(12) United States Patent
Lerchen et al.

(10) Patent No.: US 11,071,788 B2
(45) Date of Patent: Jul. 27, 2021

(54) ANTIBODY DRUG CONJUGATES OF KINESIN SPINDEL PROTEIN (KSP) INHIBITORS WITH ANTIB7H3-ANTIBODIES

(71) Applicant: BAYER PHARMA AKTIENGESELLSCHAFT, Berlin (DE)

(72) Inventors: Hans-Georg Lerchen, Leverkusen (DE); Anne-Sophie Rebstock, Champagne au Mont d'Or (FR); Yolanda Cancho Grande, Leverkusen (DE); Sven Wittrock, Berlin (DE); Sandra Berndt, Hohen Neuendorf (DE); Uwe Gritzan, Cologne (DE); Jenny Fitting, Cologne (DE); Beatrix Stelte-Ludwig, Wülfrath (DE); Patrick Jones, Oakland, CA (US); Christoph Mahlert, Wuppertal (DE); Christian Votsmeier, Cologne (DE); Dorian Schönfeld, Cologne (DE); Mark Trautwein, Whippany, NJ (US); Ernst Weber, Langenfeld (DE); Nikolaus Pawlowski, Cologne (DE); Simone Greven, Dormagen (DE); Julian Marius Glück, Meerbusch (DE); Stefanie Hammer, Berlin (DE); Lisa Dietz, Wuppertal (DE); Stephan Märsch, Cologne (DE)

(73) Assignee: BAYER PHARMA AKTIENGESELLSCHAFT, Berlin (DE)

(*) Notice: Subject to any disclaimer, the term of this patent is extended or adjusted under 35 U.S.C. 154(b) by 626 days.

(21) Appl. No.: 15/739,471

(22) PCT Filed: Jun. 20, 2016

(86) PCT No.: PCT/EP2016/064158
§ 371 (c)(1),
(2) Date: Dec. 22, 2017

(87) PCT Pub. No.: WO2016/207104
PCT Pub. Date: Dec. 29, 2016

(65) Prior Publication Data
US 2020/0138970 A1 May 7, 2020

(30) Foreign Application Priority Data
Jun. 23, 2015 (EP) .................................. 15173485

(51) Int. Cl.
*A61K 47/68* (2017.01)
*A61K 31/40* (2006.01)

(52) U.S. Cl.
CPC .......... *A61K 47/6849* (2017.08); *A61K 31/40* (2013.01); *A61K 47/6803* (2017.08)

(58) Field of Classification Search
None
See application file for complete search history.

(56) References Cited

U.S. PATENT DOCUMENTS

| 4,474,893 A | 10/1984 | Reading |
| 4,714,681 A | 12/1987 | Reading |

(Continued)

FOREIGN PATENT DOCUMENTS

| EP | 2121008 A2 | 11/2009 |
| WO | WO-9100360 A1 | 1/1991 |

(Continued)

OTHER PUBLICATIONS

International Search Report for PCT/EP2016/064158, dated Sep. 16, 2016, 10 pages.

(Continued)

*Primary Examiner* — Karl J Puttlitz
(74) *Attorney, Agent, or Firm* — Wilson Sonsini Goodrich & Rosati

(57) ABSTRACT

The present application relates to novel binder drug conjugates (ADCs), to active metabolites of these ADCs, to (Continued)

Internalization behaviour of specific B7H3 antibodies in the human renal cancer cell line A498

The kinetic progress of the internalization of fluorescence-labelled B7H3 antibodies over 24 hours is shown. For the detection of target-independent internalization, a fluorescence-labelled isotype control was used in parallel. Detailed experimental conditions are described under C-2b (x-axis: time in hours; y-axis: granule number per cell)

processes for preparing these ADCs, to the use of these ADCs for the treatment and/or prophylaxis of diseases and to the use of these ADCs for preparing medicaments for treatment and/or prophylaxis of diseases, in particular hyperproliferative and/or angiogenic disorders such as, for example, cancer diseases. Such treatments can be effected as monotherapy or else in combination with other medicaments or further therapeutic measures.

32 Claims, 8 Drawing Sheets

Specification includes a Sequence Listing.

(56) References Cited

U.S. PATENT DOCUMENTS

| | | | |
|---|---|---|---|
| 4,816,397 | A | 3/1989 | Boss et al. |
| 4,816,567 | A | 3/1989 | Cabilly et al. |
| 4,925,648 | A | 5/1990 | Hansen et al. |
| 5,573,920 | A | 11/1996 | Randle |
| 5,601,819 | A | 2/1997 | Wong et al. |
| 6,965,018 | B2 | 11/2005 | Mikesell et al. |
| 10,022,453 | B2 * | 7/2018 | Lerchen ............ A61K 47/6811 |
| 2016/0346402 | A1 * | 12/2016 | Lerchen ............ C07K 16/2875 |
| 2019/0351066 | A1 | 11/2019 | Lerchen et al. |

FOREIGN PATENT DOCUMENTS

| | | |
|---|---|---|
| WO | WO-9205793 A1 | 4/1992 |
| WO | WO-9208802 A1 | 5/1992 |
| WO | WO-9317715 A1 | 9/1993 |
| WO | WO-9708320 A1 | 3/1997 |
| WO | WO-03040979 A1 | 5/2003 |
| WO | WO-03049527 A2 | 6/2003 |
| WO | WO-03060064 A2 | 7/2003 |
| WO | WO-2005051922 A1 | 6/2005 |
| WO | WO-2005081711 A2 | 9/2005 |
| WO | WO-2006002236 A1 | 1/2006 |
| WO | WO-2006044825 A2 | 4/2006 |
| WO | WO-2006060737 A2 | 6/2006 |
| WO | WO-2007070538 A2 | 6/2007 |
| WO | WO-2008116219 A2 | 9/2008 |
| WO | WO-2009000786 A2 | 12/2008 |
| WO | WO 2009/020933 | 2/2009 |
| WO | WO 2009/140177 | 11/2009 |
| WO | WO-2012171020 A1 | 12/2012 |
| WO | WO 2014/093640 | 6/2014 |
| WO | WO 2014/151030 | 9/2014 |
| WO | WO 2015/054659 | 4/2015 |
| WO | 2015096982 * | 7/2015 |
| WO | WO 2015/096982 | 7/2015 |
| WO | WO 2015/138615 | 9/2015 |
| WO | WO 2015/189143 | 12/2015 |
| WO | WO 2016/020791 | 2/2016 |
| WO | 2016033225 * | 3/2016 |
| WO | WO 2016/096610 | 6/2016 |
| WO | WO-2016207104 A1 | 12/2016 |

OTHER PUBLICATIONS

Hong Zhou et al., "The TWEAK Receptor Fn14 is a Therapeutic Target in Melanoma: Immunotoxins Targeting Fn14 Receptor for Malignant Melanoma Treatment", Journal of Investigative Dermatology, vol. 133. No. 4, Nov. 29, 2012, pp. 1052-1062.
Hong Zhou et al., "Development and characterization of a potent immunoconjugate targeting the Fn14 receptor on solid tumor cells", Molecular Cancer Therapeutics, vol. 10, No. 7, Jul. 1, 2011, pp. 1276-1288.
Chothia et al. Canonical structures for the hypervariable regions of immunoglobulins. J Mol Biol 196:901-917 (1987).
Clackson et al. Making antibody fragments using phage display libraries. Nature 352(6336):624-628 (1991).
Doronina et al. Development of potent monoclonal antibody auristatin conjugates for cancer therapy. Nat Biotechnol 21:778-784 (2003).
Ducry et al. Antibody-drug conjugates: linking cytotoxic payloads to monoclonal antibodies. Bioconjug Chem. 21(1):5-13 (2010).
Hoogenboom. Selecting and screening recombinant antibody libraries. Nat Biotechnol. 23(9):1105-16 (2005).
Junutula et al. Site-specific conjugation of a cytotoxic drug to an antibody improves the therapeutic index. Nat Biotechnol. 26(8):925-32 (2008).
Kohler et al. Continuous cultures of fused cells secreting antibody of predefined specificity. Nature256(5517):495-497 (1975).
Kostelny et al. Formation of a bispecific antibody by the use of leucine zippers. J. Immunol. 148(5):1547-1553 (1992).
Mayer et al. Small molecule inhibitor of mitotic spindle bipolarity identified in a phenotype-based screen. Science 286(5441):971-974 (1999).
Peterson et al. Cathepsin substrates as cleavable peptide linkers in bioconjugates, selected from a fluorescence quench combinatorial library. Bioconjugate Chem. 9:618-626 (1998).
Polson et al. Antibody-drug conjugates for the treatment of non-Hodgkin's lymphoma: target and linker-drug selection. Cancer Res. 69(6):2358-64 (2009).
Polson et al. Antibody-drug conjugates targeted to CD79 for the treatment of non-Hodgkin lymphoma. Blood 110(2):616-623 (2007).
Qin et al. B7-H3 is a new cancer-specific endothelial marker in clear cell renal cell carcinoma. Onco Targets Ther 6:1667-73 (2013).
Queen et al. A humanized antibody that binds to the interleukin 2 receptor. PNAS USA 86:10029-10032 (1989).
Rashidian et al. Enzymatic labeling of proteins: techniques and approaches. Bioconjugate Chem. 24:1277-1294 (2013).
Söderlind et al. Recombining germline-derived CDR sequences for creating diverse single-framework antibody libraries. Nature Biotechnology 18:852-856 (Aug. 1, 2000).
Tao et al. Induction of apoptosis by an inhibitor of the mitotic kinesin KSP requires both activation of the spindle assembly checkpoint and mitotic slippage. Cancer Cell 8(1):49-59 (2005).
Tutt et al. Trispecific F(ab')3 derivatives that use cooperative signaling via the TCR/CD3 complex and CD2 to activate and redirect resting cytotoxic T cells. J Immunol. 147(1):60-69 (Jul. 1, 1991).
Wang et al. B7-H3-mediated tumour immunology: Friend or foe? : B7—H3-Mediated Tumour Immunology. Int J Cancer 134(12):2764-71 (2014).

* cited by examiner

Fig. 1 Internalization behaviour of specific B7H3 antibodies in the human renal cancer cell line A498

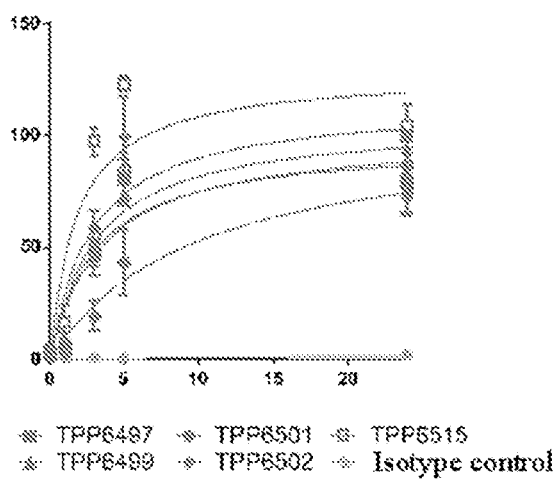

The kinetic progress of the internalization of fluorescence-labelled B7H3 antibodies over 24 hours is shown. For the detection of target-independent internalization, a fluorescence-labelled isotype control was used in parallel. Detailed experimental conditions are described under C-2b (x-axis: time in hours; y-axis: granule number per cell)

Fig. 2A: Sequence listing

<SEQ ID NO:1>
EVQLLESGGGLVQPGGSLRLSCAASGFTFRSYAMSWVRQAPGKGLEWVSSVSGSGGSALYADSVKG
RFTISRDNSKNTLYLQMNSLRAEDTAVYYCTRLTGTSFDYWGQGTLVTVSS

<SEQ ID NO:2>
SYAMS

<SEQ ID NO:3>
SVSGSGGSALYADSVKG

<SEQ ID NO:4>
LTGTSFDY

<SEQ ID NO:5>
QSVLTQPPSASGTPGQRVTISCSGSSSNIGSNPVNWYQQLPGTAPKLLIYGNSNRPSGVPDRFSGS
KSGTSASLAISGLRSEDEADYYCQSFDSSLKKVFGGGTKLTVL

<SEQ ID NO:6>
SGSSSNIGSNPVN

<SEQ ID NO:7>
GNSNRPS

<SEQ ID NO:8>
QSFDSSLKKV

<SEQ ID NO:9>
EVQLLESGGGLVQPGGSLRLSCAASGFTFRSYAMSWVRQAPGKGLEWVSSVSGSGGSALYADSVKG
RFTISRDNSKNTLYLQMNSLRAEDTAVYYCTRLTGTSFDYWGQGTLVTVSSASTKGPSVFPLAPSS
KSTSGGTAALGCLVKDYFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPG

<SEQ ID NO:10>
QSVLTQPPSASGTPGQRVTISCSGSSSNIGSNPVNWYQQLPGTAPKLLIYGNSNRPSGVPDRFSGS
KSGTSASLAISGLRSEDEADYYCQSFDSSLKKVFGGGTKLTVLGQPKAAPSVTLFPPSSEELQANK
ATLVCLISDFYPGAVTVAWKADSSPVKAGVETTTPSKQSNNKYAASSYLSLTPEQWKSHRSYSCQV
THEGSTVEKTVAPTECS

<SEQ ID NO:11>
EVQLLESGGGLVQPGGSLRLSCAASGFTFRDFYMNWIRQAPGKGLEWVSSISASGKYTYYADSVKG
RFTISRDNSKNTLYLQMNSLRAEDTAVYYCAREWGYCTNDVCRNWFDPWGQGTLVTVSS

<SEQ ID NO:12>
DFYMN

<SEQ ID NO:13>
SISASGKYTYYADSVKG

Fig. 2B: Sequence listing

<SEQ ID NO:14>
EWGYCTNDVCRNWFDP

<SEQ ID NO:15>
QSVLTQPPSASGTPGQRVTISCSGGYSNVGGNNVNWYQQLPGTAPKLLIYGNSNRPSGVPDRFSGS
KSGTSASLAISGLRSEDEADYYCQSYDSSLSGSVFGGGTKLTVL

<SEQ ID NO:16>
SGGYSNVGGNNVN

<SEQ ID NO:17>
GNSNRPS

<SEQ ID NO:18>
QSYDSSLSGSV

<SEQ ID NO:19>
EVQLLESGGGLVQPGGSLRLSCAASGFTFRDFYMNWIRQAPGKGLEWVSSISASGKYTYYADSVKG
RFTISRDNSKNTLYLQMNSLRAEDTAVYYCAREWGYCTNDVCRNWFDPWGQGTLVTVSSASTKGPS
VFPLAPSSKSTSGGTAALGCLVKDYFPEPVTVSWNSGALTSGVHTFPAVLQSSGLYSLSSVVTVPS
SSLGTQTYICNVNHKPSNTKVDKKVEPKSCDKTHTCPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEYKCK
VSNKALPAPIEKTISKAKGQPREPQVYTLPPSRDELTKNQVSLTCLVKGFYPSDIAVEWESNGQPE
NNYKTTPPVLDSDGSFFLYSKLTVDKSRWQQGNVFSCSVMHEALHNHYTQKSLSLSPG

<SEQ ID NO:20>
QSVLTQPPSASGTPGQRVTISCSGGYSNVGGNNVNWYQQLPGTAPKLLIYGNSNRPSGVPDRFSGS
KSGTSASLAISGLRSEDEADYYCQSYDSSLSGSVFGGGTKLTVLGQPKAAPSVTLFPPSSEELQAN
KATLVCLISDFYPGAVTVAWKADSSPVKAGVETTTPSKQSNNKYAASSYLSLTPEQWKSHRSYSCQ
VTHEGSTVEKTVAPTECS

<SEQ ID NO:21>
EVQLLESGGGLVQPGGSLRLSCAASGFTFSSYGMHWVRQAPGKGLEWVSAISGSGGSTYYADSVKG
RFTISRDNSKNTLYLQMNSLRAEDTAVYYCARGSNYLGMDVWGQGTLVTVSS

<SEQ ID NO:22>
SYGMH

<SEQ ID NO:23>
AISGSGGSTYYADSVKG

<SEQ ID NO:24>
GSNYLGMDV

<SEQ ID NO:25>
QSVLTQPPSASGTPGQRVTISCSGSSSNIGRNIVNWYQQLPGTAPKLLIYRSNQRPSGVPDRFSGS
KSGTSASLAISGLRSEDEADYYCQTWGTGWVFGGGTKLTVL

<SEQ ID NO:26>
SGSSSNIGRNIVN

Fig. 2C: Sequence listing

<SEQ ID NO:27>
RSNQRPS

<SEQ ID NO:28>
QTWGTGWV

<SEQ ID NO:29>
EVQLLESGGGLVQPGGSLRLSCAASGFTFSSYGMHWVRQAPGKGLEWVSAISGSGGSTYYADSVKG
RFTISRDNSKNTLYLQMNSLRAEDTAVYYCARGSNYLGMDVWGQGTLVTVSSASTKGPSVFPLAPS
SKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPG

<SEQ ID NO:30>
QSVLTQPPSASGTPGQRVTISCSGSSSNIGRNIVNWYQQLPGTAPKLLIYRSNQRPSGVPDRFSGS
KSGTSASLAISGLRSEDEADYYCQTWGTGWVFGGGTKLTVLGQPKAAPSVTLFPPSSEELQANKAT
LVCLISDFYPGAVTVAWKADSSPVKAGVETTTPSKQSNNKYAASSYLSLTPEQWKSHRSYSCQVTH
EGSTVEKTVAPTECS

<SEQ ID NO:31>
EVQLLESGGGLVQPGGSLRLSCAASGFTFSTYGMHWVRQAPGKGLEWVSAISGSGGSTYYADSVKG
RFTISRDNSKNTLYLQMNSLRAEDTAVYYCTRGYYYYGMDVWGQGTLVTVSS

<SEQ ID NO:32>
TYGMH

<SEQ ID NO:33>
AISGSGGSTYYADSVKG

<SEQ ID NO:34>
GYYYYGMDV

<SEQ ID NO:35>
QSVLTQPPSASGTPGQRVTISCSGGSSNIGSNPVNWYQQLPGTAPKLLIYGNSKRPSGVPDRFSGS
KSGTSASLAISGLRSEDEADYYCQSYDSSLSGWVFGGGTKLTVL

<SEQ ID NO:36>
SGGSSNIGSNPVN

<SEQ ID NO:37>
GNSKRPS

<SEQ ID NO:38>
QSYDSSLSGWV

Fig. 2D: Sequence listing

```
<SEQ ID NO:39>
EVQLLESGGGLVQPGGSLRLSCAASGFTFSTYGMHWVRQAPGKGLEWVSAISGSGGSTYYADSVKG
RFTISRDNSKNTLYLQMNSLRAEDTAVYYCTRGYYYYGMDVWGQGTLVTVSSASTKGPSVFPLAPS
SKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPG

<SEQ ID NO:40>
QSVLTQPPSASGTPGQRVTISCSGGSSNIGSNPVNWYQQLPGTAPKLLIYGNSKRPSGVPDRFSGS
KSGTSASLAISGLRSEDEADYYCQSYDSSLSGWVFGGGTKLTVLGQPKAAPSVTLFPPSSEELQAN
KATLVCLISDFYPGAVTVAWKADSSPVKAGVETTTPSKQSNNKYAASSYLSLTPEQWKSHRSYSCQ
VTHEGSTVEKTVAPTECS

<SEQ ID NO:41>
EVQLLESGGGLVQPGGSLRLSCAASGFTFSSYGMHWVRQVPGKGLEWVSAISGSGGTTYYADSVKG
RFTISRDNSKNTLYLQMNSLRAEDTAVYYCARGGYHFLFDYWGQGTLVTVSS

<SEQ ID NO:42>
SYGMH

<SEQ ID NO:43>
AISGSGGTTYYADSVKG

<SEQ ID NO:44>
GGYHFLFDY

<SEQ ID NO:45>
QSVLTQPPSASGTPGQRVTISCSGSSSNIGSNTVNWYQQLPGTAPKLLIYRNDQRLLGVPDRFSGS
KSGTSASLAISGLRSEDEADYYCQSYDSSLSGWVFGGGTKLTVL

<SEQ ID NO:46>
SGSSSNIGSNTVN

<SEQ ID NO:47>
RNDQRLL

<SEQ ID NO:48>
QSYDSSLSGWV

<SEQ ID NO:49>
EVQLLESGGGLVQPGGSLRLSCAASGFTFSSYGMHWVRQVPGKGLEWVSAISGSGGTTYYADSVKG
RFTISRDNSKNTLYLQMNSLRAEDTAVYYCARGGYHFLFDYWGQGTLVTVSSASTKGPSVFPLAPS
SKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPG
```

Fig. 2E: Sequence listing

```
<SEQ ID NO:50>
QSVLTQPPSASGTPGQRVTISCSGSSSNIGSNTVNWYQQLPGTAPKLLIYRNDQRLLGVPDRFSGS
KSGTSASLAISGLRSEDEADYYCQSYDSSLSGWVFGGGTKLTVLGQPKAAPSVTLFPPSSEELQAN
KATLVCLISDFYPGAVTVAWKADSSPVKAGVETTTPSKQSNNKYAASSYLSLTPEQWKSHRSYSCQ
VTHEGSTVEKTVAPTECS

<SEQ ID NO:51>
EQAPGTAPCSRGSSWSADLDKCMDCASCRARPHSDFCLGCAAAPPAPFRLLWPIEGRMDPKSCDKT
HTCPPCPAPELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDKSRWQQGN
VFSCSVMHEALHNHYTQKSLSLSPGKHHHHHH

<SEQ ID NO:52>
GALEVQVPEDPVVALVGTDATLCCSFSPEPGFSLAQLNLIWQLTDTKQLVHSFAEGQDQGSAYANR
TALFPDLLAQGNASLRLQRVRVADEGSFTCFVSIRDFGSAAVSLQVAAPYSKPSMTLEPNKDLRPG
DTVTITCSSYQGYPEAEVFWQDGQGVPLTGNVTTSQMANEQGLFDVHSILRVVLGANGTYSCLVRN
PVLQQDAHSSVTITPQRSPTGAVEVQVPEDPVVALVGTDATLRCSFSPEPGFSLAQLNLIWQLTDT
KQLVHSFTEGRDQGSAYANRTALFPDLLAQGNASLRLQRVRVADEGSFTCFVSIRDFGSAAVSLQV
AAPYSKPSMTLEPNKDLRPGDTVTITCSSYRGYPEAEVFWQDGQGVPLTGNVTTSQMANEQGLFDV
HSVLRVVLGANGTYSCLVRNPVLQQDAHGSVTITGQPMT

<SEQ ID NO:53>
VEVQVSEDPVVALVDTDATLRCSFSPEPGFSLAQLNLIWQLTDTKQLVHSFTEGRDQGSAYSNRTA
LFPDLLVQGNASLRLQRVRVTDEGSYTCFVSIQDFDSAAVSLQVAAPYSKPSMTLEPNKDLRPGNM
VTITCSSYQGYPEAEVFWKDGQGVPLTGNVTTSQMANERGLFDVHSVLRVVLGANGTYSCLVRNPV
LQQDAHGSVTITGQPLTF

<SEQ ID NO:54>
EVQLLESGGGLVQPGGSLRLSCAASGFTFRSYAMSWVRQAPGKGLEWVSSVSGSGGSALYADSVKG
RFTISRDNSKNTLYLQMNSLRAEDTAVYYCTRLTGTSFDYWGQGTLVTVSSASTKGPSVFPLAPSS
KSTSGGTAALGCLVKDYFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPKDTLMISRTPEVTCVVV
DVSHEDPEVKFNWYVDGVEVHNAKTKPREEQYASTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPG

<SEQ ID NO:55>
EVQLLESGGGLVQPGGSLRLSCAASGFTFSSYAMSWVRQAPGKGLEWVSSISGSGGSTLYADSVKG
RFTISRDNSKNTLYLQMNSLRAEDTAVYYCAKLTGTSFDYWGQGTLVTVSS

<SEQ ID NO:56>
SISGSGGSTLYADSVKG

<SEQ ID NO:57>
QSVLTQPPSASGTPGQRVTISCSGSSSNIGSNPVNWYQQLPGTAPKLLIYSNNQRPSGVPDRFSGS
KSGTSASLAITGLQSEDEADYYCQSFDSSLKKVFGGGTKLTVL

<SEQ ID NO:58>
SNNQRPS
```

Fig. 2F: Sequence listing

<SEQ ID NO:59>
EVQLLESGGGLVQPGGSLRLSCAASGFTFSSYAMSWVRQAPGKGLEWVSSISGSGGSTLYADSVKG
RFTISRDNSKNTLYLQMNSLRAEDTAVYYCAKLTGTSFDYWGQGTLVTVSSASTKGPSVFPLAPSS
KSTSGGTAALGCLVKDYFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPG

<SEQ ID NO:60>
QSVLTQPPSASGTPGQRVTISCSGSSSNIGSNPVNWYQQLPGTAPKLLIYSNNQRPSGVPDRFSGS
KSGTSASLAITGLQSEDEADYYCQSFDSSLKKVFGGGTKLTVLGQPKAAPSVTLFPPSSEELQANK
ATLVCLISDFYPGAVTVAWKADSSPVKAGVETTTPSKQSNNKYAASSYLSLTPEQWKSHRSYSCQV
THEGSTVEKTVAPTECS

<SEQ ID NO:61>
EVQLLESGGGLVQPGGSLRLSCAASGFTFSSYAMSWVRQAPGKGLEWVSSISGSGGSTLYADSVKG
RFTISRDNSKNTLYLQMNSLRAEDTAVYYCAKLTGTSFDYWGQGTLVTVSSASTKGPSVFPLAPSS
KSTSGGTAALGCLVKDYFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPKDTLMISRTPEVTCVVV
DVSHEDPEVKFNWYVDGVEVHNAKTKPREEQYASTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPG

<SEQ ID NO:62>
EVQLLESGGGLVQPGGSLRLSCAASGFTFSSYAMSWVRQAPGKGLEWVSSISGSGGSTLYADSVKG
RFTISRDNSKNTLYLQMNSLRAEDTAVYYCAKLTGTSFDYWGQGTLVTVSSASTKGPSVFPLAPSS
KSTSGGTAALGCLVKDYFPEPVTVSWNSGALTSGVHTFPAVLQSSGLYSLSSVVTVPSSSLGTQTY
ICNVNHKPSNTKVDKKVEPKSCDKTHTCPPCPAPELLGGPSVFLFPPKPKDTLMISRTPEVTCVVV
DVSHEDPEVKFNWYVDGVEVHNAKTKPREEQYQSTYRVVSVLTVLHQDWLNGKEYKCKVSNKALPA
PIEKTISKAKGQPREPQVYTLPPSRDELTKNQVSLTCLVKGFYPSDIAVEWESNGQPENNYKTTPP
VLDSDGSFFLYSKLTVDKSRWQQGNVFSCSVMHEALHNHYTQKSLSLSPG

<SEQ ID NO:63>
EVQLLESGGGLVQPGGSLRLSCAASGFTFSSYGMHWVRQAPGKGLEWVSAISGSGGSTYYADSVKG
RFTISRDNSKNTLYLQMNSLRAEDTAVYYCARGYYYYGMDVWGQGTLVTVSS

<SEQ ID NO:64>
SYGMH

<SEQ ID NO:65>
EVQLLESGGGLVQPGGSLRLSCAASGFTFSSYGMHWVRQAPGKGLEWVSAISGSGGSTYYADSVKG
RFTISRDNSKNTLYLQMNSLRAEDTAVYYCARGYYYYGMDVWGQGTLVTVSSASTKGPSVFPLAPS
SKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYNSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPG

Fig. 2G: Sequence listing

```
<SEQ ID NO:66>
EVQLLESGGGLVQPGGSLRLSCAASGFTFSSYGMHWVRQAPGKGLEWVSAISGSGGSTYYADSVKG
RFTISRDNSKNTLYLQMNSLRAEDTAVYYCARGYYYYGMDVWGQGTLVTVSSASTKGPSVFPLAPS
SKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYASTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPG

<SEQ ID NO:67>
EVQLLESGGGLVQPGGSLRLSCAASGFTFSSYGMHWVRQAPGKGLEWVSAISGSGGSTYYADSVKG
RFTISRDNSKNTLYLQMNSLRAEDTAVYYCARGYYYYGMDVWGQGTLVTVSSASTKGPSVFPLAPS
SKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYQSTYRVVSVLTVLHQDWLNGKEYKCKVSNKALP
APIEKTISKAKGQPREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPG

<SEQ ID NO:68>
QSVLTQPPSASGTPGQRVTISCSGGSSNIGSNPVNWYQQLPGTAPKLLIYGNNKRPSGVPDRFSGS
KSGTSASLAISGLRSEDEADYYCQSYDSSLSGWVFGGGTKLTVL

<SEQ ID NO:69>
GNNKRPS

<SEQ ID NO:70>
QSVLTQPPSASGTPGQRVTISCSGGSSNIGSNPVNWYQQLPGTAPKLLIYGNNKRPSGVPDRFSGS
KSGTSASLAISGLRSEDEADYYCQSYDSSLSGWVFGGGTKLTVLGQPKAAPSVTLFPPSSEELQAN
KATLVCLISDFYPGAVTVAWKADSSPVKAGVETTTPSKQSNNKYAASSYLSLTPEQWKSHRSYSCQ
VTHEGSTVEKTVAPTECS
```

ANTIBODY DRUG CONJUGATES OF KINESIN SPINDEL PROTEIN (KSP) INHIBITORS WITH ANTIB7H3-ANTIBODIES

This application is the U.S. national phase of International Application No. PCT/EP2016/064158 filed 20 Jun. 2016, which designated the U.S. and claims priority to EP Patent Application No. 15173485.2 filed 23 Jun. 2015, the entire contents of each of which are hereby incorporated by reference.

SEQUENCE LISTING

The instant application contains a Sequence Listing which has been submitted electronically in ASCII format and is hereby incorporated by reference in its entirety. Said ASCII copy, created on May 23, 2018, is named 6487-0184_SL.txt and is 96,440 bytes in size.

INTRODUCTION AND STATE OF THE ART

The invention relates to binder drug conjugates (ADCs) of kinesin spindle protein inhibitors, to active metabolites of these ADCs, to processes for preparing these ADCs, to the use of these ADCs for the treatment and/or prophylaxis of diseases and to the use of these ADCs for preparing medicaments for treatment and/or prevention of diseases, in particular hyperproliferative and/or angiogenic disorders such as, for example, cancer diseases. Such treatments can be effected as monotherapy or else in combination with other medicaments or further therapeutic measures.

Cancers are the consequence of uncontrolled cell growth of the most diverse tissues. In many cases the new cells penetrate into existing tissue (invasive growth), or they metastasize into remote organs. Cancers occur in a wide variety of different organs and often have tissue-specific courses. The term "cancer" as a generic term therefore describes a large group of defined diseases of different organs, tissue and cell types.

Some tumours at early stages can be removed by surgical and radiotherapy measures. Metastased tumours as a rule can only be treated palliatively by chemotherapeutics. The aim here is to achieve the optimum combination of an improvement in the quality of life and prolonging of life.

Conjugates of binder proteins with one or more active compound molecules are known, in particular in the form of antibody drug conjugates (ADCs) in which an internalising antibody directed against a tumour-associated antigen is covalently attached via a linker to a cytotoxic agent. Following introduction of the ADCs into the tumour cell and subsequent dissociation of the conjugate, either the cytotoxic agent itself or a cytotoxic metabolite formed therefrom is released within the tumour cell and can unfold its action therein directly and selectively. In this manner, m contrast to conventional chemotherapy, damage to normal tissue is contained in significantly narrower limits [see, for example, J. M. Lambert, Curr. Opin Pharmacol. 5, 543-549 (2005); A. M. Wu and P. D. Senter, Nat. Biotechnol. 23, 1137-1146 (2005); P. D. Senter, Curr. Opin. Chem. Biol. 13, 235-244 (2009); L. Ducry and B. Stump, Bioconjugate Chem. 21, 5-13 (2010)]. Thus, WO2012/171020 describes ADCs in which a plurality of toxophor molecules are attached via a polymeric linker to an antibody. As possible toxophors, WO2012/171020 mentions, among others, the substances SB 743921, SB 715992 (Ispinesib), MK-0371, AZD8477, AZ3146 and ARRY-520.

The substances mentioned last are kinesin spindle protein inhibitors. Kinesin spindle protein (KSP, also known as Eg5, HsEg5, KNSL1 or KIF11) is a kinesin-like motorprotein which is essential for the bipolar mitotic spindle to function. Inhibition of KSP leads to mitotic arrest and, over a relatively long term, to apoptosis (Tao et al., Cancer Cell 2005 Jul. 8(1), 39-59). After the discovery of the first cell-permeable KSP inhibitor, monastrol, KSP inhibitors have established themselves as a class of novel chemotherapeutics (Mayer et al., Science 286: 971-974, 1999) and have been the subject of a number of patent applications (e.g. WO2006/044825; WO2006/002236; WO2005/051922; WO2006/060737; WO03/060064; WO03/040979; and WO03/049527). However, since KSP unfolds its action only during a relatively short period of time during the mitosis phase, KSP inhibitors have to be present in a sufficiently high concentration during this phase. WO2014/151030 discloses ADCs including certain KSP inhibitors.

SUMMARY OF THE INVENTION

Against this background it is an object of the present invention to provide substances which, after administration at a relatively low concentration, unfold apoptotic action and may therefore be of benefit for cancer therapy.

To achieve this object, the invention provides conjugates of a glycosylated or aglycosylated anti-B7H3 antibody with compounds of the formula (I) below, where one or more of the compounds of the formula (I) are attached to the antibody via a linker L. In this case, aglycosylated antibodies do not have any glycans at the conserved N-binding site in the CH2 domain of the Fc region and therefore do not bind to NK cells. An aglycosylated antibody therefore does not support NK cell-mediated cellular cytotoxicity. The antibody is preferably a human, humanized or chimeric monoclonal antibody. Particular preference is given to anti-B7H3 antibodies which specifically bind the human Ig4 and/or the human and/or murine Ig2 isoform of B7H3, in particular the anti-B7H3 antibodies TPP-6497, TPP-6499, TPP-6501, TTP-6502, TPP-6515, TPP-7611, TPP-8382, TPP-8564, TPP-8567, TPP-8322, TPP-8565, TPP-8568, TPP-8748 and TPP-8750.

Formula (I):

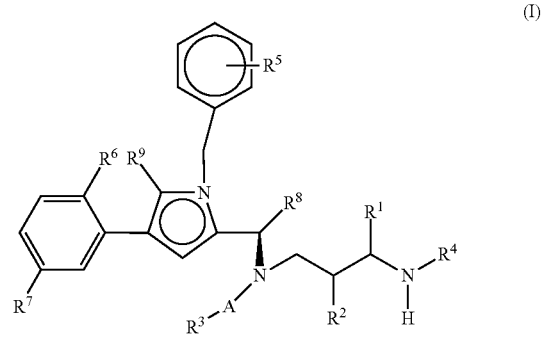

where $R^1$ represents H, -L-#1, -MOD or $-(CH_2)_{0-3}Z$, where Z represents $-H$, $-NHY^3$, $-OY^3$, $-SY^3$, halogen, $-CO-NY^1Y^2$ or $-CO-OY^3$, where $Y^1$ and $Y^2$ independently of one another represent H, $NH_2$, $-(CH_2CH_2O)_{0-3}-(CH_2)_{0-3}Z'$ (e.g. $-(CH_2)_{0-3}Z'$) or $-CH(CH_2W)Z'$, and $Y^3$ represents H or $-(CH_2)_{0-3}Z'$, where Z' represents H, $NH_2$, $SO_3H$, COOH, —NH—CO—$CH_2$—$CH_2$—$CH(NH_2)COOH$ or —(CO—NH—$CHY^4)_{1-3}COOH$, where W represents H or OH, where $Y^4$ represents straight-chain or branched $C_{1-6}$ alkyl which is optionally substituted by —$NHCONH_2$, or represents aryl or benzyl which are optionally substituted by —$NH_2$;

$R^2$ represents H, -MOD, —CO—$CHY^4$—$NHY^5$ or —$(CH_2)_{0-3}Z$, where Z represents —H, halogen, —$OY^3$, —$SY^3$, $NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;

where $Y^4$ represents straight-chain or branched $C_{1-6}$-alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;

$R^4$ represents H, -L-#1, —$SG_{lys}$-$(CO)_{0-1}$—$R^{4'}$, —CO—$CHY^4$—$NHY^5$ or —$(CH_2)_{0-3}Z$, wherein $SG_{lys}$ is a group cleavable by a lysosomal enzyme, in particular a group consisting of a dipeptide or tripeptide, $R^{4'}$ is a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, heteroarylalkoxy, $C_{1-10}$-alkoxy, $C_{6-10}$-aryloxy or $C_{6-10}$-aralkoxy, $C_{5-10}$-heteroaralkoxy, $C_{1-10}$-alkyl-O—$C_{6-10}$-aryloxy, $C_{5-10}$-heterocycloalkoxy group, which may be substituted once or more than once by —$NH_2$, —NH-alkyl, —$N(alkyl)_2$, NH—CO-alkyl, N(alkyl)-CO-alkyl, —$SO_3H$, —$SO_2NH_2$, —$SO_2$—$N(alkyl)_2$, —COOH, —$CONH_2$, —$CON(alkyl)_2$, or —OH, —H or a group —$O_x$—$(CH_2CH_2O)_y$—$R^{4''}$, (where x is 0 or 1 and v is a number from 1 to 10, and $R^{4''}$ is —H, -alkyl (preferably $C_{1-12}$-alkyl), —$CH_2$—COOH, —$CH_2$—$CH_2$—COOH, or —$CH_2$—$CH_2$—$NH_2$), wherein a primary amino group is present after cleavage (corresponding to $R^4$=H);

where Z represents —H, halogen, —$OY^3$, —$SY^3$, $NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;

where $Y^4$ represents straight-chain or branched $C_{1-6}$-alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;

or $R^2$ and $R^4$ together (with formation of a pyrrolidine ring) represent —$CH_2$—$CHR^{11}$— or —$CHR^{11}$—$CH_2$—, where $R^{11}$ represents H, $NH_2$, $SO_3H$, COOH, SH, halogen (in particular F or Cl), $C_{1-4}$-alkyl, $C_{1-4}$-haloalkyl, $C_{1-4}$-alkoxy, hydroxyl-substituted $C_{1-4}$-alkyl, COO($C_{1-4}$-alkyl) or OH;

A represents CO, SO, $SO_2$, $SO_2NH$ or $CNNH_2$;

$R^3$ represents -L-#1, -MOD or an optionally substituted alkyl, cycloalkyl, aryl, heteroaryl, heteroalkyl, heterocycloalkyl group, preferably -L-#1 or a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —$S(O)_n$-alkyl groups, 1-3 —$SO_2$—NH-alkyl groups, 1-3 —NH-alkyl groups, 1-3 —$N(alkyl)_2$ groups, 1-3 —$NH_2$ groups or 1-3 —$(CH_2)_{0-3}Z$ groups, n represents 0, 1 or 2, where Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}Z'$ and $Y^3$ represents H, —$(CH_2)_{0-3}$—CH $(NHCOCH_3)Z'$, —$(CH_2)_{0-3}$—$CH(NH_2)Z$ or —$(CH_2)_{0-3}Z'$, where Z' represents H, $SO_3H$, $NH_2$ or COOH (where "alkyl" preferably represents $C_{1-10}$-alkyl);

$R^5$ represents H, $NH_2$, $NO_2$, halogen (in particular F, Cl, Br), —CN, $CF_3$, —$OCF_3$, —$CH_2F$, —$CH_2F$, SH or —$(CH_2)_{0-3}Z$, where Z represents —H, —$OY^3$, —$SY^3$, halogen, $NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;

$R^6$ and $R^7$ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy, $NO_2$, $NH_2$, COOH or halogen (in particular F, Cl, Br), $R^8$ represents (optionally fluorinated) $C_{1-10}$-alkyl, (optionally fluorinated) $C_{2-10}$-alkenyl, (optionally fluorinated) $C_{2-10}$-alkynyl, (optionally fluorinated) $C_{4-10}$-cycloalkyl or —$(CH_2)_{0-2}$—$(HZ^2)$, where $HZ^2$ represents a 4- to 7-membered heterocycle having up to two heteroatoms selected from the group consisting of N, O and S, where each of these groups may be substituted by —OH, $CO_2H$ or $NH_2$;

$R^9$ represents H, F, $CH_3$, $CF_3$, $CH_2F$ or $CHF_2$;

where one of the substituents $R^1$, $R^3$ or $R^4$ represents or (in the case of $R^8$) contains -L-#1, L represents the linker and #1 represents the bond to the binder or derivative thereof, where -MOD represents —$(NR^{10})_n$-$(G1)_o$-G2-G3, where $R^{10}$ represents H or $C_1$-$C_3$-alkyl;

G1 represents —NHCO— or —CONH— (where, if G1 represents —NHCO—, $R^{10}$ does not represent $NH_2$);

n represents 0 or 1;

o represents 0 or 1; and

G2 represents a straight-chain and/or branched hydrocarbon group which has 1 to 10 carbon atoms and which may be interrupted once or more than once by one or more of the groups —O—, —S—, —SO—, $SO_2$, —$NR^y$—, —$NR^yCO$—, $CONR^y$—, —$NR^yNR^y$—, —$SO_2NR^yNR^y$—, —$CONR^yNR^y$— (where $R^y$ represents H, phenyl, $C_1$-$C_{10}$-alkyl, $C_2$-$C_{10}$-alkenyl or $C_2$-$C_{10}$-alkynyl, each of which may be substituted by $NHCONH_2$, —COOH, —OH, —$NH_2$, NH—$CNNH_2$, sulphonamide, sulphone, sulphoxide or sulphonic acid), —CO—, or —$CR^x$=N—O— (where Rx represents H, $C_1$-$C_3$-alkyl or phenyl), where the hydrocarbon chain including any side chains may be substituted by —$NHCONH_2$, —COOH, —OH, —$NH_2$, NH—$CNNH_2$, sulphonamide, sulphone, sulphoxide or sulphonic acid, G3 represents —H or —COOH, and where the group -MOD preferably has at least one group —COOH, and the salts, solvates, salts of the solvates and epimers thereof.

The conjugates according to the invention can have chemically labile linkers, enzymatically labile linkers or stable linkers. Particular preference is given to stable linkers and linkers which can be cleaved by a protease.

The invention furthermore provides processes for preparing the conjugates according to the invention, and also precursors and intermediates for the preparation.

The preparation of the conjugates according to the invention regularly comprises the following steps:

preparation of a linker precursor which optionally carries protective groups and has a reactive group which is capable of coupling to the antibody;

conjugation of the linker precursor to the derivative, which optionally carries protective groups, of a KSP inhibitor of the formula (I), where in these formulae there is as yet no bond to a linker, giving a reactive KSP inhibitor/linker conjugate which optionally carries protective groups;

removal of any protective groups present in the KSP inhibitor/linker conjugate and conjugation of the antibody to the KSP inhibitor/linker conjugate, giving the antibody/KSP inhibitor conjugate according to the invention.

Attachment of the reactive group may also take place after the construction of an optionally protected KSP inhibitor/linker precursor conjugate.

Depending on the linker, succinimide-linked ADCs may, after conjugation, be converted according to Scheme 26 into the open-chain succinamides, which have an advantageous stability profile.

As illustrated above, conjugation of the linker precursor to a low-molecular-weight KSP inhibitor can be by substitution of a hydrogen atom at $R^1$, $R^3$ or $R^4$ in formula (I) by the linker. In the synthesis steps prior to the conjugation, any functional groups present may also be present in protected form. Prior to the conjugation step, these protective groups are removed by known methods of peptide chemistry. The conjugation can take place chemically by various routes, as shown in an exemplary manner in Schemes 20 to 31 in the examples. In particular, it is optionally possible to modify the low-molecular weight KSP inhibitor for conjugation to the linker, for example by introduction of protective groups or leaving groups to facilitate substitution.

In particular, the invention provides novel low-molecular-weight KSP inhibitors conjugated to an anti-B7H3 antibody. These KSP inhibitors or their antibody conjugates have the following general formula (II):

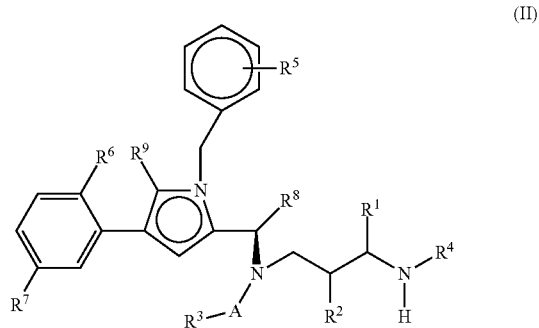

(II)

where $R^1$ represents H, -L-BINDER, -MOD or $—(CH_2)_{0-3}Z$, where Z represents —H, $—NHY^3$ $—OY^3$, $—SY^3$, halogen, $—CO—NY^1Y^2$ or $—CO—OY^3$,
where
$Y^1$ and $Y^2$ independently of one another represent H, $NH_2$, $—(CH_2CH_2O)_{0-3}—(CH_2)_{0-3}$ Z' (e.g. $—(CH_2)_{0-3}Z'$) or $—CH(CH_2W)Z'$,
$Y^3$ represents H or $—(CH_2)_{0-3}Z'$,
Z' represents H, NFL, $SO_3H$, COOH, $—NH—CO—CH_2—CH_2—CH(NH_2)COOH$ or $—(CO—NH—CHY^4)_{0-3}COOH$;
W represents H or OH,
$Y^4$ represents straight-chain or branched $C_{1-6}$ alkyl which is optionally substituted by $—NH—C(=O)—NH_2$, or represents aryl or benzyl which are optionally substituted by $—NH_2$;

$R^2$ represents H, -MOD, $—C(=O)—CHY^4—NHY^5$ or $—(CH_2)_{0-3}Z$, or
$R^2$ and $R^4$ together (with formation of a pyrrolidine ring) represent $—CH_2—CHR^{11}—$ or $—CHR^{11}—CH_2—$,
where
$R^{11}$ represents —H, $—NH_2$, $—SO_3H$, —COOH, —SH, halogen (in particular F or Cl), $C_{1-4}$-alkyl, $C_{1-4}$-haloalkyl, $C_{1-4}$-alkoxy, hydroxyl-substituted $C_{1-4}$-alkyl, COO($C_{1-4}$-alkyl) or OH;
Z represents —H, halogen, $—OY^3$, $—SY^3$, $NHY^3$, $—CO—NY^1Y^2$ or $—CO—OY^3$,
$Y^1$ and $Y^2$ independently of one another represent H, $NH_2$ or $—(CH_2)_{0-3}Z'$, and $Y^3$ represents H or $—(CH_2)_{0-3}Z'$,
where Z' represents H, $SO_3H$, $NH_2$ or COOH;
where $Y^4$ represents straight-chain or branched $C_{1-6}$-alkyl which is optionally substituted by $—NHCONH_2$, or represents aryl or benzyl which are optionally substituted by $—NH_2$, and $Y^5$ represents H or $—CO—CHY^6—NH_2$, where $Y^6$ represents straight-chain or branched $C_{1-6}$-alkyl;
$R^4$ represents H, -L-BINDER, $—SG_{lys}$-$(CO)_{0-1}—R^{4'}$, $—CO—CHY^4—NHY^5$ or $—(CH_2)_{0-3}Z$,
wherein $SG_{lys}$ is a group cleavable by a lysosomal enzyme, in particular a group consisting of a dipeptide or tripeptide,
$R^{4'}$ is a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, heteroarylalkoxy, $C_{1-10}$-alkoxy, $C_{6-10}$-aryloxy or $C_{6-10}$-aralkoxy, $C_{5-10}$-heteroaralkoxy, $C_{1-10}$-alkyl-O—$C_{6-10}$-aryloxy, $C_{5-10}$-heterocycloalkoxy group, which may be substituted once or more than once by $—NH_2$, —NH-alkyl, —N(alkyl)$_2$, NH—CO-alkyl, N(alkyl)-COalkyl, $—SO_3H$, $—SO_2NH_2$, $—SO_2—N(alkyl)_2$, —COOH, $—CONH_2$, $—CON(alkyl)_2$, or —OH, —H or a group $—O_x—(CH_2CH_2O)_y—R^{4''}$, (where x is 0 or 1 and v is a number from 1 to 10, and $R^{4''}$ is —H, -alkyl (preferably $C_{1-12}$-alkyl), $—CH_2—COOH$, $—CH_2—CH_2—COOH$, or $—CH_2—CH_2—NH_2$), wherein a primary amine group is present after cleavage (corresponding to $R^4=H$);
where Z represents —H, halogen, $—OY^3$, $—SY^3$, $NHY^3$, $—CO—NY^1Y^2$ or $—CO—OY^3$, where $Y^1$ and $Y^2$ independently of one another represent H, $NH_2$ or $—(CH_2)_{0-3}Z'$, and $Y^3$ represents H or $—(CH_2)_{0-3}Z'$, where Z' represents H, $SO_3H$, $NH_2$ or COOH;
where $Y^4$ represents straight-chain or branched $C_{1-6}$-alkyl which is optionally substituted by $—NHCONH_2$, or represents aryl or benzyl which are optionally substituted by $—NH_2$, and $Y^5$ represents H or $—CO—CHY^6—NH_2$, where $Y^6$ represents straight-chain or branched $C_{1-6}$-alkyl;
or $R^2$ and $R^4$ together (with formation of a pyrrolidine ring) represent $—CH_2—CHR^{11}—$ or $—CHR^{11}—CH_2—$, where $R^{11}$ represents H, $NH_2$, $SO_3H$, COOH, SH, halogen (in particular F or Cl), $C_{1-4}$-alkyl, $C_{1-4}$-haloalkyl, $C_{1-4}$-alkoxy, hydroxyl-substituted $C_{1-4}$-alkyl, COO($C_{1-4}$-alkyl) or OH;
A represents $—C(=O)—$, $—S(=O)—$, $—S(=O)_2—$, $—S(=O)_2—NH$ or $—CNNH_2—$;
$R^3$ represents -L-BINDER, -MOD or an optionally substituted alkyl, cycloalkyl, aryl, heteroaryl, heteroalkyl, heterocycloalkyl group, preferably -L-BINDER or a $C_{1-10}$-alkyl, $C_{5-10}$-aryl or $C_{5-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 $—S(O)_n$-alkyl groups, 1-3 $—SO_2—$NH-alkyl groups, 1-3 —NH-alkyl groups, 1-3 —N(alkyl)$_2$ groups, 1-3 $—NH_2$ groups or 1-3 $—(CH_2)_{0-3}Z$ groups, where Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z' and Y$^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH (where "alkyl" preferably represents C$_{1-10}$-alkyl);

n represents 0, 1 or 2,

R$^5$ represents H, NH$_2$, NO$_2$, halogen (in particular F, Cl, Br), —CN, CF$_3$, —OCF$_3$, —CH$_2$F, —CH$_2$F, SH or —(CH$_2$)$_{0-3}$Z, where Z represents —H, —OY$^3$, —SY$^3$, halogen, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

R$^8$ represents (optionally fluorinated) C$_{1-10}$-alkyl, (optionally fluorinated) C$_{2-10}$-alkenyl, (optionally fluorinated) C$_{2-10}$-alkynyl, (optionally fluorinated) C$_{4-10}$-cycloalkyl or —(CH$_2$)$_{0-2}$—(HZ$^2$), where HZ$^2$ represents a 4- to 7-membered heterocycle having up to two heteroatoms selected from the group consisting of N, O and S (preferably oxetane), where each of these groups may be substituted by —OH, CO$_2$H or NH$_2$;

R$^9$ represents H, F, CH$_3$, CF$_3$, CH$_2$F or CHF$_2$;

where L represents a linker and BINDER represents an (aglycosylated) anti-B7H3 antibody, where the binder may optionally be attached to a plurality of active compound molecules, where one representative of R$^1$, R$^3$ and R$^4$ represents -L-BINDER, R$^6$ and R$^7$ independently of one another represent H, cyano, (optionally fluorinated) C$_{1-10}$-alkyl, (optionally fluorinated) C$_{2-10}$-alkenyl, (optionally fluorinated) C$_{2-10}$-alkynyl, hydroxy, NO$_2$, NH$_2$, COOH or halogen (in particular F, Cl, Br), where -MOD represents —(NR$^{10}$)$_n$-(G1)$_o$-G2-G3, where R$^{10}$ represents H or C$_1$-C$_3$-alkyl;

G1 represents —NHCO— or —CONH— (where, if G1 represents —NHCO—, R$^{10}$ does not represent NH$_2$);

n represents 0 or 1;

o represents 0 or 1; and

G2 represents a straight-chain and/or branched hydrocarbon group which has 1 to 10 carbon atoms and which may be interrupted once or more than once by one or more of the groups —O—, —S—, —SO—, SO$_2$, —NRy-, —NRyCO—, CONRy-, —NRyNRy-, —SO$_2$NRyNRy-, —CONRyNRy- (where R$^y$ represents H, phenyl, C1-C10-alkyl, C2-C10-alkenyl or C2-C10-alkynyl, each of which may be substituted by NHCONH$_2$, —COOH, —OH, —NH$_2$, NH—CNNH$_2$, sulphonamide, sulphone, sulphoxide or sulphonic acid), —CO—, —CR$^x$=N—O— (where Rx represents H, C1-C3-alkyl or phenyl), where the hydrocarbon chain including any side chains may be substituted by —NHCONH$_2$, —COOH, —OH, —NH$_2$, NH—CNNH$_2$, sulphonamide, sulphone, sulphoxide or sulphonic acid, G3 represents —H or —COOH, where the group -MOD preferably has at least one group —COOH;

and the salts, solvates, salts of the solvates and epimers thereof.

DESCRIPTION OF THE FIGURES

FIG. 1: Internalization behaviour of specific B7H3 antibodies in the human renal cancer cell line A498.

The kinetic progress of the internalization of fluorescence-labelled B7H3 antibodies over 24 hours is shown. For the detection of target-independent internalization, a fluorescence-labelled isotype control was used in parallel. Detailed experimental conditions are described under C-2b (x-axis. time in hours; y-axis: granula number per cell).

FIGS. 2A-2G: Sequence protocol

DETAILED DESCRIPTION OF THE INVENTION

The invention provides conjugates of an anti-B7H3 antibody and aglycosylated and/or humanized variants thereof with one or more active compound molecules, the active compound molecule being a kinesin spindle protein inhibitor (KSP inhibitor) attached to the antibody via a linker L.

The conjugate according to the invention can be represented by the general formula

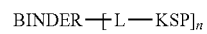

where BINDER represents the anti-B7H3 antibody, L represents the linker, KSP represents the KSP inhibitor and n represents a number from 1 to 50, preferably from 1.2 to 20 and particularly preferably from 2 to 8. Here, n is the mean of the number of KSP inhibitor/linker conjugates per BINDER. Preferably, KSP-L has the formula (I) shown above. Furthermore, the linker is preferably attached to different amino acids of the antibody. Particular preference is given to binding to different cysteine residues of the binder. The antibody is preferably a human, humanized or chimeric monoclonal anti-B7H3 antibody or an antigen-binding fragment thereof. Particular preference is given to anti-B7H3 antibodies which specifically bind the human Ig4 isoform, in particular the human anti-B7H3 antibodies TPP-6497, TPP-6499, TPP-6501, TPP-6502, TPP-6515. In a further preferred embodiment, the anti-B7H3 antibody or the antigen-binding fragment is present in aglycosylated form.

Antibodies which can be used according to the invention, KSP inhibitors which can be used according to the invention and linkers which can be used according to the invention which can be used in combination without any limitation are described below. In particular, the binders represented in each case as preferred or particularly preferred can be employed in combination with the KSP inhibitors represented in each case as preferred or particularly preferred, optionally in combination with the linkers represented in each case as preferred or particularly preferred.

KSP Inhibitors and their Binder Conjugates

Definitions

The term "substituted" signifies that one or more hydrogens on the designated atom or the designated group has/have been replaced by a selection from the group specified with the proviso that the normal valency of the designated atom is not exceeded under the given circumstances. Combinations of substituents and/or variables are permitted.

The term "optionally substituted" signifies that the number of substituents may be the same or different from zero. Unless otherwise stated, optionally substituted groups may be substituted by as many optional substituents as can be accommodated by replacing a hydrogen atom by a non-hydrogen substituent at any desired available carbon or nitrogen or sulphur atom. Normally, the number of optional substituents (if present) may be 1, 2, 3, 4 or 5, in particular 1, 2 or 3.

For instance, as used here, the expression "mono- or poly-" signifies "1, 2, 3, 4 or 5, preferably 1, 2, 3 or 4, particularly preferably 1, 2 or 3, especially preferably 1 or 2", for example in the definitions of the substituents of the compounds of the general formulae of the present invention.

If residues in the compounds according to the invention are substituted, the residues may be monosubstituted or polysubstituted unless stated otherwise. In the scope of protection of the present invention, the definitions of all residues which occur more than once are mutually independent. Preference is given to substitution by one, two or three identical or different substituents. Substitution by one substituent is particularly preferred.

Alkyl

Alkyl is a linear or branched, saturated monovalent hydrocarbon residue having 1 to 10 carbon atoms ($C_1$-$C_{10}$-alkyl), generally 1 to 6 ($C_1$-$C_6$-alkyl), preferably 1 to 4 ($C_1$-$C_4$-alkyl), and particularly preferably 1 to 3 carbon atoms ($C_1$-$C_3$-alkyl).

Preferred examples include:

Methyl, ethyl, propyl, butyl, pentyl, hexyl, isopropyl, isobutyl, sec-butyl, tert-Butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl and 1,2-dimethylbutyl.

Particular preference is given to a methyl, ethyl, propyl, isopropyl and tert-Butyl residue.

Heteroalkyl

Heteroalkyl is a straight-chain and/or branched hydrocarbon chain having 1 to 10 carbon atoms, which may be interrupted once or more than once by one or more of the groups —O—, —S—, —C(=O)—, —S(=O)—, —S(=O)$_2$—, —NR$^y$—, —NR$^y$C(=O)—, —C(=O)—NR$^y$—, —NR$^y$NR$^y$—, —S(=O)$_2$—NR$^y$NR$^y$—, —C(=O)—NR$^y$NR$^y$—, —CR$^x$=N—O—, and where the hydrocarbon chain, including the side chains if present, may be substituted with —NH—C(=O)—NH$_2$, —C(=O)—OH, —OH, —NH$_2$, —NH—C(=NNH$_2$)—, sulfonamide, sulfone, sulfoxide or sulfonic acid, Here, R$^y$ is in each case —H, phenyl, $C_1$-$C_{10}$-alkyl, $C_2$-$C_{10}$-alkenyl or $C_2$-$C_{10}$-alkynyl, which may each in turn be substituted with —NH—C(=O)—NH$_2$, —C(=O)—OH, —OH, —NH$_2$, —NH—C(=NNH$_2$), sulfonamide, sulfone, sulfoxide or sulfonic acid.

Here, R$^x$ is —H, $C_1$-$C_3$-alkyl or phenyl.

Alkenyl

Alkenyl is a straight-chain or branched monovalent hydrocarbon chain having one or two double bonds and 2, 3, 4, 5, 6, 7, 8, 9 or 10 carbon atoms ($C_2$-$C_{10}$-alkenyl), in particular 2 or 3 carbon atoms ($C_2$-$C_3$-alkenyl), in which it is understood that, if the alkenyl group comprises more than one double bond, the double bonds may be isolated from each other or conjugated with each other. The alkenyl group is, for example, an ethenyl (or vinyl), prop-2-en-1-yl (or "allyl"), prop-1-en-1-yl, but-3-enyl, but-2-enyl, but-1-enyl, pent-4-enyl, pent-3-enyl, pent-2-enyl, pent-1-enyl, hex-5-enyl, hex-4-enyl, hex-3-enyl, hex-2-enyl, hex-1-enyl, prop-1-en-2-yl (or "isopropenyl"), 2-methylprop-2-enyl, 1-methylprop-2-enyl, 2-methylprop-1-enyl, 1-methylprop-1-enyl, 3-methylbut-3-enyl, 2-methylbut-3-enyl, 1-methylbut-3-enyl, 3-methylbut-2-enyl, 2-methylbut-2-enyl, 1-methylbut-2-enyl, 3-methylbut-1-enyl, 2-methylbut-1-enyl, 1-methylbut-1-enyl, 1,1-dimethylprop-2-enyl, 1-ethylprop-1-enyl, 1-propylvinyl, 1-isopropylvinyl, 4-methylpent-4-enyl, 3-methylpent-4-enyl, 2-methylpent-4-enyl, 1-methylpent-4-enyl, 4-methylpent-3-enyl, 3-methylpent-3-enyl, 2-methylpent-3-enyl, 1-methylpent-3-enyl, 4-methylpent-2-enyl, 3-methylpent-2-enyl, 2-methylpent-2-enyl, 1-methylpent-2-enyl, 4-methylpent-1-enyl, 3-methylpent-1-enyl, 2-methylpent-1-enyl, 1-methylpent-1-enyl, 3-ethylbut-3-enyl, 2-ethylbut-3-enyl, 1-ethylbut-3-enyl, 3-ethylbut-2-enyl, 2-ethylbut-2-enyl, 1-ethylbut-2-enyl, 3-ethylbut-1-enyl, 2-ethylbut-1-enyl, 1-ethylbut-1-enyl, 2-propylprop-2-enyl, 1-propylprop-2-enyl, 2-isopropylprop-2-enyl, 1-isopropylprop-2-enyl, 2-propylprop-1-enyl, 1-propylprop-1-enyl, 2-isopropylprop-1-enyl, 1-isopropylprop-1-enyl, 3,3-dimethylprop-1-enyl, 1-(1,1-dimethylethyl)ethenyl, buta-1,3-dienyl, penta-1,4-dienyl or hexa-1-5-dienyl group. In particular the group is vinyl or allyl.

Alkynyl

Alkynyl is a straight-chain or branched monovalent hydrocarbon chain having a triple bond and having 2, 3, 4, 5, 6, 7, 8, 9 or 10 carbon atoms ($C_2$-$C_{10}$-alkynyl), particularly 2 or 3 carbon atoms ($C_2$-$C_3$-alkynyl). The $C_2$-$C_6$-alkynyl group is, for example, an ethynyl, prop-1-ynyl, prop-2-ynyl (or propargyl), but-1-ynyl, but-2-ynyl, but-3-ynyl, pent-1-ynyl, pent-2-ynyl, pent-3-ynyl, pent-4-ynyl, hex-1-ynyl, hex-2-ynyl, hex-3-ynyl, hex-4-ynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-ynyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl or 3,3-dimethylbut-1-ynyl group. In particular, the alkynyl group is ethynyl, prop-1-ynyl or prop-2-ynyl.

Cycloalkyl

Cycloalkyl is a saturated monovalent monocyclic or bicyclic hydrocarbon residue having 3-12 carbon atoms ($C_3$-$C_{12}$-cycloalkyl).

Here, a monocyclic hydrocarbon residue is a monovalent hydrocarbon residue having generally 3 to 10 ($C_3$-$C_{10}$-cycloalkyl), preferably 3 to 8 ($C_3$-$C_8$-cycloalkyl), and particularly preferably 3 to 7 ($C_3$-$C_7$-cycloalkyl) carbon atoms.

Preferred examples of a monocyclic hydrocarbon residue include: cyclopropyl, cyclobutyl, cyclopentyl, cyclohexyl, cycloheptyl and cyclooctyl.

Particular preference is given to a cyclopropyl, cyclobutyl, cylopentyl, cyclohexyl and cycloheptyl. Here, a bicyclic hydrocarbon residue is a hydrocarbon residue generally having 3 to 12 carbon atoms ($C_3$-$C_{12}$-cycloalkyl), wherein a fusion of two saturated ring systems is to be understood here, which together share two directly adjacent atoms. Preferred examples of a bicyclic hydrocarbon residue include: bicyclo[2.2.0]hexyl, bicyclo[3.3.0]octyl, bicyclo[4.4.0]decyl, bicyclo[5.4.0]undecyl, bicyclo[3.2.0]heptyl, bicyclo[4.2.0]octyl, bicyclo[5.2.0]nonyl, bicyclo[6.2.0]decyl, bicyclo[4.3.0]nonyl, bicyclo[5.3.0]decyl, bicyclo[6.3.0]undecyl and bicyclo[5.4.0]undecyl.

Heterocycloalkyl

Heterocycloalkyl is a non-aromatic monocyclic or bicyclic ring system having one, two, three or four heteroatoms, which may be the same or different. The heteroatoms may be nitrogen atoms, oxygen atoms or sulphur atoms.

A monocyclic ring system according to the present invention may have 3 to 8, preferably 4 to 7, particularly preferably 5 or 6 ring atoms.

Preferred examples of a heterocycloalkyl having 3 ring atoms include:

aziridinyl.

Preferred examples of a heterocycloalkyl having 4 ring atoms include:
azetidinyl, oxetanyl.
Preferred examples of a heterocycloalkyl having 5 ring atoms include:
pyrrolidinyl, imidazolidinyl, pyrazolidinyl, pyrrolinyl, dioxolanyl and tetrahydrofuranyl.
Preferred examples of a heterocycloalkyl having 6 ring atoms include:
piperidinyl, piperazinyl, morpholinyl, dioxanyl, tetrahydropyranyl and thiomorpholinyl.
Preferred examples of a heterocycloalkyl having 7 ring atoms include:
azepanyl, oxepanyl, 1,3-diazepanyl, 1,4-diazepanyl.
Preferred examples of a heterocycloalkyl having 8 ring atoms include:
oxocanyl, azocanyl.

Monocyclic heterocycloalkyls are preferably 4- to 7-membered saturated heterocyclyl residues having up to two heteroatoms from the series of O, N and S.

Particular preference is given to morpholinyl, piperidinyl, pyrrolidinyl and tetrahydrofuranyl.

A bicyclic ring system having one, two, three or four heteroatoms, which may be the same or different, may have in accordance with the present invention 6 to 12, preferably 6 to 10 ring atoms, in which one, two, three or four carbon atoms may be exchanged for the same or different heteroatoms from the series of O, N and S.

Examples include: azabicyclo[3.3.0]octyl, azabicyclo [4.3.0]nonyl, diazabicyclo[4.3.0]nonyl, oxazabicyclo[4.3.0] nonyl, thiazabicyclo[4.3.0]nonyl or azabicyclo[4.4.0]decyl and also residues derived from further possible combinations according to the definition.

Particular preference is given to perhydrocyclopenta[c] pyrrolyl, perhydrofuro[3,2-c]pyridinyl, perhydropyrrolo[1, 2-a]pyrazinyl, perhydropyrrolo[3,4-c]pyrrolyl and 3,4-methylenedioxyphenyl.

Aryl

Aryl signifies a monovalent monocyclic or bicyclic aromatic ring system consisting of carbon atoms. Examples are naphthyl and phenyl; preference is given to phenyl or a phenyl residue.

$C_6$-$C_{10}$-Aralkyl $C_{6-10}$-Aralkyl in the scope of the invention is a monocyclic aromatic aryl, phenyl for example, to which a $C_1$-$C_4$-alkyl group is attached.

An example of a $C_{6-10}$-aralkyl group is benzyl.

Heteroaryl

Heteroaryl signifies a monovalent monocyclic, bicyclic or tricyclic aromatic ring system having 5, 6, 8, 9, 10, 11, 12, 13 or 14 ring atoms (a "5- to 14-membered heteroaryl" group), in particular is understood to mean 5, 6, 9 or 10 ring atoms comprising at least one ring heteroatom and optionally one, two or three further ring heteroatoms from the group of N, O and S and which is attached via a ring carbon atom or optionally (if valency allows) via a ring nitrogen atom.

The heteroaryl group can be a 5-membered heteroaryl group such as thienyl, furyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group such as pyridinyl, pyridazinyl, pyrimidinyl, pyrazinyl or triazinyl; or a tricyclic heteroaryl group such as carbazolyl, acridinyl or phenazinyl; or a 9-membered heteroaryl group such as benzofuranyl, benzothienyl, benzoxazolyl, benzisoxazolyl, benzimidazolyl, benzothiazolyl, benzotriazolyl, indazolyl, indolyl, isoindolyl, indolizinyl or purinyl; or a 10-membered heteroaryl group such as quinolinyl, quinazolinyl, isoquinolinyl, cinnolinyl, phthalazinyl, quinoxalinyl or pteridinyl.

In general, and if not stated otherwise, the heteroaryl residues include all possible isomeric forms thereof, e.g. tautomers and positional isomers in relation to the attachment point to the rest of the molecule. Therefore, as an illustrative non-inclusive example, the term pyridinyl encompasses pyridin-2-yl, pyridin-3-yl and pyridin-4-yl; or the term thienyl encompasses thien-2-yl and thien-3-yl.

$C_5$-$C_{10}$-Heteroaryl $C_{5-10}$-Heteroaryl in the scope of the invention is a monocyclic or bicyclic aromatic ring system having one, two, three or four heteroatoms, which may be the same or different. The heteroatoms can be: N, O, S, S(=O) and/or S(=O)$_2$. The bond valency can be located at any aromatic carbon atom or at a nitrogen atom.

A monocyclic heteroaryl residue according to the present invention has 5 or 6 ring atoms. Preference is given to those heteroaryl residues having one or two heteroatoms. Particular preference here is given to one or two nitrogen atoms.

Heteroaryl residues having 5 ring atoms include, for example, the rings:
thienyl, thiazolyl, furyl, pyrrolyl, oxazolyl, imidazolyl, pyrazolyl, isoxazolyl, isothiazolyl, oxadiazolyl, triazolyl, tetrazolyl and thiadiazolyl.

Heteroaryl residues having 6 ring atoms include, for example, the rings:
pyridinyl, pyridazinyl, pyrimidinyl, pyrazinyl and triazinyl.

A bicyclic heteroaryl residue according to the present invention has 9 or 10 ring atoms.

Heteroaryl residues having 9 ring atoms include, for example, the rings:
phthalidyl, thiophthalidyl, indolyl, isoindolyl, indazolyl, benzothiazolyl, benzofuryl, benzothienyl, benzimidazolyl, benzoxazolyl, azocinyl, indolizinyl, purinyl, indolinyl.

Heteroaryl residues having 10 ring atoms include, for example, the rings:
isoquinolinyl, quinolinyl, quinolizinyl, quinazolinyl, quinoxalinyl, cinnolinyl, phthalazinyl, 1,7- and 1,8-naphthyridinyl, pteridinyl, chromanyl.

Heteroalkoxy

Heteroalkoxy is a straight-chain and/or branched hydrocarbon chain having 1 to 10 carbon atoms, which is attached via —O— to the rest of the molecule, and which may be further interrupted once or more than once by one or more of the groups —O—, —S—, —C(=O)—, —S(=O)—, —S(=O)$_2$—, —NR$^y$—, —NR$^y$C(=O)—, —C(=O)—NR$^y$—, —NR$^y$NR$^y$—, —S(=O)$_2$—NR$^y$NR$^y$—, —C(=O)—NR$^y$NR$^y$—, —CR$^x$=N—O—, and in which the hydrocarbon chain, including the side chains if present, may be substituted with —NH—C(=O)—NH$_2$, —C(=O)—OH, —OH, —NH$_2$, —NH—C(=NNH$_2$)—, sulfonamide, sulfone, sulfoxide or sulfonic acid.

Here, R$^y$ is in each case —H, phenyl, $C_1$-$C_{10}$-alkyl, $C_2$-$C_{10}$-alkenyl or $C_2$-$C_{10}$-alkynyl, which may in turn each be substituted with —NH—C(=O)—NH$_2$, —C(=O)—OH, —OH, —NH$_2$, —NH—C(=NNH$_2$)—, sulfonamide, sulfone, sulfoxide or sulfonic acid.

Here, R$^x$ is —H, $C_1$-$C_3$-alkyl or phenyl.

Halogen or halogen atom in the scope of the invention is fluorine (—F), chlorine (—Cl), bromine (—Br) or iodine (—I).

Fluoroalkyl, fluoroalkenyl and fluoroalkynyl signifies that the alkyl, alkenyl and alkynyl may be monosubstituted or polysubstituted by fluorine.

The conjugation of the KSP inhibitor to the antibody can take place chemically by various routes, as shown in an exemplary manner in Schemes 20 to 31 in the examples. In particular, it is optionally possible to modify the low-molecular weight KSP inhibitor for the conjugation to the linker, for example by introducing protective groups or leaving groups to facilitate substitution (such that in the reaction said leaving group, and not a hydrogen atom, is substituted by the linker). The KSP inhibitor—linker molecule obtained in this manner (where the linker has a reactive group for coupling to the binder) can then be reacted with the binder to give a binder conjugate according to the invention. In the experimental section, this procedure is illustrated in an exemplary manner by a large number of examples.

Other particularly preferred compounds have the formula (I) or (Ia) below:

Formula (I):

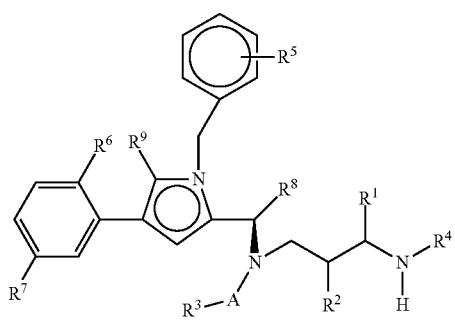
(I)

where
$R^1$ represents H, -L-#1, -MOD or —$(CH_2)_{0-3}$Z, where Z represents —H, —NHY$^3$, —OY$^3$, —SY$^3$, halogen, —CO—NY$^1$Y$^2$ or —CO—OY$^3$,
where Y$^1$ and Y$^2$ independently of one another represent H, NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', and Y$^3$ represents H or —(CH$_2$)$_{0-3}$Z', where Z' represents H, NH$_2$, SO$_3$H, COOH, —NH—CO—CH$_2$—CH$_2$—CH(NH$_2$)COOH or (—CO—NH—CHY$^4$)$_{1-3}$COOH, where W represents H or OH,
where Y$^4$ represents straight-chain or branched C$_{1-6}$ alkyl which is optionally substituted by —NHCONH$_2$, or represents aryl or benzyl which are optionally substituted by —NH$_2$;
$R^2$ represents H, -MOD, —CO—CHY$^4$—NHY$^5$ or —(CH$_2$)$_{0-3}$Z,
where Z represents —H, halogen, —OY$^3$, —SY$^3$, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;
where Y$^4$ represents straight-chain or branched C$_{1-6}$-alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-6}$-alkyl;
$R^4$ represents H, -L-#1, —SG$_{lys}$-(CO)$_{0-1}$—R$^{4'}$, —CO—CHY$^4$—NHY$^5$ or —(CH$_2$)$_{0-3}$Z, wherein SG$_{lys}$ is a group cleavable by a lysosomal enzyme, in particular a group consisting of a dipeptide or tripeptide, R$^{4'}$ is a C$_{1-10}$-alkyl, C$_{5-10}$-aryl or C$_{6-10}$-aralkyl, C$_{5-10}$-heteroalkyl, C$_{1-10}$-alkyl-O—C$_{6-10}$-aryl, C$_{5-10}$-heterocycloalkyl, heteroaryl, heteroarylalkyl, heteroarylalkoxy, C$_{1-10}$-alkoxy, C$_{6-10}$-aryloxy or C$_{6-10}$-aralkoxy, C$_{5-10}$-heteroaralkoxy, C$_{1-10}$-alkyl-O—C$_{6-10}$-aryloxy, C$_{5-10}$-heterocycloalkoxy group, which may be substituted once or more than once by —NH$_2$, —NH-alkyl, —N(alkyl)$_2$, NH—CO-alkyl, N(alkyl)-COalkyl, —SO$_3$H, —SO$_2$NH$_2$, —SO$_2$—N(alkyl)$_2$, —COOH, —CONH$_2$, —CON(alkyl)$_2$, or —OH, —H or a group —O$_x$—(CH$_2$CH$_2$O)$_y$—R$^{4''}$, (where x is 0 or 1 and v is a number from 1 to 10, and R$^{4''}$ is —H, -alkyl (preferably C$_{1-4}$-alkyl), —CH$_2$—COOH, —CH$_2$—CH$_2$—COOH, or —CH$_2$—CH$_2$—NH$_2$);
where Z represents —H, halogen, —OY$^3$, —SY$^3$, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;
where Y$^4$ represents straight-chain or branched C$_{1-6}$-alkyl which is optionally substituted by —NHCONH$_2$, or represents aryl or benzyl which are optionally substituted by —NH$_2$, and Y$^5$ represents H or —CO—CHY$^6$—NH$_2$, where Y$^6$ represents straight-chain or branched C$_{1-6}$-alkyl;
or R$^2$ and R$^4$ together (with formation of a pyrrolidine ring) represent —CH$_2$—CHR$^{11}$— or —CHR$^{11}$—CH$_2$—, where R$^{11}$ represents H, NH$_2$, SO$_3$H, COOH, SH, halogen (in particular F or Cl), C$_{1-4}$-alkyl, C$_{1-4}$-haloalkyl, C$_{1-4}$-alkoxy, hydroxyl-substituted C$_{1-4}$-alkyl, COO(C$_{1-4}$-alkyl) or OH;
A represents CO, SO, SO$_2$, SO$_2$NH or CNNH$_2$;
$R^3$ represents -L-#1, -MOD or an optionally substituted alkyl, cycloalkyl, aryl, heteroaryl, heteroalkyl, heterocycloalkyl group, preferably a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —SO$_2$—NH-alkyl groups, 1-3 —NH-alkyl groups, 1-3 —N(alkyl)$_2$ groups, 1-3 —NH((CH$_2$CH$_2$O)1-20H) groups, 1-3 —NH$_2$ groups or 1-3 —(CH$_2$)$_{0-3}$Z groups, where n represents 0, 1 or 2, Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z' and Y$^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH (where "alkyl" is preferably C$_{1-10}$-alkyl);
$R^5$ represents H, -MOD, NH$_2$, NO$_2$, halogen (in particular F, Cl, Br), —CN, CF$_3$, —OCF$_3$, —CH$_2$F, —CH$_2$F, SH or —(CH$_2$)$_{0-3}$Z, where Z represents —H, —OY$^3$, —SY$^3$, halogen, NHY$^3$, —CO—NY$^1$Y$^2$ or —CO—OY$^3$,
where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;
$R^6$ and $R^7$ independently of one another represent H, cyano, (optionally fluorinated) C$_{1-10}$-alkyl, (optionally fluorinated) C$_{2-10}$-alkenyl, (optionally fluorinated) C$_{2-10}$-alkynyl, hydroxy, NO$_2$, NH$_2$, COOH or halogen (in particular F, Cl, Br),
$R^8$ represents (optionally fluorinated) C$_{1-10}$-alkyl, (optionally fluorinated) C$_{2-10}$-alkenyl, (optionally fluorinated) C$_{2-10}$-alkynyl, (optionally fluorinated) C$_{4-10}$-cycloalkyl or -<CH$_2$)$_{0-2}$—(HZ$^2$), where HZ$^2$ represents a 4- to 7-membered heterocycle having up to two heteroatoms selected from the group consisting of N, O and S (preferably oxetane), where each of these groups may be substituted by —OH, CO$_2$H or NH$_2$;
where one of the substituents R$^1$, R$^3$ and R$^4$ represents -L-#1,
L represents the linker and #1 represents the bond to the antibody,
R$^9$ represents H, F, CH$_3$, CF$_3$, CH$_2$F or CHF$_2$;
where -MOD represents —(NR$^{10}$)$_n$-(G1)$_o$-G2-G3, where
R$^{10}$ represents H or C$_1$-C$_3$-alkyl;
G1 represents —NHCO— or —CONH— (where, if G1 represents —NHCO—, R$^{10}$ does not represent NH$_2$);
n represents 0 or 1;
o represents 0 or 1; and
G2 represents a straight-chain and/or branched hydrocarbon group which has 1 to 10 carbon atoms and which may be interrupted once or more than once by one or more of the groups —O—, —S—, —SO—, SO$_2$, —NRy-, —NRyCO—, CONRy-, —NRyNRy-, —SO$_2$NRyNRy-, —CONRyNRy- (where R$^y$ represents H, phenyl, C1-C10-alkyl, C2-C10-alkenyl or C2-C10-alkynyl, each of which may be substituted by NHCONH$_2$, —COOH, —OH, —NH$_2$, NH—CNNH$_2$, sulphonamide, sulphone, sulphoxide or sulphonic acid), —CO—, or —CR$^x$=N—O— (where Rx represents H, C1-C3-alkyl or phenyl), where the hydrocarbon chain including any side chains may be substituted by —NHCONH$_2$, —COOH, —OH, —NH$_2$, NH—CNNH$_2$, sulphonamide, sulphone, sulphoxide or sulphonic acid, where G3 represents —H or —COOH, and where the group -MOD preferably has at least one group —COOH;
and the salts, solvates, salts of the solvates and epimers thereof.

In a preferred embodiment of the formula (I), one of the substituents R$^1$ or R$^3$ represents -L-#1. In this embodiment it is particularly preferred if R$^4$ represents H or -SG$_{lys}$-(CO)$_{0-1}$—R$^{4'}$, where SG$_{lys}$ and R$^{4'}$ have the same meaning as above. In another preferred embodiment of the formula (I), the substituent R$^4$ represents -L-#1, where the linker is a linker which can be cleaved at the nitrogen atom which binds to R$^4$, so that a primary amino group is present after cleavage (corresponds to R$^4$ =H). Such cleavable groups are described in detail below.

If R$^1$ does not represent H, the carbon atom to which R$^1$ is attached is a stereocentre which may be present in the L and/or D configuration, preferably in the L configuration.

If R$^2$ does not represent H, the carbon atom to which R$^2$ is attached is a stereocentre which may be present in the L and/or D configuration.

Formula (Ia):

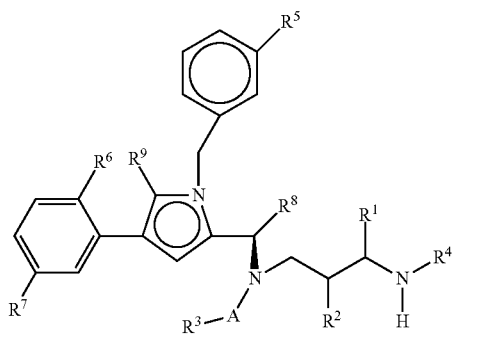

(Ia)

where
R$^1$ represents H, -L-#1 or —(CH$_2$)$_{0-3}$Z, where Z represents —H, —NHY$^3$, —OY$^3$, —SY$^3$, halogen, —CO—NY$^1$Y$^2$ or —CO—OY$^3$,
where Y$^1$ and Y$^2$ independently of one another represent H, NH$_2$, —(CH$_2$CH$_2$O)$_{0-3}$—(CH$_2$)$_{0-3}$Z' (e.g. —(CH$_2$)$_{0-3}$Z') or —CH(CH$_2$W)Z', and Y$^3$ represents H or —(CH$_2$)$_{0-3}$Z',
where Z' represents H, NH$_2$, SO$_3$H, COOH, —NH—CO—CH$_2$—CH$_2$—CH(NH$_2$)COOH or —(CO—NH—CHY$^4$)$_{1-3}$COOH, where W represents H or OH;
where Y$^4$ represents straight-chain or branched C$_{1-6}$ alkyl which is optionally substituted by —NHCONH$_2$, or represents aryl or benzyl which are optionally substituted by —NH$_2$.
R$^2$ and R$^4$ independently of one another represent H, —SG$_{lys}$-(CO)$_{0-1}$—R$^{4'}$, —CO—CHY$^4$—NHY$^5$ or —(CH$_2$)$_{0-3}$Z,
wherein SG$_{lys}$ is a group cleavable by a lysosomal enzyme, in particular a group consisting of a dipeptide or tripeptide, R$^{4'}$ is a C$_{1-10}$-alkyl, C$_{5-10}$-aryl or C$_{6-10}$-aralkyl, C$_{5-10}$-heteroalkyl, C$_{1-10}$-alkyl-O—C$_{6-10}$-aryl, C$_{5-10}$-heterocycloalkyl, heteroaryl, heteroarylalkyl, heteroarylalkoxy, C$_{1-10}$-alkoxy, C$_{6-10}$-aryloxy or C$_{6-10}$-aralkoxy, C$_{5-10}$-heteroaralkoxy, C$_{1-10}$-alkyl-O—C$_{6-10}$-aryloxy, C$_{5-10}$-heterocycloalkoxy group, which may each be substituted once or more than once by —NH$_2$, —NH— alkyl, —N(alkyl)$_2$, NH—CO-alkyl, N(alkyl)-COalkyl, —SO$_3$H, —SO$_2$NH$_2$, —SO$_2$—N(alkyl)$_2$, —COOH, —CONH$_2$, —CON(alkyl)$_2$, or —OH, —H or a group —O$_x$—(CH$_2$CH$_2$O)$_y$—R$^{4''}$, (where x is 0 or 1 and v is a number from 1 to 10, and R$^{4''}$ is —H, -alkyl (preferably C$_{1-12}$-alkyl), —CH$_2$—COOH, —CH$_2$—CH$_2$—COOH, or —CH$_2$—CH$_2$—NH$_2$);
or R$^2$ and R$^4$ together represent (with formation of a pyrrolidine ring) —CH$_2$—CHR$^{11}$— or —CHR$^{11}$—CH$_2$—, where R$^{11}$ represents H, NH$_2$, SO$_3$H, COOH, SH, halogen (in particular F or Cl), C$_{1-4}$-alkyl, C$_{1-4}$-haloalkyl, C$_{1-4}$-alkoxy, hydroxyl-substituted C$_{1-4}$-alkyl, COO(C$_{1-4}$-alkyl) or OH; or R$^2$ represents H, —CO—CHY$^4$—NHY$^5$ or —(CH$_2$)$_{0-3}$Z and R$^4$ represents -L-#1 darstellt, and where Z represents —H, halogen, —OY$^3$, —SY$^3$, —NHY$^3$, —CO—NY$_1$Y$_2$ or —CO—OY$^3$,
where Y$^1$ and Y$^2$ independently of one another represent H, NH$_2$ or —(CH$_2$)$_{0-3}$Z', and Y$^3$ represents H or —(CH$_2$)$_{0-3}$Z',
where Z' represents H, SO$_3$H, NH$_2$ or COOH;
where Y$^4$ independently of one another represents straight-chain or branched C$_{1-6}$-alkyl which is optionally substituted by —NHCONH$_2$ or represents aryl or benzyl which are optionally substituted by —NFL, where Y$^4$ represents straight-chain or branched C$_{1-5}$-alkyl which is optionally substituted by —NHCONH$_2$ or represents aryl or benzyl which are optionally substituted by —NH$_2$ and Y$^5$ represents H or —CO—CHY$^6$—NH$_2$, where Y$^6$ represents straight-chain or branched C$_{1-6}$-alkyl;
A represents CO, SO, SO$_2$, SO$_2$NH or CNNH$_2$;
R$^3$ represents an optionally substituted alkyl, aryl, heteroaryl, heteroalkyl, heterocycloalkyl group, preferably -L-#1 or a C$_{1-10}$-alkyl, C$_{6-10}$-aryl or C$_{6-10}$-aralkyl, C$_{5-10}$-heteroalkyl, C$_{1-10}$-alkyl-O—C$_{6-10}$-aryl or C$_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —SO$_2$—NH-alkyl groups, 1-3 —NH-alkyl groups, 1-3 —N(alkyl)$_2$ groups, 1-3 —NH$_2$ groups or 1-3 —(CH$_2$)$_{0-3}$Z groups, where n represents 0, 1 or 2, Z represents —H, halogen, —OY$^3$, —SY$^3$, —NHY$^3$, —CO—NY$^1$Y$^2$ or —CO—OY$^3$, where Y$^1$ and Y$^2$ independently of one another represent H, NH$_2$ or —(CH$_2$)$_{0-3}$Z' and Y$^3$ represents H, —(CH$_2$)$_{0-3}$—CH(NHCOCH$_3$)Z', —(CH$_2$)$_{0-3}$—CH(NH$_2$)Z' or —(CH$_2$)$_{0-3}$Z', where Z' represents H, SO$_3$H, NH$_2$ or COOH (where "alkyl" preferably represents C$_{1-10}$-alkyl);

R$^5$ represents H, F, NH$_2$, NO$_2$, halogen, SH or —(CH$_2$)$_{0-3}$Z, where Z represents —H, halogen, —OY$^3$, —SY$^3$, NHY$^3$, —CO—NY$^1$Y$^2$ or —CO—OY$^3$, where Y$^1$ and Y$^2$ independently of one another represent H, NH$_2$ or —(CH$_2$)$_{0-3}$Z', and Y$^3$ represents H or —(CH$_2$)$_{0-3}$Z', where Z' represents H, SO$_3$H, NH$_2$ or COOH;

R$^6$ and R$^7$ independently of one another represent H, cyano, (optionally fluorinated) C$_{1-10}$-alkyl, (optionally fluorinated) C$_{2-10}$-alkenyl, (optionally fluorinated) C$_{2-10}$-alkynyl, hydroxy or halogen, R$^8$ represents (optionally fluorinated) C$_{1-10}$-alkyl, (optionally fluorinated) C$_{4-10}$-cycloalkyl or optionally substituted oxetane; and R$^9$ represents H, F, CH$_3$, CF$_3$, CH$_2$F or CHF$_2$;

and the salts, solvates, salts of the solvates and epimers thereof.

By substitution of a hydrogen atom at R$^1$, R$^3$ or R$^4$, it is possible to attach a compound of the formula (I) or (Ia) in which none of the substituents R$^1$, R$^3$ and R$^4$ represents -L-#1 to a linker in a manner known to the person skilled in the art. This gives conjugates of the formula (I) or (Ia) where one of the substituents R$^1$, R$^3$ or R$^4$ represents -L-#1, L represents the linker and #1 represents the bond to the antibody. If the KSP inhibitor according to formula (I) or (Ia) is conjugated with a binder, one of the substituents R$^1$, R$^3$ or R$^4$ thus represents -L-#1, where L represents the linker and #1 represents the bond to the antibody. That is, in the case of the conjugates one of the substituents R$^1$, R$^3$ or R$^4$ represents -L-#1, where -L-#1 represents the bond to the antibody. In a preferred embodiment of the formula (I) or (Ia), one of the substituents R$^1$ or R$^3$ represents -L-#1. In this embodiment it is particularly preferred if R$^4$ represents H or -SG$_{lys}$-(CO)$_{0-1}$—R$^4$, where SG$_{lys}$ and R$^4$ have the same meaning as above. In another preferred embodiment of the formula (I), the substituent R$^4$ represents -L-#1, where the linker is a linker which can be cleaved at the nitrogen atom which binds to R$^4$, so that a primary amino group is present after cleavage (corresponds to R$^4$=H). Such cleavable groups are described in detail below. The binder is preferably a human, humanized or chimeric monoclonal antibody or an antigen-binding fragment thereof. Particular preference is given to anti-B7H3 antibodies which specifically bind the human Ig4 and/or the human and/or murine Ig2 isoform of B7H3, in particular the anti-B7H3 antibodies TPP-6497, TPP-6499, TPP-6501, TPP-6502, TPP-6515. In a likewise preferred embodiment, the anti-B7H3 antibody is present in aglycosylated form.

Instead of -L-#1, it is also possible for the group -L-#3 to be present in the compound, where L represents the linker and #3 represents the reactive group for binding to the antibody. Compounds comprising -L-#3 are reactive compounds which react with the antibody. #3 is preferably a group which reacts with an amino or thiol group with formation of a covalent bond, preferably with the cysteine residue in a protein. The cysteine residue in a protein may be present naturally in the protein, may be introduced by biochemical methods or, preferably, may be generated by prior reduction of disulphides of the binder.

For A, preference is given to CO (carbonyl).

Preferred for R$^1$ are -L-#1, H, —COOH, —CONHNH$_2$, —(CH$_2$)$_{1-3}$NH$_2$, —CONZ"(CH$_2$)$_{1-3}$NH$_2$ and —CONZ"CH$_2$COOH, where Z" represents H or NH$_2$.

Preferred for R$^2$ and R$^4$ is H, or R$^2$ and R$^4$ together (with formation of a pyrrolidine ring) represent —CH$_2$—CHR$^{11}$— or —CHR$^{11}$—CH$_2$—, where R$^{11}$ represents H or F. Also preferred for R$^4$ is -L-#1, where -L-#1 is a cleavable linker, preferably a linker which can be cleaved intracellularly by enzymes.

Preferred for R$^3$ is -L-#1 or C$_{1-10}$-alkyl-, which may optionally be substituted by —OH, O-alkyl, SH, S-alkyl, O—CO-alkyl, O—CO—NH-alkyl, NH—CO-alkyl, NH—CO—NH-alkyl, S(O)$_n$-alkyl, SO$_2$—NH-alkyl, NH-alkyl, N(alkyl)$_2$ or NH$_2$ (where alkyl is preferably C$_{1-3}$-alkyl).

Preferred for R$^5$ is H or F.

Preferred for R$^6$ and R$^7$, independently of one another, are H, (optionally fluorinated) C$_{1-3}$-alkyl, (optionally fluorinated) C$_{2-4}$-alkenyl, (optionally fluorinated) C$_{2-4}$-alkynyl, hydroxy or halogen.

Preferred for R$^8$ is a branched C$_{1-5}$-alkyl group, in particular a group of the formula —C(CH$_3$)$_2$—(CH$_2$)$_{0-2}$—R$_y$, where R$_y$ represents —H, —OH, CO$_2$H or NH$_2$, or an (optionally fluorinated) C$_{5-7}$-cycloalkyl. Particular preference is given to a group of the formula —C(CH$_3$)$_3$ or a cyclohexyl group.

Preferred for R$^9$ is H or F.

Especially preferred are compounds of the formula (I) or (Ia) in which

A represents CO (carbonyl);

R$^1$ represents H, -L-#1, —COOH, —CONHNH$_2$, —(CH$_2$)$_{1-3}$NH$_2$, —CONZ"(CH$_2$)$_{1-3}$NH$_2$ or —CONZ"CH$_2$COOH, where Z" represents H or NH$_2$;

R$^2$ and R$^4$ represent H or R$^2$ and R$^4$ together (with formation of a pyrrolidine ring) represent —CH$_2$—CHR$^{11}$— or —CHR$^{11}$—CH$_2$—, where R$^{1'}$ represents H; or R$^4$ represents -L-#1 and R$^2$ represents H;

R$^3$ represents -L-#1 or a phenyl group which may be mono- or polysubstituted by halogen (in particular F) or optionally fluorinated C$_{1-3}$-alkyl, or represents an optionally fluorinated C$_{1-10}$-alkyl group which may optionally be substituted by —OY$^4$, —SY$^4$, —O—CO—Y$^4$, —O—CO—NH—Y$^4$, NH—CO—Y$^4$, —NH—CO—NH—Y$^4$, S(O)$_n$—Y$^4$ (where n represents 0, 1 or 2), —SO$_2$—NH—Y$^4$, NH—Y$^4$ or N(Y$^4$)$_2$, where Y$^4$ represents H, phenyl (optionally mono- or polysubstituted by halogen (in particular F) or optionally fluorinated C$_{1-3}$-alkyl), or alkyl (where the alkyl group may be substituted by —OH, —COOH, and/or —NHCO—C$_{1-3}$-alkyl and where alkyl preferably represents C$_{1-3}$-alkyl); where particularly preferably R$^3$ may be substituted by —OH, O-alkyl, SH, S-alkyl, O—CO-alkyl, O—CO—NH-alkyl, NH—CO-alkyl, NH—CO—NH-alkyl, S(O)$_n$-alkyl, SO$_2$—NH-alkyl, NH-alkyl, N(alkyl)$_2$ or NH$_2$ (where alkyl preferably means C$_{1-3}$-alkyl);

R$^5$ represents H or F;

R$^6$ and R$^7$ independently of one another represent H, (optionally fluorinated) C$_{1-3}$-alkyl, (optionally fluorinated) C$_{2-4}$-alkenyl, (optionally fluorinated) C$_{2-4}$-alkynyl, hydroxy or halogen;

R$^8$ represents a branched C$_{1-5}$-alkyl group or cyclohexyl; and

R$^9$ represents H or F.

Furthermore, it is preferred when (alone or in combination)
$R^1$ represents -L-#1, COOH or H,
$R^2$ and $R^4$ represent H or $R^2$ and $R^4$ together (with formation of a pyrrolidine ring) represent —$CH_2$—$CHR^{11}$— or —$CHR^{11}$—$CH_2$—, where $R^{11}$ represents H, or $R^4$ represents -L-#1 and $R^2$ represents H;
A represents CO,
$R^3$ represents —$(CH_2)OH$, —$CH(CH_3)OH$, —$CH_2SCH_2CH(COOH)NHCOCH_3$, —$CH(CH_3)OCH_3$, a phenyl group which may be substituted by 1-3 halogen atoms, 1-3 amino groups or 1-3 alkyl groups (which may optionally be halogenated), or represents -L-#1,
$R^5$ represents or H,
$R^6$ and $R^7$ independently of one another represent H, $C_{1-3}$-alkyl or halogen; in particular, $R^6$ and $R^7$ represent F;
$R^8$ represents $C_{1-4}$-alkyl (preferably tert-Butyl) or cyclohexyl; and/or
$R^9$ represents H.

Additionally, in accordance with the invention it is preferred when
$R^1$ represents -L-#1, COOH or H,
$R^2$ and $R^4$ represent H or $R^2$ and $R^4$ together (with formation of a pyrrolidine ring) represent —$CH_2$—$CHR^{11}$— or —$CHR^{11}$—$CH_2$—, where $R^{11}$ represents H,
A represents CO,
$R^3$ represents —$(CH_2)OH$, —$CH(CH_3)OH$, —$CH_2SCH_2CH(COOH)NHCOCH_3$, —$CH(CH_3)OCH_3$, a phenyl group which may be substituted by 1-3 halogen atoms, 1-3 amino groups or 1-3 alkyl groups (which may optionally be halogenated), or represents -L-#1,
$R^5$ represents H,
$R^6$ and $R^7$ independently of one another represent H, $C_{1-3}$-alkyl or halogen; in particular, $R^6$ and $R^7$ represent F;
$R^8$ represents $C_{1-4}$-alkyl (preferably tert-Butyl); and
$R^9$ represents H.

Other particularly preferred compounds have the formula (II) or (IIa) below:

Formula (II):

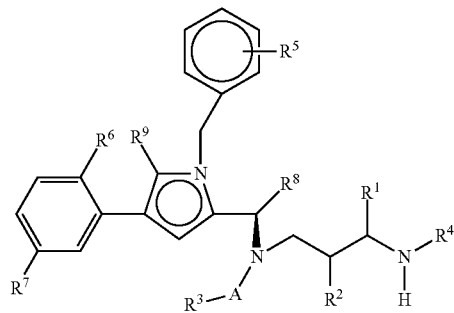

(II)

where
$R^1$ represents H, -L-BINDER, -MOD or —$(CH_2)_{0-3}Z$, where Z represents —H, —$NHY^3$, —$OY^3$, —$SY^3$, halogen, —CO—$NY^1Y^2$ or —CO—$OY^3$,
where $Y^1$ and $Y^2$ independently of one another represent H, $NH_2$, —$(CH_2CH_2O)_{0-3}$—$(CH_2)_{0-3}Z'$ (e.g. —$(CH_2)_{0-3}Z'$) or —$CH(CH_2W)Z'$, and $Y^3$ represents H or —$(CH_2)_{0-3}Z'$, where Z' represents H, $NH_2$, $SO_3H$, —COOH, —NH—CO—$CH_2$—$CH_2$—$CH(NH_2)COOH$ or —(CO—NH—$CHY^4)_{1-3}COOH$, where W represents H or OH,
where $Y^4$ represents straight-chain or branched $C_{1-6}$ alkyl which is optionally substituted by —$NHCONH_2$, or represents aryl or benzyl which are optionally substituted by —$NH_2$;

$R^2$ represents H, -MOD, —CO—$CHY^4$—$NHY^5$ or —$(CH_2)_{0-3}Z$, where $Y^4$ represents straight-chain or branched $C_{1-6}$ alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl,
where Z represents —H, halogen, —$OY^3$, —$SY^3$, $NHY^3$, —CO—$NY^1Y^2$ or —CO—$OY^3$,
where $Y^1$ and $Y^2$ independently of one another represent H, $NH_2$ or —$(CH_2)_{0-3}Z'$, and $Y^3$ represents H or —$(CH_2)_{0-3}Z'$,
where Z' represents H, $SO_3H$, $NH_2$ or COOH;
$R^4$ represents H, -L-BINDER, —$SG_{lys}$-$(CO)_{0-1}$—$R^{4'}$, —CO—$CHY^4$—$NHY^5$ or —$(CH_2)_{0-3}Z$, wherein $SG_{lys}$ is a group cleavable by lysosomal enzymes, in particular a group consisting of a dipeptide or tripeptide, $R^{4'}$ is a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, heteroarylalkoxy, $C_{1-10}$-alkoxy, $C_{6-10}$-aryloxy or $C_{6-10}$-aralkoxy, $C_{5-10}$-heteroaralkoxy, $C_{6-10}$-alkyl-O—$C_{6-10}$-aryloxy, $C_{5-10}$-heterocycloalkoxy group, which may be substituted once or more than once by —$NH_2$, —NH-alkyl, —N(alkyl)$_2$, NH—CO-alkyl, N(alkyl)-COalkyl, —$SO_3H$, —$SO_2NH_2$, —$SO_2$—N(alkyl)$_2$, —COOH, —$CONH_2$, —CON(alkyl)$_2$, or —OH, —H or a group —$O_x$—$(CH_2CH_2O)_y$—$R^{4''}$, (where x is 0 or 1 and v is a number from 1 to 10, and $R^{4''}$ is —H, -alkyl (preferably $C_{1-12}$-alkyl), —$CH_2$—COOH, —$CH_2$—$CH_2$—COOH, or —$CH_2$—$CH_2$—$NH_2$);
where Z represents —H, halogen, —$OY^3$, —$SY^3$, $NHY^3$, —CO—$NY^1Y^2$ or —CO—$OY^3$,
where $Y^1$ and $Y^2$ independently of one another represent H, $NH_2$ or —$(CH_2)_{0-3}Z'$, and $Y^3$ represents H or —$(CH_2)_{0-3}Z'$,
where Z' represents H, $SO_3H$, $NH_2$ or COOH;
where $Y^4$ represents straight-chain or branched $C_{1-6}$-alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;
or $R^2$ and $R^4$ together (with formation of a pyrrolidine ring) represent —$CH_2$—$CHR^1$— or —$CHR^1$—$CH_2$—, where $R^{11}$ represents H, $NH_2$, $SO_3H$, COOH, SH, halogen (in particular F or Cl), $C_{1-4}$-alkyl, $C_{1-4}$-haloalkyl, $C_{1-4}$-alkoxy, hydroxyl-substituted $C_{1-4}$-alkyl, COO($C_{1-4}$-alkyl) or OH;
A represents CO, SO, $SO_2$, $SO_2NH$ or $CNNH_2$;
$R^3$ represents -L-BINDER, -MOD or an optionally substituted alkyl, cycloalkyl, aryl, heteroaryl, heteroalkyl, heterocycloalkyl group, preferably -L-BINDER or a $C_{1-10}$-alkyl, $C_{6-10}$-aryl or $C_{5-10}$-aralkyl, $C_{5-10}$-heteroalkyl, $C_{1-10}$-alkyl-O—$C_{5-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —$SO_2$—NH-alkyl groups, 1-3 —NH-alkyl groups, 1-3 —N(alkyl)$_2$ groups, 1-3 —$NH_2$ groups or 1-3 —$(CH_2)_{0-3}Z$ groups, where Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}Z'$ and $Y^3$ represents H, —$(CH_2)_{0-3}$—$CH(NHCOCH_3)Z'$, —$(CH_2)_{0-3}$—$CH(NH_2)Z'$ or —$(CH_2)_{0-3}Z'$, where Z' represents H, $SO_3H$, $NH_2$ or COOH
(where "alkyl" preferably represents $C_{1-10}$-alkyl);
$R^5$ represents H, $NH_2$, $NO_2$, halogen (in particular F, Cl, Br), —CN, $CF_3$, —$OCF_3$, —$CH_2F$, —$CH_2F$, SH or —$(CH_2)_{0-3}Z$, where Z represents —H, —$OY^3$, —$SY^3$, halogen, $NHY^3$, —CO—$NY^1Y^2$ or —CO—$OY^3$, where $Y^1$ and $Y^2$ independently of one another represent H, $NH_2$ or $—(CH_2)_{0-3}Z'$, and $Y^3$ represents H or $—(CH_2)_{0-3}Z$, where Z' represents H, $SO_3H$, $NH_2$ or COOH;

$R^6$ and $R^7$ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy, $NO_2$, $NH_2$, COOH or halogen (in particular F, Cl, Br), $R^8$ represents (optionally fluorinated) $C_{1-10}$-alkyl, (optionally fluorinated) $C_{2-10}$-alkenyl, (optionally fluorinated) $C_{2-10}$-alkynyl, (optionally fluorinated) $C_{4-10}$-cycloalkyl or $—(CH_2)_{0-2}—(HZ^2)$, where $HZ^2$ represents a 4- to 7-membered heterocycle having up to two heteroatoms selected from the group consisting of N, O and S, where each of these groups may be substituted by —OH, $CO_2H$ or $NH_2$;

$R^9$ represents H, F, $CH_3$, $CF_3$, $CH_2F$ or $CHF_2$;

where -MOD represents $—(NR^{10})_n—(G1)_o—G2—G3$, where $R^{10}$ represents H or $C_1-C_3$-alkyl;

G1 represents —NHCO— or —CONH— (where, if G1 represents —NHCO—, $R^{10}$ does not represent $NH_2$);

n represents 0 or 1;

o represents 0 or 1; and

G2 represents a straight-chain and/or branched hydrocarbon group which has 1 to 10 carbon atoms and which may be interrupted once or more than once by one or more of the groups —O—, —S—, —SO—, $SO_2$, —NRy—, —NRyCO—, CONRy-, —NRyNRy-, —$SO_2$NRyNRy-, —CONRyNRy- (where $R^y$ represents H, phenyl, C1-C10-alkyl, C2-C10-alkenyl or C2-C10-alkynyl, each of which may be substituted by $NHCONH_2$, —COOH, —OH, —$NH_2$, NH—$CNNH_2$, sulphonamide, sulphone, sulphoxide or sulphonic acid), —CO—, or —$CR^x$=N—O— (where Rx represents H, C1-C3-alkyl or phenyl), where the hydrocarbon chain including any side chains may be substituted by —$NHCONH_2$, —COOH, —OH, —$NH_2$, NH—$CNNH_2$, sulphonamide, sulphone, sulphoxide or sulphonic acid, G3 represents —H or —COOH, and where the group -MOD preferably has at least one group —COOH;

and the salts, solvates, salts of the solvates and epimers thereof.

In the case of binder conjugates of the KSP inhibitors of the formula (II), at most one representative of $R^1$, $R^3$ and $R^4$ (alternatively to one of the conditions given above) may represent -L-BINDER, where L represents a linker and BINDER represents an antibody, where the antibody may optionally be attached to a plurality of active compound molecules.

Formula (IIa):

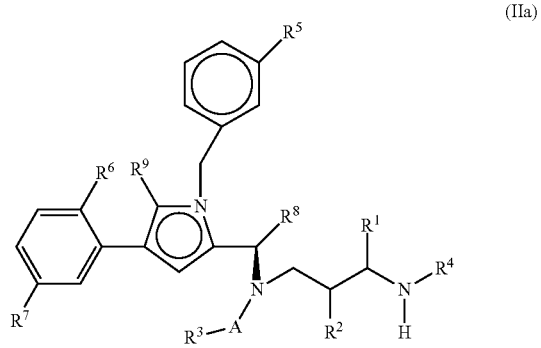

(IIa)

where $R^1$ represents -L-BINDER, H or $—(CH_2)_{0-3}Z$, where Z represents —H, —$NHY^3$, —$OY^3$, —$SY^3$, halogen, —CO—$NY^1Y^2$ or —CO—$OY^3$, where $Y^1$ and $Y^2$ independently of one another represent H, $NH_2$, $—(CH_2CH_2O)_{0-3}—(CH_2)_{0-3}Z'$ or —$CH(CH_2W)Z'$, and $Y^3$ represents H or $—(CH_2)_{0-3}Z'$, where Z' represents H, $NH_2$, $SO_3H$, COOH, —NH—CO—$CH_2$—$CH_2$—$CH(NH_2)$COOH or —(CO—NH—$CHY^4)_{1-3}$COOH; where W represents H or OH; where $Y^4$ represents straight-chain or branched $C_{1-6}$ alkyl which is optionally substituted by —$NHCONH_2$, or represents aryl or benzyl which are optionally substituted by —$NH_2$;

$R^2$ and $R^4$ independently of one another represent H, —$SG_{lys}$-$(CO)_{0-1}$—$R^4$, —CO—$CHY^4$—$NHY^5$ or $—(CH_2)_{0-3}Z$, or $R^2$ and $R^4$ together (with formation of a pyrrolidine ring) represent —$CH_2$—$CHR^{11}$— or —$CHR^{11}$—$CH_2$—, or $R^2$ represents H, —CO—$CHY^4$—$NHY^5$ or $—(CH_2)_{0-3}Z$ and $R^4$ represents -L-#1, where $R^{11}$ represents H, $NH_2$, $SO_3H$, COOH, SH, halogen (in particular F or Cl), $C_{1-4}$-alkyl, $C_{1-4}$-haloalkyl, $C_{1-4}$-alkoxy, hydroxyl-substituted $C_{1-4}$-alkyl, COO($C_{1-4}$-alkyl) or OH;

wherein $SG_{lys}$ is a group cleavable by lysosomal enzymes, in particular a group consisting of a dipeptide or tripeptide, $R^{4'}$ is a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, heteroarylalkoxy, $C_{1-10}$-alkoxy, $C_{6-10}$-aryloxy or $C_{6-10}$-aralkoxy, $C_{5-10}$-heteroaralkoxy, $C_{1-10}$-alkyl-O—$C_{6-10}$-aryloxy, $C_{5-10}$-heterocycloalkoxy group, which may be substituted once or more than once by —$NH_2$, —NH-alkyl, —N(alkyl)$_2$, NH—CO-alkyl, N(alkyl)-COalkyl, —$SO_3H$, —$SO_2NH_2$, —$SO_2$—N(alkyl)$_2$, —COOH, —$CONH_2$, —CON(alkyl)$_2$, or —OH, —H or a group —$O_x$—$(CH_2CH_2O)_y$—$R^{4''}$, (where x is 0 or 1 and v is a number from 1 to 10, and $R^{4''}$ is —H, -alkyl (preferably $C_{1-12}$-alkyl), —$CH_2$—COOH, —$CH_2$—$CH_2$—COOH, or —$CH_2$—$CH_2$—$NH_2$);

where Z represents —H, halogen, —$OY^3$, —$SY^3$, $NHY^3$, —CO—$NY^1Y^2$ or —CO—$OY^3$, where $Y^1$ and $Y^2$ independently of one another represent H, $NH_2$ or $—(CH_2)_{0-3}Z'$, and $Y^3$ represents H or $—(CH_2)_{0-3}Z'$, where Z' represents H, $SO_3H$, $NH_2$ or COOH;

where $Y^4$ represents straight-chain or branched $C_{1-4}$-alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;

A represents CO, SO, $SO_2$, $SO_2$NH or $CNNH_2$;

$R^3$ represents -L-BINDER or an optionally substituted alkyl, aryl, heteroaryl, heteroalkyl, heterocycloalkyl group, preferably -L-BINDER or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —$S(O)_n$-alkyl groups, 1-3 —$SO_2$—NH-alkyl groups, 1-3 —NH-alkyl groups, 1-3 —N(alkyl)$_2$ groups, 1-3 —$NH_2$ groups or 1-3 $—(CH_2)_{0-3}Z$ groups, where Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or $—(CH_2)_{0-3}Z'$ and $Y^3$ represents H, $—(CH_2)_{0-3}$—$CH(NHCOCH_3)Z'$, $—(CH_2)_{0-3}$—$CH(NH_2)Z'$ or $—(CH_2)_{0-3}Z'$, where Z' represents H, $SO_3H$, $NH_2$ or COOH (where "alkyl" preferably represents $C_{1-10}$-alkyl);

R⁵ represents H, F, $NH_2$, $NO_2$, halogen, SH or —$(CH_2)_{0-3}$Z, where Z represents —H, halogen, —$OY^3$, —$SY^3$, —$NHY^3$, —CO—$NY^1Y^2$ or —CO—$OY^3$,
where $Y^1$ and $Y^2$ independently of one another represent H, $NH_2$ or —$(CH_2)_{0-3}$Z', and $Y^3$ represents H or —$(CH_2)_{0-3}$Z', where Z' represents H, $SO_3H$, $NH_2$ or COOH;
where L represents a linker and BINDER represents a binder or a derivative thereof, where the binder may optionally be attached to a plurality of active compound molecules,
$R^6$ and $R^7$ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy or halogen,
$R^8$ represents (optionally fluorinated) $C_{1-10}$-alkyl, (optionally fluorinated) $C_{4-10}$-cycloalkyl or optionally substituted oxetane; and
$R^9$ represents H, F, $CH_3$, $CF_3$, $CH_2F$ or $CHF_2$;
and the salts, solvates, salts of the solvates and epimers thereof.

Preference according to the invention is furthermore given to the KSP inhibitor/antibody conjugates below:

Formula (IIb):

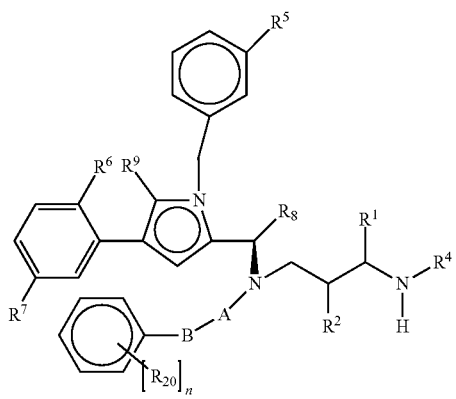

where $R^1$, $R^2$, $R^4$, $R^5$, $R^6$, $R^7$, $R^8$ and $R^9$ have the same meaning as in formula (II) or (IIa), A represents CO, B represents a single bond, —O—$CH_2$— or —$CH_2$—O— and $R^{20}$ represents $NH_2$, F, $CF_3$ or $CH_3$, and n represents 0, 1 or 2.

Formula (IIc):

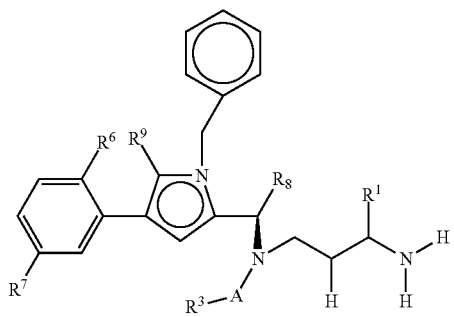

where A, $R^1$, $R^3$, $R^6$, $R^7$, $R^8$ and $R^9$ have the same meaning as in formula (II) or (IIa), where A preferably represents CO and $R^3$ represents —$CH_2OH$, —$CH_2OCH_3$, $CH(CH_3)OH$ or $CH(CH_3)OCH_3$.

Formula (IId):

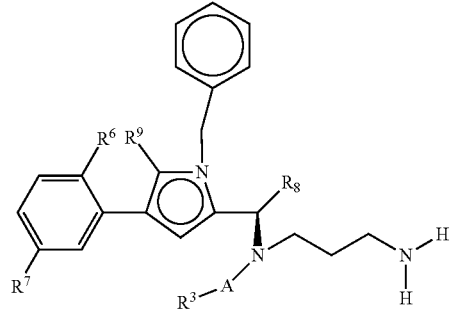

where A, $R^3$, $R^6$, $R^7$, $R^8$ and $R^9$ have the same meaning as in formula (II) or (IIa), where A preferably represents CO and $R^3$ represents —$CH_2$—$S_x$—$(CH_2)_{0-4}$—$CHY^5$—COOH, where x represents 0 or 1 and $Y^5$ represents H or $NHY^6$, where $Y^6$ represents H or —$COCH_3$.

Formula (IIe):

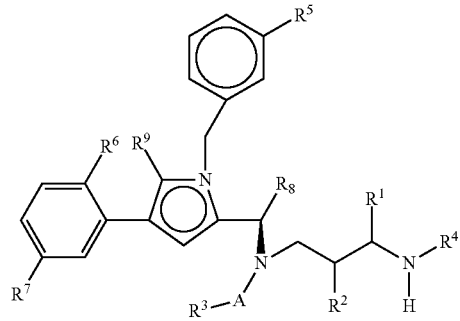

where A, $R^2$, $R^3$, $R^4$, $R^6$, $R^7$, $R^8$ and $R^9$ have the same meaning as in formula (II) or (IIa) and $R^1$ represents -L-BINDER.

Formula (IIi):

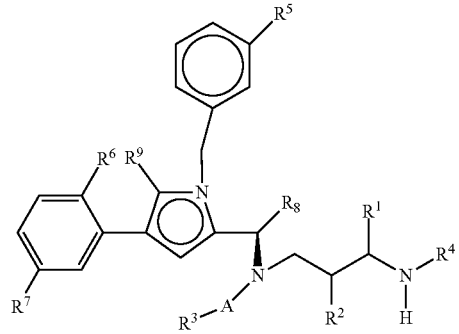

where A, $R^1$, $R^2$, $R^3$, $R^6$, $R^7$, $R^8$ and $R^9$ have the same meaning as in formula (II) or (IIa) and $R^4$ represents -L-BINDER, preferably an enzymatically cleavable binder, so that after cleavage $R^4$ =H. $R^1$ or $R^3$ particularly preferably represent -MOD.

Formula (IIj):

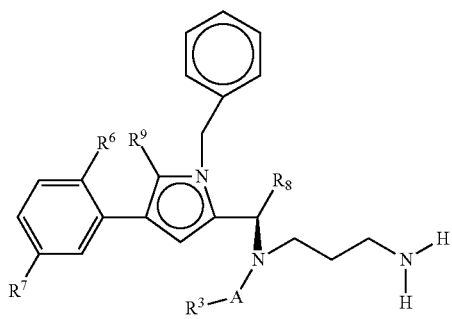

where
R³ represents -L-#1;
A represents CO; and
R⁶, R⁷, R⁸ and R⁹ have the same meaning as in formula (I)

Formula (IIk):

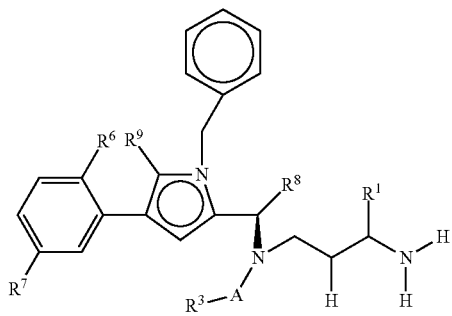

where
R¹ represents -L-#1;
A represents CO and R³ represents —CH₂OH;
R³, R⁶, R⁷, R⁸ and R⁹ have the same meaning as in formula (I).

Furthermore, it is preferred when in the compounds of the formulae (II), (IIa), (IIb), (IIe), (IId), (IIe), (IIi), (IIj) and (IIk) (alone or in combination):
Z represents Cl or Br;
R¹ represents —(CH₂)₀₋₃Z, where Z represents COOH or —CO—NY¹Y², where Y² represents —(CH₂CH₂O)₀₋₃—(CH₂)₀₋₃Z' and Y¹ represents H, NH₂ or —(CH₂CH₂O)₀₋₃—(CH₂)₀₋₃Z';
Y¹ represents H, Y² represents —(CH₂CH₂O)₃—CH₂CH₂Z' and Z' represents —COOH;
Y¹ represents H, Y² represents —CH₂CH₂Z' and Z' represents —(CONHCHY⁴)₂COOH;
Y¹ represents H, Y² represents —CH₂CH₂Z', Z' represents —(CONHCHY⁴)₂COOH and one of the Y⁴ radicals represents i-propyl and the other —(CH₂)₃—NHCONH₂;
Y¹ represents H, Y² represents —CH₂CH₂Z', Z' represents —(CONHCHY⁴)₂COOH and one of the Y⁴ radicals represents —CH₃ and the other —(CH₂)₃—NHCONH₂;
Y⁴ represents straight-chain or branched C₁₋₆-alkyl which is optionally substituted by —NHCONH₂; at least one Y⁴ representative is selected from the group consisting of i-propyl and —CH₃;

Y¹ represents H, Y² represents —CH₂CH₂Z', Z' represents —CONHCHY⁴COOH and Y⁴ represents aryl or benzyl which are optionally substituted by —NH₂;
Y⁴ represents aminobenzyl;
R² represents —(CH₂)₀₋₃Z and Z represents —SY³;
R⁴ represents —CO—CHY⁴—NHY⁵ and Y⁵ represents H;
R⁴ represents —CO—CHY⁴—NHY⁵ and Y⁵ represents —CO—CHY⁶—NH₂; or
Y⁴ represents straight-chain or branched C₁₋₆-alkyl which is optionally substituted by —NHCONH₂.

Furthermore, it is preferred when in the formula (I) or (II) R¹, R² or R³ represents -MOD. Particularly preferably, R³ represents -MOD and R¹ or R⁴ represents -L-#1 or -L-BINDER,
where -MOD represents —(NR¹⁰)ₙ-(G1)ₒ-G2-G3, where R¹⁰ represents H or C₁-C₃-alkyl;
G1 represents —NHCO— or —CONH— (where, if G1 represents —NHCO—, R¹⁰ does not represent NH₂);
n represents 0 or 1;
o represents 0 or 1; and
G2 represents a straight-chain and/or branched hydrocarbon group which has 1 to 10 carbon atoms and which may be interrupted once or more than once by one or more of the groups —O—, —S—, —SO—, SO₂, —NRy-, —NRyCO—, CONRy-, —NRyNRy-, —SO₂NRyNRy-, —CONRyNRy- (where Rʸ represents H, phenyl, C1-C10-alkyl, C2-C10-alkenyl or C2-C10-alkynyl, each of which may be substituted by NHCONH₂, —COOH, —OH, —NH₂, —NH—CNNH₂, sulphonamide, sulphone, sulphoxide or sulphonic acid), —CO—, or —CRˣ=N—O— (where Rx represents H, C1-C3-alkyl or phenyl), where the hydrocarbon chain including any side chains may be substituted by NHCONH₂, —COOH, —OH, —NH₂, NH—CNNH₂, sulphonamide, sulphone, sulphoxide or sulphonic acid, where G3 represents —H or —COOH, and where the group-MOD preferably has at least one group —COOH;
Particularly preferably, the group -MOD has a (preferably terminal) —COOH group, for example in a betaine group. Preferably, the group -MOD has the formula —CH₂—Sₓ—(CH₂)₀₋₄—CHY⁵—COOH where x is 0 or 1, and Y⁵ represents H or NHY⁶, where Y⁶ represents H or —COCH₃.
Other particularly preferred compounds have the formula (III) below:

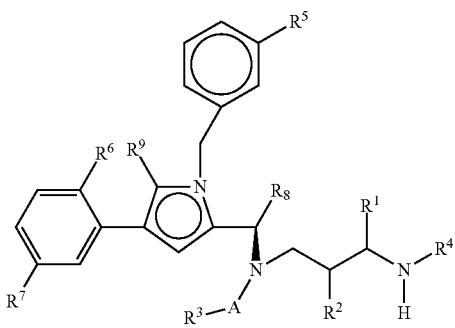

where
R¹ represents -L-BINDER, H or —(CH₂)₀₋₃Z, where Z represents —H, —NHY³, —OY³, —SY³, halogen, —CO—NY¹Y² or —CO—OY³,
where Y¹ and Y² independently of one another represent H, NH₂, —(CH₂CH₂O)₀₋₃—(CH₂)₀₋₃Z' or —CH(CH₂W)Z', and Y³ represents H or —(CH₂)₀₋₃Z', where Z' represents H, $NH_2$, $SO_3H$, COOH, —NH—CO—$CH_2$—$CH_2$—$CH(NH_2)$ COOH or —(CO—NH—$CHY^4$)$_{1-3}$COOH;
where $Y^4$ represents straight-chain or branched $C_{1-6}$ alkyl which is optionally substituted by —$NHCONH_2$, or represents aryl or benzyl which are optionally substituted by —$NH_2$;
$R^2$ and $R^4$ independently of one another represent H, —$SG_{lys}$-(CO)$_{0-1}$—$R^{4'}$, —CO—$CHY^4$—$NHY^5$ or —($CH_2$)$_{0-3}$Z, or $R^2$ and $R^4$ together (with formation of a pyrrolidine ring) represent —$CH_2$—$CHR^{11}$— or —$CHR^{11}$—$CH_2$—, where $R^{11}$ represents H, $NH_2$, $SO_3H$, COOH, SH, halogen (in particular F or Cl), $C_{1-4}$-alkyl, $C_{1-4}$-haloalkyl, $C_{1-4}$-alkoxy, hydroxyl-substituted $C_{1-4}$-alkyl, COO($C_{1-4}$-alkyl) or OH;
wherein $SG_{lys}$ is a group cleavable by lysosomal enzymes, in particular a group consisting of a dipeptide or tripeptide, $R^{4'}$ is a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, heteroarylalkoxy, $C_{1-10}$-alkoxy, $C_{6-10}$-aryloxy or $C_{6-10}$-aralkoxy, $C_{5-10}$-heteroaralkoxy, $C_{1-10}$-alkyl-O—$C_{6-10}$-aryloxy, $C_{5-10}$-heterocycloalkoxy group, which may be substituted once or more than once by —$NH_2$, —NH-alkyl, —N(alkyl)$_2$, NH—CO-alkyl, N(alkyl)-COalkyl, —$SO_3H$, —$SO_2NH_2$, —$SO_2$—N(alkyl)$_2$, —COOH, —$CONH_2$, —CON(alkyl)$_2$, —OH, —H or a group —$O_x$—($CH_2CH_2O$)$_y$—$R^{4''}$, (where x is 0 or 1 and v is a number from 1 to 10, and $R^{4''}$ is —H, -alkyl (preferably $C_{1-12}$-alkyl), —$CH_2$—COOH, —$CH_2$—$CH_2$—COOH, or —$CH_2$—$CH_2$—$NH_2$);
where Z represents —H, halogen, —$OY^3$, —$SY^3$, $NHY^3$, —CO—$NY^1Y^2$ or —CO—$OY^3$,
where $Y^1$ and $Y^2$ independently of one another represent H, $NH_2$ or —($CH_2$)$_{0-3}$Z', and $Y^3$ represents H or —($CH_2$)$_{0-3}$Z', where Z' represents H, $SO_3H$, $NH_2$ or COOH;
where $Y^4$ represents straight-chain or branched $C_{1-6}$-alkyl which is optionally substituted by —$NHCONH_2$, or represents aryl or benzyl which are optionally substituted by —$NH_2$, and Y represents H or —CO—$CHY^6$—$NH_2$, where $Y^6$ represents straight-chain or branched $C_{1-6}$-alkyl; A represents CO, SO, $SO_2$, $SO_2NH$ or $CNNH_2$;
$R^3$ represents -L-BINDER or an optionally substituted alkyl, aryl, heteroaryl, heteroalkyl, heterocycloalkyl group, or —$CH_2$—$S_x$—($CH_2$)$_{0-4}$—$CHY^5$—COOH, where x represents 0 or 1 and $Y^5$ represents H or $NHY^6$, where $Y^6$ represents H or —$COCH_3$, preferably -L-BINDER or a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —S(O)$_n$-alkyl groups, 1-3 —$SO_2$—NH-alkyl groups, 1-3 —NH-alkyl groups, 1-3 —N(alkyl)$_2$ groups, 1-3 —$NH_2$ groups or 1-3 —($CH_2$)$_{0-3}$Z groups, where Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —($CH_2$)$_{0-3}$Z' and $Y^3$ represents H, —($CH_2$)$_{0-3}$—CH($NHCOCH_3$)Z', —($CH_2$)$_{0-3}$—CH($NH_2$)Z' or —($CH_2$)$_{0-3}$Z', where Z' represents H, $SO_3H$, $NH_2$ or COOH, (where "alkyl" preferably represents $C_{1-10}$-alkyl);
$R^5$ represents H, F, $NH_2$, $NO_2$, halogen, SH or —($CH_2$)$_{0-3}$Z, where Z represents —H, halogen, —$OY^3$, —$SY^3$, —$NHY^3$, —CO—$NY^1Y^2$ or —CO—$OY^3$,
where $Y^1$ and $Y^2$ independently of one another represent H, $NH_2$ or —($CH_2$)$_{0-3}$Z', and $Y^3$ represents H or —($CH_2$)$_{0-3}$Z', where Z' represents H, $SO_3H$, $NH_2$ or COOH;

where L represents a linker and BINDER represents the antibody, where the binder may optionally be attached to a plurality of active compound molecules,
$R^6$ and $R^7$ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy or halogen,
$R^8$ represents (optionally fluorinated) $C_{1-10}$-alkyl, (optionally fluorinated) $C_{4-10}$-cycloalkyl or optionally substituted oxetane; and
$R^9$ represents H, F, $CH_3$, $CF_3$, $CH_2F$ or $CHF_2$;
and the salts, solvates, salts of the solvates and epimers thereof.
Furthermore, it is preferred when (alone or in combination) in the formula (I), (—($CH_2$)$_{0-3}$Z), (II), (IIa), (IIb), (IIe), (IId), (IIe), (IIi), (IIj), (IIk) or (III):
Z represents Cl or Br;
$R^1$ represents —($CH_2$)$_{0-3}$Z, where Z represents —CO—$NY^1Y^2$, where $Y^2$ represents —($CH_2CH_2O$)$_{0-3}$—($CH_2$)$_{0-3}$Z' and $Y^1$ represents H, $NH_2$ or —($CH_2CH_2O$)$_{0-3}$—($CH_2$)$_{0-3}$Z';
$Y^1$ represents H, $Y^2$ represents —($CH_2CH_2O$)$_3$—$CH_2CH_2$Z' and Z represents —COOH,
$Y^1$ represents H, $Y^2$ represents —$CH_2CH_2$Z' and Z' represents —($CONHCHY^4$)$_2$COOH;
$Y^1$ represents H, $Y^2$ represents —$CH_2CH_2$Z', Z' represents —($CONHCHY^4$)$_2$COOH and one $Y^4$ representative represents i-propyl and the other represents —($CH_2$)$_3$—$NHCONH_2$;
$Y^1$ represents H, $Y^2$ represents —$CH_2CH_2$Z', Z' represents —($CONHCHY^4$)$_2$COOH and one $Y^4$ representative represents —$CH_3$ and the other represents —($CH_2$)$_3$—$NHCONH_2$;
$Y^4$ represents straight-chain or branched $C_{1-6}$-alkyl which is optionally substituted by —$NHCONH_2$; at least one $Y^4$ representative is selected from the group consisting of i-propyl and —$CH_3$,
$Y^1$ represents H, $Y^2$ represents —$CH_2CH_2$Z', Z' represents —$CONHCHY^4$COOH and $Y^4$ represents aryl or benzyl which are optionally substituted by —$NH_2$;
$Y^4$ represents aminobenzyl;
$R^2$ represents —($CH_2$)$_{0-3}$Z and Z represents —$SY^3$;
$R^4$ represents —CO—$CHY^4$—$NHY^5$ and $Y^5$ represents H;
$R^4$ represents —CO—$CHY^4$—$NHY^5$ and $Y^5$ represents —CO—$CHY^6$—$NH_2$; and/or
$Y^4$ represents straight-chain or branched $C_{1-6}$-alkyl which is optionally substituted by —$NHCONH_2$.
Preference is furthermore given to compounds of the formula (I), (Ia), (II), (IIa) or (III)
where
$R^1$ represents H, -L-#1 or -L-BINDER, -MOD or —($CH_2$)$_{0-3}$Z, where Z represents —H, —$NHY^3$, —$OY^3$, —$SY^3$, halogen, —CO—$NY^1Y^2$ or —CO—$OY^3$,
where $Y^1$ and $Y^2$ independently of one another represent H, $NH_2$, —($CH_2CH_2O$)$_{0-3}$—($CH_2$)$_{0-3}$Z' (e.g. —($CH_2$)$_{0-3}$Z') or —CH($CH_2$W)Z and $Y^3$ represents H or —($CH_2$)$_{0-3}$Z', where Z' represents H, $NH_2$, $SO_3H$, COOH, —NH—CO—$CH_2$—$CH_2$—CH($NH_2$)COOH or —(CO—NH—$CHY^4$)$_{1-3}$COOH,
where W represents H or OH,
where $Y^4$ represents straight-chain or branched $C_{1-6}$ alkyl which is optionally substituted by —$NHCONH_2$, or represents aryl or benzyl which are optionally substituted by —$NH_2$;
$R^2$ represents H, —CO—$CHY^4$—$NHY^5$ or —($CH_2$)$_{0-3}$Z, where Z represents —H, halogen, —$OY^3$, —$SY^3$, $NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;

where $Y^4$ independently of one another represents straight-chain or branched $C_{1-6}$-alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;

$R^4$ represents H or -L-#1 or -L-BINDER (where -L-#1 or -L-BINDER is an enzymatically cleavable linker leading to the conversion of $R^4$ into H);

A represents CO, SO, $SO_2$, $SO_2NH$ or $CNNH_2$;

$R^3$ represents -L-#1 or -L-BINDER, -MOD or an optionally substituted alkyl, cycloalkyl, aryl, heteroaryl, heteroalkyl, heterocycloalkyl group, preferably a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —$S(O)_n$-alkyl groups, 1-3 —$SO_2$—NH-alkyl groups, 1-3 —NH-alkyl groups, 1-3 —N(alkyl)$_2$ groups, 1-3 —NH(($CH_2CH_2O$)1-20H) groups, 1-3 —$NH_2$ groups or 1-3 —$(CH_2)_{0-3}Z$ groups, where Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}Z'$ and $Y^3$ represents H, —$(CH_2)_{0-3}$—CH(NHCOCH$_3$)Z', —$(CH_2)_{0-3}$—CH(NH$_2$)Z' or —$(CH_2)_{0-3}Z'$, where Z' represents H, $SO_3H$, $NH_2$ or COOH (where "alkyl" is preferably $C_{1-10}$-alkyl);

$R^5$ represents H, -MOD, $NH_2$, $NO_2$, halogen (in particular F, Cl, Br), —CN, $CF_3$, —$OCF_3$, —$CH_2F$, —$CH_2F$, SH or —$(CH_2)_{0-3}Z$, where Z represents —H, —$OY^3$, —$SY^3$, halogen, $NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;

$R^6$ and $R^7$ independently of one another represent H, cyano, (optionally fluorinated) $C_{1-10}$-alkyl, (optionally fluorinated) $C_{2-10}$-alkenyl, (optionally fluorinated) $C_{2-10}$-alkynyl, hydroxy, $NO_2$, $NH_2$, COOH or halogen (in particular F, Cl, Br), $R^8$ represents (optionally fluorinated) $C_{1-10}$-alkyl, (optionally fluorinated) $C_{2-10}$-alkenyl, (optionally fluorinated) $C_{2-10}$-alkynyl or (optionally fluorinated) C4-10-cycloalkyl;

where one of the substituents $R^1$ and $R^3$ represents -L-#1 or -L-BINDER,

L represents the linker and #1 represents the bond to the antibody and BINDER represents the antibody, $R^9$ represents H, F, $CH_3$, $CF_3$, $CH_2F$ or $CHF_2$;

where -MOD represents —$(NR^{10})_n$-(G1)$_o$-G2-G3, where $R^{10}$ represents H or $C_1$-$C_3$-alkyl;

G1 represents —NHCO— or —CONH— (where, if G1 represents —NHCO—, $R^{10}$ does not represent $NH_2$);

n represents 0 or 1;

o represents 0 or 1; and

G2 represents a straight-chain and/or branched hydrocarbon group which has 1 to 10 carbon atoms and which may be interrupted once or more than once by one or more of the groups —O—, —S—, —SO—, $SO_2$, —NRy-, —NRyCO—, CONRy-, —NRyNRy-, —$SO_2$NRyNRy-, —CONRyNRy- (where R$^y$ represents H, phenyl, $C_1$-$C_{10}$-alkyl, C2-C10-alkenyl or C2-C10-alkynyl, each of which may be substituted by $NHCONH_2$, —COOH, —OH, —$NH_2$, NH—$CNNH_2$, sulphonamide, sulphone, sulphoxide or sulphonic acid), —CO—, or —$CR^x$=N—O— (where Rx represents H, C1-C3-alkyl or phenyl), where the hydrocarbon chain including any side chains may be substituted by —$NHCONH_2$, —COOH, —OH, —$NH_2$, NH—$CNNH_2$, sulphonamide, sulphone, sulphoxide or sulphonic acid, where G3 represents —H or —COOH, and the group -MOD preferably has at least one group —COOH;

and the salts, solvates, salts of the solvates and epimers thereof.

Preference is furthermore given to compounds of the formula (I), (Ia), (II), (IIa) or (III) in which $R^1$ represents H, -L-#1 or -L-BINDER, -MOD or —$(CH_2)_{0-3}Z$, where Z represents —H, —$NHY^3$, —$OY^3$, —$SY^3$, halogen, —CO—$NY^1Y^2$ or —CO—$OY^3$, where $Y^1$ and $Y^2$ independently of one another represent H, $NH_2$, —$(CH_2CH_2O)_{0-3}$—$(CH_2)_{0-3}Z'$ (e.g. —$(CH_2)_{0-3}Z'$) or —CH(CH$_2$W)Z', and $Y^3$ represents H or —$(CH_2)_{0-3}Z'$, where Z' represents H, $NH_2$, $SO_3H$, COOH, —NH—CO—$CH_2$—$CH_2$—CH($NH_2$)COOH or —(CO—NH—$CHY^4$)$_{1-3}$COOH, where W represents H or OH, where $Y^4$ represents straight-chain or branched $C_{1-6}$ alkyl which is optionally substituted by —$NHCONH_2$, or represents aryl or benzyl which are optionally substituted by —$NH_2$;

$R^2$ represents H, —CO—$CHY^4$—$NHY^5$ or —$(CH_2)_{0-3}Z$, where Z represents —H, halogen, —$OY^3$, —$SY^3$, $NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;

where $Y^4$ represents straight-chain or branched $C_{1-6}$-alkyl which is optionally substituted by —$NHCONH_2$, or represents aryl or benzyl which are optionally substituted by —$NH_2$, and $Y^5$ represents H or —CO—$CHY^6$—$NH_2$, where $Y^6$ represents straight-chain or branched $C_{1-6}$-alkyl;

$R^4$ represents H,

A represents CO, SO, $SO_2$, $SO_2NH$ or $CNNH_2$;

$R^3$ represents -L-#1 or -L-BINDER, -MOD or an optionally substituted alkyl, cycloalkyl, aryl, heteroaryl, heteroalkyl, heterocycloalkyl group, preferably a $C_{1-10}$-alkyl, $C_{6-10}$-aryl or $C_{6-10}$-aralkyl, $C_{5-10}$-heteroalkyl, $C_{1-10}$-alkyl-O—$C_{6-10}$-aryl or $C_{5-10}$-heterocycloalkyl group which may be substituted by 1-3 —OH groups, 1-3 halogen atoms, 1-3 halogenated alkyl groups (each having 1-3 halogen atoms), 1-3 O-alkyl groups, 1-3 —SH groups, 1-3 —S-alkyl groups, 1-3 —O—CO-alkyl groups, 1-3 —O—CO—NH-alkyl groups, 1-3 —NH—CO-alkyl groups, 1-3 —NH—CO—NH-alkyl groups, 1-3 —$S(O)_n$-alkyl groups, 1-3 —$SO_2$—NH-alkyl groups, 1-3 —NH-alkyl groups, 1-3 —N(alkyl)$_2$ groups, 1-3 —NH(($CH_2CH_2O$)1-20H) groups, 1-3 —$NH_2$ groups or 1-3 —$(CH_2)_{0-3}Z$ groups, where Z represents —H, halogen, —$OY^3$, —$SY^3$, —$NHY^3$, —CO—$NY^1Y^2$ or —CO—$OY^3$, where $Y^1$ and $Y^2$ independently of one another represent H, $NH_2$ or —$(CH_2)_{0-3}Z'$ and $Y^3$ represents H, —$(CH_2)_{0-3}$—CH(NHCOCH$_3$)Z', —$(CH_2)_{0-3}$—CH(NH$_2$)Z' or —$(CH_2)_{0-3}Z'$, where Z' represents H, $SO_3H$, $NH_2$ or COOH (where "alkyl" is preferably $C_{1-10}$-alkyl);

$R^5$ represents H, -MOD, $NH_2$, $NO_2$, halogen (in particular F, Cl, Br), —CN, $CF_3$, —$OCF_3$, —$CH_2F$, —$CH_2F$, SH or —$(CH_2)_{0-3}Z$, where Z represents —H, —$OY^3$, —$SY^3$, halogen, $NHY^3$, —CO—$NY^1Y^2$ or —CO—$OY^3$, where $Y^1$ and $Y^2$ independently of one another represent H, $NH_2$ or —$(CH_2)_{0-3}Z'$, and $Y^3$ represents H or —$(CH_2)_{0-3}Z'$, where Z' represents H, $SO_3H$, $NH_2$ or COOH;

$R^6$ and $R^7$ independently of one another represent H or halogen (in particular F, Cl, Br);

$R^8$ represents (optionally fluorinated) $C_{1-10}$-alkyl;

where one of the substituents $R^1$ and $R^3$ represents -L-#1 or -L-BINDER,

L represents the linker and #1 represents the bond to the antibody and BINDER represents the antibody, $R^9$ represents H, F, $CH_3$, $CF_3$, $CH_2F$ or $CHF_2$;

where -MOD represents $-CH_2-S_x-(CH_2)_{0-4}-CHY^5-COOH$ where x is 0 or 1, and Y represents H or $NHY^6$, where $Y^6$ represents H or $-COCH_3$, and the salts, solvates and salts of the solvates thereof.

Preference is furthermore given to the following compounds which may optionally be present together with an acid such as, for example, trifluoroacetic acid. These compounds may be attached via the positions corresponding to the positions $R^1$, $R^3$ and $R^4$ via a linker to the antibody (where a hydrogen atom is substituted by the linker):

N-(3-Aminopropyl)-N-{(1R)-1-[1-benzyl-4-(2,5-difluorophenyl)-1H-pyrrol-2-yl]-2,2-dimethylpropyl}-2-hydroxyacetamide;

(2S)-2-amino-4-[{(1R)-1-[1-benzyl-4-(2,5-difluorophenyl)-1H-pyrrol-2-yl]-2,2-dimethylpropyl}(glycoloyl)amino]-N-methylbutanamide (1:1);

N-(3-aminopropyl)-N-{(1S)-1-[1-benzyl-4-(2,5-difluorophenyl)-1H-pyrrol-2-yl]-2,2-dimethylpropyl}acetamide;

N-(3-aminopropyl)-N-{(1S)-1-[1-benzyl-4-(2,5-difluorophenyl)-1H-pyrrol-2-yl]-2,2-dimethylpropyl}-2-hydroxyacetamide;

S-(1-{2-[(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)amino]ethyl}-2,5-dioxopyrrolidin-3-yl)-L-cysteine;

S-(1-{2-[(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)amino]ethyl}-2,5-dioxopyrrolidin-3-yl)-L-cysteine;

S-[1-(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)-2,5-dioxopyrrolidin-3-yl]-L-cysteine;

N-[19-(3(R/S){[(2R)-2-amino-2-carboxyethyl]sulphanyl}-2,5-dioxopyrrolidin-1-yl)-17-oxo-4,7,10,13-tetraoxa-16-azanonadecan-1-oyl]-R/S-{2-[(3-aminopropyl){(1R)-1-[1-benzyl-4-(2,5-difluorophenyl)-1H-pyrrol-2-yl]-2,2-dimethylpropyl}amino]-2-oxoethyl}homocysteine;

S-{(3R/S)-1-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-2,5-dioxopyrrolidin-3-yl}-L-cysteine;

S-[(3R/S)-1-(2-{[6-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)hexanoyl]amino}ethyl)-2,5-dioxopyrrolidin-3-yl]-L-cysteine;

S-{1-[2-({[(1R,3S)-3-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)cyclopentyl]carbonyl}amino)ethyl]-2,5-dioxopyrrolidin-3-yl}-L-cysteine;

S-(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)-L-cysteine;

$N^6$—(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-$N^2$—{N-[6-(3-{[(2R)-2-amino-2-carboxyethyl]sulphanyl}-2,5-dioxopyrrolidin-1-yl)hexanoyl]-L-valyl-L-alanyl}-L-lysine;

N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-L-glutamine;

$N^6$—(N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-L-lysine;

N-(3-aminopropyl)-N-{(1R)-1-[1-benzyl-4-(2,5-difluorophenyl)-1H-pyrrol-2-yl]-2,2-dimethylpropyl}-3,3,3-trifluoropropanamide;

N-(3-aminopropyl)-N-{(1R)-1-[1-benzyl-4-(2,5-difluorophenyl)-1H-pyrrol-2-yl]-2,2-dimethylpropyl}-4-fluorobenzamide;

N-(3-aminopropyl)-N-{(1R)-1-[1-benzyl-4-(2,5-difluorophenyl)-1H-pyrrol-2-yl]-2,2-dimethylpropyl}acetamide;

N-(3-aminopropyl)-N-{(1R)-1-[1-benzyl-4-(2,5-difluorophenyl)-1H-pyrrol-2-yl]-2,2-dimethylpropyl}-4-(trifluoromethyl)benzamide;

(2S)-2-amino-4-[{(1R)-1-[1-benzyl-4-(2,5-difluorophenyl)-1H-pyrrol-2-yl]-2,2-dimethylpropyl}(glycoloyl)amino]butanoic acid;

(2S)-2-amino-N-(2-aminoethyl)-4-[{(1R)-1-[1-benzyl-4-(2,5-difluorophenyl)-1H-pyrrol-2-yl]-2,2-dimethylpropyl}(glycoloyl)amino]butanamide;

4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-{[(2R)-2-amino-2-carboxyethyl]sulphanyl}-4-oxobutanoic acid;

4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-2-{[(2R)-2-amino-2-carboxyethyl]sulphanyl}-4-oxobutanoic acid;

N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-beta-alanine;

N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-L-serine;

N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}-L-alanine;

N-{(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}glycine;

N-(3-aminopropyl)-N-{(1R)-1-[1-benzyl-4-(2,5-difluorophenyl)-1H-pyrrol-2-yl]-2,2-dimethylpropyl}-4-methylbenzamide;

N-(3-aminopropyl)-N-{(1R)-1-[1-benzyl-4-(2,5-difluorophenyl)-1H-pyrrol-2-yl]-2,2-dimethylpropyl}-4-(methylsulphanyl)benzamide;

(2S)—N-(3-aminopropyl)-N-{(1R)-1-[1-benzyl-4-(2,5-difluorophenyl)-1H-pyrrol-2-yl]-2,2-dimethylpropyl}-2-hydroxypropanamide;

N-(3-aminopropyl)-N-{(1R)-1-[1-benzyl-4-(2,5-difluorophenyl)-1H-pyrrol-2-yl]-2,2-dimethylpropyl}-2-(methylsulphanyl)acetamide;

(2S)—N-(3-aminopropyl)-N-{(1R)-1-[4-benzyl-1-(2,5-difluorophenyl)-1H-pyrazol-3-yl]-2,2-dimethylpropyl}-2-hydroxypropanamide;

methyl 4-[(3-aminopropyl){(1R)-1-[1-benzyl-4-(2,5-difluorophenyl)-1H-pyrrol-2-yl]-2,2-dimethylpropyl}amino]-4-oxobutanoate;

4-[(3-aminopropyl){(1R)-1-[1-benzyl-4-(2,5-difluorophenyl)-1H-pyrrol-2-yl]-2,2-dimethylpropyl}amino]-4-oxobutanoic acid;

(2R)-22-[(3R/S)-3-{[(2R)-2-amino-2-carboxyethyl]sulphanyl}-2,5-dioxopyrrolidin-1-yl]-2-[({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)methyl]-4,20-dioxo-7,10,13,16-tetraoxa-3,19-diazadocosan-1-oic acid;

N-acetyl-S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cysteine;

N-acetyl-S-[2-([3-(L-alanylamino)propyl]{(1R)-1-[1-benzyl-4-(2,5-difluorophenyl)-1H-pyrrol-2-yl]-2,2-dimethylpropyl}amino)-2-oxoethyl]-L-cysteine;

(2S)—N-(3-aminopropyl)-N-{(1R)-1-[1-benzyl-4-(2,5-difluorophenyl)-1H-pyrrol-2-yl]-2,2-dimethylpropyl}tetrahydrofuran-2-carboxamide;

3-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)propanoic acid;

S-{2-[(3-aminopropyl){(1R)-1-[1-benzyl-4-(2,5-difluorophenyl)-1H-pyrrol-2-yl]-2,2-dimethylpropyl}amino]-2-oxoethyl}homocysteine;

4-amino-N-(3-aminopropyl)-N-{(1R)-1-[1-benzyl-4-(2,5-difluorophenyl)-1H-pyrrol-2-yl]-2,2-dimethylpropyl}benzamide;

4-[(2-{[(2R)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-2-carboxyethyl]amino}-2-oxoethyl)amino]-3-{[(2R)-2-amino-2-carboxyethyl]sulphanyl}-4-oxobutanoic acid;

4-[(2-{[(2R)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-2-carboxyethyl]amino}-2-oxoethyl)amino]-2-{[(2R)-2-amino-2-carboxyethyl]sulphanyl}-4-oxobutanoic acid.

Particular preference according to the invention is given to the following compounds of the formula IV where $R^1$, $R^2$, $R^3$, $R^4$ and $R^5$ have the meanings mentioned above (as mentioned, for example for formula (I) or (II)):

Formula IV

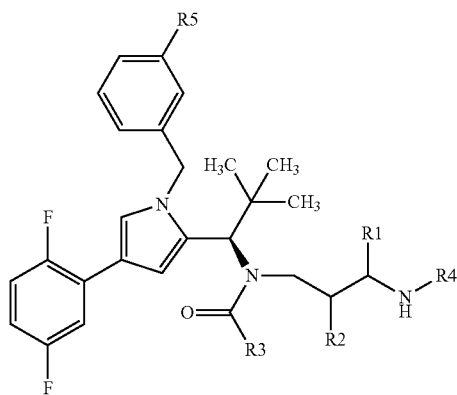

Particular preference is given to the compounds of the formula IV where $R^1$ and $R^5$ represent H or -L-#1; $R^2$ and $R^4$ represent H or $R^2$ and $R^4$ together (with formation of a pyrrolidine ring) represent —CH$_2$—CHR$^{11}$— or —CHR$^{11}$—CH$_2$—, where $R^{11}$ represents H; and $R^3$ represents CH$_2$OH, CH(CH$_3$)OH or -L-#1, where one of the substituents $R^1$ and $R^3$ represents -L-#1. In addition, particular preference is given to the compounds of the formula IV where $R^1$ represents H or COOH; $R^2$ and $R^5$ represent H; $R^4$ represents -L-#1; and $R^3$ represents CH$_2$OH or CH(CH$_3$)OH, where -L-#1 is an enzymatically cleavable linker leading to the conversion of $R^4$ into H.

Linkers

The literature discloses various options for covalently coupling (conjugating) organic molecules to binders such as, for example antibodies (see, for example, K. Lang and J. W. Chin. Chem. Rev. 2014, 114, 4764-4806, M. Rashidian et al. Bioconjugate Chem. 2013, 24, 1277-1294). Preference according to the invention is given to conjugation of the KSP inhibitors to an antibody via one or more sulphur atoms of cysteine residues of the antibody which are either already present as free thiols or generated by reduction of disulphide bridges, and/or via one or more NH groups of lysine residues of the antibody. However, it is also possible to attach the KSP inhibitor to the antibody via tyrosine residues, via glutamine residues, via residues of unnatural amino acids, via free carboxyl groups or via sugar residues of the antibody. For coupling, use is made of linkers. Linkers can be categorized into the group of the linkers which can be cleaved in vivo and the group of the linkers which are stable in vivo (see L. Ducry and B. Stump, *Bioconjugate Chem.* 21, 5-13 (2010)). The linkers which can be cleaved in vivo have a group which can be cleaved in vivo, where, in turn, a distinction may be made between groups which are chemically cleavable in vivo and groups which are enzymatically cleavable in vivo. "Chemically cleavable in vivo" and "enzymatically cleavable in vivo" means that the linkers or groups are stable in circulation and are cleaved only at or in the target cell by the chemically or enzymatically different environment therein (lower pH; elevated glutathione concentration; presence of lysosomal enzymes such as cathepsin or plasmin, or glycosidases such as, for example, β-glucuronidases), thus releasing the low-molecular weight KSP inhibitor or a derivative thereof. Groups which can be cleaved chemically in vivo are in particular disulphide, hydrazone, acetal and aminal; groups which can be cleaved enzymatically in vivo, m particular those which can be cleaved by lysosomal enzymes, are in particular the 2-8-oligopeptide group, especially a tri- or dipeptide group or glycoside. Peptide cleaving sites are disclosed in *Bioconjugate Chem.* 2002, 13, 855-869 and *Bioorganic & Medicinal Chemistry Letters* 8 (1998) 3341-3346 and also *Bioconjugate Chem.* 1998, 9, 618-626. These include, for example, valine-alanine, valine-lysine, valine-citrulline, alanine-lysine and phenylalanine-lysine (optionally with additional amide group).

Linkers which are stable in vivo are distinguished by a high stability (less than 5% metabolites after 24 hours in plasma) and do not have the chemically or enzymatically in vivo cleavable groups mentioned above.

The linker -L- preferably has one of the basic structures (i) to (iv) below:

(i) —(C═O)$_m$-SG1-L1-L2-
(ii) —(C═O)$_m$-L1-SG-L1-L2-
(iii) —(C═O)$_m$-L1-L2-
(iv) —(C═O)$_m$-L1-SG-L2 where m is 0 or 1; SG is a (chemically or enzymatically) in vivo cleavable group (in particular disulphide, hydrazone, acetal and aminal; or a 2-8-oligopeptide group which can be cleaved by a protease), SG1 is an oligopeptide group or preferably a dipeptide group, L1 independently of one another represent in vivo stable organic groups, and L2 represents a coupling group to the binder or a single bond. Here, coupling is preferably to a cysteine residue or a lysine residue of the antibody. Alternatively, coupling can be to a tyrosine residue, glutamine residue or to an unnatural amino acid of the antibody. The unnatural amino acids may contain, for example, aldehyde or keto groups (such as, for example, formylglycine) or azide or alkyne groups (see Lan & Chin, Cellular Incorporation of Unnatural Amino Acids and Bioorthogonal Labeling of Proteins, Chem. Rev. 2014, 114, 4764-4806).

Particular preference according to the invention is given to the basic linker structure (iii). Via metabolization, the administration of a conjugate according to the invention having a basic linker structure (iii) and coupling of the linker to a cysteine or lysine residue of the antibody leads to cysteine or lysine derivatives of the formulae below:

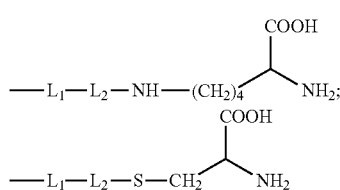

where L1 is in each case attached to the low-molecular weight KSP inhibitor, for example a compound of the formula (I), (Ia), (II), (IIa), (IIb), (IIca), (IId), (IIe), (IIf), (III) or (IV).

Preference according to the invention is also given to the basic linker structures (ii) and (iv), in particular when attachment is at position $R^1$, in particular when group L1 has one of the following structures:

(a) —NH—$(CH_2)_{0-4}$—$(CHCH_3)_{0-4}$—$CHY^5$—CO—$Y^7$, where $Y^5$ represents H or $NHY^6$, where $Y^6$ represents H or —$COCH_3$, and $Y^7$ represents a single bond or —NH—$(CH_2)_{0-4}$—$CHNH_2$—CO—, so that after cleavage the corresponding structure —NH—$(CH_2)_{0-4}$—$(CHCH_3)_{0-4}$—$CHY^5$—COOH or —NH—$(CH_2)_{0-4}$—$(CHCH_3)_{0-4}$—$CHY^5$—CO—NH—$(CH_2)_{0-4}$—$CHNH_2$—COOH is obtained.

(b) —$CH_2$—$S_x$—$(CH_2)_{0-4}$—$CHY^5$—CO—, where x is 0 or 1, and $Y^5$ represents H or $NHY^6$, where $Y^6$ represents H or —$COCH_3$, such that after cleavage the corresponding structure —$CH_2$—$S_x$—$(CH_2)_{0-4}$—$CHY^5$—COOH is obtained.

Preference according to the invention is also given to the basic linker structure (i) when attached to position $R^4$, in particular if m=0.

If the linker is attached to a cysteine side chain or a cysteine residue, L2 is preferably derived from a group which reacts with the sulphhydryl group of the cysteine. These include haloacetyls, maleimides, aziridines, acryloyls, arylating compounds, vinylsulphones, pyridyl disulphides, TNB thiols and disulphide-reducing agents. These groups generally react in an electrophilic manner with the sulphhydryl bond, forming a sulphide (e.g. thioether) or disulphide bridge. Preference is given to stable sulphide bridges. L2 is preferably

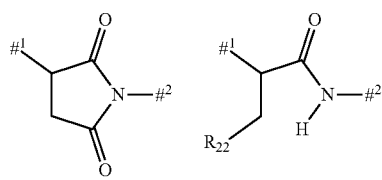

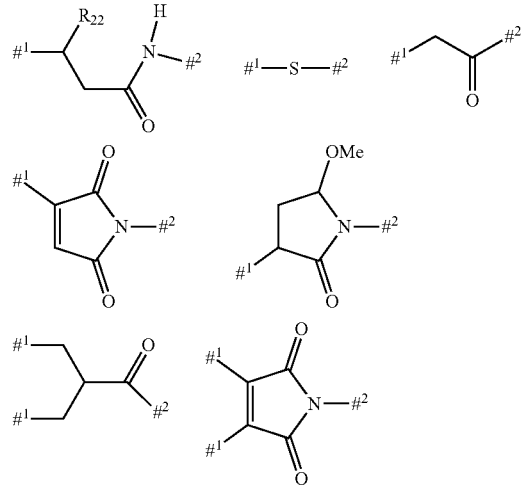

where $\#^1$ denotes the point of attachment to the sulphur atom of the antibody, $\#^2$ denotes the point of attachment to group $L^1$, and $R^{22}$ represents COOH, COOR, COR, CONHR, $CONR_2$ (where R in each case represents $C_{1-3}$-alkyl), $CONH_2$, preferably COOH.

Particularly preferred for L2 is:

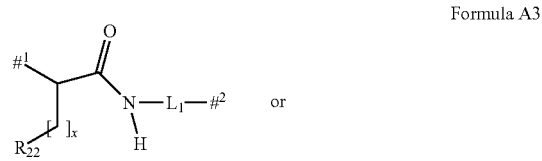

Formula A3

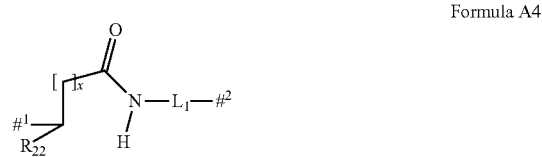

Formula A4 where $\#^1$ denotes the point of attachment to the sulphur atom of the antibody, $\#^2$ denotes the point of attachment to the active compound, x represents 1 or 2, and $R^{22}$ represents COOH, COOR, COR, $CONR_2$, CONHR (where R in each case represents $C_{1-3}$-alkyl), $CONH_2$, preferably COOH. It is preferred when x=1 and $R^{22}$ represents COOH.

In a conjugate according to the invention or in a mixture of the conjugates according to the invention, the bonds to a cysteine residue of the antibody are present, to an extent of preferably more than 80%, particularly preferably more than 90% (in each case based on the total number of bonds of the linker to the antibody), particularly preferably as one of the two structures of the formula A3 or A4. Here, the structures of the formula A3 or A4 are generally present together, preferably in a ratio of from 60:40 to 40:60, based on the number of bonds to the antibody. The remaining bonds are then present as the structure

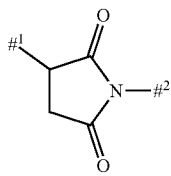

According to the invention, L1 is preferably represented by the formula $$\#^1-(NR^{10})_n-(G1)_o-G2-\#^2$$

where
$R^{10}$ represents H, $NH_2$ or $C_1$-$C_3$-alkyl;
G1 represents —NHCO—, —CONH— or

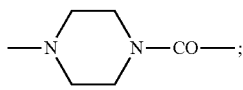

($R^{10}$ is preferably not $NH_2$, if G1 represents NHCO or

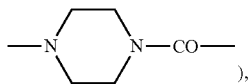

n represents 0 or 1;
o represents 0 or 1; and
G2 represents a straight-chain or branched hydrocarbon chain which has 1 to 100 carbon atoms from arylene groups and/or straight-chain and/or branched and/or cyclic alkylene groups and which may be interrupted once or more than once by one or more of the groups —O—, —S—, —SO—, $SO_2$, —NRy-, —NRyCO—, —C(NH)NRy-, CONRy-, —NRyNRy-, —$SO_2$NRyNRy-, —CONRyNRy- (where $R^y$ represents H, phenyl, C1-C10-alkyl, C2-C10-alkenyl or C2-C10-alkynyl, each of which may be substituted by $NHCONH_2$, —COOH, —OH, —$NH_2$, NH—$CNNH_2$, sulphonamide, sulphone, sulphoxide or sulphonic acid), —CO—, —$CR^x$=N—O— (where $R^x$ represents H, C1-C3-alkyl or phenyl) and/or a 3to 10-membered aromatic or non-aromatic heterocycle having up to 4 heteroatoms selected from the group consisting of N, O and S, —SO— or —$SO_2$— (preferably

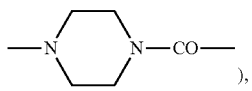

where the hydrocarbon chain including any side chains may be substituted by —$NHCONH_2$, —COOH, —OH, —$NH_2$, NH—$CNNH_2$, sulphonamide, sulphone, sulphoxide or sulphonic acid.

G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe-, —NHNH—, —$SO_2$NHNH—, —CONHNH— and a 5- to 10-membered aromatic or non-aromatic heterocycle having up to 4 heteroatoms selected from the group consisting of N, O and S, or —SO— (preferably

where the side chains, if present, may be substituted by —$NHCONH_2$, —COOH, —OH, —$NH_2$, NH—$CNNH_2$, sulphonamide, sulphone, sulphoxide or sulphonic acid.

G2 preferably represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe-, —NHNH—, —$SO_2$NHNH—, —CONHNH—, —$CR^x$=N—O— (where $R^x$ represents H, C1-C3-alkyl or phenyl) and a 3- to 10-membered, for example 5- to 10-membered, aromatic or non-aromatic heterocycle having up to 4 heteroatoms selected from the group consisting of N, O and S, —SO— or —$SO_2$— (preferably

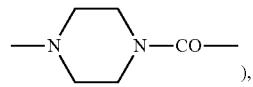

where the hydrocarbon chain including the side chains, if present, may be substituted by —$NHCONH_2$, —COOH, —OH, —$NH_2$, NH—$CNNH_2$, sulphonamide, sulphone, sulphoxide or sulphonic acid.

Further interrupting groups in G2 are preferably

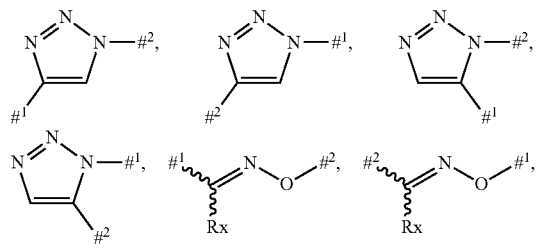

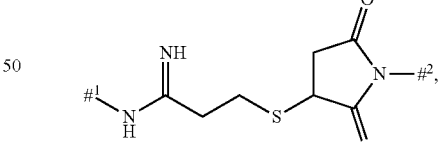

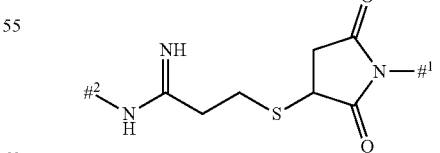

where $R^x$ represents H, $C_1$-$C_3$-alkyl or phenyl.

Here, $\#^1$ is the bond to the KSP inhibitor and $\#^2$ is the bond to the coupling group to the antibody (e.g. L2).

A straight-chain or branched hydrocarbon chain of arylene groups and/or straight-chain and/or branched and/or cyclic alkylene groups generally comprises a α,ω-divalent alkyl radical having the respective number of carbon atoms stated. The following may be mentioned by way of example and as preferred: methylene, ethane-1,2-diyl (1,2-ethylene), propane-1,3-diyl (1,3-propylene), butane-1,4-diyl (1,4-butylene), pentane-1,5-diyl (1,5-pentylene), hexane-1,6-diyl (1,6-hexylene), heptane-1,7-diyl (1,7-hexylene), octane-1,8-diyl (1,8-octylene), nonane-1,9-diyl (1,9-nonylene), decane-1,10-diyl (1,10-decylene). However, the alkylene groups in the hydrocarbon chain may also be branched, i.e. one or more hydrogen atoms of the straight-chain alkylene groups mentioned above may optionally be substituted by $C_{1-10}$-alkyl groups, thus forming side chains. The hydrocarbon chain may furthermore contain cyclic alkylene groups (cycloalkanediyl), for example 1,4-cyclohexanediyl or 1,3-cyclopentanediyl. These cyclic groups may be unsaturated. In particular, aromatic groups (arylene groups), for example phenylene, may be present in the hydrocarbon group. In turn, in the cyclic alkylene groups and the arylene groups, too, one or more hydrogen atoms may optionally be substituted by C1-10-alkyl groups. In this way, an optionally branched hydrocarbon chain is formed. This hydrocarbon chain has a total of 0 to 100 carbon atoms, preferably 1 to 50, particularly preferably 2 to 25 carbon atoms.

The side chains, if present, may be substituted once or more than once, identically or differently, by —NHCONH$_2$, —COOH, —OH, —NH$_2$, NH—CNNH$_2$, sulphonamide, sulphone, sulphoxide or sulphonic acid.

The hydrocarbon chain may be interrupted once or more than once, identically or differently, by one or more of the groups —O—, —S—, —SO—, SO$_2$, —NH—, —CO—, —NHCO—, —CONH—, —NMe-, —NHNH—, —SO$_2$NHNH—, —CONHNH— and a 5- to 10-membered aromatic or non-aromatic heterocycle having up to 4 heteroatoms selected from the group consisting of N, O and S, —SO— or —SO$_2$—.

Further interrupting groups in G2 are preferably

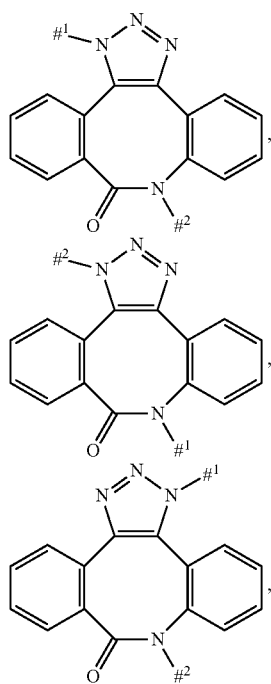

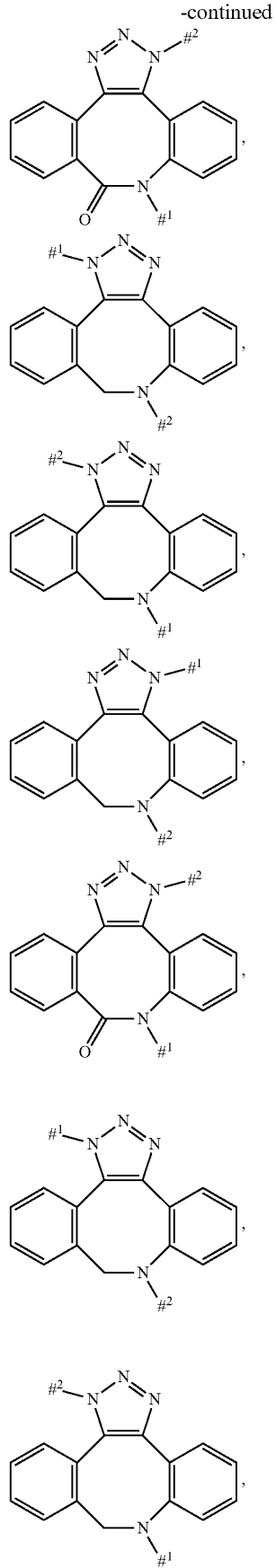

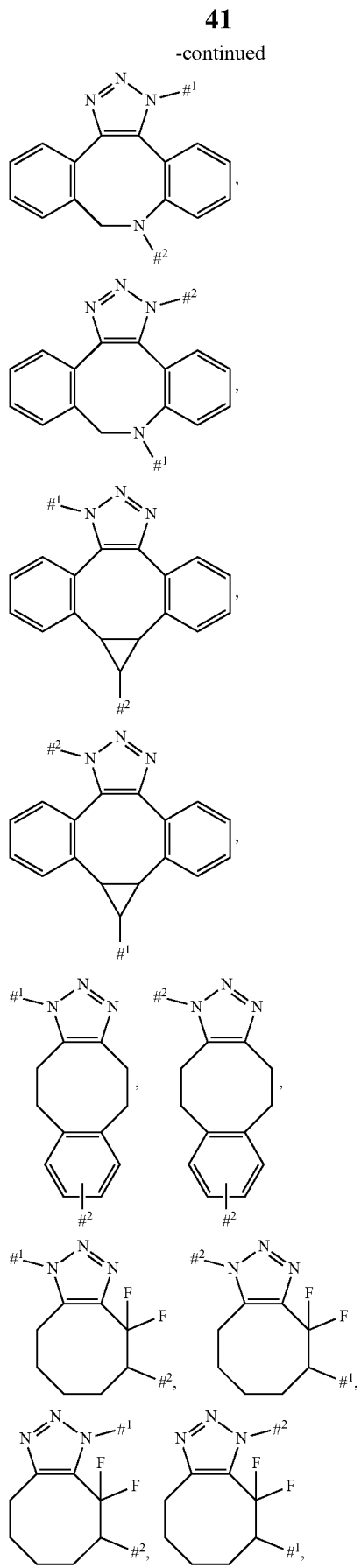

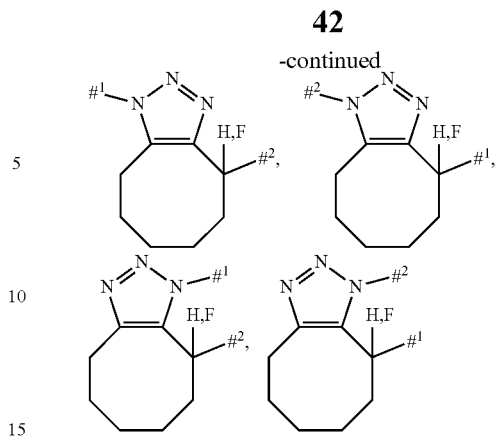

Preferably, the linker corresponds to the formula below:

§ —(CO)m-L1-L2-§ § where m represents 0 or 1;

§ represents the bond to the active compound molecule and

§ § represents the bond to the binder peptide or protein, and

L1 and L2 have the meaning given above.

Particularly preferably, L1 has the formula —NR11B—, where

R$^{11}$ represents H or NH$_2$;

B represents —[(CH$_2$)$_x$—(X$^4$)$_y$]$_w$—(CH$_2$)$_z$—, w=0 to 20;

x=0 to 5;

y=0 or 1;

z=0 to 5; and

X$^4$ represents —O—, —CONH—, —NHCO— or

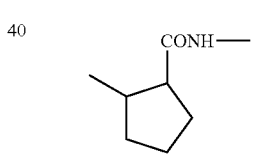

Linkers L which are preferred in accordance with the invention have the formula below:

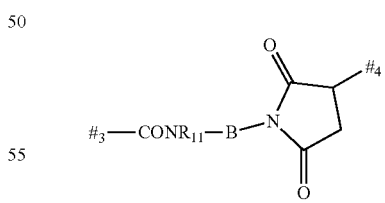

where

3 represents the bond to the active compound molecule,

4 represents the bond to the binder peptide or protein,

R11 represents H or NH$_2$;

B represents —[(CH$_2$)$_x$—(X$^4$)$_y$]$_w$—(CH$_2$)$_z$—, w=0 to 20;

x=0 to 5;

y=0 or 1;
z=1 to 5; and
X⁴ represents —O—, —CONH—, —NHCO— or

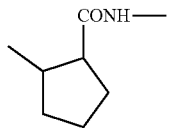

The linkers mentioned above are especially preferred in conjugates of the formula (I) or (II) in which the linker couples by substitution of a hydrogen atom at R1 or in combination with a cleavable linker SG1 at R4, i.e. R1 represents -L-#1 or R4 represents —SG1-L-#1, where #1 represents the bond to the antibody.

Preference in accordance with the invention is furthermore given to the linkers below: In a conjugate according to the invention or in a mixture of the conjugates according to the invention, the bonds to a cysteine residue of the antibody are present, to an extent of preferably more than 80%, particularly preferably more than 90% (in each case based on the total number of bonds of the linker to the antibody), particularly preferably as one of the two structures of the formula A5 or A6:

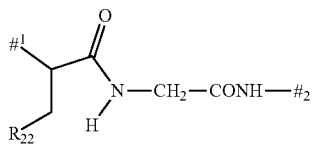
Formula A5

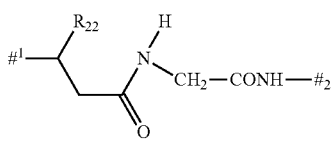
Formula A6 where
¹ denotes the point of attachment to the sulphur atom of the antibody,
² denotes the point of attachment to group L¹, and
R²² represents COOH, COOR, COR, CONR₂, CONHR (where R in each case represents C1-3-alkyl), CONH₂, preferably COOH.

Here, the structures of the formula A5 or A6 are generally present together, preferably in a ratio of from 60:40 to 40:60, based on the number of bonds to the antibody. The remaining bonds are then present as the structure

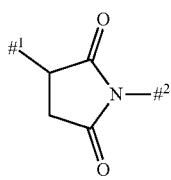

Other linkers -L- attached to a cysteine side chain or cysteine residue have the formula below:

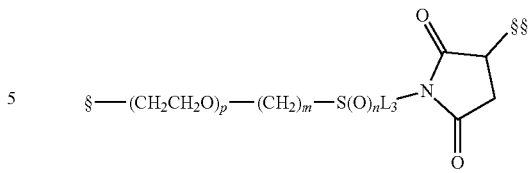

where
§ represents the bond to the active compound molecule and §§ represents the bond to the binder peptide or protein,
m represents 0, 1, 2 or 3;
n represents 0, 1 or 2;
p represents 0 to 20; and
L3 represents

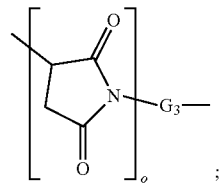

where
o represents 0 or 1;
and
G3 represents a straight-chain or branched hydrocarbon chain having 1 to 100 carbon atoms from arylene groups and/or straight-chain and/or cyclic alkylene groups and which may be interrupted once or more than once by one or more of the groups —O—, —S—, —SO—, SO₂, —NH—, —CO—, —NHCO—, —CONH—, —NMe-, —NHNH—, —SO₂NHNH—, —CONHNH— and a 3- to 10-membered (preferably 5- to 10-membered) aromatic or non-aromatic heterocycle having up to 4 heteroatoms selected from the group consisting of N, O and S, —SO— or SO₂, where the side chains, if present, may be substituted by —NHCONH₂, —COOH, —OH, —NH₂, NH—CNNH₂, sulphonamide, sulphone, sulphoxide or sulphonic acid.

In the formula above, preferably
m represents 1;
p represents 0;
n represents 0;
and L3 represents

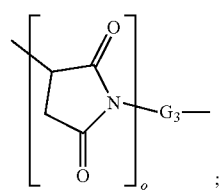

where
o represents 0 or 1; and
G3 represents —(CH₂CH₂O)ₛ(CH₂)ₜ(CONH)ᵤ CH₂CH₂O)ᵥ (CH₂)ᵥᵥ—, where
s, t, v and w each independently of one another are from 0 to 20 and u is 0 or 1.

Preferred groups L1 in the formula § —(CO)m-L1-L2-§§ above are those below, where r in each case independently of one another represents a number from 0 to 20, preferably from 0 to 15, particularly preferably from 1 to 20, especially preferably from 2 to 10:

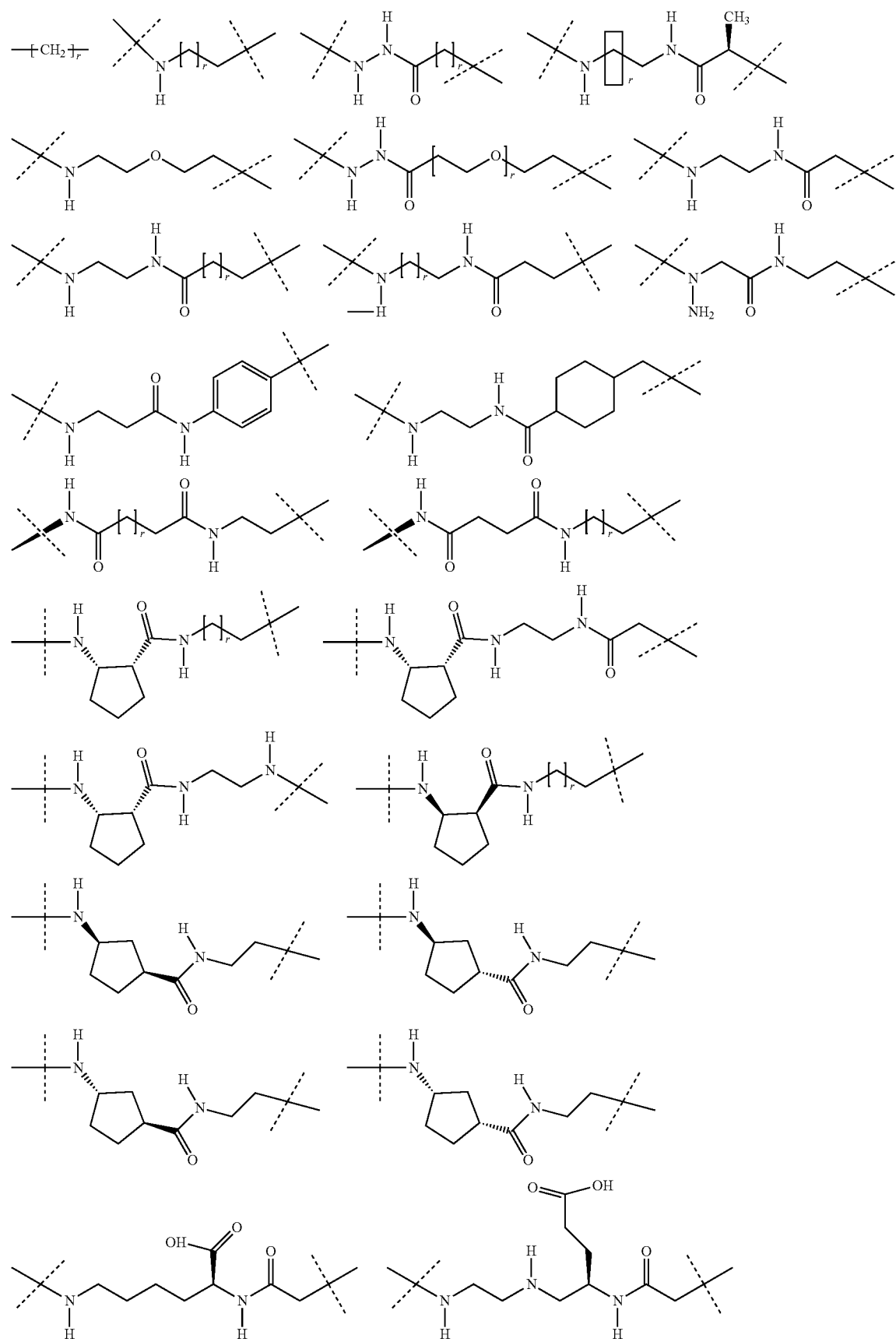

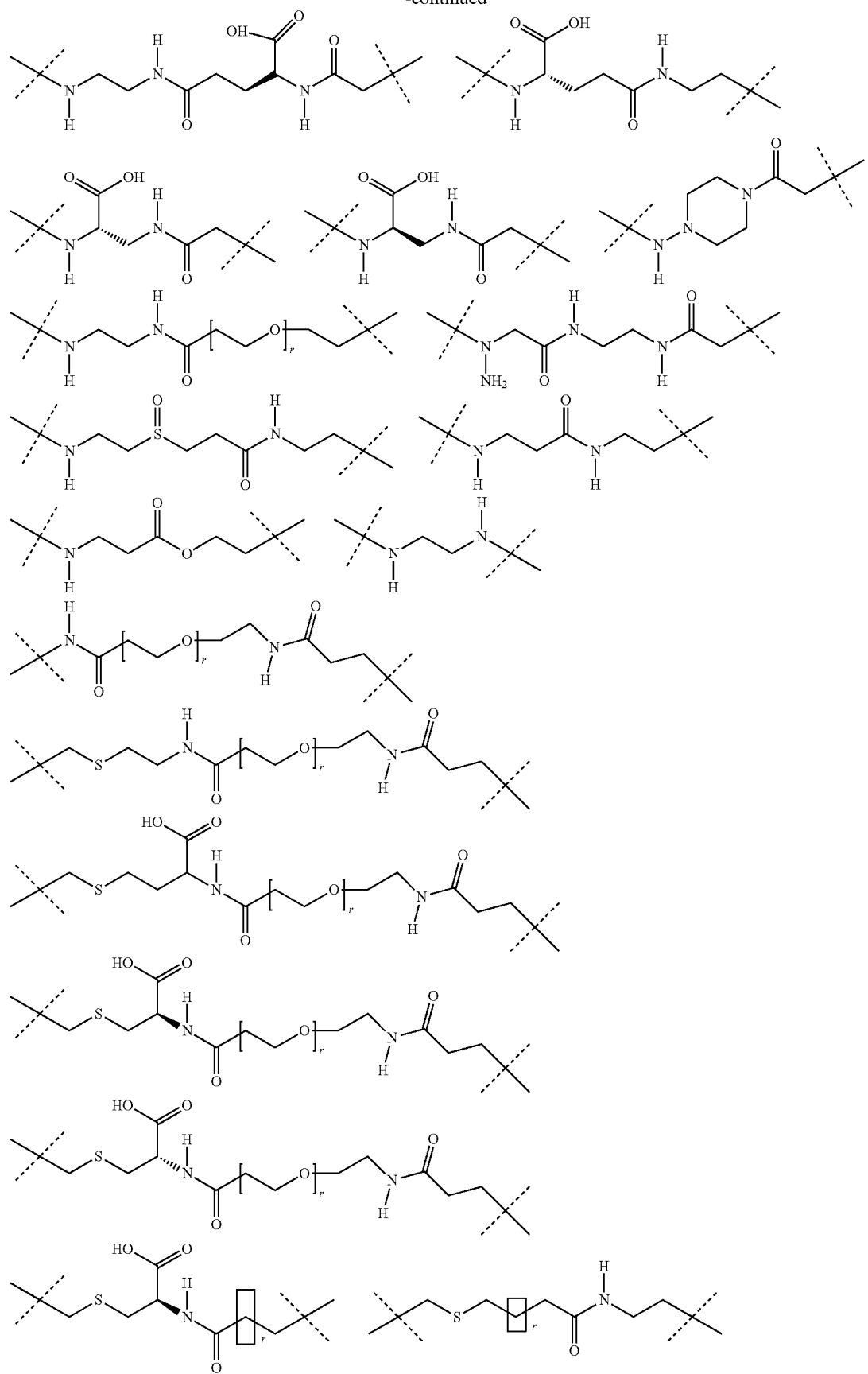

-continued
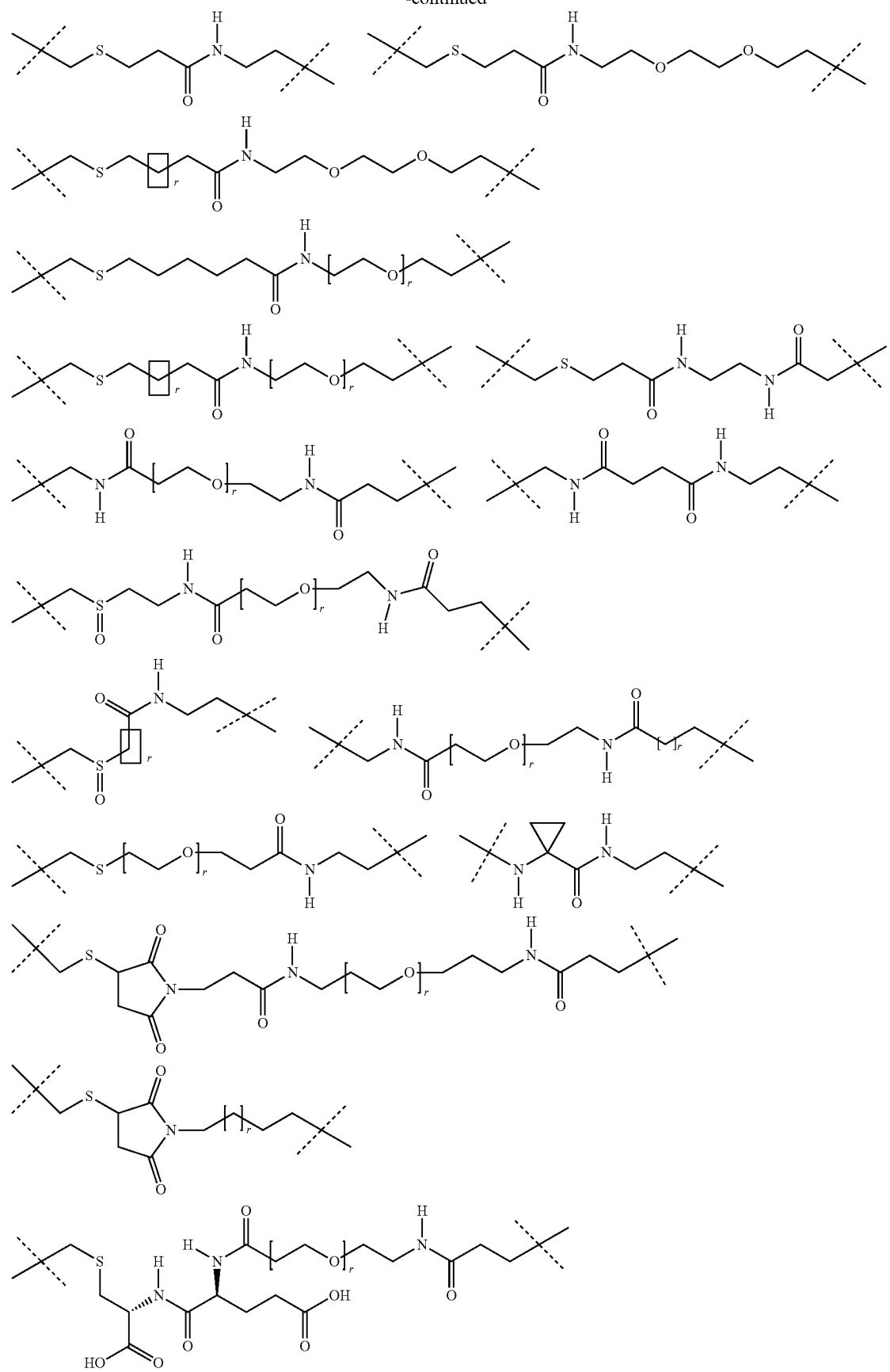

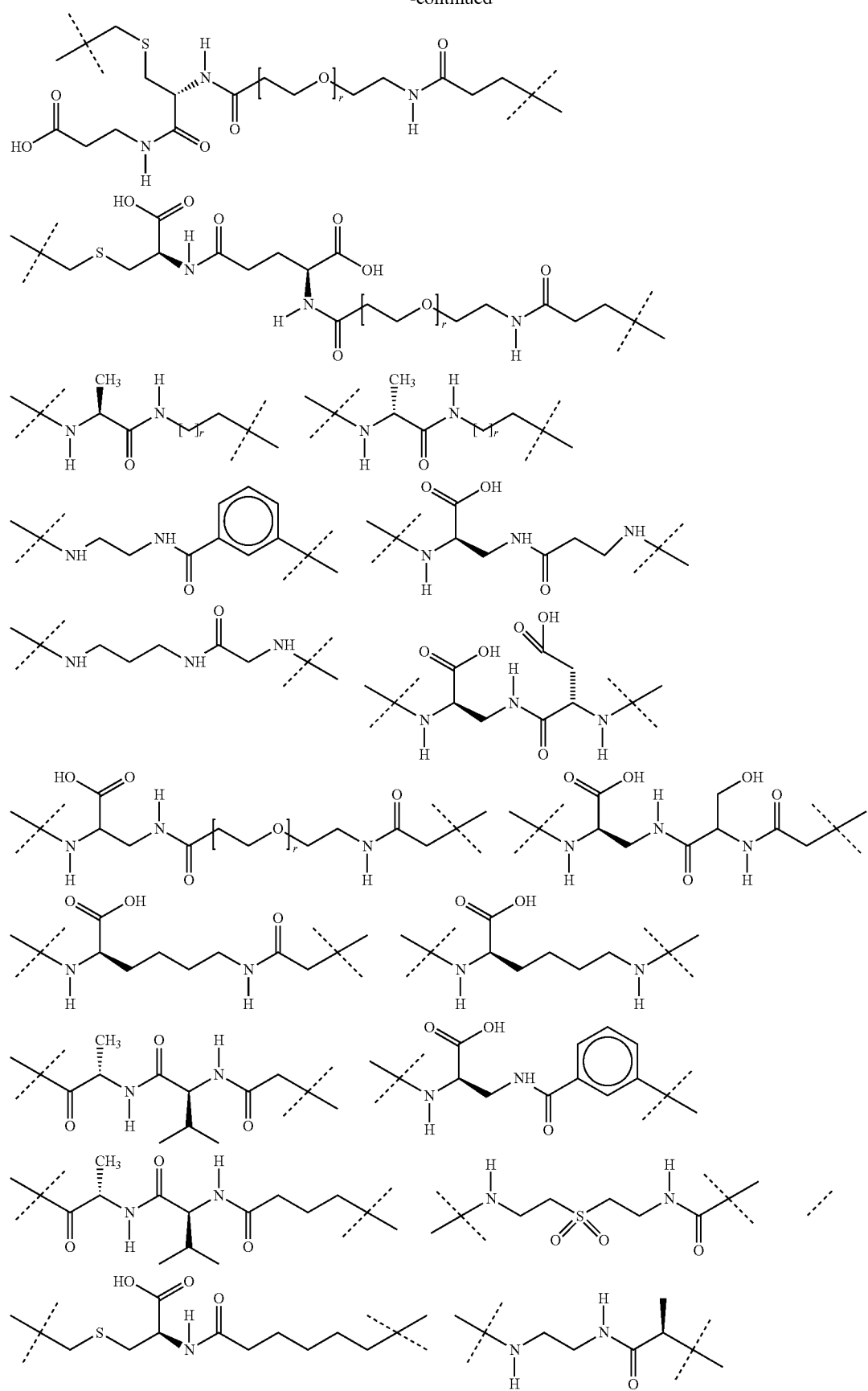

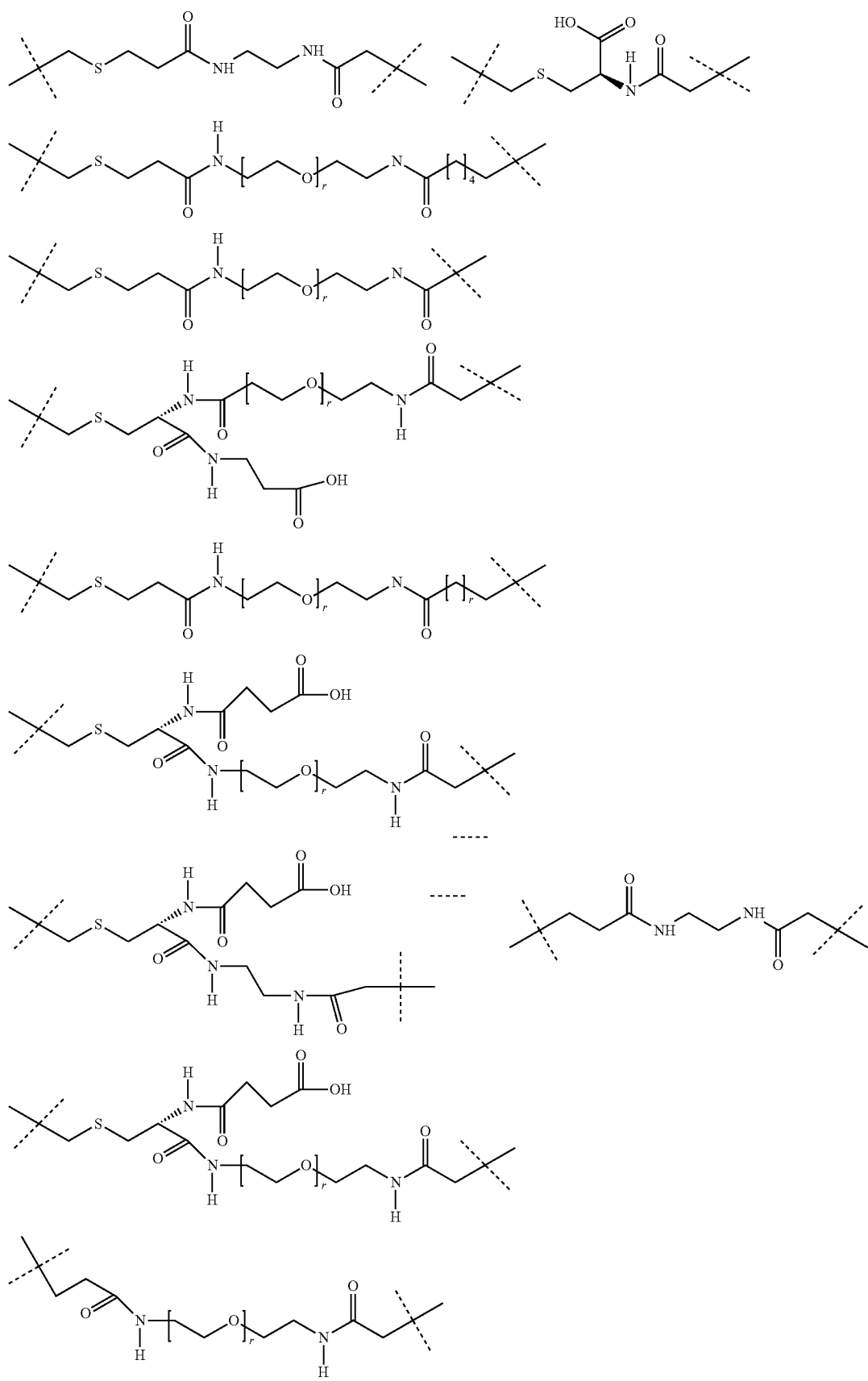

-continued

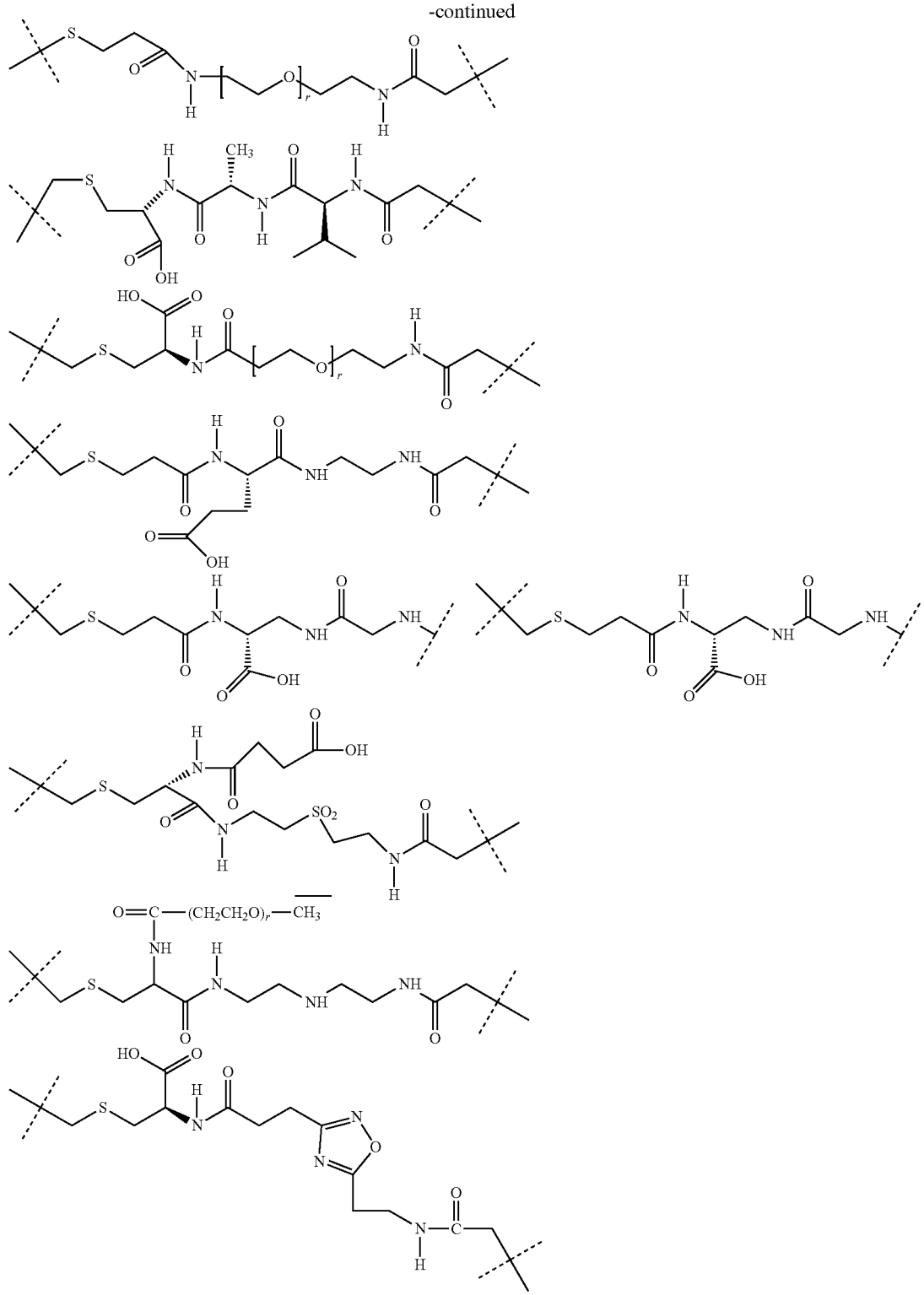

Further examples of L1 are given in Table C, in which this group is highlighted in a box.

Examples of a linker moiety L1 are given in Tables A and A' below. The table furthermore states with which group L2 these examples of L1 are preferably combined, and also the preferred coupling point ($R^1$ or $R^3$ or $R^4$) and the preferred value for m, this is whether there is a carbonyl group in front of L1 or not (cf. § —(CO)m-L1-L2-§ §). These linkers are preferably coupled to a cysteine residue. If L2 is a succinimide or derived therefrom, this imide may also be fully or partially in the form of the hydrolysed open-chain succinamide, as described above. Depending on L1, this hydrolysis to open-chain succinamides may be more or less pronounced or not present at all.

TABLE A

| Subst. | m | L1 | L2 |
|---|---|---|---|
| R¹ | 1 | propylamine linker (-NH-CH₂CH₂CH₂-) | maleimide/succinimide (N-pyrrolidine-2,5-dione) |
| R¹ | 1 | hydrazide-hexanoyl linker (-NH-NH-C(=O)-(CH₂)₅-) | succinimide |
| R¹ | 1 | -NH-(CH₂)₆-NH-C(=O)-CH(CH₃)- linker | succinimide |
| R¹ | 1 | -NH-CH₂CH₂-O-CH₂CH₂- linker | succinimide |
| R¹ | 1 | -NH-NH-C(=O)-CH₂CH₂-O-CH₂CH₂-O-CH₂CH₂-O-CH₂CH₂- linker | succinimide |
| R¹ | 1 | -NH-CH₂CH₂-NH-CH₂CH₂- linker | succinimide (See note**) |
| R¹ | 1 | -NH-CH₂CH₂-NH-C(=O)-CH(CH₂CH₂COOH)-NH-C(=O)-CH₂CH₂- linker (glutamic acid-containing) | succinimide (See note**) |
| R¹ | 1 | -NH-NH-C(=O)-CH₂-NH-C(=O)-CH₂CH₂- (hydrazinoacetyl) linker | succinimide |

TABLE A-continued

| Subst. | m | L1 | L2 |
|---|---|---|---|
| R¹ | 1 | –NH–CH₂CH₂–C(O)–NH–(4-phenyl)– | succinimide |
| R¹ | 1 | –NH–CH₂CH₂–NH–C(O)–(cyclohexyl-CH₂CH₂)– | succinimide |
| R¹ | 1 | –NH–(cyclopentyl)–C(O)–NH–CH₂CH₂– (trans) | succinimide |
| R¹ | 1 | –NH–(cyclopentyl)–C(O)–NH–CH₂CH₂– (cis) | succinimide |
| R¹ | 1 | lysine linker (–NH–(CH₂)₄–CH(COOH)–NH–C(O)–CH₂–) | succinimide (See note**) |
| R¹ | 1 | piperazine–C(O)–CH₂– linker | succinimide (See note**) |
| R¹ | 1 | –NH–CH₂CH₂–NH–C(O)–CH₂–(OCH₂CH₂)₃– | succinimide |
| R¹ | 1 | –N(NH₂)–CH₂–C(O)–NH–CH₂CH₂–NH–C(O)– | succinimide (See note**) |

TABLE A-continued

| Subst. | m | L1 | L2 |
|---|---|---|---|
| R¹ | 1 | (structure) | (succinimide) |
| R¹ | 1 | (structure) | (succinimide) |
| R¹ | 1 | (structure) | —C(O)—CH₂— |
| R¹ | 1 | (structure) | (succinimide) |
| R³ | 0 | (structure) | (succinimide) |
| R¹ | 1 | (structure) | (succinimide) |
| R³ | 0 | (structure) | (succinimide) |
| R¹ | 1 | (structure) | (succinimide) |

TABLE A-continued

| Subst. | m | L1 | L2 |
|---|---|---|---|
| R¹ | 1 | (structure) | (structure) |
| R³ | 0 | (structure) | (structure) |
| R³ | 0 | (structure) | (structure) |
| R¹ | 1 | (structure) | (structure) |
| R³ | 0 | (structure) | (structure) |
| R³ | 0 | (structure) | (structure) |
| R³ | 0 | (structure) | (structure) |
| R³ | 0 | (structure) | (structure) |

TABLE A-continued

| Subst. | m | L1 | L2 |
|---|---|---|---|
| R¹ | 1 | (structure: -NH-CH(CH₃)-C(=O)-NH-CH₂-C(CH₃)₃) | (succinimide structure) |
| R¹ | 1 | (structure: -NH-CH(CH₃)-C(=O)-NH-CH₂-C(CH₃)₃) | (succinimide structure) |
| R³ | 0 | (structure: -S-CH(NH-C(=O)-CH₂-CH₂-C(=O)-OH)-C(=O)-NH-CH₂-CH₂-SO₂-CH₂-CH₂-NH-C(=O)-) | (succinimide structure) See note** |
| R³ | 0 | (structure: -S-CH(NH-C(=O)-(CH₂CH₂O)ᵣ-CH₃)-C(=O)-NH-CH₂-CH₂-NH-CH₂-CH₂-NH-C(=O)-) | (succinimide structure) See note** |
| R³ | 0 | (structure with oxadiazole: -S-CH(COOH)(NH-C(=O)-CH₂-CH₂-[oxadiazole]-CH₂-CH₂-NH-C(=O)-) | (succinimide structure) See note** |

**With particular preference, the linkers L1 given in these rows are attached to a linker L2 selected from:

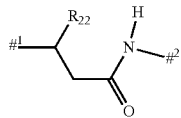

Formula A7 and/or

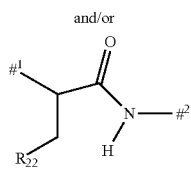

Formula A8 where #[1] denotes the point of attachment to the sulphur atom of the binder, #[2] denotes the point of attachment to group $L^1$, $R^{22}$ preferably represents COOH. In a conjugate according to the invention or in a mixture of the conjugates according to the invention, the bonds to a cysteine residue of the binder are present, to an extent of preferably more than 80%, particularly preferably more than 90% (in each case based on the total number of bonds of the linker to the binder), particularly preferably as one of the two structures of the formula A7 or A8. Here, the structures of the formula A7 or A8 are generally present together, preferably in a ratio of from 60:40 to 40:60, based on the number of bonds to the binder. The remaining bonds are then present as the structure

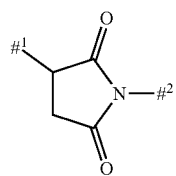

TABLE A'

| Subst. | m | L1 | L2 |
|---|---|---|---|
| $R^1$ | 1 | (structure with carboxylic acid and amide linker) | (succinimide structure) |
| $R^1$ | 1 | (cyclopentane diamine/amide structure) | (succinimide structure) |
| $R^1$ | 1 | (cyclopentane diamine/amide structure) | (succinimide structure) |
| $R^1$ | 1 | (ethylenediamine structure) | $-\overset{O}{\underset{}{C}}-CH_2-$ |
| $R^1$ | 1 | (cyclopentane diamine/amide structure) | (succinimide structure) |
| $R^1$ | 1 | (cyclopentane diamine/amide structure) | (succinimide structure) |

TABLE A'-continued
| Subst. | m | L1 | L2 |
|---|---|---|---|
| R³ | 0 | 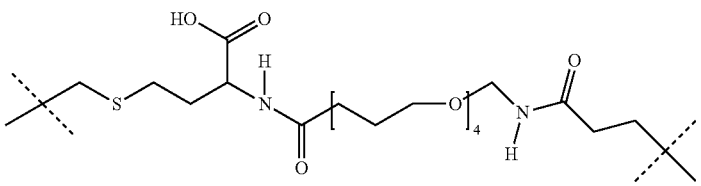 | 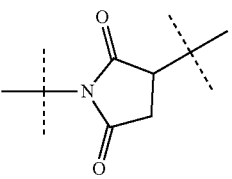 |
| R³ | 0 | 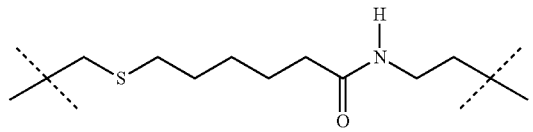 | 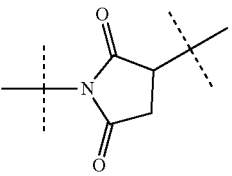 |
| R³ | 0 | 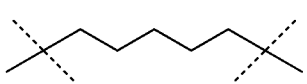 | 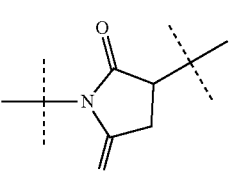 |
| R³ | 0 | 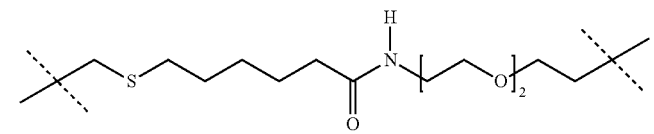 | 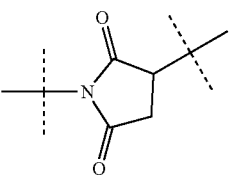 |
| R³ | 0 | 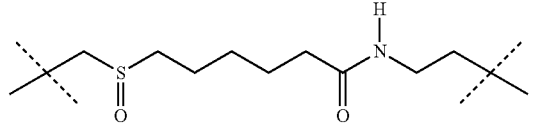 | 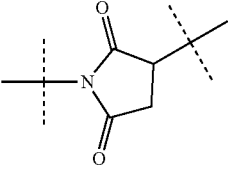 |
| R¹ | 1 | 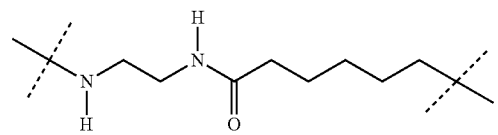 | 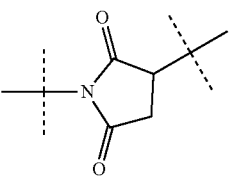 |
| R¹ | 1 | 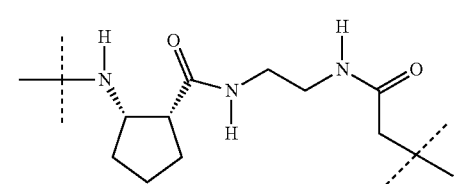 | 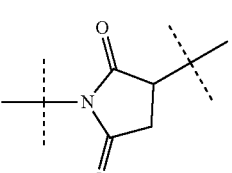 See note** |
| R¹ | 1 | 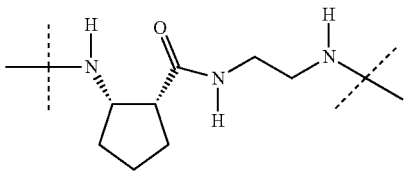 | 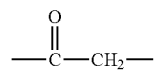 |

TABLE A'-continued
| Subst. | m | L1 | L2 |
|---|---|---|---|
| R¹ | 1 | 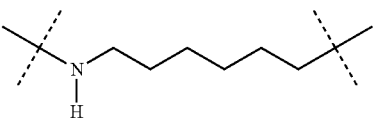 | 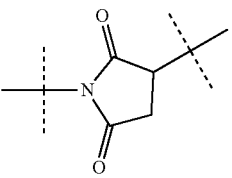 |
| R¹ | 1 | 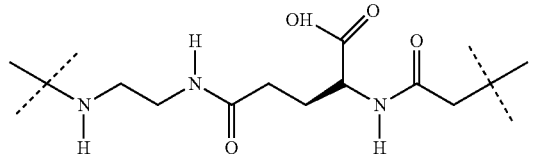 | 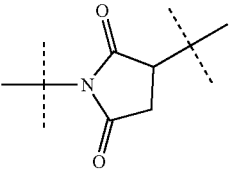 See note** |
| R¹ | 1 | 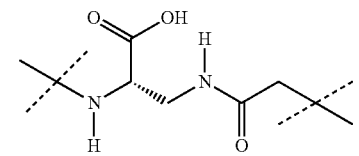 | 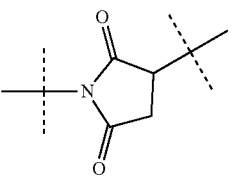 See note** |
| R¹ | 1 | 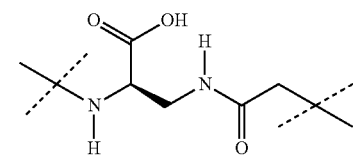 | 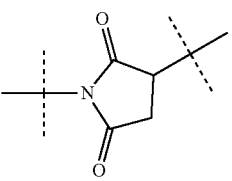 See note** |
| R¹ | 0 | 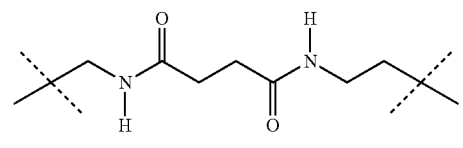 | 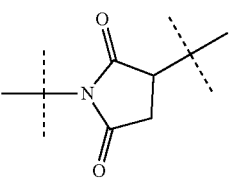 |
| R¹ | 1 | 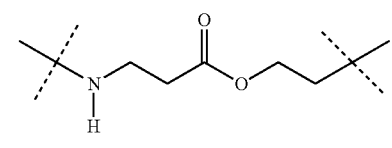 | 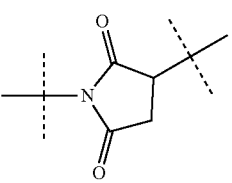 |

TABLE A'-continued

| Subst. | m | L1 | L2 |
|---|---|---|---|
| R¹ | 1 | (structure: -NH-CH₂CH₂-NH-C(O)-C(CH₃)₂-) | (structure with carboxylic acid) and (second isomer structure)  See note*** |
| R¹ | 1 | (structure: -NH-CH₂CH₂-NH-C(O)-C(CH₃)₂-) | (structure with carboxylic acid) |
| R¹ | 1 | (structure: -NH-CH₂CH₂-NH-C(O)-C(CH₃)₂-) | (structure with carboxylic acid)  identical to the two above |
| R¹ | 1 | (structure: -NH-CH₂CH₂-NH-C(O)-CH₂CH₂-) | (succinimide structure) |
| R³ | 0 | (Cys-PEG₄-amide structure) | (succinimide structure) |
| R³ | 0 | (Cys-PEG₄-amide structure) | (succinimide structure) |

TABLE A'-continued

| Subst. | m | L1 | L2 |
|---|---|---|---|
| R³ | 0 | | |
| R³ | 0 | | |
| R³ | 0 | | See note** |
| R³ | 0 | | |
| R³ | 0 | | |
| R³ | 0 | | See note** |
| R³ | 0 | | |

TABLE A'-continued

| Subst. | m | L1 | L2 |
|---|---|---|---|
| R² | 0 | (structure: -NH-C(=O)-CH₂-CH₂-C(=O)-NH-) | (structure: succinimide ring) |
| R¹ | 1 | (structure: -NH-CH₂-CH₂-NH-C(=O)-CH₂-) | (structure: -C(=O)-NH-CH(-)-CH₂-C(=O)-R₂₂) where R₂₂ = —OH or —NH₂ |
| R¹ | 1 | (structure: -NH-CH₂-CH₂-NH-C(=O)-CH₂-) | (structure: -NH-C(=O)-CH₂-CH(-)-C(=O)-R₂₂) where R₂₂ = —OH or —NH₂ |
| R¹ | 1 | (structure: -NH-CH₂-CH₂-) | (structure: -C(=O)-NH-CH(-)-CH₂-COOH) and (structure: -NH-C(=O)-CH₂-CH(-)-COOH) See note*** |
| R¹ | 1 | (structure: -NH-CH₂-CH₂-) | (structure: -C(=O)-NH-CH(-)-CH₂-COOH) |
| R¹ | 1 | (structure: -NH-CH₂-CH₂-) | (structure: -NH-C(=O)-CH₂-CH(-)-COOH) |

TABLE A'-continued
| Subst. | m | L1 | L2 |
|---|---|---|---|
| R¹ | 1 | 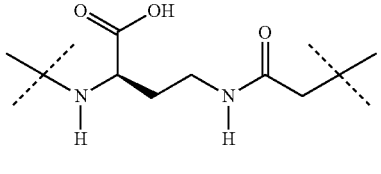 | 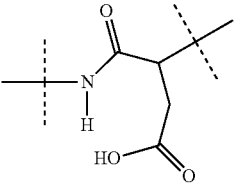 and 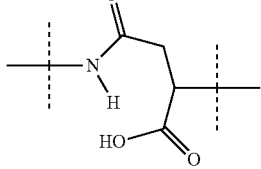 See note*** |
| R¹ | 1 | 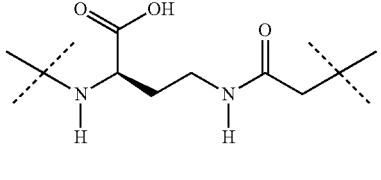 | 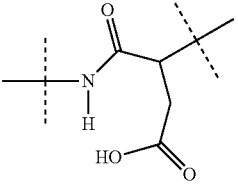 |
| R¹ | 1 | 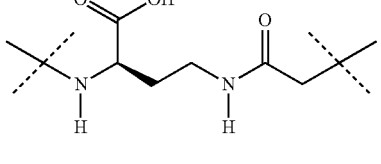 | 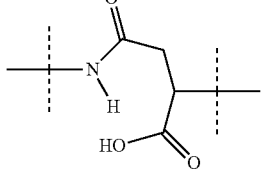 |
| R³ | 0 | 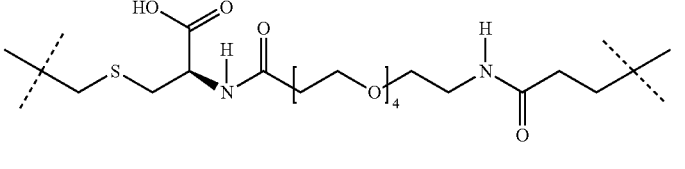 | 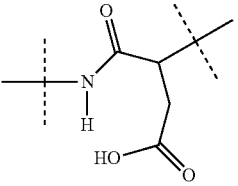 and 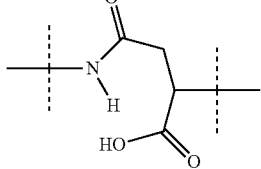 See note*** |
| R³ | 0 | 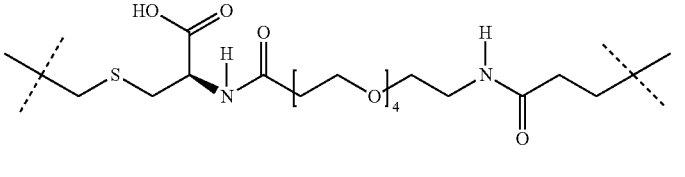 | 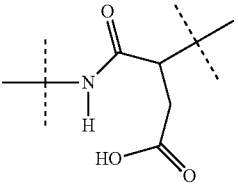 |

TABLE A'-continued
| Subst. | m | L1 | L2 |
|---|---|---|---|
| R³ | 0 | 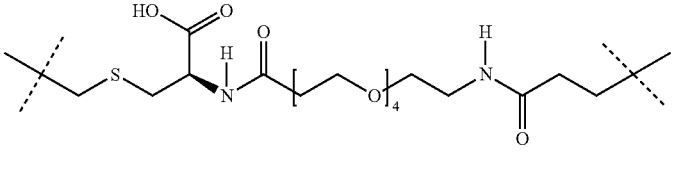 | 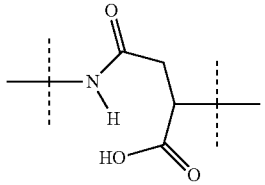 |
| R³ | 0 | 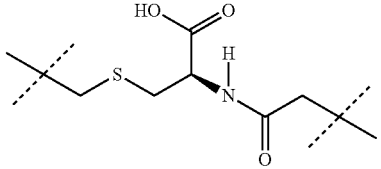 | 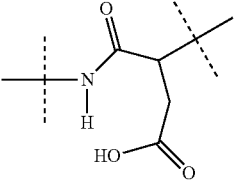 and 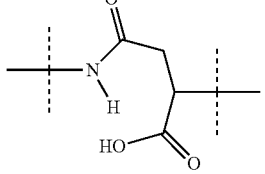 See note*** |
| R³ | 0 | 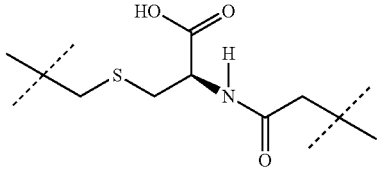 | 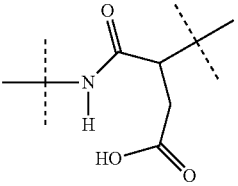 |
| R³ | 0 | 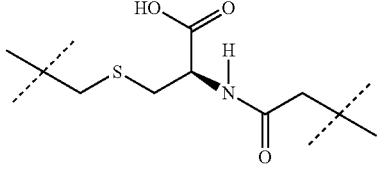 | 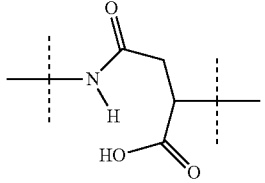 |
| R³ | 0 | 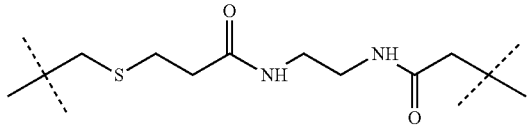 | 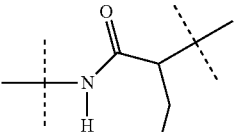 and 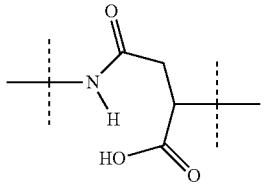 See note*** |

TABLE A'-continued

| Subst. | m | L1 | L2 |
|---|---|---|---|
| R³ | 0 | (structure: -CH₂-S-CH₂-C(O)-NH-CH₂-CH₂-NH-C(O)-CH₂-C(CH₃)₂-) | (structure: -NH-C(O)-CH(CH₂COOH)-) |
| R³ | 0 | (structure: -CH₂-S-CH₂-C(O)-NH-CH₂-CH₂-NH-C(O)-CH₂-C(CH₃)₂-) | (structure: -NH-C(O)-CH₂-CH(COOH)-) |
| R¹ | 1 | (structure: -NH-CH₂CH₂-NH-C(O)-CH₂-NH-) | $-\overset{O}{\underset{\|}{C}}-CH_2-$ |
| R¹ | 1 | (structure: -NH-CH₂CH₂CH₂-NH-C(O)-CH₂-) | (structure: -NH-C(O)-CH(CH₂COOH)-) and (structure: -NH-C(O)-CH₂-CH(COOH)-) See note*** |
| R¹ | 1 | (structure: -NH-CH₂CH₂CH₂-NH-C(O)-CH₂-) | (structure: -NH-C(O)-CH(CH₂COOH)-) |
| R¹ | 1 | (structure: -NH-CH₂CH₂CH₂-NH-C(O)-CH₂-) | (structure: -NH-C(O)-CH₂-CH(COOH)-) |

TABLE A'-continued

| Subst. | m | L1 | L2 |
|---|---|---|---|
| R¹ | 1 | [structure: –NH–CH₂CH₂–O–CH₂CH₂–NH–C(O)–CH₂–] | [structure: –NH–C(O)–CH(–)–CH₂–C(O)OH] and [structure: –NH–C(O)–CH₂–CH(–)–C(O)OH] See note*** |
| R¹ | 1 | [structure: –NH–CH₂CH₂–O–CH₂CH₂–NH–C(O)–CH₂–] | [structure: –NH–C(O)–CH(–)–CH₂–C(O)OH] |
| R¹ | 1 | [structure: –NH–CH₂CH₂–O–CH₂CH₂–NH–C(O)–CH₂–] | [structure: –NH–C(O)–CH(–)–CH₂–C(O)OH] |
| R³ | 0 | [structure: –CH₂–S–CH₂–CH(NH₂)–C(O)–NH–CH₂CH₂–NH–C(O)–(CH₂)₄–] | [succinimide structure: N-linked 2,5-dioxopyrrolidine] |
| R¹ | 0 | [structure: –NH–C(O)–CH₂CH₂–C(O)–NH–CH₂CH₂–NH–C(O)–CH₂–] | [structure: –NH–C(O)–CH(–)–CH₂–C(O)OH] and [structure: –NH–C(O)–CH₂–CH(–)–C(O)OH] See note*** |

TABLE A'-continued

| Subst. | m | L1 | L2 |
|---|---|---|---|
| R¹ | 0 | (structure: −NH−C(O)−CH₂CH₂−C(O)−NH−CH₂CH₂−NH−C(O)−) | (structure: −NH−C(O)−CH(CH₂COOH)−) |
| R¹ | 0 | (structure: −NH−C(O)−CH₂CH₂−C(O)−NH−CH₂CH₂−NH−C(O)−) | (structure: −NH−C(O)−CH₂−CH(COOH)−) |
| R¹ | 1 | (structure: −NH−CH₂CH₂−NH−C(O)−CH₂−) | (structure: −NH−C(O)−CH(CH₂COOH)−) and (structure: −NH−C(O)−CH₂−CH(COOH)−) |
| R¹ | 1 | (structure: −NH−CH₂CH₂−O−CH₂CH₂−) | (structure: succinimide: N-pyrrolidine-2,5-dione) |
| R¹ | 1 | (structure: −NH−CH₂CH₂−NH−C(O)−(m-phenylene)−) | (structure: −NH−C(O)−CH(CH₂COOH)−) and (structure: −NH−C(O)−CH₂−CH(COOH)−) |
| R¹ | 1 | (structure: −NH−CH(COOH)−CH₂−NH−C(O)−CH₂CH₂−NH−) | −C(O)−CH₂− |

TABLE A'-continued

| Subst. | m | L1 | L2 |
|---|---|---|---|
| R¹ | 1 | (structure: -NH-(CH₂)₃-NH-C(O)-CH₂-NH-) | -C(O)-CH₂- |
| R¹ | 1 | (dipeptide structure with two carboxylic acid groups) | -C(O)-CH₂- |
| R¹ | 1 | (structure with PEG₄ linker between amino acid residues) | (succinic acid amide structure) and (succinic acid amide structure) See note*** |
| R¹ | 1 | (tripeptide structure with serine) | (succinimide structure) See note** |
| R¹ | 1 | (lysine-based structure) | (succinic acid amide structure) and (succinic acid amide structure) See note*** |

TABLE A'-continued
| Subst. | m | L1 | L2 |
|---|---|---|---|
| R¹ | 1 | 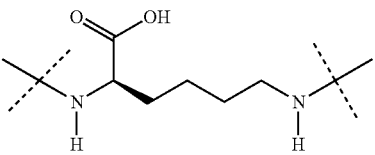 | 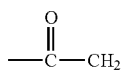 |
| R⁴ | 0 | 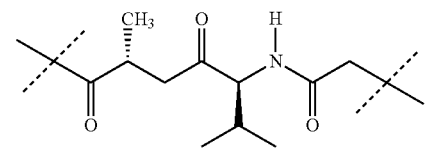 | 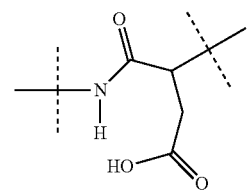 and 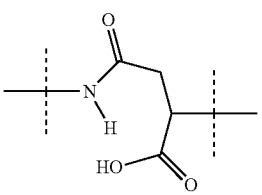 See note*** |
| R¹ | 1 | 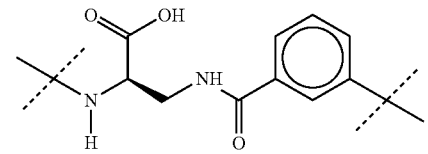 | 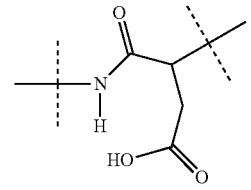 and 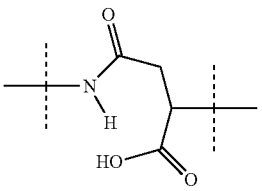 See note*** |
| R⁴ | 0 | 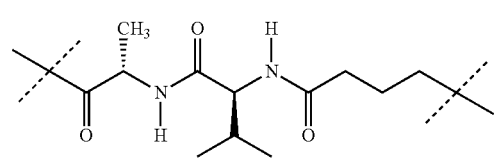 | 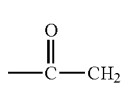 |

TABLE A'-continued
| Subst. | m | L1 | L2 |
|---|---|---|---|
| R¹ | 1 | 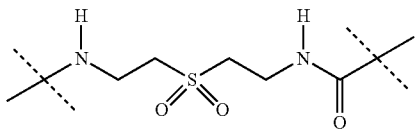 | 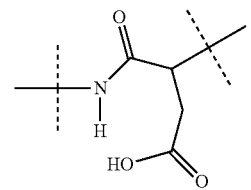<br>and<br>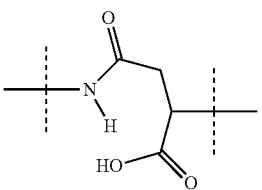<br>See note** |
| R³ | 0 | 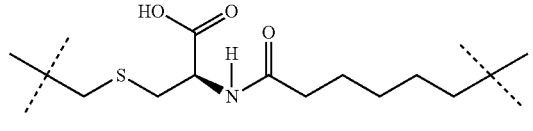 | 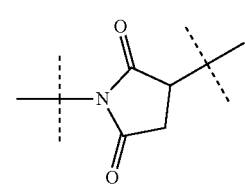<br>See note** |
| R¹ | 1 | 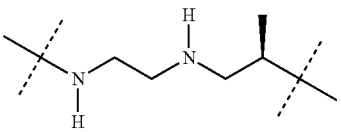 | 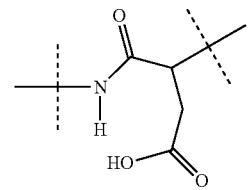<br>and<br>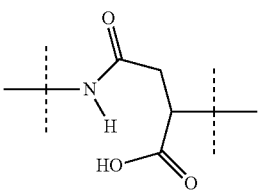<br>See note** |

TABLE A'-continued
| Subst. | m | L1 | L2 |
|---|---|---|---|
| R³ | 0 | 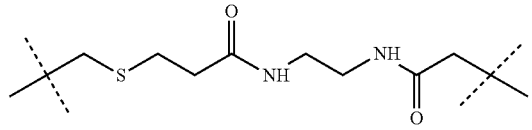 | 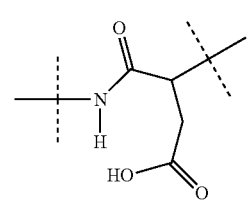
and
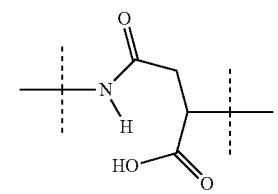
See note*** |
| R³ | 0 | 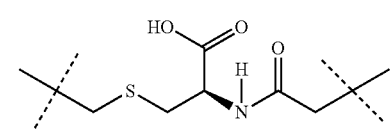 | 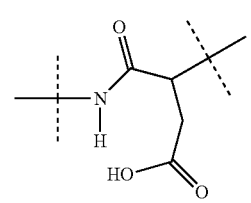
and
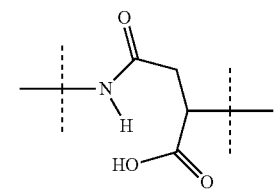
See note*** |
| R³ | 0 | 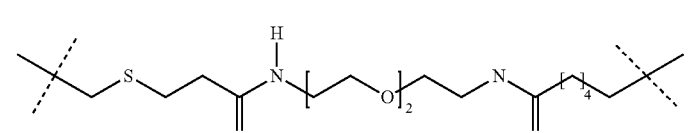 | 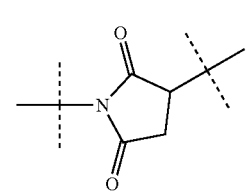
See note** |

TABLE A'-continued
| Subst. | m | L1 | L2 |
|---|---|---|---|
| R³ | 0 | 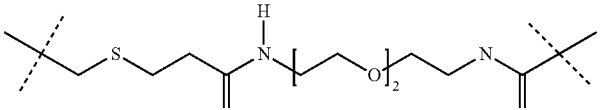 | 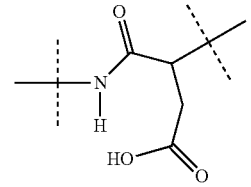<br>and<br>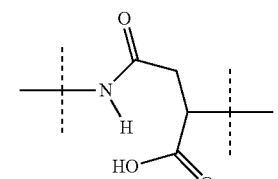<br>See note*** |
| R³ | 0 | 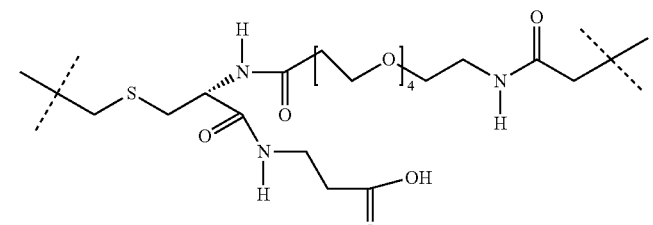 | 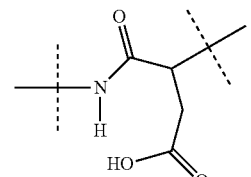<br>and<br>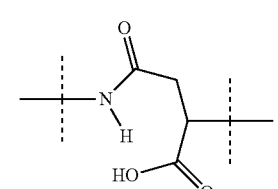<br>See note*** |
| R³ | 0 | 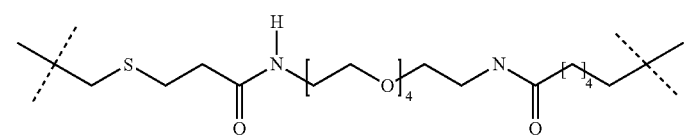 | 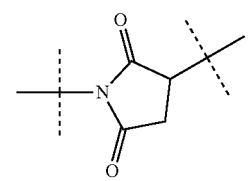<br>See note** |

TABLE A'-continued
| Subst. | m | L1 | L2 |
|---|---|---|---|
| R³ | 0 | 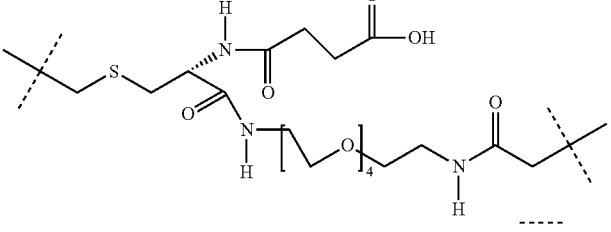 | 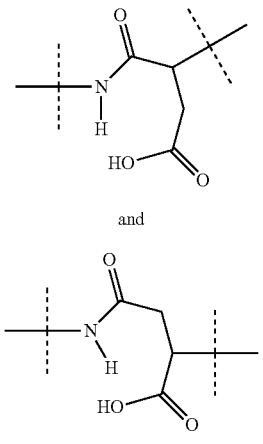<br>and<br>See note*** |
| R³ | 0 | 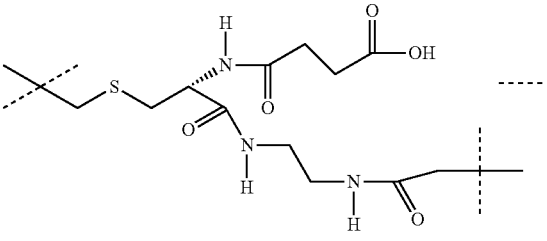 | 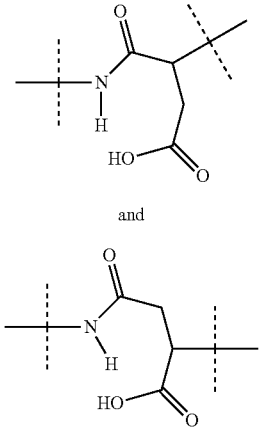<br>and<br>See note*** |
| R³ | 0 | 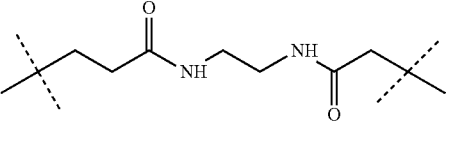 | 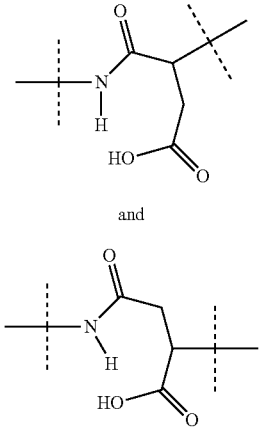<br>and<br>See note*** |

TABLE A'-continued

| Subst. | m | L1 | L2 |
|---|---|---|---|
| R³ | 0 | (structure) | (structures) and See note*** |
| R³ | 0 | (structure) | (structures) and See note*** |
| R³ | 0 | (structure) | (structures) and See note*** |

TABLE A'-continued

| Subst. | m | L1 | L2 |
|---|---|---|---|
| R³ | 0 | (structure) | (structure) and (structure) See note*** |
| R³ | 0 | (structure) | (structure) and (structure) See note*** |
| R³ | 0 | (structure) | (structure) and (structure) See note*** |

TABLE A'-continued

| Subst. | m | L1 | L2 |
|---|---|---|---|
| R³ | 0 | (structure) | (structures) and See note*** |
| R³ | 0 | (structure) | —C(O)—CH₂— |

See note  for Table A.

***When this structure L2 is present, there may simultaneously be a structure L2 of the formula below:

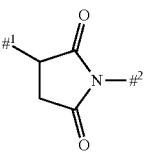

Examples of conjugates having corresponding linkers have the following structures, where X1 represents CH, X2 represents C and X3 represents N and L1 has the meaning given above, L2 and L3 have the same meaning as L1, AK1 represents an (aglycosylated) anti-B7H3 antibody attached via a cysteine residue and n is a number from 1 to 10. AK1 is preferably a human, humanized or chimeric monoclonal antibody or an antigen-binding fragment thereof. With particular preference, AK1 is an anti-B7H3 antibody which specifically binds the human Ig4 and/or the human and/or murine Ig2 isoform of B7H3, in particular one of the anti-B7H3 antibodies TPP-6497, TPP-6499, TPP-6501, TPP-6502, TPP-6515. In a further preferred embodiment, the anti-B7H3 antibody or the antigen-binding fragment is present in aglycosylated form.

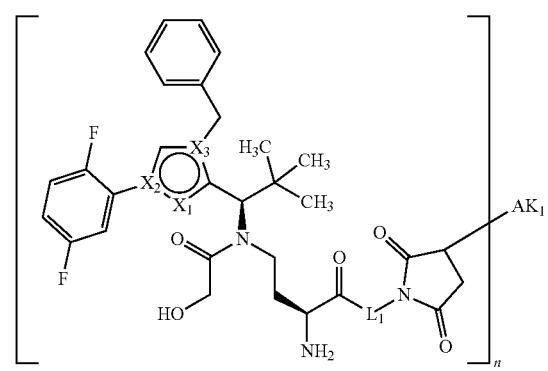

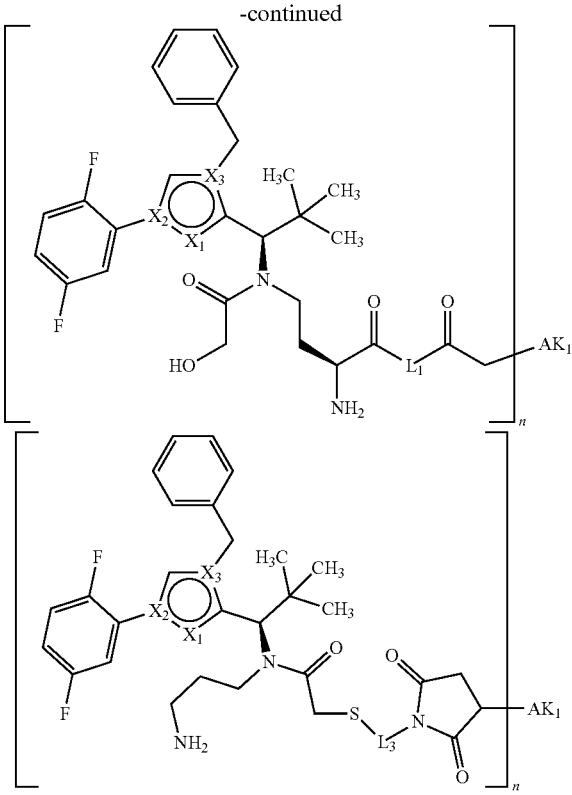

If the linker is attached to a lysine side chain or a lysine residue, it preferably has the formula below:

-§-(SG)$_x$-L4-CO-§§ where
§ represents the bond to the active compound molecule and
§ § represents the bond to the binder peptide or protein,
x represents 0 or 1,
SG represents a cleavable group, preferably a 2-8 oligopeptide, particularly preferably a dipeptide, and
L4 represents a single bond or a group —(CO)$_y$-G4-, where y represents 0 or 1, and
G4 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO$_2$, —NH—, —CO—, —NHCO—, —CONH—, —NMe-, —NHNH—, —SO$_2$NHNH—, —CONHNH— and a 5- to 10-membered aromatic or non-aromatic heterocycle having up to 4 heteroatoms selected from the group consisting of N, O and S, —SO— or —SO$_2$— (preferably

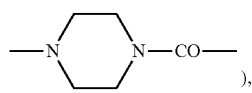
), where the side chains, if present, may be substituted by —NHCONH$_2$, —COOH, —OH, —NH$_2$, NH—CNNH$_2$, sulphonamide, sulphone, sulphoxide or sulphonic acid.

Table B below gives examples of linkers to a lysine residue. The table furthermore gives the preferred coupling point (R$^1$—R$^5$). The first column furthermore states the example numbers in which the corresponding linkers are used.

TABLE B lysine linker
-§-(SG)$_x$-L4-CO-§§

| Ex. | Subst. | (SG)$_x$-L4 |
|---|---|---|
| 194, 294 | R$^4$ | 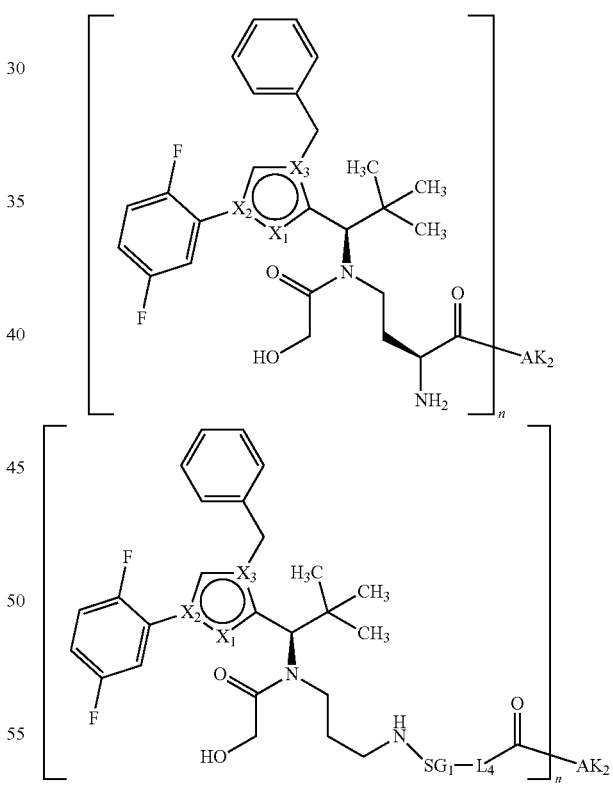 |

Examples of conjugates having corresponding linkers have the following structures, where X1 represents CH, X2 represents C and X3 represents N and L4 has the meaning given above, AK2 represents an antibody attached via a lysine residue and n is a number from 1 to 10. AK2 is preferably a human, humanized or chimeric monoclonal anti-B7H3 antibody or an antigen-binding fragment thereof. Particular preference is given to anti-B7H3 antibodies which specifically bind the human Ig4 and/or the human and/or murine Ig2 isoform of B7H3, in particular the anti-B7H3 antibodies TPP-6497, TPP-6499, TPP-6501, TPP-6502, TPP-6515. In a further preferred embodiment, the anti-B7H3 antibody or the antigen-binding fragment is present in aglycosylated form.

Preference according to the invention is furthermore given to the basic structure (i), (ii) or (iv), where SG1 or SG represents a group which can be cleaved by a protease and L1 and L2 have the meanings given above. Particular preference is given to the following groups:
-Val-Ala-CONH— (hereby cleavage of the amide bond at the C-terminal amide of alanine)
—NH-Val-Lys-CONH— (cleavage of the amide bond at the C-terminal amide of lysine)

—NH-Val-Cit-CONH— (cleavage of the amide bond at the C-terminal amide of citrulline)

—NH-Phe-Lys-CONH (cleavage of the amide bond at the C-terminal amide of lysine)

—NH-Ala-Lys-CONH— (cleavage of the amide bond at the C-terminal amide of lysine)

—NH-Ala-Cit-CONH— (cleavage of the amide bond at the C-terminal amide of citrulline)

SG1 or SG is particularly preferably

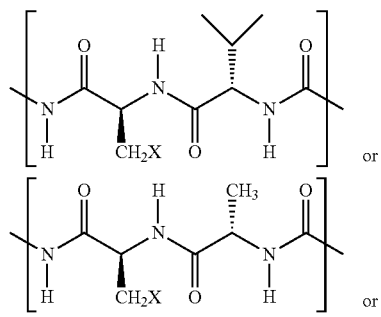

or

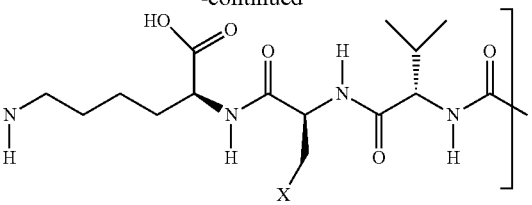

where X represents H or a $C_{1-10}$-alkyl group which may optionally be substituted by —NHCONH$_2$, —COOH, —OH, NH$_2$, —NH—CNNH$_2$ or sulphonic acid.

Table C below gives examples of a linker moiety —SG1-L1- or -L1-SG-L1-, where SG1 and SG are groups which can be cleaved by a protease. Table C furthermore states with which group L2 these examples of —SG1-L1- and -L1-SG-L1-are preferably combined, and also the preferred coupling point ($R^1$—$R^5$) and the preferred value for m, thus whether there is a carbonyl group in front of L1 or not (cf. § —(CO)m-L1-L2-§ §). These linkers are preferably coupled to a cysteine residue. The L1 group is highlighted in a box. However, these groups L1 can be replaced by one of the groups L1 given for formula § —(CO)m-L1-L2-§ § above. If L2 is a succinamide or derived therefrom, this amide may also be fully or partially in the form of the hydrolysed open-chain succinamide, as described above.

TABLE C

| Sub St. | m | -SG1-L1- or -L1-SG-L1- | L2 |
|---|---|---|---|
| $R^1$ | 1 | 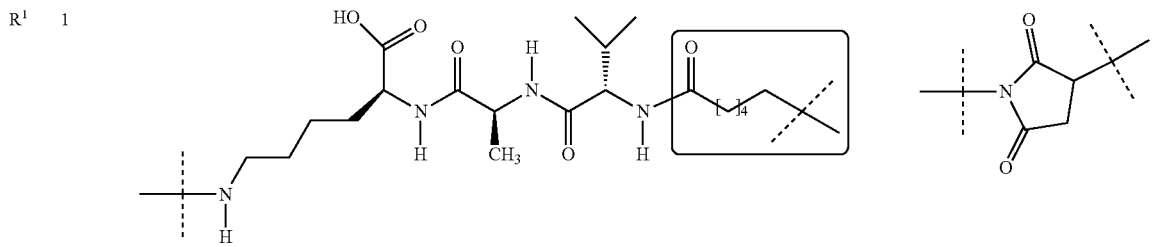 | |
| $R^1$ | 1 | 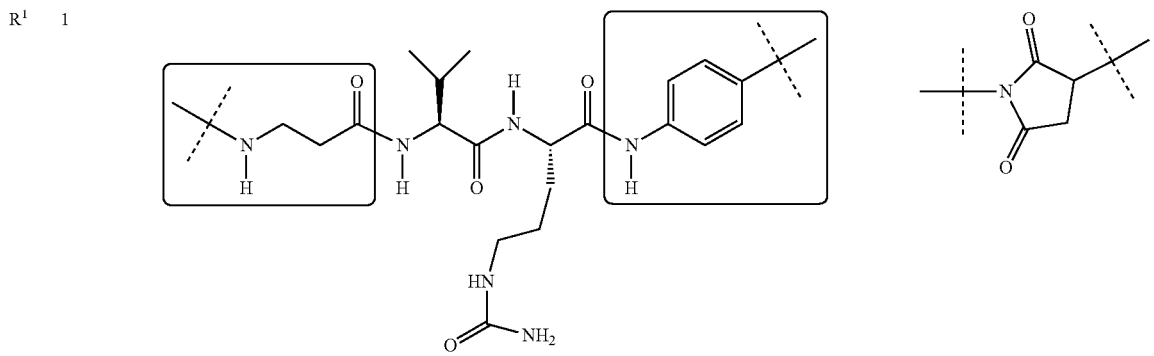 | |

TABLE C-continued
| Sub St. | m | -SG1-L1- or -L1-SG-L1- | L2 |
|---|---|---|---|
| R[1] | 1 | 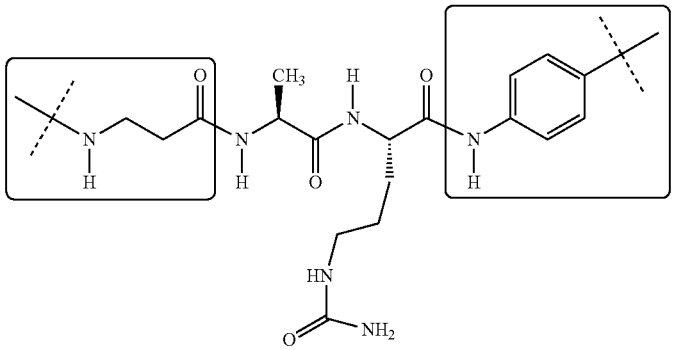 | 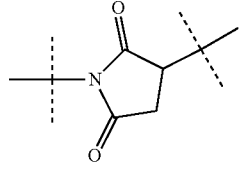 |
| R[1] | 1 | 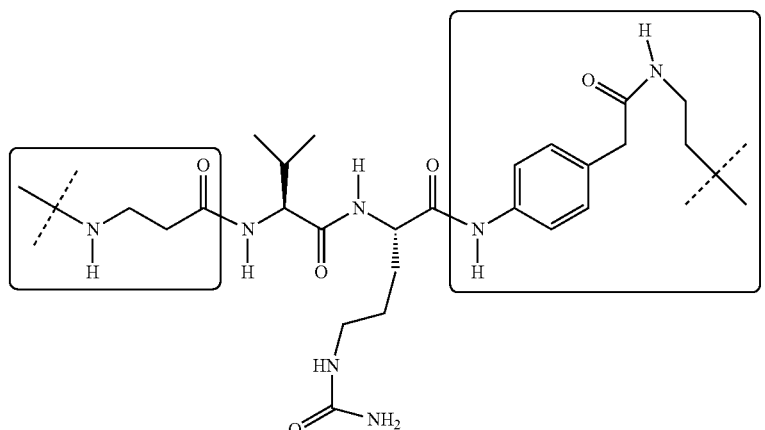 | 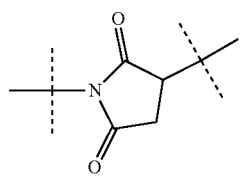 |
| R[1] | 1 | 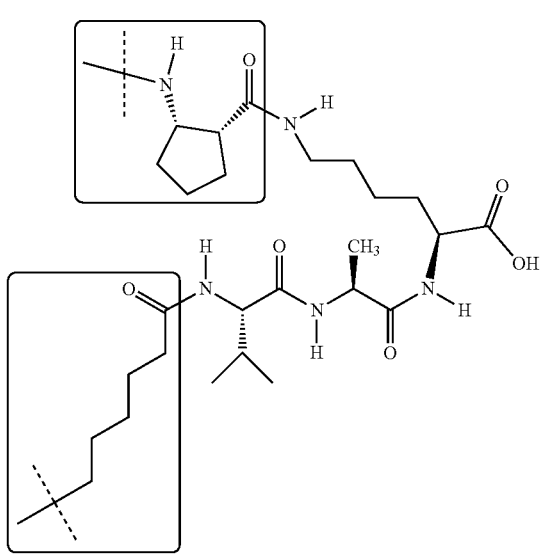 | 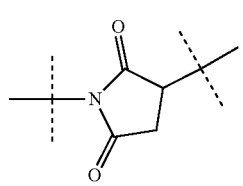 |

TABLE C-continued
| Sub St. | m | -SG1-L1- or -L1-SG-L1- | L2 |
|---|---|---|---|
| R¹ | 1 | 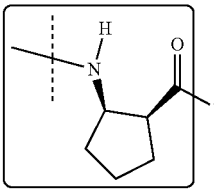 | 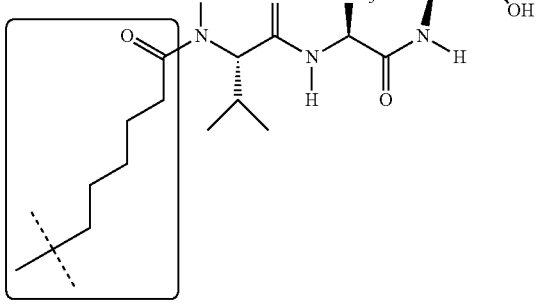 |
| R¹ | 1 | 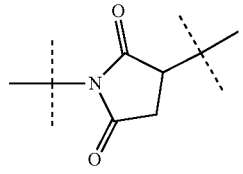 | 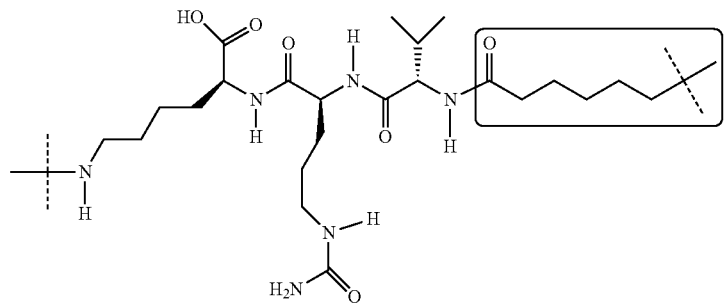 |
| R¹ | 1 | 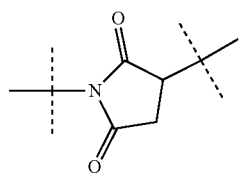 | 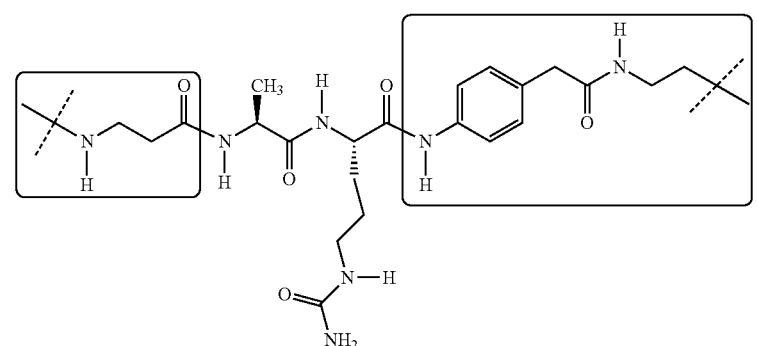 |
| R¹ | 1 | 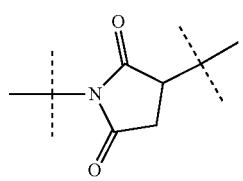 | 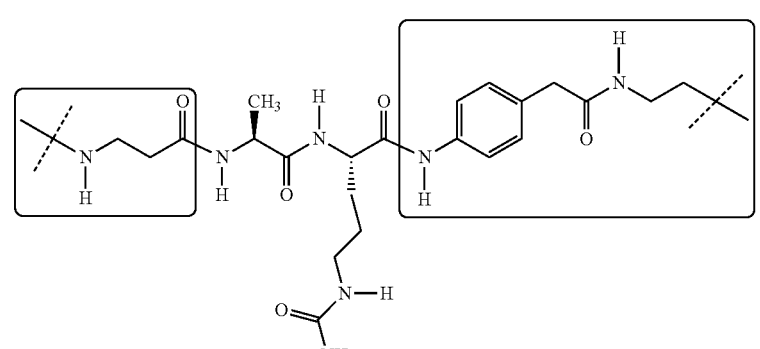 |

TABLE C-continued

| Sub St. | m | -SG1-L1- or -L1-SG-L1- | L2 |
|---|---|---|---|
| R¹ | 1 | | |
| R¹ | 1 | | |
| R¹ | 1 | | |
| R¹ | 1 | | |
| R¹ | 0 | | |

TABLE C-continued
| Sub St. | m | -SG1-L1- or -L1-SG-L1- | L2 |
|---|---|---|---|
| $R^1$ | 1 | 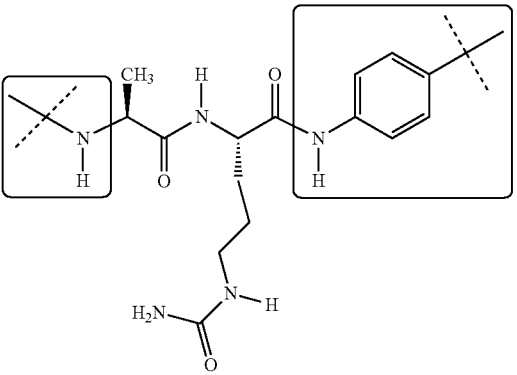 | 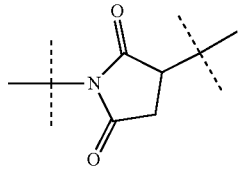 |
| $R^1$ | 0 | 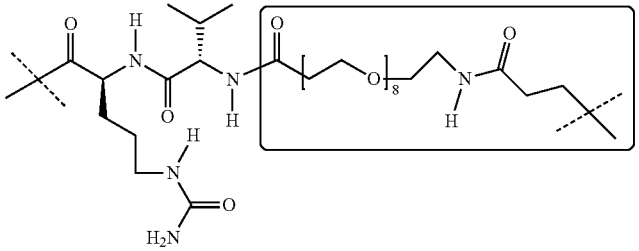 | 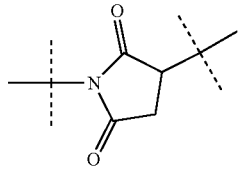 |
| $R^1$ | 0 | 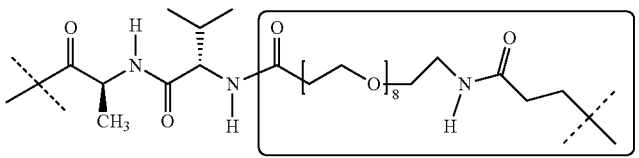 | 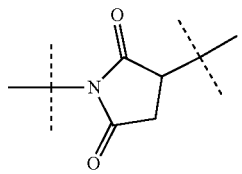 |
| $R^1$ | 0 | 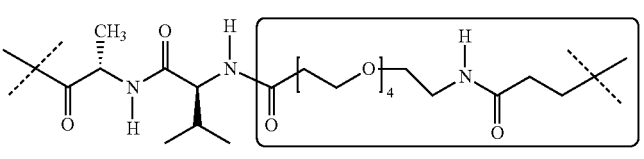 | 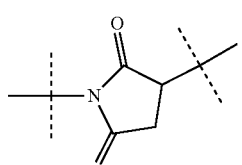 |
| $R^1$ | 0 | 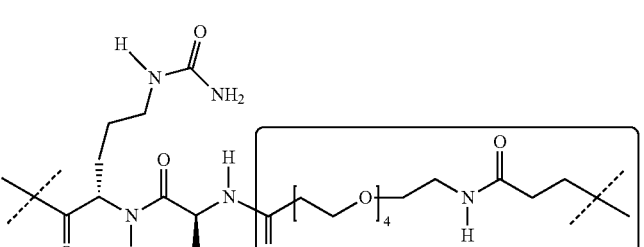 | 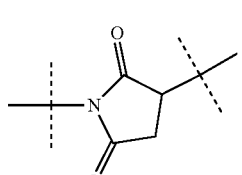 |
| $R^1$ | 0 | 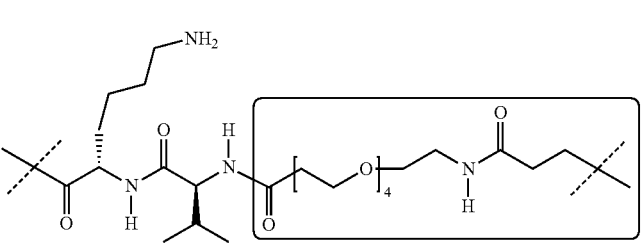 | 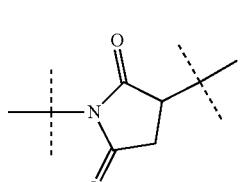 |

US 11,071,788 B2
TABLE C-continued
| Sub St. | m | -SG1-L1- or -L1-SG-L1- | L2 |
|---|---|---|---|
| R¹ | 0 | 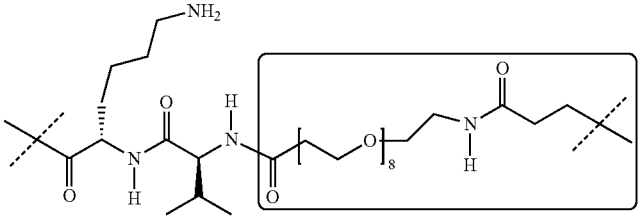 | 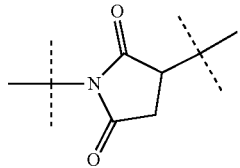 |
| R¹ | 0 | 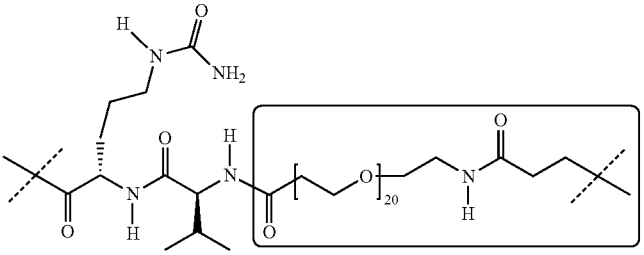 | 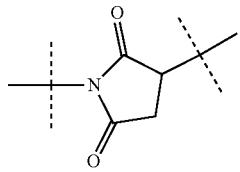 |
| R³ | 0 | 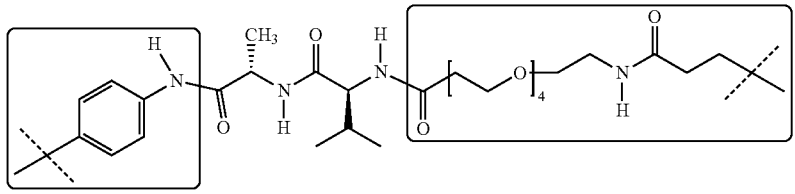 | 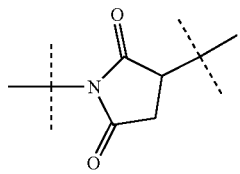 |
| R³ | 0 | 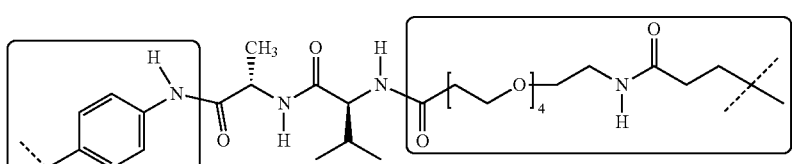 | 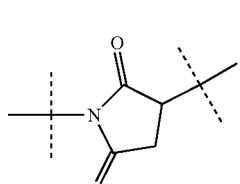 |
| R¹ | 1 | 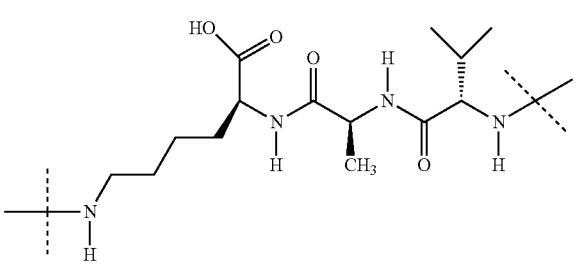 | 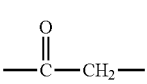 |
| R¹ | 1 | 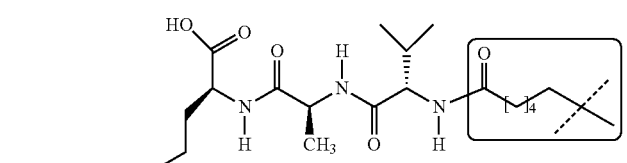 | 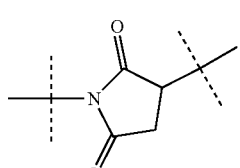 |

TABLE C-continued
| Sub St. | m | -SG1-L1- or -L1-SG-L1- | L2 |
|---|---|---|---|
| R¹ | 1 | 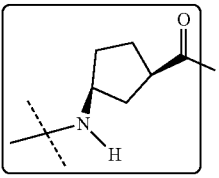 | 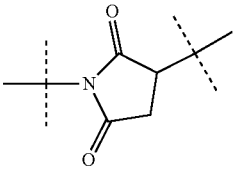 |
| R³ | 0 | 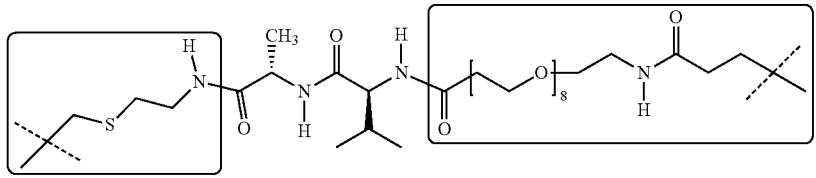 | 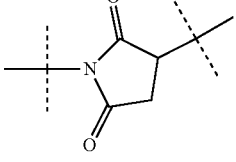 |
| R¹ | 1 | 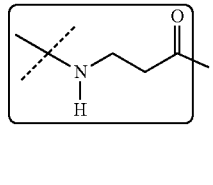 | 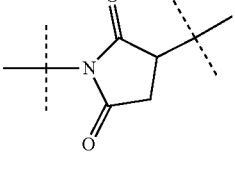 |
| R¹ | 1 | 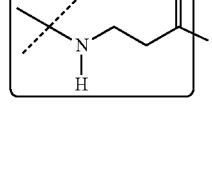 | 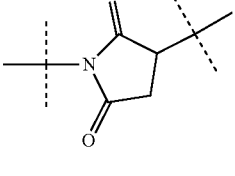 |
| R¹ | 1 | 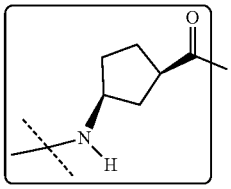 | 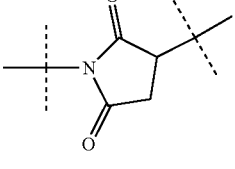 |
| R¹ | 1 | 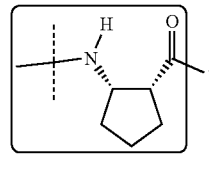 | 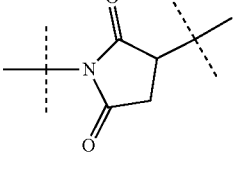 |

TABLE C-continued
| Sub St. | m | -SG1-L1- or -L1-SG-L1- | L2 |
|---|---|---|---|
| R¹ | 1 | 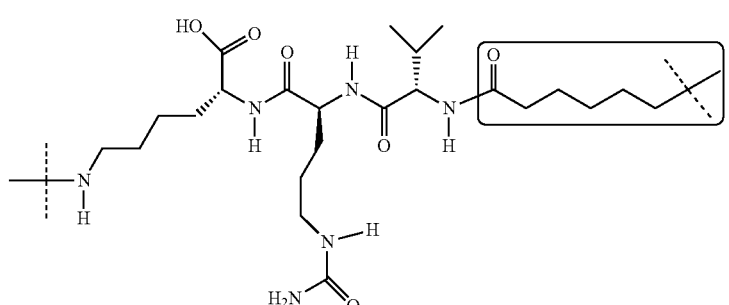 | 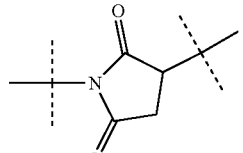 |
| R¹ | 1 | 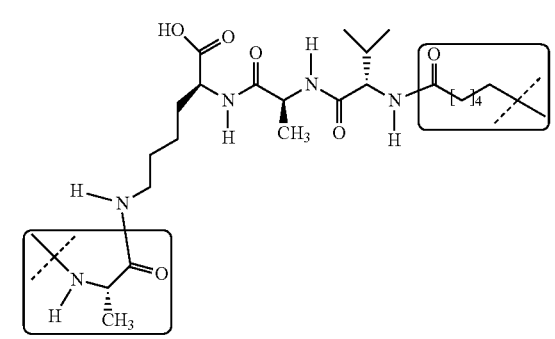 | 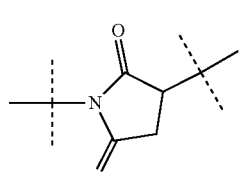 |
| R¹ | 1 | 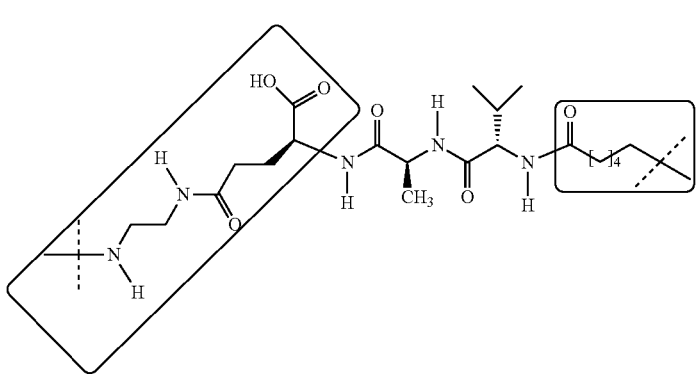 | 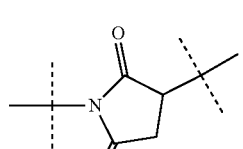 |
| R¹ | 1 | 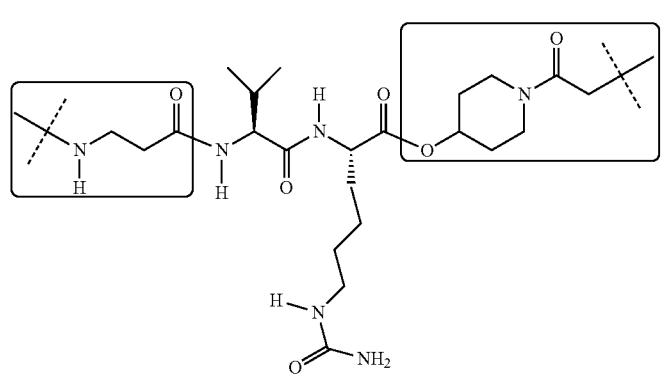 | 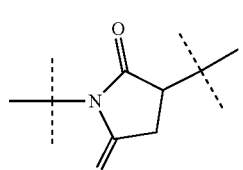 |

TABLE C-continued

| Sub St. | m | -SG1-L1- or -L1-SG-L1- | L2 |
|---|---|---|---|
| R¹ | 1 | | |
| R¹ | 1 | | |
| R³ | 0 | | |
| R¹ | 1 | | and |
| R³ | 0 | | |

Examples of conjugates having basic structure (i) have the following structure, where X1 represents CH, X2 represents C and X3 represents N, L4 has the same meaning as L1, AK1 represents an anti-B7H3 antibody attached via a cysteine residue and n is a number from 1 to 10. The antibody is preferably an aglycosylated human, humanized or chimeric monoclonal anti-B7H3 antibody or an antigen-binding fragment thereof. Particular preference is given to an anti-B7H3 antibody which specifically binds the human Ig4 isoform, in particular one of the anti-B7H3 antibodies TPP-6497, TPP-6499, TPP-6501, TPP-6502 and TPP-6515. In a further preferred embodiment, the anti-B7H3 antibody or the antigen-binding fragment is present in aglycosylated form.

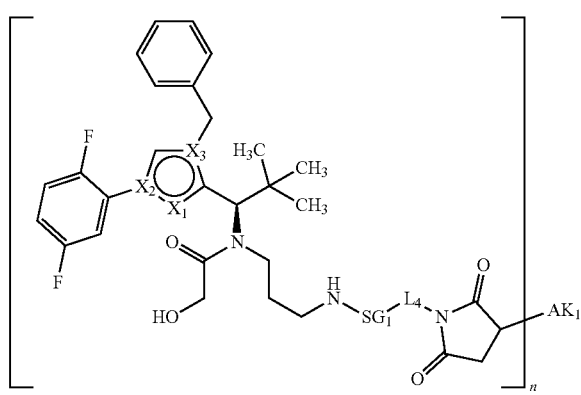

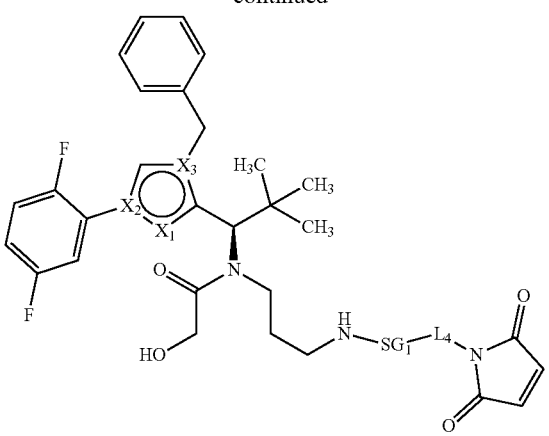

KSP Inhibitor-Linker-Intermediates and Preparation of the Conjugates

The conjugates according to the invention are prepared by initially providing the low-molecular weight KSP inhibitor with a linker. The intermediate obtained in this manner is then reacted with the binder (preferably antibody).

Preferably, for coupling to a cysteine residue, one of the compounds below is reacted with the cysteine-containing binder such as an antibody, which is optionally partially reduced for this purpose:

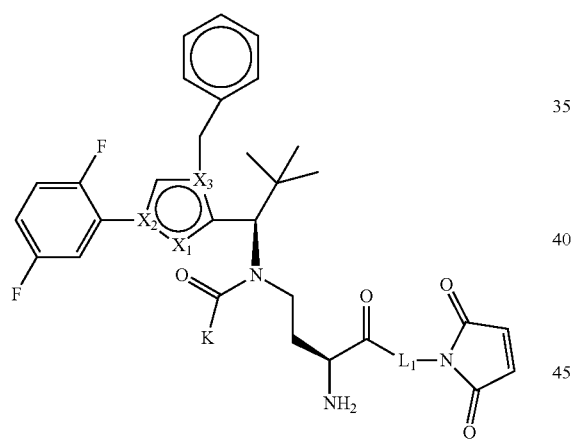

TFA

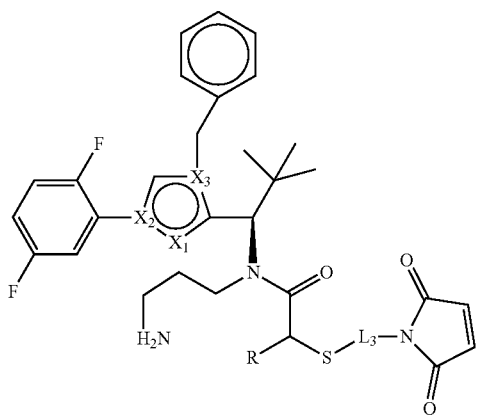

TFA

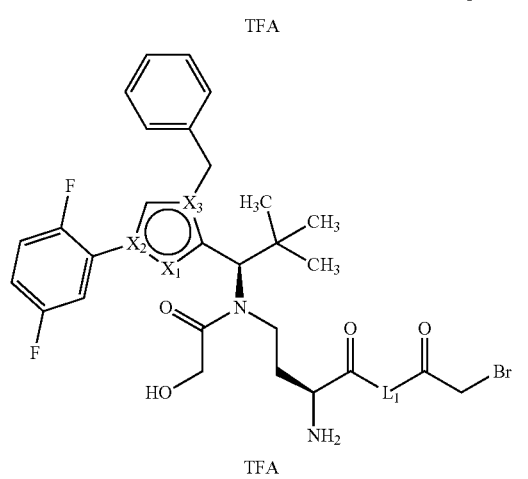

TFA

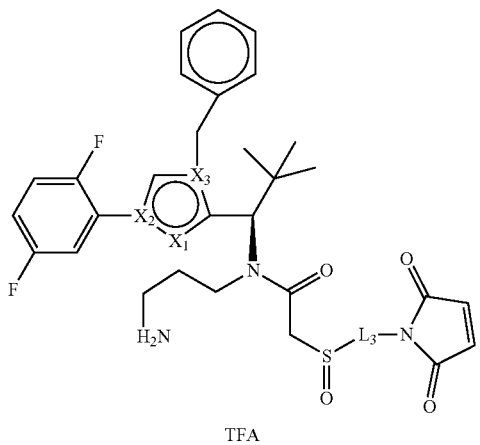

TFA

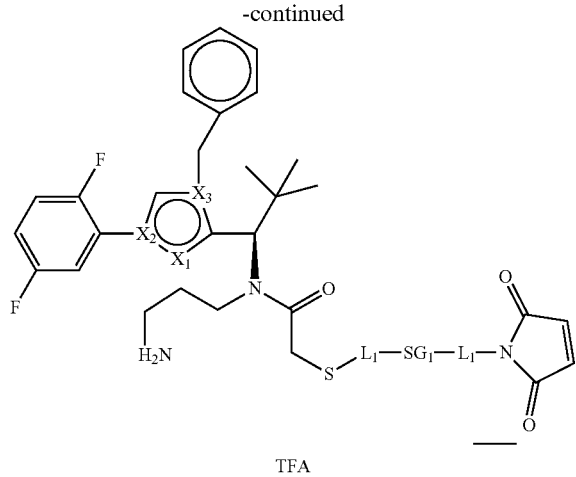

TFA

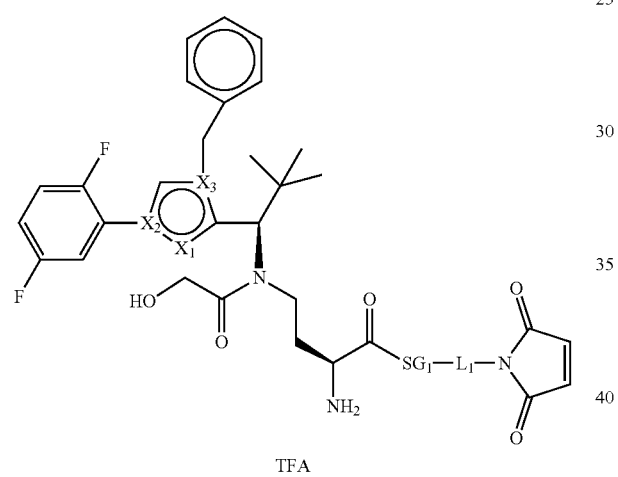

TFA

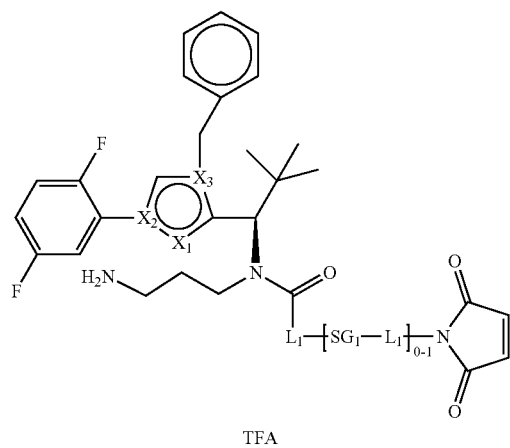

TFA where R represents —H or —COOH, where K represents straight-chain or branched $C_1$-$C_6$ alkyl which is optionally substituted by $C_1$-$C_6$-alkoxy or —OH, and where X1 represents CH, X2 represents C and X3 represents N, SG1, L1, L2, L3 and L4 have the same meaning as described above.

In each of the above compounds and in the compounds below, the tert-Butyl group may be replaced by cyclohexyl.

The compound may be employed, for example, in the form of its trifluoroacetic acid salt. For the reaction with the binder such as, for example, the antibody, the compound is preferably used in a 2- to 12-fold molar excess with respect to the binder.

Preferably, for coupling to a lysine residue, one of the compounds below is reacted with the lysine-containing binder such as an antibody:

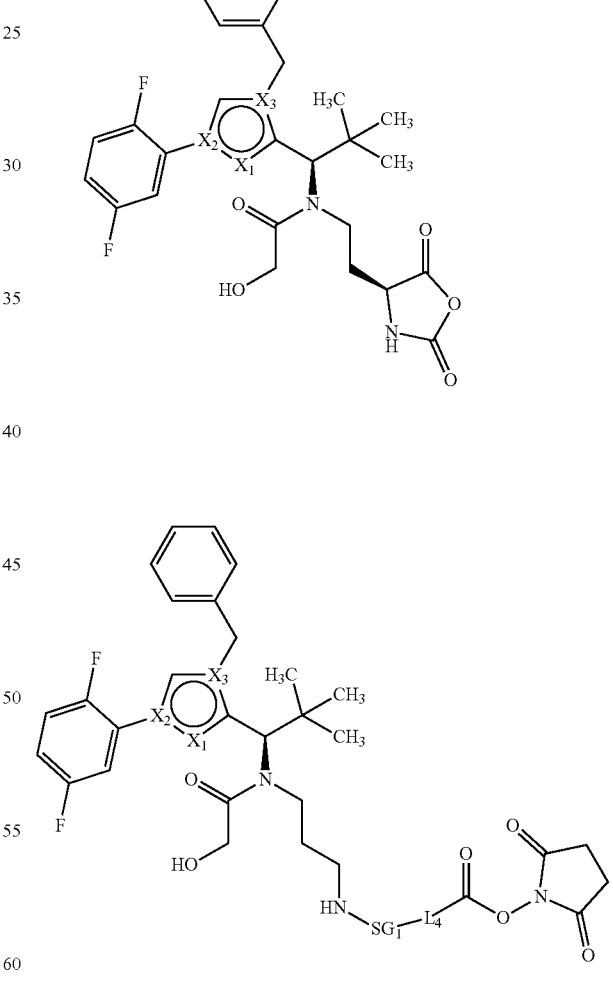

where X1 represents CH, X2 represents C and X3 represents N and L4 has the same meaning as L1 and L1 has the same meaning as described above.

For an intermediate coupling to a cysteine residue, the reactions can be illustrated as follows:

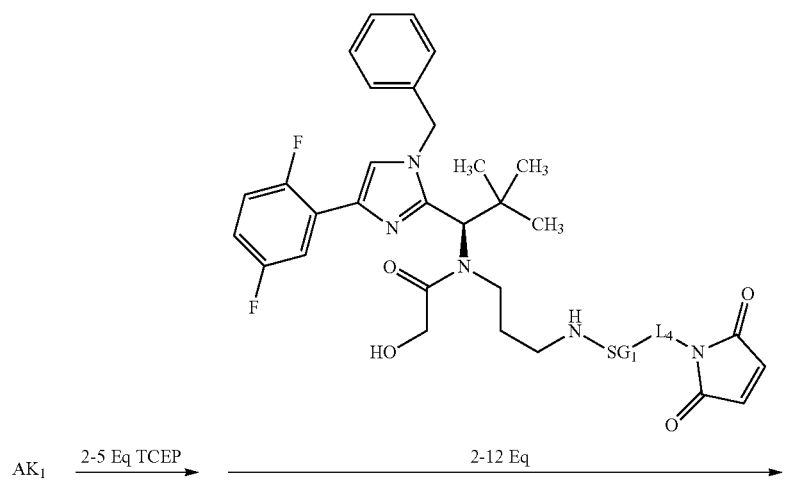
AK₁ —2-5 Eq TCEP→ —2-12 Eq→
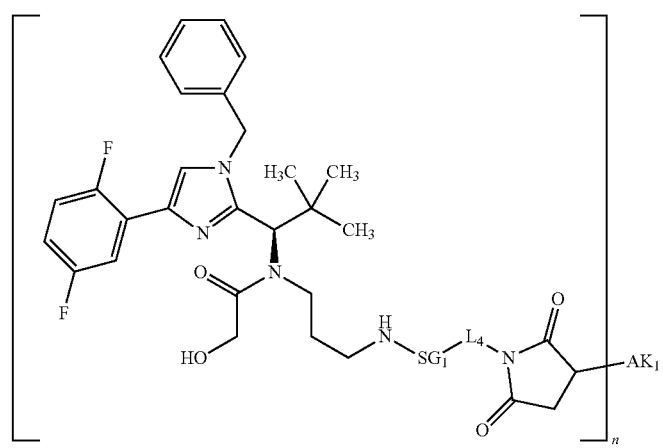
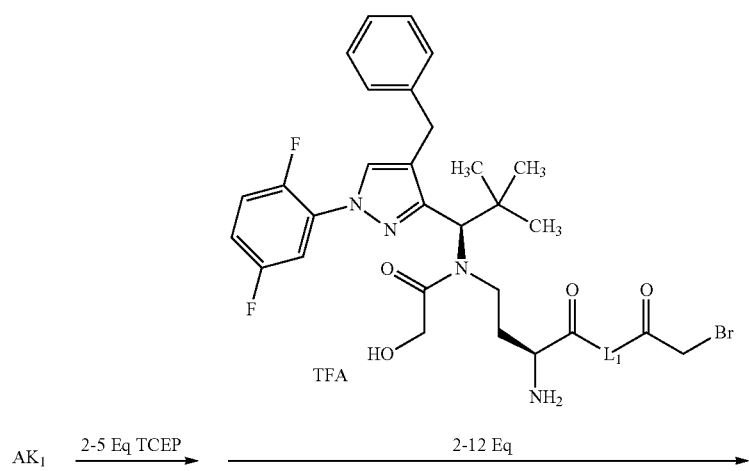
AK₁ —2-5 Eq TCEP→ —2-12 Eq→

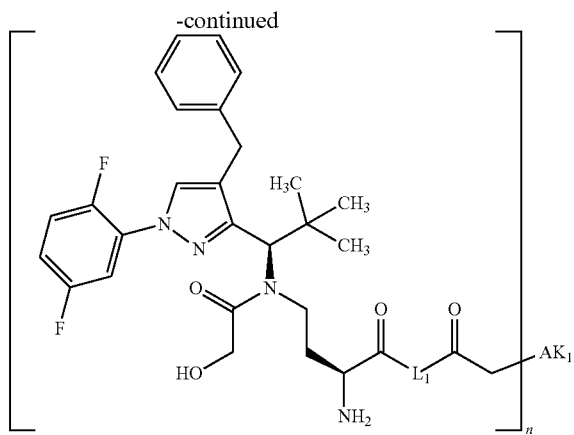
The other intermediates and other antibodies can be reacted correspondingly.
For an intermediate coupling to a lysine residue, the reaction can be illustrated as follows:
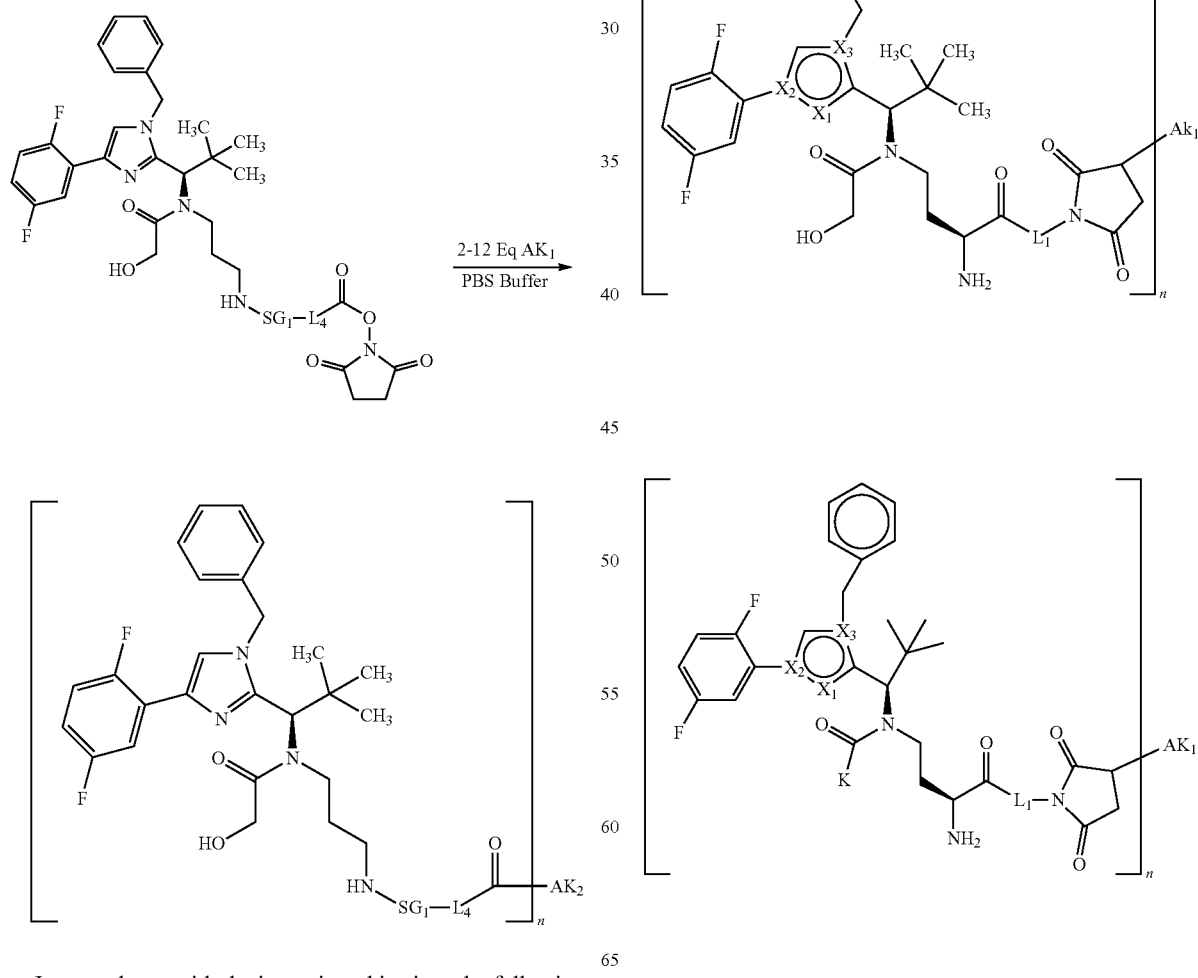
In accordance with the invention, this gives the following conjugates:

135
-continued
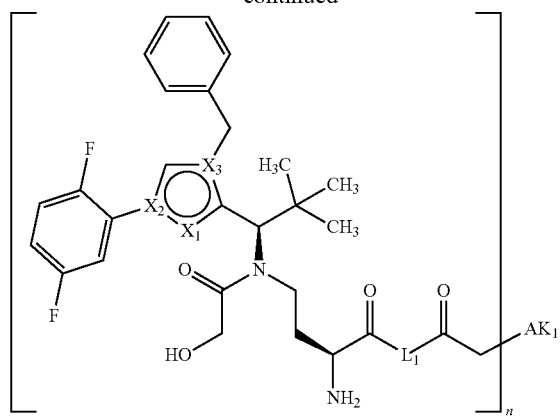
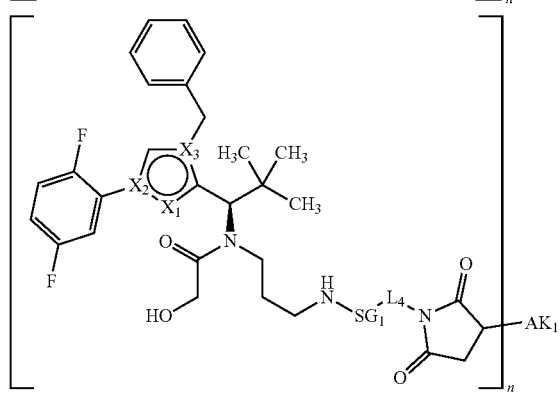
136
-continued
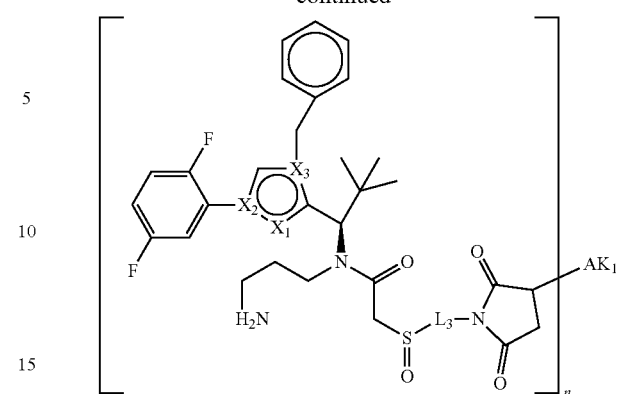
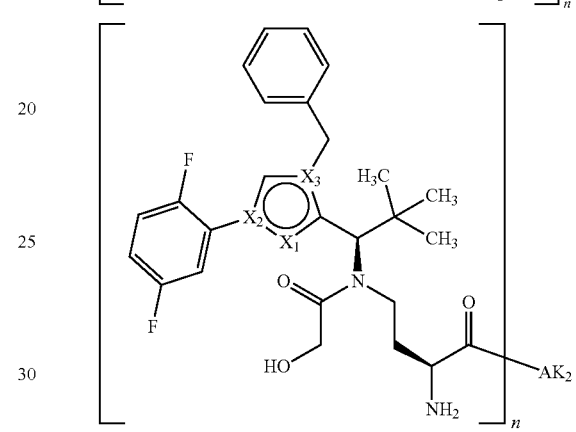
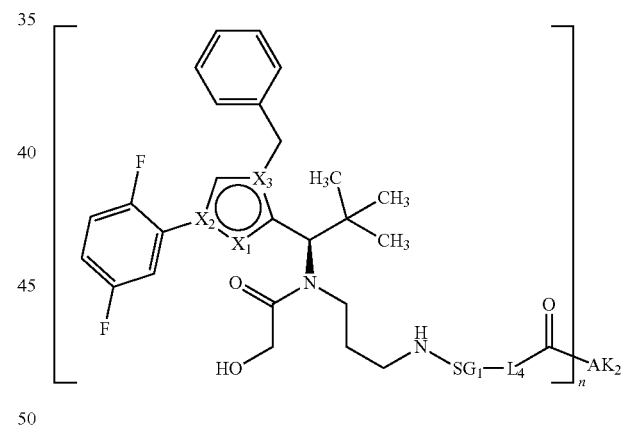
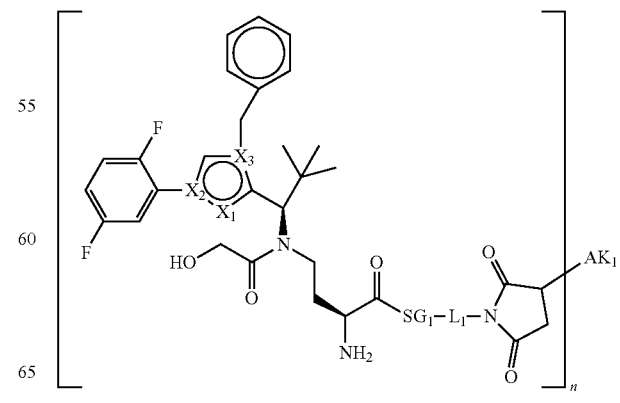

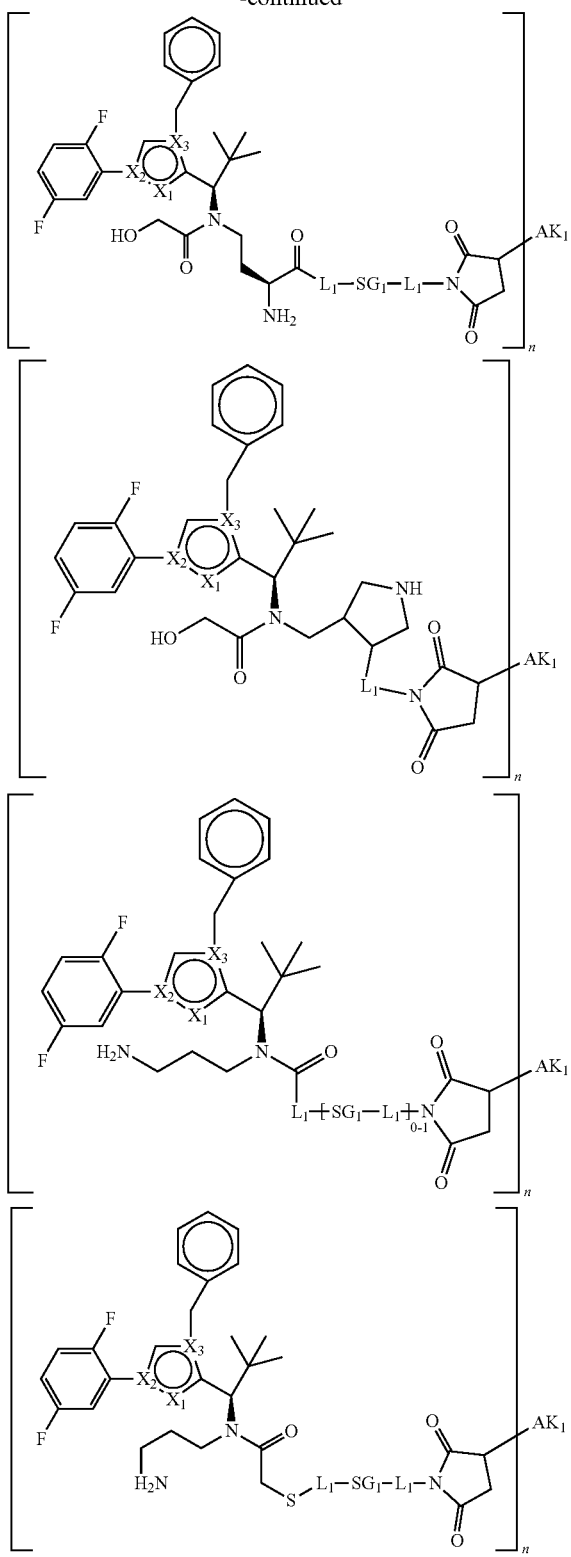
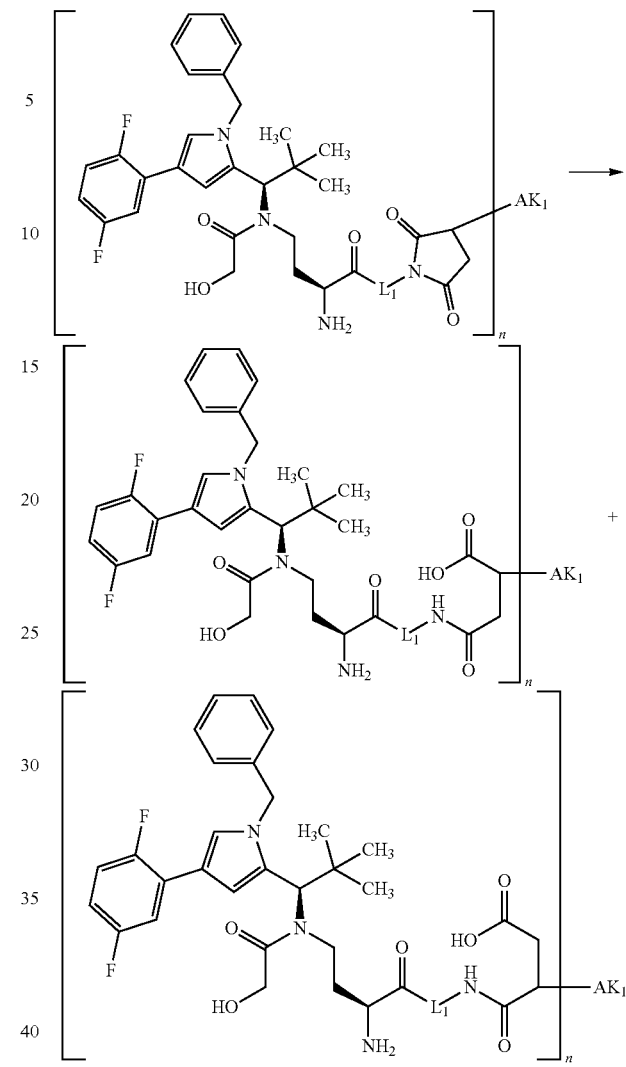

Depending on the linker, succinimide-linked ADCs may, after conjugation, be converted into the open-chain succinamides, which have an advantageous stability profile.

This reaction (ring opening) can be carried out at pH 7.5 to 9, preferably at pH 8, at a temperature of from 25° C. to 37° C., for example by stirring. The preferred stirring time is 8 to 30 hours.

In the above formulae, X1 represents CH, X2 represents C and X3 represents N, SG1 and L1 have the same meaning as described above and L2, L3 and L4 have the same meaning as L1; R and K have the same meaning as described above. AK1 is an anti-B7H3 antibody coupled via a cysteine residue or an antigen-binding fragment thereof, and AK2 is an anti-B7H3 antibody coupled via a lysine residue or an antigen-binding fragment thereof. With particular preference, AK1 and AK2 are anti-B7H3 antibodies which specifically bind the human Ig4 isoform, in particular one of the anti-B7H3 antibodies TPP-6497, TPP-6499, TPP-6501, TPP-6502 and TPP-6515. In a further preferred embodiment, the antibodies or antigen-binding fragments are present in aglycosylated form.

Anti-B7H3 Antibodies

The anti-B7H3 antibody is preferably a human, humanized or chimeric monoclonal antibody or an antigen-binding fragment thereof. Particular preference is given to anti-B7H3 antibodies or antigen-binding fragments which specifically bind the human Ig4 and/or the human and/or murine Ig2 isoform of B7H3, in particular the anti-B7H3 antibodies TPP-6497, TTP-6499, TPP-6501, TPP-6502, TPP-6515. In a further preferred embodiment, the antibodies or antigen-binding fragments are present in aglycosylated form. Here, aglycosyl or aglycosylated antibodies have no glycans at the conserved N-binding site in the CH2 domain of the Fc region.

The literature also discloses various options of covalent coupling (conjugation) of organic molecules to antibodies. Preference according to the invention is given to the conjugation of the toxophores to the antibody via one or more sulphur atoms of cysteine residues of the antibody and/or via one or more NH groups of lysine residues of the antibody. However, it is also possible to bind the toxophor to the antibody via free carboxyl groups or via sugar residues of the antibody.

The antibody can be attached to the linker via a bond. Attachment of the antibody can be via a heteroatom of the binder. Heteroatoms according to the invention of the antibody which can be used for attachment are sulphur (in one embodiment via a sulphhydryl group of the antibody), oxygen (according to the invention by means of a carboxyl or hydroxyl group of the antibody) and nitrogen (in one embodiment via a primary or secondary amine group or amide group of the antibody). These heteroatoms may be present in the natural antibody or are introduced by chemical methods or methods of molecular biology. According to the invention, the attachment of the antibody to the toxophor has only a minor effect on the binding activity of the antibody with respect to the target molecule. In a preferred embodiment, the attachment has no effect on the binding activity of the antibody with respect to the target molecule.

In accordance with the present invention, the term "antibody" is to be understood in its broadest meaning and comprises immunoglobulin molecules, for example intact or modified monoclonal antibodies, polyclonal antibodies or multispecific antibodies (e.g. bispecific antibodies). An immunoglobulin molecule preferably comprises a molecule having four polypeptide chains, two heavy chains (H chains) and two light chains (L chains) which are typically linked by disulphide bridges. Each heavy chain comprises a variable domain of the heavy chain (abbreviated VH) and a constant domain of the heavy chain. The constant domain of the heavy chain may, for example, comprise three domains CH1, CH2 and CH3. Each light chain comprises a variable domain (abbreviated VL) and a constant domain. The constant domain of the light chain comprises a domain (abbreviated CL). The VH and VL domains may be subdivided further into regions having hypervariability, also referred to as complementarity determining regions (abbreviated CDR) and regions having low sequence variability (framework region, abbreviated FR). Typically, each VH and VL region is composed of three CDRs and up to four FRs. For example from the amino terminus to the carboxy terminus in the following order: FR1, CDR1, FR2, CDR2, FR3, CDR3, FR4. An antibody may be obtained from any suitable species, e.g. rabbit, llama, camel, mouse or rat. In one embodiment, the antibody is of human or murine origin. An antibody may, for example, be human, humanized or chimeric.

The term "monoclonal" antibody refers to antibodies obtained from a population of substantially homogeneous antibodies, i.e. individual antibodies of the population are identical except for naturally occurring mutations, of which there may be a small number. Monoclonal antibodies recognize a single antigenic binding site with high specificity. The term monoclonal antibody does not refer to a particular preparation process.

The term "intact" antibody refers to antibodies comprising both an antigen-binding domain and the constant domain of the light and heavy chain. The constant domain may be a naturally occurring domain or a variant thereof having a number of modified amino acid positions.

The term "modified intact" antibody refers to intact antibodies fused via their amino terminus or carboxy terminus by means of a covalent bond (e.g. a peptide bond) with a further polypeptide or protein not originating from an antibody. Furthermore, antibodies may be modified such that, at defined positions, reactive cysteines are introduced to facilitate coupling to a toxophor (see Junutula et al. Nat Biotechnol. 2008 August; 26(8):925-32).

The term "human" antibody refers to antibodies which can be obtained from a human or which are synthetic human antibodies. A "synthetic" human antibody is an antibody which is partially or entirely obtainable in silico from synthetic sequences based on the analysis of human antibody sequences. A human antibody can be encoded, for example, by a nucleic acid isolated from a library of antibody sequences of human origin. An example of such an antibody can be found in Söderlind et al., Nature Biotech. 2000, 18:853-856.

The term "humanized" or "chimeric" antibody describes antibodies consisting of a non-human and a human portion of the sequence. In these antibodies, part of the sequences of the human immunoglobulin (recipient) is replaced by sequence portions of a non-human immunoglobulin (donor). In many cases, the donor is a murine immunoglobulin. In the case of humanized antibodies, amino acids of the CDR of the recipient are replaced by amino acids of the donor. Sometimes, amino acids of the framework, too, are replaced by corresponding amino acids of the donor. In some cases the humanized antibody contains amino acids present neither in the recipient nor in the donor, which were introduced during the optimization of the antibody. In the case of chimeric antibodies, the variable domains of the donor immunoglobulin are fused with the constant regions of a human antibody.

The term complementarity determining region (CDR) as used herein refers to those amino acids of a variable antibody domain which are required for binding to the antigen. Typically, each variable region has three CDR regions referred to as CDR1, CDR2 and CDR3. Each CDR region may embrace amino acids according to the definition of Rabat and/or amino acids of a hypervariable loop defined according to Chotia. The definition according to Rabat comprises, for example, the region from about amino acid position 24-34 (CDR1), 50-56 (CDR2) and 89-97 (CDR3) of the variable light chain and 31-35 (CDR1), 50-65 (CDR2) and 95-102 (CDR3) of the variable heavy chain (Rabat et al., Sequences of Proteins of Immunological Interest, 5th Ed. Public Health Service, National Institutes of Health, Bethesda, Md. (1991)). The definition according to Chotia comprises, for example, the region from about amino acid position 26-32 (CDR1), 50-52 (CDR2) and 91-96 (CDR3) of the variable light chain and 26-32 (CDR1), 53-55 (CDR2) and 96-101 (CDR3) of the variable heavy chain (Chothia and Lesk; J Mol Biol 196: 901-917 (1987)). In some cases, a CDR may comprise amino acids from a CDR region defined according to Rabat and Chotia.

Depending on the amino acid sequence of the constant domain of the heavy chain, antibodies may be categorized into different classes. There are five main classes of intact antibodies: IgA, IgD, IgE, IgG and IgM, and several of these can be divided into further subclasses. (Isotypes), e.g. IgG1, IgG2, IgG3, IgG4, IgA1 and IgA2. The constant domains of the heavy chain, which correspond to the different classes, are referred to as [alpha/a], [delta/8], [epsilon/e], [gamma/y] and [my/p]. Both the three-dimensional structure and the subunit structure of antibodies are known.

The term "functional fragment" or "antigen-binding antibody fragment" of an antibody/immunoglobulin is defined as a fragment of an antibody/immunoglobulin (e.g. the variable domains of an IgG) which still comprise the antigen binding domains of the antibody/immunoglobulin. The "antigen binding domain" of an antibody typically comprises one or more hypervariable regions of an antibody, for example the CDR, CDR2 and/or CDR3 region. However, the "framework" or "skeleton" region of an antibody may also play a role during binding of the antibody to the antigen. The framework region forms the skeleton of the CDRs. Preferably, the antigen binding domain comprises at least amino acids 4 to 103 of the variable light chain and amino acids 5 to 109 of the variable heavy chain, more preferably amino acids 3 to 107 of the variable light chain and 4 to 111 of the variable heavy chain, particularly preferably the complete variable light and heavy chains, i.e. amino acids 1-109 of the VL and 1 to 113 of the VH (numbering according to WO97/08320).

"Functional fragments" or "antigen-binding antibody fragments" of the invention encompass, non-conclusively, Fab, Fab', F(ab')$_2$ and Fv fragments, diabodies, Single Domain Antibodies (DAbs), linear antibodies, individual chains of antibodies (single-chain Fv, abbreviated to scFv); and multispecific antibodies, such as bi and tri-specific antibodies, for example, formed from antibody fragments C. A. K Borrebaeck, editor (1995) Antibody Engineering (Breakthroughs in Molecular Biology), Oxford University Press; R. Kontermann & S. Duebel, editors (2001) Antibody Engineering (Springer Laboratory Manual), Springer Verlag. Antibodies other than "multispecific" or "multifunctional" antibodies are those having identical binding sites. Multispecific antibodies may be specific for different epitopes of an antigen or may be specific for epitopes of more than one antigen (see, for example, WO 93/17715; WO 92/08802; WO 91/00360; WO 92/05793; Tutt, et al., 1991, J. Immunol. 147:60 69; U.S. Pat. Nos. 4,474,893; 4,714,681; 4,925,648; 5,573,920; 5,601,819; or Kostelny et ah, 1992, J. Immunol. 148: 1547 1553). An F(ab')$_2$ or Fab molecule may be constructed such that the number of intermolecular disulphide interactions occurring between the Chi and the CL domains can be reduced or else completely prevented.

"Epitopes" refer to protein determinants capable of binding specifically to an immunoglobulin or T cell receptors. Epitopic determinants usually consist of chemically active surface groups of molecules such as amino acids or sugar side chains or combinations thereof, and usually have specific 3-dimensional structural properties and also specific charge properties.

"Functional fragments" or "antigen-binding antibody fragments" may be fused with another polypeptide or protein, not originating from an antibody, via the amino terminus or carboxyl terminus thereof, by means of a covalent bond (e.g. a peptide linkage). Furthermore, antibodies and antigen-binding fragments may be modified by introducing reactive cysteines at defined locations, in order to facilitate coupling to a toxophore (see Junutula et ah Nat Biotechnol. 2008 August; 26(8):925-32).

Polyclonal antibodies can be prepared by methods known to a person of ordinary skill in the art. Monoclonal antibodies may be prepared by methods known to a person of ordinary skill in the art (Köhler and Milstein, Nature, 256, 495-497, 1975). Human and humanized monoclonal antibodies may be prepared by methods known to a person of ordinary skill in the art (Olsson et ah, Meth Enzymol. 92, 3-16 or Cabilly et al U.S. Pat. No. 4,816,567 or Boss et al U.S. Pat. No. 4,816,397).

A person of ordinary skill in the art is aware of diverse methods for preparing human antibodies and fragments thereof, such as, for example, by means of transgenic mice (N Lonberg and D Huszar, Int Rev Immunol. 1995; 13(1): 65-93) or phage display technologies (Clackson et ah, Nature. 1991 Aug. 15; 352(6336):624-8). Antibodies of the invention may be obtained from recombinant antibody libraries consisting for example of the amino acid sequences of a multiplicity of antibodies compiled from a large number of healthy volunteers. Antibodies may also be produced by means of known recombinant DNA technologies. The nucleic acid sequence of an antibody can be obtained by routine sequencing or is available from publically accessible databases.

An "isolated" antibody or binder has been purified to remove other constituents of the cell. Contaminating constituents of a cell which may interfere with a diagnostic or therapeutic use are, for example, enzymes, hormones, or other peptidic or non-peptidic constituents of a cell. A preferred antibody or binder is one which has been purified to an extent of more than 95% by weight, relative to the antibody or binder (determined for example by Lowry method, UV-Vis spectroscopy or by SDS capillary gel electrophoresis). Moreover an antibody which has been purified to such an extent that it is possible to determine at least 15 amino acids of the amino terminus or of an internal amino acid sequence, or which has been purified to homogeneity, the homogeneity being determined by SDS-PAGE under reducing or non-reducing conditions (detection may be determined by means of Coomassie Blau staining or preferably by silver coloration). However, an antibody is normally prepared by one or more purification steps.

The term "specific binding" or "binds specifically" refers to an antibody or binder which binds to a predetermined antigen/target molecule. Specific binding of an antibody or binder typically describes an antibody or binder having an affinity of at least $10^{-7}$ M (as Kd value: i.e. preferably those with Kd values smaller than $10^{-7}$ M), with the antibody or binder having an at least two times higher affinity for the predetermined antigen/target molecule than for a non-specific antigen/target molecule (e.g. bovine serum albumin, or casein) which is not the predetermined antigen/target molecule or a closely related antigen/target molecule. The antibodies preferably have an affinity of at least $10^{-7}$ M (as Kd value; in other words preferably those with smaller Kd values than $10^{-7}$ M), preferably of at least $10^{-8}$ M, more preferably in the range from $10^{-9}$ M to $10^{-11}$ M. The Kd values may be determined, for example, by means of surface plasmon resonance spectroscopy.

The antibody-drug conjugates of the invention likewise exhibit affinities in these ranges. The affinity is preferably not substantially affected by the conjugation of the drugs (in general, the affinity is reduced by less than one order of magnitude, in other words, for example, at most from $10^{-8}$ M to $10^{-7}$ M).

The antibodies used in accordance with the invention are also notable preferably for a high selectivity. A high selectivity exists when the antibody of the invention exhibits an affinity for the target protein which is better by a factor of at least 2, preferably by a factor of 5 or more preferably by a factor of 10, than for an independent other antigen, e.g. human serum albumin (the affinity may be determined, for example, by means of surface plasmon resonance spectroscopy).

Furthermore, the antibodies of the invention that are used are preferably cross-reactive. In order to be able to facilitate and better interpret preclinical studies, for example toxicological or activity studies (e.g. in xenograft mice), it is advantageous if the antibody used in accordance with the invention not only binds the human target protein but also binds the species target protein in the species used for the studies. In one embodiment the antibody used in accordance with the invention, in addition to the human target protein, is cross-reactive to the target protein of at least one further species. For toxicological and activity studies it is preferred to use species of the families of rodents, dogs and non-human primates. Preferred rodent species are mouse and rat. Preferred non-human primates are rhesus monkeys, chimpanzees and long-tailed macaques.

In one embodiment the antibody used in accordance with the invention, in addition to the human target protein, is cross-reactive to the target protein of at least one further species selected from the group of species consisting of mouse, rat and long-tailed macaque (*Macaca fascicularis*). Especially preferred are antibodies used in accordance with the invention which in addition to the human target protein are at least cross-reactive to the mouse target protein. Preference is given to cross-reactive antibodies whose affinity for the target protein of the further non-human species differs by a factor of not more than 50, more particularly by a factor of not more than ten, from the affinity for the human target protein.

Antibodies Directed Against a Cancer Target Molecule

The target molecule towards which the binder, for example an antibody or an antigen-binding fragment thereof, is directed is preferably a cancer target molecule. The term "cancer target molecule" describes a target molecule which is more abundantly present on one or more cancer cell species than on non-cancer cells of the same tissue type. Preferably, the cancer target molecule is selectively present on one or more cancer cell species compared with non-cancer cells of the same tissue type, where selectively describes an at least two-fold enrichment on cancer cells compared to non-cancer cells of the same tissue type (a "selective cancer target molecule"). The use of cancer target molecules allows the selective therapy of cancer cells using the conjugates according to the invention.

Particular preference is given here to the extracellular cancer target molecule B7H3 (SEQ ID NO: 52).

Antibodies which bind cancer target molecules may be prepared by a person of ordinary skill in the art using known processes, such as, for example, chemical synthesis or recombinant expression. Binders for cancer target molecules may be acquired commercially or may be prepared by a person of ordinary skill in the art using known processes, such as, for example, chemical synthesis or recombinant expression. Further processes for preparing antibodies or antigen-binding antibody fragments are described in WO 2007/070538 (see page 22 "Antibodies"). The person skilled in the art knows how processes such as phage display libraries (e.g. Morphosys HuCAL Gold) can be compiled and used for discovering antibodies or antigen-binding antibody fragments (see WO 2007/070538, page 24 ff and AK Example 1 on page 70, AK. Example 2 on page 72). Further processes for preparing antibodies that use DNA libraries from B cells are described for example on page 26 (WO 2007/070538). Processes for humanizing antibodies are described on page 30-32 of WO2007070538 and in detail in Queen, et al., Pros. Natl. Acad. Sci. USA 86:10029-10033, 1989 or in WO 90/0786. Furthermore, processes for the recombinant expression of proteins in general and of antibodies in particular are known to the person skilled in the art (see, for example, in Berger and Kimmel (Guide to Molecular Cloning Techniques, Methods in Enzymology, Vol. 152, Academic Press, Inc.); Sambrook, et ah, (Molecular Cloning: A Laboratory Manual, (Second Edition, Cold Spring Harbor Laboratory Press; Cold Spring Harbor, N.Y.; 1989) Vol. 1-3); Current Protocols in Molecular Biology, (F. M. Ausabel et ah [Eds.], Current Protocols, Green Publishing Associates, Inc./John Wiley & Sons, Inc.); Harlow et ah, (Monoclonal Antibodies: A Laboratory Manual, Cold Spring Harbor Laboratory Press (19881, Paul [Ed.]); Fundamental Immunology, (Lippincott Williams & Wilkins (1998)); and Harlow, et ah, (Using Antibodies: A Laboratory Manual, Cold Spring Harbor Laboratory Press (1998)). The person skilled in the art knows the corresponding vectors, promoters and signal peptides which are necessary for the expression of a protein/antibody. Commonplace processes are also described in WO 2007/070538 on pages 41-45. Processes for preparing an IgG1 antibody are described for example in WO 2007/070538 in Example 6 on page 74 ff. Processes which allow the determination of the internalization of an antibody after binding to its antigen are known to the skilled person and are described for example in WO 2007/070538 on page 80. The person skilled in the art is able to use the processes described in WO 2007/070538 that have been used for preparing carboanhydrase IX (Mn) antibodies in analogy for the preparation of antibodies with different target molecule specificity.

The antibodies according to the invention are glycosylated or aglycosylated, i.e. in the latter case they have no glycans at the conserved N-binding site in the CH2 domain of the Fc region.

Anti-B7H3 Antibodies

According to the invention, use is made of an anti-B7H3 antibody or an antigen-binding fragment thereof, preferably TPP6497, 6499, 6501, 6502, 6515 or antibodies derived therefrom. In addition, the person skilled in the art is familiar with antibodies binding to B7H3, see e.g. U.S. Pat. No. 6,965,018 or EP2121008. The invention relates in particular to conjugates with antibodies, antigen-binding antibody fragments thereof or variants thereof, having the following properties: binding to human B7H3, i.e. no binding to human B7H2 or human B7H4; effective and specific killing of B7H3-expressing tumour cells in vitro and in vivo. The antibodies according to the invention bind to epitopes which are particularly suitable for internalization after binding has taken place. At the same time, the antibodies according to the invention are distinguished by low immunogenicity when used in humans by virtue of the fact that the amino acid sequence of the antibodies is as similar as possible to human germ line sequences.

Generation of Anti-B7H3 Antibodies

A fully human antibody phage bank (Bioinvent n-CoDeR Fab lambda library) was used to isolate B7H3-specific human monoclonal antibodies of the present invention by protein panning (Hoogenboom H. R., Nat Biotechnol 2005; 23(3):1105-16) using murine B7H3 as immobilized target protein.

TABLE 1

List of antigens employed

| Nomenclature | Description | SEQ ID NO |
|---|---|---|
| TPP-3762 | Recombinant Mouse B7-H3 (R&D Systems; 1397-B3) | 53 |
| TPP-2202 | Off-target (TweakR-ECD-hIgG1Fc-His) | 51 |

Following the instructions of the supplier, the antigens were desalted using an approximately two-fold molar excess of biotin-LC-NHS (Pierce; Cat. No. 21347) and Zeba desalting columns (Pierce; Cat. No. 89889). Washed magnetic beads (Dynabeads) were incubated with 800 nM of biotinylated protein at 4 degrees Celsius overnight and then blocked for an hour at 4 degrees Celsius using blocking buffer (PBS with 3% milk powder, 0.05% Tween-20). For depletion of unspecific binders, the blocked Fab-phage bank was added to blocked beads (Dynabeads streptavidin M280-Invitrogen 112-06D) loaded with TPP2202 and incubated at room temperature for 5 minutes. This depletion step was repeated four times. The depleted Fab-phage bank was added to blocked beads loaded with TPP3762 and incubated at room temperature for 60 minutes. After stringent washing (3× in blocking buffer and 9× in PBS (150 mM NaCl; 8 mM Na$_2$HPO$_4$; 1.5 mM KH$_2$PO$_4$; pH=7.4-7.6) with 0.05% Tween-20), TPP-3762-specific binders were resuspended in PBS and, for amplification, used directly for infecting the *Escherichia coli* strain TG1. In the second selection round, the concentration of TPP-3762 was lowered to 400 nM to increase the selection pressure for highly affinic binders. Alternatively, a second and third selection round were carried out on cell lines expressing human B7H3. In the second and the third round, the human renal carcinoma cell line A498 (ATCC, HTB-44) and the human adenocarcinoma cell line MCF-7 (ATCC, HTB-22) were used as selection antigens, with 1×10$^7$ cells. The cells were cultivated in 80% (v/v) RPMI 1640 GlutaMAX-I medium (Life Technologies, Cat. No. 61870-010) supplemented with 20% (v/v) foetal calf serum (FBS, Life Technologies, Cat. No. 10091-148) at 37 degrees Celsius, 5% CO$_2$, and every 3-4 days passaged in a ratio of 1:5. The cells were washed three times with 10 ml of ice-cold PBS and blocked for two hours using PBS, 2% milk powder. The Fab phage particles from the first selection round were added to the blocked cells and incubated on a rotating platform at 4 degrees Celsius for one hour. Cells and bound phages were centrifuged at 1000×g for two minutes. Non-binders and unspecific binders were washed off using in each case five alternating short and long (5 minutes) washing steps with pre-cooled PBS. The cells were then resuspended in 15 ml of pre-warmed PBS and incubated at 37 degrees Celsius for 15 minutes to allow internalization. The cell membrane-bound Fab-phages were removed by incubation with 1 ml of 76 mM citric acid. The cells were washed again and centrifuged as above. The internalized Fab phages were obtained by incubating the cell pellet with 1 ml of lysis buffer (100 mM triethylamine) for 10 minutes and neutralization in 0.5 ml of 1M Tris-HCl, pH 7,5. The lysate fractions were amplified by infection of TG1 cells. The phages obtained in this manner were sequenced, and appropriate DNA sequences were cloned in a mammalian IgG expression vector and expressed as complete IgGs. These constructs were expressed, for example, transiently in mammalian cells, as described by Tom et al., chapter 12 in Methods Express: Expression Systems edited by Michael R. Dyson and Yves Durocher, Scion Publishing Ltd, 2007. The antibodies were purified by protein A chromatography and binding to human B7H3 as well as human B7H2 and B7H4 was characterized by Elisa, as described in AK-Example 1. TPP 6497, TPP6499, TPP6501, TPP6502 and TPP6515 in particular showed attractive binding properties. Furthermore, the efficacy of active compound conjugates with these antibodies was tested in vitro and in vivo, as described in AK-Example C-1 and C-2. Furthermore, comparison of the amino acid sequences of these antibodies with frequent human germ line sequences identified a number of amino acid substitutions which would make the antibody sequences even more similar to human germ line sequences.

Particular Embodiments of Anti-B7H3 Antibodies

In the present application, reference is made to the following preferred antibodies, as shown in the table below: TPP-6497, TPP-6499, TPP-6501, TPP-6502, TPP-6515, TPP-7611, TPP-8382, TPP-8564, TPP-8567, TPP-8322, TPP-8565, TPP-8568, TPP-8748 and TPP-8750.

| Antibody | VH | H-CDR1 | H-CDR2 | H-CDR3 | VL | L-CDR1 | L-CDR2 | L-CDR3 | Heavy Chain (IgG) | Light Chain (IgG) |
|---|---|---|---|---|---|---|---|---|---|---|
| TPP-6497 | 1 | 2 | 3 | 4 | 5 | 6 | 7 | 8 | 9 | 10 |
| TPP-6499 | 11 | 12 | 13 | 14 | 15 | 16 | 17 | 18 | 19 | 20 |
| TPP-6501 | 21 | 22 | 23 | 24 | 25 | 26 | 27 | 28 | 29 | 30 |
| TPP-6502 | 31 | 32 | 33 | 34 | 35 | 36 | 37 | 38 | 39 | 40 |
| TPP-6515 | 41 | 42 | 43 | 44 | 45 | 46 | 47 | 48 | 49 | 50 |
| TPP-7611 | 1 | 2 | 3 | 4 | 5 | 6 | 7 | 8 | 54 | 10 |
| TPP-8382 | 55 | 2 | 56 | 4 | 57 | 6 | 58 | 8 | 59 | 60 |
| TPP-8564 | 55 | 2 | 56 | 4 | 57 | 6 | 58 | 8 | 61 | 60 |
| TPP-8567 | 55 | 2 | 56 | 4 | 57 | 6 | 58 | 8 | 62 | 60 |
| TPP-8322 | 63 | 64 | 33 | 34 | 35 | 36 | 37 | 38 | 65 | 40 |
| TPP-8565 | 63 | 64 | 33 | 34 | 35 | 36 | 37 | 38 | 66 | 40 |
| TPP-8568 | 63 | 64 | 33 | 34 | 35 | 36 | 37 | 38 | 67 | 40 |
| TPP-8748 | 63 | 64 | 33 | 34 | 68 | 36 | 69 | 38 | 65 | 70 |
| TPP-8750 | 63 | 64 | 33 | 34 | 68 | 36 | 69 | 38 | 67 | 70 |

TPP-6497 is an antibody comprising a region of the heavy chain corresponding to SEQ ID NO: 9 and a region of the light chain corresponding to SEQ ID NO: 10.

TPP-6499 is an antibody comprising a region of the heavy chain corresponding to SEQ ID NO: 19 and a region of the light chain corresponding to SEQ ID NO: 20.

TPP-6501 is an antibody comprising a region of the heavy chain corresponding to SEQ ID NO: 29 and a region of the light chain corresponding to SEQ ID NO: 30.

TPP-6502 is an antibody comprising a region of the heavy chain corresponding to SEQ ID NO: 39 and a region of the light chain corresponding to SEQ ID NO: 40.

TPP-6515 is an antibody comprising a region of the heavy chain corresponding to SEQ ID NO: 49 and a region of the light chain corresponding to SEQ ID NO: 50.

TPP-6497 is: an antibody comprising a variable region of the heavy chain corresponding to SEQ ID NO: 1 and a variable region of the light chain corresponding to SEQ ID NO: 5.

TPP-6499 is: an antibody comprising a variable region of the heavy chain corresponding to SEQ ID NO: 11 and a variable region of the light chain corresponding to SEQ ID NO: 15.

TPP-6501 is: an antibody comprising a variable region of the heavy chain corresponding to SEQ ID NO: 21 and a variable region of the light chain corresponding to SEQ ID NO: 25.

TPP-6502 is: an antibody comprising a variable region of the heavy chain corresponding to SEQ ID NO: 31 and a variable region of the light chain corresponding to SEQ ID NO: 35.

TPP-6515 is: an antibody comprising a variable region of the heavy chain corresponding to SEQ ID NO: 41 and a variable region of the light chain corresponding to SEQ ID NO: 45.

TPP-7611 is: an antibody comprising a variable region of the heavy chain corresponding to SEQ ID NO: 1 and a variable region of the light chain corresponding to SEQ ID NO: 5.

TPP-8382 is: an antibody comprising a variable region of the heavy chain corresponding to SEQ ID NO: 55 and a variable region of the light chain corresponding to SEQ ID NO: 57.

TPP-8564 is: an antibody comprising a variable region of the heavy chain corresponding to SEQ ID NO: 55 and a variable region of the light chain corresponding to SEQ ID NO: 57.

TPP-8567 is: an antibody comprising a variable region of the heavy chain corresponding to SEQ ID NO: 55 and a variable region of the light chain corresponding to SEQ ID NO: 57.

TPP-8322 is: an antibody comprising a variable region of the heavy chain corresponding to SEQ ID NO: 63 and a variable region of the light chain corresponding to SEQ ID NO: 35.

TPP-8565 is: an antibody comprising a variable region of the heavy chain corresponding to SEQ ID NO: 63 and a variable region of the light chain corresponding to SEQ ID NO: 35.

TPP-8568 is: an antibody comprising a variable region of the heavy chain corresponding to SEQ ID NO: 63 and a variable region of the light chain corresponding to SEQ ID NO: 35.

TPP-8748 is: an antibody comprising a variable region of the heavy chain corresponding to SEQ ID NO: 63 and a variable region of the light chain corresponding to SEQ ID NO: 68.

TPP-8750 is: an antibody comprising a variable region of the heavy chain corresponding to SEQ ID NO: 63 and a variable region of the light chain corresponding to SEQ ID NO: 68.

Preferred embodiments of the anti-B7H3 antibody for coupling with linkers and/or toxophores according to the invention are the antibodies below:
1. An anti-B7H3 antibody or antigen-binding fragment thereof which binds to a polypeptide as shown in SEQ ID NO: 52, where the antibody is preferably aglycosylated. SEQ ID NO: 52 represents the amino acid sequence of the extracellular domain of the human B7H3 polypeptide.
2. An antibody binding to B7H3 or an antigen-binding fragment thereof, comprising:
   a variable heavy chain comprising the variable CDR1 sequence of the heavy chain, as shown in SEQ ID NO: 2, the variable CDR2 sequence of the heavy chain, as shown in SEQ ID NO: 3, and the variable CDR3 sequence of the heavy chain, as shown in SEQ ID NO: 4 and
   a variable light chain comprising the variable CDR1 sequence of the light chain, as shown in SEQ ID NO: 6, the variable CDR2 sequence of the light chain, as shown in SEQ ID NO: 7, and the variable CDR3 sequence of the light chain, as shown in SEQ ID NO: 8, or
   a variable heavy chain comprising the variable CDR1 sequence of the heavy chain, as shown in SEQ ID NO: 12, the variable CDR2 sequence of the heavy chain, as shown in SEQ ID NO: 13, and the variable CDR3 sequence of the heavy chain, as shown in SEQ ID NO: 14 and
   a variable light chain comprising the variable CDR1 sequence of the light chain, as shown in SEQ ID NO: 16, the variable CDR2 sequence of the light chain, as shown in SEQ ID NO: 17, and the variable CDR3 sequence of the light chain, as shown in SEQ ID NO: 18, or
   a variable heavy chain comprising the variable CDR1 sequence of the heavy chain, as shown in SEQ ID NO: 22, the variable CDR2 sequence of the heavy chain, as shown in SEQ ID NO: 23, and the variable CDR3 sequence of the heavy chain, as shown in SEQ ID NO: 24 and
   a variable light chain comprising the variable CDR1 sequence of the light chain, as shown in SEQ ID NO: 26, the variable CDR2 sequence of the light chain, as shown in SEQ ID NO: 27, and the variable CDR3 sequence of the light chain, as shown in SEQ ID NO: 28, or
   a variable heavy chain comprising the variable CDR1 sequence of the heavy chain, as shown in SEQ ID NO: 32, the variable CDR2 sequence of the heavy chain, as shown in SEQ ID NO: 33, and the variable CDR3 sequence of the heavy chain, as shown in SEQ ID NO: 34 and
   a variable light chain comprising the variable CDR1 sequence of the light chain, as shown in SEQ ID NO: 36, the variable CDR2 sequence of the light chain, as shown in SEQ ID NO: 37, and the variable CDR3 sequence of the light chain, as shown in SEQ ID NO: 38, or
   a variable heavy chain comprising the variable CDR1 sequence of the heavy chain, as shown in SEQ ID NO: 42, the variable CDR2 sequence of the heavy chain, as shown in SEQ ID NO: 43 and the variable CDR3 sequence of the heavy chain, as shown in SEQ ID NO: 44 and
   a variable light chain comprising the variable CDR1 sequence of the light chain, as shown in SEQ ID NO: 46, the variable CDR2 sequence of the light chain, as shown in SEQ ID NO: 47 and the variable CDR3 sequence of the light chain, as shown in SEQ ID NO: 48, or a variable heavy chain comprising the variable CDR1 sequence of the heavy chain, as shown in SEQ ID NO: 2, the variable CDR2 sequence of the heavy chain, as shown in SEQ ID NO: 56 and the variable CDR3 sequence of the heavy chain, as shown in SEQ ID NO: 4 and a variable light chain comprising the variable CDR1 sequence of the light chain, as shown in SEQ ID NO: 6, the variable CDR2 sequence of the light chain, as shown in SEQ ID NO: 58 and the variable CDR3 sequence of the light chain, as shown in SEQ ID NO: 8.

3. The antibody according to embodiment 2, or an antigen-binding fragment thereof, comprising:
   a variable sequence of the heavy chain, as shown in SEQ ID NO:1, and also a variable sequence of the light chain, as shown in SEQ ID NO:5, or
   a variable sequence of the heavy chain, as shown in SEQ ID NO: 11, and also a variable sequence of the light chain, as shown in SEQ ID NO: 15, or
   a variable sequence of the heavy chain, as shown in SEQ ID NO:21, and also a variable sequence of the light chain, as shown in SEQ ID NO:25, or
   a variable sequence of the heavy chain, as shown in SEQ ID NO:31, and also a variable sequence of the light chain, as shown in SEQ ID NO:35, or
   a variable sequence of the heavy chain, as shown in SEQ ID NO: 41, and also a variable sequence of the light chain, as shown in SEQ ID NO: 45, or
   a variable sequence of the heavy chain, as shown in SEQ ID NO: 55 and a variable sequence of the light chain, as shown in SEQ ID NO: 57.

4. The antibody according to any of the preceding embodiments or an antigen-binding fragment thereof, comprising:
   a sequence of the heavy chain, as shown in SEQ ID NO:9, and also a sequence of the light chain, as shown in SEQ ID NO: 10, or
   a sequence of the heavy chain, as shown in SEQ ID NO: 19, and also a sequence of the light chain, as shown in SEQ ID NO:20, or
   a sequence of the heavy chain, as shown in SEQ ID NO:29, and also a sequence of the light chain, as shown in SEQ ID NO: 30, or
   a sequence of the heavy chain, as shown in SEQ ID NO:39, and also a sequence of the light chain, as shown in SEQ ID NO:40, or
   a sequence of the heavy chain, as shown in SEQ ID NO: 49, and also a sequence of the light chain, as shown in SEQ ID NO: 50, or
   a sequence of the heavy chain, as shown in SEQ ID NO: 59 and a sequence of the light chain, as shown in SEQ ID NO: 60, or
   a sequence of the heavy chain, as shown in SEQ ID NO: 61 and a sequence of the light chain, as shown in SEQ ID NO: 60, or
   a sequence of the heavy chain, as shown in SEQ ID NO: 62 and a sequence of the light chain, as shown in SEQ ID NO: 60.

5. The antibody according to any of the preceding embodiments, or an antigen-binding fragment thereof, where the anti-B7H3 antibody is a humanized variant of one of the antibodies TPP-6497, TPP-6499, TPP-6501, TPP-6502, TPP-6515, TPP-7611, TPP-8382, TPP-8564, TPP-8567, TPP-8322, TPP-8565, TPP-8568, TPP-8748 and TPP-8750.

6. The antibody according to any of the preceding embodiments, or an antigen-binding fragment thereof, where the anti-B7H3 antibody is one of the antibodies TPP-8382, TPP-8564 and TPP-8567.

7. The antibody according to any of the preceding embodiments or an antigen-binding fragment thereof, comprising:
   a sequence of the heavy chain, as shown in SEQ ID NO:9, which contains at least one amino acid substitution selected from a group comprising the substitutions R30S, S50A, V51I, A58T, L59Y, T97A, R98K and
   a sequence of the light chain, as shown in SEQ ID NO: 10, which contains at least one amino acid substitution selected from a group comprising the substitutions P33T, G51S, S53N, N54Q, S77T, R80Q, S81A, Q90A, S91A, F92W, F92Y, S94D, K97N, K97S, K98G, K105Q, or
   a sequence of the heavy chain, as shown in SEQ ID NO: 19, which contains at least one amino acid substitution selected from a group comprising the substitutions R30S, D31S, F32Y, Y33A, N35S, I37V, S50A, S50Y, A53G, A53S, K56G, K56S, Y57S, Y57T, P114S, P114Y and
   a sequence of the light chain, as shown in SEQ ID NO:20, which contains at least one amino acid substitution selected from a group comprising the substitutions G25S, Y26S, V29I, G31S, N33Y, N33T, N35Y, G51R, S53N, N54Q, S77T, R80Q, S81A, Q90A, S91A, Y92W, S94D, K106Q, or
   a sequence of the heavy chain, as shown in SEQ ID NO: 29, which contains at least one amino acid substitution selected from a group comprising the substitutions G33A, H35S, N101Y, L103Y, L103N, L113T and
   a sequence of the light chain, as shown in SEQ ID NO:30, which contains at least one amino acid substitution selected from a group comprising the substitutions R31S, I33Y, I33T, N35Y, S52N, Q90A, T91A, G93D, T94D, G95S, W96L, V97S, F98G, K103Q, or
   a sequence of the heavy chain, as shown in SEQ ID NO:39, which contains at least one amino acid substitution selected from a group comprising the substitutions T31S, G33A, H35S, T97A, R98K, L113T and
   a sequence of the light chain, as shown in SEQ ID NO:40, which contains at least one amino acid substitution selected from a group comprising the substitutions G25S, P33Y, P33T, N35Y, G51R, S53N, K54Q, Q90A, S91A, Y92W, S94D, W99V, G103E, K106E, or
   a sequence of the heavy chain, as shown in SEQ ID NO:49, which contains at least one amino acid substitution selected from a group comprising the substitutions G33A, H35S, V40A, T57S, L104Y, L104W, Y107S and
   a sequence of the light chain, as shown in SEQ ID NO: 50, which contains at least one amino acid substitution selected from a group comprising the substitutions T33Y, N35Y, D53N, L56P, L57S, Q90A, S91A, Y92W, S94D, W99V, G103E, K106E.

8. The antibody according to any of the preceding embodiments which is an IgG antibody.

9. The antibody according to any of the preceding embodiments, comprising: The antigen-binding fragment according to any of the preceding embodiments or an antigen-binding fragment of an antibody according to any of the preceding embodiments which is an scFv, Fab, Fab fragment or a F(ab)₂ fragment.

10. The antibody or the antigen-binding fragment according to any of the preceding embodiments which is a monoclonal antibody or an antigen-binding fragment thereof.

11. The antibody or the antigen-binding fragment according to any of the preceding embodiments which is a human, humanized or chimeric antibody or an antigen-binding fragment.

Particular preference is given to the anti-B7H3 antibodies TPP-6497, TPP-6499, TPP-6501, TPP-6502 and TPP-6515. Accordingly, the present invention also provides humanized variants of the anti-B7H3 antibodies according to the invention having the amino acid substitutions listed below, where P33T means a substitution of P by T in amino acid position 33 of the respective chain of the antibody, G51S means a substitution of G by S in position 51 of the respective chain of the antibody in question, etc.

| Anti-B7H3 antibody | Localization of the substitution | Amino acid substitutions |
|---|---|---|
| TPP-6497 | light chain | P33T, G51S, S53N, N54Q, S77T, R80Q, S81A, Q90A, S91A, F92W, F92Y, S94D, K97N, K97S, K98G, K105Q |
|  | heavy chain | R30S, S50A, V51I, A58T, L59Y, T97A, R98K |
| TPP-6499 | light chain | G25S, Y26S, V29I, G31S, N33Y, N33T, N35Y, G51R, S53N, N54Q, S77T, R80Q, S81A, Q90A, S91A, Y92W, S94D, K106Q |
|  | heavy chain | R30S, D31S, F32Y, Y33A, N35S, I37V, S50A, S50Y, A53G, A53S, K56G, K56S, Y57S, Y57T, P114S, P114Y |
| TPP-6501 | light chain | R31S, I33Y, I33T, N35Y, S52N, Q90A, T91A, G93D, T94D, G95S, W96L, V97S, F98G, K103Q. |
|  | heavy chain | G33A, H35S, N101Y, L103Y, L103N, L113T |
| TPP-6502 | light chain | G25S, P33Y, P33T, N35Y, G51R, S53N, K54Q, Q90A, S91A, Y92W, S94D, W99V, G103E, K106E |
|  | heavy chain | T31S, G33A, H35S, T97A, R98K, L113T |
| TPP-6515 | light chain | T33Y, N35Y, D53N, L56P, L57S, Q90A, S91A, Y92W, S94D, W99V, G103E, K106E |
|  | heavy chain | G33A, H35S, V40A, T57S, L104Y, L104W, Y107S |

Isotopes, Salts, Solvates, Isotopic Variants

The present invention also encompasses all suitable isotopic variants of the compounds of the invention. An isotopic variant of a compound of the invention is understood here to mean a compound in which at least one atom within the compound of the invention has been exchanged for another atom of the same atomic number, but with a different atomic mass from the atomic mass which usually or predominantly occurs in nature. Examples of isotopes which can be incorporated into a compound of the invention are those of hydrogen, carbon, nitrogen, oxygen, phosphorus, sulphur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$I, $^{124}$I, $^{129}$I and $^{131}$I. Particular isotopic variants of a compound of the invention, especially those in which one or more radioactive isotopes have been incorporated, may be beneficial, for example, for the examination of the mechanism of action or of the active ingredient distribution in the body; due to comparatively easy preparability and detectability, especially compounds labelled with $^3$H or $^{14}$C isotopes are suitable for this purpose.

In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds of the invention may therefore in some cases also constitute a preferred embodiment of the present invention. Isotopic variants of the compounds of the invention can be prepared by the processes known to those skilled in the art, for example by the methods described further down and the procedures described in the working examples, by using corresponding isotopic modifications of the respective reagents and/or starting compounds.

Preferred salts in the context of the present invention are physiologically acceptable salts of the compounds according to the invention. Also encompassed are salts which are not themselves suitable for pharmaceutical applications but can be used, for example, for isolation or purification of the compounds of the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, benzenesulphonic acid, toluenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylpiperidine, N-methylmorpholine, arginine, lysine and 1,2-ethylenediamine.

Designated as solvates in the context of the invention are those forms of the compounds according to the invention which form a complex in the solid or liquid state by coordination with solvent molecules. Hydrates are a specific form of the solvates in which the coordination is with water. Solvates preferred in the context of the present invention are hydrates.

The present invention additionally also encompasses prodrugs of the compounds of the invention. The term "prodrugs" in this context refers to compounds which may themselves be biologically active or inactive but are converted (for example metabolically or hydrolytically) to compounds of the invention during their residence time in the body.

Particular Embodiments

The following embodiments are particularly preferred:

Embodiment A

An ADC of the formula $$\text{BINDER} - [\text{L} - \text{KSP}]_n$$

where KSP-L- represents a compound of the formula (I), (Ia), (II), (IIa), (IIb), (IIc), (IId), (IIe), (IIi), (IIj), (IIk) below or of the formula (IIf) below, the binder is an anti-B7H3 antibody, which can be aglycosylated, or an antigen-binding fragment thereof. Particular preference is given here to anti-B7H3 antibodies which specifically bind the human Ig4 and/or the human and/or murine Ig2 isoform of B7H3, in particular the anti-B7H3 antibodies TPP-6497, TPP-6499, TPP-6501, TPP-6502, TPP-6515, where n represents a number from 1 to 10:

Formula (IIf):

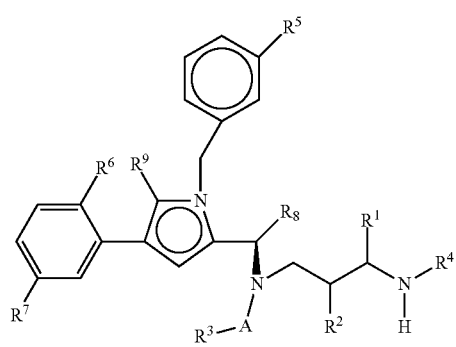

(IIf)

where

A represents CO (carbonyl);

$R^1$ represents -L-#1, H, —COOH, —CONHNH$_2$, —(CH$_2$)$_{1-3}$NH$_2$, —CONZ"(CH$_2$)$_{1-3}$ NH$_2$ and —CONZ"CH$_2$COOH, where Z" represents H or NH$_2$;

$R^2$ and $R^4$ represent H, or $R^2$ and $R^4$ together (with formation of a pyrrolidine ring) represent —CH$_2$—CHR$^{11}$— or —CHR$^{11}$—CH$_2$—, where $R^{11}$ represents H;

$R^3$ represents -L-#1 or a C1-10-alkyl-, which may optionally be substituted by —OH, O-alkyl, SH, S-alkyl, O—CO-alkyl, O—CO—NH-alkyl, NH—CO-alkyl, NH—CO—NH-alkyl, S(O)$_n$-alkyl, SO$_2$—NH— alkyl, NH-alkyl, N(alkyl)$_2$ or NH$_2$ (where alkyl is preferably C$_{1-3}$-alkyl);

$R^5$ represents H or F;

$R^6$ and $R^7$ independently of one another represent H, (optionally fluorinated) C$_{1-3}$-alkyl, (optionally fluorinated) C$_{2-4}$-alkenyl, (optionally fluorinated) C$_{2-4}$-alkynyl, hydroxy or halogen;

$R^8$ represents a branched C$_{1-5}$-alkyl group; and $R^9$ represents H or F, where one of the substituents $R^1$ and $R^3$ represents -L-#1, and -L- represents the linker and #1 represents the bond to the antibody, and salts, solvates and salts of the solvates of the ADC.

The linker is preferably a linker

§ —(CO)m-L1-L2-§ § where m represents 0 or 1;

§ represents the bond to KSP and

§ § represents the bond to the antibody, and

L2 represents

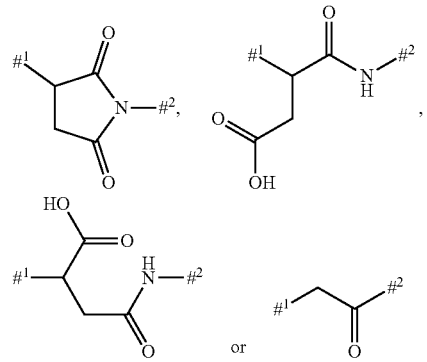

where

$^1$ denotes the point of attachment to the sulphur atom of the antibody,

$^2$ denotes the point of attachment to group L$^1$, and L1 is represented by formula

$^1$—(NR$^{10}$)$_n$-(G1)$_o$-G2-#$^2$ where $R^{10}$ represents H, NH$_2$ or C1-C3-alkyl;

G1 represents —NHCO— or

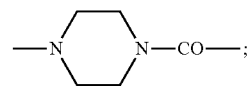

n represents 0 or 1;

o represents 0 or 1; and

G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO$_2$, —NH—, —CO—, —NHCO—, —CONH—, —NMe-, —NHNH—, —SO$_2$NHNH—, —CONHNH— and a 3- to 10-membered aromatic or non-aromatic heterocycle having up to 4 heteroatoms selected from the group consisting of N, O and S, or —SO— (preferably

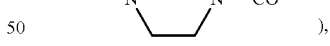

), where the Side chains, if present, may be substituted by —NHCONH$_2$, —COOH, —OH, —NH$_2$, NH—CNNH$_2$, sulphonamide, sulphone, sulphoxide or sulphonic acid.

Here, #1 is the bond to the KSP inhibitor and #2 is the bond to the coupling group to the antibody (e.g. L2).

Embodiment B

An ADC of the formula

BINDER—[L—KSP]$_n$ where KSP-L- represents a compound of the formula (I), (Ia), (II), (IIa), (IIb), (IIc), (IId), (IIe), (IIf), (IIi), (IIj), (IIk)

below or of the formula (IIg) below, the binder is an anti-B7H3 antibody which in a preferred embodiment is aglycosylated, and n represents a number from 1 to 10:

Formula (IIg):

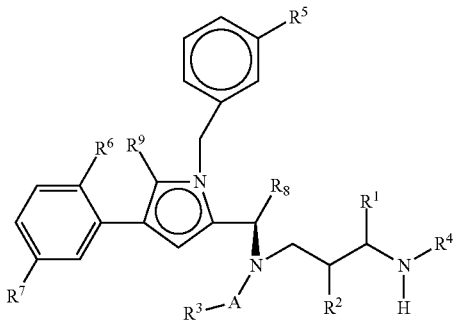

(IIg)

where

A represents —C(=O)—;

R$^1$ represents -L-#1, H, —COOH, —CONHNH$_2$, —(CH$_2$)$_{1-3}$NH$_2$, —CONZ"(CH$_2$)$_{1-3}$ NH$_2$ and —CONZ"CH$_2$COOH, where Z" represents H or NH$_2$;

R$^2$ and R$^4$ represent H, or R$^2$ and R$^4$ together (with formation of a pyrrolidine ring) represent —CH$_2$—CHR$^{11}$— or —CHR$^{11}$—CH$_2$—, where R$^{11}$ represents H;

R$^3$ represents -L-#1 or a C$_{1-10}$-alkyl-, which may optionally be substituted by —OH, O-alkyl, SH, S-alkyl, O—CO-alkyl, O—CO—NH-alkyl, NH—CO-alkyl, NH—CO—NH-alkyl, S(O)$_n$-alkyl, SO$_2$—NH-alkyl, NH-alkyl, N(alkyl)$_2$ or NH$_2$ (where alkyl is preferably C$_{1-3}$-alkyl);

R$^5$ represents H or F;

R$^6$ and R$^7$ independently of one another represent H, (optionally fluorinated) C$_{1-3}$-alkyl, (optionally fluorinated) C$_{2-4}$-alkenyl, (optionally fluorinated) C$_{2-4}$-alkynyl, hydroxy or halogen;

R$^8$ represents a branched C$_{1-5}$-alkyl group; and

R$^9$ represents H or F, where one of the substituents R$^1$ and R$^3$ represents -L-#1, and -L- represents the linker and #1 represents the bond to the antibody, where -L- is represented by § —(CO)$m$-L1-L2-§ § where m represents 0 or 1;

§ represents the bond to KSP and

§ § represents the bond to the antibody, and

L2 represents

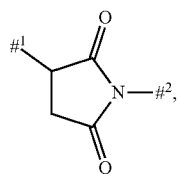

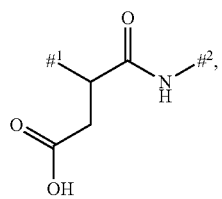

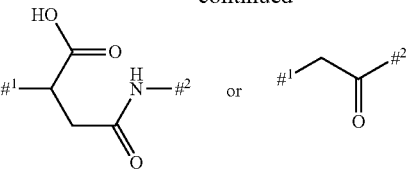

where

$^1$ denotes the point of attachment to the sulphur atom of the antibody,

$^2$ denotes the point of attachment to group L$^1$, and L1 is represented by formula

$^1$—(NR$^{10}$)$_n$-(G1)$_o$-G2-#$^2$ where

R$^{10}$ represents H, NH$_2$ or C1-C3-alkyl;

G1 represents —NHCO— or

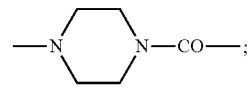

n represents 0 or 1;

o represents 0 or 1; and

G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, SO$_2$, —NH—, —CO—, —NHCO—, —CONH—, —NMe-, —NHNH—, —SO$_2$NHNH—, —CONHNH— and a 3- to 10-membered aromatic or non-aromatic heterocycle having up to 4 heteroatoms selected from the group consisting of N, O and S, or —SO— (preferably

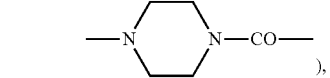), where the side chains, if present, may be substituted by —NHCONH$_2$, —COOH, —OH, —NH$_2$, NH—CNNH$_2$, sulphonamide, sulphone, sulphoxide or sulphonic acid,

$^1$ is the bond to the KSP inhibitor and #$^2$ is the bond to the coupling group to the antibody (e.g. L2), and salts, solvates and salts of the solvates of the ADC.

Embodiment C

An ADC of the formula

BINDER—[L—KSP]$_n$ where KSP-L- represents a compound of the formula (II), (IIa), (IIb), (IIc), (IId), (IIe), (IIf), (IIg), (IIi), (IIj), (IIk) below or of the formula (IIh) below, the binder is an anti-B7H3 antibody which in a preferred embodiment is aglycosylated, and n represents a number from 1 to 10:

Formula (IIh):

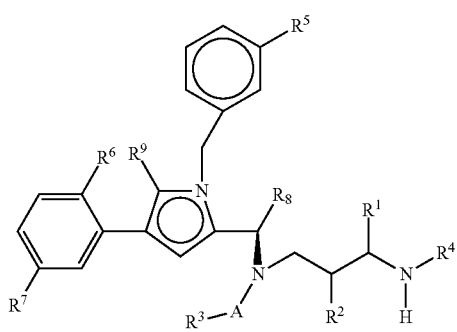

where
A represents CO (carbonyl);
$R^1$ represents -L-#1;
$R^2$ and $R^4$ represent H, or $R^2$ and $R^4$ together (with formation of a pyrrolidine ring) represent —$CH_2$—$CHR^{11}$— or —$CHR^{11}$—$CH_2$—, where $R^{11}$ represents H;
$R^3$ represents $C_{1-10}$-alkyl-, which may optionally be substituted by —OH, O-alkyl, SH, S-alkyl, O—CO-alkyl, O—CO—NH-alkyl, NH—CO-alkyl, NH—CO—NH-alkyl, $S(O)_n$-alkyl, $SO_2$—NH-alkyl, NH-alkyl, N(alkyl)$_2$ or $NH_2$ (where alkyl is preferably $C_{1-3}$-alkyl), or -MOD;
where -MOD represents —$(NR^{10})_n$-$(G1)_o$-G2-G3, where $R^{10}$ represents H or $C_1$-$C_3$-alkyl;
G1 represents —NHCO— or —CONH— (where, if G1 represents —NHCO—, $R^{10}$ does not represent $NH_2$);
n represents 0 or 1;
o represents 0 or 1; and
G2 represents a straight-chain or branched hydrocarbon group which has 1 to 10 carbon atoms and which may be interrupted once or more than once by one or more of the groups —O—, —S—, —SO—, S02, —NRy-, —NRyCO—, CONRy-, —NRyNRy-, —$SO_2$NRyNRy-, —CONRyNRy- (where $R^y$ represents H, phenyl, C1-C10-alkyl, C2-C10-alkenyl or C2-C10-alkynyl, each of which may be substituted by $NHCONH_2$, —COOH, —OH, —$NH_2$, NH—$CNNH_2$, sulphonamide, sulphone, sulphoxide or sulphonic acid), —CO—, —$CR^x$=N—O— (where Rx represents H, C1-C3-alkyl or phenyl), where the hydrocarbon chain including any side chains may be substituted by —$NHCONH_2$, —COOH, —OH, —$NH_2$, NH—$CNNH_2$, sulphonamide, sulphone, sulphoxide or sulphonic acid, G3 represents —H or —COOH, where the group -MOD preferably has at least one group —COOH;
$R^5$ represents H or F;
$R^6$ and $R^7$ independently of one another represent H, (optionally fluorinated) $C_{1-3}$-alkyl, (optionally fluorinated) $C_{2-4}$-alkenyl, (optionally fluorinated) $C_{2-4}$-alkynyl, hydroxy or halogen;
$R^8$ represents a branched $C_{1-5}$-alkyl group; and
$R^9$ represents H or F,
where -L- represents the linker and #1 represents the bond to the antibody,
where -L- is represented by § —(CO)m-L1-L2-§ § where
m represents 0 or 1;
§ represents the bond to KSP and
§ § represents the bond to the antibody, and L2 represents

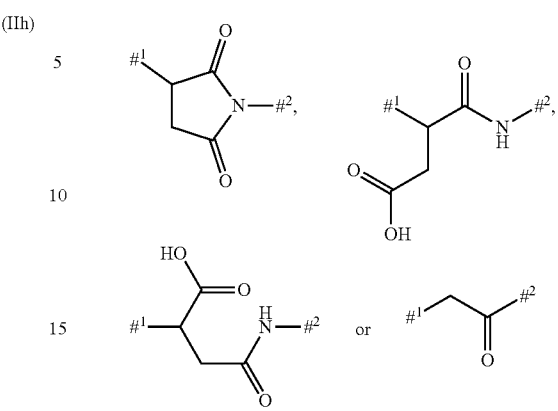

where
$^1$ denotes the point of attachment to the sulphur atom of the antibody,
$^2$ denotes the point of attachment to group $L^1$,
and L1 is represented by formula

$^1$—$(NR^{10})_n$-$(G1)_o$-G2-#$^2$ where
$R^{10}$ represents H, $NH_2$ or C1-C3-alkyl;
G1 represents-NHCO— or

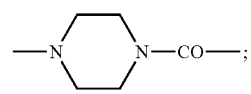

n represents 0 or 1;
o represents 0 or 1; and
G2 represents a straight-chain or branched hydrocarbon chain having 1 to 100 carbon atoms from arylene groups and/or straight-chain and/or branched and/or cyclic alkylene groups and which may be interrupted once or more than once by one or more of the groups —O—, —S—, —SO—, $SO_2$, —NH—, —CO—, —NHCO—, —CONH—, —NMe-, —NHNH—, —$SO_2$NHNH—, —CONHNH—, —$CR^x$=N—O— (where Rx represents H, C1-C3-alkyl or phenyl) and a 3- to 10-membered aromatic or non-aromatic heterocycle having up to 4 heteroatoms selected from the group consisting of N, O and S, —SO— or —$SO_2$-(preferably

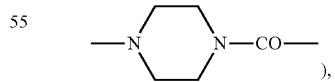

), where the hydrocarbon chain including the side chains, if present, may be substituted by —$NHCONH_2$, —COOH, —OH, —$NH_2$, NH—$CNNH_2$, sulphonamide, sulphone, sulphoxide or sulphonic acid,
1 is the bond to the KSP inhibitor and #2 is the bond to the coupling group to the antibody (e.g. L2),
and salts, solvates, salts of the solvates and epimers of the ADC.

Embodiment D

The invention also provides binder/active compound conjugates of the general formula below:

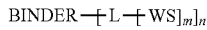
BINDER—[L—[WS]$_m$]$_n$ where BINDER represents the (preferably aglycosylated) anti-B7H3 antibody, L represents the linker, WS represents the active compound, preferably a KSP inhibitor such as, for example, a KSP inhibitor according to the invention of one of the formulae (I), (Ia), (II), (IIa), (IIb), (IIc), (IId), (IIe), (IIf), (IIg), (IIh) or (IIi), m represents a number from 1 to 2, preferably 1, and n represents a number from 1 to 50, preferably from 1.2 to 20 and particularly preferably from 2 to 8, where L has one of the structures below. Here, m represents the number of active compound molecules per linker and n a mean of the number of active compound/linker conjugates per BINDER. The sum of all WS present in a conjugate molecule is therefore the product of m and n.

WS is an active compound which has local or systemic therapeutic action in animals, preferably in humans. These active compounds generally have a molecular weight below 5 kDa, preferably below 1.5 kDa. Preferred active compounds are vinca alkaloids, auristatins, tubulysins, duocarmycins, kinase inhibitors, MEK inhibitors and KSP inhibitors.

Here, L represents one of the formulae A3 and A4 below

Formula A3
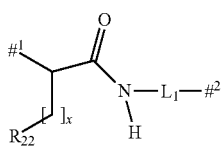

Formula A4
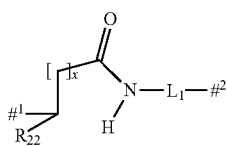

where #$^1$ denotes the point of attachment to the sulphur atom of the binder, #$^2$ denotes the point of attachment to the active compound, x represents 1 or 2, and R22 represents COOH, COOR, COR (where R in each case represents C1-3-alkyl), CONH$_2$, Br, preferably COOH.
L1 has the same meaning as above. Preferably, -L1-#$^2$ is represented by the formula below:

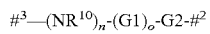
$^3$—(NR$^{10}$)$_n$-(G1)$_o$-G2-#$^2$ where
3 denotes the point of attachment to the nitrogen atom,
R$^{10}$ represents H, NH$_2$ or C$_1$-C$_3$-alkyl;
G1 represents —NHCO—, —CONH— or

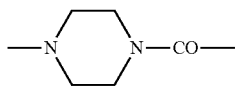

(where, if G1 represents NHCO or

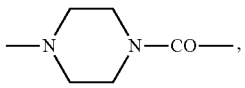

R10 does not represent NH$_2$),
n represents 0 or 1;
o represents 0 or 1; and
G2 represents a straight-chain or branched hydrocarbon chain which has 1 to 100 carbon atoms from arylene groups and/or straight-chain and/or branched and/or cyclic alkylene groups and which may be interrupted once or more than once by one or more of the groups —O—, —S—, —SO—, SO$_2$, —NRy-, —NRyCO—, —C(NH)NRy-, CONRy-, —NRyNRy-, —SO$_2$NRyNRy-, —CONRyNRy- (where R$^y$ represents H, phenyl, C1-C10-alkyl, C2-C10-alkenyl or C2-C10-alkynyl, each of which may be substituted by NHCONH$_2$, —COOH, —OH, —NH$_2$, NH—CNNH$_2$, sulphonamide, sulphone, sulphoxide or sulphonic acid), —CO—, —CR$^x$=N—O— (where R$^x$ represents H, C1-C3-alkyl or phenyl) and/or a 3- to 10-membered aromatic or non-aromatic heterocycle having up to 4 heteroatoms selected from the group consisting of N, O and S, —SO— or —SO$_2$— (preferably

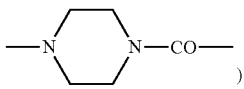

), where the hydrocarbon chain including any side chains may be substituted by —NHCONH$_2$, —COOH, —OH, —NH$_2$, NH—CNNH$_2$, sulphonamide, sulphone, sulphoxide or sulphonic acid.

Further interrupting groups in G2 are preferably

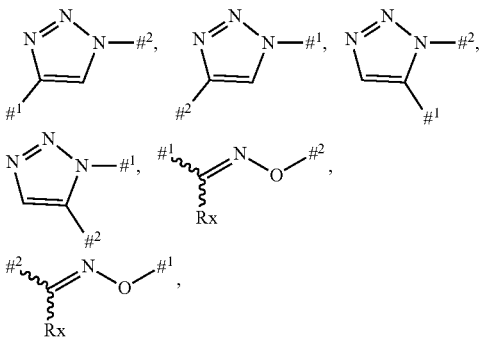

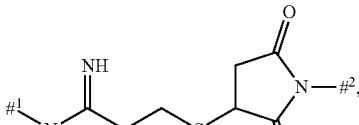

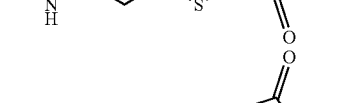

where R$^x$ represents H, C$_1$-C$_3$-alkyl or phenyl.

In the conjugate according to the invention or in a mixture of the conjugates according to the invention, the bonds to a cysteine residue of the antibody are present, to an extent of preferably more than 80%, particularly preferably more than 90% (in each case based on the total number of bonds of the linker to the antibody) as one of the two structures of the formula A3 or A4.

The conjugates with the linkers of formula A3 or A4 can be obtained by coupling the antibodies to the appropriate bromine derivatives of the formulae A3' and A4', respectively, below:

Formula A3'

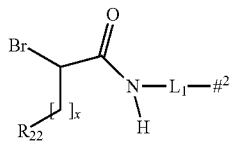

Formula A4'

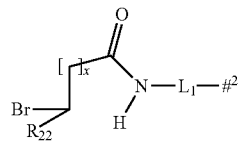

These bromine derivatives of the formula A3' or A4' can be obtained by reacting $HOOCCH_2CHBrCOOR_{22}$ or $HOOCCHBrCH_2COOR_{22}$ with an amine group of the binder, as illustrated in an exemplary manner in Schemes 30 to 32 below.

Scheme 30

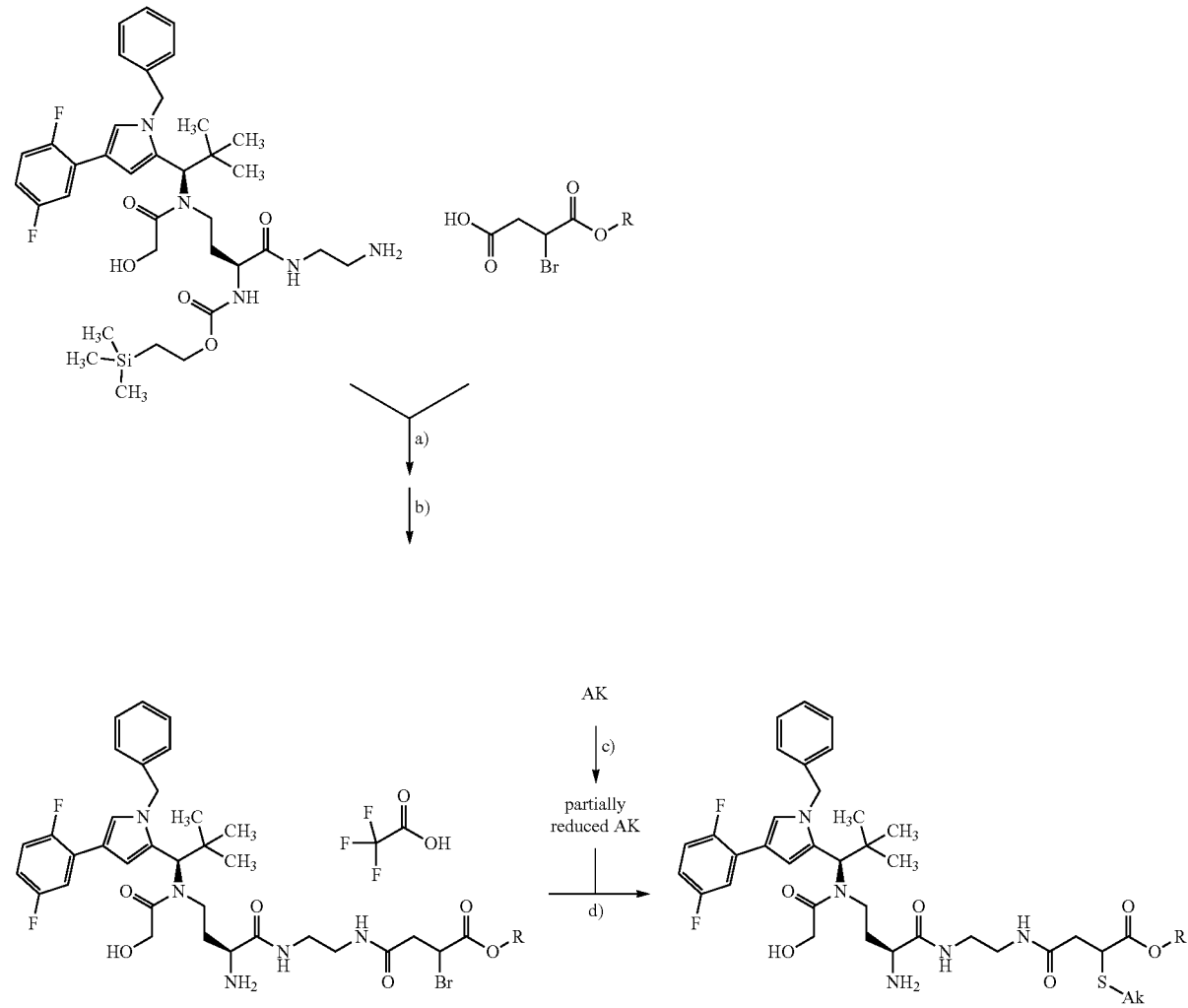

R = CH$_3$

[a): 2-bromo-1-ethylpyridinium tetrafluoroborate (BEP), DCM, pyridine, RT; b) zinc chloride, trifluoroethanol, 50° C., EDTA; c) 3-4 equivalents of TCEP, PBS buffer; d) PBS buffer, 20 h RT.]

Scheme 31
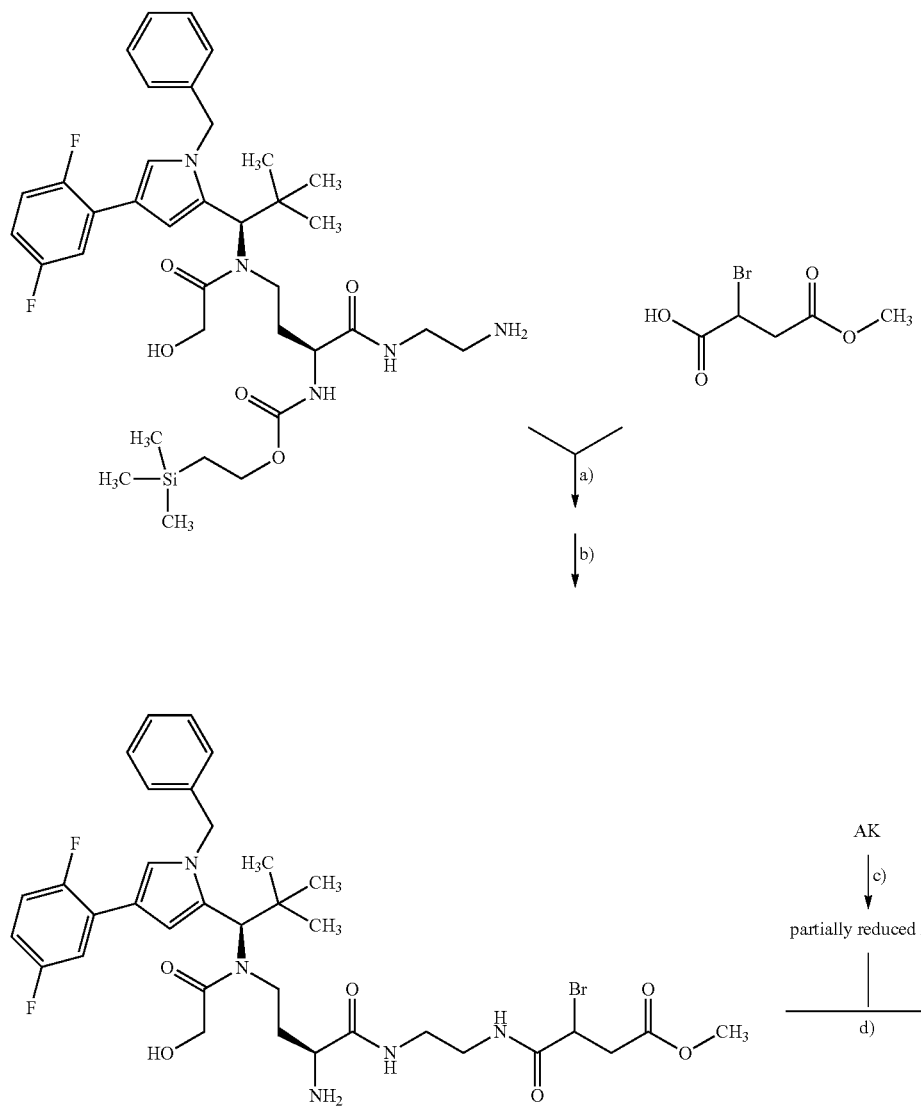
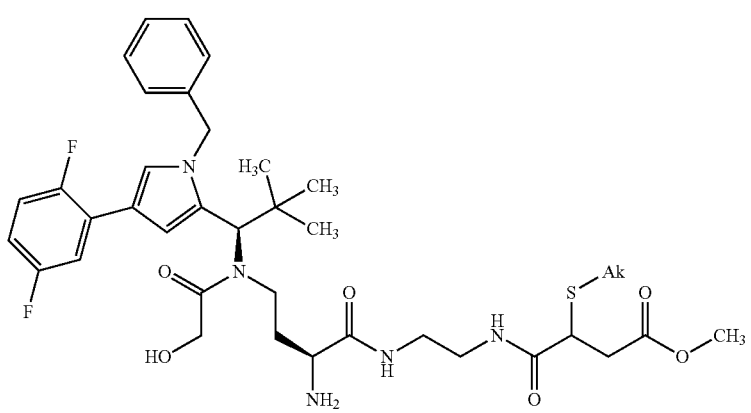
[a]: 2-bromo-1-ethylpyridinium tetrafluoroborate (BEP), DCM, pyridine, RT; b) zinc chloride, trifluoroethanol, 50° C., EDTA; c) 3-4 equivalents of TCEP, PBS buffer; d) PBS buffer, 20 h RT.]

Embodiment E

The invention also provides binder/active compound conjugates of the general formula below:

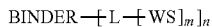

where BINDER represents the preferably aglycosylated anti-B7H3 antibody, L represents the linker, WS represents the active compound, preferably a KSP inhibitor such as, for example, a KSP inhibitor according to the invention of one of the formulae (I), (Ia), (II), or (IIa), m represents a number from 1 to 2, preferably 1, and n represents a number from 1 to 50, preferably from 1.2 to 20 and particularly preferably from 2 to 8, where L has one of the structures below. Here, m represents the number of active compound molecules per linker and n a mean of the number of active compound/linker conjugates per BINDER. The sum of all WS present in a conjugate molecule is therefore the product of m and n.

Here, L represents:

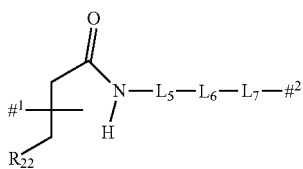

Formula A where $\#^1$ denotes the point of attachment to the sulphur atom of the antibody, $\#^2$ denotes the point of attachment to the active compound and $R^{22}$ represents COOH, COOR, COR (where R in each case represents $C_{1-3}$-alkyl), $CONH_2$, Br, preferably COOH. The link to the sulphur atom of the binder may thus have one of the structures below:

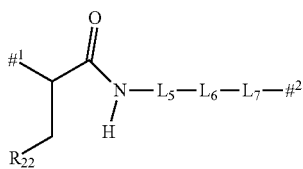

Formula A1

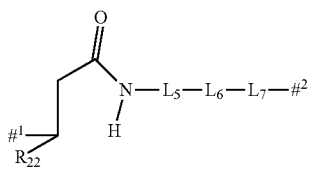

Formula A2

In the case of antibody drug conjugates containing more than one active compound molecule WS per antibody drug conjugate, both structures according to the formulae A1 and/or A2 may be present in an antibody drug conjugate. Since the antibody drug conjugates according to the invention may be mixtures of different antibody drug conjugates, it is also possible for this mixture to comprise both antibody drug conjugates of formula A1 or formula A2 and those of formula A1 and A2.

$L_5$ is a group selected from $-(CH_2)_m-(CHRS)_n-(OCH_2CH_2)_o-(X)_p-(CH_2)_q-$, where m, n, o, p and q independently of one another have the following values: m=0-10; n=0 or 1; o=0-10; p=0 or 1; and q=0-10, where m+n+o=1-15, preferably 1-6. X represents a 5- or 6-membered aromatic or nonaromatic hetero- or homocycle, preferably $-C_6H_4-$ or $-C_6H_{10}-$. RS represents an acid group, preferably —COOH or $SO_3H$.

$L_6$ is a group selected from —CONH—, —OCONH—, —NHCO—, —NHCOO—,

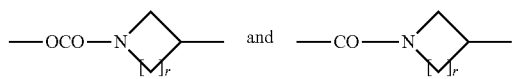

where r is 1, 2 or 3.

$L_7$ is a single bond or a group selected from a straight-chain or branched hydrocarbon chain which has 1 to 100 (preferably 1 to 10) carbon atoms from arylene groups and/or straight-chain and/or branched and/or cyclic alkylene groups and which may be interrupted once or more than once by one or more of the groups —O—, —S—, —SO—, $SO_2$, —NRy-, —NRyCO—, —C(NH)NRy-, CONRy-, —NRyNRy-, —$SO_2$NRyNRy-, —CONRyNRy- (where $R^y$ represents H, phenyl, $C_1$-$C_{10}$-alkyl, C2-C10-alkenyl or C2-C10-alkynyl, each of which may be substituted by $NHCONH_2$, —COOH, —OH, —$NH_2$, NH—$CNNH_2$, sulphonamide, sulphone, sulphoxide or sulphonic acid), —CO—, —$CR^x$=N—O -(where Rx represents H, C1-C3-alkyl or phenyl) and/or a 3- to 10-membered, preferably 5- to 10-membered aromatic or non-aromatic heterocycle having up to 4 heteroatoms selected from the group consisting of N, O and S, —SO— or —$SO_2$—, where the hydrocarbon chain including any side chains may be substituted by —$NHCONH_2$, —COOH, —OH, —$NH_2$, NH—$CNNH_2$, sulphonamide, sulphone, sulphoxide or sulphonic acid.

$L_5$ is preferably a group $-(CH_2)_m-(CHRS)_n-(OCH_2CH_2)_o-(X)_p-(CH_2)_q-$ where m=1-3, n=0, o=0-7, p=0 and q=0 or 1. Particular preference is given to a group $-(CH_2)_m-(CHRS)_n-(OCH_2CH_2)_o-(X)_p-(CH_2)_q-$ where m=1 or 2, n=0, o=0 or 1, p=0 and q=0 or 1.

$L_6$ is preferably a group selected from —CONH— and —NHCO—.

$L_7$ is preferably a single bond or $-[(CH_2)_x-(X^4)_y]w-(CH_2)_z-$, where
w=0 to 20;
x=0 to 5;
y=0 or 1;
z=1 to 5; and
$X^4$ represents —O—, —CONH—, —NHCO— or

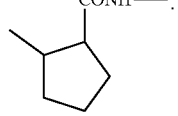

Particularly preferably, $L_7$ is a single bond or a group $-[(CH_2)_x-NHCO-]$, where x=1 to 5.

Particularly preferably, -$L_5$-$L_6$-$L_7$- represents $-(CH_2)_m-(CHRS)_n-(OCH_2CH_2)_o-(X)_p-(CH_2)_q-$NHCO$-[(CH_2)_x-NHCO-)]$, where m=1 or 2, n=0, o=0 or 1, p=0, and q=0 or 1, and x=1-5.

However, it is also possible that these two structures are jointly present in the conjugate according to the invention.

According to the invention, these antibody drug conjugates can be prepared from the compounds of the formula

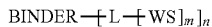

where L has the formula A' below:

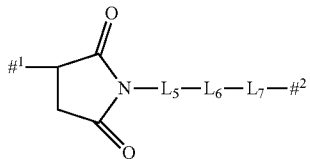

Formula A'

Preferably, the conversion of A' into A is carried out by stirring in a pH buffer having a pH of from 7.5 to 8.5, preferably 8, at a temperature below 37° C., preferably from 10 to 25° C., over a period of up to 40 hours, preferably 1 to 15 hours.

Embodiment I

An antibody conjugate of the formula

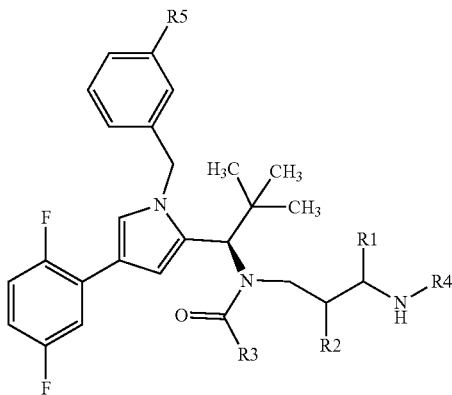

where
R2, R4 and R5 represent H;
R3 represents —CH$_2$OH;
R1 represents-L1-L2-BINDER, where
L1 represents

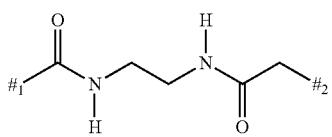

where #2 represents the attachment to L2 and #1 represents the attachment to the other attachment;
and L2 represents one or both of the structures of the formulae A5 and A6 below:

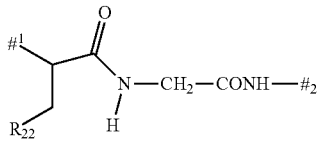

Formula A5

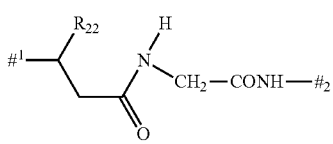

Formula A6 where
$^1$ denotes the point of attachment to the sulphur atom of the antibody,
$^2$ denotes the point of attachment to group L$^1$, and
R$^{22}$ represents COOH, COOR, COR, CONHR (where R in each case represents C1-3-alkyl), CONH$_2$, preferably COOH.

In a conjugate according to the invention or in a mixture of the conjugates according to the invention, the bonds to a cysteine residue of the antibody are present, to an extent of preferably more than 80%, particularly preferably more than 90% (in each case based on the total number of bonds of the linker to the antibody), particularly preferably as one of the two structures of the formula A5 or A6:

Here, the structures of the formula A5 or A6 are generally present together, preferably in a ratio of from 60:40 to 40:60, based on the number of bonds to the antibody. The remaining bonds are then present as the structure

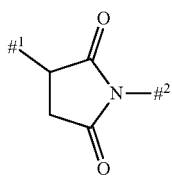

The antibody is preferably an anti-B7H3 antibody or an antigen-binding fragment thereof which specifically binds the human Ig4 and/or murine Ig2 isoform of B7H3, in particular the anti-B7H3 antibodies TPP-6497, TPP-6499, TPP-6501, TPP-6502, TPP-6515. In a preferred embodiment, the anti-B7H3 antibody is present in aglycosylated form.

Specific Embodiments

Antibody conjugates according to one of the formulae below are provided, where n is a number from 1 to 20 and AK and AK$_2$ are antibodies. AK represents an antibody linked via cysteine, AK$_2$ an antibody linked via lysine.

The antibody (AK or AK$_2$) is preferably an anti-B7H3 antibody or an antigen-binding fragment thereof, which specifically binds the human Ig4 and/or the human and/or murine Ig2 isoform of B7H3, particularly the anti-B7H3 antibodies TPP-6497, TTP-6499, TPP-6501, TPP-6502, TPP-6515, TPP-7611, TPP-8382, TPP-8564, TPP-8567, TPP-8322, TPP-8565, TPP-8568, TPP-8748 and TPP-8750. In a preferred embodiment, the anti-B7H3 antibody is aglycosylated.

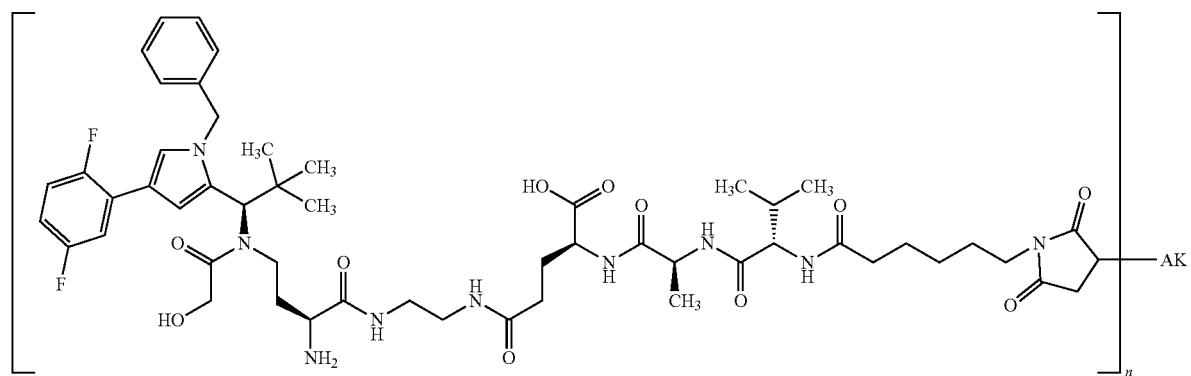
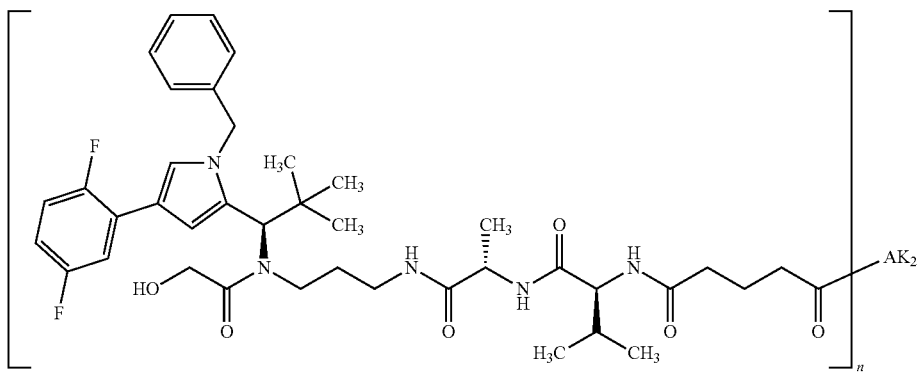
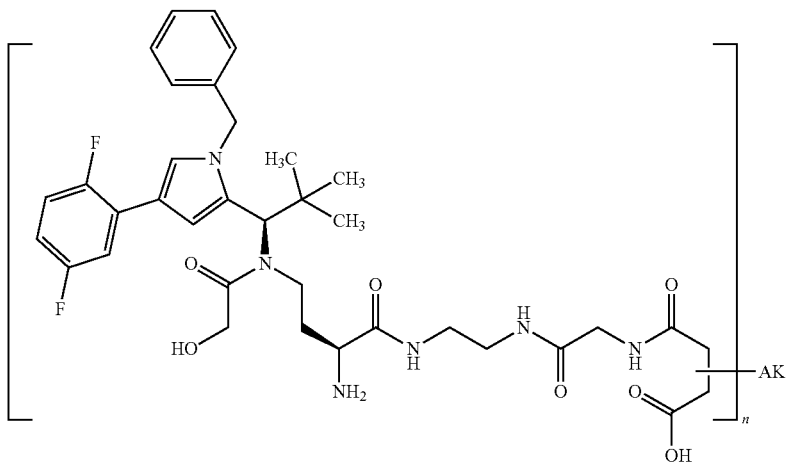
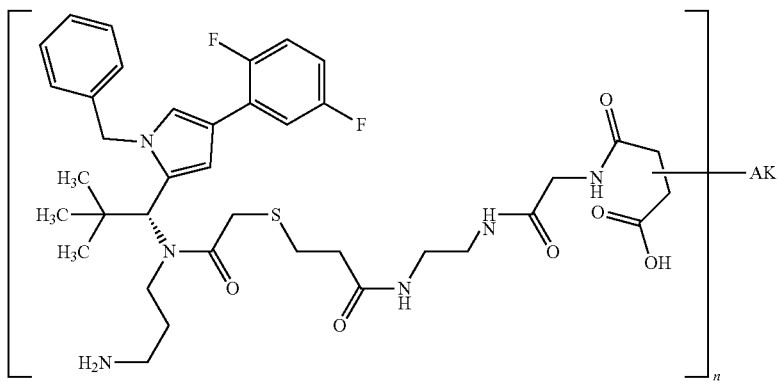

-continued
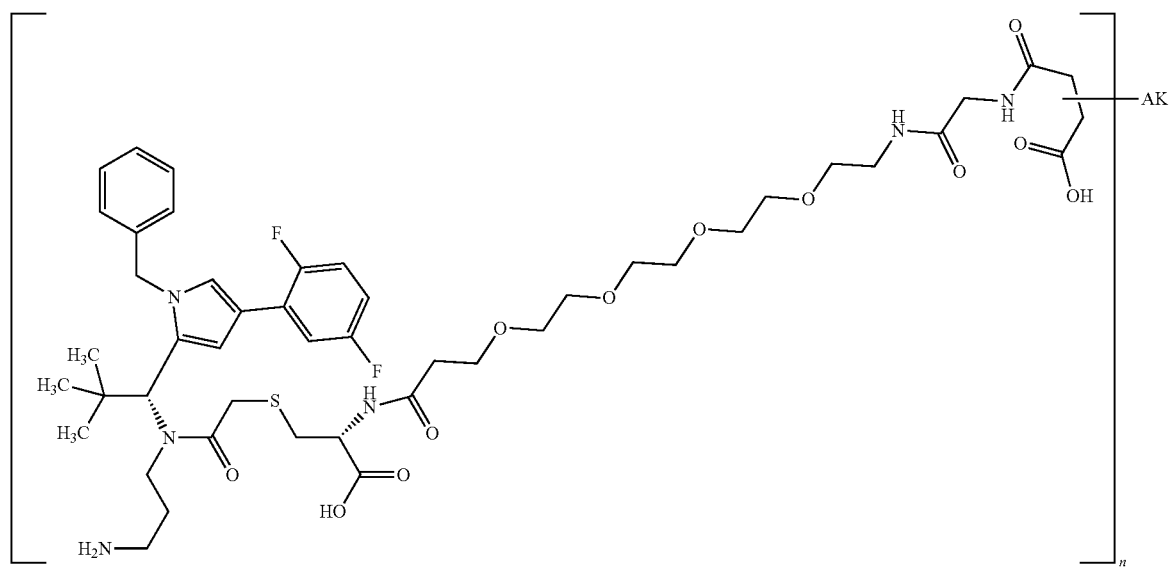
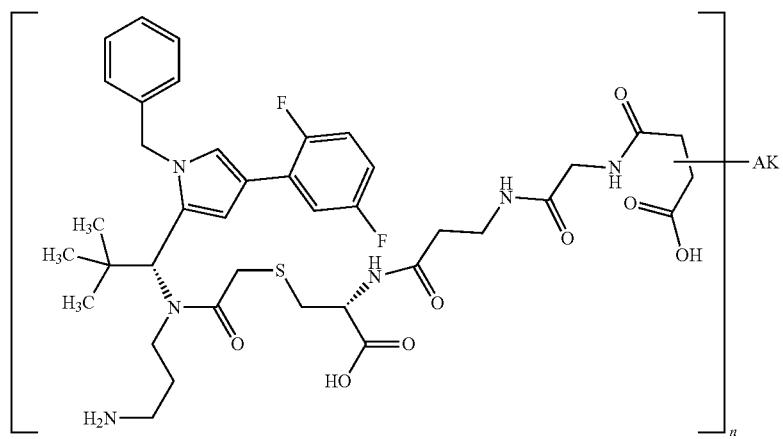
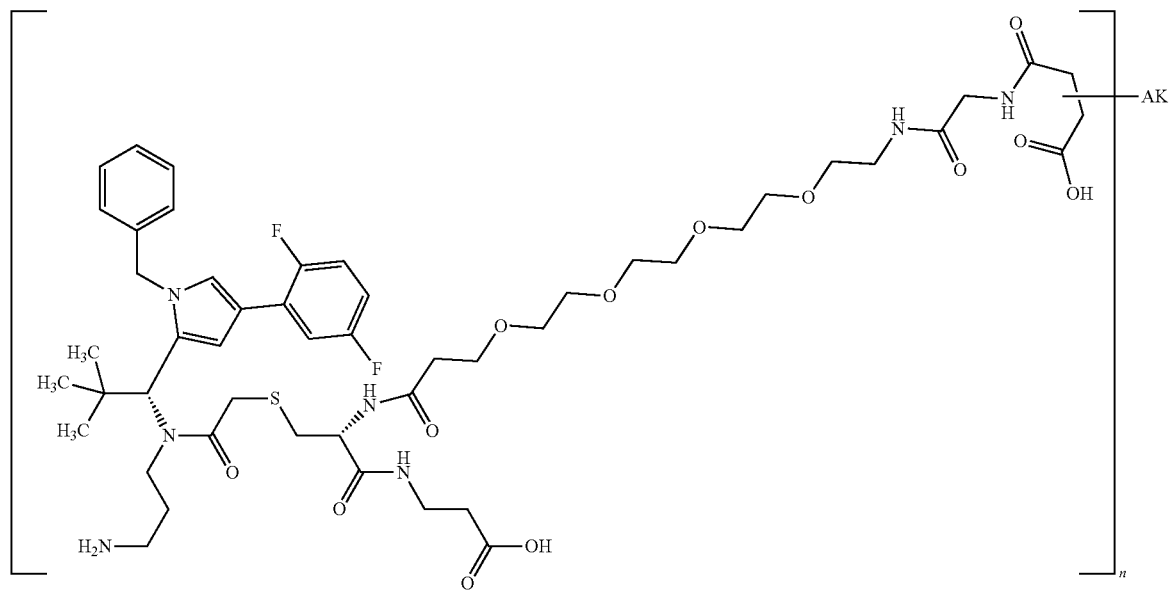

173
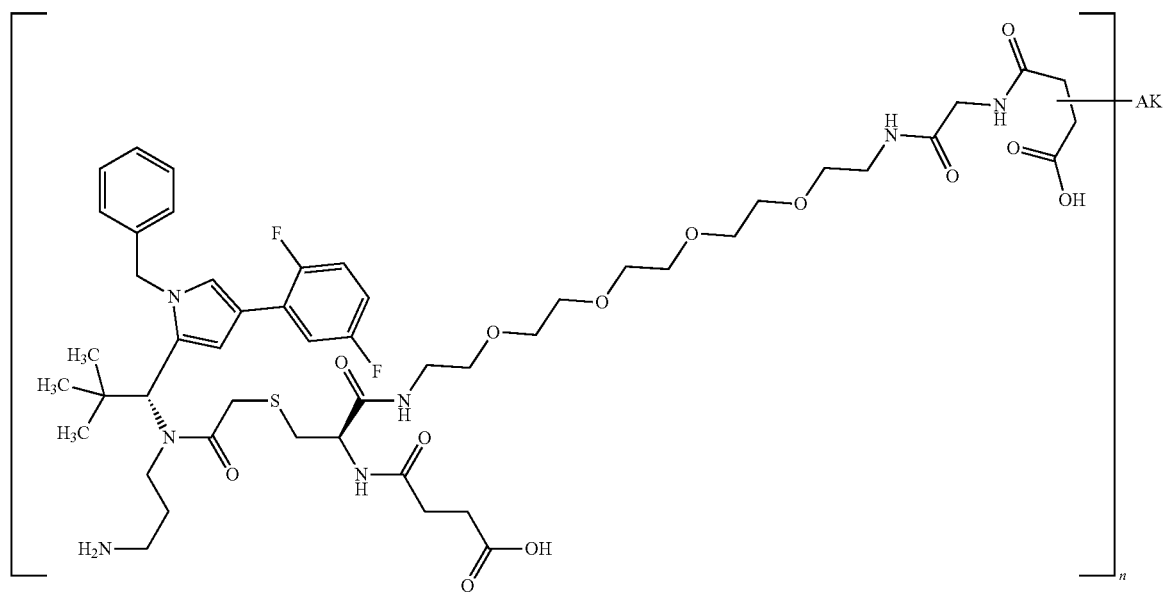
174
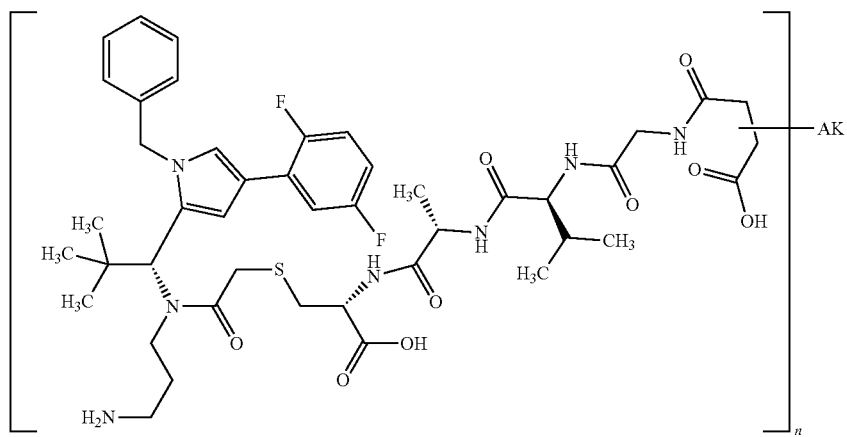
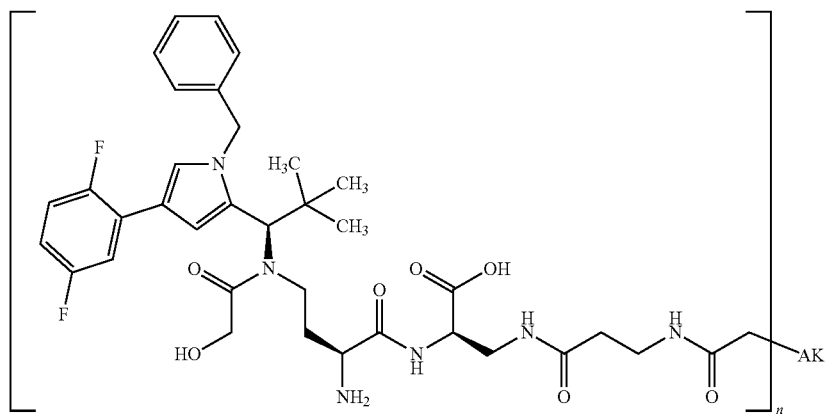

-continued
175
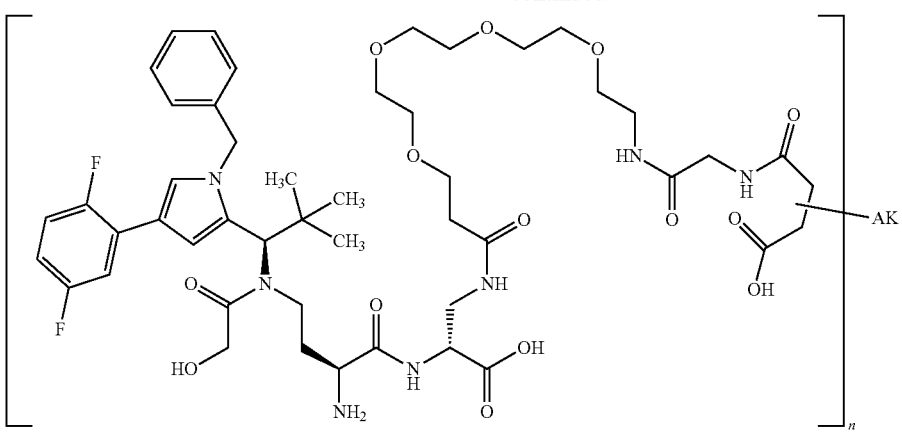
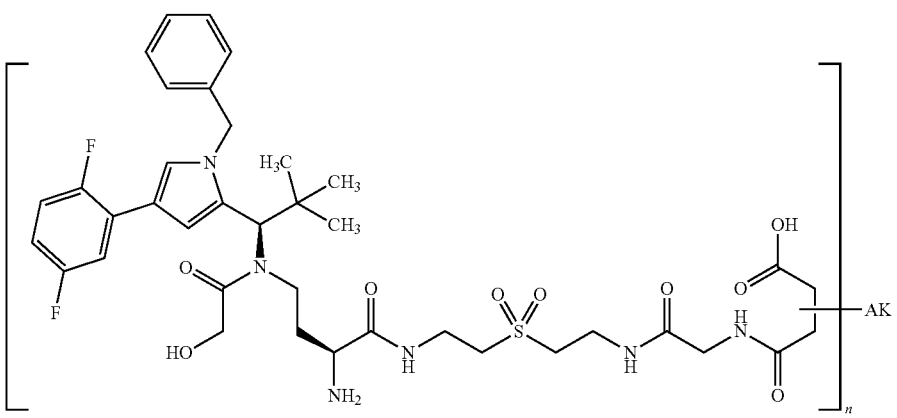
176
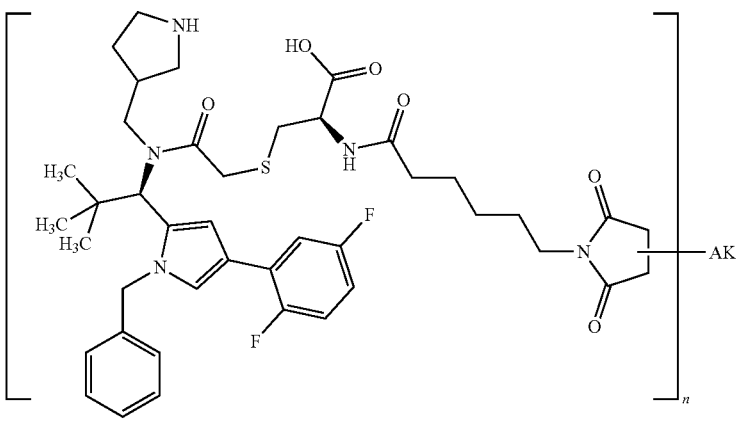

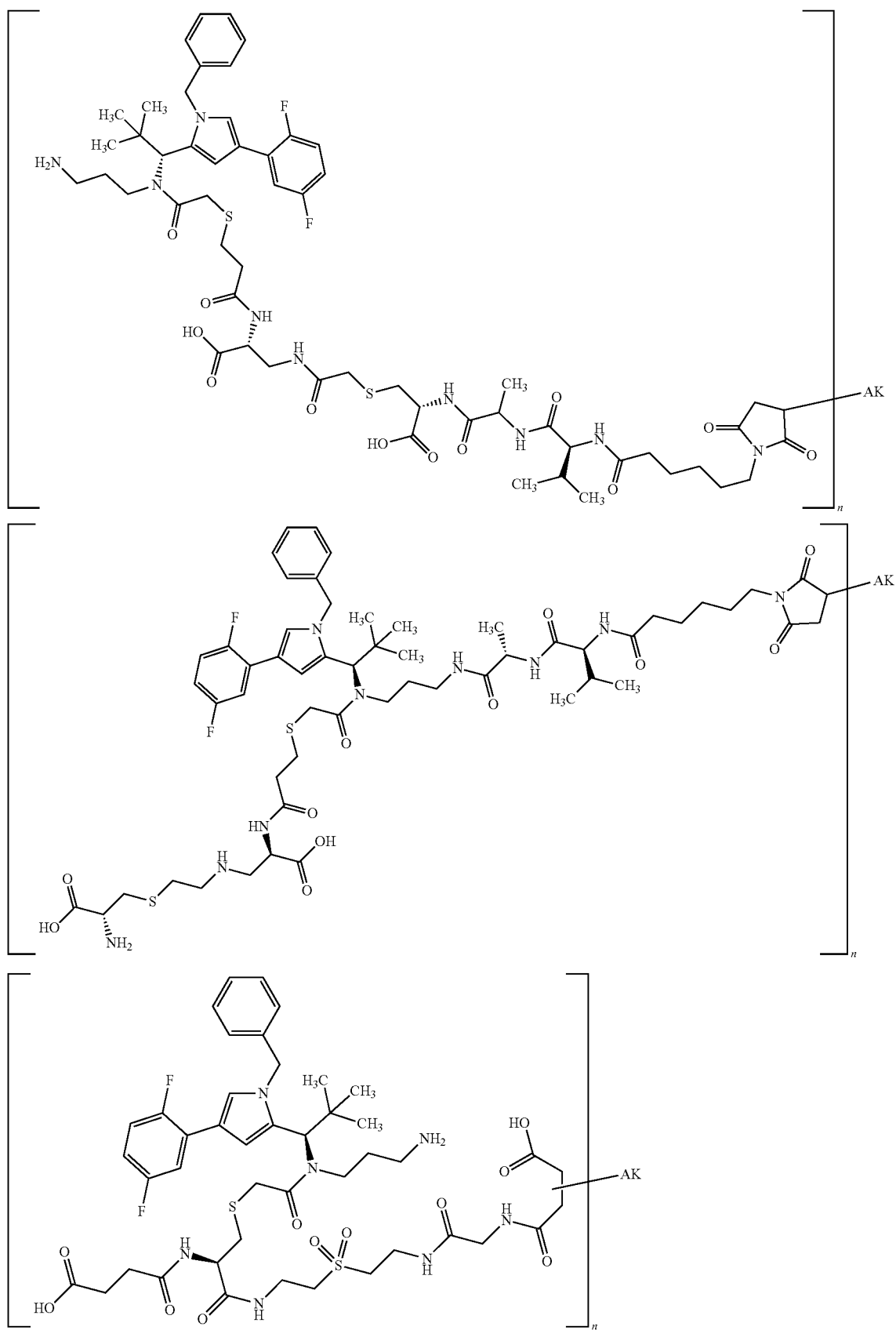

179 180
-continued
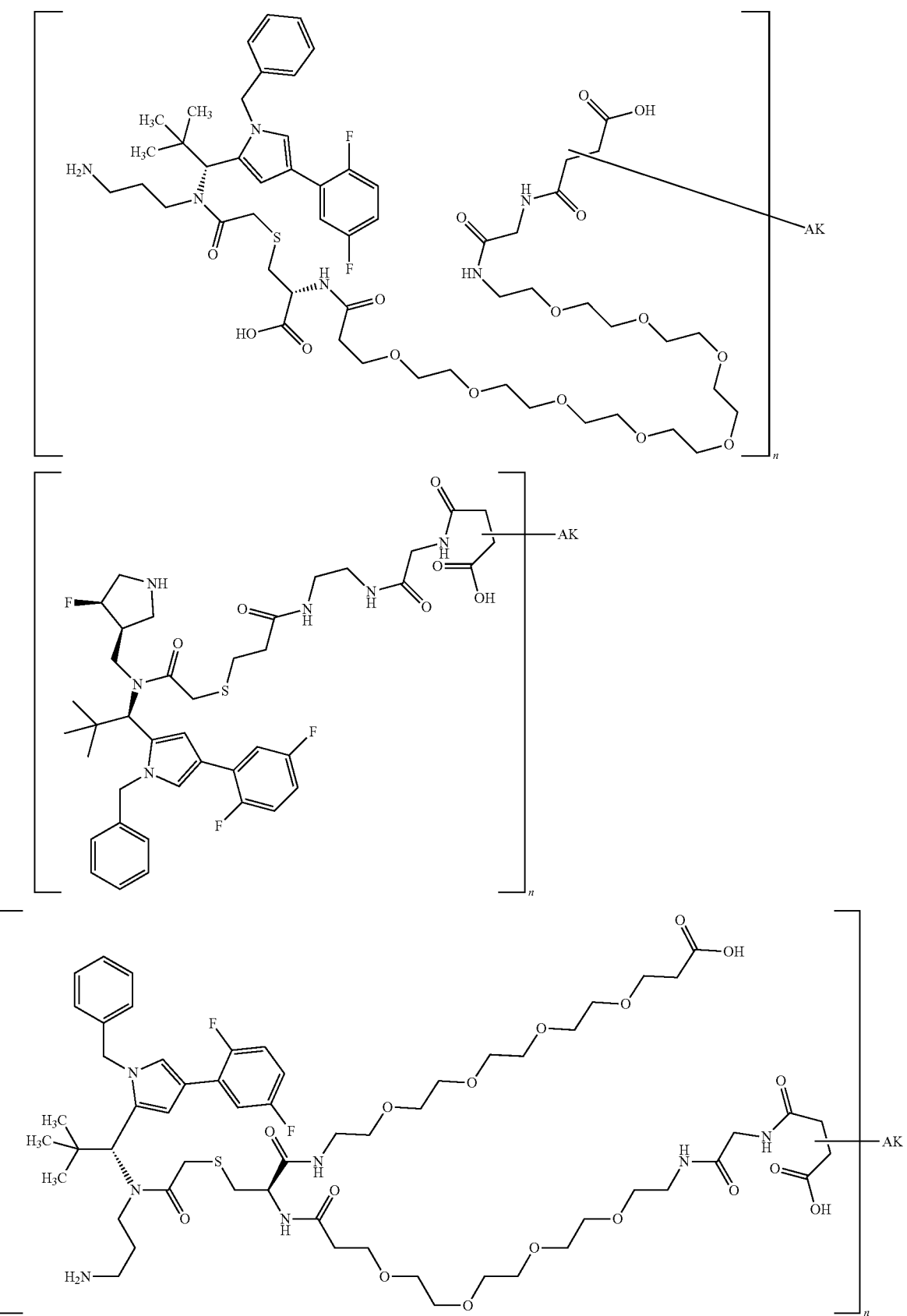

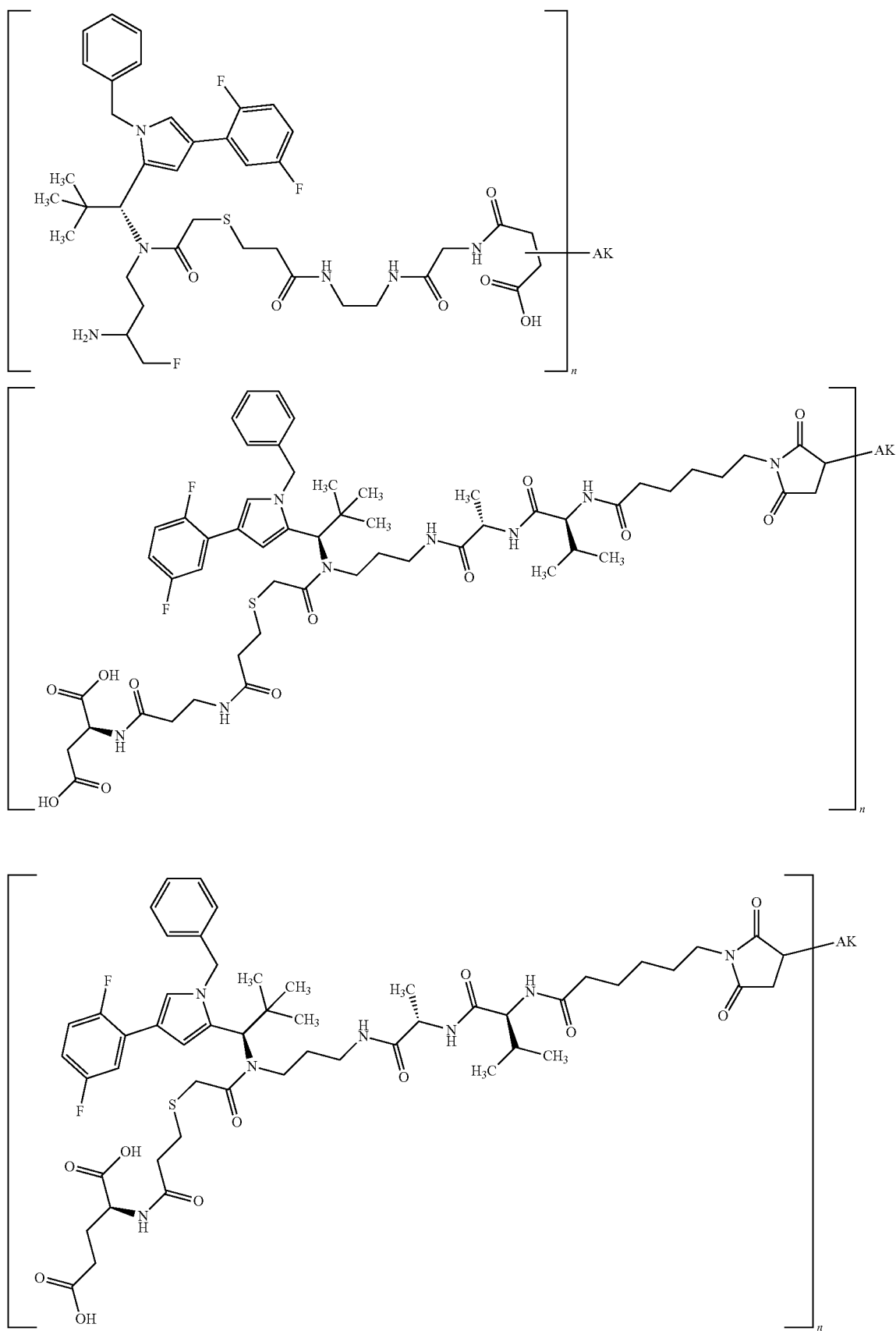

183
184
-continued
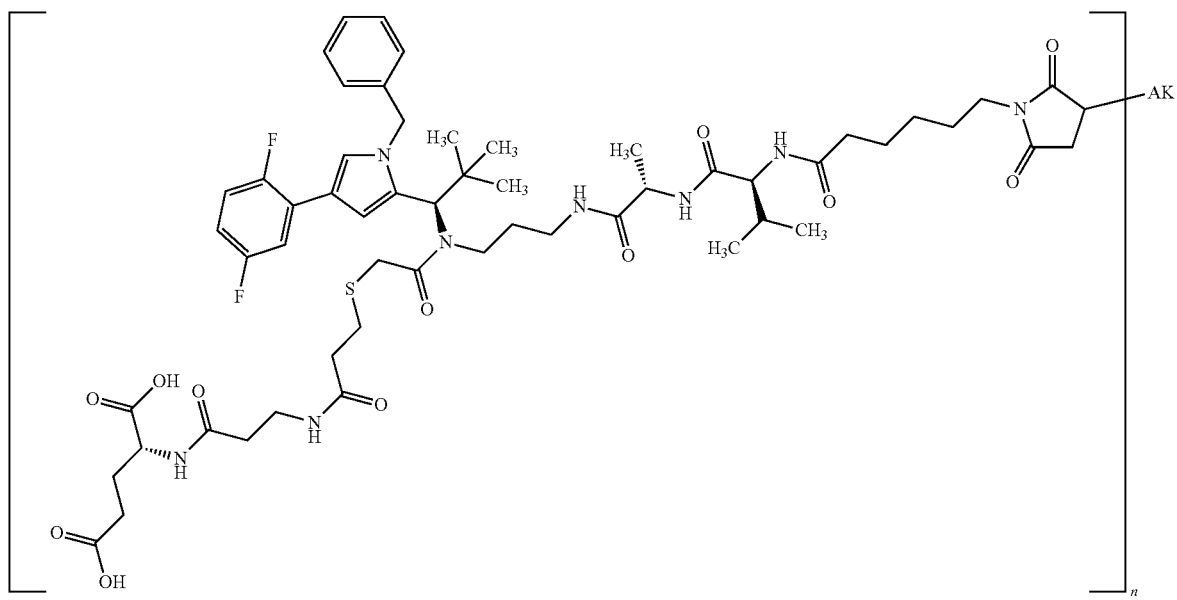
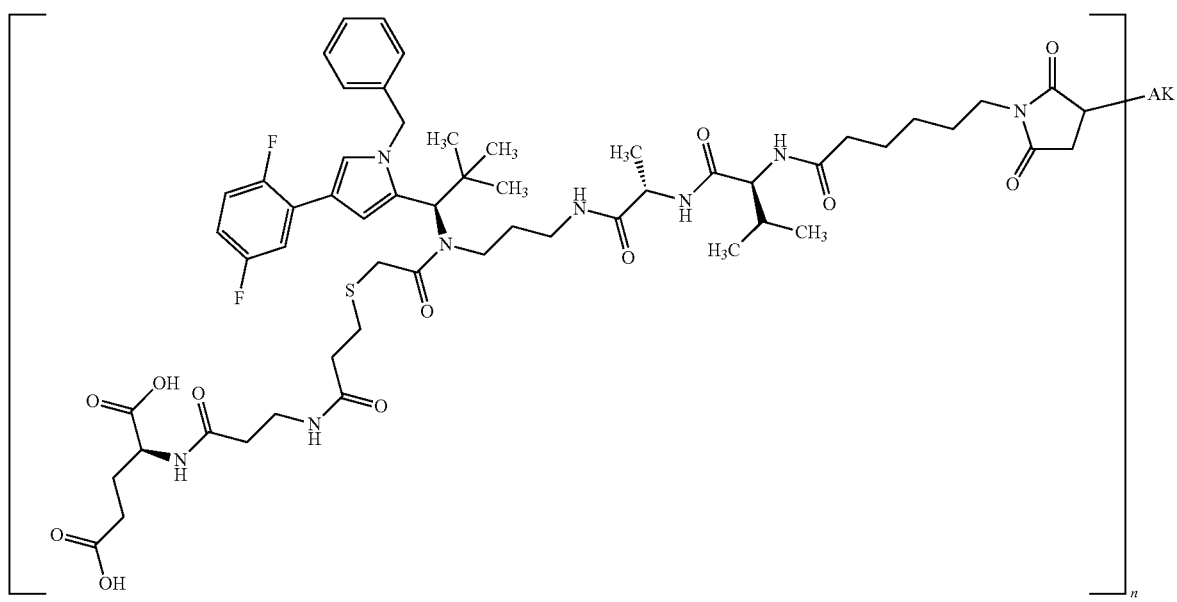

185
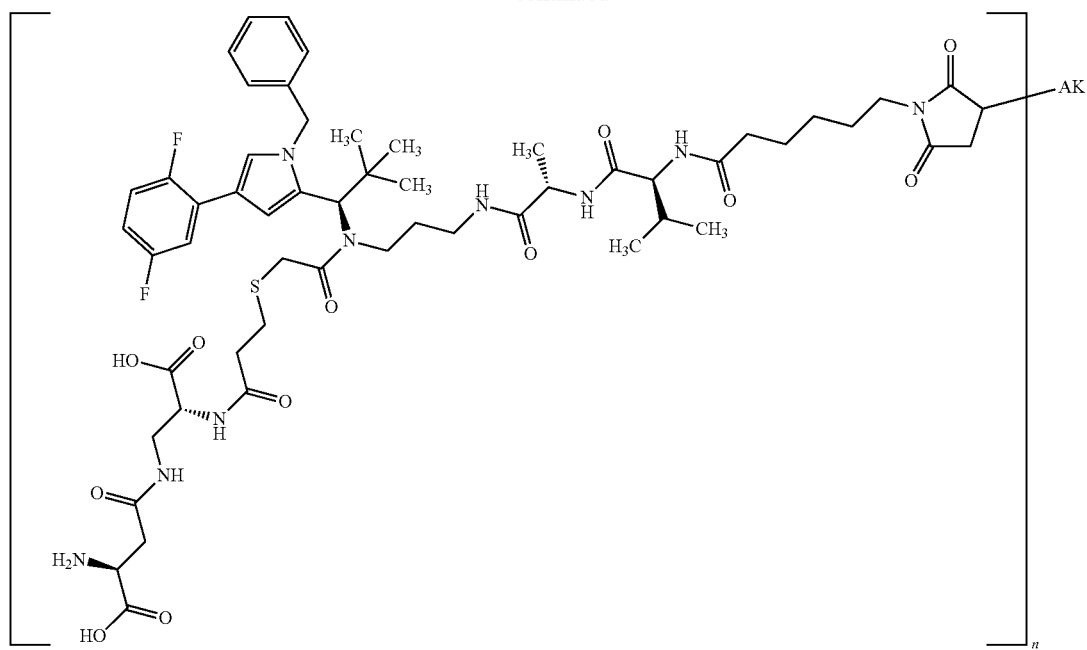
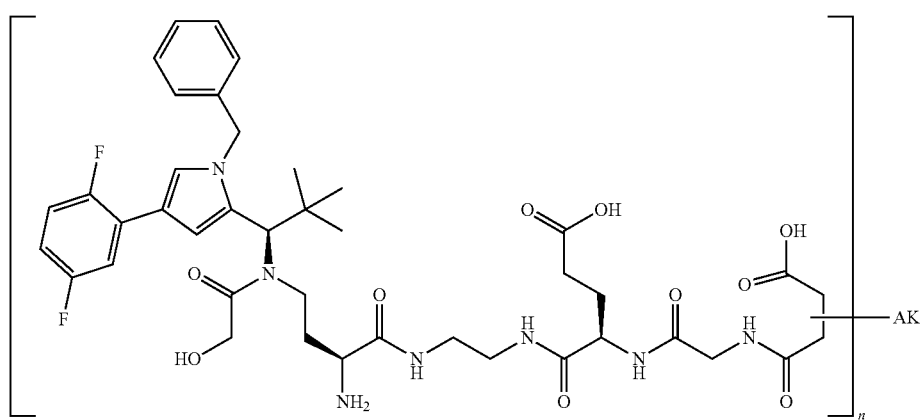
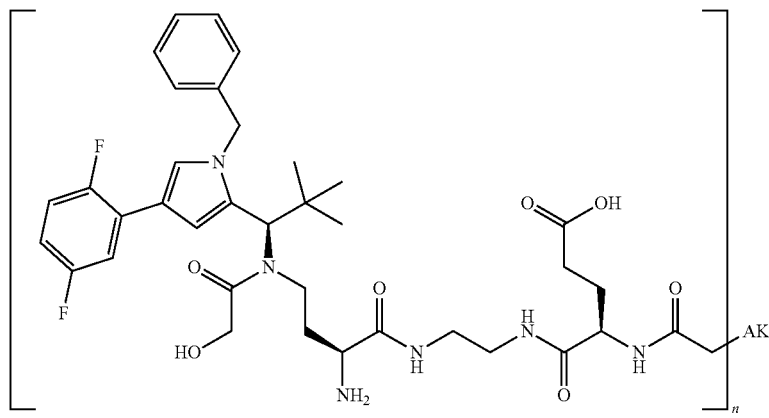

Other Conjugates
Other conjugates may have one of the formulae below:
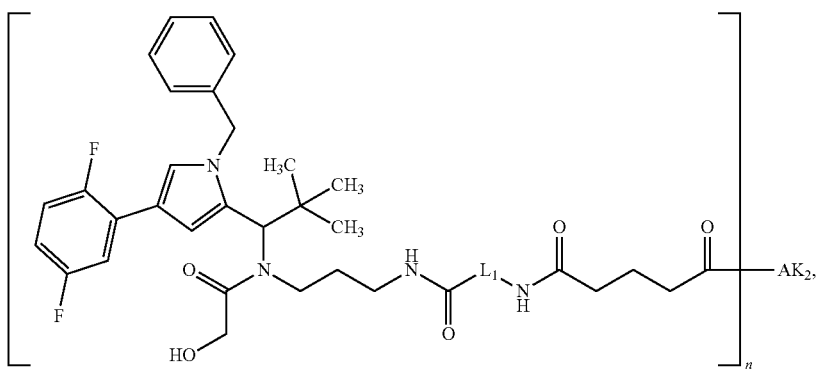
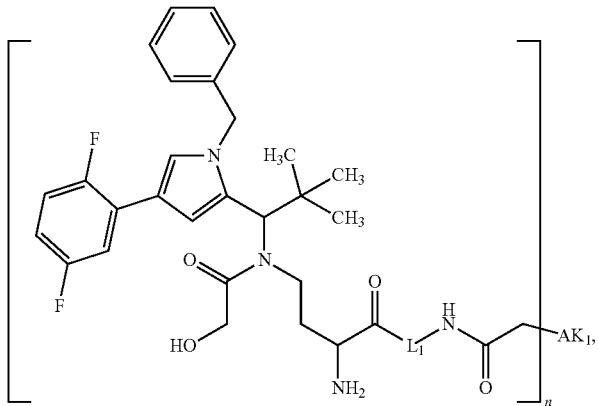
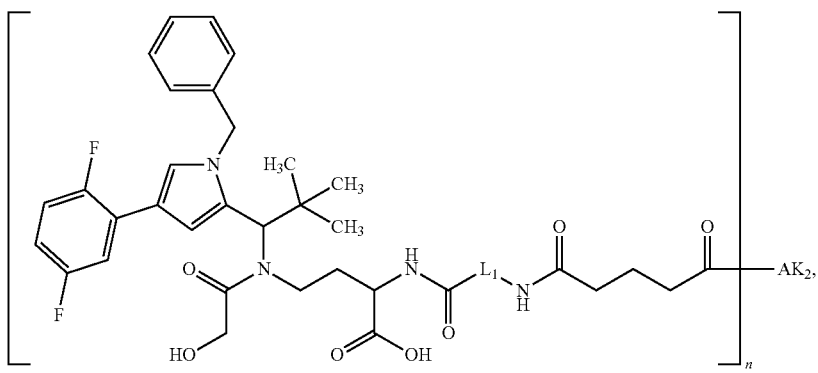
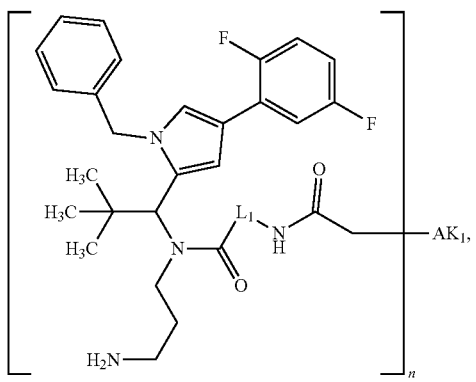
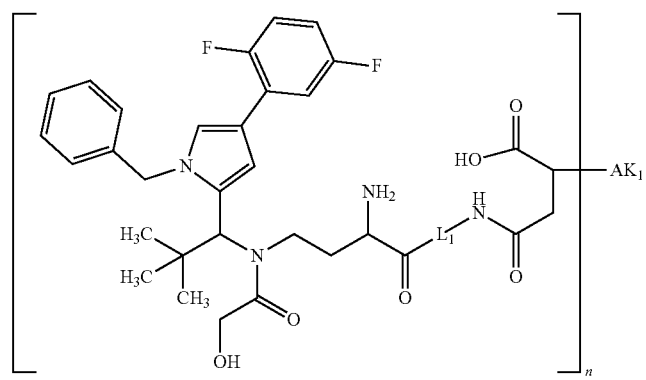

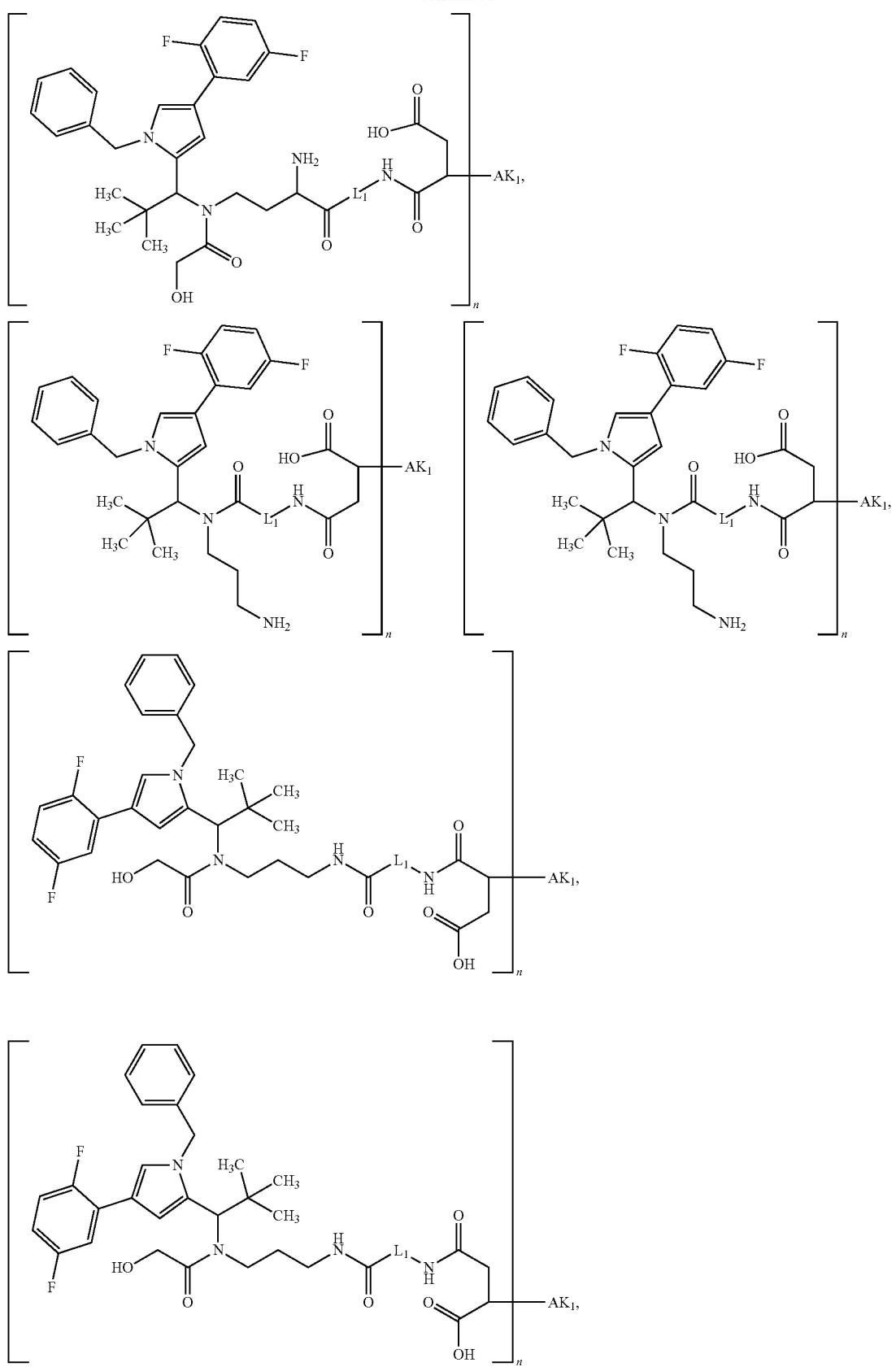

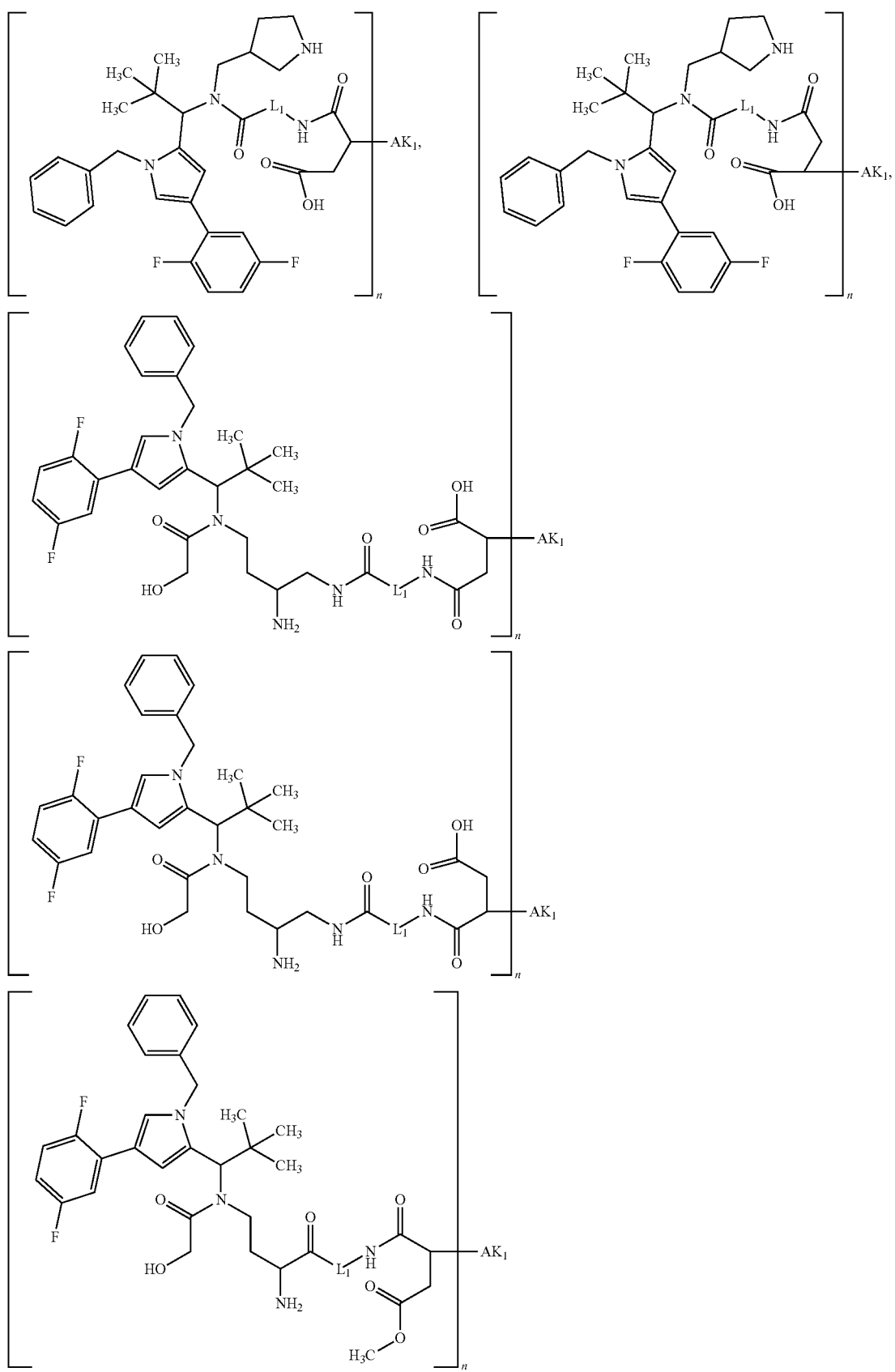

193
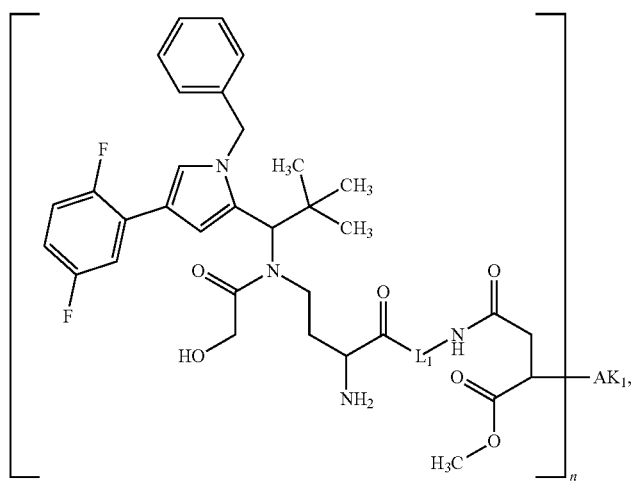
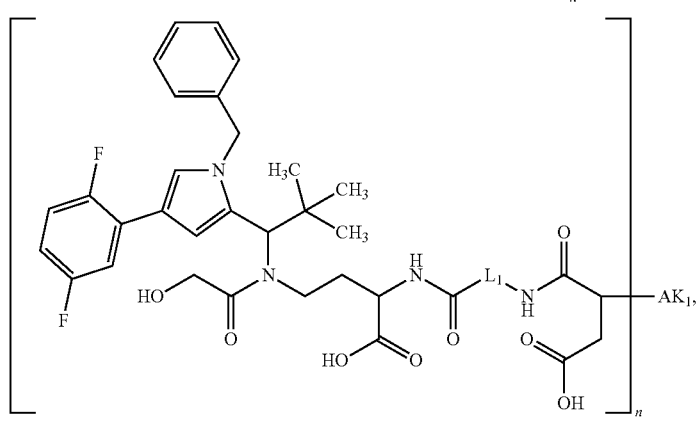
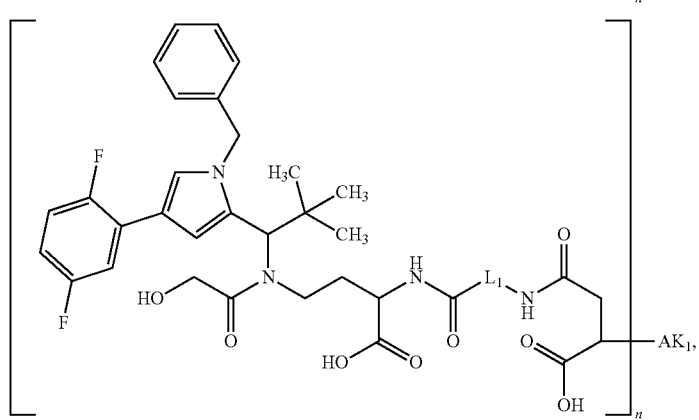
-continued
194
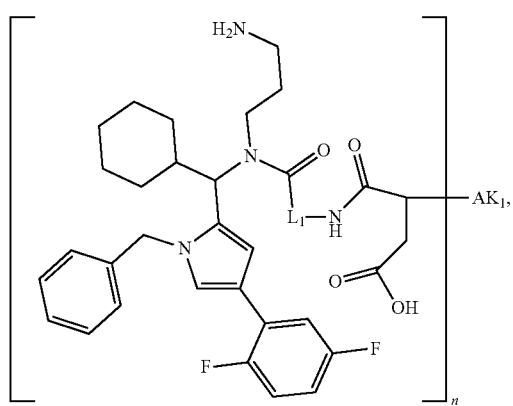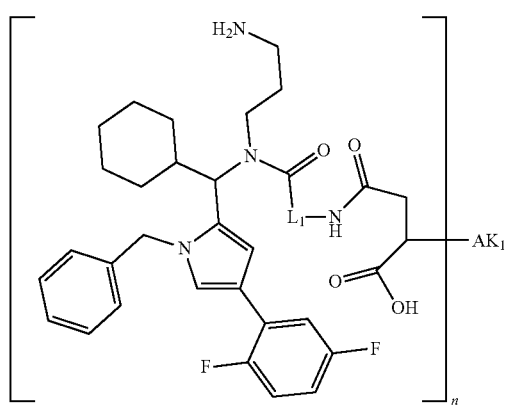

-continued
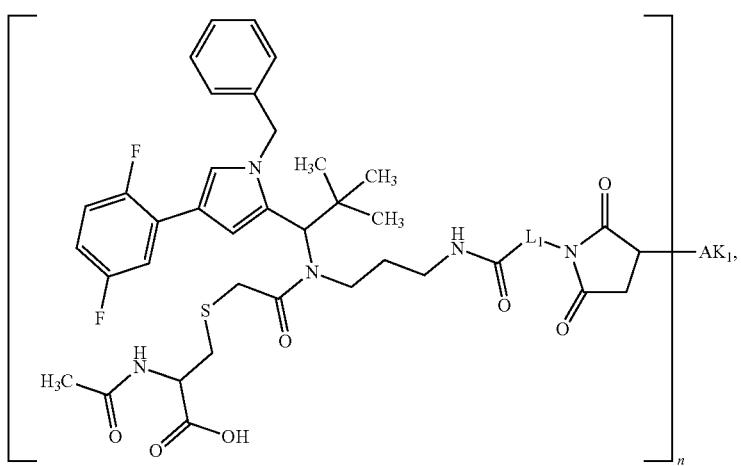
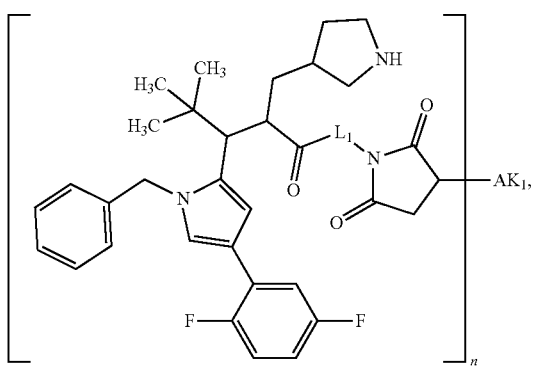
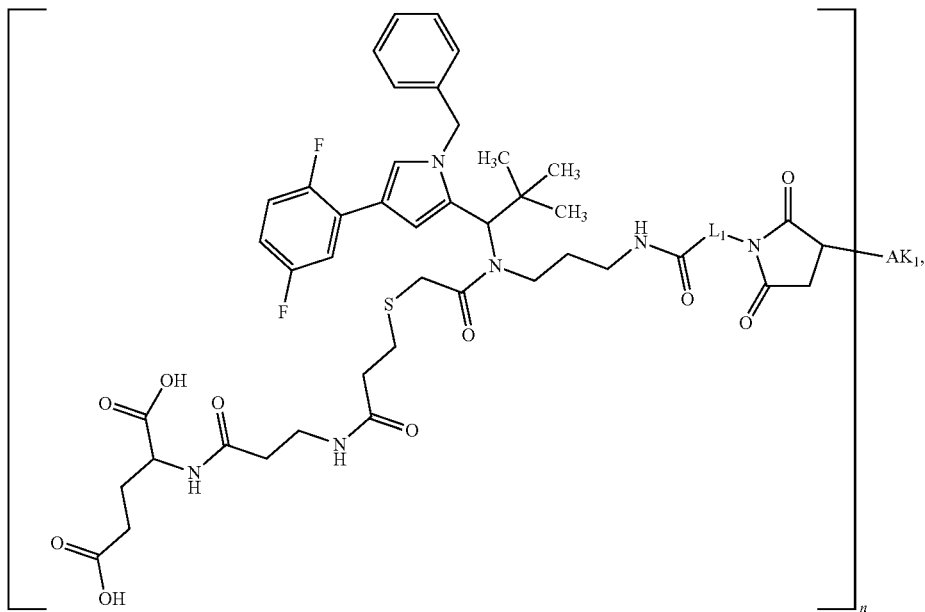

197
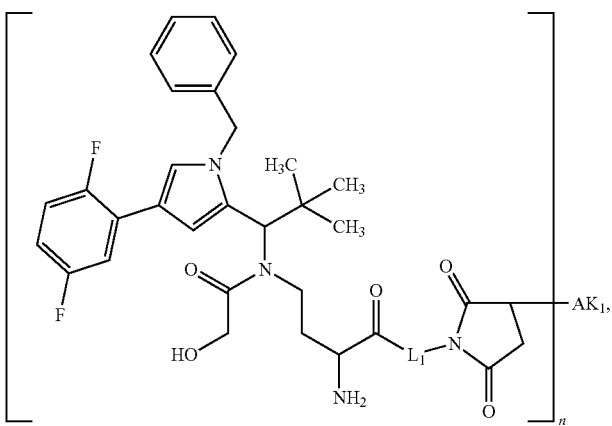
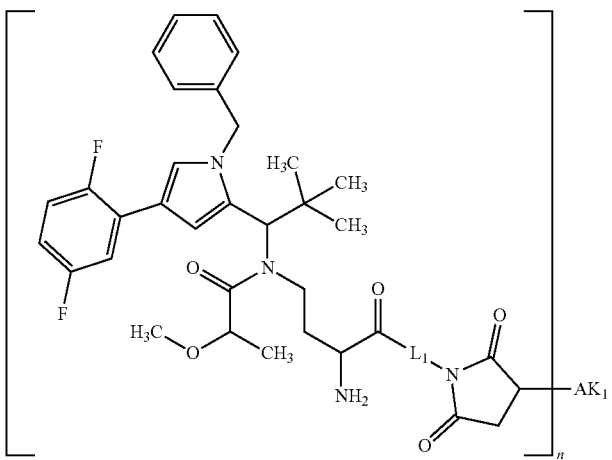
198
-continued
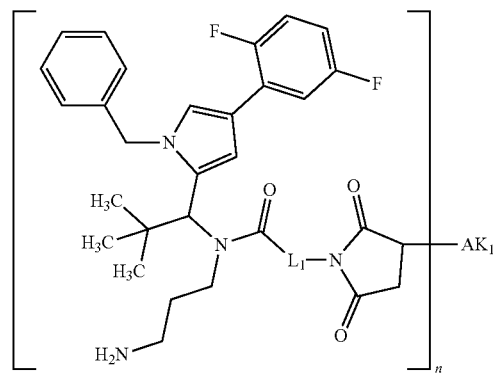
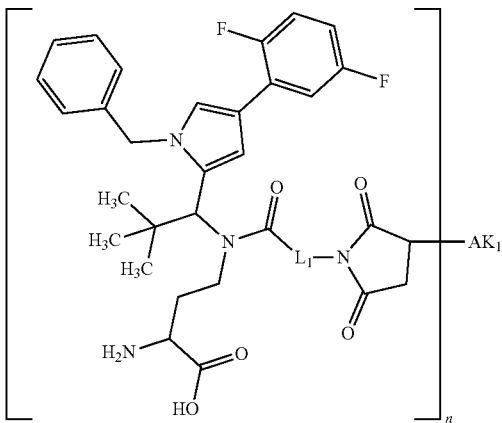
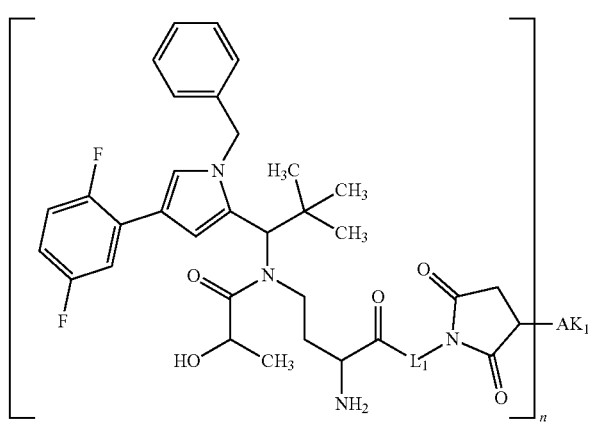

-continued
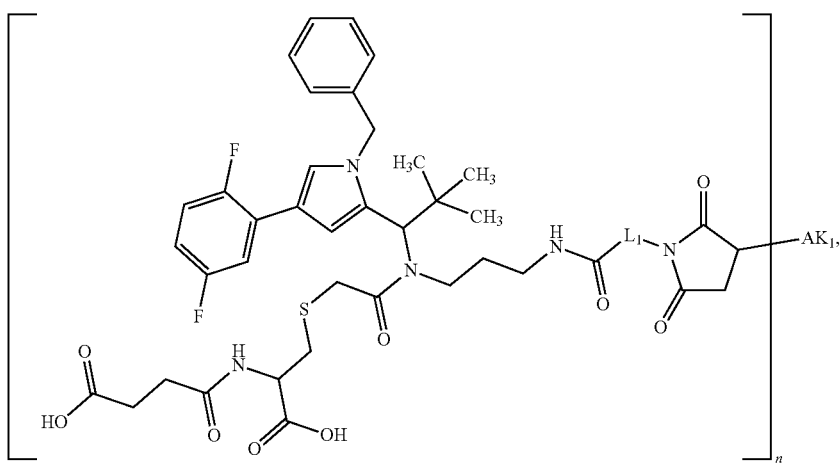
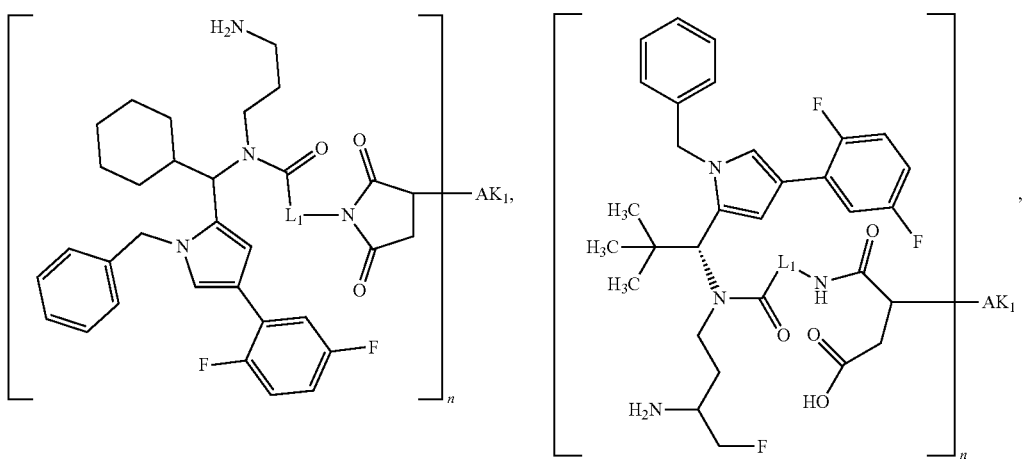
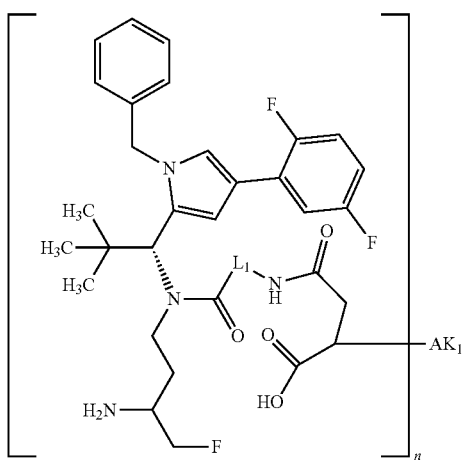

-continued
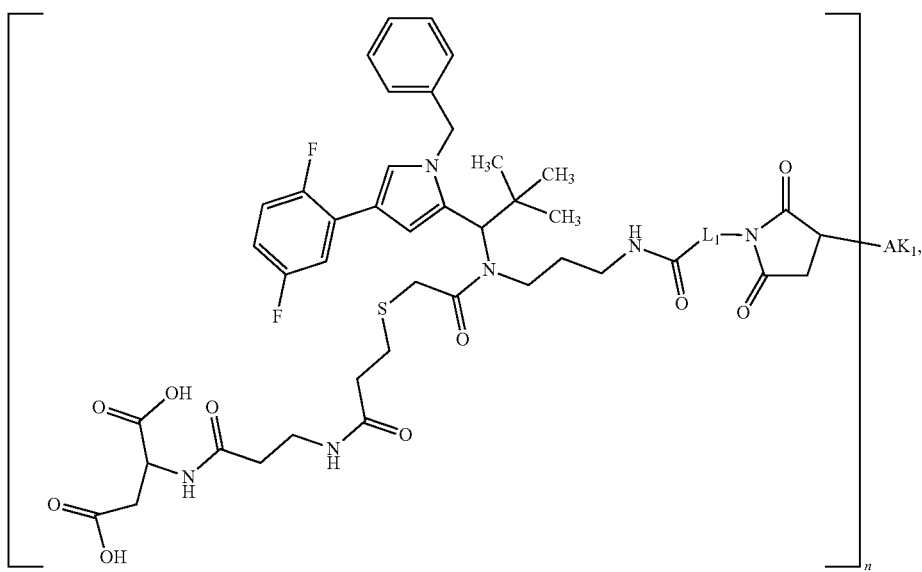
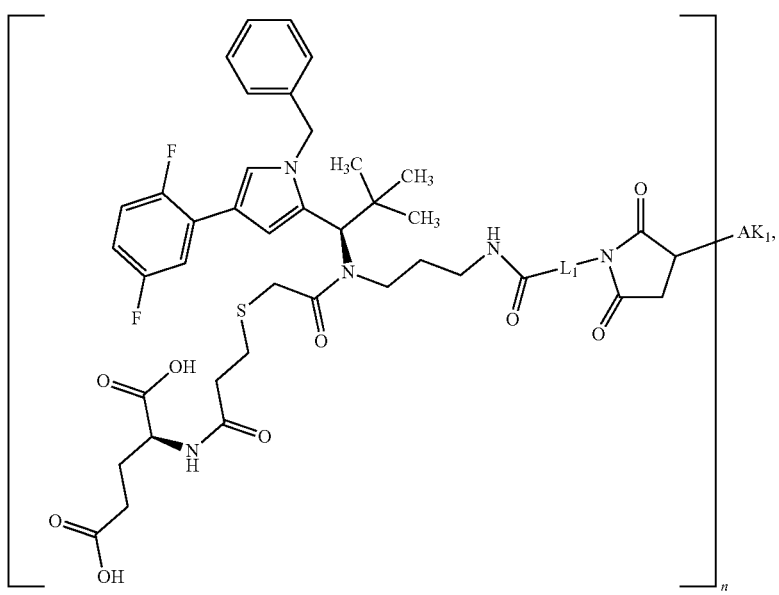

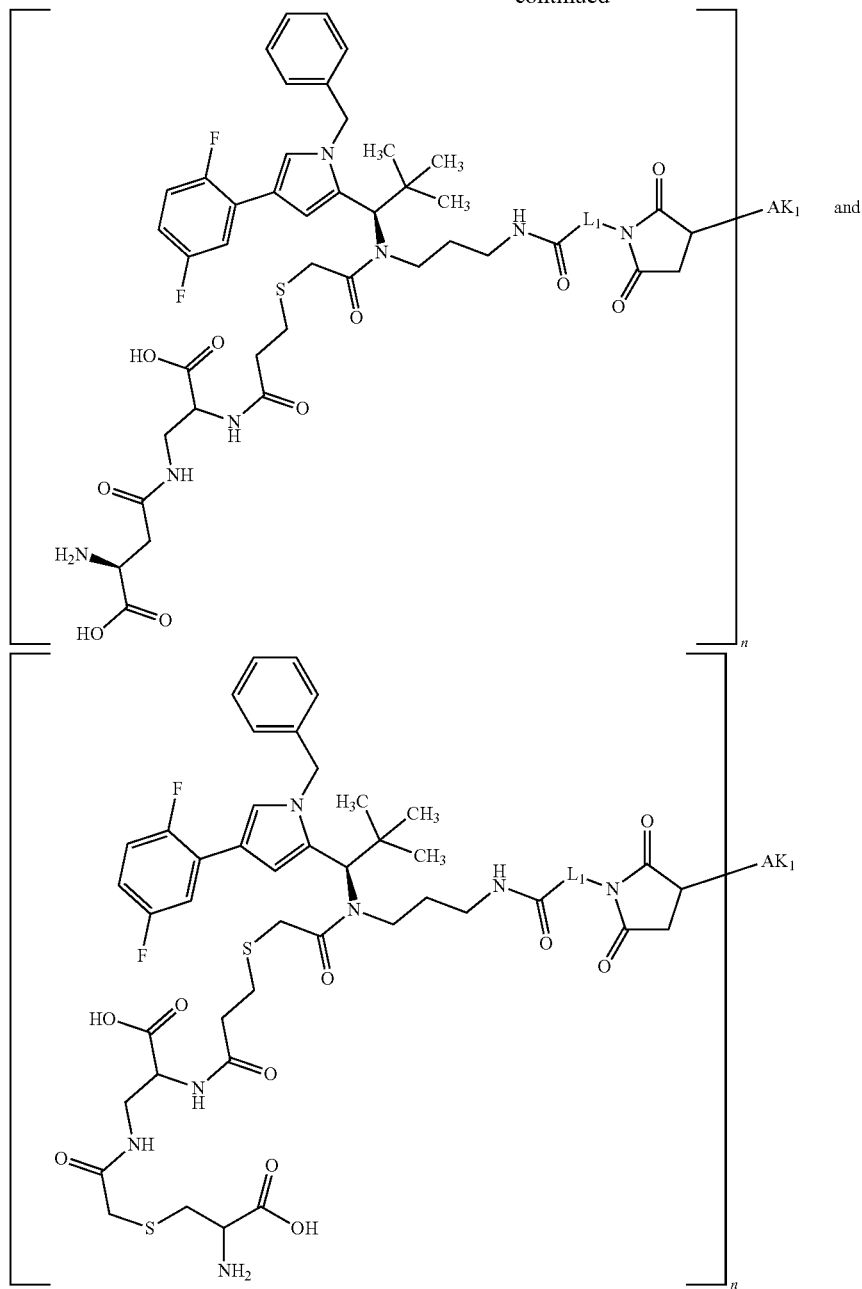

where

AK1 represents an antibody linked via cysteine and

AK2 represents an antibody linked via lysine, which binds to B7H3 and is a chimeric or humanized variant of the antibody TPP-6497, n is a number from 1 to 20; and $L_1$ is a straight-chain or branched hydrocarbon chain having 1 to 30 carbon atoms, which may be interrupted once or more than once, identically or differently, by —O—, —S—, —C(=O)—, —S(=O)$_2$—, —NH—, cyclopentyl, piperidinyl, phenyl, where the straight-chain or branched hydrocarbon chain may be substituted with —COOH, or —NH$_2$, and salts, solvates, salts of the solvates and epimers thereof.

Here, the linker $L_1$ preferably represents the group

§—NH—(CH$_2$)$_2$—§§;  §—NH—(CH$_2$)$_6$—§§;  §—NH—(CH$_2$)$_2$—O—(CH$_2$)$_2$—§§;  §—NH—CH(COOH)—(CH$_2$)$_4$—§§;

§—NH—NH—C(=O)—(CH$_2$)$_5$—§§;  §—NH—(CH$_2$)$_2$—C(=O)—O—(CH$_2$)$_2$—§§;  §—NH—(CH$_2$)$_2$—C(=O)—NH—(CH$_2$)$_2$—§§;

-continued

§—NH—(CH₂)₂—NH—C(=O)—CH₂—§§; §—NH—(CH₂)₃—NH—C(=O)—CH₂—§§;

§—NH—(CH₂)₂—NH—C(=O)—(CH₂)₂—§§; §—NH—(CH₂)₂—NH—C(=O)—(CH₂)₅—§§;

§—NH—(CH₂)₂—NH—C(=O)—CH(CH₃)—§§; §—NH—(CH₂)₂—O—(CH₂)₂—NH—C(=O)—CH₂—§§;

§—NH—CH(COOH)—CH₂—NH—C(=O)—CH₂—§§; §—NH—CH(COOH)—(CH₂)₂—NH—C(=O)—CH₂—§§;

§—NH—CH(COOH)—(CH₂)₄—NH—C(=O)—CH₂—§§; §—NH—CH(COOH)—CH₂—NH—C(=O)—(CH₂)₂—§§;

§—NH—(CH₂)₂—NH—C(=O)—CH(C₂H₄COOH)—§§; §—NH—(CH₂)₂—NH—C(=O)—((CH₂)₂—O)₃—(CH₂)₂—§§;

§—NH—(CH₂)₂—S(=O)₂—(CH₂)₂—NH—C(=O)—CH₂—§§;

§—NH—(CH₂)₂—NH—C(=O)—CH₂—NH—C(=O)—CH₂—§§;

§—NH—(CH₂)₃—NH—C(=O)—CH₂—NH—C(=O)—CH₂—§§;

§—NH—CH(COOH)—CH₂—NH—C(=O)—CH(CH₂COOH)—§§;

§—NH—(CH₂)₂—NH—C(=O)—CH(C₂H₄COOH)—NH—C(=O)—CH₂—§§;

§—NH—CH(COOH)—CH₂—NH—C(=O)—(CH₂)₂—NH—C(=O)—CH₂—§§;

§—NH—(CH₂)₂—NH—C(=O)—(CH₂)₂—CH(COOH)—NH—C(=O)—CH₂—§§;

§—NH—CH(COOH)—CH₂—NH—C(=O)—CH(CH₂OH)—NH—C(=O)—CH₂—§§;

§—NH—CH[C(=O)—NH—(CH₂)₂—O)₄—(CH₂)₂COOH]—CH₂—NH—C(=O)—CH₂—§§;

§—NH—CH(COOH)—CH₂—NH—C(=O)—((CH₂)₂—O)₄—(CH₂)₂—NH—C(=O)—CH₂—§§;

§—NH—(CH₂)₄—CH(COOH)—NH—C(=O)—CH(CH₃)—NH—C(=O)—CH(isoC₃H₇)—§§;

§—NH—(CH₂)₄—CH(COOH)—NH—C(=O)—CH(CH₃)—NH—C(=O)—CH(isoC₃H₇)—NH—C(=O)—(CH₂)₅—§§;

§—NH—(CH₂)₂—C(=O)—NH—(CH₂)₄—CH(COOH)—NH—C(=O)—CH(CH₃)—NH—C(=O)—CH(isoC₃H₇)—NH—C(=O)—CH₂—§§;

§—NH—(CH₂)₂—C(=O)—NH—(CH₂)₄—CH(COOH)—NH—C(=O)—CH(CH₃)—NH—C(=O)—CH(isoC₃H₇)—NH—C(=O)—(CH₂)₅—§§;

§—NH—(CH₂)₄—CH(COOH)—NH—C(=O)—CH[(CH₂)₃—NH—C(=O)—NH₂]—NH—C(=O)—CH(isoC₃H₇)—NH—C(=O)—(CH₂)₅—§§;

§—NH—(CH₂)₂—NH—C(=O)—(CH₂)₂—CH(COOH)—NH—C(=O)—CH(CH₃)—NH—C(=O)—CH(isoC₃H₇)—NH—C(=O)—(CH₂)₅—§§; §—NH—CH(CH₃)—C(=O)—NH—(CH₂)₄—CH(COOH)—NH—C(=O)—CH(CH₃)—NH—C(=O)—CH(isoC₃H₇)—NH—C(=O)—(CH₂)₅—§§;

§—NH—(CH₂)₂—C(=O)—NH—(CH₂)₄—CH(COOH)—NH—C(=O)—CH[(CH₂)₃—NH—C(=O)—NH₂]—NH—C(=O)—CH(isoC₃H₇)—NH—C(=O)—(CH₂)₅—§§;

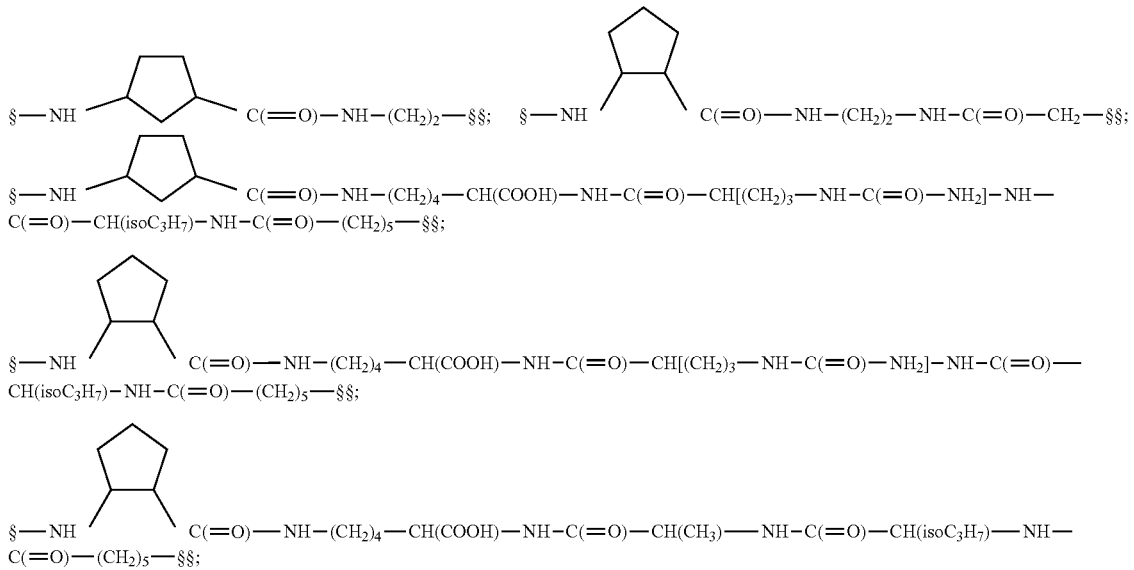

-continued

§—NH—(CH₂)₂—C(=O)—NH—CH(isoC₃H₇)—C(=O)—NH—CH[(CH₂)₃—NH—C(=O)—NH₂]—C(=O)—O

[4-methylpiperidine]—C(=O)—CH₂—§§;

§—NH—(CH₂)₂—C(=O)—NH—CH(isoC₃H₇)—C(=O)—NH—CH(CH₃)—C(=O)—O—[piperidine]—C(=O)—CH₂—§§;

§—NH—(CH₂)₂—NH—C(=O)—[m-phenylene]—§§;  §—NH—CH(COOH)—CH₂—NH—C(=O)—[m-phenylene]—[p-tolyl]—§§;

§—NH—(CH₂)₂—C(=O)—NH—CH(CH₃)—C(=O)—NH—CH[(CH₂)₃—NH—C(=O)—NH₂]—C(=O)—NH—[p-tolyl]—§§;
§—(CH₂)₂—C(=O)—NH—(CH₂)₂—§§;  §—(CH₂)₂—C(=O)—NH—(CH₂)₂—NH—C(=O)—CH₂—§§;
§—CH(CH₃)—NH—C(=O)—CH(isoC₃H₇)—§§;  §—CH(CH₃)—NH—C(=O)—CH(isoC₃H₇)—NH—C(=O)—CH₂—§§;
§—CH(CH₃)—NH—C(=O)—CH(isoC₃H₇)—NH—C(=O)—(CH₂)₅—§§;
§—(CH₂)₂—C(=O)—NH—((CH₂)₂—O)₄—(CH₂)₂—NH—C(=O)—CH₂—§§;
§—CH(CH₃)—NH—C(=O)—CH(isoC₃H₇)—NH—C(=O)—((CH₂)₂—O)₄—(CH₂)₂—NH—C(=O)—(CH₂)₂—§§;

§—[p-phenylene]—NH—C(=O)—CH(CH₃)—NH—C(=O)—CH(isoC₃H₇)—NH—C(=O)—((CH₂)₂—O)₄—(CH₂)₂—NH—C(=O)—(CH₂)₂—§§;  §—CH₂—S—(CH₂)₂—C(=O)—NH—(CH₂)₂—§§;  §—CH₂—S—(CH₂)₅—C(=O)—NH—(CH₂)₂—§§;
§—CH₂—S—CH₂CH(COOH)—NH—C(=O)—CH₂—§§;  §—CH₂—S—CH₂CH(COOH)—NH—C(=O)—(CH₂)₅—§§;
§—CH₂—S—(CH₂)₂—C(=O)—NH—((CH₂)₂—O)₂—(CH₂)₂—§§;
§—CH₂—S—(CH₂)₂—C(=O)—NH—((CH₂)₂—O)₂—(CH₂)₅—§§;
§—CH₂—S—(CH₂)₂—C(=O)—NH—(CH₂)₂—NH—C(=O)—CH₂—§§;
§—CH₂—S—(CH₂)₂—C(=O)—NH—(CH₂)₂—NH—C(=O)—CH₅—§§;
§—CH₂—S—CH₂CH(COOH)—NH—C(=O)—(CH₂)₂—NH—C(=O)—CH₂—§§;
§—CH₂—S—CH₂CH(NH₂)—C(=O)—NH—(CH₂)₂—NH—C(=O)—(CH₂)₅—§§;
§—CH₂—S—(CH₂)₂—C(=O)—NH—CH(COOH)—CH₂—NH—C(=O)—CH₂—§§;
§—CH₂—S—(CH₂)₂—C(=O)—NH—((CH₂)₂—O)₂—(CH₂)₂—NH—C(=O)—CH₂—§§;
§—CH₂—S—(CH₂)₂—C(=O)—NH—((CH₂)₂—O)₄—(CH₂)₂—NH—C(=O)—CH₂—§§;
§—CH₂—S—(CH₂)₂—C(=O)—NH—((CH₂)₂—O)₂—(CH₂)₂—NH—C(=O)—(CH₂)₅—§§;
§—CH₂—S—(CH₂)₂—C(=O)—NH—((CH₂)₂—O)₄—(CH₂)₂—NH—C(=O)—(CH₂)₅—§§;
§—CH₂—S—CH₂CH(COOH)—NH—C(=O)—((CH₂)₂—O)₂—(CH₂)₂—NH—C(=O)—CH₂—§§;
§—CH₂—S—CH₂CH(COOH)—NH—C(=O)—((CH₂)₂—O)₄—(CH₂)₂—NH—C(=O)—CH₂—§§;
§—CH₂—S—CH₂CH(COOH)—NH—C(=O)—((CH₂)₂—O)₈—(CH₂)₂—NH—C(=O)—CH₂—§§;
§—CH₂—S—CH₂CH(COOH)—NH—C(=O)—((CH₂)₂—O)₄—(CH₂)₂—NH—C(=O)—(CH₂)₂—§§;
§—CH₂—S—(CH₂)₂—CH(COOH)—NH—C(=O)—((CH₂)₂—O)₄—(CH₂)₂—NH—C(=O)—(CH₂)₂—§§;
§—CH₂—S—(CH₂)₂—C(=O)—NH—CH(C₂H₄COOH)—C(=O)—NH—(CH₂)₂—NH—C(=O)—CH₂—§§;
§—CH₂—S—CH₂CH[NH—C(=O)—(CH₂)₂—COOH]—C(=O)—NH—(CH₂)₂—NH—C(=O)—CH₂—§§;
§—CH₂—S—CH₂CH[NH—C(=O)—((CH₂)₂—O)₄—CH₃]—C(=O)—NH—(CH₂)₂—NH—C(=O)—CH₂—§§;
§—CH₂—S—CH₂CH(COOH)—NH—C(=O)—CH(CH₃)—NH—C(=O)—CH(isoC₃H₇)—NH—C(=O)—CH₂—§§;
§—CH₂—S—CH₂CH[NH—C(=O)—(CH₂)₂—COOH]—C(=O)—NH—(CH₂)₂—S(=O)₂—(CH₂)₂—NH—C(=O)—CH₂—  §§;
§—CH₂—S—CH₂CH[NH—C(=O)—(CH₂)₂—COOH]—C(=O)—NH—((CH₂)₂—O)₄—(CH₂)₂—NH—C(=O)—CH₂—§§;
§—CH₂—S—CH₂CH[C(=O)—NH—(CH₂)₂—COOH]—NH—C(=O)—((CH₂)₂—O)₄—(CH₂)₂—NH—C(=O)—CH₂—§§;
§—CH₂—S—CH₂CH[C(=O)—NH—(CH₂)₂—COOH]—NH—C(=O)—((CH₂)₂—O)₄—(CH₂)₂—NH—C(=O)—(CH₂)₂—  §§;

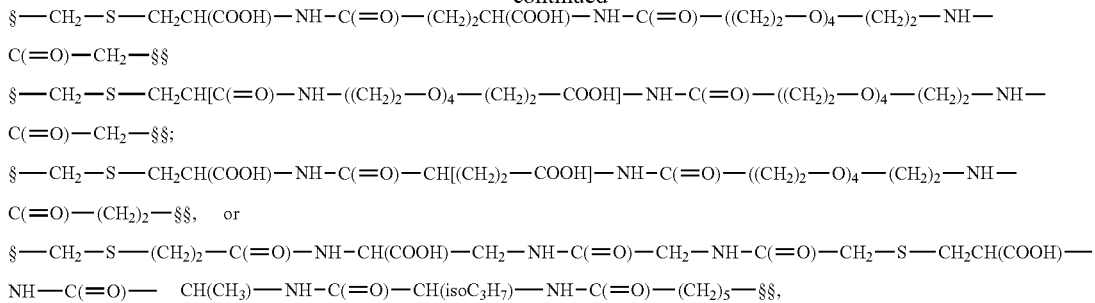

where
§ represents the bond to the drug molecule and
§ § represents the bond to the antibody and
isoC$_3$H$_7$ represents an isopropyl residue,
and salts, solvates, salts of the solvates and epimers thereof.

Therapeutic Use

The hyper-proliferative diseases, for the treatment of which the compounds according to the invention may be employed, include in particular the group of cancer and tumour diseases. In the context of the present invention, these are understood to mean especially the following diseases, but without any limitation thereto: mammary carcinomas and mammary tumours (mammary carcinomas including ductal and lobular forms, also in situ), tumours of the respiratory tract (small-cell and non-small-cell pulmonary carcinoma, bronchial carcinoma), cerebral tumours (e.g. of the brain stem and of the hypothalamus, astrocytoma, ependymoma, glioblastoma, glioma, medulloblastoma, meningioma and neuro-ectodermal and pineal tumours), tumours of the digestive organs (carcinomas of the oesophagus, stomach, gall bladder, small intestine, large intestine, rectum and anal carcinomas), liver tumours (inter alia hepatocellular carcinoma, cholangiocarcinoma and mixed hepatocellular cholangiocarcinoma), tumours of the head and neck region (larynx, hypopharynx, nasopharynx, oropharynx, lips and oral cavity carcinomas, oral melanomas), skin tumours (basaliomas, spinaliomas, squamous cell carcinomas, Kaposi's sarcoma, malignant melanoma, non-melanomatous skin cancer, Merkel cell skin cancer, mast cell tumours), tumours of the stroma and connective tissue (inter alia soft tissue sarcomas, osteosarcomas, malignant fibrous histiocytomas, chondrosarcomas, fibrosarcomas, haemangiosarcomas, leiomyosarcomas, liposarcomas, lymphosarcomas and rhabdomyosarcomas), tumours of the eyes (inter alia intraocular melanoma and retinoblastoma), tumours of the endocrine and exocrine glands (e.g. of the thyroid and parathyroid glands, pancreas and salivary gland carcinomas, adenocarcinomas), tumours of the urinary tract (tumours of the bladder, penis, kidney, renal pelvis and ureter) and tumours of the reproductive organs (carcinomas of the endometrium, cervix, ovary, vagina, vulva and uterus in women and carcinomas of the prostate and testes in men). These also include proliferative diseases of the blood, the lymph system and the spinal cord, in solid form and as circulating cells, such as leukaemias, lymphomas and myeloproliferative diseases, for example acute myeloid, acute lymphoblastic, chronic lymphocytic, chronic myelogenous and hairy cell leukaemia, and AIDS-correlated lymphomas, Hodgkin's lymphomas, non-Hodgkin's lymphomas, cutaneous T cell lymphomas, Burkitt's lymphomas and lymphomas in the central nervous system.

These well-characterized diseases in humans can also occur with a comparable aetiology in other mammals and can likewise be treated there with the compounds of the present invention.

The treatment of the cancer diseases mentioned above with the compounds according to the invention comprises both a treatment of the solid tumors and a treatment of metastasizing or circulating forms thereof.

In the context of this invention, the term "treatment" or "treat" is used in the conventional sense and means attending to, caring for and nursing a patient with the aim of combating, reducing, attenuating or alleviating a disease or health abnormality, and improving the living conditions impaired by this disease, as, for example, in the event of a cancer.

The present invention thus further provides for the use of the compounds of the invention for treatment and/or prevention of disorders, especially of the aforementioned disorders.

The present invention further provides for the use of the compounds according to the invention for producing a medicament for the treatment and/or prevention of disorders, especially of the aforementioned disorders.

The present invention further provides for the use of the compounds of the invention in a method for treatment and/or prevention of disorders, especially of the aforementioned disorders.

The present invention further provides a process for treatment and/or prevention of disorders, especially of the aforementioned disorders, using an effective amount of at least one of the compounds according to the invention.

The compounds of the invention can be used alone or, if required, in combination with one or more other pharmacologically active substances, provided that this combination does not lead to undesirable and unacceptable side effects. Accordingly, the present invention further provides medicaments comprising at least one of the compounds of the invention and one or more further active ingredients, especially for treatment and/or prevention of the aforementioned disorders.

For example, the compounds of the present invention can be combined with known anti-hyper-proliferative, cytostatic or cytotoxic substances for the treatment of cancer diseases. Examples of suitable combination active compounds include:

131I-chTNT, abarelix, abiraterone, aclarubicin, adotrastuzumab emtansin, afatinib, aflibercept, aldesleukin, alemtuzumab, alendronic acid, alitretinoin, altretamine, amifostine, aminoglutethimide, hexyl-5-aminolevulinate, amrubicin, amsacrine, anastrozole, ancestim, anethole dithiolethione, angiotensin II, antithrombin III, aprepitant, arcitumomab, arglabin, arsenic trioxide, asparaginase, axitinib, azacitidine, belotecan, bendamustine, belinostat, bevacizumab, bexarotene, bicalutamide, bisantrene, bleomycin, bortezomib, buserelin, bosutinib, brentuximab vedotin, busulfan, cabazitaxel, cabozantinib, calcium folinate, calcium levofolinate, capecitabine, capromab, carboplatin, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, copanlisib, crisantaspase, crizotinib, cyclophosphamide, cyproterone, cytarabine, dacarbazine, dactinomycin, dabrafenib, dasatinib, daunorubicin, decitabine, degarelix, denileukin diftitox, denosumab, depreotide, deslorelin, dexrazoxane, dibrospidium chloride, dianhydrogalactitol, diclofenac, docetaxel, dolasetron, doxifluridine, doxorubicin, doxorubicin+estrone, dronabinol, edrecolomab, elliptinium acetate, endostatin, enocitabine, enzalutamide, epirubicin, epitiostanol, epoetin alfa, epoetin beta, epoetin zeta, eptaplatin, eribulin, erlotinib, esomeprazole, estramustine, etoposide, everolimus, exemestane, fadrozole, fentanyl, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine salt, gadoversetamide, gadoxetic acid disodium salt (Gd-EOB-DTPA disodium salt), gallium nitrate, ganirelix, gefitinib, gemcitabine, gemtuzumab, glucarpidase, glutoxim, goserelin, granisetron, granulocyte colony stimulating factor (G-CSF), granulocyte macrophage colony stimulating factor (GM-CSF), histamine dihydrochloride, histrelin, hydroxycarbamide, I-125 seeds, ibandronic acid, ibritumomab tiuxetan, ibrutinib, idarubicin, ifosfamide, imatinib, imiquimod, improsulfan, indisetron, incadronic acid, ingenolmebutate, interferon alpha, interferon beta, interferon gamma, iobitridol, iobenguane (123I), iomeprole, ipilimumab, irinotecan, itraconazole, ixabepilone, lanreotide, lansoprazole, lapatinib, lasocholine, lenalidomide, lentinan, letrozole, leuprorelin, levamisole, levonorgestrel, levothyroxine-sodium, lipegfilgrastim, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methyl aminolevulinate, methylprednisolone, methyltestosterone, metirosin, mifamurtide, miltefosine, miriplatin, mitobronitol, mitoguazone, mitolactol, mitomycin, mitotane, mitoxantrone, mogamulizumab, molgramostim, mopidamole, morphine hydrochloride, morphine sulphate, nabilon, nabiximols, nafarelin, naloxone+pentazocine, naltrexone, nartograstim, nedaplatin, nelarabine, neridronic acid, nivolumabpentetreotide, nilotinib, nilutamide, nimorazole, nimotuzumab, nimustine, nitracrine, nivolumab, obinutuzumab, octreotide, ofatumumab, omacetaxin-mepesuccinate, omeprazole, ondansetron, orgotein, orilotimode, oxaliplatin, oxycodone, oxymetholone, ozogamicin, p53 gene therapy, paclitaxel, palladium-103 seed, palonosetron, pamidronic acid, panitumumab, pantoprazole, pazopanib, pegaspargase, pembrolizumab, peginterferon alfa 2b, pemetrexed, pentostatin, peplomycin, perflubutane, perfosfamide, pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223-chloride, radotinib, raloxifene, raltitrexed, ramosetron, ramucirumab, ranimustine, rasburicase, razoxane, refametinib, regorafenib, risedronic acid, rhenium-186 etidronate, rituximab, romidepsin, romurtide, roniciclib, samarium (153Sm) lexidronam, satumomab, secretin, sipuleucel-T, sizofiran, sobuzoxane, sodium glycididazole, sorafenib, stanozolol, streptozocin, sunitinib, talaporfm, tamibarotene, tamoxifen, tapentadole, tasonermin, teceleukin, technetium (99mTc) nofetumomab merpentane, 99mTc-HYNIC-[Tyr3]-octreotide, tegafur, tegafur+gimeracil+oteracil, temoporfm, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, tramadol, trastuzumab, treosulfan, tretinoin, trifluridine+tipiracil, trametinib, trilostane, triptorelin, trofosfamide, thrombopoietin, ubenimex, valrubicin, vandetanib, vapreotide, valatinib, vemurafenib, vinblastine, vincristine, vindesine, vinflunine, vinorelbine, vismodegib, vorinostat, yttrium-90 glass microspheres, zinostatin, zinostatin stimalamer, zoledronic acid, zorubicin.

In addition, the compounds of the present invention can be combined, for example, with binders which, by way of example, can bind to the following targets: OX-40, CD137/4-1BB, DR3, IDO1/IDO2, LAG-3, CD40.

In addition, the compounds according to the invention can also be used in combination with radiotherapy and/or surgical intervention.

Generally, the following aims can be pursued with the combination of compounds of the present invention with other cytostatically or cytotoxically active agents:
improved efficacy in slowing the growth of a tumour, in reducing its size or even in completely eliminating it, compared with treatment with an individual active compound;
the possibility of using the chemotherapeutics used in a lower dosage than in the case of monotherapy;
the possibility of a more tolerable therapy with fewer side effects compared with individual administration;
the possibility of treatment of a broader spectrum of neoplastic disorders;
the achievement of a higher rate of response to the therapy;
a longer survival time of the patient compared with present-day standard therapy.

In addition, the compounds according to the invention can also be used in combination with radiotherapy and/or surgical intervention.

The present invention further provides medicaments which comprise at least one compound of the invention, typically together with one or more inert, nontoxic, pharmaceutically suitable excipients, and for the use thereof for the aforementioned purposes.

The compounds of the invention can act systemically and/or locally. For this purpose, they can be administered in a suitable manner, for example parenterally, possibly inhalatively or as implants or stents.

The compounds of the invention can be administered in administration forms suitable for these administration routes.

Parenteral administration can bypass an absorption step (for example intravenously, intraarterially, intracardially, intraspinally or intralumbally) or include an absorption (for example intramuscularly, subcutaneously, intracutaneously, percutaneously or intraperitoneally). Administration forms suitable for parenteral administration include preparations for injection and infusion in the form of solutions, suspensions, emulsions or lyophilizates. Preference is given to parenteral administration, especially intravenous administration.

In general, it has been found to be advantageous in the case of parenteral administration to administer amounts of about 0.001 to 1 mg/kg, preferably about 0.01 to 0.5 mg/kg, of body weight to achieve effective results.

It may nevertheless be necessary in some cases to deviate from the stated amounts, specifically as a function of body weight, route of administration, individual response to the active ingredient, nature of the preparation and time or interval over which administration takes place. Thus, in some cases less than the abovementioned minimum amount may be sufficient, while in other cases the upper limit mentioned must be exceeded. In the case of administration of greater amounts, it may be advisable to divide them into several individual doses over the day.

EXAMPLES

The examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are based in each case on volume.

If, in the description of experiments, the temperature at which the reaction is carried out is not stated, room temperature can be assumed.

Synthesis Routes:

Exemplary for the working examples, the schemes below show exemplary synthesis routes leading to the working examples:

Scheme 20: Synthesis of Cysteine-Linked ADCs

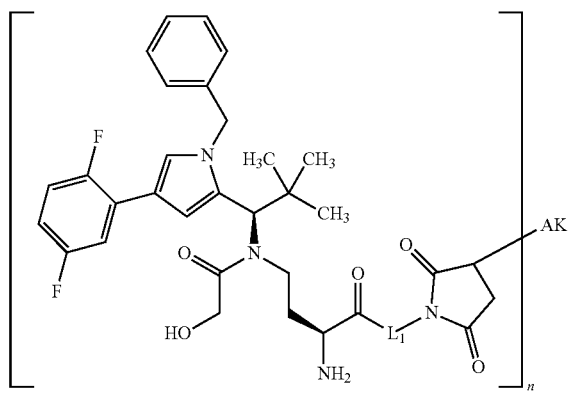

Scheme 21: Synthesis of Cysteine-Linked ADCs

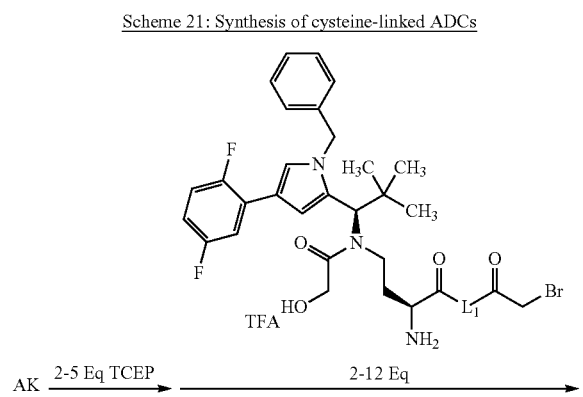

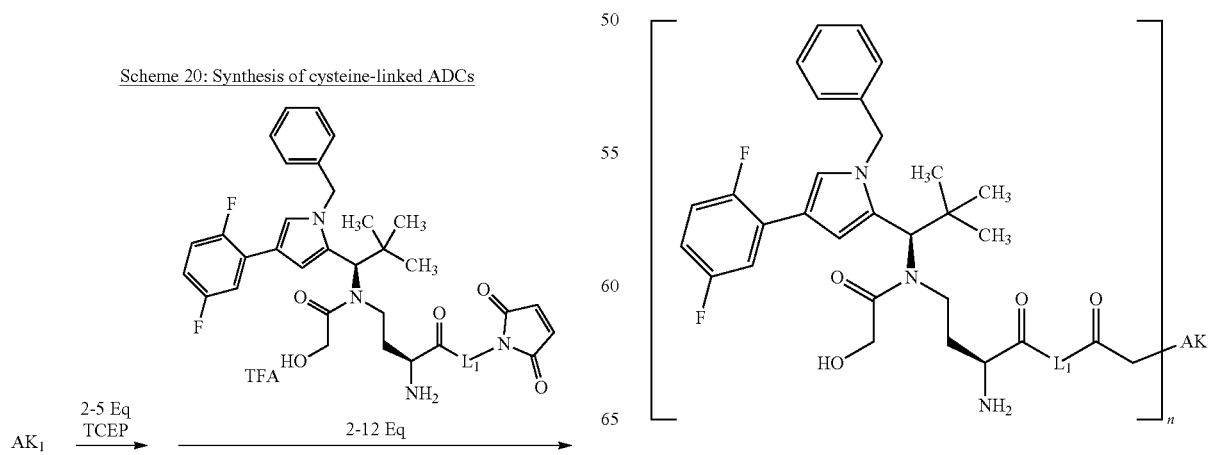

Scheme 22: Synthesis of intermediates
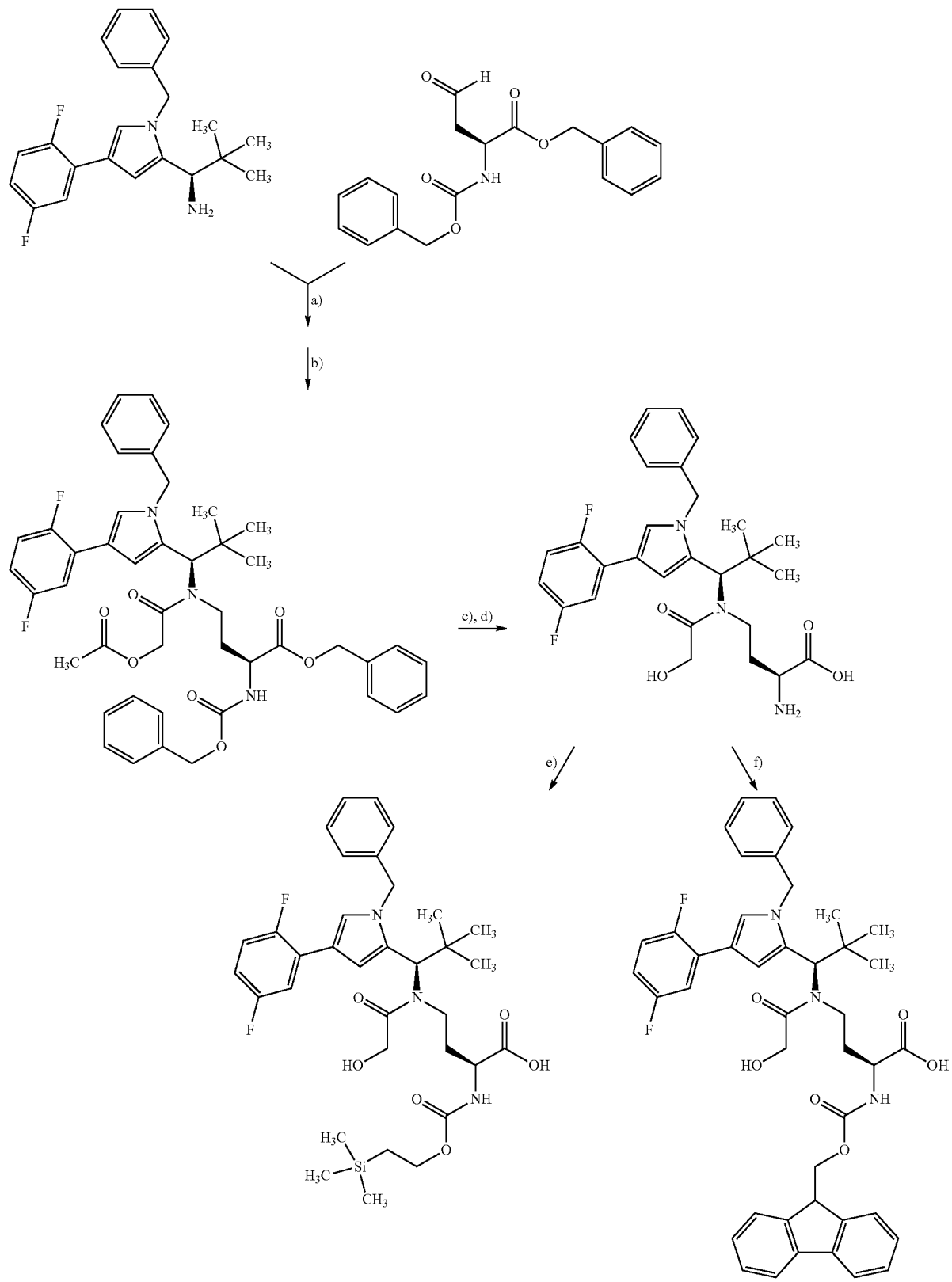
[a): for example sodium triacetoxyborohydride, acetic acid, DCM, RT; b) for example acetoxyacetyl chloride, NEt3, DCM, RT; c) for example LiOH, THF/water, RT; d) for example H2, Pd-C, EtOH, RT; e) for example Teoc-OSu, NEt3, dioxane, RT; f) for example Fmoc-Cl, dissopropylethylamine, dioxane/water 2:1, RT]

Scheme 24: Synthesis of intermediates
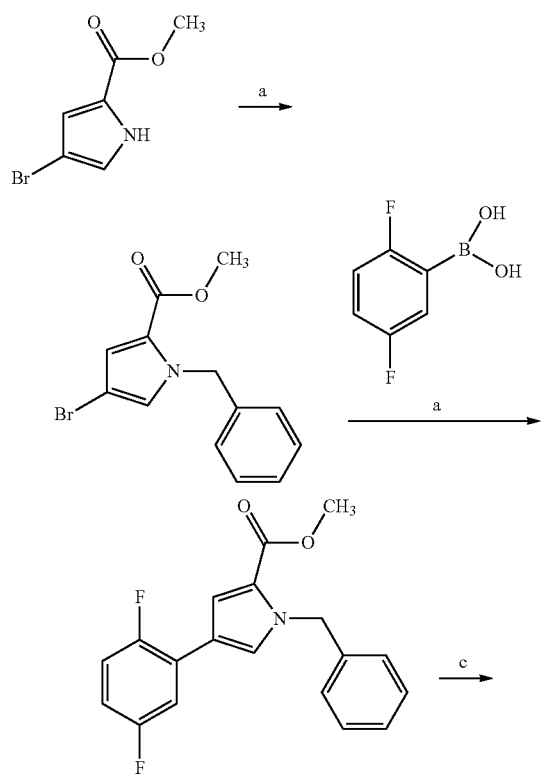
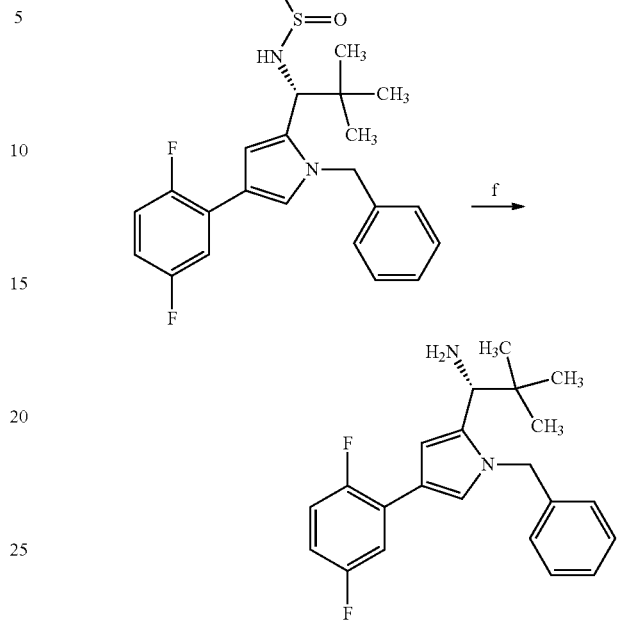
[a): for example benzyl bromide, Cs$_2$CO$_3$, DMF, RT; b) for example Pd(dppf)$_2$Cl$_2$, DMF, Na$_2$CO$_3$, 85° C.; c) for example LiAlH$_4$, THF, 0° C.; MnO$_2$, DCM, RT; d) for example Ti(iOPr)$_4$, THF, RT; e) for example tBuLi, THF, -78° C.; MeOH, NH$_4$Cl; f) for example HCl/1,4-dioxane]
Scheme 25: Synthesis of cysteine-linked ADCs
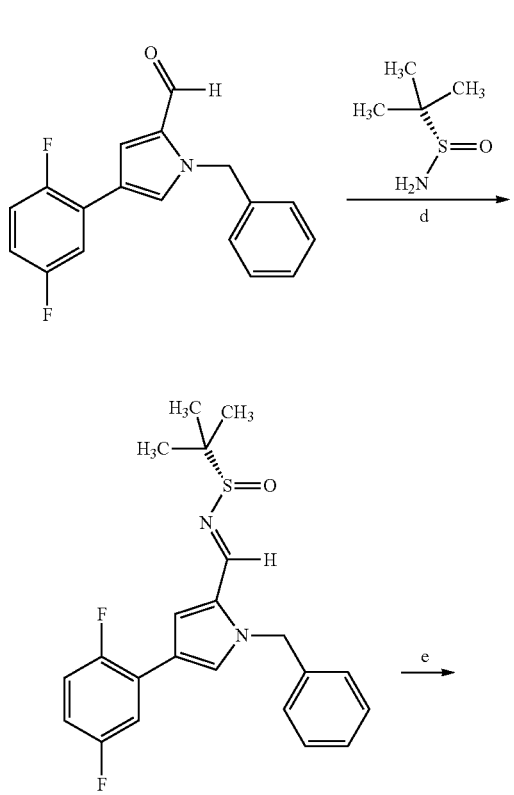
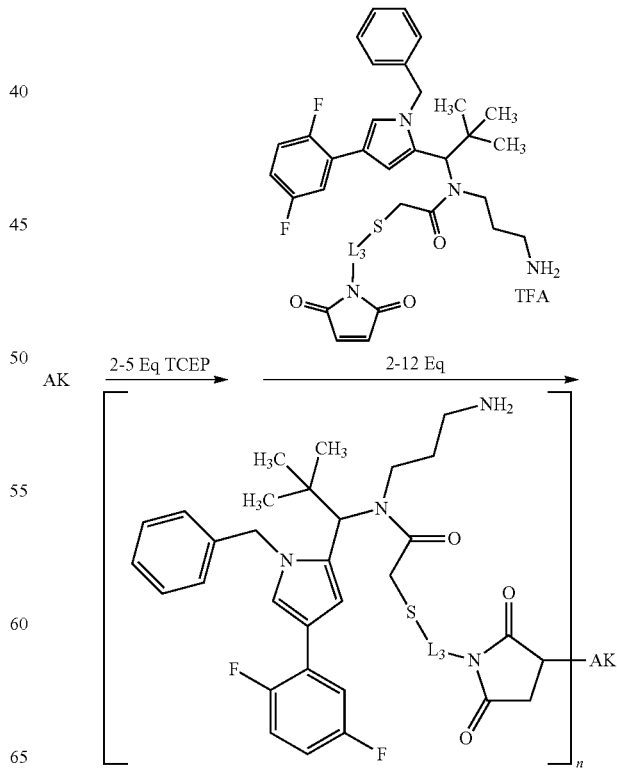

219
Scheme 26: Synthesis of cysteine-linked ADCs via hydrolyzed succinamides
This process was used in particular for ADCs where L1 = CH$_2$ or L1 = CH-CH$_3$ or where L1 = phenyl to convert these ADCs into the open-chain linking forms.
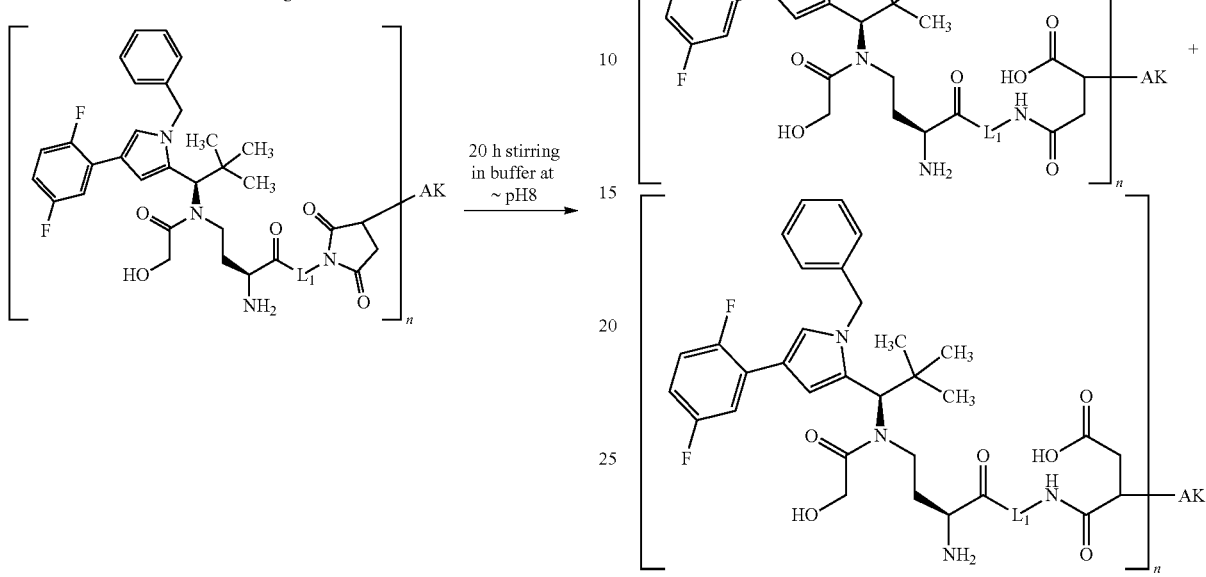
220
-continued
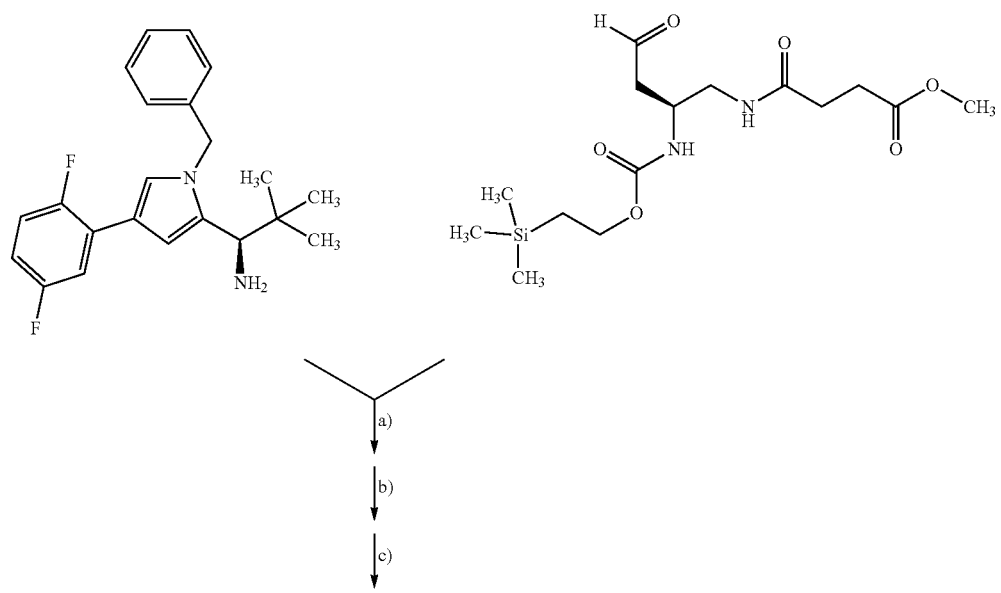
Scheme 27: Synthesis of ADC precursor molecules

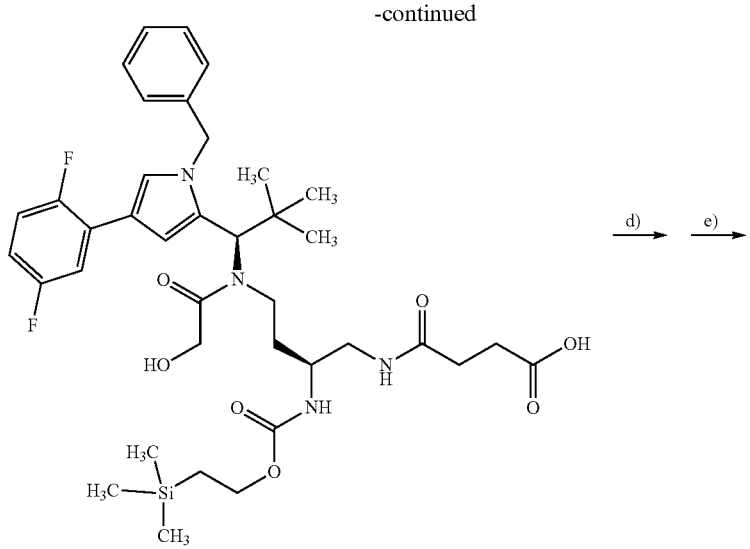

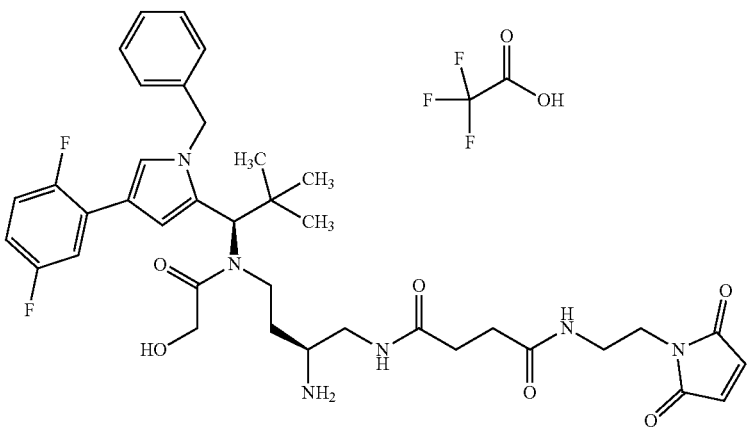

[a]: sodium triacetoxyborohydride, acetic acid, DCM, RT; b) acetoxyacetyl chloride, diisopropylethylamine, DCM, RT; c) LiOH, MeOH, RT; d) trifluoroacetic acid/ 1-(2-aminoethyl)-1H-pyrrole-2,5-dione (1:1) HATU, DMF, diisopropylethylamine, RT; e) zinc chloride, trifluoroethanol, 50° C., EDTA.]

Scheme 28: Synthesis of ADC precursor molecules

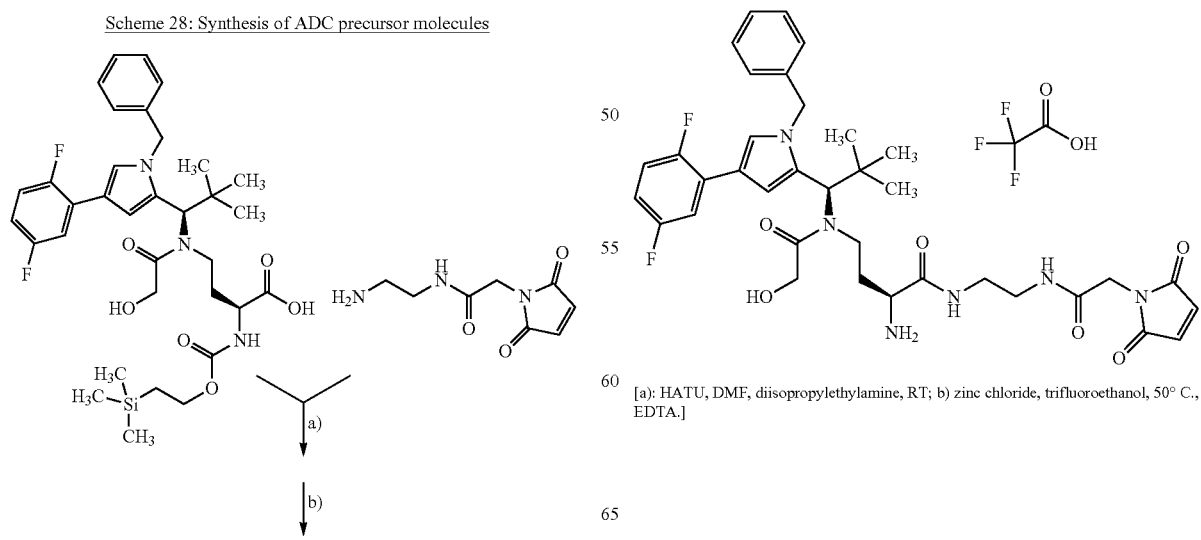

[a]: HATU, DMF, diisopropylethylamine, RT; b) zinc chloride, trifluoroethanol, 50° C., EDTA.]

Scheme 29: Synthesis of ADC precursor molecules
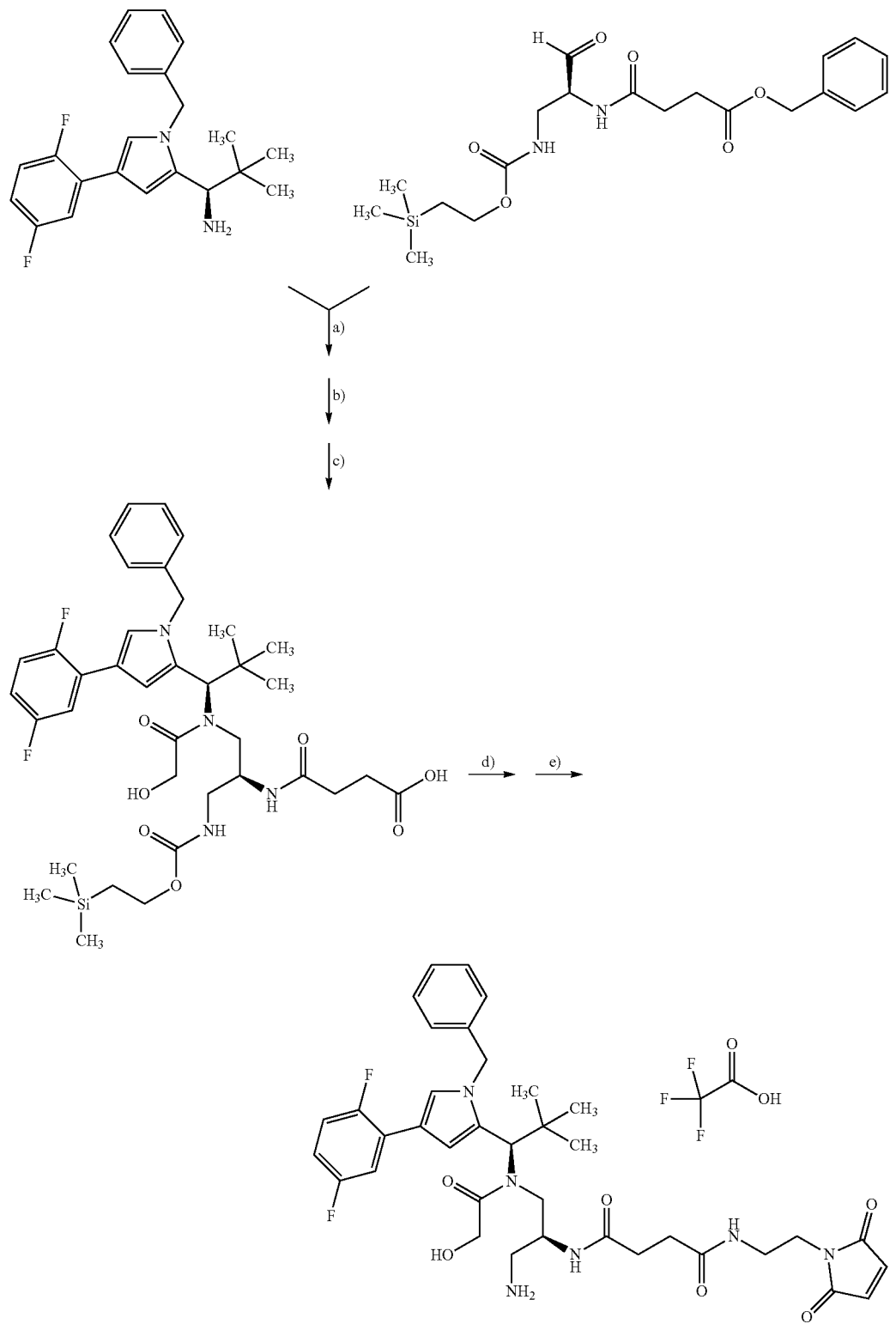
[a]: sodium triacetoxyborohydride, acetic acid, DCM, RT; b) acetoxyacetyl chloride, triethylamine, DCM, RT; c) LiOH, MeOH, RT; d) trifluoroacetic acid/1-(2-aminoethyl)-1H-pyrrole-2,5-dione (1:1) HATU, DMF, diisopropylethylamine, RT; e) zinc chloride, trifluoroethanol, 50° C., EDTA.]

Scheme 30: Synthesis of ADCs
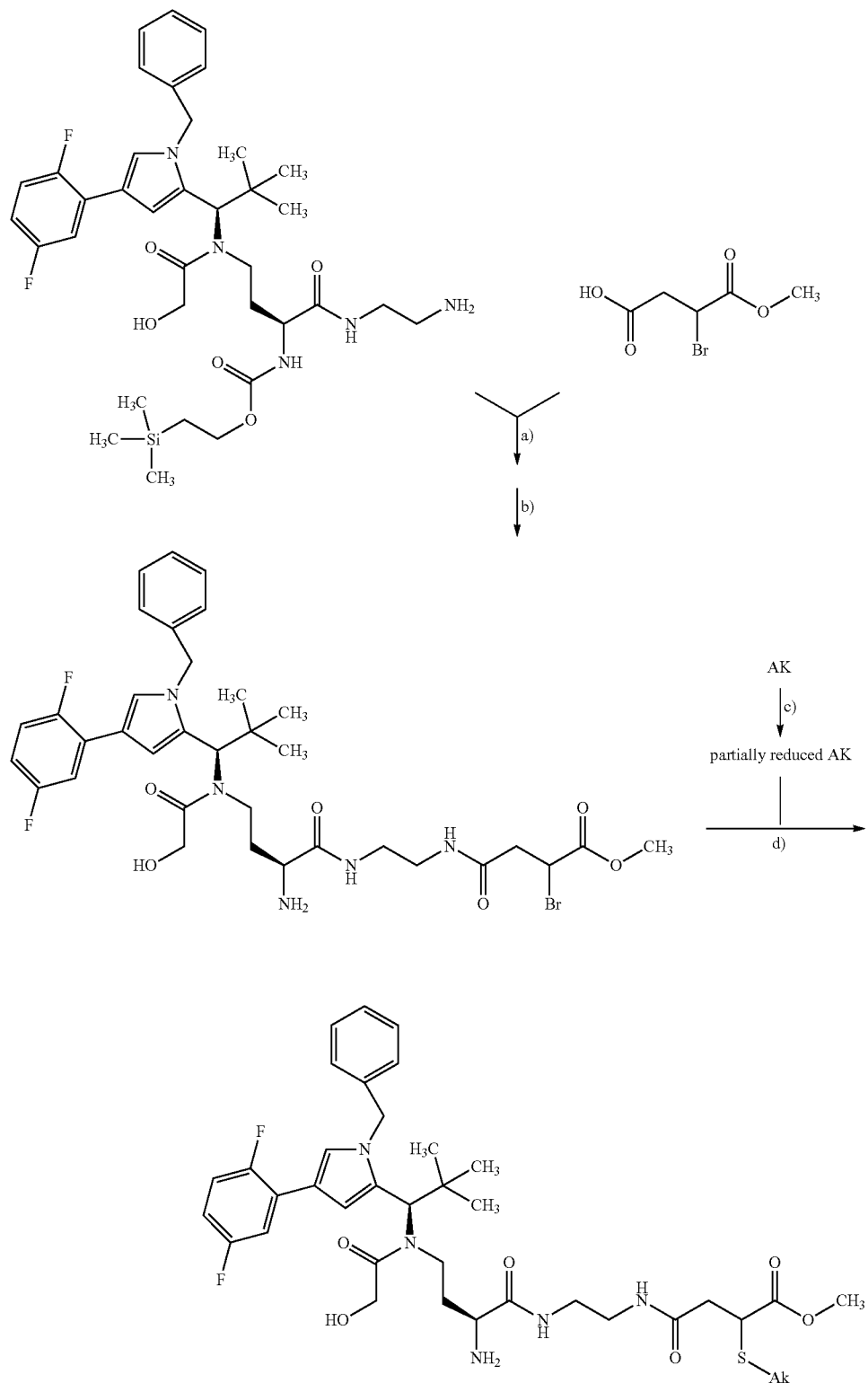
[a]: 2-bromo-1-ethylpyridinium tetrafluoroborate (BEP), DCM, pyridine, RT; b) zinc chloride, trifluoroethanol, 50° C., EDTA; c) 3-4 equivalents of TCEP, PBS buffer; d) PBS buffer, 20 h RT.]

Scheme 31: Synthesis of ADCs
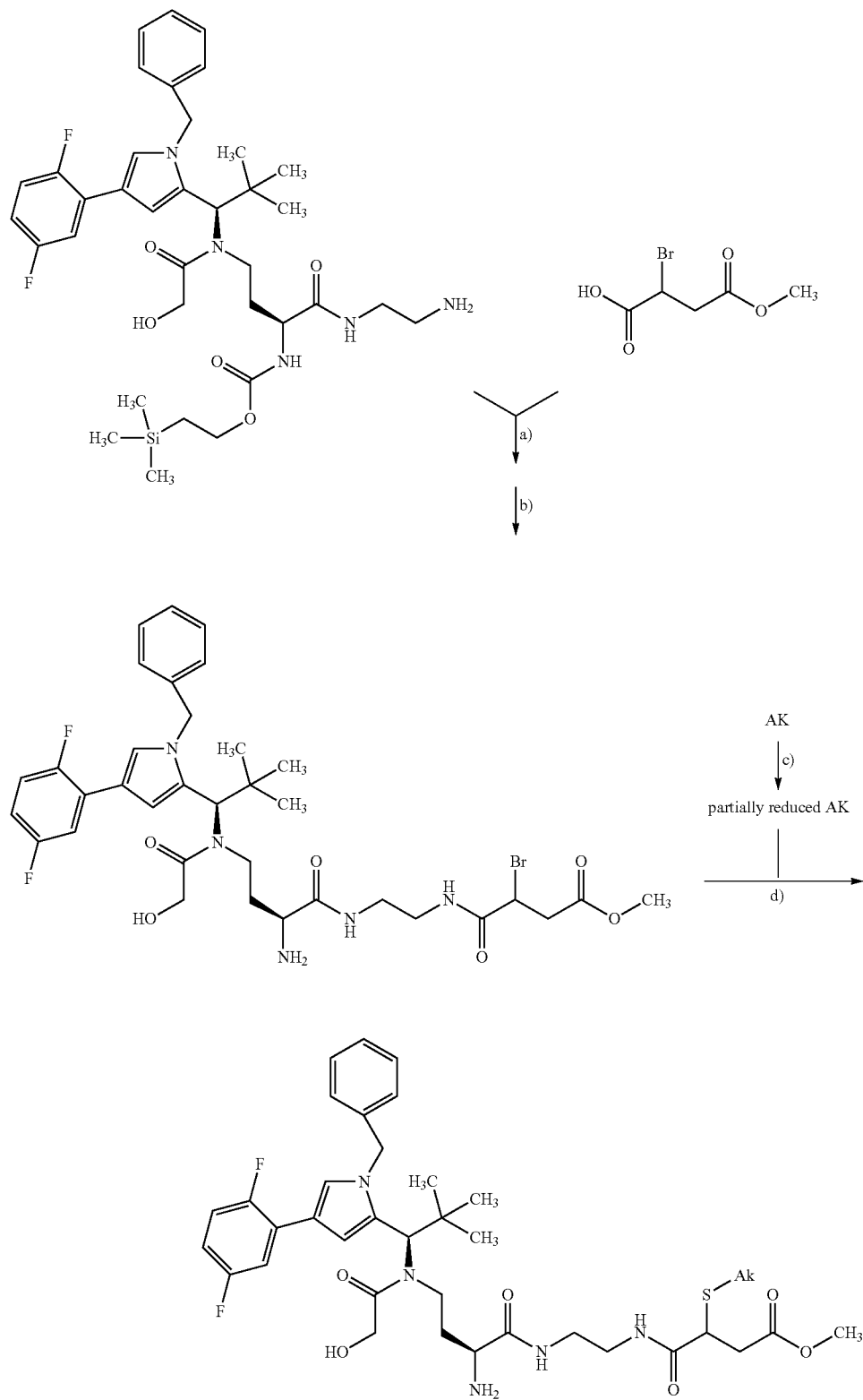
[a]: 2-bromo-1-ethylpyridinium tetrafluoroborate (BEP), DCM, pyridine, RT; b) zinc chloride, trifluoroethanol, 50° C., EDTA; c) 3-4 equivalents of TCEP, PBS buffer; d) PBS buffer, 20 h RT.]

Scheme 32: Synthesis of intermediates
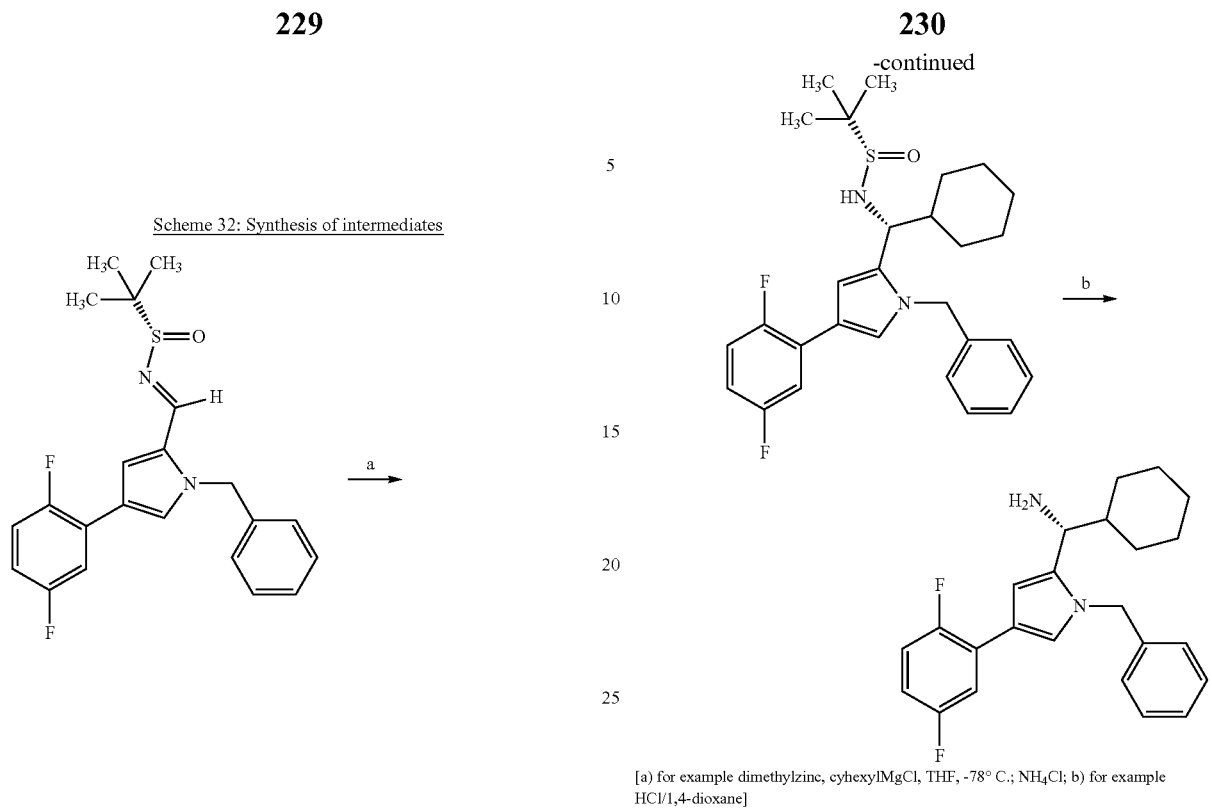
[a) for example dimethylzinc, cyhexylMgCl, THF, -78° C.; NH4Cl; b) for example HCl/1,4-dioxane]
Scheme 33: Synthesis of ADC precursor molecules
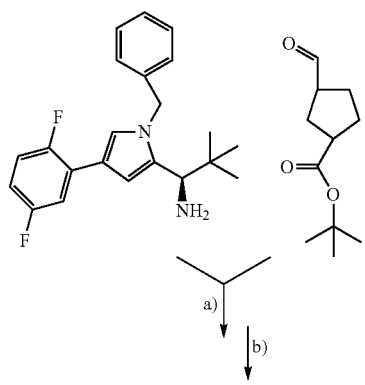

231 232
-continued
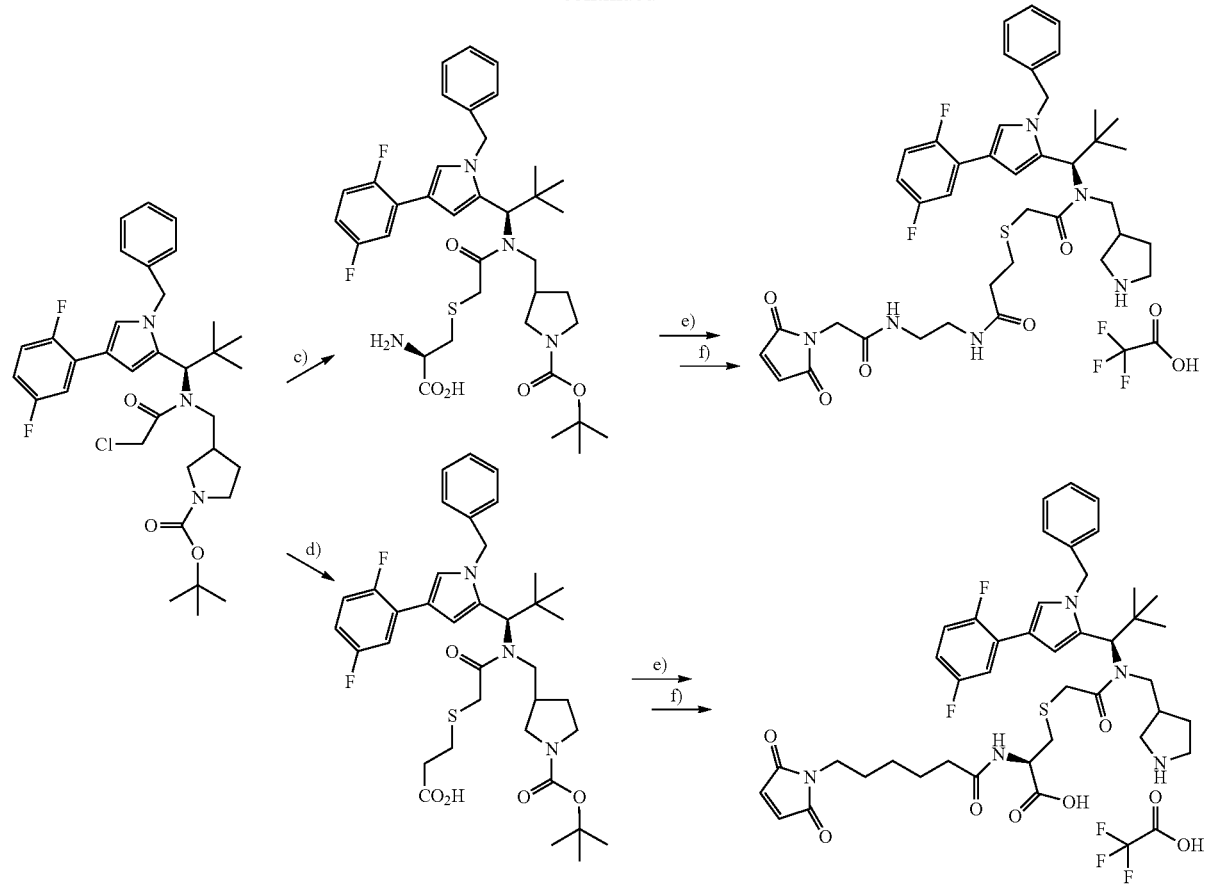
[a]: sodium triacetoxyborohydride, acetic acid, DC, RT; b) acetoxyacetyl chloride, triethylamine, DCM, RT; c) L-cysteine NaHCO₃, DBU, isopropanol/water, RT; d) 3-sulphanylpropanoic acid, K₂CO₃, RT; e) linker, HATU, DMF, diisopropylethylamine, RT; e) zinc chloride, trifluoroethanol, 50° C., EDTA.]
Scheme 34: Synthesis of lysine-linked ADCs
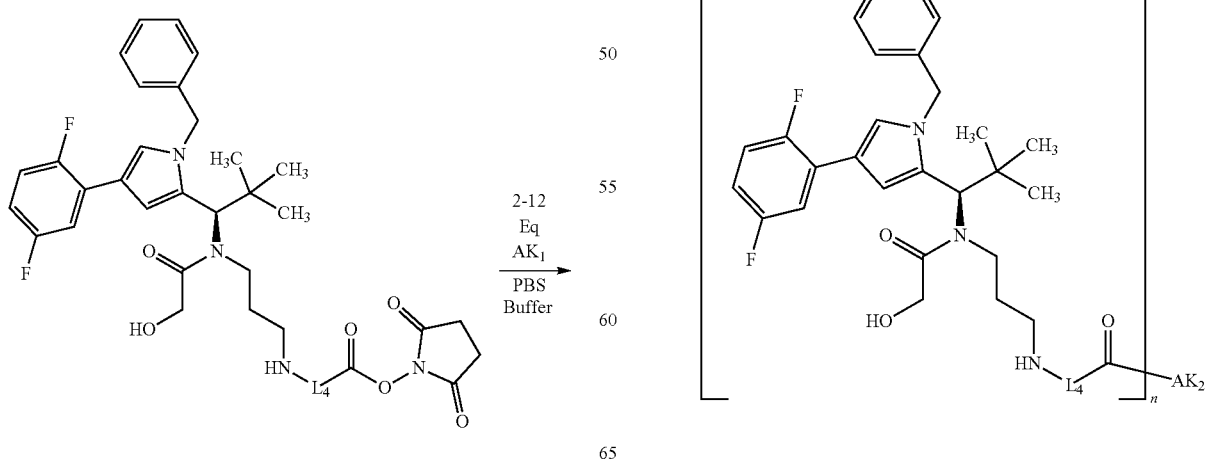

Scheme 35: Synthesis of lysine-linked ADCs

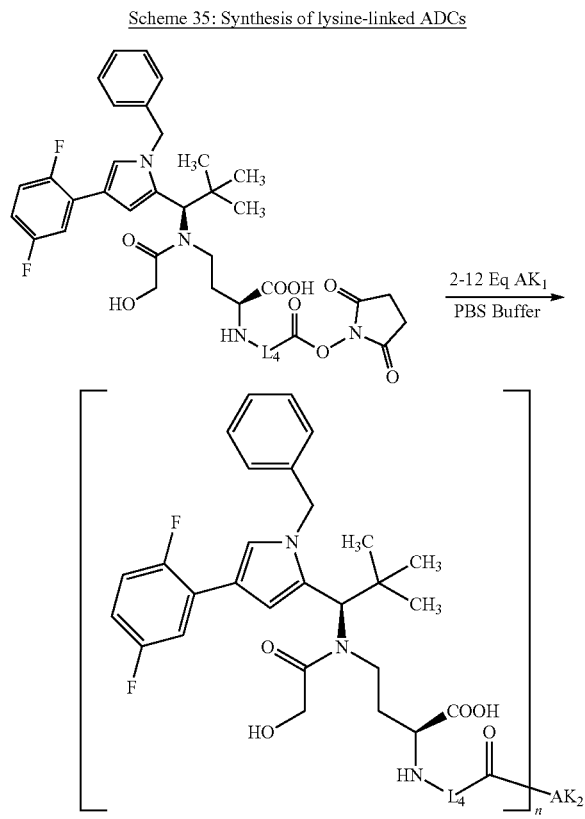

A. Examples
Abbreviations and Acronyms:
A43 INS human tumour cell line
A549 human tumour cell line
A498 human tumour cell line
ABCB1 ATP-binding cassette sub-family B member 1 (synonym for P-gp and MDR1)
abs. absolute
Ac acetyl
ACN acetonitrile
aq. aqueous, aqueous solution
ATP adenosine triphosphate
BCRP breast cancer resistance protein, an efflux transporter
BEP 2-bromo-1-ethylpyridinium tetrafluoroborate
Boc tert-butoxy carbonyl
br. broad (in NMR)
Ex. Example
CI chemical ionization (in MS)
d doublet (in NMR)
d day(s)
TLC thin-layer chromatography
DCI direct chemical ionization (in MS)
dd doublet of doublets (in NMR)
DMAP 4-N,N-dimethylaminopyridine
DME 1,2-dimethoxyethane
DMEM Dulbecco's Modified Eagle Medium (standardized nutrient medium for cell culture)
DMF N,N-dimethylformamide
DMSO dimethyl sulphoxide
DPBS, D-PBS, PBS Dulbecco's phosphate-buffered salt solution
  PBS=DPBS=D-PBS, pH 7.4, from Sigma, No D8537
  Composition:
  0.2 g KCl
  0.2 g $KH_2PO_4$ (anhyd)
  8.0 g NaCl
  1.15 g $Na_2HPO_4$ (anhyd)
  made up ad 1 l with $H_2O$
dt doublet of triplets (in NMR)
DTT DL-dithiothreitol
EDC N'-(3-dimethylaminopropyl)-7V-ethylcarbodiimide hydrochloride
EGFR epidermal growth factor receptor
EI electron impact ionization (in MS)
ELISA enzyme-linked immunosorbent assay
eq. equivalent(s)
ESI electrospray ionization (in MS)
ESI-MicroTofq ESI—MicroTofq (name of the mass spectrometer with Tof=time of flight and q=quadrupol)
FCS foetal calf serum
Fmoc (9H-fluoren-9-ylmethoxy (carbonyl
sat. saturated
GTP guanosine-5'-triphosphate
h hour(s)
HATU O-(7-azabenzotriazol-1-yl)-N,N,N',N'-tetramethyluronium hexafluorophosphate
HCT-116 human tumour cell line
HEPES 4-(2-hydroxyethyl)piperazine-1-ethanesulphonic acid
HOAc acetic acid
HOAt 1-hydroxy-7-azabenzotriazole
HOBt 1-hydroxy-1H-benzotriazole hydrate
HOSu TV-hydroxysuccinimide
HPLC high-pressure, high-performance liquid chromatography
HT29 human tumour cell line
$IC_{50}$ half-maximal inhibitory concentration
i.m. intramuscularly, administration into the muscle
i.v. intravenously, administration into the vein
conc. concentrated
LC-MS liquid chromatography-coupled mass spectrometry
LLC-PK1 cells Lewis lung carcinoma pork kidney cell line
L-MDR human MDR1 transfected LLC-PK1 cells
m multiplet (in NMR)
Me methyl;
MDR1 Multidrug resistance protein 1
MeCN acetonitrile
min minute(s)
MS mass spectrometry MTT 3-(4,5-dimethylthiazol-2-yl)-2,5-diphenyl-2H-tetrazolium bromide 3
NCI-H292 human tumour cell line
NCI-H520 human tumour cell line
NMM N-methylmorpholine
NMP N-methyl-2-pyrrolidinone
NMR nuclear magnetic resonance spectrometry
NMRI mouse strain originating from the Naval Medical Research Institute (NMRI)
Nude mice nude mice (experimental animals)
NSCLC non small cell lung cancer
PBS phosphate-buffered salt solution
Pd/C palladium on activated carbon
P-gp P-gycoprotein, a transporter protein
PNGaseF enzyme for cleaving sugar
quant. quantitative (in yield)
quart quartet (in NMR)
quint quintet (in NMR)
$R_f$ retention index (in TLC)
RT room temperature
$R_t$ retention time (in HPLC)
s singlet (in NMR)

s.c. subcutaneously, administration under the skin
SCC-4 human tumour cell line
SCC-9 human tumour cell line
SCID mice test mice with severe combined immunodeficiency
t triplet (in NMR)
TBAF tetra-n-butylammonium fluoride
TEMPO (2,2,6,6-tetramethylpiperidin-1-yl)oxyl
tert tertiary
TFA trifluoroacetic acid
THF tetrahydrofuran
T3P® 2,4,6-tripropyl-1,3,5,2,4,6-trioxatriphosphinane 2,4,6-trioxide
UV ultraviolet spectrometry
v/v volume to volume ratio (of a solution)
Z benzyloxycarbonyl
786-O human tumour cell line
HPLC and LC-MS Methods:
Method 1 (LC-MS):
Instrument: Waters ACQUITY SQD UPLC System; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A oven: 50° C.; flow rate: 0.40 ml/min; UV detection: 208-400 nm.
Method 2 (LC-MS):
MS instrument type: Waters Synapt G2S; UPLC instrument type: Waters Acquity I-CLASS; column: Waters, BEH300, 2.1×150 mm, C18 1.7 μm; mobile phase A: 1 l of water+0.01% formic acid, mobile phase B: 1 l of acetonitrile+0.01% formic acid; gradient: 0.0 min 2% B→1.5 min 2% B→8.5 min 95% B→10.0 min 95% B; oven: 50° C.; flow rate: 0.50 ml/min; UV detection: 220 nm
Method 3 (LC-MS):
MS instrument: Waters (Micromass) QM; HPLC instrument: Agilent 1100 Series; column: Agilent ZORBAX Extend-C18 3.0×50 mm 3.5-micron; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; oven: 40° C.; flow rate: 1.75 ml/min; UV detection: 210 nm
Method 4 (LC-MS):
MS instrument type: Waters Synapt G2S; UPLC instrument type: Waters Acquity I-CLASS; column: Waters, HSST3, 2.1×50 mm, C18 1.8 μm; mobile phase A: 1 l of water+0.01% formic acid, mobile phase B: 1 l of acetonitrile+0.01% formic acid; gradient: 0.0 min 10% B→0.3 min 10% B→1.7 min 95% B→2.5 min 95% B; oven: 50° C.; flow rate: 1.20 ml/min; UV detection: 210 nm
Method 5 (LC-MS):
Instrument: Waters ACQUITY SQD UPLC System; column: Waters Acquity UPLC HSS T3 1.8μ 50×1 mm; mobile phase A: 1 l of water+0.25 ml of 99% strength formic acid, mobile phase B: 1 l of acetonitrile+0.25 ml of 99% strength formic acid; gradient: 0.0 min 95% A→6.0 min 5% A→7.5 min 5% A oven: 50° C.; flow rate: 0.35 ml/min; UV detection: 210-400 nm.
Method 6 (LC-MS):
Instrument: Micromass Quattro Premier with Waters UPLC Acquity; column: Thermo Hypersil GOLD 1.9μ 50×1 mm; mobile phase A: 1 l of water+0.5 ml of 50% strength formic acid, mobile phase B: 1 l of acetonitrile+0.5 ml of 50% strength formic acid; gradient: 0.0 min 97% A→0.5 min 97% A→3.2 min 5% A→4.0 min 5% A oven: 50° C.; flow rate: 0.3 ml/min; UV detection: 210 nm.
Method 7 (LC-MS):
Instrument: Agilent MS Quad 6150; HPLC: Agilent 1290; column: Waters Acquity UPLC HSS T3 1.8μ 50×2.1 mm; mobile phase A: 1 l of water+0.25 ml of 99% strength formic acid, mobile phase B: 1 l of acetonitrile+0.25 ml of 99% strength formic acid; gradient: 0.0 min 90% A→0.3 min 90% A→1.7 min 5% A→3.0 min 5% A oven: 50° C.; flow rate: 1.20 ml/min; UV detection: 205-305 nm.
Method 8 (LC-MS):
MS instrument type: Waters Synapt G2S; UPLC instrument type: Waters Acquity I-CLASS; column: Waters, HSST3, 2.1×50 mm, C18 1.8 μm; mobile phase A: 1 l of water+0.01% formic acid; mobile phase B: 1 l of acetonitrile+0.01% formic acid; gradient: 0.0 min 2% B→2.0 min 2% B→13.0 min 90% B→15.0 min 90% B; oven: 50° C.; flow rate: 1.20 ml/min; UV detection: 210 nm
Method 9: LC-MS-Prep Purification Method for Examples 181-191 (Method LIND-LC-MS-Prep)
MS instrument: Waters, HPLC instrument: Waters (column Waters X-Bridge C18, 19 mm×50 mm, 5 μm, mobile phase A: water+0.05% ammonia, mobile phase B: acetonitrile (ULC) with gradient; flow rate: 40 ml/min; UV detection: DAD; 210-400 nm).
or:
MS instrument: Waters, HPLC instrument: Waters (column Phenomenex Luna 5μ C18(2) 100A, AXIA Tech. 50×21.2 mm, mobile phase A: water+0.05% formic acid, mobile phase B: acetonitrile (ULC) with gradient; flow rate: 40 ml/min; UV detection: DAD; 210-400 nm).
Method 10: LC-MS Analysis Method for Examples 181-191 (LIND_SQD_SB_AQ)
MS instrument: Waters SQD; Instrument HPLC: Waters UPLC; column: Zorbax SB-Aq (Agilent), 50 mm×2.1 mm, 1.8 μm; mobile phase A: water+0.025% formic acid, mobile phase B: acetonitrile (ULC)+0.025% formic acid; gradient: 0.0 min 98% A—0.9 min 25% A—1.0 min 5% A—1.4 min 5% A—1.41 min 98% A—1.5 min 98% A; oven: 40° C.; flow rate: 0.600 ml/min; UV detection: DAD; 210 nm.
Method 11 (HPLC):
Instrument: HP1100 Series
column: Merck Chromolith SpeedROD RP-18e, 50-4.6 mm, Cat. No. 1.51450.0001, precolumn Chromolith Guard Cartridge Kit, RP-18e, 5-4.6 mm, Cat. No. 1.51470.0001
gradient: flow rate 5 ml/min
  injection volume 5 μl
  solvent A: HClO4 (70% strength) in water (4 ml/l)
  solvent B: acetonitrile
  start 20% B
  0.50 min 20% B
  3.00 min 90% B
  3.50 min 90% B
  3.51 min 20% B
  4.00 min 20% B
  column temperature: 40° C.
wavelength: 210 nm
Method 12 (LC-MS):
MS instrument type: Thermo Scientific FT-MS; UHPLC+ instrument type: Thermo Scientific UltiMate 3000; column: Waters, HSST3, 2.1×75 mm, C18 1.8 μm; mobile phase A: 1 l of water+0.01% formic acid; mobile phase B: 1 l of acetonitrile+0.01% formic acid; gradient: 0.0 min 10% B→2.5 min 95% B→3.5 min 95% B; oven: 50° C.; flow rate: 0.90 ml/min; UV detection: 210 nm/optimum integration path 210-300 nm
Method 13: (LC-MS):
MS instrument: Waters (Micromass) Quattro Micro; Instrument Waters UPLC Acquity; column: Waters BEH C18 1.7μ 50×2.1 mm; mobile phase A: 1 l of water+0.01 mol ammonium formate, mobile phase B: 1 l of acetonitrile; gradient: 0.0 min 95% A→0.1 min 95% A→2.0 min 15% A→2.5 min 15% A→2.51 min 10% A→3.0 min 10% A; oven: 40° C.; flow rate: 0.5 ml/min; UV detection: 210 nm
Method 14: (LC-MS):

MS instrument type: ThermoFisherScientific LTQ-Orbitrap-XL; HPLC instrument type: Agilent 1200SL; column: Agilent, POROSHELL 120, 3×150 mm, SB—C18 2.7 μm; mobile phase A: 1 l water+0.1% trifluoroacetic acid; mobile phase B: 1 l acetonitrile+0.1% trifluoroacetic acid; gradient: 0.0 min 2% B→0.3 min 2% B→5.0 min 95% B→10.0 min 95% B; oven: 40° C.; flow rate: 0.75 ml/min; UV detection: 210 nm All reactants or reagents whose preparation is not described explicitly hereinafter were purchased commercially from generally accessible sources. For all other reactants or reagents whose preparation likewise is not described hereinafter and which were not commercially obtainable or were obtained from sources which are not generally accessible, a reference is given to the published literature in which their preparation is described.

Starting Materials and Intermediates:

Intermediate C2 tert-Butyl (2S)-4-({(1R)-1-[1-benzyl-4-(2,5-difluorophenyl)-1H-imidazol-2-yl]-2,2-dimethylpropyl}amino)-2-[(tert-butoxycarbonyl)amino]butanoate

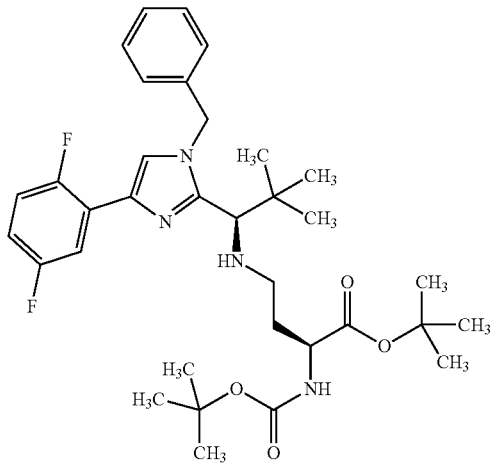 [SMILES: CC(C)(C)OC(=O)N[C@@H](CCN[C@@H](c1nc(-c2cc(F)ccc2F)cn1Cc1ccccc1)C(C)(C)C)C(=O)OC(C)(C)C]

4.22 g (14.5 mmol) of tert-Butyl N-(tert-butoxycarbonyl)-L-homoserinate were dissolved in 180 ml of dichloromethane, and 3.5 ml of pyridine and 9.2 g (21.7 mmol) of 1,1,1-triacetoxy-1lambda$^5$,2-benziodoxol-3(1H)-one were then added. The mixture was stirred at RT for 1 h and then diluted with 500 ml of dichloromethane and extracted twice with 10% strength sodium thiosulphate solution and then in succession twice with 5% strength citric acid and twice with 10% strength sodium bicarbonate solution. The organic phase was separated off, dried over magnesium sulphate and then concentrated under reduced pressure. The residue was taken up in DCM, and a mixture of diethyl ether and n-pentane was added. The precipitate was filtered off and the filtrate was then concentrated and lyophilized from acetonitrile/water. This gave 3.7 g (93%) of tert-Butyl-(2S)-2-[(tert-butoxycarbonyl)amino]-4-oxobutanoate which was used for the next step without further purification. ($R_f$ value: 0.5 (DCM/methanol 95/5).

3.5 g (9.85 mmol) of Intermediate C1 were dissolved in 160 ml of DCM, and 3.13 g (14.77 mmol) of sodium triacetoxyborohydride and 0.7 ml of acetic acid were added. After 5 min of stirring at RT, 3.23 g (11.85 mmol) of tert-Butyl (2S)-2-[(tert-butoxycarbonyl)amino]-4-oxobutanoate were added and the mixture was stirred at RT for a further 30 min. The solvent was then evaporated under reduced pressure and the residue was taken up in acetonitrile/water. The precipitated solid was filtered off and dried, giving 5.46 g (84%) of the title compound.

HPLC (Method 11): $R_t$=2.5 min;
LC-MS (Method 1): $R_t$=1.13 min; MS (ESIpos): m/z=613 (M+H)$^+$.

Intermediate C11

R/S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-homocysteine/trifluoroacetate (1:1)

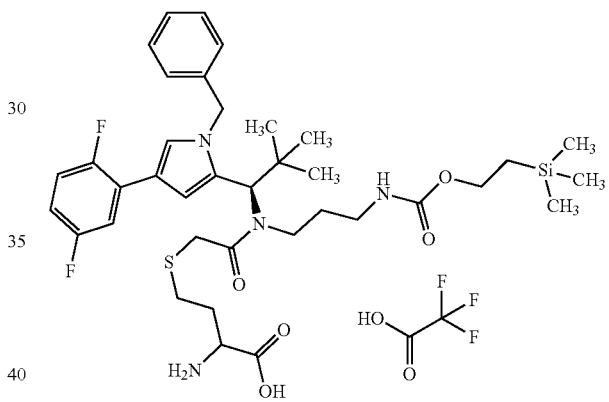

990.0 mg (2.79 mmol) of (1R)-1-[1-benzyl-4-(2,5-difluorophenyl)-1H-pyrrol-2-yl]-2,2-dimethylpropan-1-amine were initially charged in 15.0 ml of dichloromethane, and 828.8 mg (3.91 mmol) of sodium triacetoxyborohydride and 129.9 mg (3.21 mmol) of acetic acid were added, and the mixture was stirred at RT for 5 min. 698.1 mg (3.21 mmol) of 2-(trimethylsilyl)ethyl (3-oxopropyl)carbamate (Intermediate L58) dissolved in 15.0 ml of dichloromethane were added, and the reaction mixture was stirred at RT overnight. The reaction mixture was diluted with ethyl acetate and the organic phase was washed in each case twice with saturated sodium carbonate solution and saturated NaCl solution. The organic phase was dried over magnesium sulphate and the solvent was evaporated under reduced pressure. The residue was purified on silica gel (mobile phase: dichloromethane/methanol=100:2). The solvents were evaporated under reduced pressure and the residue was dried under high vacuum. This gave 1.25 g (73% of theory) of the compound 2-(trimethylsilyl)ethyl [3-({(1R)-1-[1-benzyl-4-(2,5-difluorophenyl)-1H-pyrrol-2-yl]-2,2-dimethyl-propyl}amino)propyl]carbamate.

LC-MS (Method 1): $R_t$=1.09 min; MS (ESIpos): m/z=556 (M+H)$^+$.

151.4 mg (1.5 mmol) of triethylamine and 161.6 mg (1.43 mmol) of chloroacetyl chloride were added to 400.0 mg (0.65 mmol) of 2-(trimethylsilyl)ethyl [3-({(1R)-1-[1-benzyl-4-(2,5-difluorophenyl)-1H-pyrrol-2-yl]-2,2-dimethylpropyl}amino)propyl]carbamate. The reaction mixture was stirred at RT overnight. Ethyl acetate was added to the reaction mixture and the organic phase was washed three times with water and once with saturated NaCl solution. The organic phase was dried over magnesium sulphate and the solvent was evaporated under reduced pressure. The residue was purified by silica gel chromatography (mobile phase: cyclohexane/ethyl acetate=3:1). The solvents were evaporated under reduced pressure and the residue was dried under high vacuum. This gave 254.4 mg (57% of theory) of the compound 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate.

LC-MS (Method 1): $R_t$=1.49 min; MS (ESIneg): m/z=676 $(M+HCOO^-)^-$.

117.4 mg (0.19 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate were dissolved in 10.0 ml of isopropanol, and 928.4 µl of 1M NaOH and 50.2 mg (0.37 mmol) of DL-homocysteine were added. The reaction mixture was stirred at 50° C. for 4.5 h. Ethyl acetate was added to the reaction mixture and the organic phase was washed with saturated sodium bicarbonate solution and saturated NaCl solution. The organic phase was dried over magnesium sulphate and the solvent was evaporated under reduced pressure. The residue was purified by preparative RP-HPLC (column: Reprosil 250×40; 10µ, flow rate: 50 ml/min, MeCN/water, 0.1% TFA). The solvents were evaporated under reduced pressure and the residue was dried under high vacuum. This gave 75.3 mg (48% of theory) of the title compound.

LC-MS (Method 1): $R_t$=1.24 min; MS (ESIpos): m/z=731 $(M+H)^+$.

$^1$H-NMR (400 MHz, DMSO-$d_6$): δ [ppm]=0.03 (s, 9H), 0.40 (m, 1H), 0.75-0.91 (m, 11H), 1.30 (m, 1H), 1.99-2.23 (m, 2H), 2.63-2.88 (m, 4H), 3.18-3.61 (m, 5H), 3.79-4.10 (m, 3H), 4.89 (d, 1H), 4.89 (d, 1H), 5.16 (d, 1H), 5.56 (s, 1H), 6.82 (m, 1H), 6.91 (s, 1H), 6.97 (m, 1H), 7.13-7.38 (m, 6H), 7.49 (s, 1H), 7.63 (m, 1H), 8.26 (s, 3H).

Intermediate C12

R/S-[(8S)-11-{(1R)-1-[1-Benzyl-4-(2,5-difluorophenyl)-1H-pyrrol-2-yl]-2,2-dimethylpropyl}-8-carboxy-2,2-dimethyl-6,12-dioxo-5-oxa-7,11-diaza-2-silatridecan-13-yl]homocysteine

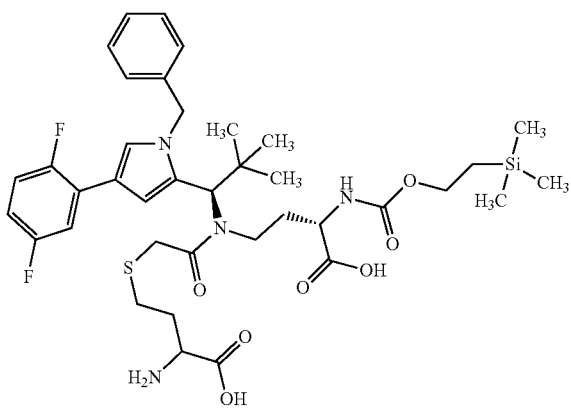 [SMILES: CC(C)(C)[C@H](c1cc(-c2cc(F)ccc2F)cn1Cc1ccccc1)N(CC[C@H](NC(=O)OCC[Si](C)(C)C)C(=O)O)C(=O)CSCCC(N)C(=O)O]

The synthesis was carried out analogously to the synthesis of Intermediate C11 using methyl (2S)-4-oxo-2-({[2-(trimethylsilyl)ethoxy]carbonyl}amino)butanoate (Intermediate L57) and Intermediate C52 as starting materials.

LC-MS (Method 1): $R_t$=1.18 min; MS (ESIpos): m/z=775 $(M+H)^+$.

Intermediate C52

(1R)-1-[1-Benzyl-4-(2,5-difluorophenyl)-1H-pyrrol-2-yl]-2,2-dimethylpropan-1-amine

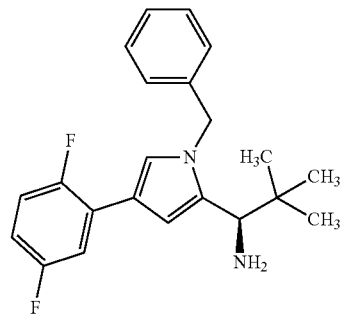 [SMILES: CC(C)(C)[C@@H](N)c1cc(-c2cc(F)ccc2F)cn1Cc1ccccc1]

10.00 g (49.01 mmol) of methyl 4-bromo-1H-pyrrole-2-carboxylate were initially charged in 100.0 ml of DMF, and 20.76 g (63.72 mmol) of caesium carbonate and 9.22 g (53.91 mmol) of benzyl bromide were added. The reaction mixture was stirred at RT overnight. The reaction mixture was partitioned between water and ethyl acetate and the aqueous phase was extracted with ethyl acetate. The combined organic phases were dried over magnesium sulphate and the solvent was evaporated under reduced pressure. The reaction was repeated with 90.0 g of methyl 4-bromo-1H-pyrrole-2-carboxylate.

The two combined reactions were purified by preparative RP-HPLC (column: Daiso 300×100; 10µ, flow rate: 250 ml/min, MeCN/water). The solvents were evaporated under reduced pressure and the residue was dried under high vacuum. This gave 125.15 g (87% of theory) of the compound methyl 1-benzyl-4-bromo-1H-pyrrole-2-carboxylate.

LC-MS (Method 1): $R_t$=1.18 min; MS (ESIpos): m/z=295 $[M+H]^+$.

Under argon, 4.80 g (16.32 mmol) of methyl 1-benzyl-4-bromo-1H-pyrrole-2-carboxylate were initially charged in DMF, and 3.61 g (22.85 mmol) of (2,5-difluorophenyl)boronic acid, 19.20 ml of saturated sodium carbonate solution and 1.33 g (1.63 mmol) of [1,1-bis(diphenylphosphino)ferrocene]-dichloropalladium(II):dichloromethane were added. The reaction mixture was stirred at 85° C. overnight. The reaction mixture was filtered through Celite and the filter cake was washed with ethyl acetate. The organic phase was extracted with water and then washed with saturated NaCl solution. The organic phase was dried over magnesium sulphate and the solvent was evaporated under reduced pressure. The residue was purified by silica gel chromatography (mobile phase: cyclohexane/ethyl acetate 100:3). The solvents were evaporated under reduced pressure and the residue was dried under high vacuum. This gave 3.60 g (67% of theory) of the compound methyl 1-benzyl-4-(2,5-difluorophenyl)-1H-pyrrole-2-carboxylate.

LC-MS (Method 7): $R_t$=1.59 min; MS (ESIpos): m/z=328 $[M+H]^+$.

3.60 g (11.00 mmol) of methyl 1-benzyl-4-(2,5-difluorophenyl)-1H-pyrrole-2-carboxylate were initially charged in 90.0 ml of THF, and 1.04 g (27.50 mmol) of lithium aluminium hydride (2.4 M in THF) were added at 0° C. The reaction mixture was stirred at 0° C. for 30 minutes. At 0° C., saturated potassium sodium tartrate solution was added, and ethyl acetate was added to the reaction mixture. The organic phase was extracted three times with saturated potassium sodium tartrate solution. The organic phase was washed once with saturated NaCl solution and dried over magnesium sulphate. The solvent was evaporated under reduced pressure and the residue was dissolved in 30.0 ml of dichloromethane. 3.38 g (32.99 mmol) of manganese(IV) oxide were added, and the mixture was stirred at RT for 48 h. Another 2.20 g (21.47 mmol) of manganese(IV) oxide were added, and the mixture was stirred at RT overnight. The reaction mixture was filtered through Celite and the filter cake was washed with dichloromethane. The solvent was evaporated under reduced pressure and the residue 2.80 g of (1-benzyl-4-(2,5-difluorophenyl)-1H-pyrrole-2-carbaldehyde) was used without further purification in the next step of the synthesis.

LC-MS (Method 7): $R_t$=1.48 min; MS (ESIpos): m/z=298 [M+H]$^+$.

28.21 g (94.88 mmol) of 1-benzyl-4-(2,5-difluorophenyl)-1H-pyrrole-2-carbaldehyde together with 23.00 g (189.77 mmol) of (R)-2-methylpropane-2-sulphinamide were initially charged in 403.0 ml of absolute THF, and 67.42 g (237.21 mmol) of titanium(IV) isopropoxide were added and the mixture was stirred at RT overnight. 500.0 ml of saturated NaCl solution and 1000.0 ml of ethyl acetate were added, and the mixture was stirred at RT for 1 h. The mixture was filtered through kieselguhr and the filtrate was washed twice with saturated NaCl solution. The organic phase was dried over magnesium sulphate, the solvent was evaporated under reduced pressure and the residue was purified using Biotage Isolera (silica gel, column 1500+340 g SNAP, flow rate 200 ml/min, ethyl acetate/cyclohexane 1:10).

LC-MS (Method 7): $R_t$=1.63 min; MS (ESIpos): m/z=401 [M+H]$^+$.

25.00 g (62.42 mmol) of (R)—N—{(E/Z)-[1-benzyl-4-(2,5-difluorophenyl)-1H-pyrrol-2-yl]methylene}-2-methylpropane-2-sulphinamide were initially charged in absolute THF under argon and cooled to −78° C. 12.00 g (187.27 mmol) of tert-Butyllithium (1.7 M solution in pentane) were then added at −78° C., and the mixture was stirred at this temperature for 3 h. At −78° C. 71.4 ml of methanol and 214.3 ml of saturated ammonium chloride solution were then added in succession, and the reaction mixture was allowed to warm to RT and stirred at RT for 1 h. The mixture was diluted with ethyl acetate and washed with water. The organic phase was dried over magnesium sulphate and the solvent was evaporated under reduced pressure. The residue (R)—N-{(1R)-1-[1-benzyl-4-(2,5-difluorophenyl)-1H-pyrrol-2-yl]-2,2-dimethylpropyl}-2-methylpropane-2-sulphinamide was used without further purification in the next step of the synthesis.

LC-MS (Method 6): $R_t$=2.97 min; MS (ESIpos): m/z=459 [M+H]$^+$.

28.00 g (61.05 mmol) of (R)—N-{(1R)-1-[1-benzyl-4-(2,5-difluorophenyl)-1H-pyrrol-2-yl]-2,2-dimethylpropyl}-2-methylpropane-2-sulphinamide were initially charged in 186.7 ml of 1,4-dioxane, and 45.8 ml of HCl in 1,4-dioxane solution (4.0 M) were then added. The reaction mixture was stirred at RT for 2 h and the solvent was evaporated under reduced pressure. The residue was purified by preparative RP-HPLC (column: Kinetix 100×30; flow rate: 60 ml/min, MeCN/water). The acetonitrile was evaporated under reduced pressure and dichloromethane was added to the aqueous residue. The organic phase was washed with sodium bicarbonate solution and dried over magnesium sulphate. The solvent was evaporated under reduced pressure and the residue was dried under high vacuum. This gave 16.2 g (75% of theory) of the title compound.

LC-MS (Method 6): $R_t$=2.10 min; MS (ESIpos): m/z=338 [M-NH$_2$]$^+$, 709 [2M+H]$^+$.

$^1$H-NMR (400 MHz, DMSO-de): δ [ppm]=0.87 (s, 9H), 1.53 (s, 2H), 3.59 (s, 1H), 5.24 (d, 2H), 6.56 (s, 1H), 6.94 (m, 1H), 7.10 (d, 2H), 7.20 (m, 1H), 7.26 (m, 2H), 7.34 (m, 2H), 7.46 (m, 1H).

Intermediate C53

(2S)-4-[{(1R)-1-[1-Benzyl-4-(2,5-difluorophenyl)-1H-pyrrol-2-yl]-2,2-dimethylpropyl}(glycoloyl)amino]-2-{[(9H-fluoren-9-ylmethoxy)carbonyl]amino}butanoic acid

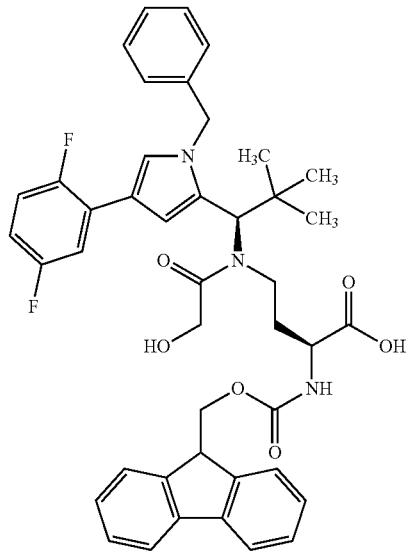 [SMILES: CC(C)(C)[C@H](c1cc(-c2cc(F)ccc2F)cn1Cc1ccccc1)N(CC[C@H](NC(=O)OCC1c2ccccc2-c2ccccc21)C(=O)O)C(=O)CO]

First, intermediate C52 was reductively alkylated with benzyl (2S)-2-{[(benzyloxy)carbonyl]amino}-4-oxobutanoate analogously to intermediate C2. The secondary amino group was then acylated with 2-chloro-2-oxoethyl acetate as described for Intermediate C27, and the two ester groups were then hydrolysed with 2M lithium hydroxide solution in methanol. The intermediate obtained in this manner was dissolved in ethanol, palladium on carbon (10%) was added and the mixture was hydrogenated at RT with hydrogen under standard pressure for 1 h. The deprotected compound was taken up in dioxane/water 2:1 and in the last step the Fmoc protective group was introduced using 9H-fluoren-9-ylmethyl chlorocarbonate in the presence of N,N-diisopropylethylamine.

LC-MS (Method 1): $R_t$=1.37 min; MS (ESIpos): m/z=734 (M−H)$^−$.

243

Intermediate C54

N-[(2S)-4-[{(1R)-1-[1-Benzyl-4-(2,5-difluorophenyl)-1H-pyrrol-2-yl]-2,2-dimethylpropyl}(glycoloyl)amino]-2-{[(9H-fluoren-9-ylmethoxy)carbonyl]amino}butanoyl]-beta-alanine

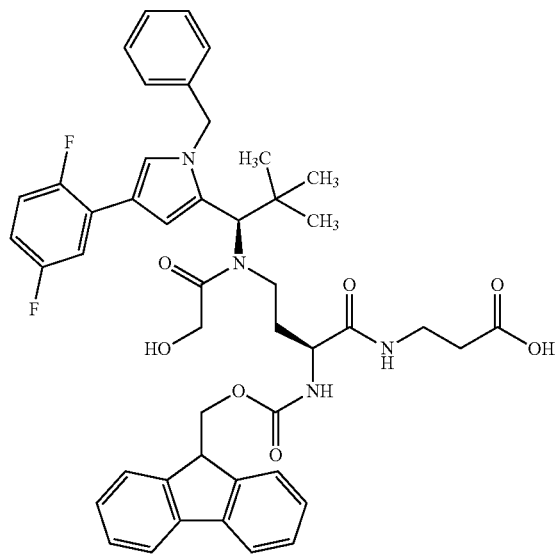 [SMILES: CC(C)(C)[C@H](c1cc(-c2cc(F)ccc2F)cn1Cc1ccccc1)N(CC[C@H](NC(=O)OCC1c2ccccc2-c2ccccc21)C(=O)NCCC(=O)O)C(=O)CO]

First, Intermediate C52 was reductively alkylated with benzyl N-[(2S)-2-{[(benzyloxy)carbonyl]amino}-4-oxobutanoyl]-beta-alaninate analogously to Intermediate C2. The secondary amino group was then acylated with 2-chloro-2-oxoethyl acetate as described for Intermediate C27. The intermediate obtained in this manner was dissolved in methanol, palladium on carbon (10%) was added and the mixture was hydrogenated at RT with hydrogen under standard pressure for 1 h. The ester group was then hydrolyzed with 2M lithium hydroxide solution in methanol. The deprotected compound was taken up in dioxane/water 2:1 and in the last step the Fmoc protective group was introduced using 9H-fluoren-9-ylmethyl chlorocarbonate in the presence of N,N-diisopropylethylamine. 48 mg of the title compound were obtained.

LC-MS (Method 1): $R_t$=1.38 min; MS (ESIpos): m/z=807 (M+H)$^+$.

244

Intermediate C58

(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoic acid

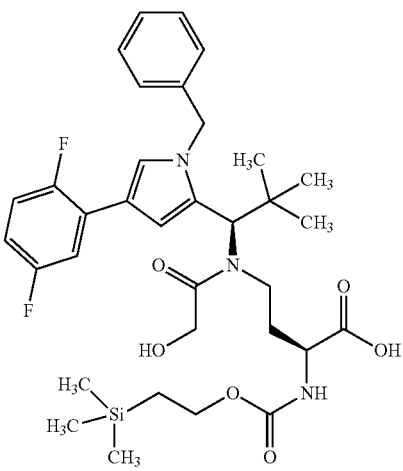 [SMILES: CC(C)(C)[C@H](c1cc(-c2cc(F)ccc2F)cn1Cc1ccccc1)N(CC[C@H](NC(=O)OCC[Si](C)(C)C)C(=O)O)C(=O)CO]

First, Intermediate C52 was reductively alkylated with benzyl (2S)-2-{[(benzyloxy)carbonyl]amino}-4-oxobutanoate analogously to Intermediate C2. The secondary amino group was then acylated with 2-chloro-2-oxoethyl acetate as described for Intermediate C27, and the two ester groups were then hydrolysed with 2M lithium hydroxide solution in methanol. The intermediate obtained in this manner was dissolved in ethanol, palladium on carbon (10%) was added and the mixture was hydrogenated at RT with hydrogen under standard pressure for 1 h.

500 mg (0.886 mmol) of this fully deprotected intermediate were taken up in 60 ml of dioxane, and 253 mg (0.975 mmol) of 1-({[2-(trimethylsilyl)ethoxy]carbonyl}oxy)pyrrolidine-2,5-dione and 198 µl of triethylamine were added. After 24 h of stirring at RT, the reaction was concentrated and the residue was purified by preparative HPLC. Combination of the appropriate fractions, concentration under reduced pressure and drying under high vacuum gave 312 mg (50% of theory) of the title compound.

LC-MS (Method 5): $R_t$=4.61 min; MS (ESIpos): m/z=658 (M+H)$^-$.

Intermediate C59

(2S)-4-({(1R)-1-[1-Benzyl-4-(2,5-difluorophenyl)-1H-pyrrol-2-yl]-2,2-dimethylpropyl}[(2S)-2-methoxypropanoyl]amino)-2-{[(9H-fluoren-9-ylmethoxy)carbonyl]amino}butanoic acid

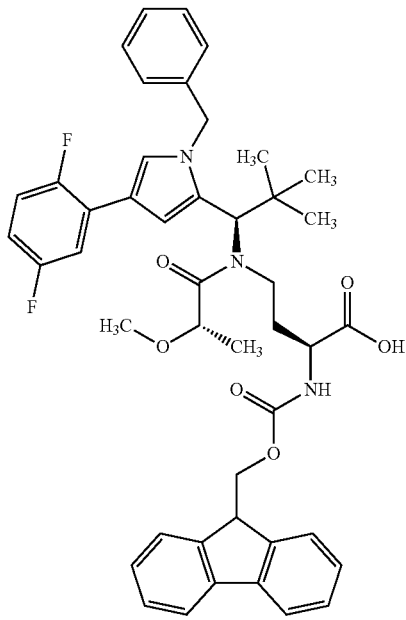 [SMILES: CO[C@@H](C)C(=O)N(CC[C@H](NC(=O)OCC1c2ccccc2-c2ccccc21)C(=O)O)[C@@H](c1cc(-c2cc(F)ccc2F)cn1Cc1ccccc1)C(C)(C)C]

Initially, the secondary amino group of benzyl (2S)-4-({(1R)-1-[1-benzyl-4-(2,5-difluorophenyl)-1H-pyrrol-2-yl]-2,2-dimethylpropyl}amino)-2-{[(benzyloxy)carbonyl]amino}butanoate was acylated with (2S)-2-methoxypropanoyl chloride (intermediate of Intermediate C53) in the presence of triethylamine as described for Intermediate C53. The intermediate obtained was taken up in ethanol, palladium on carbon (10%) was added and the mixture was hydrogenated at RT with hydrogen under standard pressure for 1 h. The deprotected compound was taken up in dioxane/water 2:1 and in the last step the Fmoc protective group was introduced using 9H-fluoren-9-ylmethyl chlorocarbonate in the presence of N,N-diisopropylethylamine.

LC-MS (Method 1): $R_t$=1.39 min; MS (ESIpos): m/z=764 (M–H)$^-$.

Intermediate C60

(2S)-4-({(1R)-1-[1-Benzyl-4-(2,5-difluorophenyl)-1H-pyrrol-2-yl]-2,2-dimethylpropyl}[(2S)-2-methoxypropanoyl]amino)-2-{[(9H-fluoren-9-ylmethoxy)carbonyl]amino}butanoic acid

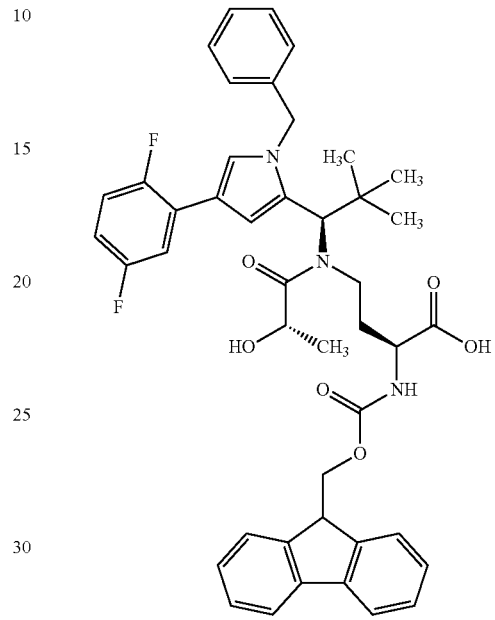

The synthesis was carried out analogously to Intermediate C53.

LC-MS (Method 1): $R_t$=1.41 min; MS (ESIpos): m/z=750 (M+H)$^+$.

Intermediate C61

N-[(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-beta-alanine

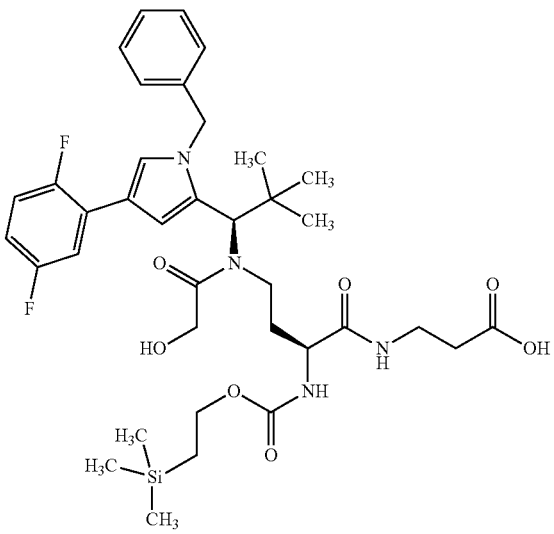 [SMILES: CC(C)(C)[C@H](c1cc(-c2cc(F)ccc2F)cn1Cc1ccccc1)N(CC[C@H](NC(=O)OCC[Si](C)(C)C)C(=O)NCCC(=O)O)C(=O)CO]

The title compound was prepared by coupling 60 mg (0.091 mmol) of Intermediate C58 with methyl β-alaninate, followed by ester cleavage with 2M lithium hydroxide solution. This gave 67 mg (61% of theory) of the title compound over 2 steps.

LC-MS (Method 1): $R_t$=1.29 min; MS (ESIpos): m/z=729 (M+H)$^+$.

Intermediate C62

N-[(2S)-4-[{(1R)-1-[1-Benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-D-alanine

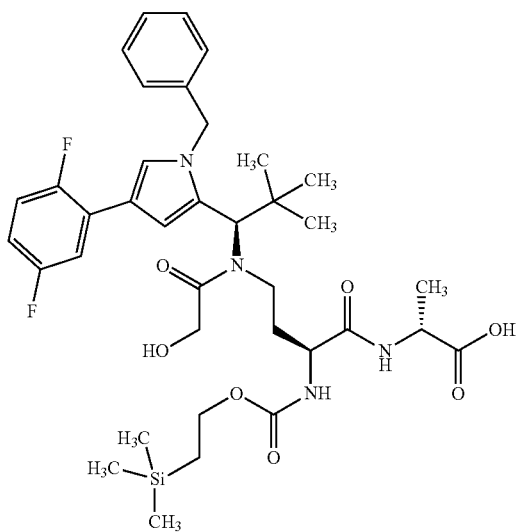 [SMILES: C[C@@H](NC(=O)[C@H](CCN(C(=O)CO)[C@@H](c1cc(-c2cc(F)ccc2F)cn1Cc1ccccc1)C(C)(C)C)NC(=O)OCC[Si](C)(C)C)C(=O)O]

The title compound was prepared analogously to Intermediate C61 from Intermediate C58 and methyl D-alaninate.

LC-MS (Method 1): $R_t$=1.32 min; MS (ESIpos): m/z=729 (M+H)$^+$.

Intermediate C64

Trifluoroacetic acid/2-(trimethylsilyl)ethyl {(2S)-1-[(2-aminoethyl)amino]-4-[{(1R)-1-[1-benzyl-4-(2,5-difluorophenyl)-1H-pyrrol-2-yl]-2,2-dimethylpropyl}(glycoloyl)amino]-1-oxobutan-2-yl}carbamate (1:1)

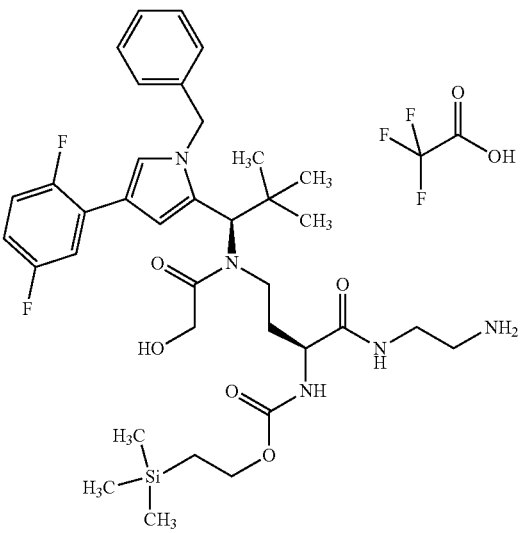 [SMILES: CC(C)(C)[C@H](c1cc(-c2cc(F)ccc2F)cn1Cc1ccccc1)N(CC[C@H](NC(=O)OCC[Si](C)(C)C)C(=O)NCCN)C(=O)CO ; O=C(O)C(F)(F)F]

The title compound was prepared from Intermediate C58 analogously to Intermediate C63.

HPLC (Method 11): $R_t$=2.4 min;
LC-MS (Method 1): $R_t$=1.01 min; MS (ESIpos): m/z=700 (M+H)$^+$.

Intermediate C65

(8S)-8-{2-[{(1R)-1-[1-Benzyl-4-(2,5-difluorophenyl)-1H-pyrrol-2-yl]-2,2-dimethylpropyl}-(glycoloyl)amino]ethyl}-2,2-dimethyl-6,11-dioxo-5-oxa-7,10-diaza-2-silatetradecan-14-oic acid

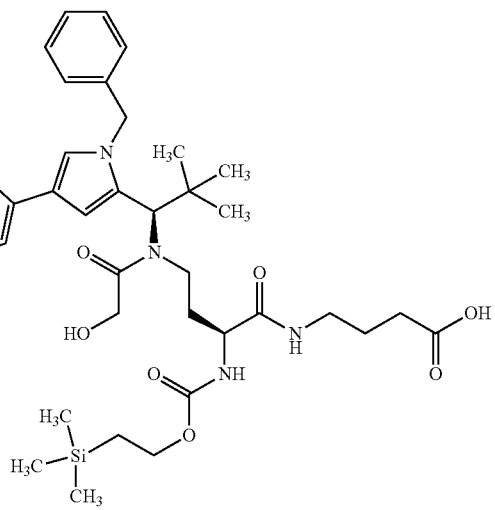

215 mg (0.59 mmol) of Intermediate L66 were initially charged in 25 ml of dichloromethane, and 377 mg (0.89 mmol) of Dess-Martin periodinane and 144 µl (1.78 mmol) of pyridine were added. The mixture was stirred at RT for 30 min. The reaction was then diluted with 300 ml of dichloromethane and the organic phase was washed in each case twice with 10% strength $Na_2S_2O_3$ solution, 10% strength citric acid solution and saturated sodium bicarbonate solution. The organic phase was dried over magnesium sulphate and the solvent was evaporated under reduced pressure. This gave 305 mg of the aldehyde which was reacted without further purification.

175 mg (0.49 mmol) of Intermediate C52 were dissolved in 50 ml of dichloromethane, and 147 mg (0.69 mmol) of sodium triacetoxyborohydride and 32.5 µl of acetic acid were added. After 5 min of stirring at RT, 214 mg (0.593 mmol) of the aldehyde described above were added, and the reaction was stirred at RT overnight. Here, instead of the expected product, 2-(trimethylsilyl)ethyl [(2S)-4-({(1R)-1-[1-benzyl-4-(2,5-difluorophenyl)-1H-pyrrol-2-yl]-2,2-dimethylpropyl}amino)-1-(2,5-dioxopyrrolidin-1-yl)butan-2-yl]carbamate was formed. Since this imide can also be converted into the title compound, the reaction was concentrated and the residue was purified by preparative HPLC. After combination of the appropriate imide-containing fractions, the solvent was evaporated under reduced pressure and the residue was dried under high vacuum. This gave 195 mg (58%) of the imide named above.

LC-MS (Method 5): $R_t$=3.32 min; MS (ESIpos): m/z=667 (M+H)$^+$.

65 mg (97.5 µmol) of this imide were taken up in 15 ml of dichloromethane, and 367 µl (3.4 mmol) of acetoxyacetyl chloride and 595 µl of N,N-diisopropylethylamine were added. After 30 min of stirring at RT, the reaction was concentrated without heating under reduced pressure and the residue was purified by preparative HPLC. The appropriate fractions were combined giving, after evaporation of the solvents and drying under high vacuum, 28 mg (37% of theory) of (8S)-11-{(1R)-1-[1-benzyl-4-(2,5-difluorophenyl)-1H-pyrrol-2-yl]-2,2-dimethylpropyl}-8-[(2,5-dioxopyrrolidin-1-yl)methyl]-2,2-dimethyl-6,12-dioxo-5-oxa-7,11-diaza-2-silatridecan-13-yl acetate.

LC-MS (Method 1): $R_t$=1.44 min; MS (ESIpos): m/z=767 (M+H)$^+$.

28 mg (37 µmol) of this intermediate were dissolved in 3 ml of methanol, and 548 µl of a 2M lithium hydroxide solution were added. After 10 min of stirring at RT, the reaction was adjusted to pH 4 with trifluoroacetic acid and then concentrated. The residue was purified by preparative HPLC. The appropriate fractions were combined, the solvent was evaporated and the residue was dried under high vacuum, giving 26 mg (96% of theory) of the title compound as a white solid.

LC-MS (Method 1): $R_t$=1.33 min; MS (ESIpos): m/z=743 (M+H)$^+$.

Intermediate C66

2-(Trimethylsilyl)ethyl [(2S)-4-[{(1R)-1-[1-benzyl-4-(2,5-difluorophenyl)-1H-pyrrol-2-yl]-2,2-dimethylpropyl}(glycoloyl)amino]-1-{[2-(glycylamino)ethyl]amino}-1-oxobutan-2-yl]carbamate

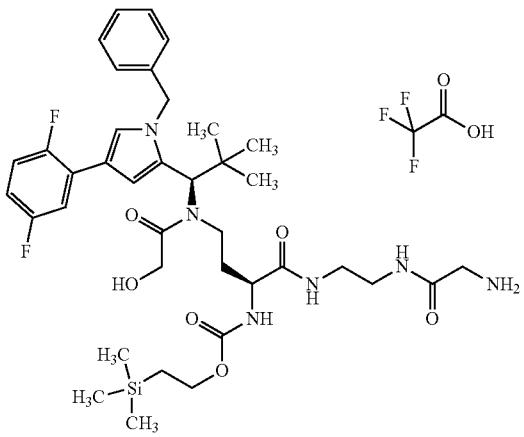 [SMILES: CC(C)(C)[C@H](c1cc(-c2cc(F)ccc2F)cn1Cc1ccccc1)N(CC[C@H](NC(=O)OCC[Si](C)(C)C)C(=O)NCCNC(=O)CN)C(=O)CO ; O=C(O)C(F)(F)F]

First, trifluoroacetic acid/benzyl {2-[(2-aminoethyl)amino]-2-oxoethyl}carbamate (1:1) was prepared from N-[(benzyloxy)carbonyl]glycine and tert-Butyl (2-aminoethyl)carbamate according to classical methods of peptide chemistry (HATU coupling and Boc removal). 13 mg (0.036 mmol) of this intermediate and 25 mg (0.033 mmol) of Intermediate C58 were taken up in 3 ml of DMF, and 19 mg (0.05 mmol) of HATU and 17 µl of N,N-diisopropylethylamine were added. After 10 min of stirring at RT, the mixture was concentrated and the residue was purified by preparative HPLC. This gave 17.8 mg (60% of theory) of the intermediate.

LC-MS (Method 1): $R_t$=1.36 min; MS (ESIpos): m/z=891 (M+H)$^+$.

17 mg (0.019 mmol) of this intermediate were dissolved in 10 ml of ethanol, palladium on carbon (10%) was added and the mixture was hydrogenated at RT with hydrogen at standard pressure for 2 h. The catalyst was filtered off, the solvents were evaporated under reduced pressure and the residue was dried under high vacuum. This gave 9 mg (62% of theory) of the title compound.

LC-MS (Method 1): $R_t$=1.03 min; MS (ESIpos): m/z=757 (M+H)$^+$.

Intermediate C67

9H-Fluoren-9-ylmethyl [3-({(1R)-1-[1-benzyl-4-(2,5-difluorophenyl)-1H-pyrrol-2-yl]-2,2-dimethylpropyl}amino)propyl]carbamate

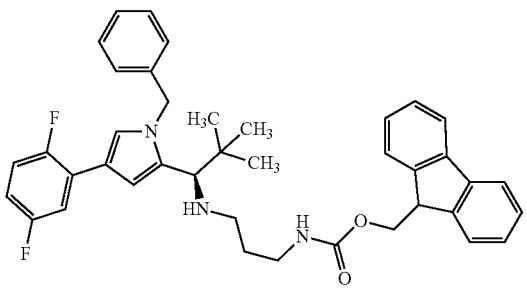 [SMILES: CC(C)(C)[C@@H](NCCCNC(=O)OCC1c2ccccc2-c2ccccc21)c1cc(-c2cc(F)ccc2F)cn1Cc1ccccc1]

605.3 mg (1.71 mmol) of (1R)-1-[1-benzyl-4-(2,5-difluorophenyl)-1H-pyrrol-2-yl]-2,2-dimethylpropan-1-amine (Intermediate C52) were initially charged in 10.0 ml of dichloromethane, and 506.7 mg (2.39 mmol) of sodium triacetoxyborohydride and 117.9 mg (1.96 mmol) of acetic acid were added and the mixture was stirred at RT for 5 min. 580.0 mg (1.96 mmol) of 9H-fluoren-9-ylmethyl (3-oxopropyl)carbamate (Intermediate L70) dissolved in 10.0 ml of dichloromethane were added and the reaction mixture stirred at RT overnight. The reaction mixture was diluted with ethyl acetate and the organic phase was washed in each case twice with saturated sodium carbonate solution and saturated NaCl solution. The organic phase was dried over magnesium sulphate and the solvent was evaporated under reduced pressure. The residue was purified by silica gel chromatography (mobile phase: cyclohexane/ethyl acetate 3:1). The solvents were evaporated under reduced pressure and the residue was dried under high vacuum. This gave 514.7 mg (46% of theory) of the title compound.

LC-MS (Method 1): $R_t$=1.10 min; MS (ESIpos): m/z=634 (M+H)$^+$.

Intermediate C69

11-{(1R)-1-[1-Benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid

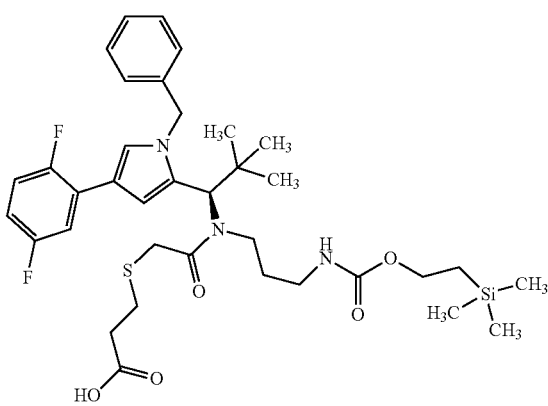 [SMILES: CC(C)(C)[C@H](c1cc(-c2cc(F)ccc2F)cn1Cc1ccccc1)N(CCCNC(=O)OCC[Si](C)(C)C)C(=O)CSCCC(=O)O]

117.0 mg (0.19 mmol) of (2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70) and 21.6 mg (0.20 mmol) of 3-sulphanylpropanoic acid were initially charged in 3.0 ml of methanol, 89.5 mg (0.65 mmol) of potassium carbonate were added and the mixture was stirred at 50° C. for 4 h. The reaction mixture was diluted with ethyl acetate and the organic phase was washed with water and saturated NaCl solution. The organic phase was dried over magnesium sulphate, the solvent was evaporated under reduced pressure and the residue was dried under high vacuum. The residue was used without further purification in the next step of the synthesis. This gave 106.1 mg (73% of theory) of the title compound.

LC-MS (Method 1): $R_t$=1.42 min; MS (ESIneg): m/z=700 (M−H)$^-$.

Intermediate C70

(2-(Trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate

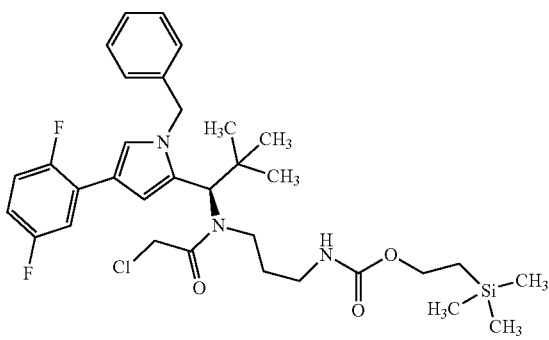 [SMILES: CC(C)(C)[C@H](c1cc(-c2cc(F)ccc2F)cn1Cc1ccccc1)N(CCCNC(=O)OCC[Si](C)(C)C)C(=O)CCl]

908.1 mg (1.63 mmol) of 2-(trimethylsilyl)ethyl [3-({(1R)-1-[1-benzyl-4-(2,5-difluorophenyl)-1H-pyrrol-2-yl]-2,2-dimethylpropyl}amino)propyl]carbamate (see synthesis of Intermediate C11) and 545.6 mg (5.39 mmol) of triethylamine were initially charged in 10.0 ml of dichloromethane, and the mixture was cooled to 0° C. At this temperature, 590.5 mg (5.23 mmol) of chloroacetyl chloride were added and the mixture was stirred at RT overnight. The reaction mixture was diluted with ethyl acetate and the organic phase was washed in each case three times with saturated sodium bicarbonate solution and saturated ammonium chloride solution. The organic phase was washed with saturated NaCl solution and dried over magnesium sulphate. The residue was purified by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 673.8 mg (65% of theory) of the title compound.

LC-MS (Method 1): $R_t$=1.53 min; MS (ESIneg): m/z=676 (M+HCOO$^-$)$^-$.

Intermediate C71

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1)

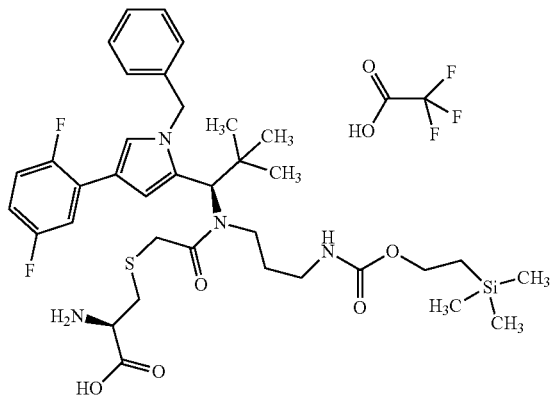 [SMILES: CC(C)(C)[C@H](c1cc(-c2cc(F)ccc2F)cn1Cc1ccccc1)N(CCCNC(=O)OCC[Si](C)(C)C)C(=O)CSC[C@H](N)C(=O)O ; O=C(O)C(F)(F)F]

536.6 mg (4.43 mmol) of L-cysteine were suspended in 2.5 ml of water together with 531.5 mg (6.33 mmol) of sodium bicarbonate. 400.0 mg (0.63 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (Intermediate C70) dissolved in 25.0 ml of isopropanol and 1.16 g (7.59 mmol) of 1,8-diazabicyclo[5.4.0]undec-7-ene were added. The reaction mixture was stirred at 50° C. for 1.5 h. Ethyl acetate was added to the reaction mixture and the organic phase was washed repeatedly with saturated sodium bicarbonate solution and once with sat. NaCl solution. The organic phase was dried over magnesium sulphate, the solvent was evaporated under reduced pressure and the residue was dried under high vacuum. The residue was purified by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 449.5 mg (86% of theory) of the title compound.

LC-MS (Method 1): $R_t$=1.20 min; MS (ESIpos): m/z=717 (M+F1)$^+$.

Intermediate C72

(9S)-9-{[{(1R)-1-[1-Benzyl-4-(2,5-difluorophenyl)-1H-pyrrol-2-yl]-2,2-dimethylpropyl}(glycoloyl)amino]methyl}-2,2-dimethyl-6,11-dioxo-5-oxa-7,10-diaza-2-silatetradecan-14-oic acid

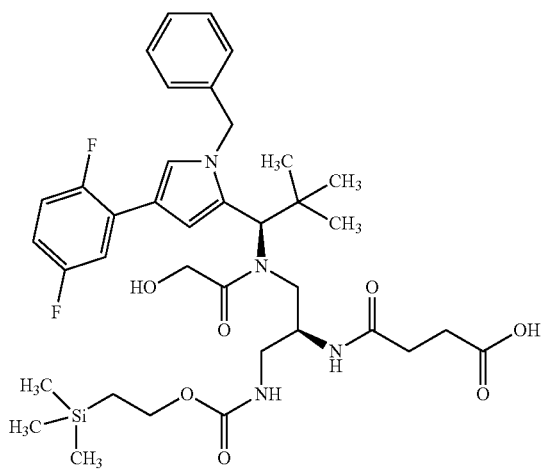 [SMILES: CC(C)(C)[C@H](c1cc(-c2cc(F)ccc2F)cn1Cc1ccccc1)N(C[C@H](CNC(=O)OCC[Si](C)(C)C)NC(=O)CCC(=O)O)C(=O)CO]

90 mg (0.212 mmol) of Intermediate L72 were initially charged in 6 ml of dichloromethane, and 86 µl (1.06 mmol) of pyridine and 135 mg (0.318 mmol) of Dess-Martin periodinane were added. The mixture was stirred at RT for 30 min. The reaction was then diluted with 30 ml of dichloromethane and the organic phase was washed twice with 10% strength $Na_2S_2O_3$ solution and once with 5% strength citric acid solution. The organic phase was dried over magnesium sulphate and the solvent was evaporated under reduced pressure. The aldehyde obtained in this manner was reacted without further purification.

63 mg (0.177 mmol) of Intermediate C52 were dissolved in 15 ml of dichloromethane, and 52.4 mg (0.247 mmol) of sodium triacetoxyborohydride and 20.2 µl of acetic acid were added. After 5 min of stirring at RT, 89.6 mg (0.212 mmol) of the aldehyde described above were added, and the reaction was stirred at RT for 20 min. The reaction was concentrated under reduced pressure and the residue was purified by preparative HPLC. After combination of the appropriate fractions, the solvent was evaporated under reduced pressure and the residue was lyophilized from acetonitrile/water. This gave 71 mg (53% of theory over 2 steps) of benzyl (9R)-9-[({(1R)-1-[1-benzyl-4-(2,5-difluorophenyl)-1H-pyrrol-2-yl]-2,2-dimethylpropyl}amino)methyl]-2,2-dimethyl-6,11-dioxo-5-oxa-7,10-diaza-2-silatetradecan-14-oate.

LC-MS (Method 1): $R_t$=1.21 min; MS (ESIpos): m/z=761 (M+H)$^+$.

70 mg (92 µmol) of this intermediate were taken up in 15 ml of dichloromethane, the mixture was cooled to 10° C., and 54 µl of triethylamine and 25.5 µl (0.23 mmol) of acetoxyacetyl chloride were added. After 1 h of stirring at RT, the same amounts of acid chloride and triethylamine were added, and once more after a further hour of stirring at RT. The reaction was then stirred at RT for a further 30 min and then concentrated under reduced pressure, and the residue was purified by preparative HPLC. The appropriate fractions were combined giving, after evaporation of the solvents and lyophilization of the residue from acetonitrile/water, 46.5 mg (59% of theory) of the acylated intermediate.

LC-MS (Method 1): $R_t$=1.53 min; MS (ESIpos): m/z=861 (M+H)$^+$.

46 mg (53 µmol) of this intermediate were dissolved in 5 ml of methanol, and 2.7 ml of a 2M lithium hydroxide solution were added. After 10 min of stirring at RT, the reaction was adjusted to pH 3-4 with acetic acid and then diluted with 15 ml of water. The aqueous phase was extracted with ethyl acetate and the organic phase was dried over magnesium sulphate and concentrated. The residue was lyophilized from acetonitrile/water giving, after drying of the residue under high vacuum, 37 mg (90% of theory) of the title compound as a white solid.

LC-MS (Method 1): $R_t$=1.32 min; MS (ESIpos): m/z=729 (M+H)$^+$.

Intermediate C73

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[3-(trimethylsilyl)propanoyl]-L-cysteine

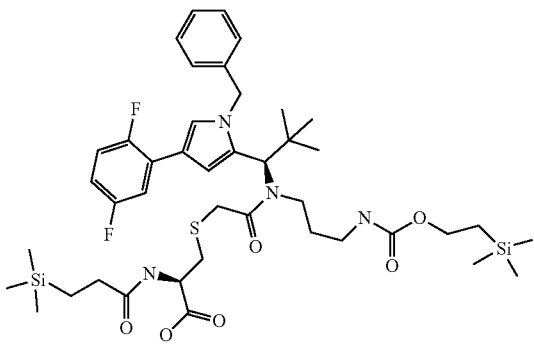

619 mg (0.86 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) were initially charged in 8.8 ml of dichloromethane, and 87 mg (0.86 mmol) of triethylamine and 224 mg (0.86 mmol) of N-[2-(trimethylsilyl)ethoxycarbonyloxy]pyrrolidine-2,5-dione were added. After 1 h, 45 mg (0.17 mmol) of N-[2-(trimethylsilyl)ethoxycarbonyloxy]pyrrolidine-2,5-dione were added. The reaction mixture was stirred at RT for 1 h. The mixture was concentrated under reduced pressure, the residue was taken up in dichloromethane and the organic phase was then washed twice with water and a saturated sodium bicarbonate solution. The organic phase was dried over magnesium sulphate, concentrated on a rotary evaporator and dried under high vacuum. The residue was used further without further purification. This gave 602 mg (71%, purity 87%) of the title compound.

LC-MS (Method 1): $R_t$=1.58 min; MS (ESIpos): m/z=861 (M+H)$^+$.

Intermediate C74

Trifluoroacetic acid 2-(trimethylsilyl)ethyl 3-amino-N-[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-D-alaninate (1:1)

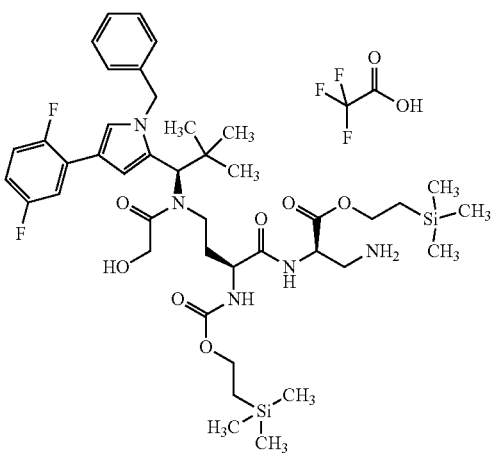 [SMILES: CC(C)(C)[C@H](c1cc(-c2cc(F)ccc2F)cn1Cc1ccccc1)N(CC[C@H](NC(=O)OCC[Si](C)(C)C)C(=O)N[C@H](CN)C(=O)OCC[Si](C)(C)C)C(=O)CO ; O=C(O)C(F)(F)F]

75 mg (0.114 mmol) of Intermediate C58 were taken up in 12.5 ml of DMF and coupled with 78 mg (0.171 mmol) of Intermediate L75 in the presence of 65 mg (0.11 mmol) of HATU and 79 µl of N,N-diisopropylethylamine. After purification by preparative HPLC, the intermediate was taken up in 20 ml of ethanol and hydrogenated over 10% palladium on activated carbon at RT under hydrogen standard pressure for 1 h. The catalyst was then filtered off, the solvent was removed under reduced pressure and the product was purified by preparative HPLC. Lyophilization from acetonitrile/water 1:1 gave 63 mg (64% of theory over 2 steps) of the title compound.

LC-MS (Method 1): $R_t$=1.16 min; MS (EIpos): m/z=844 [M+H]$^+$.

Intermediate C75

Methyl (2S)-4-[(acetoxyacetyl){(1R)-1-[1-benzyl-4-(2,5-difluorophenyl)-1H-pyrrol-2-yl]-2,2-dimethylpropyl}amino]-2-({[2-(trimethylsilyl)ethoxy]carbonyl}amino)butanoate

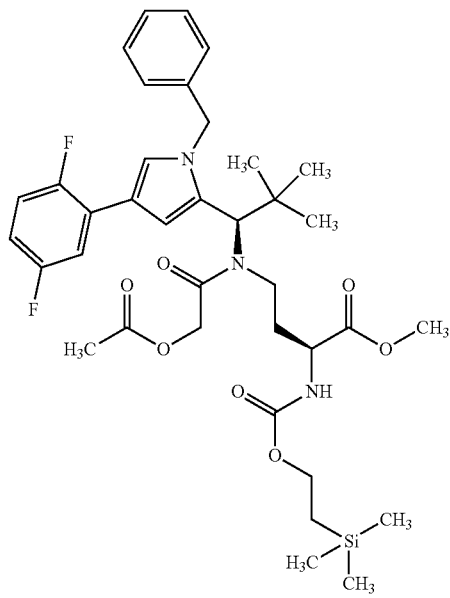 [SMILES: COC(=O)[C@H](CCN(C(=O)COC(C)=O)[C@@H](c1cc(-c2cc(F)ccc2F)cn1Cc1ccccc1)C(C)(C)C)NC(=O)OCC[Si](C)(C)C]

4.3 g (12.2 mmol) of Intermediate C52 were dissolved in 525 ml of DCM, and 3.63 g (17.12 mmol) of sodium triacetoxyborohydride and 8.4 ml of acetic acid were added. After 5 min of stirring at RT, 3.23 g (11.85 mmol) of methyl (2S)-4-oxo-2-({[2-(trimethylsilyl)ethoxy]carbonyl}amino)butanoate (prepared from (3S)-3-amino-4-methoxy-4-oxobutanoic acid by classical methods) dissolved in 175 ml of DCM were added, and the mixture was stirred at RT for a further 45 min. The mixture was then diluted with DCM and extracted twice with 100 ml of saturated sodium bicarbonate solution and then with saturated sodium chloride solution. The organic phase was dried over magnesium sulphate, filtered and concentrated. The residue was purified by preparative HPLC. Combination of the appropriate fractions, concentration and drying of the residue under high vacuum gave 4.6 g (6184% of theory) of the intermediate.

LC-MS (Method 12): $R_t$=1.97 min; MS (ESIpos): m/z=614.32 (M+H)$^+$.

200 mg (0.33 mmol) of this intermediate were dissolved in 10 ml of DCM, and 105 µl of triethylamine and 77 µl (0.717 mmol) of acetoxyacetyl chloride were then added. The mixture was stirred at RT overnight and then concentrated under reduced pressure. The residue was taken up in ethyl acetate and extracted twice with saturated sodium bicarbonate solution and then with saturated sodium chloride solution. The organic phase was dried over magnesium sulphate and then concentrated. This gave 213 mg (75%) of the title compound as a beige foam.

LC-MS (Method 1): R$_t$=1.46 min; MS (ESIpos): m/z=714 (M+H)$^+$.

Intermediate C76

N-[(Benzyloxy)carbonyl]-L-valyl-N-{(1S)-3-[{(1R)-1-[1-benzyl-4-(2,5-difluorophenyl)-1H-pyrrol-2-yl]-2,2-dimethylpropyl}(glycoloyl)amino]-1-carboxypropyl}-L-alaninamide

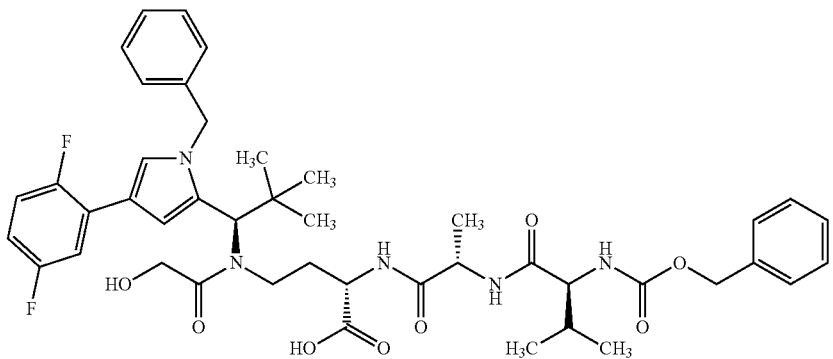 [SMILES: CC(C)[C@H](NC(=O)OCc1ccccc1)C(=O)N[C@@H](C)C(=O)N[C@@H](CCN(C(=O)CO)[C@@H](c1cc(-c2cc(F)ccc2F)cn1Cc1ccccc1)C(C)(C)C)C(=O)O]

The title compound was prepared from Intermediate C75 according to classical methods of peptide chemistry (removal of the Teoc protective group with zinc chloride, acylation with N-[(benzyloxy)carbonyl]-L-valyl-L-alanine in the presence of HATU and ester cleavage with lithium hydroxide in THF/water).

LC-MS (Method 1): R$_t$=1.23 min; MS (ESIpos): m/z=818 (M+H)$^+$.

Intermediate C77

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine

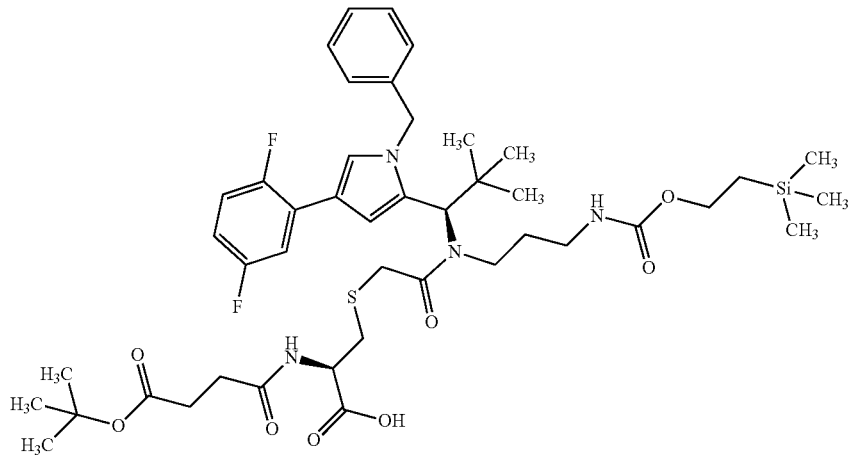 [SMILES: CC(C)(C)OC(=O)CCC(=O)N[C@@H](CSCC(=O)N(CCCNC(=O)OCC[Si](C)(C)C)[C@@H](c1cc(-c2cc(F)ccc2F)cn1Cc1ccccc1)C(C)(C)C)C(=O)O]

4-tert-Butoxy-4-oxobutanoic acid (8.39 mg, 48.1 µmol) was initially charged in 1.0 ml of DMF, 7.37 mg (48.1 µmol) of 1-hydroxy-1H-benzotriazole hydrate, 15.5 mg ((48.1 µmol) of (benzotriazol-1-yloxy)bisdimethylaminomethylium fluoroborat and 8.60 µl (48.1 µmol) of N,N-diisopropylethylamine were added and the mixture was stirred at RT for 10 minutes. 40.0 mg (0.048 mmol)S-(11-{(1R)-1-[1-Benzyl-4-(2,5-difluorphenyl)-1H-pyrrol-2-yl]-2,2-dimethyl-propyl}-2,2-dimethyl-6,12-dioxo-5-oxa-7,11-diaza-2-silatridecan-13-yl)-L-cysteine trifluoroacetic acid (1:1) (Intermediate C71) were initially charged in 1.0 ml of DMF, 25.4 µl (141.9 µmol) of N,N-diisopropylethylamine were added, the mixture was added to the reaction and the reaction mixture was stirred at RT for 4 h. The reaction mixture was purified directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 35.0 mg (83% of theory) of the title compound.

LC-MS (Method 12): $R_t$=2.76 min; MS (ESIpos): m/z=873 [M+H]$^+$

Intermediate C78

11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecane-15-acid

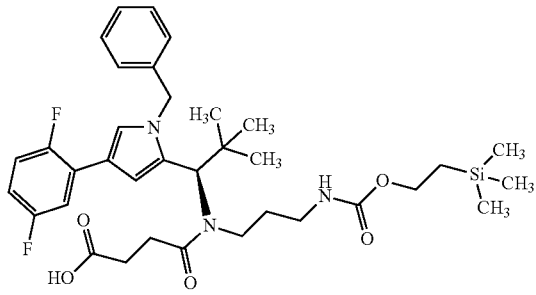 [SMILES: CC(C)(C)[C@H](c1cc(-c2cc(F)ccc2F)cn1Cc1ccccc1)N(CCCNC(=O)OCC[Si](C)(C)C)C(=O)CCC(=O)O]

197 mg (0.354 mmol) of 2-(trimethylsilyl)ethyl [3-({(1R)-1-[1-benzyl-4-(2,5-difluorophenyl)-1H-pyrrol-2-yl]-2,2-dimethylpropyl}amino)propyl]carbamate (see synthesis of Intermediate C11) were initially charged in 5.0 ml of dichloromethane, and the mixture was heated to 40° C. At this temperature, 240 µl (3.0 mmol) of pyridine and 220 µl (1.8 mmol) of methyl 4-chloro-4-oxobutanoate were added, and the mixture was stirred at RT for 1 h. 240 µl (3.0 mmol) of pyridine and 220 µl (1.8 mmol) of methyl 4-chloro-4-oxobutanoate were then added, and the mixture was stirred at RT for 1 h. 240 µl (3.0 mmol) of pyridine and 220 µl (1.8 mmol) of methyl 4-chloro-4-oxobutanoate were then added, and the mixture was stirred at RT for 1 h. The reaction mixture was diluted with ethyl acetate and the organic phase was extracted in each case three times with 5% strength KHSO$_4$ solution. The organic phase was washed with saturated NaCl solution and dried over magnesium sulphate. The solvents were evaporated under reduced pressure. The residue was purified by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 74.1 mg (31% of theory) of methyl 11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecan-15-oate.

LC-MS (Method 1): $R_t$=1.49 min; MS (ESIpos): m/z=670 [M+H]$^+$78.3 mg (117 µmol) of methyl 11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecan-15-oate were initially charged in 4.0 ml of THF, and 800 µl of methanol, 160 µl of water and 230 µl (230 µmol) of aqueous LiOH solution (1M) were added. The reaction mixture was stirred at RT for 3 h, quenched with acetic acid and purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 64.8 mg (85% of theory) of the title compound.

LC-MS (Method 12): $R_t$=2.61 min; MS (ESIneg): m/z=654 [M−H]$^-$

Intermediate C79

Trifluoroacetic acid 2-(trimethylsilyl)ethyl 3-amino-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-D-alaninate (1:1)

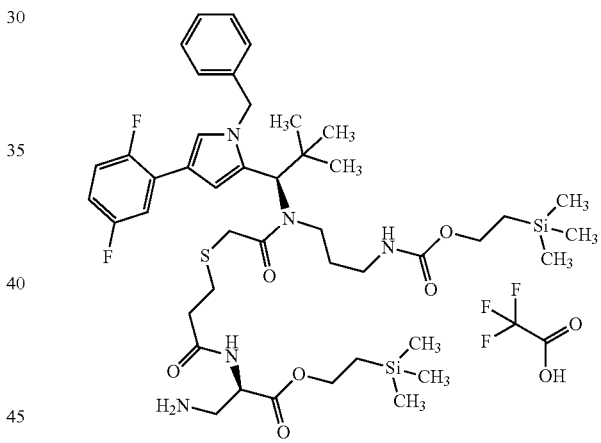

57.4 mg (81.8 µmol) of H-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged in 5.7 ml of DMF, 74.0 mg (164 µmol) of trifluoroacetic acid 2-(trimethylsilyl)ethyl 3-{[(benzyloxy)carbonyl]amino}-D-alaninate (1:1) (Intermediate L75), 43 µl (250 µmol) of N,N-diisopropylethylamine and 62.2 mg (164 µmol) of HATU were added and the mixture was stirred at RT for 1 h. The reaction mixture was stirred at RT for 1 h, quenched with acetic acid and purified directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 52.4 mg (63% of theory) of the compound 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-{[(benzyloxy)carbonyl]amino}-D-alaninate.

LC-MS (Method 1): $R_t$=1.64 min; MS (ESIpos): m/z=1022 [M]$^+$

Under argon, 6.23 mg (27.7 μmol) of palladium(II) acetate: were initially charged in 3.0 ml of dichloromethane, 12 μl (83 μmol) of triethylamine and 89 μl (550 μmol) of triethylsilane were added and the mixture was stirred for 5 minutes. 56.7 mg (55.5 μmol) of 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-{[(benzyloxy)carbonyl]amino}-D-alaninate in 3.0 ml of dichloromethane were then added, and the mixture was stirred at RT overnight. The mixture was concentrated almost to dryness, acetonitrile/water was added, and the mixture was filtered and purified by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 37.4 mg (67% of theory) of the title compound.

LC-MS (Method 12):): $R_t$=2.15 min; MS (ESIpos): m/z=888 [M+H]$^+$

Intermediate C80

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-(glycylamino)-4,7,10,13-tetraoxapentadecan-1-oyl]-L-cysteine trifluoroacetic acid (1:1)

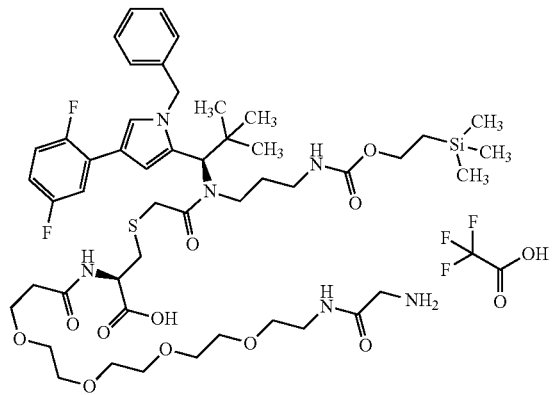 [SMILES: CC(C)(C)[C@H](c1cc(-c2cc(F)ccc2F)cn1Cc1ccccc1)N(CCCNC(=O)OCC[Si](C)(C)C)C(=O)CSC[C@H](NC(=O)CCOCCOCCOCCOCCNC(=O)CN)C(=O)O ; O=C(O)C(F)(F)F]

Under argon, 43.4 mg (95.1 μmol) of 1-({N-[(benzyloxy)carbonyl]glycyl}amino)-3,6,9,12-tetraoxapentadecan-15-oic acid (Intermediate L90) were initially charged in 2.5 ml of DMF, 14.6 mg (95.1 μmol) of 1-hydroxy-1H-benzotriazole hydrate, 30.5 mg (95.1 μmol) of (benzotriazol-1-yloxy)bisdimethylaminomethylium fluoroborate and 16.5 μl (95.1 μmol) of N,N-diisopropylethylamine were added and the mixture was stirred for 10 min. 79.0 mg (95.1 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine trifluoroacetic acid (1:1) (Intermediate C71) were dissolved in 2.5 ml of DMF, 49.5 μl (285.3 μmol) of N,N-diisopropylethylamine were added and the mixture was added to the reaction. The reaction mixture was stirred at RT for 2 h and purified directly by preparative RP-HPLC (column: Reprosil 125× 30; 10μ, flow rate: 50 ml/min, MeCN/water, 0.1% TFA). The solvents were evaporated under reduced pressure and the residue was dried under high vacuum. This gave 44.2 mg (40% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-({N-[(benzyloxy)carbonyl]glycyl}amino)-4,7,10,13-tetraoxapentadecan-1-oyl]-L-cysteine.

LC-MS (Method 12): $R_t$=2.57 min; MS (ESIpos): m/z=1156 [M+H]$^+$ 60.2 mg (52.1 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-({N-[(benzyloxy)carbonyl]glycyl}amino)-4,7,10,13-tetraoxapentadecan-1-oyl]-L-cysteine were suspended in 3.0 ml of ethanol, 6.0 mg of palladium on activated carbon (10%) were added and the mixture was hydrogenated with hydrogen at RT and standard pressure for 1 h. Twice, 6.0 mg of palladium on activated carbon (10%) were added and the mixture was hydrogenated with hydrogen at RT and standard pressure for 1 h. The catalyst was filtered off and the reaction mixture was freed from the solvent under reduced pressure and dried under high vacuum. The residue was purified by preparative RP-HPLC (column: Reprosil 125× 30; 10μ, flow rate: 50 ml/min, MeCN/water, 0.1% TFA). The solvents were evaporated under reduced pressure and the residue was dried under high vacuum. This gave 29.4 mg (50% of theory) of the title compound.

LC-MS (Method 5): $R_t$=3.77 min; MS (ESIpos): m/z=1021 [M+H]$^+$

Intermediate C81

(R)-1-[1-Benzyl-4-(2,5-difluorophenyl)-1H-pyrrol-2-yl]-1-cyclohexylmethanamine

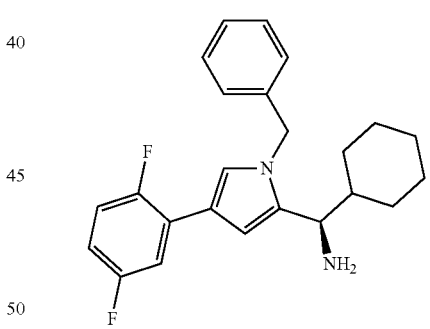

Under argon and at −78° C., 18.7 ml (37.45 mmol) of cyclohexylmagnesium chloride in diethyl ether (2M) were added to a solution of 3.12 ml (6.24 mmol) of dimethylzinc in toluene (2.0 M), and the mixture was stirred at −78° C. for 30 minutes. A solution of 5.0 g (12.48 mmol) of (R)—N-{(E/Z)-[1-benzyl-4-(2,5-difluorophenyl)-1H-pyrrol-2-yl]methylene}-2-methylpropane-2-sulphinamide in THF was then added at −78° C., and the reaction mixture was stirred at this temperature for 1 h and then at RT for 4 h. At −78° C., ml of saturated ammonium chloride solution were then added and the reaction mixture was allowed to warm to RT. The mixture was diluted with ethyl acetate and washed with water. The organic phase was dried over magnesium sulphate and the solvent was evaporated under reduced pressure. The residue was purified using Biotage Isolera (silica gel, ethyl acetate/cyclohexane 25:75). This gave 1.59 g (26% of theory) of the intermediate.

LC-MS (Method 12): $R_t$=2.76 min; MS (ESIneg): m/z=483 [M−H]⁻

Under argon, 264.0 mg (0.54 mmol) of this intermediate were initially charged in 0.5 ml of 1,4-dioxane, and 1.36 ml of HCl in 1,4-dioxane solution (4.0 M) were then added. The reaction mixture was stirred at RT for 1 h. Dichloromethane was added, and the reaction mixture was washed with an aqueous 1M sodium hydroxide solution. The organic phase was dried with magnesium sulphate and the solvent was evaporated under reduced pressure. The residue was purified using Biotage Isolera (silica gel, methanol/dichloromethane 98:2). The solvent was evaporated under reduced pressure and the residue was dissolved in dichloromethane, washed with a sodium bicarbonate solution and dried over sodium sulphate. The solvent was evaporated under reduced pressure and the residue was dried under high vacuum. This gave 148 mg (72% of theory) of the title compound.

LC-MS (Method 13): $R_t$=2.07 min; MS (ESIpos): m/z=364 [M−NH$_2$]⁺

Intermediate C82

2-(Trimethylsilyl)ethyl (3-{[(R)-[1-benzyl-4-(2,5-difluorophenyl)-1H-pyrrol-2-yl](cyclohexyl)methyl]amino}propyl)carbamate

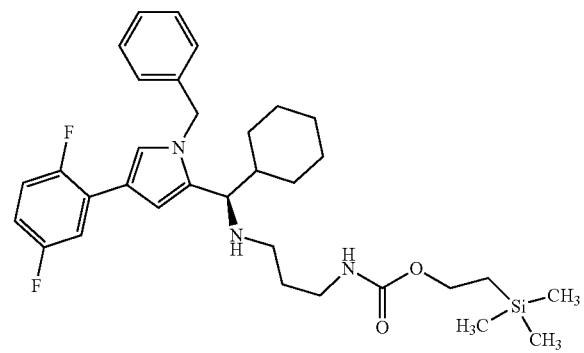 [SMILES: C[Si](C)(C)CCOC(=O)NCCCN[C@@H](c1cc(-c2cc(F)ccc2F)cn1Cc1ccccc1)C1CCCCC1]

Under argon, 392.2 mg (1.85 mmol) of sodium triacetoxyborohydride and 91.29 mg (1.52 mmol) of acetic acid were added to a solution of 503.0 mg (1.32 mmol) of 1-[1-benzyl-4-(2,5-difluorophenyl)-1H-pyrrol-2-yl]-1-cyclohexylmethanamine (Intermediate C81) in 1.4 ml of dichloromethane, and the reaction mixture was stirred at RT for 10 minutes. A solution of 574.6 (2.38 mmol) of 2-(trimethylsilyl)ethyl (3-oxopropyl)carbamate in dichloromethane was then added, and the mixture was stirred at RT overnight. After addition of 143 mg (0.66 mmol) of 2-(trimethylsilyl)ethyl (3-oxopropyl)carbamate, the mixture was stirred for a further 2 h. The reaction mixture was diluted with dichloromethane and the organic phase was washed in each case twice with saturated sodium carbonate solution and with saturated NaCl solution, dried over sodium sulphate and concentrated. The residue was purified by preparative HPLC. The solvents were evaporated under reduced pressure and the residue was dried under high vacuum. This gave 488 g (63% of theory) of the title compound.

LC-MS (Method 12): $R_t$=1.89 min; MS (ESIpos): m/z=582 (M+H)⁺.

Intermediate C83

2-(Trimethylsilyl)ethyl (3-{[(R)-[1-benzyl-4-(2,5-difluorophenyl)-1H-pyrrol-2-yl](cyclohexyl)methyl](chloroacetyl)amino}propyl)carbamate

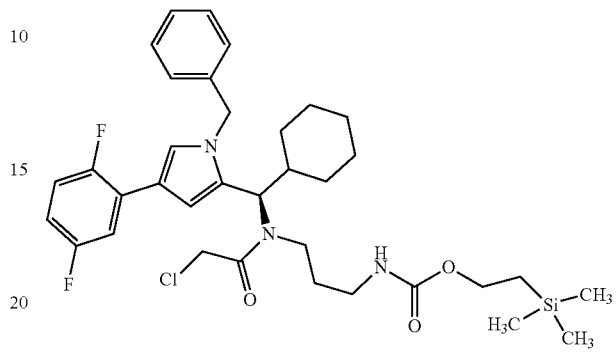

280.0 mg (2.77 mmol) of triethylamine and 397.8 mg (3.52 mmol) of chloroacetyl chloride were added to a solution of 487.9 mg (0.84 mmol) 2-(trimethylsilyl)ethyl (3-{[(R)-[1-benzyl-4-(2,5-difluorophenyl)-1H-pyrrol-2-yl](cyclohexyl)methyl]amino}propyl)carbamate (Intermediate C82) in 8.40 ml of dichloromethane with 4 Å molecular sieve, and the reaction mixture was stirred at RT for 6 h. The reaction mixture was diluted with dichloromethane and the organic phase was washed with saturated sodium bicarbonate solution and saturated ammonium chloride solution. The organic phase was dried over sodium sulphate and concentrated. The residue was used further without purification. This gave 470 mg (85% of theory) of the title compound.

LC-MS (Method 12): $R_t$=2.88 min; MS (ESIpos): m/z=680 (M+Na)⁺.

Intermediate C84

S-{11-[(R)-[1-Benzyl-4-(2,5-difluorophenyl)-1H-pyrrol-2-yl](cyclohexyl)methyl]-2,2-dimethyl-6,12-dioxo-5-oxa-7,11-diaza-2-silatridecan-13-yl}-L-cysteine

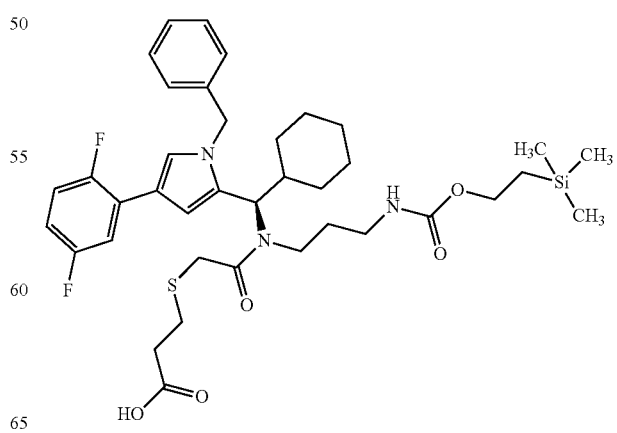

161.65 mg (1.17 mmol) of potassium carbonate were added to a mixture of 220.0 mg (0.33 mmol) of 2-(trimethylsilyl)ethyl (3-{[(R)-[1-benzyl-4-(2,5-difluorophenyl)-1H-pyrrol-2-yl](cyclo-hexyl)methyl](chloroacetyl)amino}propyl)carbamate (Intermediate C83) and 39.02 mg (0.37 mmol) of 3-sulphanylpropanoic acid in 7.45 ml of methanol and a few drops of water. The reaction mixture was stirred at 50° C. for 4 h. Ethyl acetate was added to the reaction mixture and the organic phase was washed repeatedly with water and with saturated NaCl solution. The organic phase was dried over sodium sulphate and the solvent was evaporated under reduced pressure. The residue was used further without work-up. This gave 201 mg (83% of theory) of the title compound.

LC-MS (Method 12): $R_t$=2.72 min; MS (ESIneg): m/z=726 (M−H)⁻.

Intermediate C87

2-(Trimethylsilyl)ethyl {13-[(R)-[1-benzyl-4-(2,5-difluorophenyl)-1H-pyrrol-2-yl](cyclo-hexyl)methyl]-1-(2,5-dioxo-2,5-dihydro-1H-pyrrol-1-yl)-2,7,12-trioxo-10-thia-3,6,13-triazahexadecan-16-yl}carbamate

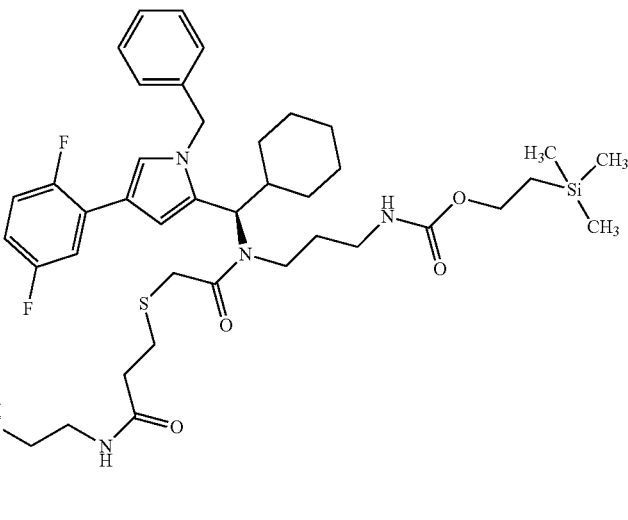

54.18 mg (0.28 mmol) of N-(2-aminoethyl)-2-(2,5-dioxo-2,5-dihydro-1H-pyrrol-1-yl)acetamide (Intermediate L1), 71.01 mg (0.50 mmol) of N,N-diisopropylethylamine, 104.46 mg (0.27 mmol) of HATU and 0.23 ml (0.14 mmol) of 1-hydroxy-7-azabenzotriazole 0.5 M in DMF were added to a solution of 100 mg (0.14 mmol) of 11-[(R)-[1-benzyl-4-(2,5-difluorophenyl)-1H-pyrrol-2-yl](cyclohexyl)methyl]-2,2-dim ethyl-6,12-dioxo-5-oxa-14-thia-7,11-diaza-2-silaheptadecan-17-oic acid (Intermediate C86) in 1.37 ml of DMF. The reaction mixture was stirred at RT for 5 h. Without further work-up, the mixture was purified by preparative HPLC. This gave 41 mg (33% of theory) of the title compound.

LC-MS (Method 12): $R_t$=2.61 min; MS (ESIpos): m/z=907 (M+H)⁺.

Intermediate C88 tert-Butyl 3 —[({(1R)-1-[1-benzyl-4-(2,5-difluorophenyl)-1H-pyrrol-2-yl]-2,2-dimethylpropyl}amino)methyl]pyrrolidine-1-carboxylate trifluoroacetic acid (1:1)

Mixture of stereoisomers

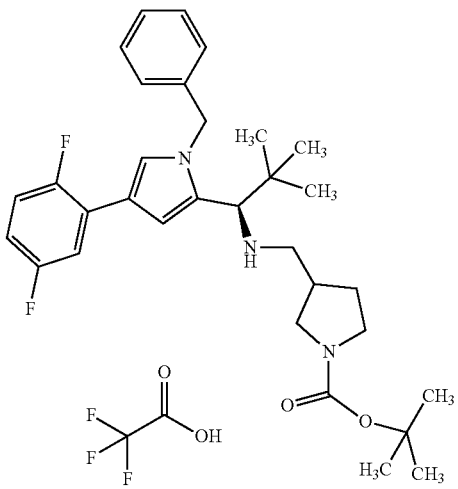 [SMILES: CC(C)(C)OC(=O)N1CCC(CN[C@@H](c2cc(-c3cc(F)ccc3F)cn2Cc2ccccc2)C(C)(C)C)C1 ; O=C(O)C(F)(F)F]

1.71 g (8.05 mmol) of sodium triacetoxyborohydride and 0.40 g (6.61 mmol) of acetic acid were added to a solution of 2.04 mg (5.75 mmol) of (1R)-1-[1-benzyl-4-(2,5-difluorophenyl)-1H-pyrrol-2-yl]-2,2-dimethylpropane-1-amine in 51 ml of dichloromethane, and the reaction mixture was stirred at RT for 5 minutes. A solution of 1.32 g (6.61 mmol) of tert-Butyl 3-formylpyrrolidine-1-carboxylate in 20 ml of dichloromethane was then added, and the mixture was stirred at RT overnight. The reaction mixture was diluted with ethyl acetate and the organic phase was washed in each case twice with saturated sodium carbonate solution and with saturated NaCl solution, dried over magnesium sulphate and concentrated. The residue was purified by preparative HPLC. The solvents were evaporated under reduced pressure and the residue was dried under high vacuum. This gave 1.86 g (50% of theory) of the title compound.

LC-MS (Method 1): $R_t$=0.99 min; MS (ESIpos): m/z=538 (M+H—CF$_3$CO$_2$H)$^+$.

Intermediate C89 tert-Butyl 3-{[{(1R)-1-[1-benzyl-4-(2,5-difluorophenyl)-1H-pyrrol-2-yl]-2,2-dimethyl-propyl}(chloroacetyl)amino]methyl}pyrrolidine-1-carboxylate

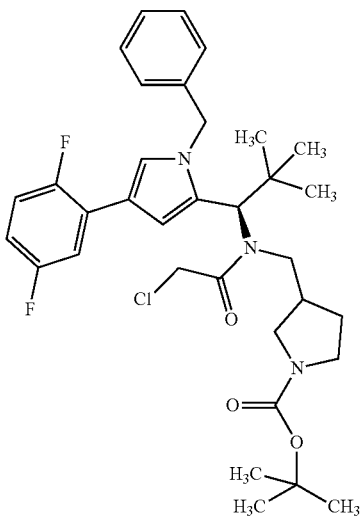 [SMILES: CC(C)(C)OC(=O)N1CCC(CN(C(=O)CCl)[C@@H](c2cc(-c3cc(F)ccc3F)cn2Cc2ccccc2)C(C)(C)C)C1]

1.36 g (13.42 mmol) of triethylamine and 2.13 g (18.87 mmol) of chloracetyl chloride were added to a solution of 2.89 g (4.19 mmol, 80% pure) of tert-Butyl 3-[({(1R)-1-[1-benzyl-4-(2,5-difluorophenyl)-1H-pyrrol-2-yl]-2,2-dimethylpropyl}amino)methyl]pyrrolidine-1-carboxylate (Intermediate C88) in 42 ml of dichloromethane with 4 Å molecular sieve. The reaction mixture was stirred at RT for 5 h. The mixture was concentrated on a rotary evaporator and the residue was purified by preparative HPLC. This gave 449 mg (17% of theory) of Isomer 1 and 442 mg (17% of theory) of Isomer 2 of the title compound.

Isomer 1 LC-MS (Method 12): $R_t$=2.74 min; MS (ESIpos): m/z=636 (M+NH$_4^+$)$^-$ Isomer 2 LC-MS (Method 12): $R_t$=2.78 min; MS (ESIpos): m/z=636 (M+NH$_4^+$)$^+$.

Intermediate C90

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-L-cysteine (Isomer 1)

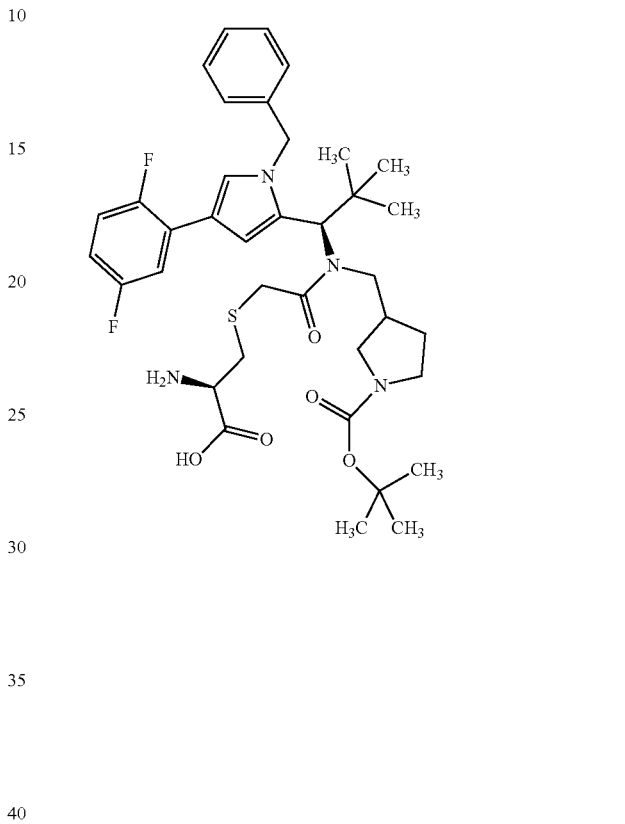

357.3 mg (0.58 mmol) of L-cysteine were suspended in 2.3 ml of water together with 488.7 mg (4.07 mmol) of sodium bicarbonate. 357.0 mg (0.58 mmol) of tert-Butyl 3-{[{(1R)-1-[1-benzyl-4-(2,5-difluorophenyl)-1H-pyrrol-2-yl]-2,2-dimethylpropyl}(chloroacetyl)amino]methyl}pyrrolidine-1-carboxylate (Intermediate C89, Isomer 1) dissolved in 23.0 ml of isopropanol and 1.06 g (6.98 mmol) of 1,8-diazabicyclo[5.4.0]undec-7-ene were added. The reaction mixture was stirred at 50° C. for 3 h. Ethyl acetate was added to the reaction mixture and the organic phase was washed repeatedly with saturated sodium bicarbonate solution and once with sat. NaCl solution. The organic phase was dried over magnesium sulphate and the solvent was evaporated under reduced pressure. The residue was used further without purification. This gave 255.0 mg (62% of theory) of the title compound.

LC-MS (Method 1): $R_t$=1.09 min; MS (ESIpos): m/z=699 (M+H)$^+$.

Intermediate C91

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-L-cysteine (Isomer 2)

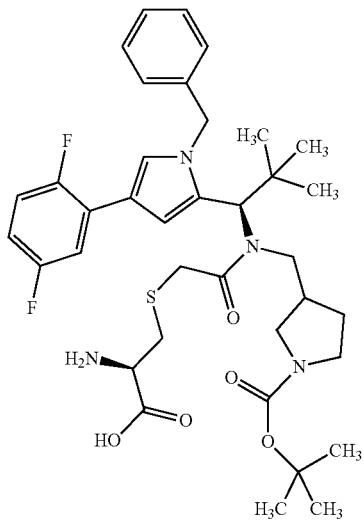 [SMILES: CC(C)(C)OC(=O)N1CCC(CN(C(=O)CSC[C@H](N)C(=O)O)[C@@H](c2cc(-c3cc(F)ccc3F)cn2Cc2ccccc2)C(C)(C)C)C1]

453.5 mg (3.74 mmol) of L-cysteine were suspended in 2.1 ml of water together with 449.2 mg (5.35 mmol) of sodium bicarbonate. 3287.4 mg (0.54 mmol) of tert-Butyl 3-{[{(1R)-1-[1-benzyl-4-(2,5-difluorophenyl)-1H-pyrrol-2-yl]-2,2-dimethylpropyl}(chloroacetyl)amino]methyl}pyrrolidine-1-carboxylate (Intermediate C89, Isomer 2) dissolved in 21.1 ml of isopropanol and 0.98 g (6.42 mmol) of 1,8-diazabicyclo[5.4.0]undec-7-ene were added. The reaction mixture was stirred at 50° C. for 3 h. Ethyl acetate was added to the reaction mixture and the organic phase was washed repeatedly with saturated sodium bicarbonate solution and once with sat. NaCl solution. The organic phase was dried over magnesium sulphate and the solvent was evaporated under reduced pressure. The residue was used further without purification. This gave 221.0 mg (59% of theory) of the title compound.

LC-MS (Method 1): $R_t$=1.12 min; MS (ESIpos): m/z=699 (M+H)$^+$.

Intermediate C92

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-N-[6-(2,5-dioxo-2,5-dihydro-1H-pyrrol-1-yl)hexanoyl]-L-cysteine (Isomer 1)

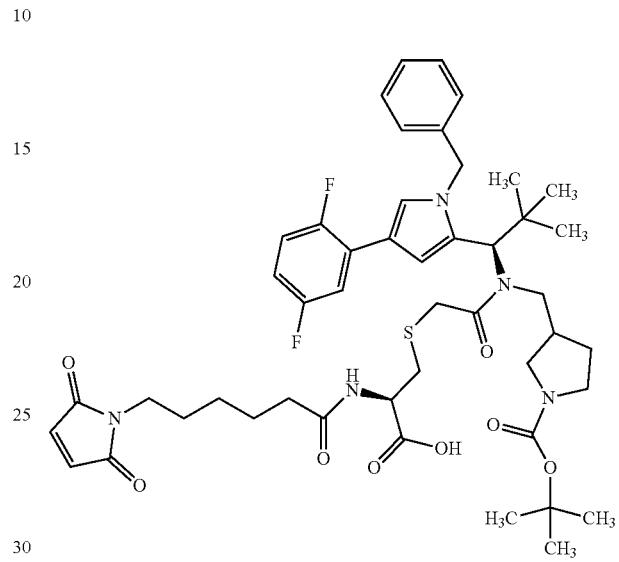

18.49 mg (0.14 mmol) of N,N-diisopropylethylamine were added to a mixture of 50 mg (0.07 mmol) of S-[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-L-cysteine (Intermediate C90) and 22.06 mg (0.07 mmol) of 1-{6-[(2,5-dioxopyrrolidin-1-yl)oxy]-6-oxohexyl}-1H-pyrrole-2,5-dione in 3.3 ml of DMF, and the reaction mixture was stirred at RT for 45 minutes. Without work-up, the mixture was purified by preparative HPLC. This gave 65 mg (100% of theory, 71% pure) of the title compound.

LC-MS (Method 1): $R_t$=1.31 min; MS (ESIpos): m/z=892 (M+H)$^+$.

Intermediate C93

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-N-[6-(2,5-dioxo-2,5-dihydro-1H-pyrrol-1-yl)hexanoyl]-L-cysteine (Isomer 2)

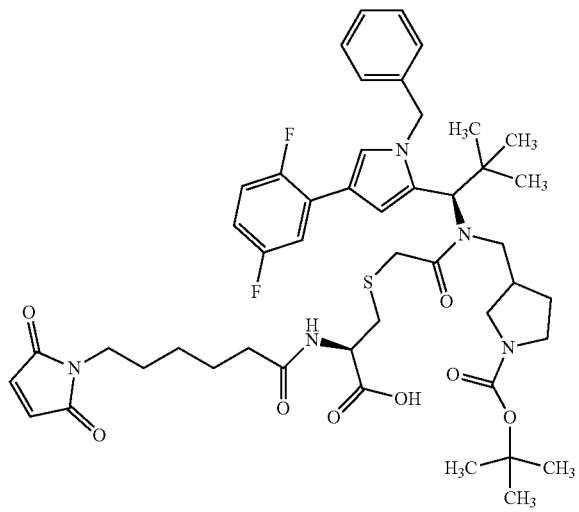 [SMILES: CC(C)(C)OC(=O)N1CCC(CN(C(=O)CSC[C@H](NC(=O)CCCCCN2C(=O)C=CC2=O)C(=O)O)[C@@H](c2cc(-c3cc(F)ccc3F)cn2Cc2ccccc2)C(C)(C)C)C1]

18.49 mg (0.14 mmol) of N,N-diisopropylethylamine were added to a mixture of 50.0 mg (0.07 mmol) of S-[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-L-cysteine (Intermediate C91) and 22.06 mg (0.07 mmol) of 1-{6-[(2,5-dioxopyrrolidin-1-yl)oxy]-6-oxohexyl}-1H-pyrrole-2,5-dione in 3.0 ml of DMF, and the reaction mixture was stirred at RT for 90 minutes. Without work-up, the mixture was purified by preparative HPLC. This gave 63 mg (98% of theory, 73% pure) of the title compound.

LC-MS (Method 1): $R_t$=1.34 min; MS (ESIpos): m/z=892 (M+H)$^+$.

Intermediate C94

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-N-[(2,5-dioxo-2,5-dihydro-1H-pyrrol-1-yl)acetyl]-L-cysteine (Isomer 1)

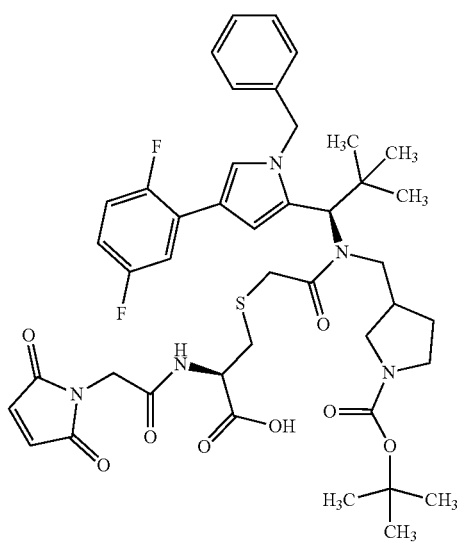 [SMILES: CC(C)(C)OC(=O)N1CCC(CN(C(=O)CSC[C@H](NC(=O)CN2C(=O)C=CC2=O)C(=O)O)[C@@H](c2cc(-c3cc(F)ccc3F)cn2Cc2ccccc2)C(C)(C)C)C1]

18.5 mg (0.14 mmol) of N,N-diisopropylethylamine were added to a mixture of 50.0 mg (0.07 mmol) of S-[2-({(1R)-1-[1-benzyl-4-(2,5-difluorophenyl)-1H-pyrrol-2-yl]-2,2-dimethylpropyl}{[-1-(tert-butoxycarbonyl)pyrrolidin-3-yl]methyl}amino)-2-oxoethyl]-L-cysteine (Intermediate C90) and 18.0 mg (0.07 mmol) of -{2-[(2,5-dioxopyrrolidin-1-yl)oxy]-2-oxoethyl}-1H-pyrrole-2,5-dione in 3.3 ml of DMF, and the reaction mixture was stirred at RT for 30 minutes. Ethyl acetate was added to the reaction mixture and the organic phase was washed repeatedly with saturated NH$_4$Cl solution and once with saturated NaCl solution. The organic phase was dried over magnesium sulphate and the solvent was evaporated under reduced pressure. The residue was employed without further purification. This gave 57 mg (81% of theory, 85% pure) of the title compound.

LC-MS (Method 1): $R_t$=0.96 min; MS (ESIpos): m/z=836 (M+H)$^+$.

Intermediate C95

3-{[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]sulphanyl}propanoic acid (Isomer 1)

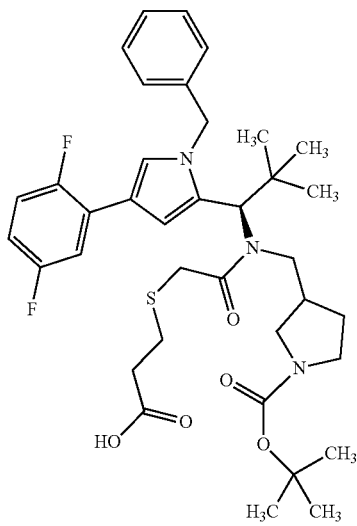 [SMILES: CC(C)(C)OC(=O)N1CCC(CN(C(=O)CSCCC(=O)O)[C@@H](c2cc(-c3cc(F)ccc3F)cn2Cc2ccccc2)C(C)(C)C)C1]

302.5 mg (2.19 mmol) of potassium carbonate were added to a mixture of 384.0 mg (0.62 mmol) of tert-Butyl 3-{[{(1R)-1-[1-benzyl-4-(2,5-difluorophenyl)-1H-pyrrol-2-yl]-2,2-dimethyl-propyl}(chloroacetyl)amino]methyl}pyrrolidine-1-carboxylate (Intermediate C89, Isomer 1) and 73.0 mg (0.69 mmol) of 3-sulphanylpropanoic acid in 14 ml of methanol and a few drops of water. The reaction mixture was stirred at 50° C. for 2.5 h. Ethyl acetate was added to the reaction mixture and the organic phase was washed repeatedly with water and with saturated NaCl solution. The organic phase was dried over magnesium sulphate, the solvent was evaporated under reduced pressure and the residue was dried under high vacuum. The residue was used further without work-up. This gave 358.0 mg (84% of theory) of the title compound.

LC-MS (Method 1): $R_t$=1.33 min; MS (ESIpos): m/z=684 (M+H)$^+$.

Intermediate C96

3-{[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]sulphanyl}propanoic acid (Isomer 2)

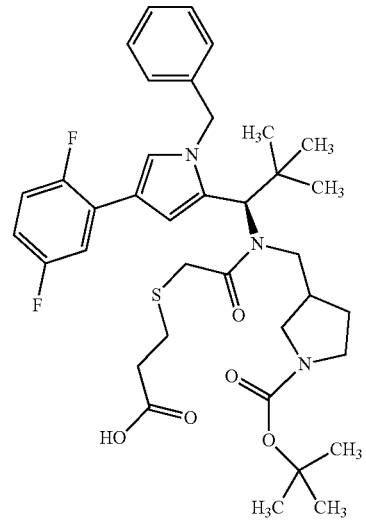 [SMILES: CC(C)(C)OC(=O)N1CCC(CN(C(=O)CSCCC(=O)O)[C@@H](c2cc(-c3cc(F)ccc3F)cn2Cc2ccccc2)C(C)(C)C)C1]

226.0 mg (1.64 mmol) of potassium carbonate were added to a mixture of 287.0 mg (0.45 mmol) of tert-Butyl 3-{[{(1R)-1-[1-benzyl-4-(2,5-difluorophenyl)-1H-pyrrol-2-yl]-2,2-dimethyl-propyl}(chloroacetyl)amino]methyl}pyrrolidine-1-carboxylate (Intermediate C89, Isomer 2) and 54.6 mg (0.51 mmol) of 3-sulphanylpropanoic acid in 14 ml of methanol and a few drops of water. The reaction mixture was stirred at 50° C. for 2.5 h. Ethyl acetate was added to the reaction mixture and the organic phase was washed repeatedly with water and with saturated NaCl solution. The organic phase was dried over magnesium sulphate, the solvent was evaporated under reduced pressure and the residue was dried under high vacuum. The residue was used further without work-up. This gave 318.7 mg (88% of theory, 88% pure) of the title compound.

LC-MS (Method 1): $R_t$=1.36 min; MS (ESIpos): m/z=684 (M+H)$^+$.

Intermediate C97 tert-Butyl 3-[2-{(1R)-1-[1-benzyl-4-(2,5-difluorophenyl)-1H-pyrrol-2-yl]-2,2-dimethylpropyl}-14-(2,5-dioxo-2,5-dihydro-1H-pyrrol-1-yl)-3,8,13-trioxo-5-thia-2,9,12-triazatetradec-1-yl]pyrrolidine-1-carboxylate (Isomer 2)

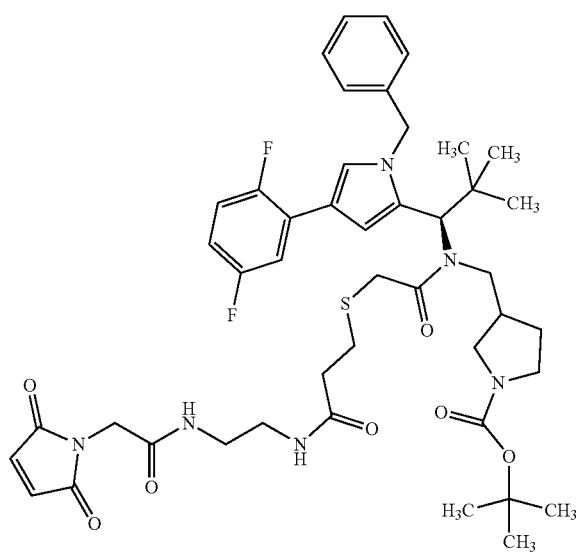 [SMILES: CC(C)(C)OC(=O)N1CCC(CN(C(=O)CSCCC(=O)NCCNC(=O)CN2C(=O)C=CC2=O)[C@@H](c2cc(-c3cc(F)ccc3F)cn2Cc2ccccc2)C(C)(C)C)C1]

Under argon, 14.17 mg (0.11 mmol) of N,N-diisopropylethylamin and 27.80 mg (0.07 mmol) of HATU were added to a solution of 25.0 mg (0.04 mmol) of 3-{[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]sulphanyl}propanoic acid (Intermediate C96) in 2.81 ml of DMF. The reaction mixture was stirred at RT for 10 minutes. A solution of 22.75 mg (0.07 mmol) of N-(2-aminoethyl)-2-(2,5-dioxo-2,5-dihydro-1H-pyrrol-1-yl)acetamide-ethane (1:1) trifluoroacetic acid (Intermediate L1) in 1.4 ml of DMF and 5 mg (0.04 mmol) of N,N-diisopropylethylamine was then added, and the mixture was stirred at RT overnight. Water was added and the mixture was extracted with dichloromethane. The organic phase was dried over magnesium sulphate and the solvent was evaporated under reduced pressure. The residue was used further without work-up. This gave 318.7 mg (88% of theory) of the title compound.

LC-MS (Method 5): $R_t$=4.39 min; MS (ESIpos): m/z=863 (M+H)$^+$.

Intermediate C98 tert-Butyl 3-[2-{(1R)-1-[1-benzyl-4-(2,5-difluorophenyl)-1H-pyrrol-2-yl]-2,2-dimethylpropyl}-18-(2,5-dioxo-2,5-dihydro-1H-pyrrol-1-yl)-3,8,13-trioxo-5-thia-2,9,12-triazaoctadec-1-yl]pyrrolidine-1-carboxylate (Isomer 2)

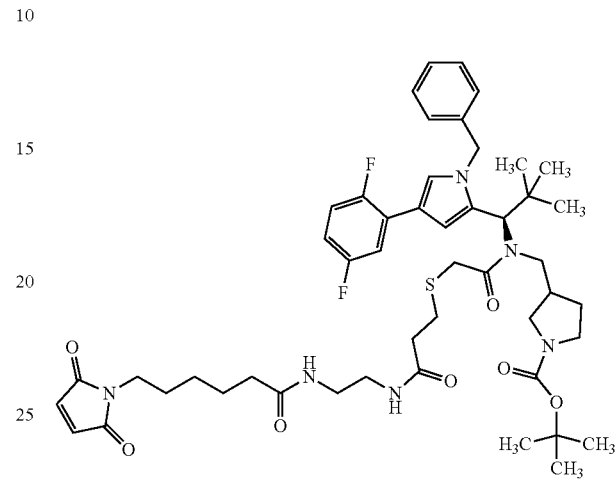

Under argon, 14.17 mg (0.11 mmol) of N,N-diisopropylethylamine and 27.80 mg (0.07 mmol) of HATU were added to a solution of 25.0 mg (0.04 mmol) of 3-{[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]sulphanyl}propanoic acid (Intermediate C96) in 2.81 ml of DMF. The reaction mixture was stirred at RT for 10 minutes. A solution of 37.30 mg (0.07 mmol) of N-(2-aminoethyl)-6-(2,5-dioxo-2,5-dihydro-1H-pyrrol-1-yl)hexanamide-ethane (1:1) trifluoroacetic acid in 1.4 ml of DMF and 5 mg (0.04 mmol) of N,N-diisopropylethylamine was then added, and the mixture was stirred at RT overnight. Water was added and the mixture was extracted with dichloromethane. The organic phase was dried over magnesium sulphate and the solvent was evaporated under reduced pressure. The residue was employed without further purification. This gave 318.7 mg (88% of theory) of the title compound.

LC-MS (Method 5): $R_t$=4.54 min; MS (ESIpos): m/z=919 (M+H)$^+$.

Intermediate C99 tert-Butyl 3-[2-{(1R)-1-[1-benzyl-4-(2,5-difluoro-phenyl)-1H-pyrrol-2-yl]-2,2-dimethylpropyl}-24-(2,5-dioxo-2,5-dihydro-1H-pyrrol-1-yl)-3,8,19-trioxo-12,15-dioxa-5-thia-2,9,18-triazatetracos-1-yl]pyrrolidine-1-carboxylate (Isomer 2)

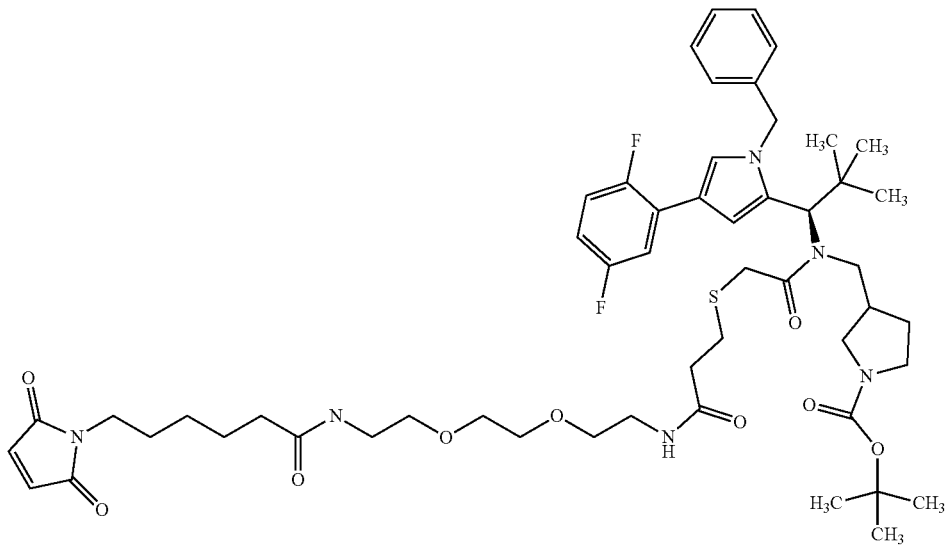 [SMILES: CC(C)(C)OC(=O)N1CCC(CN(C(=O)CSCCC(=O)NCCOCCOCCNC(=O)CCCCCN2C(=O)C=CC2=O)[C@@H](c2cc(-c3cc(F)ccc3F)cn2Cc2ccccc2)C(C)(C)C)C1]

Under argon, 14.17 mg (0.11 mmol) of N,N-diisopropylethylamine and 27.80 mg (0.07 mmol) of HATU were added to a solution of 25.0 mg (0.04 mmol) of 3-{[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]sulphanyl}propanoic acid (Intermediate C96) in 2.81 ml of DMF. The reaction mixture was stirred at RT for 10 minutes. A solution of 35.05 mg (0.07 mmol) of N-{2-[2-(2-Aminoethoxy)ethoxy]ethyl}-6-(2,5-dioxo-2,5-dihydro-1H-pyrrol-1-yl)hexanamide-ethane (1:1) trifluoroacetic acid (Intermediate L82) in 1.4 ml of DMF and 5 mg (0.04 mmol) of N,N-diisopropylethylamine was then added, and the mixture was stirred at RT overnight. Water was added and the mixture was extracted with dichloromethane. The organic phase was dried over magnesium sulphate, the solvent was evaporated under reduced pressure and the residue was dried under high vacuum. The residue was used further without work-up. This gave 25 mg (36% of theory) of the title compound.

LC-MS (Method 1): $R_t$=4.52 min; MS (ESIpos): m/z=1007 (M+H)$^+$.

Intermediate C100

2-(Trimethylsilyl)ethyl {(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2R)-2-(2,5-dioxo-2,5-dihydro-1H-pyrrol-1-yl)propanoyl]amino}ethyl)amino]-1-oxobutan-2-yl}carbamate

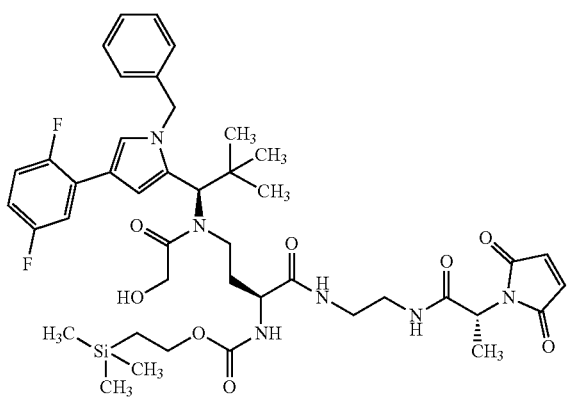 [SMILES: C[C@H](C(=O)NCCNC(=O)[C@H](CCN(C(=O)CO)[C@@H](c1cc(-c2cc(F)ccc2F)cn1Cc1ccccc1)C(C)(C)C)NC(=O)OCC[Si](C)(C)C)N1C(=O)C=CC1=O]

22.2 mg (0.068 mmol) of (2R)—N-(2-aminoethyl)-2-(2,5-dioxo-2,5-dihydro-1H-pyrrol-1-yl)propanamide (1:1) trifluoroacetic acid were added to a solution of 45 mg (0.068 mmol) of (2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoic acid (Intermediate C58) in 5.8 ml of DMF. After 30 minutes of stirring at RT, 39 mg (0.10 mmol) of HATU and 36 mg (0.27 mmol) of N,N-diisopropylethylamine were added to the mixture. The reaction mixture was stirred at RT for 1 h. Without work-up, the mixture was purified by preparative HPLC. This gave 7 mg (12% of theory) of the title compound.

LC-MS (Method 1): $R_t$=1.41 min; MS (ESIpos): m/z 851 (M+H)$^+$.

Intermediate C101

Trifluoroacetic acid methyl (2S)-4-[(acetoxyacetyl){(1R)-1-[1-benzyl-4-(2,5-difluorophenyl)-1H-pyrrol-2-yl]-2,2-dimethylpropyl}amino]-2-aminobutanoate (1:1)

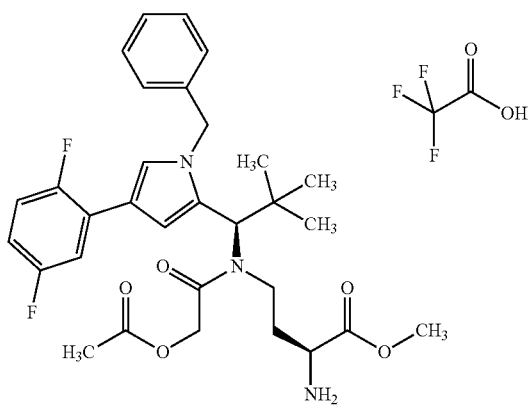 [SMILES: COC(=O)[C@@H](N)CCN(C(=O)COC(C)=O)[C@@H](c1cc(-c2cc(F)ccc2F)cn1Cc1ccccc1)C(C)(C)C ; O=C(O)C(F)(F)F]

4.3 g (12.2 mmol) of intermediate C52 were dissolved in 525 mL of DCM and 3.63 g (17.12 mmol) of sodium triacetoxyborohydride and 8.4 mL of acetic acid were added. After stirring at RT for 5 min, 3.23 g (11.85 mmol) of methyl (2S)-4-oxo-2-({[2-(trimethylsilyl)ethoxy]carbonyl}amino)butanoate (prepared from (3S)-3-amino-4-methoxy-4-oxobutanoic acid by classical methods) dissolved in 175 mL of DCM were added and the mixture was stirred at RT for a further 45 min. The mixture was then diluted with DCM and shaken twice with 100 mL of saturated sodium hydrogen carbonate solution and then with saturated sodium chloride solution. The organic phase was dried over magnesium sulfate, filtered and then concentrated. The residue was purified by preparative HPLC. After purification of the relevant fractions, concentration and drying of the residue under high vacuum, 4.6 g (61% of theory) of the intermediate was obtained.

LC-MS (Method 12): $R_t$=1.97 min; MS (ESIpos): m/z=614.32 (M+H)$^+$.

2.06 g (3.36 mmol) of this intermediate were charged in 76 mL of DCM and acylated with 0.81 mL (7.17 mmol) of 2-chloro-2-oxoethyl acetate in the presence of 2.1 ml of triethylamine. After stirring at RT for 20 h, a further 0.36 mL of 2-chloro-2-oxoethyl acetate and 0.94 ml of triethylamine were added and the mixture was stirred for a further 15 min at RT. The mixture was subsequently diluted with 500 mL of ethyl acetate and shaken successively twice with 300 mL of 5% citric acid, twice with 300 mL of saturated sodium hydrogen carbonate solution and once with 100 mL of saturated sodium chloride solution, then dried over magnesium sulfate and concentrated. After drying under high vacuum, 2.17 g (79% of theory) of the protected intermediate were obtained.

LC-MS (Method 1): $R_t$=1.48 min; MS (ESIpos): m/z=714 (M+H)$^+$.

321 mg (0.342 mmol) of this intermediate were dissolved in 7 mL of 2,2,2-trifluoroethanol. 279.5 mg (2.05 mmol) of zinc chloride were added and the mixture stirred at 50° C. for 2 h. Subsequently, 599 mg (2.05 mmol) of ethylenediamine-N,N,N',N'-tetraacetic acid and 2 mL of a 0.1% trifluoroacetic acid solution in water were added and the mixture was then concentrated under vacuum. The residue was purified by preparative HPLC. After concentrating the relevant fractions and lyophilisation of the residue of acetonitrile/water, 60 mg (26% of theory) of the title compound were obtained, which still comprised a portion of the deacetylated compound.

LC-MS (Method 1): $R_t$=0.91 min and 0.95 min; MS (ESIpos): m/z=528 and 570 (M+H)$^+$.

Intermediate C102

(2S)-4-[{(1R)-1-[1-Benzyl-4-(2,5-difluorophenyl)-1H-pyrrol-2-yl]-2,2-dimethylpropyl}(glycoloyl)amino]-2-{[(benzyloxy)carbonyl]amino}butanoic acid

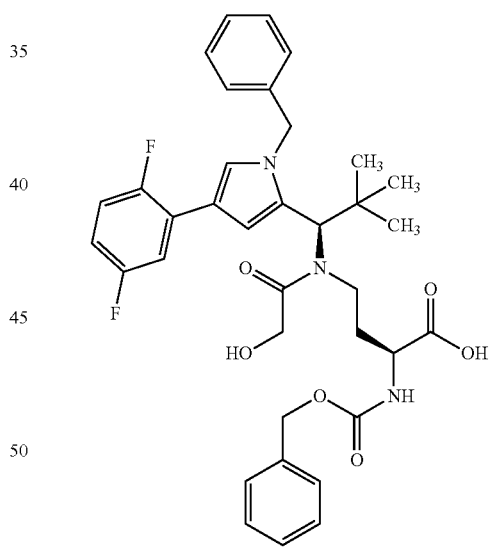

Firstly, intermediate C52 was reductively alkylated with benzyl (2S)-2-{[(benzyloxy)carbonyl]amino}-4-oxobutanoate analogously to intermediate C2. The secondary amino group was then acylated with 2-chloro-2-oxoethyl acetate and finally the two ester groups were hydrolysed with 2M lithium hydroxide solution in methanol.

LC-MS (Method 1): $R_t$=1.31 min; MS (ESIpos): m/z=646 (M−H)$^−$.

Intermediate C103

2-(Trimethylsilyl)ethyl N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-N2-{[2-(trimethylsilyl)ethoxy]carbonyl}-L-glutaminate

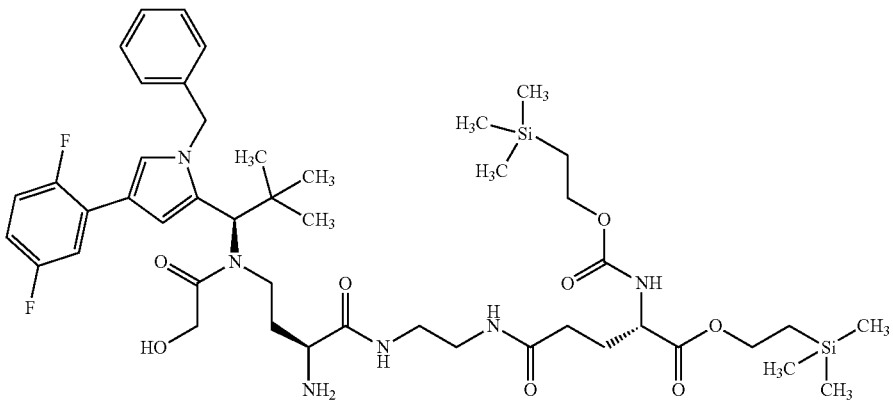 [SMILES: CC(C)(C)[C@H](c1cc(-c2cc(F)ccc2F)cn1Cc1ccccc1)N(CC[C@H](N)C(=O)NCCNC(=O)CC[C@H](NC(=O)OCC[Si](C)(C)C)C(=O)OCC[Si](C)(C)C)C(=O)CO]

The title compound was firstly prepared by coupling of 151 mg (0.23 mmol) of intermediate C102 with 128 mg (0.234 mmol) of intermediate L98 in DMF in the presence of HATU and N,N-diisopropylethylamine. The Z protecting group was then removed by a 30 minute hydrogenation over 10% palladium on active carbon under standard hydrogen pressure at RT, whereupon the title compound was obtained.

Yield: 30% of theory over 2 stages

LC-MS (Method 1): $R_t$=1.14 min; MS (ESIpos): m/z=929 (M+H)$^+$.

Intermediate C104

2-(Trimethylsilyl)ethyl (3R,4R)-3-[({(1R)-1-[1-benzyl-4-(2,5-difluorophenyl)-1H-pyrrol-2-yl]-2,2-dimethylpropyl}amino)methyl]-4-fluoropyrrolidine-1-carboxylate

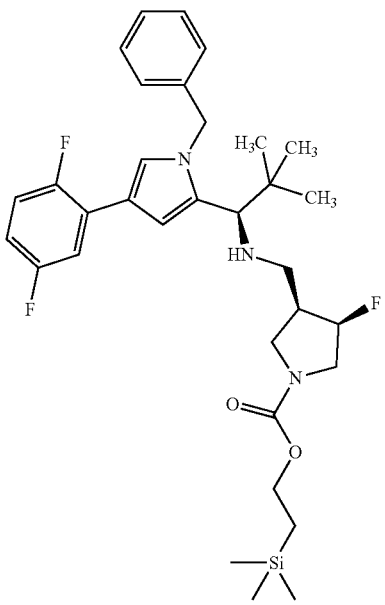 [SMILES: CC(C)(C)[C@@H](NC[C@@H]1CN(C(=O)OCC[Si](C)(C)C)C[C@@H]1F)c1cc(-c2cc(F)ccc2F)cn1Cc1ccccc1]

1.87 g (8.84 mmol) of sodium triacetoxyborohydride was added to a solution of 2.24 g (6.31 mmol) of (1R)-1-[1-benzyl-4-(2,5-difluorophenyl)-1H-pyrrol-2-yl]-2,2-dimethylpropan-1-amine in 56.0 ml of dichloromethane with 4 Å molecular sieve and the mixture was stirred at room temperature for 15 minutes. Subsequently, 2.20 g (7.58 mmol) of 2-(trimethyl silyl)ethyl (3R,4S)-3-fluoro-4-formylpyrrolidine-1-carboxylate (Ref: WO 2014/151030A1) were added and the reaction mixture was stirred at room temperature for 3.5 h. The mixture was diluted with dichloromethane and the organic phase was washed with sat. sodium hydrogen carbonate solution and water. The organic phase was dried over sodium sulfate and concentrated. The residue was purified by prep. HPLC. This gave 1.39 g (24% of theory) of the title compound.

LC-MS (Method 1): $R_t$=1.15 min; MS (ESIpos): m/z=600 (M+H)$^+$.

Intermediate C105

2-(Trimethylsilyl)ethyl (3R,4R)-3-{[{(1R)-1-[1-benzyl-4-(2,5-difluorophenyl)-1H-pyrrol-2-yl]-2,2-dimethylpropyl}(chloroacetyl)amino]methyl}-4-fluoropyrrolidine-1-carboxylate

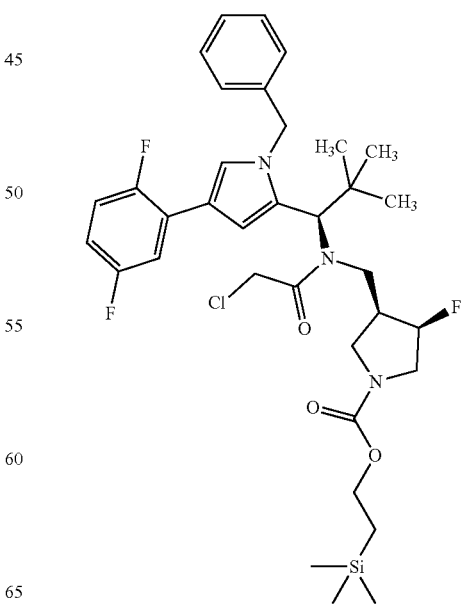

295.0 mg (2.91 mmol) of triethylamine and 418.9 mg (3.71 mmol) of chloroacetyl chloride were added to a solution of 692.8 mg (0.88 mmol) of 2-(trimethylsilyl)ethyl (3R,4R)-3-[({(1R)-1-[1-benzyl-4-(2,5-difluorophenyl)-1H-pyrrol-2-yl]-2,2-dimethylpropyl}amino)methyl]-4-fluoropyrrolidine-1-carboxylate (intermediate C104) in 8.7 ml of dichloromethane with 4 Å molecular sieve and the reaction mixture was stirred at RT for 2.5 h. The reaction mixture was diluted with dichloromethane and the organic phase was washed with sat. sodium hydrogen carbonate solution and sat. ammonium chloride solution. The organic phase was dried over sodium sulfate and concentrated. The residue was again in 8.7 ml of dichloromethane with 4 Å molecular sieve were added 295.0 mg (2.91 mmol) of triethylamine and 418.9 mg (3.71 mmol) of chloroacetyl chloride and the reaction mixture was stirred at RT for 3 h. The reaction mixture was diluted with dichloromethane and the organic phase was washed with sat. sodium hydrogen carbonate solution and sat. ammonium chloride solution. The organic phase was dried over sodium sulfate and concentrated. The organic phase was dried over sodium sulfate, concentrated and further used without purification. This gave 691 mg (74% of theory, 64% purity) of the title compound.

LC-MS (Method 1): $R_t$=1.78 min; MS (ESIpos): m/z=676 $(M+H)^+$.

Intermediate C106

3-{[2-({(1R)-1-[1-Benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]sulfanyl}propanoic acid

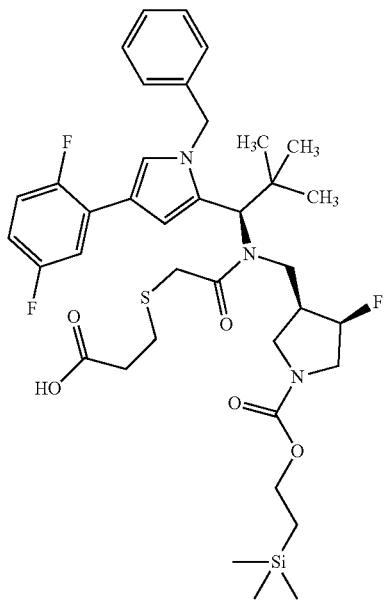 [SMILES: CC(C)(C)[C@H](c1cc(-c2cc(F)ccc2F)cn1Cc1ccccc1)N(C[C@@H]1CN(C(=O)OCC[Si](C)(C)C)C[C@@H]1F)C(=O)CSCCC(=O)O]

To a mixture of 691.0 mg (0.65 mmol) of 2-(trimethylsilyl)ethyl (3R,4R)-3-{[{(1R)-1-[1-benzyl-4-(2,5-difluorophenyl)-1H-pyrrol-2-yl]-2,2-dimethylpropyl}(chloroacetyl)amino]methyl}-4-fluoropyrrolidine-1-carboxylate (intermediate C105) and 76.3 mg (0.72 mmol) of 3-sulfanylpropanoic acid in 15 ml of methanol and a few drops of water were added 316 mg (2.29 mmol) of potassium carbonate. The reaction mixture was stirred at 50° C. for 1.5 h. Ethyl acetate was added to the reaction mixture and the org. phase was washed repeatedly with water and sat. NaCl solution. The organic phase was dried over magnesium sulfate and the solvent evaporated under vacuum and the residue dried under high vacuum. The residue was further used without processing. This gave 502 mg (67% of theory, 65% purity) of the title compound.

LC-MS (Method 1): $R_t$=1.48 min; MS (ESIneg): m/z=744 $(M-H)^-$.

Intermediate C107

S-[2-({(1R)-1-[1-Benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]-L-cysteine

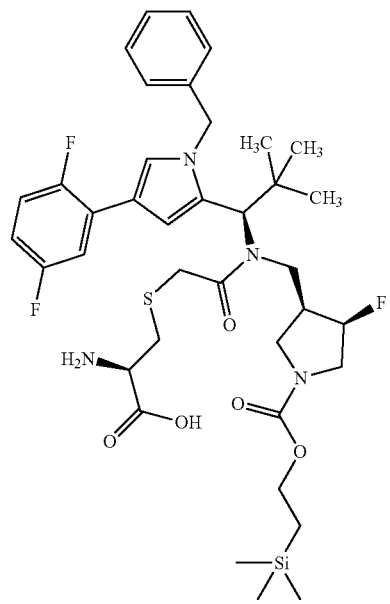 [SMILES: CC(C)(C)[C@H](c1cc(-c2cc(F)ccc2F)cn1Cc1ccccc1)N(C[C@@H]1CN(C(=O)OCC[Si](C)(C)C)C[C@@H]1F)C(=O)CSC[C@H](N)C(=O)O]

203.6 mg (1.68 mmol) of L-cysteine were suspended in 0.95 mL of water together with 201.7 mg (2.40 mmol) of sodium hydrogen carbonate. To this were added 170.0 mg (0.24 mmol) of 2-(trimethylsilyl)ethyl (3R,4R)-3-{[{(1R)-1-[1-benzyl-4-(2,5-difluorophenyl)-1H-pyrrol-2-yl]-2,2-dimethylpropyl}(chloroacetyl)amino]methyl}-4-fluoropyrrolidine-1-carboxylate (intermediate 105) dissolved in 9.5 mL of isopropanol and 438.5 mg (2.40 mmol) of 1,8-diazabicyclo(5.4.0)undec-7-ene. The reaction mixture was stirred at 50° C. for 3 h. Ethyl acetate was added to the mixture and the org. phase was washed repeatedly with sat. sodium hydrogen carbonate solution and with sat. NaCl solution. The organic phase was dried over sodium sulphate and the solvent evaporated under vacuum. The residue was further used without further purification. This gave 152 mg (83% of theory) of the title compound.

LC-MS (Method 1): $R_t$=1.26 min; MS (ESIpos): m/z=762 $(M+H)^+$.

Intermediate C115

N-[6-(2,5-Dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}{[(2-carboxyethyl)sulfanyl]acetyl}amino)propyl]-L-alaninamide

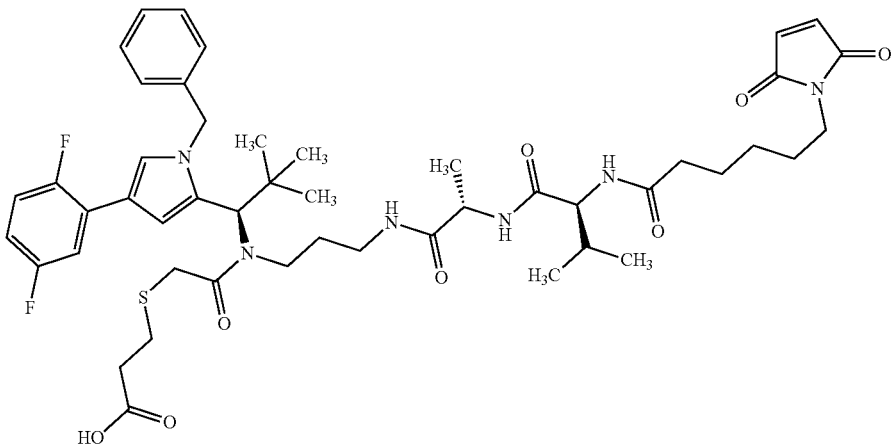 [SMILES: CC(C)[C@H](NC(=O)CCCCCN1C(=O)C=CC1=O)C(=O)N[C@@H](C)C(=O)NCCCN(C(=O)CSCCC(=O)O)[C@@H](c1cc(-c2cc(F)ccc2F)cn1Cc1ccccc1)C(C)(C)C]

11-{(1R)-1-[1-Benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (200 mg, 285 µmol) (intermediate C69) was dissolved in 10 ml of trifluoroethanol. Zinc chloride (233 mg, 1.71 mmol) was added to the reaction mixture and the mixture wash stirred at 50° C. for 1 hour. The reaction mixture was treated twice more with zinc chloride (233 mg, 1.71 mmol) and stirred at 50° C. for 1 hour. Ethylenediamine-N,N,N',N'-tetraacetic acid (1.50 g, 5.13 mmol) was added to the mixture, then water (0.1% TFA) was added and the mixture subsequently concentrated under vacuum. The residue was purified by prep. RP-HPLC (column: Reprosil 250×30; 10µ, flow: 50 mL/min, MeCN/water, 0.1% TFA). The solvents were evaporated under vacuum and the residue was dried under high vacuum. This gave 62 mg (85% of theory) of the compound 3-({2-[(3-aminopropyl){(1R)-1-[1-benzyl-4-(2,5-difluorophenyl)-1H-pyrrol-2-yl]-2,2-dimethylpropyl}amino]-2-oxoethyl}sulfanyl)propanoic acid—trifluoroacetic acid (1:1).

LC-MS (Method 1): $R_t$=0.94 min; MS (ESIneg): m/z=556 [M−H]⁻

3-({2-[(3-Aminopropyl){(1R)-1-[1-benzyl-4-(2,5-difluorophenyl)-1H-pyrrol-2-yl]-2,2-dimethylpropyl}amino]-2-oxoethyl}sulfanyl)propanoic acid—trifluoroacetic acid (1:1) (80.0 mg, 119 µmol) was dissolved in 5.0 ml of DMF and treated with 2,5-dioxopyrrolidin-1-yl-N-[6-(2,5-dioxo-2,5-dihydro-1H-pyrrol-1-yl)hexanoyl]-L-valyl-L-alaninate (69.4 mg, 82% purity, 119 µmol) (intermediate L88) and N,N-diisopropylethylamine (41 µl, 240 µmol). The reaction mixture was stirred at RT for 2 h30 and water (0.1% TFA) was added. The mixture was concentrated and purified directly by prep. RP-HPLC (column: Reprosil 250×30; 10µ, flow: 50 mL/min, MeCN/water, 0.1% TFA). The solvents were evaporated under vacuum and the residue dried under high vacuum. This gave 82.2 mg (75% of theory) of the title compound.

LC-MS (Method 1): $R_t$=1.17 min; MS (ESIpos): m/z=921 [M+H]⁺

Intermediate C116

N-[6-(2,5-Dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}[({3-[(2-carboxyethyl)amino]-3-oxopropyl}sulfanyl)acetyl]amino)propyl]-L-alaninamide

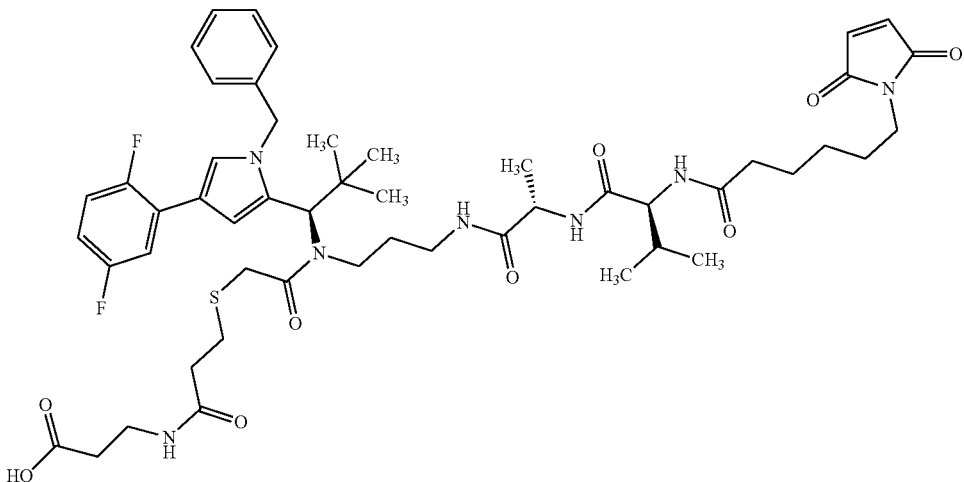 [SMILES: CC(C)[C@H](NC(=O)CCCCCN1C(=O)C=CC1=O)C(=O)N[C@@H](C)C(=O)NCCCN(C(=O)CSCCC(=O)NCCC(=O)O)[C@@H](c1cc(-c2cc(F)ccc2F)cn1Cc1ccccc1)C(C)(C)C]

N-[6-(2,5-Dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}{[(2-carboxyethyl)sulfanyl]acetyl}amino)propyl]-L-alaninamide (56.7 mg, 61.6 µmol) (intermediate C115) and tert-Butyl beta-alaninate hydrochloride (1:1) (13.4 mg, 73.9 µmol) were initially charged in 3.0 ml DMF under argon and treated with HATU (28.1 mg, 73.9 µmol) and N,N-diisopropylethylamine (32 µl, 180 µmol). The reaction mixture was stirred at RT for 10 min and then purified directly by prep. RP-HPLC (column: Reprosil 250×30; 10µ, flow: 50 mL/min, MeCN/water). The solvents were evaporated under vacuum and the residue dried under high vacuum. This gave 41.4 mg (64% of theory) of the compound N-[6-(2,5-dioxo-2,5-dihydro-1H-pyrrol-1-yl)hexanoyl]-L-valyl-N-(14-{(1R)-1-[1-benzyl-4-(2,5-difluorophenyl)-1H-pyrrol-2-yl]-2,2-dimethylpropyl}-2,2-dimethyl-4,8,13-trioxo-3-oxa-11-thia-7,14-diazaheptadecan-17-yl)-L-alaninamide.

LC-MS (Method 1): $R_t$=1.28 min; MS (ESIpos): m/z=1048 [M+H]$^+$

N-[6-(2,5-Dioxo-2,5-dihydro-1H-pyrrol-1-yl)hexanoyl]-L-valyl-N-(14-{(1R)-1-[1-benzyl-4-(2,5-difluorophenyl)-1H-pyrrol-2-yl]-2,2-dimethylpropyl}-2,2-dimethyl-4,8,13-trioxo-3-oxa-11-thia-7,14-diazaheptadecan-17-yl)-L-alaninamide (39.3 mg, 37.5 µmol) was dissolved in 2.5 ml of trifluoroethanol. Zinc chloride (30.7 mg, 225 µmol) was added to the reaction mixture and the mixture was stirred at 50° C. for 1 hour. The reaction mixture was treated once again with zinc chloride (30.7 mg, 225 µmol) and stirred at 50° C. for 1 hour. Ethylenediamine-N,N,N',N'-tetraacetic acid (131 mg, 450 µmol) was added to the mixture, then water (0.1% TFA) was added and the mixture was then concentrated under vacuum. The residue was purified by prep. RP-HPLC (column: Reprosil 250×30; 10µ, flow: 50 mL/min, MeCN/water, 0.1% TFA). The solvents were evaporated under vacuum and the residue was taken up in a little water and lyophilized. This gave 30 mg (81% of theory) of the title compound.

LC-MS (Method 1): $R_t$=1.12 min; MS (ESIpos): m/z=992 [M+H]$^+$

Intermediate L1

Trifluoroacetic acid/N-(2-aminoethyl)-2-(2,5-dioxo-2,5-dihydro-1H-pyrrol-1-yl)acetamide (1:1)

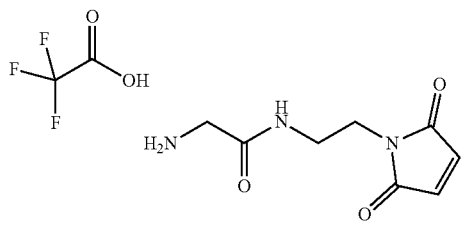 [SMILES: O=C(O)C(F)(F)F ; NCC(=O)NCCN1C(=O)C=CC1=O]

The title compound was prepared by classical methods of peptide chemistry from commercially available (2,5-dioxo-2,5-dihydro-1H-pyrrol-1-yl)acetic acid and tert-Butyl (2-amino-ethyl)carbamate.

HPLC (Method 11): $R_t$=0.19 min;

LC-MS (Method 1): $R_t$=0.17 min; MS (ESIpos): m/z=198 (M+H)$^+$.

Intermediate L2

Trifluoroacetic acid/rel-(1R,2S)-2-amino-N-[2-(2,5-dioxo-2,5-dihydro-1H-pyrrol-1-yl)ethyl]cyclopentanecarboxamide (1:1)

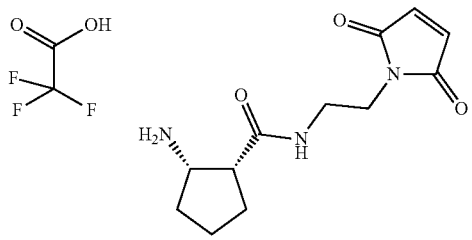 [SMILES: O=C(O)C(F)(F)F ; N[C@H]1CCC[C@H]1C(=O)NCCN1C(=O)C=CC1=O]

The title compound was prepared from 50 mg (0.214 mmol) of commercially available cis-2-[(tert-butoxycarbonyl)amino]-1-cyclopentanecarboxylic acid and 60 mg (0.235 mmol) of likewise commercially available trifluoroacetic acid/1-(2-aminoethyl)-1H-pyrrole-2,5-dione (1:1) by coupling with EDC/HOBT and subsequent deprotection with TFA. This gave 36 mg (38% of theory over 2 steps) of the title compound.

HPLC (Method 11): $R_t$=0.2 min;

LC-MS (Method 1): $R_t$=0.17 min; MS (ESIpos): m/z=252 (M+H)$^+$.

Intermediate L3

Trifluoroacetic acid/(1S,2R)-2-amino-N-[2-(2,5-dioxo-2,5-dihydro-1H-pyrrol-1-yl)ethyl]cyclopentanecarboxamide (1:1)

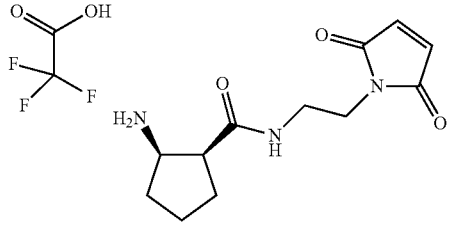

The title compound was prepared from 50 mg (0.214 mmol) of commercially available (1S,2R)-2-[(tert-butoxycarbonyl)amino]cyclopentanecarboxylic acid with 72 mg (0.283 mmol) of likewise commercially available trifluoroacetic acid/1-(2-aminoethyl)-1H-pyrrole-2,5-dione (1:1) by coupling with EDC/HOBT and subsequent deprotection with TFA. This gave 13 mg (16% of theory over 2 steps) of the title compound.

HPLC (Method 11): $R_t$=0.2 min;

LC-MS (Method 1): $R_t$=0.2 min; MS (ESIpos): m/z=252 (M+H)$^+$.

Intermediate L4

Trifluoroacetic acid/N-(2-aminoethyl)-4-(2,5-dioxo-2,5-dihydro-1H-pyrrol-1-yl)cyclohexanecarboxamide (1:1)

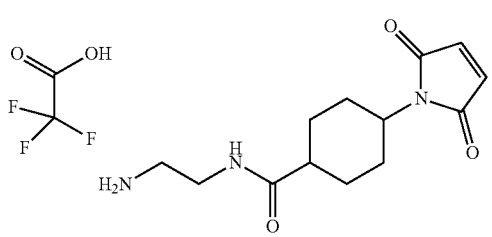

The title compound was prepared by classical methods of peptide chemistry from commercially available 1-[(4-{[(2,5-dioxopyrrolidin-1-yl)oxy]carbonyl}cyclohexyl)methyl]-1H-pyrrole-2,5-dione and tert-Butyl (2-aminoethyl)carbamate.

HPLC (Method 11): $R_t$=0.26 min;

LC-MS (Method 1): $R_t$=0.25 min; MS (ESIpos): m/z=280 (M+H)$^+$.

Intermediate L5

Trifluoroacetic acid/N-[4-(2,5-dioxo-2,5-dihydro-1H-pyrrol-1-yl)phenyl]-beta-alaninamide (1:1)

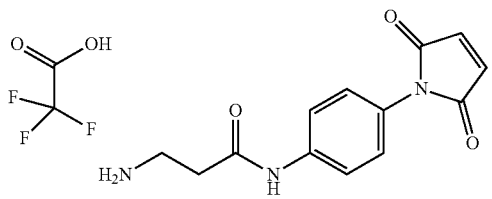

The title compound was prepared by classical methods of peptide chemistry from commercially available 1-(4-aminophenyl)-1H-pyrrole-2,5-dione and N-(tert-butoxycarbonyl)-beta-alanine.

HPLC (Method 11): $R_t$=0.22 min;

LC-MS (Method 1): $R_t$=0.22 min; MS (ESIpos): m/z=260 (M+H)$^+$.

Intermediate L6

Trifluoroacetic acid/tert-Butyl-N-[6-(2,5-dioxo-2,5-dihydro-1H-pyrrol-1-yl)hexanoyl]-L-valyl-L-alanyl-L-lysinate (1:1)

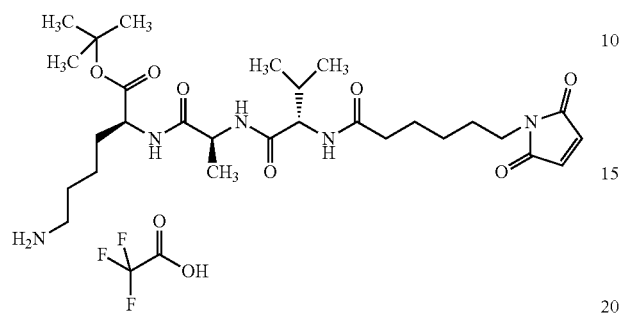

The title compound was prepared by initially coupling, in the presence of EDC/HOBT, commercially available 6-(2,5-dioxo-2,5-dihydro-1H-pyrrol-1-yl)hexanoic acid with the partially protected peptide tert-Butyl L-valyl-L-alanyl-$N^6$-(tert-butoxycarbonyl)-L-lysinate, prepared by classical methods of peptide chemistry. This was followed by deprotection at the amino group under gentle conditions by stirring in 5% strength trifluoroacetic acid in DCM at RT, which gave the title compound in a yield of 37%.

HPLC (Method 11): $R_t$=1.29 min;

LC-MS (Method 1): $R_t$=0.62 min; MS (ESIpos): m/z=566 (M+H)$^+$.

Intermediate L7

Trifluoroacetic acid/beta-alanyl-L-valyl-$N^5$-carbamoyl-N-[4-(2,5-dioxo-2,5-dihydro-1H-pyrrol-1-yl)phenyl]-L-ornithinamide (1:1)

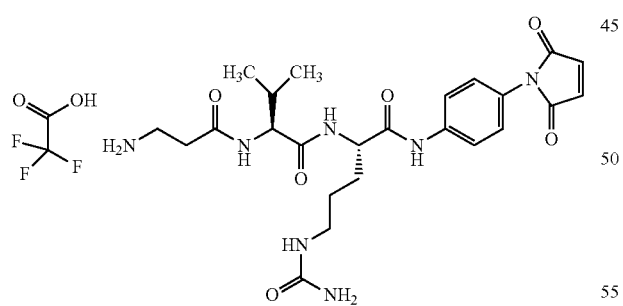

The title compound was prepared according to classical methods of peptide chemistry from commercially available 1-(4-aminophenyl)-1H-pyrrole-2,5-dione by sequential coupling with $N^2$-(tert-butoxycarbonyl)-$N^5$-carbamoyl-L-ornithine in the presence of HATU, deprotection with TFA, coupling with 2,5-dioxopyrrolidin-1-yl N-(tert-butoxycarbonyl)-L-valinate, deprotection with TFA, coupling with 2,5-dioxopyrrolidin-1-yl N-(tert-butoxycarbonyl)-beta-alaninate and another deprotection with TFA. 32 mg of the title compound were obtained.

HPLC (Method 11): $R_t$=0.31 min;

LC-MS (Method 1): $R_t$=0.47 min; MS (ESIpos): m/z=516 (M+H)$^+$.

Intermediate L8

Trifluoroacetic acid/L-alanyl-N5-carbamoyl-N-[4-(2,5-dioxo-2,5-dihydro-1H-pyrrol-1-yl)phenyl]-L-ornithinamide (1:1)

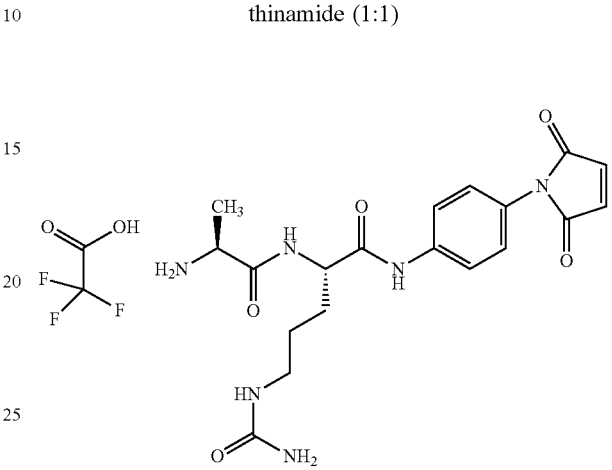

The title compound was prepared according to classical methods of peptide chemistry from commercially available 1-(4-aminophenyl)-1H-pyrrole-2,5-dione by sequential coupling with $N^2$-(tert-butoxycarbonyl)-$N^5$-carbamoyl-L-ornithine in the presence of HATU, deprotection with TFA, coupling with 2,5-dioxopyrrolidin-1-yl N-(tert-butoxycarbonyl)-L-alaninate and another deprotection with TFA. 171 mg of the title compound were obtained.

HPLC (Method 11): $R_t$=0.23 min;

LC-MS (Method 7): $R_t$=0.3 min; MS (ESIpos): m/z=417 (M+H)$^+$.

Intermediate L9

Trifluoroacetic acid/beta-alanyl-L-valyl-$N^5$-carbamoyl-N-[4-(2-methoxy-2-oxoethyl)phenyl]-L-ornithinamide (1:1)

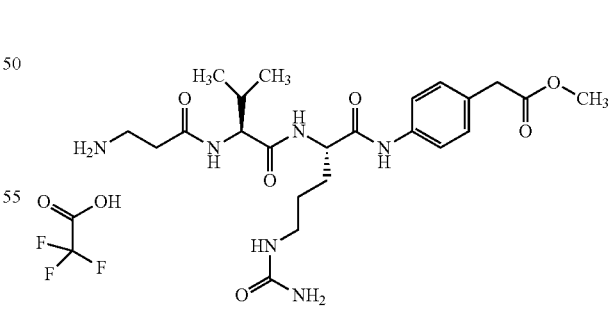

The title compound was prepared analogously to Intermediate L7 from commercially available methyl (4-aminophenyl)acetate. 320 mg of the title compound were obtained.

HPLC (Method 11): $R_t$=0.45 min;

LC-MS (Method 1): $R_t$=0.48 min; MS (ESIpos): m/z=493 (M+H)$^+$.

Intermediate L10

N-[6-(2,5-Dioxo-2,5-dihydro-1H-pyrrol-1-yl)hexanoyl]-L-valyl-L-alanyl-rel-N⁶—{[(1R,2S)-2-aminocyclopentyl]carbonyl}-L-lysine/trifluoroacetic acid (1:2)

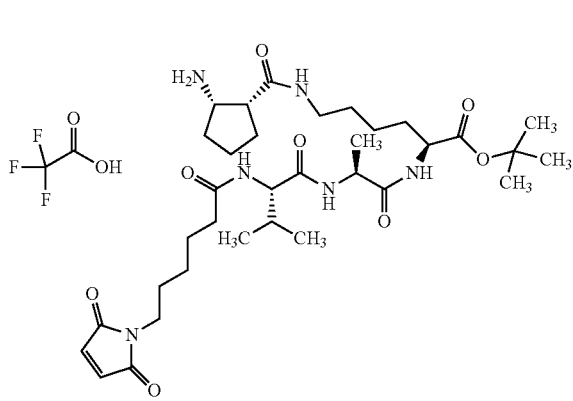 [SMILES: O=C(O)C(F)(F)F ; CC(C)[C@H](NC(=O)CCCCCN1C(=O)C=CC1=O)C(=O)N[C@@H](C)C(=O)N[C@@H](CCCCNC(=O)[C@@H]1CCC[C@@H]1N)C(=O)OC(C)(C)C]

The title compound was prepared from Intermediate L6 by coupling with cis-2-[(tert-butoxycarbonyl)amino]-1-cyclopentanecarboxylic acid with EDC/HOBT and subsequent deprotection with TFA. This gave 12 mg (52% of theory over 2 steps) of the title compound.

HPLC (Method 11): $R_t$=1.45 min;

LC-MS (Method 1): $R_t$=0.73 min; MS (ESIpos): m/z=677 (M+H)⁺.

Intermediate L11

N-[6-(2,5-Dioxo-2,5-dihydro-1H-pyrrol-1-yl)hexanoyl]-L-valyl-L-alanyl-N⁶-{[(1 S,2R)-2-aminocyclopentyl]carbonyl}-L-lysine/trifluoroacetic acid (1:2)

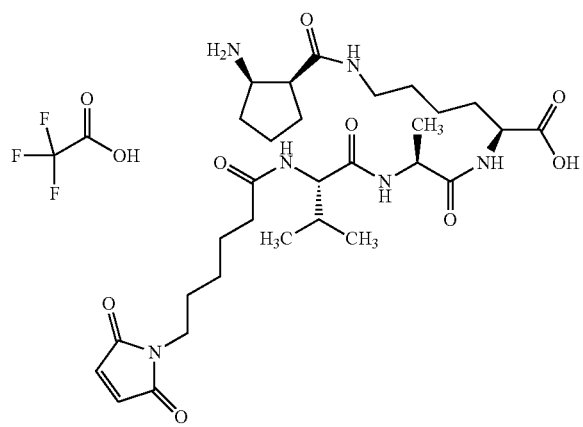 [SMILES: O=C(O)C(F)(F)F ; CC(C)[C@H](NC(=O)CCCCCN1C(=O)C=CC1=O)C(=O)N[C@@H](C)C(=O)N[C@@H](CCCCNC(=O)[C@H]1CCC[C@H]1N)C(=O)O]

The title compound was prepared from Intermediate L6 by coupling with (1S,2R)-2-[(tert-butoxycarbonyl)amino]cyclopentanecarboxylic acid with EDC/HOBT and subsequent deprotection with TFA. This gave 11 mg (39% of theory over 2 steps) of the title compound.

HPLC (Method 11): $R_t$=1.45 min;

LC-MS (Method 1): $R_t$=0.74 min; MS (ESIpos): m/z=677 (M+H)⁺.

Intermediate L12

Trifluoroacetic acid/1-[2-(2-aminoethoxy)ethyl]-1H-pyrrole-2,5-dione (1:1)

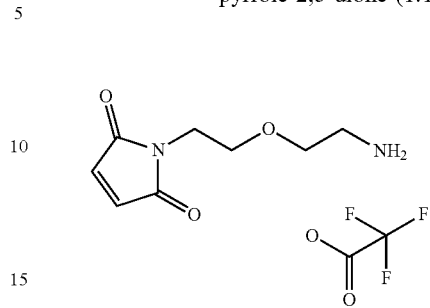

381 mg (2.46 mmol) of methyl 2,5-dioxo-2,5-dihydro-1H-pyrrole-1-carboxylate were added to 228 mg (1.12 mmol) of tert-Butyl [2-(2-aminoethoxy)ethyl]carbamate dissolved in 7 ml of dioxane/water 1:1. 1.2 ml of a saturated sodium bicarbonate solution were then added and the reaction was stirred at RT. After a total of 5 days of stirring and 2 further additions of the same amounts of the sodium bicarbonate solution, the reaction was worked up by acidification with trifluoroacetic acid, concentration on a rotary evaporator and purification of the residue by preparative HPLC. The appropriate fractions were combined, the solvent was removed under reduced pressure and the residue was lyophilized from acetonitrile/water 1:1.

The residue was taken up in 3 ml of dichloromethane, and 1 ml of trifluoroacetic acid was added. After 15 min of stirring at RT, the solvent was removed under reduced pressure and the residue was lyophilized from acetonitrile/water 1:1. This gave 70 mg (67% of theory over 2 steps) of the title compound as a resinous residue.

HPLC (Method 11): $R_t$=0.2 min;

LC-MS (Method 1): $R_t$=0.18 min; MS (ESIpos): m/z=185 (M+H)⁺.

Intermediate L13

Trifluoroacetic acid/tert-Butyl N²-[(2,5-dioxo-2,5-dihydro-1H-pyrrol-1-yl)acetyl]-L-lysinate (1:1)

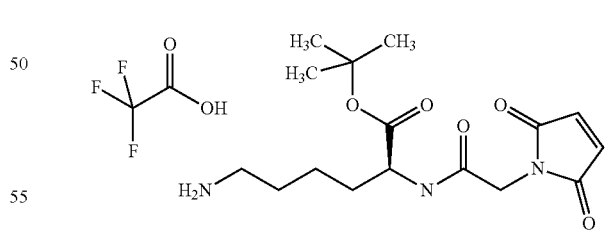

The title compound was prepared by coupling of (2,5-dioxo-2,5-dihydro-1H-pyrrol-1-yl)acetic acid with tert-Butyl N⁶-(tert-butoxycarbonyl)-L-lysinate hydrochloride (1:1) in the presence of EDC/HOBT and subsequent gentle removal of the tert-butoxycarbonyl protective group analogously to Intermediate L6.

HPLC (Method 11): $R_t$=0.42 min;

LC-MS (Method 1): $R_t$=0.43 min; MS (ESIpos): m/z=340 (M+H)⁺.

Intermediate L14

Trifluoroacetic acid/1-[2-(4-aminopiperazin-1-yl)-2-oxoethyl]-1H-pyrrole-2,5-dione (1:1)

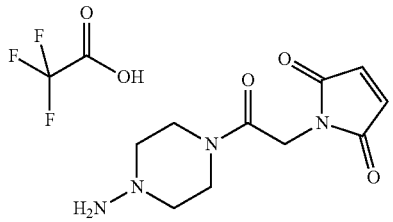 [SMILES: O=C(O)C(F)(F)F ; NN1CCN(C(=O)CN2C(=O)C=CC2=O)CC1]

The title compound was prepared analogously to Intermediate L2 over 2 steps from tert-Butyl piperazin-1-ylcarbamate and (2,5-dioxo-2,5-dihydro-1H-pyrrol-1-yl)acetic acid.

HPLC (Method 11): $R_t$=0.2 min;
LC-MS (Method 3): $R_t$=0.25 min; MS (ESIpos): m/z=239 (M+H)⁺.

Intermediate L15

Trifluoroacetic acid/N-(2-aminoethyl)-3-(2-{2-[2-(2,5-dioxo-2,5-dihydro-1H-pyrrol-1-yl)ethoxy]ethoxy}ethoxy)propanamide (1:1)

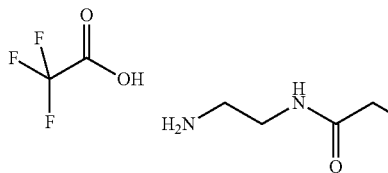

2.93 g (10.58 mmol) of tert-Butyl 3-{2-[2-(2-aminoethoxy)ethoxy]ethoxy}propanoate were dissolved in 100 ml of dioxane/water 1:1, and 3.28 g (21.15 mmol) of methyl 2,5-dioxo-2,5-dihydro-1H-pyrrole-1-carboxylate and a saturated sodium bicarbonate solution were added until a pH of 6-7 had been reached. The solution was stirred at RT for 30 min and the 1,4-dioxane was then evaporated under reduced pressure. 200 ml of water were then added, and the mixture was extracted three times with in each case 300 ml of ethyl acetate. The organic extracts were combined, dried over magnesium sulphate and filtered. Concentration gave tert-Butyl 3-(2-{2-[2-(2,5-dioxo-2,5-dihydro-1H-pyrrol-1-yl)ethoxy]ethoxy}ethoxy)propanoate as a brown oil which was then dried under high vacuum.

HPLC (Method 11): $R_t$=1.5 min;
LC-MS (Method 3): $R_t$=0.88 min; MS (ESIpos): m/z=375 (M+NH₄)⁺.

This intermediate was converted by standard methods (deprotection with TFA, coupling with tert-Butyl (2-aminoethyl)carbamate and another deprotection with TFA) into the title compound.

HPLC (Method 11): $R_t$=0.2 min;
LC-MS (Method 3): $R_t$=0.25 min; MS (ESIpos): m/z=344 (M+H)⁺.

Intermediate L16

N-[6-(2,5-Dioxo-2,5-dihydro-1H-pyrrol-1-yl)hexanoyl]-L-valyl-N⁵-carbamoyl-L-ornithine

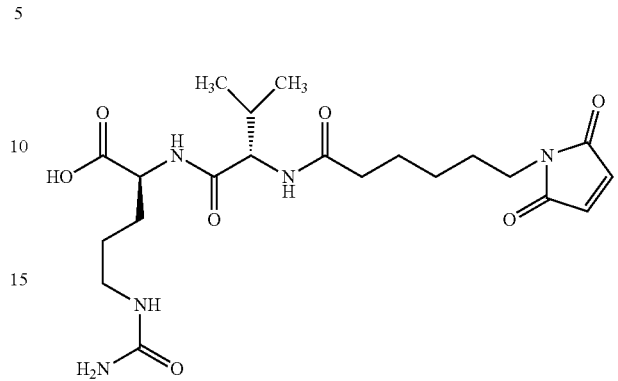

535 mg (1.73 mmol) of commercially available 1-{6-[(2,5-dioxopyrrolidin-1-yl)oxy]-6-oxohexyl}-1H-pyrrole-2,5-dione and 930 ml of N,N-diisopropylethylamine were added to a solution of 266 mg (1.33 mmol) of L-valyl-N5-carbamoyl-L-omithine in 24 ml of DMF. The reaction was treated in an ultrasonic bath for 24 h and then concentrated to dryness under reduced pressure. The residue that remained was purified by preparative HPCL and gave, after concentration of the appropriate fractions and drying of the residue under high vacuum, 337 mg (50% of theory) of the title compound.

HPLC (Method 11): $R_t$=0.4 min;
LC-MS (Method 3): $R_t$=0.58 min; MS (ESIpos): m/z=468 (M+H)⁺.

Intermediate L17

Trifluoroacetic acid/tert-Butyl N-[6-(2,5-dioxo-2,5-dihydro-1H-pyrrol-1-yl)hexanoyl]-L-valyl-N⁵-carbamoyl-L-ornithyl-L-lysinate (1:1)

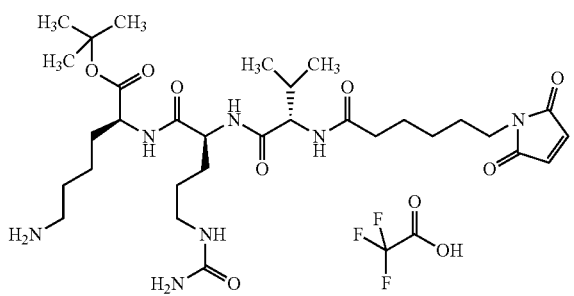 [SMILES: CC(C)[C@H](NC(=O)CCCCCN1C(=O)C=CC1=O)C(=O)N[C@@H](CCCNC(N)=O)C(=O)N[C@@H](CCCCN)C(=O)OC(C)(C)C ; O=C(O)C(F)(F)F]

The title compound was prepared by initially coupling 172 mg (0.37 mmol) of Intermediate L16 and 125 mg (0.37 mmol) of tert-Butyl N6-(tert-butoxycarbonyl)-L-lysinate hydrochloride (1:1) in the presence of EDC/HOBT and N A-diisopropylethylamine and then deprotecting the amino group under gentle conditions by stirring for 2 h in 10% strength trifluoroacetic acid in DCM at RT. Freeze-drying from acetonitrile/water gave 194 mg (49% of theory) of the title compound over 2 steps.

HPLC (Method 11): $R_t$=1.1 min;

LC-MS (Method 1): $R_t$=0.58 min; MS (ESIpos): m/z=652 (M+H)$^+$.

Intermediate L18

Trifluoroacetic acid/beta-alanyl-L-alanyl-N$^5$-carbamoyl-N-[4-(2-methoxy-2-oxoethyl)phenyl]-L-ornithinamide (1:1)

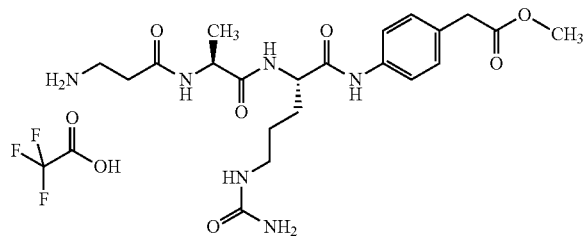

The title compound was prepared from methyl (4-aminophenyl)acetate analogously to Intermediate L7 sequentially according to classical methods of peptide chemistry by linking N$^2$-(tert-butoxycarbonyl)-N$^5$-carbamoyl-L-omithine in the presence of HATU, deprotection with TFA, coupling with 2,5-dioxopyrrolidin-1-yl N-(tert-butoxycarbonyl)-L-alaninate, deprotection with TFA, coupling with 2,5-dioxopyrrolidin-1-yl N-(tert-butoxycarbonyl)-beta-alaninate and another deprotection with TFA. 330 mg of the title compound were obtained.

HPLC (Method 11): $R_t$=0.29 min;

LC-MS (Method 1): $R_t$=0.41 min; MS (ESIpos): m/z=465 (M+H)$^+$.

Intermediate L19

Trifluoroacetic acid/L-alanyl-N5-carbamoyl-N-(4-{[(2,5-dioxo-2,5-dihydro-1H-pyrrol-1-yl)acetyl]amino}phenyl)-L-ornithinamide (1:1)

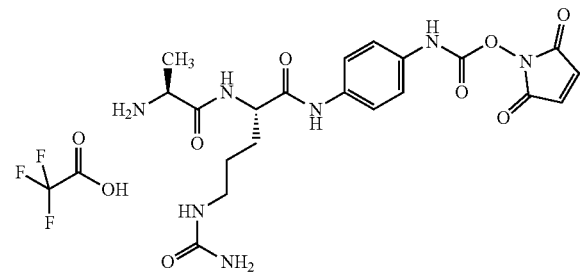 [SMILES: O=C(O)C(F)(F)F ; C[C@H](N)C(=O)N[C@@H](CCCNC(N)=O)C(=O)Nc1ccc(NC(=O)ON2C(=O)C=CC2=O)cc1]

The title compound was prepared from 1,4-phenylenediamine sequentially according to classical methods of peptide chemistry. In the first step, 942 mg (8.72 mmol) of 1,4-phenylenediamine were monoacylated with 0.8 g (2.9 mmol) of N$^2$-(tert-butoxycarbonyl)-N$^5$-carbamoyl-L-omithine in the presence of HATU and N,N-diisopropylethylamine. In the second step, in an analogous manner, the second anilinic amino group was acylated with (2,5-dioxo-2,5-dihydro-1H-pyrrol-1-yl)acetic acid in the presence of HATU and N,N-diisopropylethylamine. Deprotection with TFA, coupling with 2,5-dioxopyrrolidin-1-yl N-(tert-butoxycarbonyl)-L-alaninate and another deprotection with TFA then gave, in 3 further synthesis steps, the title compound, 148 mg of which were obtained by this route.

LC-MS (Method 1): $R_t$=0.21 min; MS (ESIpos): m/z=474 (M+H)$^+$.

LC-MS (Method 4): $R_t$=0.2 min; MS (ESIpos): m/z=474 (M+H)$^+$.

Intermediate L20

Trifluoroacetic acid/L-valyl-N$^5$-carbamoyl-N-[4-(2,5-dioxo-2,5-dihydro-1H-pyrrol-1-yl)phenyl]-L-ornithinamide (1:1)

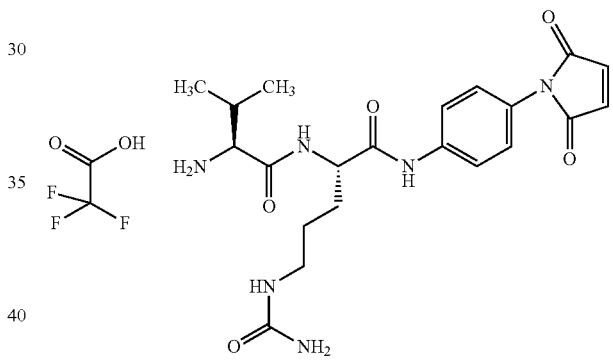

The title compound was prepared according to classical methods of peptide chemistry analogously to Intermediate L8 from commercially available 1-(4-aminophenyl)-1H-pyrrole-2,5-dione by sequential coupling with N$^2$-(tert-butoxycarbonyl)-N$^5$-carbamoyl-L-omithine in the presence of HATU, deprotection with TFA, coupling with 2,5-dioxopyrrolidin-1-yl N-(tert-butoxycarbonyl)-L-valinate and another deprotection with TFA. 171 mg of the title compound were obtained.

HPLC (Method 11): $R_t$=0.28 min;

LC-MS (Method 1): $R_t$=0.39 min; MS (ESIpos): m/z=445 (M+H)$^+$.

Intermediate L21

L-Valyl-$N^6$-(tert-butoxycarbonyl)-N-[4-(2-methoxy-2-oxoethyl)phenyl]-L-lysinamide

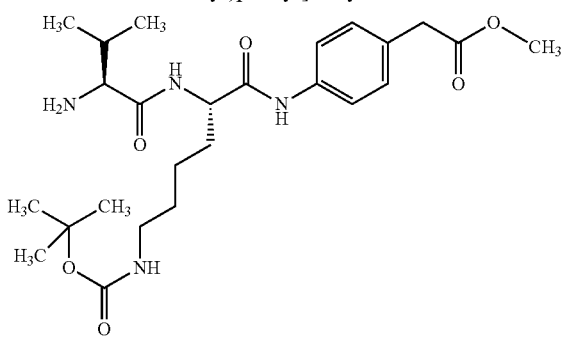

The title compound was prepared according to classical methods of peptide chemistry from commercially available 0.42 g (2.56 mmol) of methyl (4-aminophenyl)acetate by sequential coupling with N6-(tert-butoxycarbonyl)-N2-[(9H-fluoren-9-ylmethoxy)carbonyl]-L-lysine in the presence of HATU and N,N-diisopropylethylamine, deprotection with piperidine, coupling with 2,5-dioxopyrrolidin-1-yl N-[(benzyloxy)carbonyl]-L-valinate in the presence of N,N-diisopropylethylamine and subsequent hydrogenolytic removal of the benzyloxycarbonyl protective group over 10% palladium on activated carbon. This gave 360 mg (32% of theory over 4 steps) of the title compound.

HPLC (Method 11): $R_t$=1.5 min;
LC-MS (Method 1): $R_t$=0.73 min; MS (ESIpos): m/z=493 (M+H)$^+$.

Intermediate L22

Trifluoroacetic acid/N-[(9H-fluoren-9-ylmethoxy)carbonyl]-L-valyl-N-{4-[(2S)-2-amino-3-methoxy-3-oxopropyl]phenyl}-$N^5$-carbamoyl-L-ornithinamide (1:1)

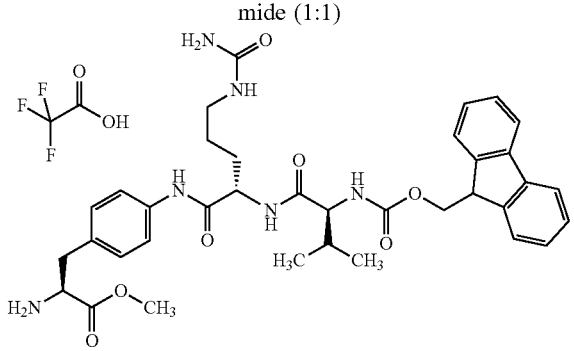

The title compound was prepared from N-(tert-butoxycarbonyl)-4-nitro-L-phenylalanine sequentially according to classical methods of peptide chemistry. 2.5 g (8.06 mmol) of this starting material were in the first step initially converted into the caesium salt and then with iodomethane in DMF into the methyl ester.

Hydrogenolytically in methanol over 10% palladium on activated carbon, the nitro group was then converted into an amino group.

The amino group generated in this manner was then acylated with N5-carbamoyl-N2-[(9H-fluoren-9-ylmethoxy)carbonyl]-L-ornithine in DMF in the presence of HATU and N,N-diisopropylethylamine. In the next step, the Fmoc group was removed with piperidine in DMF.

Coupling was then carried out in DMF with N-[(9H-fluoren-9-ylmethoxy)carbonyl]-L-valine in the presence of 1-(3-dimethylaminopropyl)-3-ethylcarbodiimide hydrochloride, 1-hydroxy-1H-benzotriazole hydrate and N,N-diisopropylethylamine and finally removal of the tert-butoxycarbonyl group with trifluoroacetic acid.

HPLC (Method 11): $R_t$=1.6 min;
LC-MS (Method 1): $R_t$=0.77 min; MS (ESIpos): m/z=673 (M+H)$^+$.

Intermediate L23

Trifluoroacetic acid/N-[2-(2,5-dioxo-2,5-dihydro-1H-pyrrol-1-yl)ethyl]-beta-alaninamide (1:1)

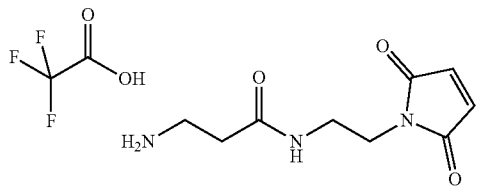 [SMILES: O=C(O)C(F)(F)F ; NCCC(=O)NCCN1C(=O)C=CC1=O]

The title compound was prepared from commercially available trifluoroacetic acid/1-(2-aminoethyl)-1H-pyrrole-2,5-dione (1:1) by coupling with N-(tert-butoxycarbonyl)-beta-alanine in the presence of EDCI/HOBT and N,N-diisopropylethylamine and subsequent deprotection with trifluoroacetic acid.

HPLC (Method 11): $R_t$=0.19 min.

Intermediate L24

Trifluoroacetic acid/1-amino-N-[2-(2,5-dioxo-2,5-dihydro-1H-pyrrol-1-yl)ethyl]cyclopropanecarboxamide (1:1)

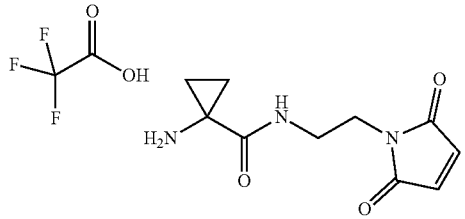

114 mg (0.67 mmol) of commercially available 1-[(tert-butoxycarbonyl)amino]cyclopropane-carboxylic acid were dissolved in 25 ml of DCM, 110 mg (0.623 mmol) of commercially available trifluoroacetic acid/1-(2-aminoethyl)-1H-pyrrole-2,5-dione (1:1) and 395 µl of N,N-diisopropylethylamine were added and the mixture was cooled to −10° C. 217 mg (0.793 mmol) of 2-bromo-1-ethylpyridinium tetrafluoroborate were then added, and the mixture was stirred at RT for 2 h. The mixture was then diluted with ethyl acetate and extracted successively with 10% strength citric acid, saturated sodium bicarbonate solution and saturated sodium chloride solution, then dried over magnesium sulphate and concentrated. Drying under high vacuum gave 152 mg of the protected intermediate.

These were then taken up in 10 ml of DCM and deprotected with 1 ml of trifluoroacetic acid. Lyophilization from acetonitrile/water gave 158 mg (71% of theory over 2 steps) of the title compound.

HPLC (Method 11): $R_t$=0.19 min.
LC-MS (Method 3): $R_t$=0.98 min; MS (ESIpos): m/z=224 (M+H)$^+$.

Intermediate L25

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-L-alanine

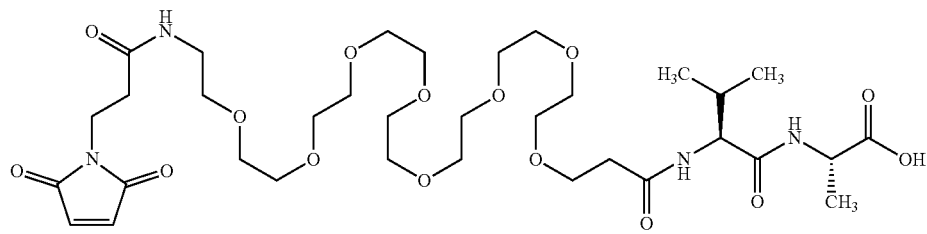 [SMILES: CC(C)[C@H](NC(=O)CCOCCOCCOCCOCCOCCOCCOCCOCCNC(=O)CCN1C(=O)C=CC1=O)C(=O)N[C@@H](C)C(=O)O]

31.4 mg (0.17 mmol) of valyl-L-alanine were dissolved in 3.0 ml of DMF, and 115.0 mg (0.17 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide and 33.7 mg (0.33 mmol) of triethylamine were added. The mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 74.1 mg (58% of theory) of the title compound.

LC-MS (Method 1): $R_t$=0.61 min; MS (ESIpos): m/z=763 [M+H]$^+$.

Intermediate L26

L-Valyl-N6-(tert-butoxycarbonyl)-L-lysine

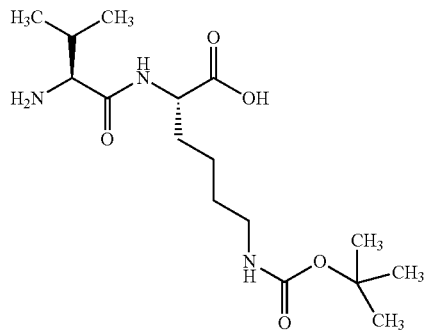 [SMILES: CC(C)[C@H](N)C(=O)N[C@@H](CCCCNC(=O)OC(C)(C)C)C(=O)O]

600.0 mg (1.58 mmol) of N2-[(benzyloxy)carbonyl]-N6-(tert-butoxycarbonyl)-L-lysine were suspended in 25.0 ml of water/ethanol/THF (1:1:0.5), palladium on carbon (10%) was added and the mixture was hydrogenated at RT with hydrogen under standard pressure for 5 h. The catalyst was filtered off and the solvents were evaporated under reduced pressure. The compound obtained was used in the next step without further purification.

LC-MS (Method 1): $R_t$=0.42 min; MS (ESIpos): m/z=247 [M+H]$^+$.

180 mg (0.73 mmol) of N6-(tert-butoxycarbonyl)-L-lysine were dissolved in 5.0 ml of DMF, and 74.0 mg (0.73 mmol) of triethylamine were added. 254.6 mg (0.73 mmol) of 2,5-dioxopyrrolidin-1-yl N-[(benzyloxy)carbonyl]-L-valinate and 74.0 mg (0.73 mmol) of triethylamine were then added. The reaction mixture was stirred at RT for 3.5 h. The reaction solution was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 294.1 mg (76% of theory) of N-[(benzyloxy)carbonyl]-L-valyl-N6-(tert-butoxycarbonyl)-L-lysine.

LC-MS (Method 1): $R_t$=0.97 min; MS (ESIpos): m/z=480 [M+H]$^+$.

272.2 mg (0.57 mmol) of N-[(benzyloxy)carbonyl]-L-valyl-N6-(tert-butoxycarbonyl)-L-lysine were initially charged in 20.0 ml of ethyl acetate/ethanol/THF (1:1:1), and 27.2 mg of palladium on activated carbon were added. The mixture was hydrogenated with hydrogen at RT under standard pressure for 5 h. The mixture was filtered off with the aid of Celite® and the filter cake was washed with ethyl acetate/ethanol/THF (1:1:1). The solvents were evaporated under reduced pressure and the residue was dried under high vacuum. The title compound (182 mg, 72% of theory) was used in the next reaction step without further purification.

LC-MS (Method 1): $R_t$=0.53 min; MS (ESIpos): m/z=346 [M+H]$^+$.

Intermediate L27

N-[31-(2,5-Dioxo-2,5-dihydro-1H-pyrrol-1-yl)-29-oxo-4,7,10,13,16,19,22,25-octaoxa-28-azahentria-contan-1-oyl]-L-valyl-N6-(tert-butoxycarbonyl)-L-lysine

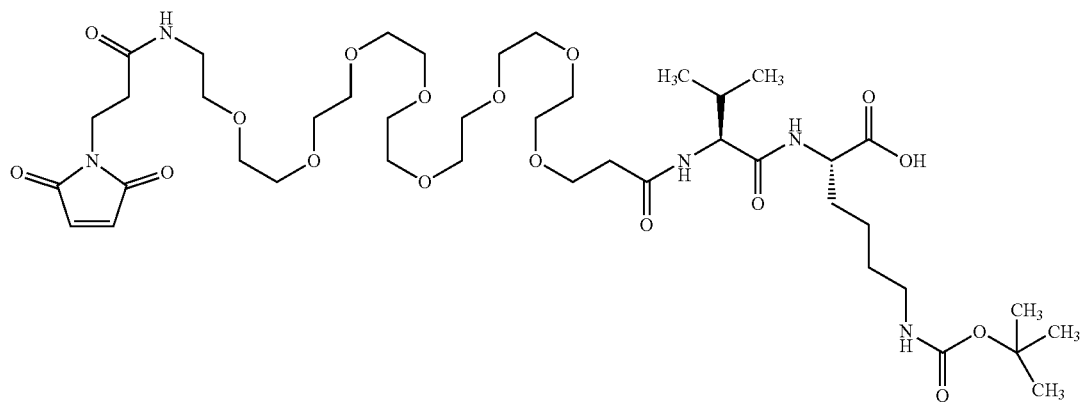 [SMILES: CC(C)[C@H](NC(=O)CCOCCOCCOCCOCCOCCOCCOCCOCCNC(=O)CCN1C(=O)C=CC1=O)C(=O)N[C@@H](CCCCNC(=O)OC(C)(C)C)C(=O)O]

30 mg (0.07 mmol) of L-valyl-N6-(tert-butoxycarbonyl)-L-lysine (Intermediate L26) and 46.1 mg (0.07 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide were initially charged in 1.5 ml of DMF, and 6.8 mg (0.07 mmol) of 4-methylmorpholine were added. The reaction solution was stirred at RT overnight. The reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 55.6 mg (90% of theory) of the title compound.

LC-MS (Method 1): $R_t$=0.77 min; MS (ESIpos): m/z=920 [M+H]$^+$.

Intermediate L28 tert-Butyl 3-formyl-4-({[2-(trimethylsilyl)ethoxy]carbonyl}amino)pyrrolidine-1-carboxylate

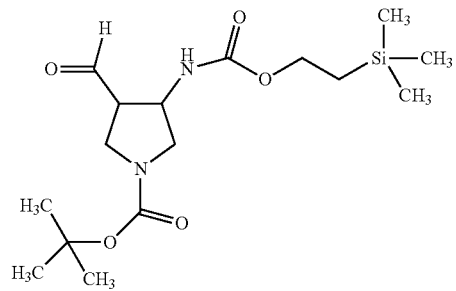 [SMILES: CC(C)(C)OC(=O)N1CC(C=O)C(NC(=O)OCC[Si](C)(C)C)C1]

461.7 mg (1.15 mmol) of 1-tert-Butyl 3-ethyl-4-({[2-(trimethylsilyl)ethoxy]carbonyl}amino)pyrrolidine-1,3-dicarboxylate (this compound was prepared according to the literature procedure of WO 2006/066896) were initially charged in 5.0 ml of absolute dichloromethane and the mixture was cooled to −78° C. 326.2 mg (2.29 mmol) of diisobutylaluminium hydride solution (1 M in THF) were then slowly added dropwise and the mixture was stirred at −78° C. for 2 h (monitored by thin-layer chromatography (petroleum ether/ethyl acetate=3:1). 1.3 g (4.59 mmol) of potassium sodium tartrate dissolved in 60 ml of water were added dropwise and the reaction mixture was allowed to warm to RT. Ethyl acetate was added to the reaction mixture and the aqueous phase was extracted three times with ethyl acetate. The combined organic phases were washed once with sat. NaCl solution and dried over magnesium sulphate. The solvent was evaporated under reduced pressure and the residue was dried under high vacuum. This gave 629.0 mg of the title compound as a crude product which was used immediately without further purification in the next reaction step.

Intermediate L29 tert-Butyl 3-formyl-4-[({[2-(trimethylsilyl)ethoxy]carbonyl}amino)methyl]pyrrolidine-1-carboxylate Mixture of Diastereomers.

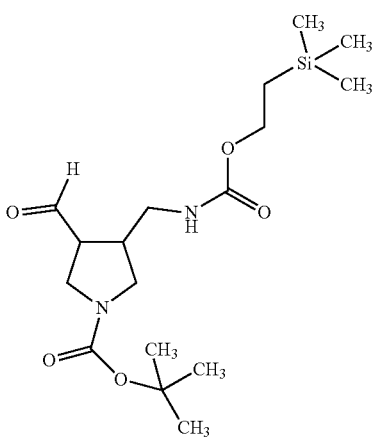 [SMILES: CC(C)(C)OC(=O)N1CC(C=O)C(CNC(=O)OCC[Si](C)(C)C)C1]

807.1 mg (2.34 mmol) of tert-Butyl 3-({[tert-Butyl(dimethyl)silyl]oxy}methyl)-4-(hydroxymethyl)pyrrolidine-1-carboxylate (prepared according to the literature procedure of WO 2006/100036) were initially charged in 8.0 ml of dichloromethane, and 236.4 mg (2.34 mmol) of triethylamine were added. At 0° C., 267.6 mg (2.34 mmol) of methanesulphonyl chloride were added dropwise, and the reaction mixture stirred at RT overnight. A further 133.8 mg (1.17 mmol) of methanesulphonyl chloride and 118.2 mg (1.17 mmol) of triethylamine were added. The reaction mixture was stirred at RT overnight. The mixture was diluted with dichloromethane and the organic phase was washed in each case once with saturated sodium bicarbonate solution, 5% strength potassium hydrogen sulphate solution and saturated NaCl solution. After drying over magnesium sulphate, the solvent was evaporated under reduced pressure and the residue was purified on Biotage Isolera (silica gel, column 50 g SNAP, flow rate 66 ml/min, cyclohexane/ethyl acetate). The solvents were evaporated under reduced pressure and the residue was dried under high vacuum. This gave 402.0 mg (41% of theory) of the compound tert-Butyl 3-({[tert-Butyl(dimethyl)silyl]oxy}methyl)-4-{[(methylsulphonyl)oxy]methyl}pyrrolidine-1-carboxylate.

LC-MS (Method 1): $R_t$=1.38 min; MS (ESIpos): m/z=424 [M+H]$^+$.

400.0 mg (0.94 mmol) of tert-Butyl 3-({[tert-Butyl(dimethyl)silyl]oxy}methyl)-4-{[(methylsulphonyl)oxy]methyl}pyrrolidine-1-carboxylate were initially charged in 5.0 ml of DMF, and 98.2 mg (1.51 mmol) of sodium azide were added. The reaction mixture was stirred at 40° C. for 10 h. Another 30.7 mg (0.47 mmol) of sodium azide were then added, and the mixture was stirred at 40° C. for a further 10 h. Ethyl acetate was added and the organic phase was washed repeatedly with water. After drying of the organic phase over magnesium sulphate, the solvent was evaporated under reduced pressure and the residue was dried under high vacuum. This gave 309.5 mg (89% of theory) of the compound tert-Butyl 3-(azidomethyl)-4-({[tert-Butyl(dimethyl)silyl]oxy}methyl)pyrrolidine-1-carboxylate. The compound was used without further purification in the next step of the synthesis.

LC-MS (Method 1): $R_t$=1.50 min; MS (ESIpos): m/z=371 [M+H]$^+$.

250 mg (0.68 mmol) of tert-Butyl 3-(azidomethyl)-4-({[tert-Butyl(dimethyl)silyl]oxy}methyl)pyrrolidine-1-carboxylate were dissolved in 10.0 ml of ethyl acetate/ethanol (1:1), and 25.0 mg of palladium on activated carbon (10%) were added. The mixture was hydrogenated with hydrogen at RT under standard pressure for 8 h. The reaction was filtered through Celite® and the filter cake was washed thoroughly with ethyl acetate. The solvent was evaporated under reduced pressure and the residue was dried under high vacuum. This gave 226.2 mg (82% of theory) of the compound tert-Butyl 3-(aminomethyl)-4-({[tert-Butyl(dimethyl)silyl]oxy}methyl)pyrrolidine-1-carboxylate. The compound was used without further purification in the next step of the synthesis.

LC-MS (Method 1): $R_t$=0.89 min; MS (ESIpos): m/z=345 [M+H]$^+$.

715.0 mg (2.08 mmol) of tert-Butyl 3-(aminomethyl)-4-({[tert-Butyl(dimethyl)silyl]oxy}methyl)pyrrolidine-1-carboxylate were dissolved in 15.0 ml of THF, and 2.28 ml (2.28 mmol) of TBAF solution (1M in THF) were added. The reaction mixture was stirred at RT overnight. The solvent was evaporated under reduced pressure and the residue (1.54 g) used without further purification in the next step of the synthesis.

LC-MS (Method 1): $R_t$=0.41 min; MS (ESIpos): m/z=231 [M+H]$^+$. 1.54 g (4.88 mmol) of tert-Butyl 3-(aminomethyl)-4-(hydroxymethyl)pyrrolidine-1-carboxylate were initially charged in 1,4-dioxane, and 541.8 mg (4.88 mmol) of calcium chloride (anhydrous) and 488.6 mg (4.88 mmol) of calcium carbonate were added and the mixture was stirred vigorously. 592.8 mg (5.86 mmol) of triethylamine and 1.52 g (5.86 mmol) of 1-({[2-(trimethylsilyl)ethoxy]carbonyl}oxy)pyrrolidine-2,5-dione were then added and the reaction mixture stirred at RT overnight. 644.9 mg (10.7 mmol) of HOAc and ethyl acetate were added. The organic phase was washed twice with water and once with saturated NaCl solution. After drying over magnesium sulphate, the solvent was evaporated under reduced pressure and the residue was purified on silica gel (mobile phase: dichloromethane/methanol=100:1). The solvents were evaporated under reduced pressure and the residue was dried under high vacuum. This gave 346.9 mg (19% of theory) of the compound tert-Butyl 3-(hydroxymethyl)-4-[({[2-(trimethylsilyl)ethoxy]carbonyl}amino)methyl]pyrrolidine-1-carboxylate.

LC-MS (Method 1): $R_t$=1.08 min; MS (ESIpos): m/z=375 [M+H]$^+$.

804.0 mg (2.15 mmol) of tert-Butyl 3-(hydroxymethyl)-4-[({[2-(trimethylsilyl)ethoxy]carbonyl}amino)methyl]pyrrolidine-1-carboxylate were initially charged in 20.0 ml of chloroform and 20.0 ml of 0.05 N potassium carbonate/0.05 N sodium bicarbonate solution (1:1). 59.7 mg (0.22 mmol) of tetra-n-butylammonium chloride, 429.9 mg (3.22 mmol) of N-chlorosuccinimide and 33.5 mg (0.22 mmol) of TEMPO were then added and the reaction mixture was stirred vigorously at RT overnight. The organic phase was separated off and freed from the solvent under reduced pressure. The residue was purified by silica gel chromatography (mobile phase: cyclohexane/ethyl acetate=3:1). This gave 517.0 mg (46% of theory) of the title compound.

LC-MS (Method 1): $R_t$=1.13 min; MS (ESIpos): m/z=373 [M+H]$^+$.

Intermediate L30 tert-Butyl 3-({[tert-Butyl(dimethyl)silyl]oxy}methyl)-4-formylpyrrolidine-1-carboxylate
Mixture of stereoisomers

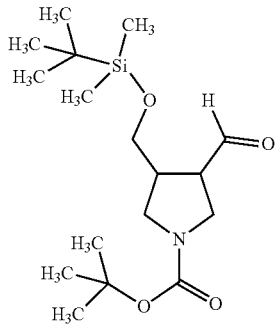 [SMILES: CC(C)(C)OC(=O)N1CC(C=O)C(CO[Si](C)(C)C(C)(C)C)C1]

250.0 mg (0.72 mmol) of tert-Butyl 3-({[tert-Butyl(dimethyl)silyl]oxy}methyl)-4-(hydroxymethyl)pyrrolidine-1-carboxylate (the compound was prepared according to the literature procedure of WO2006/100036) were initially charged in 12.5 ml of dichloromethane/DMSO (4:1), and 219.6 mg (2.17 mmol) of triethylamine were added. At 2° C., 345.5 mg (2.17 mmol) of sulphur trioxide-pyridine complex were added a little at a time and the mixture was stirred at 2° C. for 3 h. Another 345.5 mg (2.17 mmol) of sulphur trioxide-pyridine complex were added a little at a time and the mixture was stirred at RT for 17 h. The reaction mixture was partitioned between dichloromethane and water. The aqueous phase was extracted three times with dichloromethane and the combined organic phases were washed once with water and dried over magnesium sulphate. The solvent was evaporated under reduced pressure and the residue was dried under high vacuum. The residue was used without further purification in the next step of the synthesis (thin-layer chromatography: petroleum ether/ethyl acetate 7:3).

Intermediate L31

Di-tert-Butyl {[(tert-butoxycarbonyl)amino]methyl}malonate

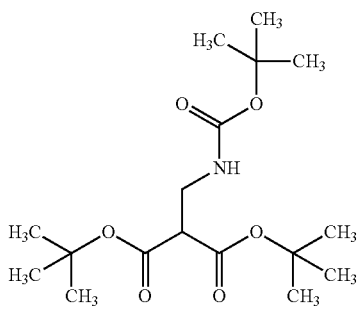 [SMILES: CC(C)(C)OC(=O)NCC(C(=O)OC(C)(C)C)C(=O)OC(C)(C)C]

57.2 g (488.27 mmol) of tert-Butyl carbamate, 51.2 ml (683.57 mmol) of a 37% strength solution of formaldehyde in water and 25.9 g (244.13 mmol) of sodium carbonate were added to 600 ml of water. The mixture was warmed until a solution was formed and then stirred at RT for 16 h. The suspension formed was extracted with 500 ml of dichloromethane and the organic phase was separated off, washed with saturated sodium chloride solution and dried over sodium sulphate. The mixture was concentrated on a rotary evaporator and the residue was dried under high vacuum, giving a crystalline solid. The residue was taken up in 1000 ml of absolute THF, and a mixture of 322 ml (3.414 mol) of acetic anhydride and 138 ml (1.707 mol) of pyridine was added dropwise at RT. The reaction mixture was stirred at RT for 16 h and then concentrated on a rotary evaporator, with the water bath at room temperature. The residue was taken up in diethyl ether and washed three times with a saturated sodium bicarbonate solution and once with a saturated sodium chloride solution. The organic phase was dried over sodium sulphate and concentrated on a rotary evaporator and the residue was dried under high vacuum for 2 d. The residue was taken up in 2000 ml of absolute THF, and 456 ml (456.52 mmol) of a 1 M solution of potassium tert-butoxide in THF were added with ice cooling. The mixture was stirred at 0° C. for 20 min, and 100.8 g (456.52 mmol) of di-tert-Butyl malonate dissolved in 200 ml of absolute THF were then added dropwise. The mixture was stirred at RT for 48 h, and water was then added. The reaction mixture was concentrated on a rotary evaporator and taken up in 500 ml of ethyl acetate. The mixture was washed with 500 ml of water and 100 ml of a saturated sodium chloride solution and the organic phase was dried over sodium sulphate. The organic phase was concentrated on a rotary evaporator and the residue was dried under high vacuum. The residue was purified by filtration on silica gel (mobile phase: cyclohexane/ethyl acetate, gradient=30:1→5:1). This gave 37.07 g (22% of theory) of the target compound.

LC-MS (Method 6): $R_t$=2.87 min; MS (ESIpos): m/z=346 [M+H]$^+$.

Intermediate L32 tert-Butyl [3-hydroxy-2-(hydroxymethyl)propyl]carbamate

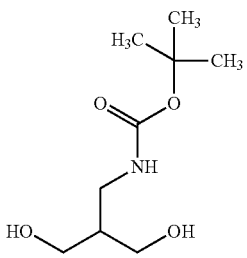

37.0 g (107.11 mmol) of di-tert-Butyl (acetoxymethyl)malonate were dissolved in 1000 ml of absolute THF, and 535.5 ml (1071.10 mmol) of a 2 M solution of lithium borohydride in THF were added dropwise with ice cooling. 19.3 ml (1071.10 mmol) of water were added dropwise and the mixture was stirred at RT for 4.5 h. The reaction mixture was concentrated on a rotary evaporator and dried under high vacuum. The residue was taken up in 1500 ml of ethyl acetate, 100 ml of water were added and the mixture was stirred with water cooling (slightly exothermic) for 30 min. The organic phase was separated off and the aqueous phase was extracted twice with 500 ml of ethyl acetate. The organic phase was concentrated on a rotary evaporator and the residue was dried under high vacuum. This gave 20.7 g (94% of theory) of the target compound.

LC-MS (Method 6): $R_t$=1.49 min; MS (EIpos): m/z=106 [M-C$_5$H$_8$O$_2$]$^+$.

Intermediate L33 tert-Butyl [3-{[tert-Butyl(dimethyl)silyl]oxy}-2-(hydroxymethyl)propyl]carbamate

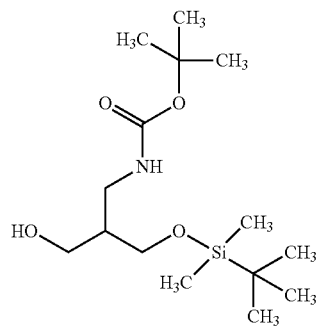 [SMILES: CC(C)(C)OC(=O)NCC(CO)CO[Si](C)(C)C(C)(C)C]

20.00 g (97.44 mmol) of tert-Butyl [3-hydroxy-2-(hydroxymethyl)propyl]carbamate were dissolved in 1000 ml of absolute dichloromethane, and 6.63 g (97.44 mmol) of imidazole and 16.16 g (107.18 mmol) of tert-Butyl(chloro)dimethylsilane were added at RT. The reaction mixture was stirred at RT for 16 h and washed with semiconcentrated sodium chloride solution. The aqueous phase was extracted with ethyl acetate and the combined organic phases were dried over sodium sulphate, concentrated on a rotary evaporator and dried under high vacuum. This gave 28.50 g (92% of theory) of the target compound.

$^1$H-NMR (400 MHz, DMSO-d$_6$): δ [ppm]=0.02 (s, 6H), 0.86 (s, 9H), 1.37 (s, 9H), 1.58-1.73 (m, 1H), 2.91 (q, 2H), 3.33-3.36 [m, (2H, hidden)], 3.53-3.58 (m, 2H), 6.65-6.72 (m, 1H).

Intermediate L34 tert-Butyl (3-{[tert-Butyl(dimethyl)silyl]oxy}-2-formylpropyl)carbamate

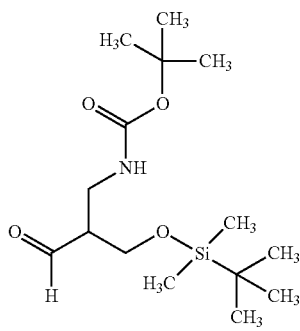 [SMILES: CC(C)(C)OC(=O)NCC(C=O)CO[Si](C)(C)C(C)(C)C]

12.65 g (39.591 mmol) of tert-Butyl [3-{[tert-Butyl(dimethyl)silyl]oxy}-2-(hydroxy-methyl)propyl]carbamate were dissolved in 200 ml of dichloromethane, and 19.31 g (45.53 mmol) of Dess-Martin periodinane dissolved in 150 ml of dichloromethane were added dropwise at RT. The mixture was stirred at room temperature for 2 h, 250 ml of a semiconcentrated sodium bicarbonate solution and 250 ml of a 10% strength sodium thiosulphate solution were then added and the mixture was stirred for 20 min. The organic phase was separated off and the aqueous phase was extracted with ethyl acetate. The combined organic phases were washed with 300 ml of water, dried over sodium sulphate, concentrated on a rotary evaporator and dried under high vacuum. This gave 11.35 g (90% of theory) of the target compound.

$^1$H-NMR (400 MHz, DMSO-d$_6$): δ [ppm]=0.02 (s, 6H), 0.84 (s, 9H), 1.36 (s, 9H), 1.48-1.51 (m, 1H), 3.08-3.32 [m, (1H, hidden)], 3.50-3.58 (m, 2H), 3.81-3.91 (m, 1H), 6.71 (t, 1H), 9.60 (d, 1H).

Intermediate L35 tert-Butyl (3-oxopropyl)carbamate

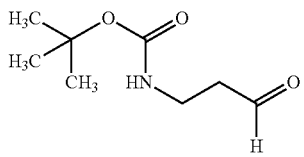

The title compound was prepared according to a method known from the literature (e.g. Jean Bastide et al. *J. Med. Chem.* 2003, 4(5)(16), 3536-3545).

Intermediate L36

N-[(Benzyloxy)carbonyl]-L-valyl-N5-carbamoyl-L-omithine

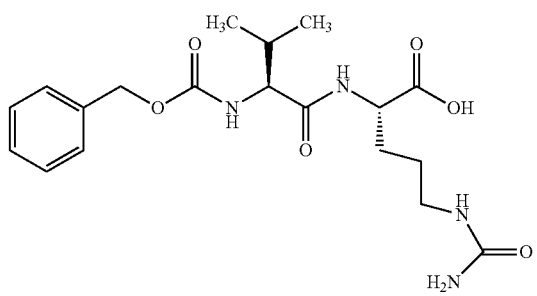 [SMILES: CC(C)[C@H](NC(=O)OCc1ccccc1)C(=O)N[C@@H](CCCNC(N)=O)C(=O)O]

100 mg (0.57 mmol) of N5-carbamoyl-L-omithine were taken up in 4.0 ml of DMF, and 0.08 ml (0.57 mmol) of triethylamine was added. 199.0 mg (0.57 mmol) of 2,5-dioxopyrrolidin-1-yl-N-[(benzyloxy)carbonyl]-L-valine and 0.08 ml (0.57 mmol) of triethylamine were then added. The mixture was stirred at RT for 48 h. The reaction mixture was purified directly by preparative RP-HPLC (column: Reprosil 250×30; 10μ, flow rate: 50 ml/min, MeCN/water with 0.1% TFA). The solvents were evaporated under reduced pressure and the residue was dried under high vacuum. This gave 75.7 mg (33% of theory) of the title compound.

LC-MS (Method 1): R$_t$=0.69 min; MS (ESIpos): m/z=409 [M+H]$^+$.

Intermediate L37

L-Valyl-N5-carbamoyl-L-omithine

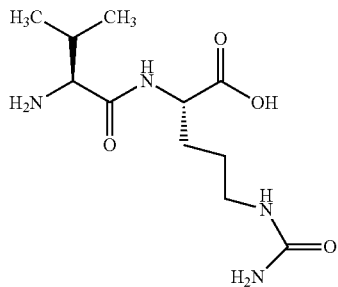 [SMILES: CC(C)[C@H](N)C(=O)N[C@@H](CCCNC(N)=O)C(=O)O]

75.7 mg (0.19 mmol) of Intermediate L36 were suspended in 25 ml of water/ethanol/THF, and 7.5 mg of palladium on activated carbon (10%) were added and the mixture was hydrogenated at RT with hydrogen under standard pressure for 4.5 h. The catalyst was filtered off and the reaction mixture was freed from the solvent under reduced pressure and dried under high vacuum. The residue was used for the next step without further purification. This gave 64.9 mg (93% of theory) of the title compound.

LC-MS (Method 6): R$_t$=0.25 min; MS (ESIpos): m/z=275 [M+H]$^+$.

Intermediate L38

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N5-carbamoyl-L-ornithine

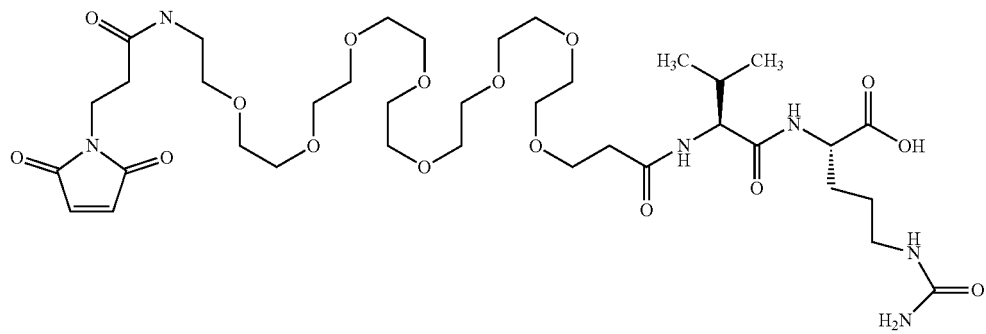 [SMILES: CC(C)[C@H](NC(=O)CCOCCOCCOCCOCCOCCOCCOCCOCCNC(=O)CCN1C(=O)C=CC1=O)C(=O)N[C@@H](CCCNC(N)=O)C(=O)O]

38.3 mg (0.14 mmol) of Intermediate L37 were initially charged in 3.0 ml of DMF, and 96.4 mg (0.14 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide and 39.0 μl (0.28 mmol) of triethylamine were added. The mixture was stirred at RT overnight. 16.0 μl (0.28 mmol) of HOAc were then added, and the reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 58.9 mg (45% of theory) of the title compound.

LC-MS (Method 1): $R_t$=0.61 min; MS (ESIpos): m/z=849 [M+H]$^+$.

300 mg (2.64 mmol) of 2-aminoethanethiol hydrochloride (1:1) were initially charged in 3.0 ml of dichloromethane, and 668.0 mg (6.60 mmol) of triethylamine and 719.1 mg (2.77 mmol) of 1-({[2-(trimethylsilyl)ethoxy]carbonyl}oxy)pyrrolidine-2,5-dione were added. The mixture was stirred at RT for 2 days (monitored by thin-layer chromatography: dichloromethane/methanol=100:1.5). Ethyl acetate was added and the reaction mixture was washed three times with water. The organic phase was washed twice with saturated NaCl solution and dried over magnesium sulphate. The solvent was evaporated under reduced pressure and the residue was dried under high vacuum. The compound was used without further purification in the next step of the synthesis.

Intermediate L39

2-(Trimethylsilyl)ethyl (2-sulphanylethyl)carbamate

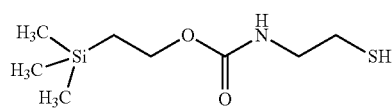

Intermediate L40

N-[31-(2,5-Dioxo-2,5-dihydro-1H-pyrrol-1-yl)-29-oxo-4,7,10,13,16,19,22,25-octaoxa-28-azahentriacontan-1-oyl]-L-valyl-N6-(tert-butoxycarbonyl)-L-lysine

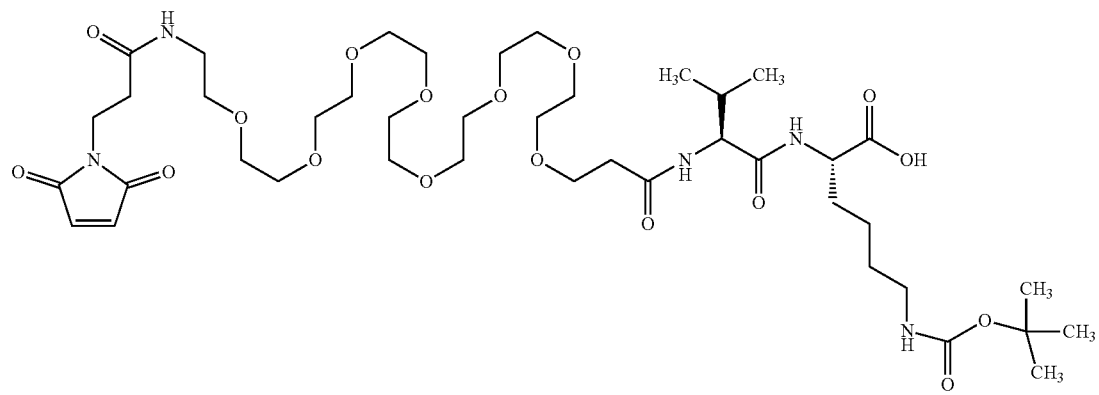 [SMILES: CC(C)[C@H](NC(=O)CCOCCOCCOCCOCCOCCOCCOCCOCCNC(=O)CCN1C(=O)C=CC1=O)C(=O)N[C@@H](CCCCNC(=O)OC(C)(C)C)C(=O)O]

600 mg (1.58 mmol) of N2-[(benzyloxy)carbonyl]-N6-(tert-butoxycarbonyl)-L-lysine were hydrogenated in 25.0 ml of water/ethanol/THF (1:1:0.5) using palladium on carbon (10%) at RT under standard pressure with hydrogen. The compound N6-(tert-butoxycarbonyl)-L-lysine is used without further purification in the next step of the synthesis.

LC-MS (Method 1): $R_f$=0.99 min; MS (ESIpos): m/z=247 [M+H]$^+$.

180.0 (0.73 mmol) of N6-(tert-butoxycarbonyl)-L-lysine were dissolved in 5.0 ml of DMF, and 74.0 mg (0.73 mmol) of triethylamine were added. 254.6 mg (0.73 mmol) of 2,5-dioxopyrrolidin-1-yl N-[(benzyloxy)carbonyl]-L-valinate and 74.0 mg (0.73 mmol) of triethylamine were added. The reaction mixture was stirred at RT for 3.5 h. The reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 294.1 mg (76% of theory) of the compound N-[(benzyloxy)carbonyl]-L-valyl-N6-(tert-butoxycarbonyl)-L-lysine.

LC-MS (Method 1): $R_f$=0.97 min; MS (ESIpos): m/z=480 [M+H]$^+$.

272.2 mg (0.57 mmol) of N-[(benzyloxy)carbonyl]-L-valyl-N6-(tert-butoxycarbonyl)-L-lysine were dissolved in 20 ml of ethyl acetate/ethanol/THF (1:1:1), 27.2 mg of palladium on activated carbon were added and the mixture was hydrogenated under standard pressure and at RT with hydrogen. The mixture was filtered through Celite® and the filter cake was washed thoroughly with ethyl acetate/ethanol/THF (1:1:1). The solvents were evaporated under reduced pressure and the residue was dried under high vacuum. This gave 182.0 mg (72% of theory) of the compound L-valyl-N6-(tert-butoxycarbonyl)-L-lysine.

LC-MS (Method 1): $R_f$=0.53 min; MS (ESIpos): m/z=346 [M+H]$^+$.

30.0 mg (0.07 mmol) of L-valyl-N6-(tert-butoxycarbonyl)-L-lysine and 46.1 mg (0.07 mmol) of 3-(2,5-dioxo-2,5-dihydro-1H-pyrrol-1-yl)-N-{27-[(2,5-dioxopyrrolidin-1-yl)oxy]-27-oxo-3,6,9,12,15,18,21,24-octaoxaheptacos-1-yl}propanamide were dissolved in 1.5 ml of DMF, and 6.8 mg (0.07 mmol) of 4-methylmorpholine were added. The reaction mixture was stirred at RT overnight. The reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 55.6 mg (90% of theory) of the title compound.

LC-MS (Method 1): $R_f$=0.77 min; MS (ESIpos): m/z=920 [M+H]$^+$.

Intermediate L41

N-[19-(2,5-Dioxo-2,5-dihydro-1H-pyrrol-1-yl)-17-oxo-4,7,10,13-tetraoxa-16-azanonadecan-1-oyl]-L-valyl-N6-(tert-butoxycarbonyl)-L-lysine

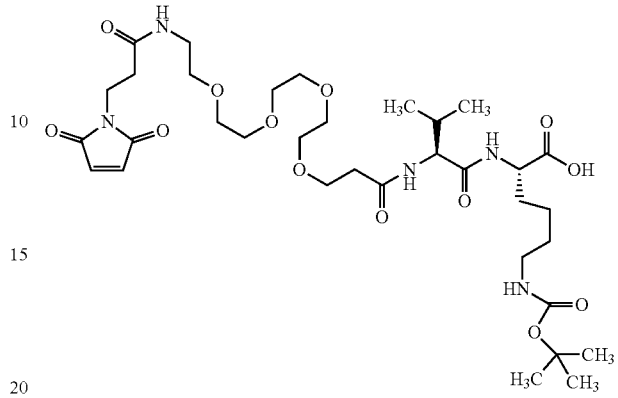

600 mg (1.58 mmol) of N2-[(benzyloxy)carbonyl]-N6-(tert-butoxycarbonyl)-L-lysine were hydrogenated in 25.0 ml of water/ethanol/THF (1:1:0.5) using palladium on carbon (10%) at RT under standard pressure with hydrogen. The compound N6-(tert-butoxycarbonyl)-L-lysine is used without further purification in the next step of the synthesis.

LC-MS (Method 1): $R_f$=0.99 min; MS (ESIpos): m/z=247 [M+F1]$^+$.

180.0 (0.73 mmol) of N6-(tert-butoxycarbonyl)-L-lysine were dissolved in 5.0 ml of DMF, and 74.0 mg (0.73 mmol) of triethylamine were added. 254.6 mg (0.73 mmol) of 2,5-dioxopyrrolidin-1-yl N-[(benzyloxy)carbonyl]-L-valinate and 74.0 mg (0.73 mmol) of triethylamine were added. The reaction mixture was stirred at RT for 3.5 h. The reaction mixture was purified directly by preparative RP-HPLC (column: Reprosil 250×30; 10µ, flow rate: 50 ml/min, MeCN/water, 0.1% TFA). The solvents were then evaporated under reduced pressure and the residue was dried under high vacuum. This gave 294.1 mg (76% of theory) of the compound N-[(benzyloxy)carbonyl]-L-valyl-N6-(tert-butoxycarbonyl)-L-lysine.

LC-MS (Method 1): $R_f$=0.97 min; MS (ESIpos): m/z=480 [M+H]$^+$.

272.2 mg (0.57 mmol) of N-[(benzyloxy)carbonyl]-L-valyl-N6-(tert-butoxycarbonyl)-L-lysine were dissolved in 20.0 ml of ethyl acetate/ethanol/THF (1:1:1), 27.2 mg of palladium on activated carbon were added and the mixture was hydrogenated under standard pressure and at RT with hydrogen. The mixture was filtered through Celite® and the filter cake was washed thoroughly with ethyl acetate/ethanol/THF (1:1:1). The solvents were evaporated under reduced pressure and the residue was dried under high vacuum. This gave 182.0 mg (72% of theory) of the compound L-valyl-N6-(tert-butoxycarbonyl)-L-lysine.

LC-MS (Method 1): $R_f$=0.53 min; MS (ESIpos): m/z=346 [M+H]$^+$.

30.0 mg (0.07 mmol) of L-valyl-N6-(tert-butoxycarbonyl)-L-lysine and 34.3 mg (0.07 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide were dissolved in 1.5 ml of DMF, and 6.8 mg (0.07 mmol) of 4-methylmorpholine were added. The reaction mixture was stirred at RT overnight. The reaction mixture was purified directly by preparative RP-HPLC (column: Reprosil 250×30; 10µ, flow rate: 50 ml/min, MeCN/water). The solvents were evaporated under reduced pressure and the residue was dried under high vacuum. This gave 40.6 mg (82% of theory) of the title compound.

LC-MS (Method 1): $R_f$=0.73 min; MS (ESIpos): m/z=744 [M+H]$^+$.

Intermediate L42

N-[19-(2,5-Dioxo-2,5-dihydro-1H-pyrrol-1-yl)-17-oxo-4,7,10,13-tetraoxa-16-azanonadecan-1-oyl]-L-valyl-N5-carbamoyl-L-ornithine

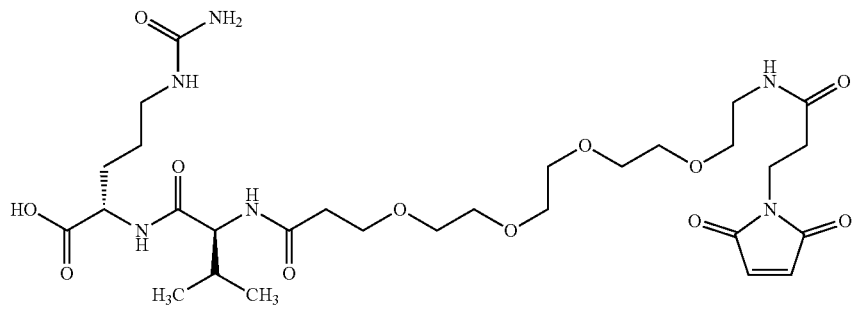 [SMILES: CC(C)[C@H](NC(=O)CCOCCOCCOCCOCCNC(=O)CCN1C(=O)C=CC1=O)C(=O)N[C@@H](CCCNC(N)=O)C(=O)O]

50.0 mg (0.18 mmol) of L-valyl-N5-carbamoyl-L-ornithine (Intermediate L37) were initially charged in DMF, and 93.6 mg (0.18 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide and 36.9 mg (0.37 mmol) of triethylamine were added. The reaction mixture was stirred at RT overnight. 21.9 mg (0.37 mmol) of HOAc were added and the reaction mixture was purified directly by preparative RP-HPLC (column: Reprosil 250× 30; 10μ, flow rate: 50 ml/min, MeCN/water). The solvents were evaporated under reduced pressure and the residue was dried under high vacuum. This gave 20.6 mg (14% of theory) of the title compound.

LC-MS (Method 1): $R_t$=0.55 min; MS (ESIpos): m/z=673 [M+H]$^+$.

Intermediate L43

N-[67-(2,5-Dioxo-2,5-dihydro-1H-pyrrol-1-yl)-65-oxo-4,7,10,13,16,19,22,25,28,31,34,37,40,43,46,49,52,55,58,61-icosaoxa-64-azaheptahexacontan-1-oyl]-L-valyl-N5-carbamoyl-L-ornithine

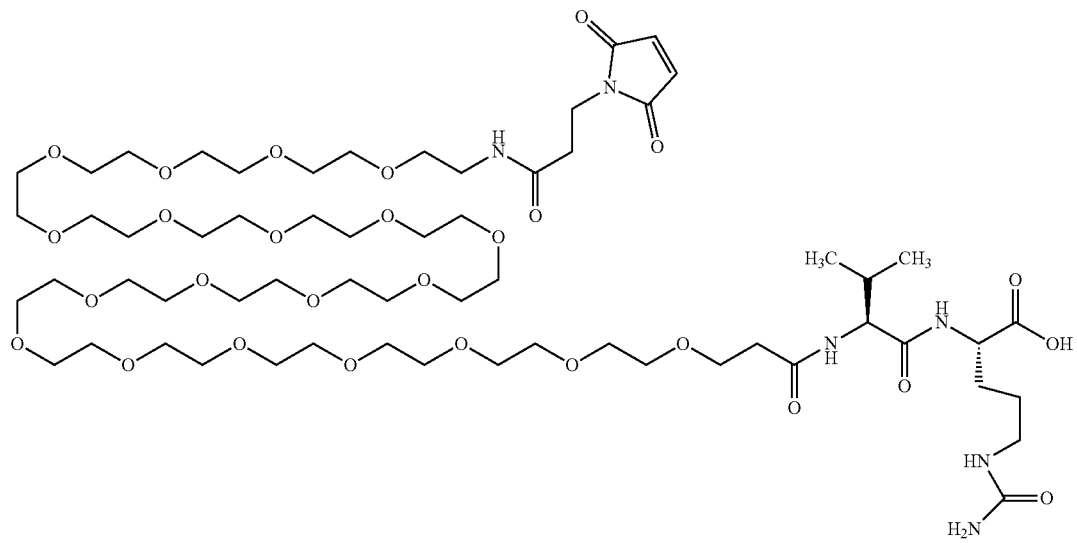 [SMILES: CC(C)[C@H](NC(=O)CCOCCOCCOCCOCCOCCOCCOCCOCCOCCOCCOCCOCCOCCOCCOCCOCCOCCOCCOCCOCCNC(=O)CCN1C(=O)C=CC1=O)C(=O)N[C@@H](CCCNC(N)=O)C(=O)O]

11.3 mg (0.04 mmol) of L-valyl-N5-carbamoyl-L-ornithine (Intermediate L37) were initially charged in DMF, and 50.0 mg (0.04 mmol) of 3-(2,5-dioxo-2,5-dihydro-1H-pyrrol-1-yl)-N-{63-[(2,5-dioxopyrrolidin-1-yl)oxy]-63-oxo-3,6,9,12,15,18,21,24,27,30,33,36,39,42,45,48,51,54,57,60-icosaoxatrihexacont-1-yl}propanamide and 8.3 mg (0.08 mmol) of triethylamine were added. The reaction mixture was stirred at RT overnight. 4.9 mg (0.08 mmol) of HOAc were added and the reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 15.8 mg (20% of theory) of the title compound.

LC-MS (Method 4): $R_t$=0.94 min; MS (ESIpos): m/z=1377 [M+H]$^+$.

Intermediate L44

N-[19-(2,5-Dioxo-2,5-dihydro-1H-pyrrol-1-yl)-17-oxo-4,7,10,13-tetraoxa-16-azanonadecan-1-oyl]-L-valyl-L-alanine

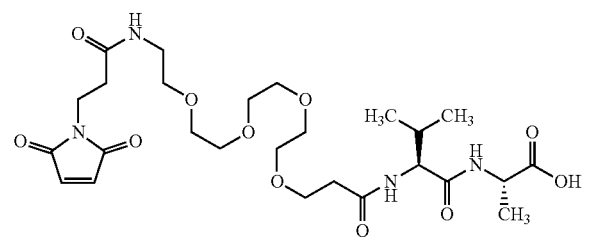 [SMILES: CC(C)[C@H](NC(=O)CCOCCOCCOCCOCCNC(=O)CCN1C(=O)C=CC1=O)C(=O)N[C@@H](C)C(=O)O]

73.3 mg (0.39 mmol) of L-valyl-L-alanine were dissolved in 7.0 ml of DMF, and 200.0 mg (0.39 mmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide and 78.8 mg (0.78 mmol) of triethylamine were added. The reaction mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 103.3 mg (45% of theory) of the title compound.

LC-MS (Method 1): $R_t$=0.58 min; MS (ESIpos): m/z=587 [M+H]$^+$.

Intermediate L45 tert-Butyl (2S)-2-[(tert-butoxycarbonyl)amino]-4-oxobutanoate

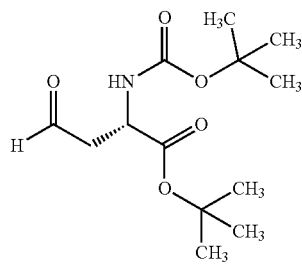 [SMILES: CC(C)(C)OC(=O)N[C@@H](CC=O)C(=O)OC(C)(C)C]

2.00 g (7.26 mmol) of tert-Butyl N-(tert-butoxycarbonyl)-L-homoserinate were dissolved in 90 ml of dichloromethane, and 1.76 ml of pyridine and 4.62 g (10.90 mmol) of 1,1,1-triacetoxy-1lambda$^5$,2-benziodoxol-3(1H)-on (Dess-Martin periodinane) were then added. The reaction was stirred at RT for 2 h and then diluted with 200 ml of dichloromethane and extracted twice with 10% strength sodium thiosulphate solution and then successively twice with 5% strength citric acid and twice with saturated sodium bicarbonate solution. The organic phase was separated off, dried over sodium sulphate and then concentrated under reduced pressure. 100 ml of diethyl ether and cyclohexane (v/v=1:1) were added to the residue and the mixture was somewhat concentrated, resulting in the formation of a white precipitate. This was filtered off with suction. The filtrate was concentrated on a rotary evaporator and dried under high vacuum, giving 1.74 g (88% of theory) of the target compound as a light-yellow oil.

LC-MS (Method 1): $R_t$=0.85 min; MS (ESIpos): m/z=274 [M+H]$^+$.

$^1$H-NMR (400 MHz, DMSO-d$_6$): δ [ppm]=1.38 (s, 18H), 2.64-2.81 (m, 2H), 4.31-4.36 (m, 1H), 7.23 (d, 1H), 9.59 (s, 1H).

Intermediate L46

Trifluoroacetic acid/tert-Butyl N-[2-(2,5-dioxo-2,5-dihydro-1H-pyrrol-1-yl)ethyl]-L-glutaminate (1:1)

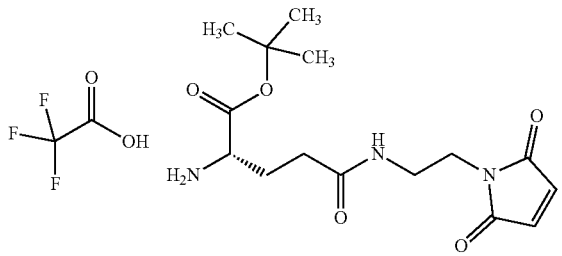 [SMILES: O=C(O)C(F)(F)F ; CC(C)(C)OC(=O)[C@@H](N)CCC(=O)NCCN1C(=O)C=CC1=O]

The title compound was prepared by first coupling 200 mg (0.79 mmol) of trifluoroacetic acid/1-(2-aminoethyl)-1H-pyrrole-2,5-dione (1:1) with 263 mg (0.87 mmol) of (4S)-5-tert-butoxy-4-[(tert-butoxycarbonyl)amino]-5-oxopentanoic acid/trifluoroacetic acid (1:1) in the presence of EDC/HOBT and N,N-diisopropylethylamine and then deprotecting the amino group under gentle conditions by stirring for 1 h in 10% strength trifluoroacetic acid in DCM at RT. Freeze-drying from acetonitrile/water gave 85 mg (20% of theory) of the title compound over 2 steps.

LC-MS (Method 1): $R_t$=0.37 min; MS (ESIpos): m/z=326 [M+H]$^+$.

Intermediate L47

Trifluoroacetic acid/beta-alanyl-L-alanyl-N5-carbamoyl-N-[4-(2,5-dioxo-2,5-dihydro-1H-pyrrol-1-yl)phenyl]-L-ornithinamide (1:1)

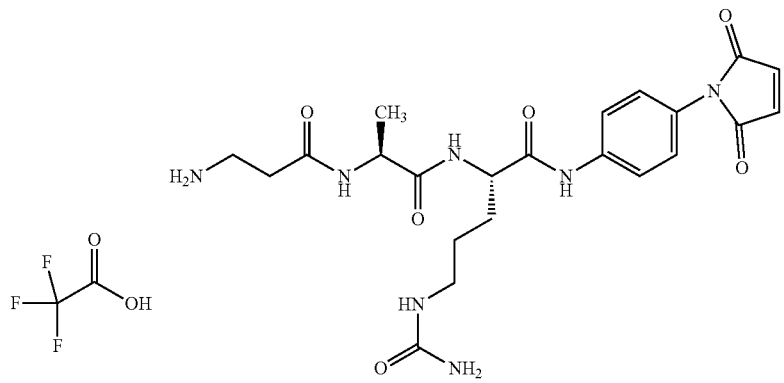 [SMILES: O=C(O)C(F)(F)F ; C[C@H](NC(=O)CCN)C(=O)N[C@@H](CCCNC(N)=O)C(=O)Nc1ccc(N2C(=O)C=CC2=O)cc1]

The title compound was prepared by coupling Intermediate L8 with 2,5-dioxopyrrolidin-1-yl N-(tert-butoxycarbonyl)-beta-alaninate and subsequent deprotection with TFA.

LC-MS (Method 3): $R_t$=1.36 min; MS (ESIpos): m/z=488 (M+H)$^+$.

Intermediate L48

Trifluoroacetic acid/(1R,2S)-2-amino-N-[2-(2,5-dioxo-2,5-dihydro-1H-pyrrol-1-yl)ethyl]cyclopentanecarboxamide (1:1)

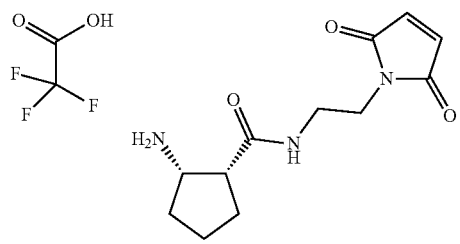 [SMILES: O=C(O)C(F)(F)F ; N[C@H]1CCC[C@H]1C(=O)NCCN1C(=O)C=CC1=O]

The title compound was prepared from commercially available (1R,2S)-2-[(tert-butoxycarbonyl)amino]cyclopentanecarboxylic acid analogously to Intermediate L2.

LC-MS (Method 3): $R_t$=1.22 min; MS (ESIpos): m/z=252 (M+H)$^+$.

Intermediate L49

Trifluoroacetic acid/tert-Butyl N-(bromoacetyl)-L-valyl-L-alanyl-L-lysinate (1:1)

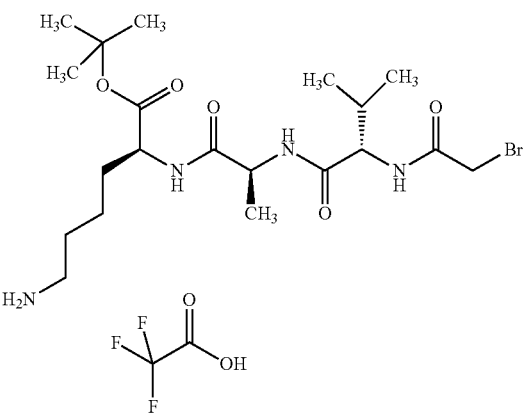 [SMILES: CC(C)[C@H](NC(=O)CBr)C(=O)N[C@@H](C)C(=O)N[C@@H](CCCCN)C(=O)OC(C)(C)C ; O=C(O)C(F)(F)F]

The title compound was prepared by first coupling commercially available bromoacetic anhydride with the partially protected peptide tert-Butyl L-valyl-L-alanyl-N$^6$-(tert-butoxycarbonyl)-L-lysinate, prepared according to classical methods of peptide chemistry, in the presence of N,N-diisopropylethylamine in dichloromethane. This was followed by deprotection at the amino group under gentle conditions by stirring in 10% strength trifluoroacetic acid in DCM at RT, giving the title compound in 49% yield over 2 steps.

LC-MS (Method 1): $R_t$=1.09 min; MS (ESIpos): m/z=593 and 595 (M+H)$^+$.

Intermediate L50

Trifluoroacetic acid/(1S,3R)-3-amino-N-[2-(2,5-dioxo-2,5-dihydro-1H-pyrrol-1-yl)ethyl]cyclopentanecarboxamide (1:1)

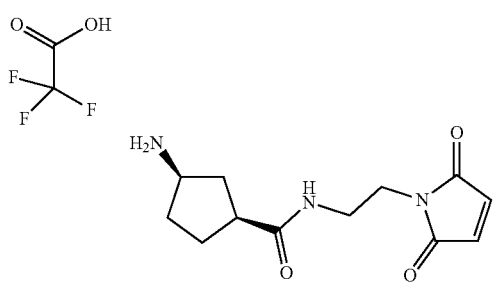 [SMILES: O=C(O)C(F)(F)F ; N[C@@H]1CC[C@H](C(=O)NCCN2C(=O)C=CC2=O)C1]

The title compound was prepared from commercially available (1S,3R)-3-[(tert-butoxycarbonyl)amino]cyclopentanecarboxylic acid and likewise commercially available trifluoroacetic acid/1-(2-aminoethyl)-1H-pyrrole-2,5-dione (1:1) by coupling with HATU in the presence of N,N-diisopropylethylamine and subsequent deprotection with TFA.

HPLC (Method 11): $R_t$=0.2 min;

LC-MS (Method 3): $R_t$=0.88 min; MS (ESIpos): m/z=252 (M+H)$^+$.

Intermediate L51

Trifluoroacetic acid/(1R,3R)-3-amino-N-[2-(2,5-dioxo-2,5-dihydro-1H-pyrrol-1-yl)ethyl]cyclopentanecarboxamide (1:1)

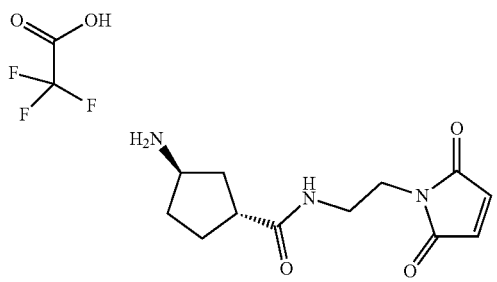 [SMILES: O=C(O)C(F)(F)F ; N[C@@H]1CC[C@@H](C(=O)NCCN2C(=O)C=CC2=O)C1]

The title compound was prepared from commercially available (1R,3R)-3-[(tert-butoxycarbonyl)amino]cyclopentanecarboxylic acid and likewise commercially available trifluoroacetic acid/1-(2-aminoethyl)-1H-pyrrole-2,5-dione (1:1) by coupling with HATU in the presence of N,N-diisopropylethylamine and subsequent deprotection with TFA.

LC-MS (Method 3): $R_t$=0.98 min; MS (ESIpos): m/z=250 (M–H)$^-$.

Intermediate L52

Trifluoroacetic acid/N-(2-aminoethyl)-2-bromoacetamide (1:1)

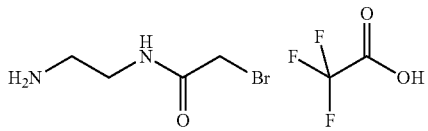

420 mg (2.62 mmol) of tert-Butyl (2-aminoethyl)carbamate were taken up in 50 ml of dichloromethane, and 817 mg (3.15 mmol) of bromoacetic anhydride and 913 μl (5.24 mmol) of N,N-diisopropylethylamine were added. The reaction was stirred at RT for 1 h and then concentrated under reduced pressure. The residue was purified by preparative HPLC. This gave 577 mg of the protected intermediate which were then taken up in 50 ml of dichloromethane, and 10 ml of trifluoroacetic acid were added. After 1 h of stirring at RT, the reaction was concentrated under reduced pressure and the residue was lyophilized from acetonitrile/water. This gave 705 mg (65% of theory) of the title compound.

LC-MS (Method 3): $R_t$=0.34 min; MS (ESIpos): m/z=181 and 183 (M+H)$^+$.

Intermediate L53

Trifluoroacetic acid/(1S,3S)-3-amino-N-[2-(2,5-dioxo-2,5-dihydro-1H-pyrrol-1-yl)ethyl]cyclopentanecarboxamide (1:1)

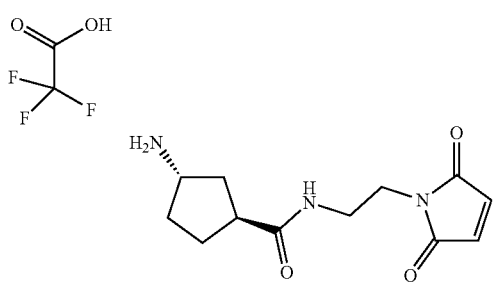 [SMILES: O=C(O)C(F)(F)F ; N[C@H]1CC[C@H](C(=O)NCCN2C(=O)C=CC2=O)C1]

The title compound was prepared from commercially available (1S,3S)-3-[(tert-butoxycarbonyl)amino]cyclopentanecarboxylic acid and likewise commercially available trifluoroacetic acid/1-(2-aminoethyl)-1H-pyrrole-2,5-dione (1:1) by coupling with HATU in the presence of N,N-diisopropylethylamine and subsequent deprotection with TFA.

HPLC (Method 11): $R_t$=0.19 min;

LC-MS (Method 3): $R_t$=0.88 min; MS (ESIpos): m/z=250 (M–H)$^-$.

Intermediate L54

Trifluoroacetic acid/(1R,3S)-3-amino-N-[2-(2,5-dioxo-2,5-dihydro-1H-pyrrol-1-yl)ethyl]cyclopentanecarboxamide (1:1)

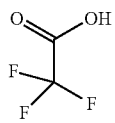
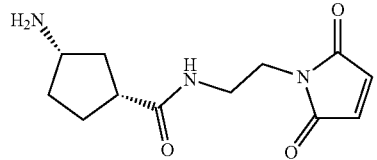

The title compound was prepared from commercially available (1R,3S)-3-[(tert-butoxycarbonyl)amino]cyclopentanecarboxylic acid and likewise commercially available trifluoroacetic acid/1-(2-aminoethyl)-1H-pyrrole-2,5-dione (1:1) by coupling with HATU in the presence of N,N-diisopropylethylamine and subsequent deprotection with TFA.

LC-MS (Method 3): $R_t$=0.89 min; MS (ESIpos): m/z=252 (M+H)$^+$.

Intermediate L55

Trifluoroacetic acid/tert-Butyl-N6-D-alanyl-N2-{N-[6-(2,5-dioxo-2,5-dihydro-1H-pyrrol-1-yl)-hexanoyl]-L-valyl-L-alanyl}-L-lysinate (1:1)

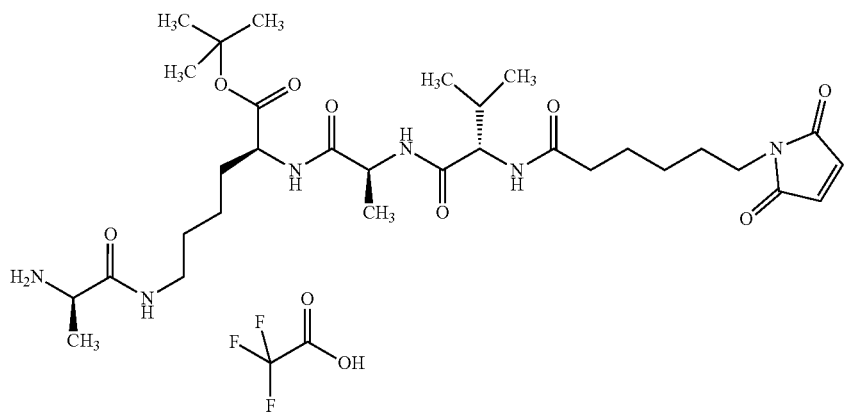 [SMILES: CC(C)[C@H](NC(=O)CCCCCN1C(=O)C=CC1=O)C(=O)N[C@@H](C)C(=O)N[C@@H](CCCCNC(=O)[C@@H](C)N)C(=O)OC(C)(C)C ; O=C(O)C(F)(F)F]

The title compound was prepared by first coupling Intermediate L6 with N-(tert-butoxycarbonyl)-D-alanine in the presence of HATU, followed by deprotection at the amino group under gentle conditions by stirring for 90 minutes in 5% strength trifluoroacetic acid in DCM at RT.

HPLC (Method 11): $R_t$=1.35 min;
LC-MS (Method 1): $R_t$=0.67 min; MS (ESIpos): m/z=637 (M+H)$^+$.

Intermediate L56

Trifluoroacetic acid/tert-Butyl-N-[6-(2,5-dioxo-2,5-dihydro-1H-pyrrol-1-yl)hexanoyl]-L-valyl-L-alanyl-N6-{[(1R,3S)-3-aminocyclopentyl]carbonyl}-L-lysinate (1:1)

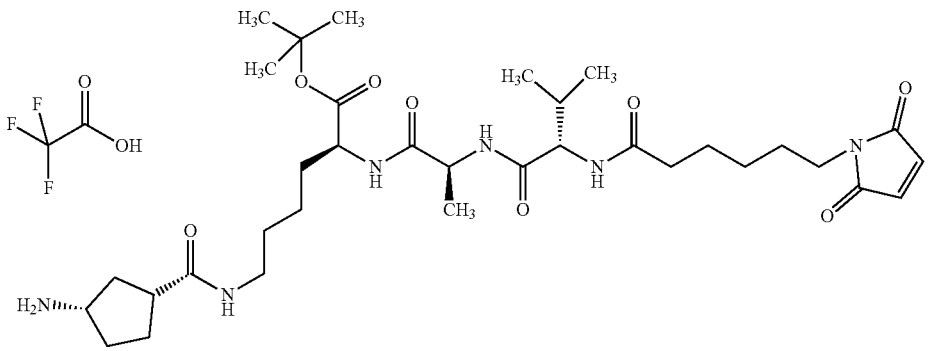

The title compound was prepared by first coupling Intermediate L6 with (1R,3S)-3-[(tert-butoxycarbonyl)amino]cyclopentanecarboxylic acid in the presence of HATU, followed by deprotection at the amino group under gentle conditions by stirring for 15 minutes in 25% strength trifluoroacetic acid in DCM at RT.

HPLC (Method 11): $R_t$=1.4 min;
LC-MS (Method 1): $R_t$=0.7 min; MS (ESIpos): m/z=677 (M+H)$^+$.

Intermediate L57

Methyl (2S)-4-oxo-2-({[2-(trimethylsilyl)ethoxy]carbonyl}amino)butanoate

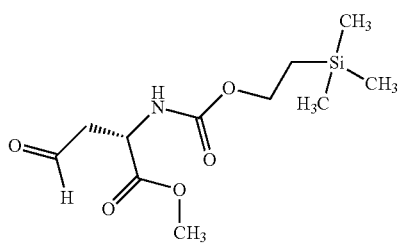 [SMILES: COC(=O)[C@H](CC=O)NC(=O)OCC[Si](C)(C)C]

500.0 mg (2.72 mmol) of methyl L-asparaginate hydrochloride and 706.3 mg (2.72 mmol) of 2-(trimethyl silyl)ethyl 2,5-dioxopyrrolidine-1-carboxylate were initially charged in 5.0 ml of 1,4-dioxane, and 826.8 mg (8.17 mmol) of triethylamine were added. The reaction mixture was stirred at RT overnight. The reaction mixture was purified directly by preparative RP-HPLC (column: Reprosil 250× 40; 10µ, flow rate: 50 ml/min, MeCN/water, 0.1% TFA). The solvents were then evaporated under reduced pressure and the residue was dried under high vacuum. This gave 583.9 mg (74% of theory) of the compound (3S)-4-methoxy-4-oxo-3-({[2-(trimethylsilyl)ethoxy]carbonyl}amino)butanoic acid.

LC-MS (Method 1): $R_t$=0.89 min; MS (ESIneg): m/z=290 (M−H)$^-$.

592.9 mg of (3S)-4-methoxy-4-oxo-3-({[2-(trimethylsilyl)ethoxy]carbonyl}amino)butanoic acid were initially charged in 10.0 ml of 1,2-dimethoxyethane, the mixture was cooled to −15° C., and 205.8 mg (2.04 mmol) of 4-methylmorpholine and 277.9 mg (2.04 mmol) of isobutyl chloroformate were added. The precipitate was filtered off with suction after 15 min and twice with in each case 10.0 ml of 1,2-dimethoxyethane. The filtrate was cooled to −10° C., and 115.5 mg (3.05 mmol) of sodium borohydride dissolved in 10 ml of water were added with vigorous stirring. The phases were separated and the organic phase was washed in each case once with saturated sodium bicarbonate solution and saturated NaCl solution. The organic phase was dried over magnesium sulphate, the solvent was evaporated under reduced pressure and the residue was dried under high vacuum. This gave 515.9 mg (91% of theory) of the compound methyl N-{[2-(trimethylsilyl)ethoxy]carbonyl}-L-homoserinate.

LC-MS (Method 1): $R_t$=0.87 min; MS (ESIpos): m/z=278 (M+H)$^+$.

554.9 mg (2.00 mmol) of methyl N-{[2-(trimethylsilyl)ethoxy]carbonyl}-L-homoserinate were initially charged in 30.0 ml of dichloromethane, and 1.27 g (3.0 mmol) of Dess-Martin periodinane and 474.7 mg (6.00 mmol) of pyridine were added. The mixture was stirred at RT overnight. After 4 h, the reaction was diluted with dichloromethane and the organic phase was washed in each case three times with 10% strength $Na_2S_2O_3$ solution, 10% strength citric acid solution and saturated sodium bicarbonate solution. The organic phase was dried over magnesium sulphate and the solvent was evaporated under reduced pressure. This gave 565.7 mg (97% of theory) of the title compound.

$^1$H-NMR (400 MHz, DMSO-d$_6$): δ [ppm]=0.03 (s, 9H), 0.91 (m, 2H), 2.70-2.79 (m, 1H), 2.88 (dd, 1H), 3.63 (s, 3H), 4.04 (m, 2H), 4.55 (m, 1H), 7.54 (d, 1H), 9.60 (t, 1H).

Intermediate L58

2-(Trimethylsilyl)ethyl (3-oxopropyl)carbamate

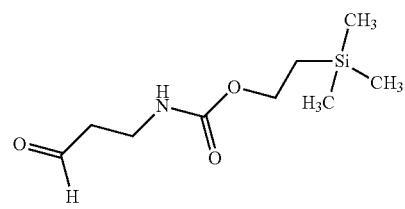

434.4 mg (5.78 mmol) of 3-amino-1-propanol and 1.50 g (5.78 mmol) of 2-(trimethylsilyl)ethyl 2,5-dioxopyrrolidine-1-carboxylate were dissolved in 10.0 ml of dichloromethane, 585.3 mg (5.78 mmol) of triethylamine were added and the mixture was stirred at RT overnight. The reaction mixture was diluted with dichloromethane and the organic phase was washed with water and saturated sodium bicarbonate solution and then dried over magnesium sulphate. The solvent was evaporated under reduced pressure. The residue 2-(trimethylsilyl)ethyl (3-hydroxypropyl)carbamate (996.4 mg, 79% of theory) was dried under high vacuum and used without further purification in the next step of the synthesis.

807.0 mg (3.68 mmol) of 2-(trimethylsilyl)ethyl (3-hydroxypropyl)carbamate were initially charged in 15.0 ml of chloroform and 15.0 ml of 0.05 N potassium carbonate/0.05 N sodium bicarbonate solution (1:1). 102.2 mg (0.37 mmol) of tetra-n-butylammonium chloride, 736.9 mg (5.52 mmol) of N-chlorosuccinimide and 57.5 mg (0.37 mmol) of TEMPO were then added and the reaction mixture was stirred vigorously at RT overnight. The reaction mixture was diluted with dichloromethane and the organic phase was washed with water and saturated NaCl solution. The organic phase was dried over magnesium sulphate and the solvent was evaporated under reduced pressure. The residue was dried under high vacuum and used without further purification in the next step of the synthesis (890.3 mg).

Intermediate L59

Trifluoroacetic acid/1-{2-[2-(2-aminoethoxy)ethoxy]ethyl}-1H-pyrrole-2,5-dione (1:1)

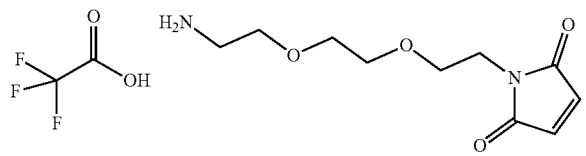 [SMILES: O=C(O)C(F)(F)F ; NCCOCCOCCN1C(=O)C=CC1=O]

300.0 mg (0.91 mmol) of tert-Butyl (2-{2-[2-(2,5-dioxo-2,5-dihydro-1H-pyrrol-1-yl)ethoxy]ethoxy}ethyl)carbamate were initially charged in dichloromethane, 4.2 g (36.54 mmol) of TFA were added and the mixture was stirred at RT for 1 h (monitored by TLC: dichloromethane/methanol 10:1). The volatile components were evaporated under reduced pressure and the residue was co-distilled four times with dichloromethane. The residue was dried under high vacuum and used without further purification in the next step of the synthesis.

LC-MS (Method 1): $R_t$=0.19 min; MS (ESIpos): m/z=229 (M+F1)$^+$.

Intermediate L60

6-(2,5-Dioxo-2,5-dihydro-1H-pyrrol-1-yl)hexanoyl chloride

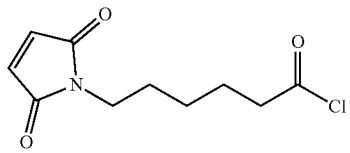 [SMILES: O=C(Cl)CCCCCN1C(=O)C=CC1=O]

200.0 mg (0.95 mmol) of 6-(2,5-dioxo-2,5-dihydro-1H-pyrrol-1-yl)hexanoic acid were dissolved in 4.0 ml of dichloromethane, and 338.0 mg (2.84 mmol) of thionyl chloride were added. The reaction mixture was stirred at RT for 3 h, and 1 drop of DMF was then added. The mixture was stirred for another 1 h. The solvent was evaporated under reduced pressure and the residue was co-distilled three times with dichloromethane. The crude product was used without further purification in the next step of the synthesis.

Intermediate L61

Trifluoroacetic acid/2-(trimethylsilyl)ethyl N-[6-(2,5-dioxo-2,5-dihydro-1H-pyrrol-1-yl)hexanoyl]-L-valyl-L-alanyl-L-lysinate (1:1)

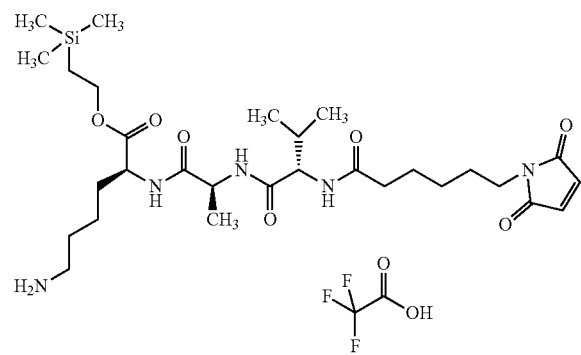 [SMILES: CC(C)[C@H](NC(=O)CCCCCN1C(=O)C=CC1=O)C(=O)N[C@@H](C)C(=O)N[C@@H](CCCCN)C(=O)OCC[Si](C)(C)C ; O=C(O)C(F)(F)F]

First, the tripeptide derivative 2-(trimethylsilyl)ethyl L-valyl-L-alanyl-N6-(tert-butoxycarbonyl)-L-lysinate was prepared from N2-[(benzyloxy)carbonyl]-N6-(tert-butoxycarbonyl)-L-lysine according to classical methods of peptide chemistry (esterification with 2-(trimethylsilylethanol using EDCI/DMAP, hydrogenolysis, coupling with N-[(benzyloxy)carbonyl]-L-valyl-L-alanine in the presence of HATU and another hydrogenolysis). The title compound was prepared by coupling this partially protected peptide derivative with commercially available 6-(2,5-dioxo-2,5-dihydro-1H-pyrrol-1-yl)hexanoic acid in the presence of HATU and N,N-diisopropylethylamine. This was followed by deprotection at the amino group under gentle conditions by stirring for 2.5 hours in 5% strength trifluoroacetic acid in DCM at RT with retention of the ester protective group. Work-up and purification by preparative HPLC gave 438 mg of the title compound.

HPLC (Method 11): $R_t$=1.69 min;

LC-MS (Method 1): $R_t$=0.78 min; MS (ESIpos): m/z=610 (M+H)$^+$.

Intermediate L62

Trifluoroacetic acid/2-(trimethylsilyl)ethyl N-[6-(2,5-dioxo-2,5-dihydro-1H-pyrrol-1-yl)hexanoyl]-L-valyl-N5-carbamoyl-L-ornithyl-L-lysinate (1:1)

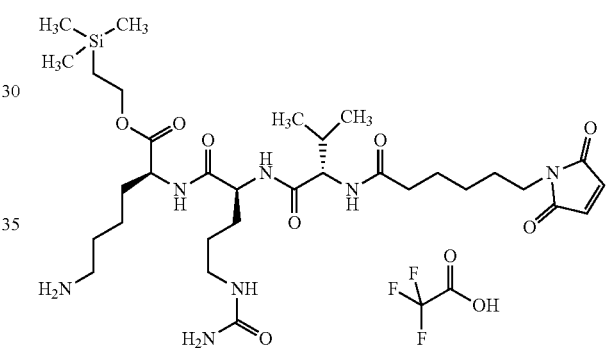

First, 2-(trimethylsilyl)ethyl N6-(tert-butoxycarbonyl)-L-lysinate was prepared from N2-[(benzyloxy)carbonyl]-N6-(tert-butoxycarbonyl)-L-lysine according to classical methods of peptide chemistry. 148 mg (0.43 mmol) of this intermediate were then coupled in the presence of 195 mg (0.51 mmol) of HATU and 149 µl of N,N-diisopropylethylamine with 200 mg (0.43 mmol) of Intermediate L16. After concentration and purification of the residue by preparative HPLC, the protected intermediate was taken up in 20 ml of DCM and the tert-butoxycarbonyl protective group was removed by addition of 2 ml of trifluoroacetic acid and 1 h of stirring at RT. Concentration and lyophilization of the residue from acetonitrile/water gave 254 mg (63% of theory over 2 steps).

HPLC (Method 11): $R_t$=1.51 min;

LC-MS (Method 1): $R_t$=0.68 min; MS (ESIpos): m/z=696 (M+H)$^+$.

Intermediate L63

(4S)-4-{[(2S)-2-{[(2S)-2-{[6-(2,5-Dioxo-2,5-dihydro-1H-pyrrol-1-yl)hexanoyl]amino}-3-methylbutanoyl]amino}propanoyl]amino}-5-oxo-5-[2-(trimethylsilyl)ethoxy]pentanoic acid

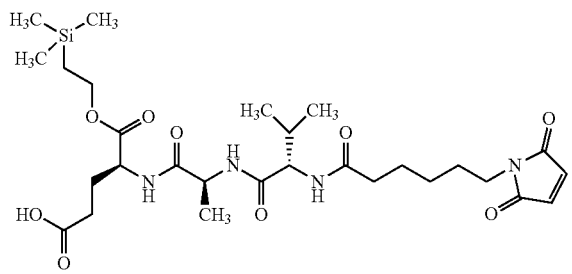 [SMILES: CC(C)[C@H](NC(=O)CCCCCN1C(=O)C=CC1=O)C(=O)N[C@@H](C)C(=O)N[C@@H](CCC(=O)O)C(=O)OCC[Si](C)(C)C]

First, the tripeptide derivative (4S)-4-{[(2S)-2-{[(2S)-2-amino-3-methylbutanoyl]amino}propanoyl]amino}-5-oxo-5-[2-(trimethylsilyl)ethoxy]pentanoic acid was prepared from (2S)-5-(benzyloxy)-2-[(tert-butoxycarbonyl)amino]-5-oxopentanoic acid according to classical methods of peptide chemistry (esterification with 2-(trimethylsilylethanol using EDCI/DMAP, removal of the Boc protective group with trifluoroacetic acid, coupling with N-[(benzyloxy)carbonyl]-L-valyl-L-alanine in the presence of HATU and hydrogenolysis in methanol over 10% palladium on activated carbon). The title compound was prepared by coupling of this partially protected peptide derivative with commercially available 1-{6-[(2,5-dioxopyrrolidin-1-yl)oxy]-6-oxohexyl}-1H-pyrrole-2,5-dione. Work-up and purification by preparative HPLC gave 601 mg of the title compound.

LC-MS (Method 1): $R_t$=0.96 min; MS (ESIpos): m/z=611 (M+H)$^+$.

Intermediate L64

(4S)-4-{[(2,5-Dioxo-2,5-dihydro-1H-pyrrol-1-yl)acetyl]amino}-5-oxo-5-[2-(trimethylsilyl)ethoxy]pentanoic acid

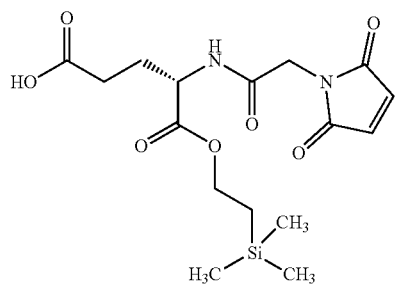 [SMILES: C[Si](C)(C)CCOC(=O)[C@H](CCC(=O)O)NC(=O)CN1C(=O)C=CC1=O]

The title compound was prepared from (2S)-5-(benzyloxy)-2-[(tert-butoxycarbonyl)amino]-5-oxopentanoic acid according to classical methods of peptide chemistry (esterification with 2-(trimethylsilylethanol using EDCI/DMAP, removal of the Boc protective group with trifluoroacetic acid, hydrogenolytic cleavage of the benzyl ester in methanol over 10% palladium on activated carbon and coupling with 1-{2-[(2,5-dioxopyrrolidin-1-yl)oxy]-2-oxoethyl}-1H-pyrrole-2,5-dione in the presence of N,N-diisopropylethylamine).

LC-MS (Method 1): $R_t$=0.84 min; MS (ESIpos): m/z=385 (M+H)$^+$.

Intermediate L65

Trifluoroacetic acid/2-(trimethylsilyl)ethyl 3-{[(benzyloxy)carbonyl]amino}-L-alaninate (1:1)

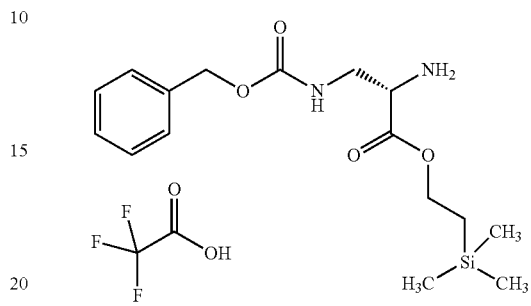

The title compound was prepared from 3-{[(benzyloxy)carbonyl]amino}-N-(tert-butoxycarbonyl)-L-alanine according to classical methods of peptide chemistry (esterification with 2-(trimethylsilylethanol using EDCI/DMAP and removal of the Boc protective group with trifluoroacetic acid. This gave 373 mg (79% of theory over 2 steps) of the title compound.

LC-MS (Method 1): $R_t$=0.72 min; MS (ESIpos): m/z=339 (M+H)$^+$.

Intermediate L66

Methyl (8S)-8-(2-hydroxyethyl)-2,2-dimethyl-6,11-dioxo-5-oxa-7,10-diaza-2-silatetradecan-14-oate

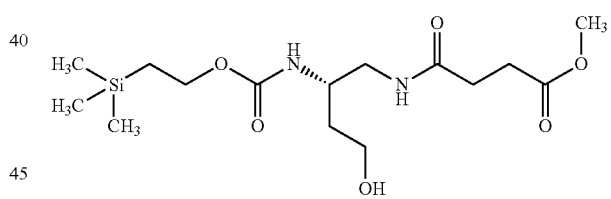

1000 mg (2.84 mmol) of (3S)-3-{[(benzyloxy)carbonyl]amino}-4-[(tert-butoxycarbonyl)amino]butanoic acid were initially charged in 10.0 ml of 1,2-dimethoxyethane, and 344.4 mg (3.4 mmol) of 4-methylmorpholine and 504 mg (3.69 mmol) of isobutyl chloroformate were added. After 10 min of stirring at RT, the reaction was cooled to 5° C., and 161 mg (4.26 mmol) of sodium borohydride dissolved in 3 ml of water were added a little at a time with vigorous stirring. After 1 h, the same amount of sodium borohydride was added again and the reaction was then slowly warmed to RT. 170 ml of water were added and the reaction was then extracted four times with in each case 200 ml of ethyl acetate. The phases were separated and the organic phase was washed once with citric acid and then with saturated sodium bicarbonate solution. The organic phase was dried over magnesium sulphate, the solvent was evaporated under reduced pressure and the residue was dried under high vacuum. This gave 760 mg (78% of theory) of the compound benzyl tert-Butyl [(2S)-4-hydroxybutane-1,2-diyl]biscarbamate.

LC-MS (Method 1): $R_t$=0.84 min; MS (ESIpos): m/z=339 (M+H)$^+$.

760 mg (2.16 mmol) of this intermediate dissolved in 13 ml of hydrogen chloride/dioxane were stirred at RT for 20 min. The reaction was then concentrated to 5 ml, and diethyl ether was added. The precipitate was filtered off and lyophilized from acetonitrile/water 1:1.

The product obtained in this manner was dissolved in 132 ml of DMF, and 345.5 mg (2.35 mmol) of 4-methoxy-4-oxobutanoic acid, 970 mg (2.55 mmol) of HATU and 1025 µl of N,N-diisopropylethylamine were added. The mixture was stirred at RT for 5 min. The solvent was removed under reduced pressure and the residue that remained was purified by preparative HPLC. The appropriate fractions were combined and the acetonitrile was evaporated under reduced pressure. The aqueous phase that remained was extracted twice with ethyl acetate and the organic phase was then concentrated and dried under high vacuum.

The intermediate obtained in this manner was taken up in methanol and hydrogenated over 10% palladium on activated carbon at RT under hydrogen standard pressure for 1 h. The catalyst was then filtered off and the solvent was removed under reduced pressure.

247 mg of this deprotected compound were taken up in 20 ml of DMF, and 352 mg (1.36 mmol) of 1-({[2-(trimethylsilyl)ethoxy]carbonyl}oxy)pyrrolidine-2,5-dione and 592 µl of N,N-diisopropylethylamine were added. The reaction mixture was stirred at RT for 1 h and then concentrated, and the residue was purified by preparative HPLC. The solvents were then evaporated under reduced pressure and the residue was dried under high vacuum. This gave, over these 5 reaction steps, 218 mg of the title compound in a total yield of 21%.

LC-MS (Method 1): $R_t$=0.74 min; MS (ESIpos): m/z=363 (M+H)$^+$.

Intermediate L67

Trifluoroacetic acid/2-(2,5-dioxo-2,5-dihydro-1H-pyrrol-1-yl)ethyl-beta-alaninate (1:1)

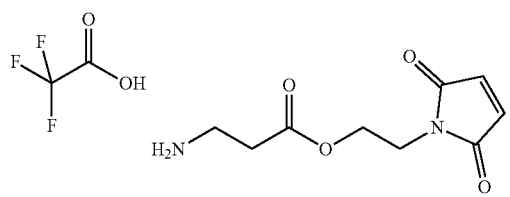 [SMILES: O=C(O)C(F)(F)F ; NCCC(=O)OCCN1C(=O)C=CC1=O]

The title compound was prepared from 50 mg (0.354 mmol) of commercially available 1-(2-hydroxyethyl)-1H-pyrrole-2,5-dione by coupling with 134 mg (0.71 mmol) of N-(tert-butoxycarbonyl)-beta-alanine in 10 ml of dichloromethane in the presence of 1.5 equivalents of EDCI and 0.1 equivalent of 4-N,N-dimethylaminopyridine and subsequent deprotection with trifluoroacetic acid.

Yield: 56 mg (48% of theory over 2 steps)

LC-MS (Method 3): $R_t$=1.15 min; MS (ESIpos): m/z=213 (M+H)$^+$.

Intermediate L68

Trifluoroacetic acid/N-(2-aminoethyl)-2-(2,5-dioxo-2,5-dihydro-1H-pyrrol-1-yl)propanamide (1:1)

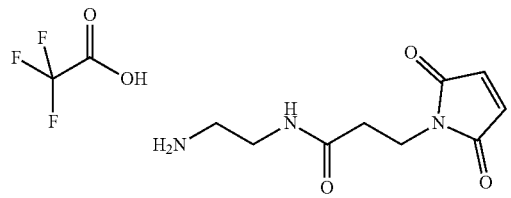 [SMILES: O=C(O)C(F)(F)F ; NCCNC(=O)CCN1C(=O)C=CC1=O]

The title compound was prepared analogously to Intermediate L1 according to classical methods of peptide chemistry from commercially available (2,5-dioxo-2,5-dihydro-1H-pyrrol-1-yl)propanoic acid and tert-Butyl (2-aminoethyl)carbamate.

LC-MS (Method 1): $R_t$=0.17 min; MS (ESIpos): m/z=212 (M+H)$^+$.

Intermediate L69

Trifluoroacetic acid/1-[(benzyloxy)carbonyl]piperidin-4-yl-L-valyl-N5-carbamoyl-L-ornithine (1:1)

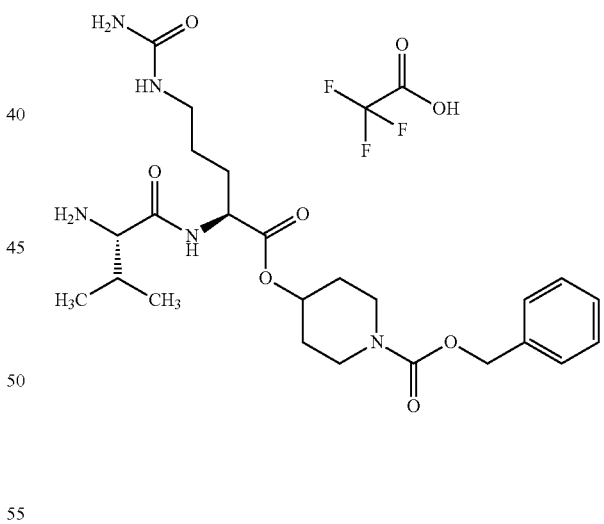

The title compound was prepared by classical methods of peptide chemistry from commercially available benzyl 4-hydroxypiperidine-1-carboxylate by esterification with N2-(tert-butoxycarbonyl)-N5-carbamoyl-L-ornithine using EDCI/DMAP, subsequent Boc removal with TFA, followed by coupling with N-[(tert-butoxy)carbonyl]-L-valine in the presence of HATU and (N,N-diisopropylethylamine and finally another Boc removal with TFA.

LC-MS (Method 1): $R_t$=0.62 min; MS (ESIpos): m/z=492 (M+H)$^+$.

Intermediate L70

9H-Fluoren-9-ylmethyl (3-oxopropyl)carbamate

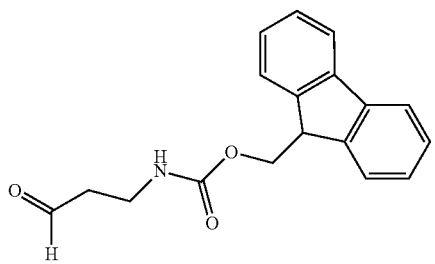 [SMILES: O=CCCNC(=O)OCC1c2ccccc2-c2ccccc21]

1000.0 mg (3.36 mmol) of 9H-fluoren-9-ylmethyl (3-hydroxypropyl)carbamate were initially charged in 15.0 ml of chloroform and 15.0 ml of 0.05 N potassium carbonate/0.05 N sodium bicarbonate solution (1:1). 93.5 mg (0.34 mmol) of tetra-n-butylammonium chloride, 673.6 mg (5.04 mmol) of N-chlorosuccinimide and 52.5 mg (0.34 mmol) of TEMPO were then added and the reaction mixture was stirred vigorously at RT overnight. The reaction mixture was diluted with dichloromethane and the organic phase was washed with water and saturated NaCl solution. The organic phase was dried over magnesium sulphate and the solvent was evaporated under reduced pressure. The residue was dried under high vacuum and purified by silica gel chromatography (mobile phase: cyclohexane/ethyl acetate 3:1-1:1). The solvents were evaporated under reduced pressure and the residue was dried under high vacuum. This gave 589.4 mg (58% of theory) of the title compound.

LC-MS (Method 6): $R_t$=2.15 min; MS (ESIpos): m/z=296 (M–H)$^+$.

Intermediate L71 tert-Butyl [4-(chlorocarbonyl)phenyl]carbamate

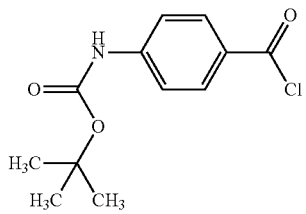 [SMILES: CC(C)(C)OC(=O)Nc1ccc(C(=O)Cl)cc1]

100.0 mg (0.42 mmol) of 4-[(tert-butoxycarbonyl)amino] benzoic acid were initially charged in 2.0 ml of dichloromethane, and 64.2 mg (0.51 mmol) of oxalyl dichloride were added. The reaction mixture was stirred at RT for 30 min (monitored by TLC: dichloromethane/methanol). Another 192.6 mg (1.53 mmol) of oxalyl dichloride and 1 drop of DMF were then added and the mixture was stirred at RT for 1 h. The solvent was evaporated under reduced pressure and the residue was co-distilled repeatedly with dichloromethane. The residue was used without further purification in the next step of the synthesis.

Intermediate L72

Benzyl (9S)-9-(hydroxymethyl)-2,2-dimethyl-6,11-dioxo-5-oxa-7,10-diaza-2-silatetradecan-14-oate

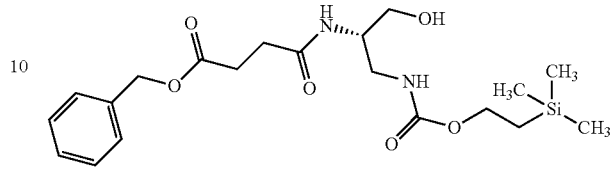

The title compound was prepared from commercially available benzyl tert-Butyl [(2S)-3-hydroxypropan-1,2-diyl] biscarbamate according to classical methods of peptide chemistry by hydrogenolytic removal of the Z protective group, subsequent coupling with 4-(benzyloxy)-4-oxobutanoic acid in the presence of EDCI/HOBT, followed by removal of the Boc protective group with TFA and finally by reaction with 1-({[2-(trimethylsilyl)ethoxy]carbonyl}oxy) pyrrolidine-2,5-dione in the presence of triethylamine.

LC-MS (Method 1): $R_t$=0.94 min; MS (ESIpos): m/z=425 [M+H]$^+$.

Intermediate L73

N-(2-Aminoethyl)-6-(2,5-dioxo-2,5-dihydro-1H-pyrrol-1-yl)hexanamide

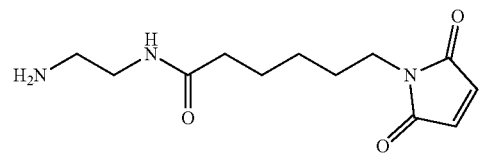 [SMILES: NCCNC(=O)CCCCCN1C(=O)C=CC1=O]

395.5 mg (1.87 mmol) of 6-(2,5-dioxo-2,5-dihydro-1H-pyrrol-1-yl)hexanoic acid, 1.21 g (9.36 mmol) of N,N-diisopropylethylamine and 854.3 mg (2.25 mmol) of HATU were added to a solution of 300 mg (1.87 mmol) of tert-Butyl (2-aminoethyl)carbamate in 20 ml of dimethylformamide. The reaction mixture was stirred at RT for 5 minutes. After concentration of the mixture, the residue was taken up in DCM and washed with water. The organic phase was washed with brine, dried over magnesium sulphate, filtered off and concentrated. This gave 408 mg (33%, purity 53%) of the title compound which were used without further purification.

LC-MS (Method 1): $R_t$=0.75 min; MS (ESIpos): m/z=354 (M+H)$^+$.

1 ml of TFA was added to a solution of tert-Butyl (2-{[6-(2,5-dioxo-2,5-dihydro-1H-pyrrol-1-yl)hexanoyl] amino}ethyl)carbamate (408 mg, 0.365 mmol) in 7 ml of dichloromethane. The reaction mixture was stirred at RT for 0.5 h. The reaction mixture was concentrated under reduced pressure and the residue was co-distilled twice with dichloromethane. The residue was used further without further purification. This gave 384 mg (94%, purity 57%) of the title compound.

LC-MS (Method 1): $R_t$=0.26 min; MS (ESIpos): m/z=254 (M+H)$^+$.

Intermediate L74

3-[2-[2-[2-[2-[[2-(2,5-Dioxopyrrol-1-yl)acetyl]amino]ethoxy]ethoxy]ethoxy]ethoxy]propanoic acid

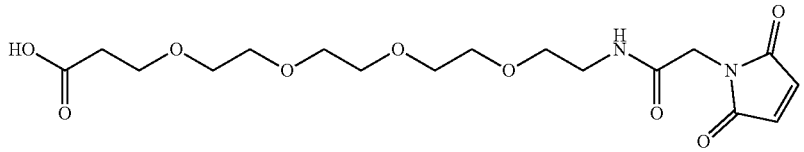 [SMILES: O=C(O)CCOCCOCCOCCOCCNC(=O)CN1C(=O)C=CC1=O]

107 mg (0.335 mmol) of tert-Butyl 3-[2-[2-[2-(2-aminoethoxy)ethoxy]ethoxy]ethoxy]propanoate and 93 mg (0.369 mmol) of (2,5-dioxopyrrolidin-1-yl) 2-(2,5-dioxopyrrol-1-yl)acetate were dissolved in 5 ml of dimethylformamide, and 0.074 ml (0.671 mmol) of N-methylmorpholine were added. The reaction mixture was stirred at RT overnight. 0.048 ml (0.838 mmol) of acetic acid were added and the reaction mixture was purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 133 mg (86%, purity 100%) of tert-Butyl 3-[2-[2-[2-[2-[[2-(2,5-dioxopyrrol-1-yl)acetyl]amino]ethoxy]ethoxy]ethoxy]ethoxy]propanoate.

LC-MS (Method 1): $R_t$=0.82 min; MS (ESIpos): m/z=459 $(M+H)^+$.

0.5 ml of TFA was added to a solution of tert-Butyl 3-[2-[2-[2-[2-[[2-(2,5-dioxopyrrol-1-yl)acetyl]amino]ethoxy]ethoxy]ethoxy]ethoxy]propanoate (130 mg, 0.284 mmol) in 5 ml of dichloromethane. The reaction mixture was stirred at RT overnight. The reaction mixture was concentrated under reduced pressure and the residue was taken up in water and lyophilized. The residue was used further without further purification. This gave 102 mg (90%, purity 100%) of the title compound.

LC-MS (Method 1): $R_t$=0.52 min; MS (ESIpos): m/z=402 $(M+H)^+$.

Intermediate L75

Trifluoroacetic acid/2-(trimethylsilyl)ethyl 3-{[(benzyloxy)carbonyl]amino}-D-alaninate (1:1)

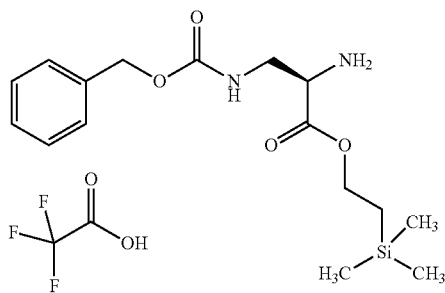

The title compound was prepared from 3-{[(benzyloxy)carbonyl]amino}-N-(tert-butoxycarbonyl)-D-alanine according to classical methods of peptide chemistry (esterification with 2-(trimethylsilylethanol using EDCI/DMAP and removal of the Boc protective group with trifluoroacetic acid. This gave 405 mg (58% of theory over 2 steps) of the title compound. LC-MS (Method 1): $R_t$=0.75 min; MS (ESIpos): m/z=339 $(M+H)^+$.

Intermediate L76

(2S)-2-Bromo-4-oxo-4-[2-(trimethylsilyl)ethoxy]butanoic acid

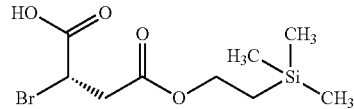

First, a suitably protected aspartic acid derivative was prepared from (3S)-4-(benzyloxy)-3-{[(benzyloxy)carbonyl]amino}-4-oxobutanoic acid according to classical methods of peptide chemistry (esterification with 2-(trimethylsilyl)ethanol using EDCI/DMAP and hydrogenolytic removal of the Z protective group and the benzyl ester. 470 mg (1.8 mmol) of the (2S)-2-amino-4-oxo-4-[2-(trimethylsilyl)ethoxy]butanoic acid obtained in this manner were suspended in 10 ml of water, and 1.8 ml of a 1 molar hydrochloric acid and 0.5 ml of concentrated sulphuric acid were added, followed by 863 mg (7.25 mmol) of potassium bromide. At 10° C., a solution of 150 mg (2.175 mmol) of sodium nitrite in 1 ml of water was then added dropwise over a period of 30 min, and the mixture was stirred at 10-15° C. for 2 h. The mixture was then extracted with 50 ml of ethyl acetate. The organic phase was washed with saturated sodium chloride solution and dried over magnesium sulphate. Evaporation of the solvent and purification of the product by preparative HPLC gave 260 mg (48% of theory) of the title compound.

LC-MS (Method 1): $R_t$=1.03 min; MS (ESIneg): m/z=295 and 297 $(M-H)^-$.

$^1$H-NMR (400 MHz, $CDCl_3$): δ [ppm]=0.03 (s, 9H), 0.95 (t, 2H), 2.94 and 3.2 (2dd, 2H), 4.18 (t, 2H), 4.57 (t, 1H).

Intermediate L77

Trifluoroacetic acid/N-[2-(2-Aminoethoxy)ethyl]-2-bromoacetamide (1:1)

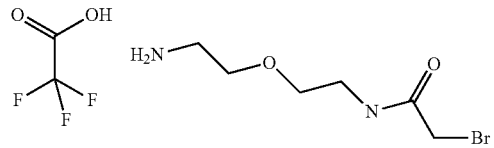 [SMILES: O=C(O)C(F)(F)F ; NCCOCCNC(=O)CBr]

418 mg (2.05 mmol) of tert-Butyl [2-(2-aminoethoxy) ethyl]carbamate were initially reacted with 638 mg (2.46 mmol) of bromoacetic anhydride, and the Boc protective group was then removed with trifluoroacetic acid. This gave 551 mg (63% of theory over 2 steps) of the title compound.

LC-MS (Method): $R_t$=0.32 min; MS (ESIpos): m/z=227 and 225 (M+H)$^+$.

Intermediate L78

N-[(2,5-Dioxo-2,5-dihydro-1H-pyrrol-1-yl)acetyl]-beta-alanine

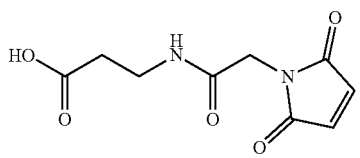 [SMILES: O=C(O)CCNC(=O)CN1C(=O)C=CC1=O]

The title compound was prepared from commercially available (2,5-dioxo-2,5-dihydro-1H-pyrrol-1-yl)acetic acid by coupling with tert-Butyl beta-alaninate hydrochloride (1:1) in the presence of EDCI/HOBt and N',N'-diisopropylethylamine and subsequent deprotection with trifluoroacetic acid.

LC-MS (Method 1): $R_t$=0.32 min; MS (ESIpos): m/z=227 (M+H)$^+$.

Intermediate L79

N-[(2,5-Dioxo-2,5-dihydro-1H-pyrrol-1-yl)hexanoyl]-beta-alanine

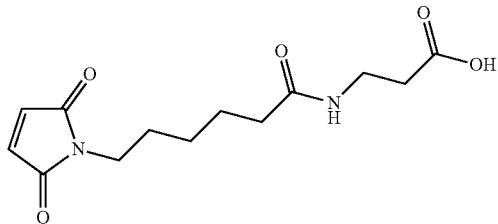 [SMILES: O=C(O)CCNC(=O)CCCCCN1C(=O)C=CC1=O]

64.8 mg (0.357 mmol) of tert-Butyl beta-alaninate hydrochloride (1:1) and 100 mg (0.324 mmol) of 1-{6-[(2,5-dioxopyrrolidin-1-yl)oxy]-6-oxohexyl}-1H-pyrrole-2,5-dione were dissolved in 4 ml of dimethylformamide, and 65.6 mg (0.649 mmol) of N-methylmorpholine were added. The reaction mixture was stirred at RT overnight. 0.048 ml (0.838 mmol) of acetic acid were added and the reaction mixture was purified directly by preparative RP-HPLC (column: Reprosil 250×30; 10µ, flow rate: 50 ml/min, MeCN/water/0.1% TFA). The solvents were evaporated under reduced pressure and the residue was dried under high vacuum. This gave 84.5 mg (77%, purity 100%) of tert-Butyl N-[6-(2S-dioxo-2,5-dihydro-1H-pyrrol-1-yl)hexanoyl]-beta-alaninate.

LC-MS (Method 1): $R_t$=0.78 min; MS (ESIpos): m/z=339 (M+H)$^+$.

1.62 ml of TFA were added to a solution of tert-Butyl N-[6-(2,5-dioxo-2,5-dihydro-1H-pyrrol-1-yl)hexanoyl]-beta-alaninate (82.8 mg, 0.244 mmol) in 8 ml of dichloromethane. The reaction mixture was stirred at RT for 2 hours. The reaction mixture was concentrated under reduced pressure and the residue was taken up in water and lyophilized. The residue was used further without further purification. This gave 62.7 mg (87%, purity 95%) of the title compound.

LC-MS (Method 1): $R_t$=0.75 min; MS (ESIpos): m/z=283 (M+H)$^+$.

Intermediate L80

2-(Trimethylsilyl)ethyl 3-[(15-amino-4,7,10,13-tetraoxapentadecan-1-oyl)amino]-N-(tert-butoxycarbonyl)-D-alaninate

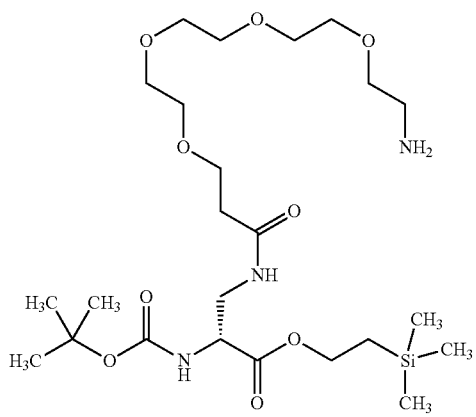 [SMILES: CC(C)(C)OC(=O)N[C@H](CNC(=O)CCOCCOCCOCCOCCN)C(=O)OCC[Si](C)(C)C]

The title compound was prepared from commercially available 3-{[(benzyloxy)carbonyl]amino}-N-(tert-butoxycarbonyl)-D-alanine/N-cyclohexylcyclohexanamine (1:1) according to classical methods of peptide chemistry (release from the salt and esterification with 2-(trimethylsilyl)ethanol using EDCI/DMAP, hydrogenolytic removal of the Z protective group, coupling with commercially available 3-oxo-1-phenyl-2,7,10,13,16-pentaoxa-4-azanonadecan-19-oic acid in the presence of HATU and N,N-diisopropylethylamine and another hydrogenolytic removal of the Z protective group).

LC-MS (Method 1): $R_t$=0.70 min; MS (ESIpos): m/z=552 (M+H)$^+$.

Intermediate L81

Trifluoroacetic acid/benzyl {2-[(2-aminoethyl)sulphonyl]ethyl}carbamate (1:1)

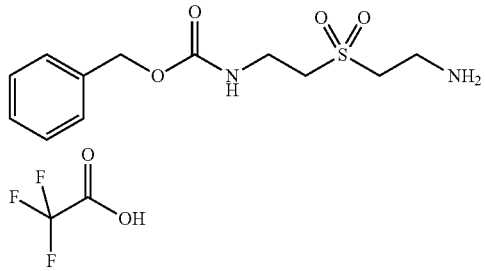

250 mg (1.11 mmol) of 2,2'-sulphonyldiethanamine were coupled with 92.3 mg (0.37 mmol) of 1-{[(benzyloxy) carbonyl]oxy}pyrrolidine-2,5-dione in the presence of N,N-diisopropylethylamine in DMF. Subsequent purification by HPLC gave 70 mg (47% of theory) of the title compound.

LC-MS (Method 12): $R_t$=0.64 min; MS (ESIpos): m/z=257.11 (M+H)$^+$.

Intermediate L82

Trifluoroacetic acid/N-{2-[2-(2-aminoethoxy) ethoxy]ethyl}-6-(2,5-dioxo-2,5-dihydro-1H-pyrrol-1-yl)hexanamide (1:1)

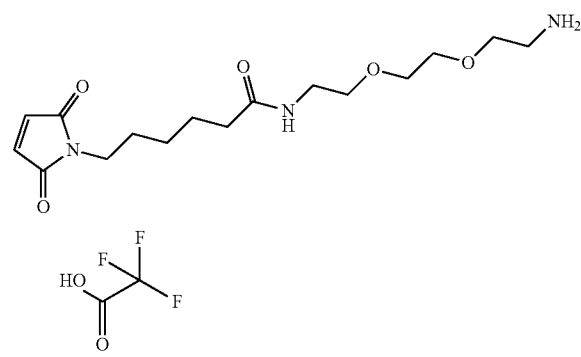

88.6 mg (0.357 mmol) of N-Boc-2,2'-(ethylenedioxy) diethylamine and 100 mg (0.324 mmol) of N-succinimidyl 6-maleimidohexanoate were dissolved in 4.0 ml of dimethylformamide, and 0.071 ml (0.650 mmol) of N-methylmorpholine were added. The reaction mixture was stirred at RT overnight. 0.048 ml (0.838 mmol) of acetic acid were added and the reaction mixture was purified directly by preparative RP-HPLC (column: Reprosil 125×30; 10μ, flow rate: 75 ml/min, MeCN/water/0.1% TFA). The solvents were evaporated under reduced pressure and the residue was dried under high vacuum. This gave 127 mg (81% of theory) of tert-Butyl {2-[2-(2-{[6-(2,5-dioxo-2,5-dihydro-1H-pyrrol-1-yl)hexanoyl]amino}ethoxy)ethoxy]ethyl}carbamate.

LC-MS (Method 1): $R_t$=0.78 min; MS (ESIpos): m/z=442 (M+H)$^+$.

2.0 ml of TFA were added to a solution of 123 mg (225 μmol) tert-Butyl {2-[2-(2-{[6-(2,5-dioxo-2,5-dihydro-1H-pyrrol-1-yl)hexanoyl]amino}ethoxy)ethoxy]ethyl}carbamate in 7.5 ml of dichloromethane. The reaction mixture was stirred at RT for 2 h. The reaction mixture was concentrated under reduced pressure and the residue was taken up in water and lyophilized. The residue was used further without further purification. This gave 111 mg (100% of theory) of the title compound.

LC-MS (Method 1): $R_t$=0.31 min; MS (ESIpos): m/z=342 (M+H)$^+$.

$^1$H-NMR (400 MHz, DMSO-d$_6$): δ [ppm]=1.17 (m, 2H), 1.47 (m, 4H), 2.04 (m, 2H), 2.98 (m, 2H), 3.19 (m, 2H), 3.39 (m, 4H), 3.56 (m, 6H), 7.01 (s, 2H), 7.72 (bs, 3H), 7.80 (m, 1H).

Intermediate L83

Trifluoroacetic acid/N-{2-[2-(2-aminoethoxy) ethoxy]ethyl}-2-(2,5-dioxo-2,5-dihydro-1H-pyrrol-1-yl)acetamide (1:1)

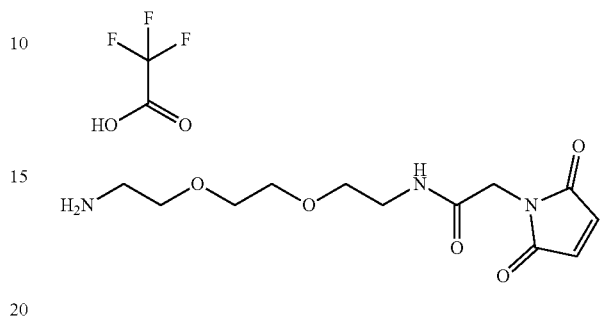

200 mg (0.805 mmol) of tert-Butyl (2-[2-(2-aminoethoxy) ethoxy]ethyl}carbamate, 150 mg (0.966 mmol) of (2,5-dioxo-2,5-dihydro-1H-pyrrol-1-yl)acetic acid and 560 μl (3.2 mmol) of N,N-diisopropylethylamine were dissolved in 10 ml of dimethylformamide, and 459 mg (1.21 mmol) of HATU were added. The reaction mixture was stirred at RT for 30 minutes. The solvents were evaporated under reduced pressure and the residue was dissolved in dichloromethane. The organic phase was washed twice with 5% strength citric acid solution and dried over magnesium sulphate, and the solvent was evaporated under reduced pressure. The residue was purified using Biotage Isolera (silica gel, column 25 g SNAP, dichloromethane:methanol 98:2). This gave 276 mg (89% of theory) of tert-Butyl {2-[2-(2-{[(2,5-dioxo-2,5-dihydro-1H-pyrrol-1-yl)acetyl]amino}ethoxy)ethoxy] ethyl}carbamate.

LC-MS (Method 1): $R_t$=0.67 min; MS (ESIpos): m/z=386 (M+H)$^+$. 4 ml of TFA were added to a solution of tert-Butyl {2-[2-(2-{[(2,5-dioxo-2,5-dihydro-1H-pyrrol-1-yl)acetyl] amino}ethoxy)ethoxy]ethyl}carbamate (275 mg, 714 μmol) in 15 ml of dichloromethane. The reaction mixture was stirred at RT for 30 minutes. The reaction mixture was concentrated under reduced pressure and the residue was taken up in water and lyophilized. This gave 281 mg (99% of theory) of the title compound.

LC-MS (Method 1): $R_t$=0.17 min; MS (ESIpos): m/z=286 (M+H)$^+$.

Intermediate L84

Trifluoroacetic acid/N-(14-amino-3,6,9,12-tetraoxa-tetradec-1-yl)-6-(2,5-dioxo-2,5-dihydro-1H-pyrrol-1-yl)hexanamide (1:1)

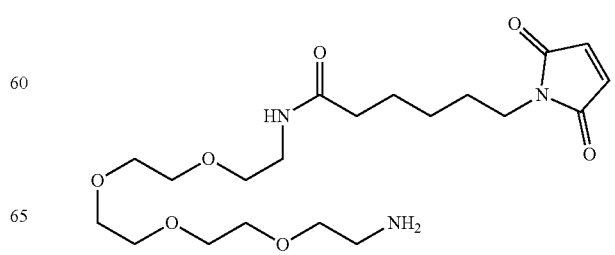

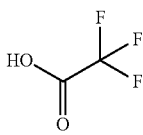

200 mg (0.594 mmol) of tert-Butyl (14-amino-3,6,9,12-tetraoxatetradec-1-yl)carbamate and 202 mg (0.654 mmol) of 1-{6-[(2,5-dioxopyrrolidin-1-yl)oxy]-6-oxohexyl}-1H-pyrrole-2,5-dione were dissolved in 4.0 ml of dimethylformamide, and 0.130 ml (1.2 mmol) of N-methylmorpholine were added. The reaction mixture was stirred at RT overnight. 0.085 ml (1.5 mmol) of acetic acid were added and the reaction mixture was purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 275 mg (73% of theory) of tert-Butyl [21-(2,5-dioxo-2,5-dihydro-1H-pyrrol-1-yl)-16-oxo-3,6,9,12-tetraoxa-15-azahenicos-1-yl]carbamate.

LC-MS (Method 1): $R_t$=0.81 min; MS (ESIpos): m/z=530 (M+H)$^+$.

780 μl (10 mmol) of TFA were added to a solution of tert-Butyl [21-(2,5-dioxo-2,5-dihydro-1H-pyrrol-1-yl)-16-oxo-3,6,9,12-tetraoxa-15-azahenicos-1-yl]carbamate (268 mg, 505 μmol) in 5.0 ml of dichloromethane. The reaction mixture was stirred at RT overnight. The reaction mixture was concentrated under reduced pressure and the residue was taken up in water and lyophilized. The residue was used further without further purification. This gave 266 mg (97% of theory) of the title compound.

LC-MS (Method 1): $R_t$=0.46 min; MS (ESIpos): m/z=430 (M+H)$^+$.

$^1$H-NMR (400 MHz, DMSO-d$_6$): δ [ppm]=1.17 (m, 2H), 1.47 (m, 4H), 2.03 (m, 2H), 2.99 (m, 2H), 3.18 (m, 2H), 3.38 (m, 4H), 3.52 (m, 8H), 3.58 (m, 6H), 7.01 (s, 2H), 7.73 (bs, 3H), 7.80 (m, 1H).

Intermediate L85

Trifluoroacetic acid/N-(14-amino-3,6,9,12-tetraoxatetradec-1-yl)-2-(2,5-dioxo-2,5-dihydro-1H-pyrrol-1-yl)acetamide (1:1)

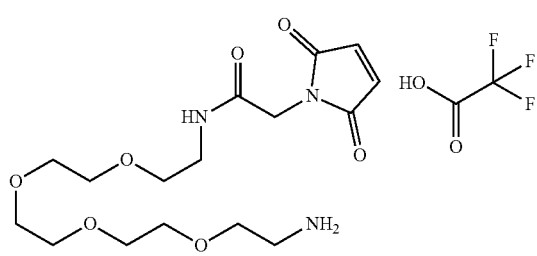

200 mg (0.594 mmol) of tert-Butyl (14-amino-3,6,9,12-tetraoxatetradec-1-yl)carbamate, 111 mg (0.713 mmol) of (2,5-dioxo-2,5-dihydro-1H-pyrrol-1-yl)acetic acid and 410 μl (2.4 mmol) of N,N-diisopropylethylamine were dissolved in 6 ml of dimethylformamide, and 339 mg (0.892 mmol) of HATU were added. The reaction mixture was stirred at RT for 1 h and purified directly by preparative RP-HPLC (column: Reprosil 250×30; 10μ, flow rate: 50 ml/min, MeCN/water/0.1% TFA). The solvents were evaporated under reduced pressure and the residue was dried under high vacuum. This gave 130 mg (43% of theory) of tert-Butyl [17-(2,5-dioxo-2,5-dihydro-1H-pyrrol-1-yl)-16-oxo-3,6,9,12-tetraoxa-15-azaheptadec-1-yl]carbamate.

LC-MS (Method 1): $R_t$=0.71 min; MS (ESIpos): m/z=474 (M+F1)$^+$.

410 μl (5.3 mmol) of TFA were added to a solution of tert-Butyl [17-(2,5-dioxo-2,5-dihydro-1H-pyrrol-1-yl)-16-oxo-3,6,9,12-tetraoxa-15-azaheptadec-1-yl]carbamate (126 mg, 267 μmol) in 4.0 ml of dichloromethane. The reaction mixture was stirred at RT overnight. The reaction mixture was concentrated under reduced pressure and the residue was dried under high vacuum. This gave 124 mg (95% of theory) of the title compound.

LC-MS (Method 13): $R_t$=0.74 min; MS (ESIpos): m/z=374 (M+H)$^+$.

$^1$H-NMR (400 MHz, DMSO-d$_6$): δ [ppm]=2.99 (m, 2H), 3.22 (m, 2H), 3.41 (m, 2H), 3.53 (m, 8H), 3.58 (m, 6H), 4.02 (s, 2H), 7.09 (s, 2H), 7.73 (bs, 3H), 8.21 (m, 1H).

Intermediate L86

N-[(2,5-Dioxo-2,5-dihydro-1H-pyrrol-1-yl)acetyl]-L-valyl-L-alanine

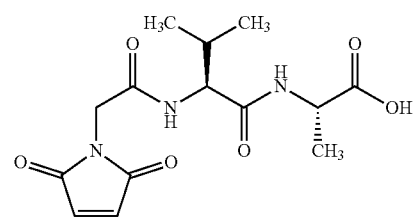 [SMILES: CC(C)[C@H](NC(=O)CN1C(=O)C=CC1=O)C(=O)N[C@@H](C)C(=O)O]

100 mg (0.531 mmol) of L-valyl-L-alanine and 134 mg (0.531 mmol) of 1-{2-[(2,5-dioxopyrrolidin-1-yl)oxy]-2-oxoethyl}-1H-pyrrole-2,5-dione were dissolved in 3 ml of dimethylformamide, and 0.150 ml (1.1 mmol) of triethylamine were added. The reaction mixture was stirred at RT for 8 h. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 71.5 mg (41% of theory) of the title compound.

LC-MS (Method 1): $R_t$=0.42 min; MS (ESIpos): m/z=326 (M+F1)$^+$.

Intermediate L87

3-[2-(2-{[(2,5-Dioxo-2,5-dihydro-1H-pyrrol-1-yl)acetyl]amino}ethoxy)ethoxy]propanoic acid

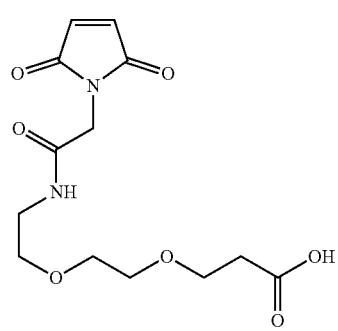 [SMILES: O=C(O)CCOCCOCCNC(=O)CN1C(=O)C=CC1=O]

250 mg (1.07 mmol) of tert-Butyl 3-[2-(2-aminoethoxy)ethoxy]propanoate, 151 mg (0.974 mmol) of 2-(2,5-dioxo-2,5-dihydro-1H-pyrrol-1-yl)acetic acid, 224 mg (1.46 mmol) of 1-hydroxy-1H-benzotriazole hydrate and 224 mg (1.17 mmol) of 1-(3-dimethylaminopropyl)-3-ethylcarbodiimide hydrochloride were dissolved in 5.0 ml of dimethylformamide. The reaction mixture was stirred at RT for 1 h. Ethyl acetate was added and the mixture was extracted twice with 5% strength citric acid solution and with saturated sodium bicarbonate solution. The organic phase was washed twice with saturated sodium chloride solution and dried over magnesium sulphate, and the solvent was evaporated under reduced pressure. The residue was purified by preparative RP-HPLC (column: Reprosil 250×40; 10μ, flow rate: 50 ml/min, MeCN/water/0.1% TFA). The solvents were evaporated under reduced pressure and the residue was dried under high vacuum. This gave 267 mg (64% of theory) of tert-Butyl 3-[2-(2-{[(2,5-dioxo-2,5-dihydro-1H-pyrrol-1-yl)acetyl]amino}ethoxy)ethoxy]propanoate.

LC-MS (Method 1): Rt=0.73 min; MS (ESIpos): m/z=371 (M+H)$^+$.

1.1 ml (14 mmol) of TFA were added to a solution of tert-Butyl 3-[2-(2-{[(2,5-dioxo-2,5-dihydro-1H-pyrrol-1-yl)acetyl]amino}ethoxy)ethoxy]propanoate (263 mg, 710 μmol) in 10 ml of dichloromethane. The reaction mixture was stirred at RT overnight. The reaction mixture was concentrated under reduced pressure and the residue was dried under high vacuum. This gave 240 mg (94% of theory) of the title compound.

LC-MS (Method 12): R$_t$=0.57 min; MS (ESIpos): m/z=315 (M+H)$^+$.

Intermediate L88

2,5-Dioxopyrrolidin-1-yl N-[6-(2,5-dioxo-2,5-dihydro-1H-pyrrol-1-yl)hexanoyl]-L-valyl-L-alaninate

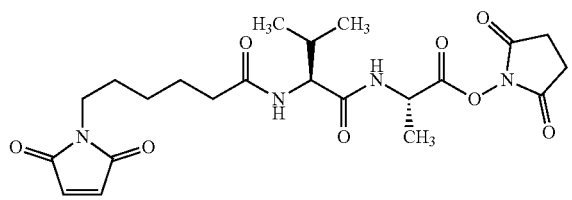 [SMILES: CC(C)[C@H](NC(=O)CCCCCN1C(=O)C=CC1=O)C(=O)N[C@@H](C)C(=O)ON1C(=O)CCC1=O]

150 mg (0.797 mmol) of L-valyl-L-alanine and 246 mg (0.797 mmol) of 1-{6-[(2,5-dioxopyrrolidin-1-yl)oxy]-6-oxohexyl}-1H-pyrrole-2,5-dione were dissolved in 4.0 ml of dimethylformamide, and 0.220 ml (1.6 mmol) of triethylamine were added. The reaction mixture was stirred at RT overnight. The reaction mixture was purified directly by preparative RP-HPLC (column: Reprosil 250×30; 10μ, flow rate: 50 ml/min, MeCN/water). The solvents were evaporated under reduced pressure and the residue was dried under high vacuum. This gave 302 mg (97% of theory) of N-[6-(2,5-dioxo-2,5-dihydro-1H-pyrrol-1-yl)hexanoyl]-L-valyl-L-alanine.

LC-MS (Method 12): R$_t$=1.02 min; MS (ESIpos): m/z=382 (M+H)$^+$.

$^1$H-NMR (400 MHz, DMSO-d$_6$): δ [ppm]=0.82 (dd, 6H), 1.17 (m, 2H), 1.27 (d, 3H), 1.48 (m, 4H), 1.94 (m, 1H), 2.13 (m, 2H), 3.38 (t, 2H), 4.17 (m, 2H), 7.00 (s, 2H), 7.75 (d, 1H), 8.19 (d, 1H).

130 mg (0.531 mmol) of N-[6-(2,5-dioxo-2,5-dihydro-1H-pyrrol-1-yl)hexanoyl]-L-valyl-L-alanine were dissolved in 6.5 ml of dichloromethane, and 58.8 mg (0.511 mmol) of 1-hydroxypyrrolidine-2,5-dione and 78.4 mg (0.409 mmol) of 1-(3-dimethylaminopropyl)-3-ethylcarbodiimide hydrochloride were added. Another 58.8 mg (0.511 mmol) of 1-hydroxypyrrolidine-2,5-dione and 78.4 mg (0.409 mmol) of 1-(3-dimethylaminopropyl)-3-ethylcarbodiimide hydrochloride were added. Dichloromethane was added and the mixture was washed three times with water. The organic phase was dried over magnesium sulphate, the solvent was evaporated under reduced pressure and the residue was dried under high vacuum. This gave 172 mg (87% of theory) of the title compound.

LC-MS (Method 12): R$_t$=1.28 min; MS (ESIpos): m/z=479 (M+H)$^+$.

Intermediate L89

1-Benzyl-5-[2-(trimethylsilyl)ethyl]-L-glutamate hydrochloride (1:1)

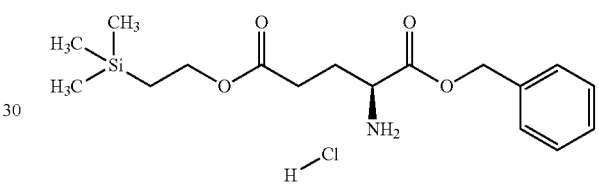

1.00 g (2.96 mmol) of (4S)-5-(benzyloxy)-4-[(tert-butoxycarbonyl)amino]-5-oxopentanoic acid was initially charged in 13.0 ml of THF, and 510 μl (3.6 mmol) of 2-(trimethylsilyl)ethanol and 109 mg (889 μmol) of 4-dimethylaminopyridine were added. The reaction mixture was cooled to 0° C., and 682 mg (3.56 mmol) of N-ethyl-N'-3-(dimethylaminopropyl)carbodiimide hydrochloride were added. The reaction mixture was stirred at RT overnight. The solvents were evaporated under reduced pressure and the residue was dissolved in ethyl acetate. The organic phase was washed twice with 0.1 N HCl solution and saturated sodium chloride solution and dried over magnesium sulphate, and the solvent was evaporated under reduced pressure. The residue was purified using Biotage Isolera (silica gel, column 25 g SNAP, cyclohexane:ethyl acetate 80:20). This gave 649 mg (50% of theory) of the compound 1-benzyl-5-[2-(trimethylsilyl)ethyl]-N-(tert-butoxycarbonyl)-L-glutamate.

LC-MS (Method 1): R$_t$=4.6 min; MS (ESIpos): m/z=438 (M+H)$^+$.

649 mg (1.48 mmol) of 1-benzyl-5-[2-(trimethylsilyl)ethyl]-N-(tert-butoxycarbonyl)-L-glutamate were dissolved in 7.0 ml of dioxane and, with ice bath cooling, 14 ml (59 mmol) of 4N HCl in dioxane were added. The reaction mixture was stirred at RT overnight. The reaction mixture was concentrated under reduced pressure and the residue was dried under high vacuum and purified by Biotage Isolera (silica gel, column 25 g SNAP, dichloromethane:methanol 90:10). This gave 320 mg (57% of theory) of the title compound.

LC-MS (Method 1): R$_t$=0.79 min; MS (ESIpos): m/z=338 (M+H)$^+$.

Intermediate L90

1-({N-[(Benzyloxy)carbonyl]glycyl}amino)-3,6,9,12-tetraoxapentadecan-15-oic acid

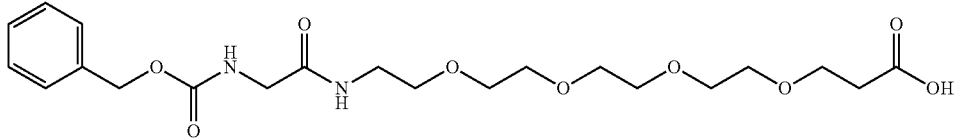 [SMILES: O=C(O)CCOCCOCCOCCOCCNC(=O)CNC(=O)OCc1ccccc1]

118 mg (566 µmol) of N-[(benzyloxy)carbonyl]glycine were initially charged in 5.0 ml of DMF, 200 mg (622 µmol) of tert-Butyl 1-amino-3,6,9,12-tetraoxapentadecan-15-oate, 130 mg (849 µmol) of 1-hydroxy-1H-benzotriazole hydrate and 130 mg (679 µmol) of 1-(3-dimethylaminopropyl)-3-ethylcarbodiimide hydrochloride were added and the mixture was stirred at RT for 1 h. Ethyl acetate was added and the mixture was extracted twice with 5% strength citric acid solution and with saturated sodium bicarbonate solution. The organic phase was washed twice with saturated sodium chloride solution and dried over magnesium sulphate. The solvents were evaporated under reduced pressure and the residue was dried under high vacuum. This gave 274 mg (95% of theory) of tert-Butyl 1-({N-[(benzyloxy)carbonyl]glycyl}amino)-3,6,9,12-tetraoxapentadecan-15-oate.

LC-MS (Method 12): $R_t$=1.69 min; MS (ESIpos): m/z=513 (M+H)$^+$.

820 µl (11 mmol) of TFA were added to a solution of 274 mg (535 µmol) of tert-Butyl 1-({N-[(benzyloxy)carbonyl]glycyl}amino)-3,6,9,12-tetraoxapentadecan-15-oate in 5.0 ml of dichloromethane. The reaction mixture was stirred at RT for 3 h. The reaction mixture was concentrated under reduced pressure and the residue was taken up in water and lyophilized. This gave 262 mg (100% of theory) of the title compound.

LC-MS (Method 12): $R_t$=1.12 min; MS (ESIpos): m/z=457 (M+H)$^+$.

Intermediate L91

Trifluoroacetic acid/2-(trimethylsilyl)ethyl 1-{[3-amino-N-(tert-butoxycarbonyl)-D-alanyl]amino}-3,6,9,12-tetraoxapentadecan-15-oate (1:1)

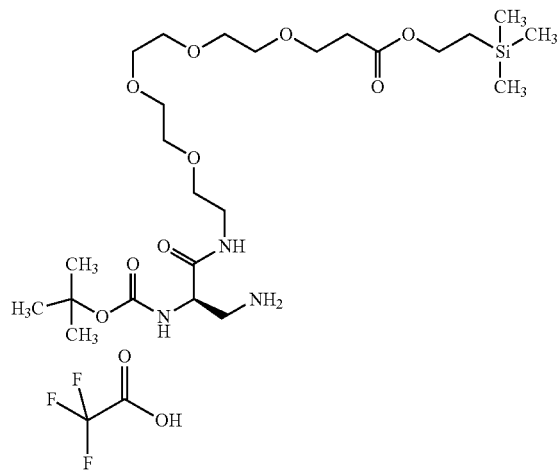

The title compound was prepared from commercially available 3-oxo-1-phenyl-2,7,10,13,16-pentaoxa-4-azanonadecan-19-oic acid by classical methods of peptide chemistry (esterification with 2-trimethylsilylethanol using EDCI/DMAP, hydrogenolytic removal of the Z protective group, coupling with commercially available N-(tert-butoxycarbonyl)-3-{[(9H-fluoren-9-ylmethoxy)carbonyl]amino}-D-alanine and removal of the Fmoc protective group).

LC-MS (Method 1): $R_t$=0.74 min; MS (ESIpos): m/z=552 (M+H)$^+$.

Intermediate L92

N-[(Benzyloxy)carbonyl]-L-alanyl-L-alanyl-L-alpha-asparagine

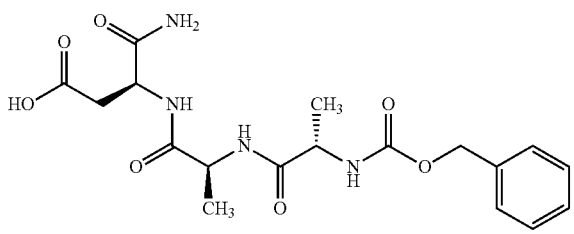 [SMILES: C[C@H](NC(=O)OCc1ccccc1)C(=O)N[C@@H](C)C(=O)N[C@@H](CC(=O)O)C(N)=O]

The title compound was prepared by classical methods of peptide chemistry by HATU coupling in the presence of N,N-diisopropylethylamine of commercially available N-[(benzyloxy)carbonyl]-L-alanyl-L-alanine with tert-Butyl L-asparaginate and subsequent deprotection of the carboxyl group with trifluoroacetic acid.

LC-MS (method 1): $R_t$=0.5 min; MS (ESIpos): m/z=409 (M+H)$^+$.

Intermediate L93

N-Acetyl-L-alanyl-L-alanyl-L-alpha-asparagine

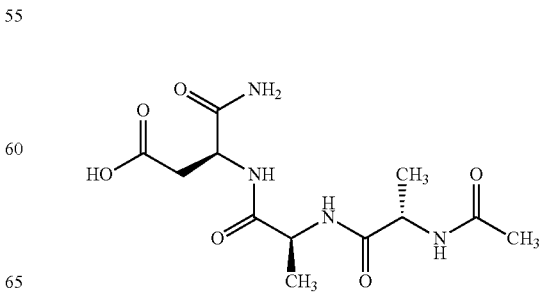

The title compound was prepared by classical methods of peptide chemistry by HATU coupling in the presence of N,N-diisopropylethylamine of commercially available N-[(benzyloxy)carbonyl]-L-alanyl-L-alanine with tert-Butyl L-asparaginate, subsequent cleavage of the Z protecting group by hydrogenation in DCM-methanol over 10% palladium on active carbon, then subsequent acetylation with acetic acid in DMF in the presence of HATU and N,N-diisopropylethylamine and finally deprotection of the carboxyl group with trifluoroacetic acid.

LC-MS (method 1): $R_t$=0.16 min; MS (ESIpos): m/z=317 (M+H)$^+$.

$^1$H-NMR (400 MHz, DMSO-d$_6$): δ [ppm]=1.19 (2d, 6H), 1.82 (s, 3H), 2.5 (m, 2H), 4.26 (m, 2H), 4.48 (q, 1H), 6.9 (s, 1H), 7.36 (s, 1H), 8.0 (m, 3H), 12.54 (s, 1H).

Intermediate L94

N-{4-Oxo-4-[2-(trimethylsilyl)ethoxy]butanoyl}-L-alanyl-L-alanyl-L-alpha-asparagine

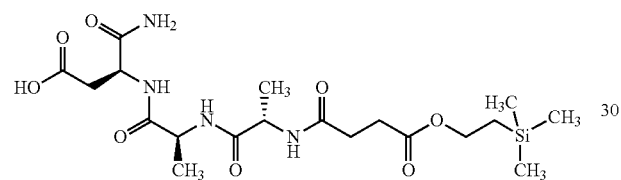

Firstly, 4-oxo-4-[2-(trimethylsilyl)ethoxy]butanoic acid was prepared by reacting 4-(benzyloxy)-4-oxobutanoic acid with 2-(trimethylsilyl)ethanol in the presence of EDCI/DMAP in DCM and subsequent cleavage of the benzyl ester by hydrogenolysis.

LC-MS (method 1): $R_t$=0.89 min; MS (ESIpos): m/z=217 (M-H)$^-$.

Then, trifluoroacetic acid—4-nitrobenzyl L-alanyl-L-alanyl-L-asparaginate (1:1) was prepared by coupling of N-(tert-butoxycarbonyl)-L-alanyl-L-alanine with 4-nitrobenzyl L-asparaginate hydrobromide (1:1) in DMF in the presence of HATU and N,N-diisopropylethylamine and subsequent deprotection of the amino group with trifluoroacetic acid in DCM.

LC-MS (Method 1): $R_t$=0.43 min; MS (ESIpos): m/z=410 (M+H)$^+$.

The title compound was then prepared by coupling of these two intermediates in DMF in the presence of HATU and N,N-diisopropylethylamine and subsequent cleavage of the p-nitrobenzyl ester by hydrogenation in DCM-methanol 1:9 over 10% palladium on active carbon.

LC-MS (method 1): $R_t$=0.79 min; MS (ESIpos): m/z=475 (M+H)$^+$.

Intermediate L95

N-[(Benzyloxy)carbonyl]-L-valyl-L-alanine

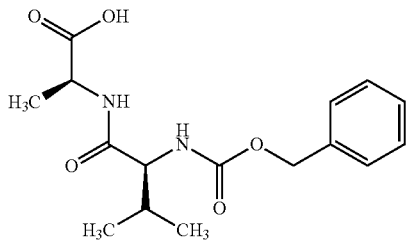 [SMILES: CC(C)[C@H](NC(=O)OCc1ccccc1)C(=O)N[C@@H](C)C(=O)O]

This intermediate was prepared using classical methods of peptide chemistry starting from N-[(benzyloxy)carbonyl]-L-valine and tert-Butyl L-alaninate hydrochloride (1:1).

LC-MS (method 12): $R_t$=1.34 min; MS (ESIpos): m/z=323.16 (M+H)$^+$.

Intermediate L96

N-Acetyl-L-valyl-N$^5$-carbamoyl-L-ornithinamide

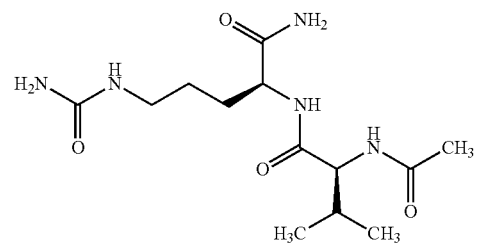 [SMILES: CC(=O)N[C@H](C(=O)N[C@@H](CCCNC(N)=O)C(N)=O)C(C)C]

This intermediate was prepared using classical methods of peptide chemistry beginning with the coupling of 2,5-dioxopyrrolidin-1-yl N-[(benzyloxy)carbonyl]-L-valinate with N$^5$-carbamoyl-L-omithine, then subsequent cleavage of the Z protecting group by hydrogenolysis over 10% palladium/active carbon in ethanol and finally by reacting the resulting dipeptide with 1-acetoxypyrrolidine-2,5-dione.

LC-MS (Method 1): $R_t$=0.25 min; MS (ESIpos): m/z=317 (M+H)$^+$.

Intermediate L97

1-(2,5-Dioxo-2,5-dihydro-1H-pyrrol-1-yl)-2-oxo-6,9,12,15,18,21,24,27-octaoxa-3-azatriacontan-30-oic acid

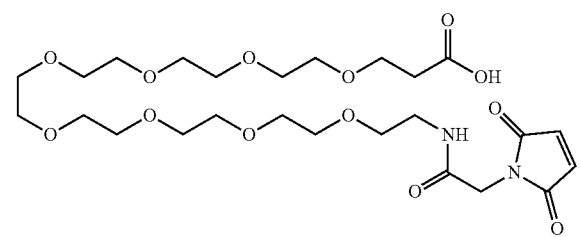 [SMILES: O=C(O)CCOCCOCCOCCOCCOCCOCCOCCOCCNC(=O)CN1C(=O)C=CC1=O]

Tert-Butyl 1-amino-3,6,9,12,15,18,21,24-octaoxaheptacosan-27-oate (100 mg, 201 μmol) was initially charged in 1.0 ml of DMF and (2,5-dioxo-2,5-dihydro-1H-pyrrol-1-yl)acetic acid (46.8 mg, 301 μmol), 1-hydroxy-1H-benzotriazole hydrate (76.9 mg, 502 μmol) and 1-(3-dimethylaminopropyl)-3-ethylcarbodiimide hydrochloride (77.0 mg, 402 μmol) were added. The reaction mixture was stirred overnight at RT and then ethyl acetate was added. The organic phase was washed twice with 5% citric acid solution, with sat. sodium hydrogen carbonate solution and then with sat. sodium chloride solution. The organic phase was dried over magnesium sulfate. The solvents were evaporated under vacuum and the residue purified by prep. RP-HPLC (column: Reprosil 125×30; 10μ, flow: 50 mL/min, MeCN/water/0.1% TFA). The solvents were evaporated under vacuum and the residue dried under high vacuum. This gave 19.1 mg (13% of theory) of the compound tert-Butyl 1-(2,5-dioxo-2,5-dihydro-1H-pyrrol-1-yl)-2-oxo-6,9,12,15,18,21,24,27-octaoxa-3-azatriacontan-30-oate.

LC-MS (Method 1): $R_t$=0.87 min; MS (ESIpos): m/z=635 [M+H]$^+$

To a solution of tert-Butyl 1-(2,5-dioxo-2,5-dihydro-1H-pyrrol-1-yl)-2-oxo-6,9,12,15,18,21,24,27-octaoxa-3-azatriacontan-30-oate (19.1 mg, 30.1 μmol) in 1.0 ml DCM was added TFA (62 μl, 600 μmol). The reaction mixture was stirred at RT for 3 h. The reaction mixture was evaporated under vacuum and the residue was taken up in water and lyophilized. The residue was further used without further purification. This gave 10.8 mg (46% of theory) of the title compound.

LC-MS (Method 1): $R_t$=0.55 min; MS (ESIneg): m/z=577 [M−H]$^−$.

Intermediate L98

2,2-Dimethylpropanoic acid—2-(trimethylsilyl)ethyl N-(2-aminoethyl)-N$^2$-{[2-(trimethylsilyl)ethoxy]carbonyl}-L-glutaminate (1:1)

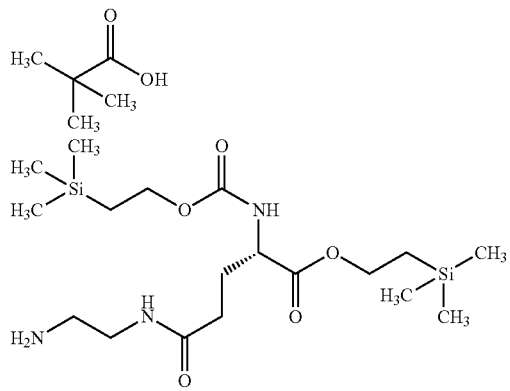

Firstly, (4S)-5-tert-butoxy-4-[(tert-butoxycarbonyl)amino]-5-oxopentanoic acid was coupled with benzyl (2-aminoethyl)carbamate in the presence of HATU and N,N-diisopropylethylamine. The Boc protecting group and the tert-Butyl ester were then cleaved off using trifluoroacetic acid in DCM. Next, the amino group was firstly protected again by reaction with 1-({[2-(trimethylsilyl)ethoxy]carbonyl}oxy)pyrrolidine-2,5-dione in DMF/water in the presence of N,N-diisopropylethylamine and subsequently the carboxyl group by reaction with 2-(trimethylsilyl)ethanol in DCM in the presence of EDCI/DMAP. In the final step, the terminal amino group was deprotected by means of hydrogenolysis over 10% palladium on active carbon in ethanol at standard pressure. After filtering off the catalyst, concentration, purification by preparative HPLC and freeze-drying of the residue from acetonitrile/water, the title compound was obtained.

LC-MS (Method 1): $R_t$=0.82 min; MS (ESIpos): m/z=434 (M+H)$^+$.

Intermediate L99

Trifluoroacetic acid—2-(trimethylsilyl)ethyl N-[(2,5-dioxo-2,5-dihydro-1H-pyrrol-1-yl)acetyl]-L-valyl-L-alanyl-beta-alanyl-L-lysinate (1:1)

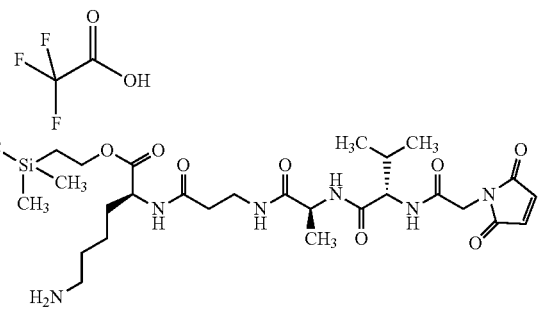

Firstly, 2-(trimethylsilyl)ethyl N6-(tert-butoxycarbonyl)-L-lysinate was prepared by classical methods of peptide chemistry starting from N2-[(benzyloxy)carbonyl]-N6-(tert-butoxycarbonyl)-L-lysine. This intermediate was then coupled with the tripeptide unit N-[(benzyloxy)carbonyl]-L-valyl-L-alanyl-beta-alanine, prepared by standard methods, in the presence of HATU and N,N-diisopropylethylamine. The Z protecting group was then removed by hydrogenolysis in methanol and the resulting intermediate coupled with (2,5-dioxo-2,5-dihydro-1H-pyrrol-1-yl)acetic acid in the presence of HATU and N,N-diisopropylethylamine. In the latter step the side-chain amino group was deprotected under mild conditions by stirring in 10% trifluoroacetic acid in DCM at RT for 1 h. After concentrating and freeze-drying from acetonitrile/water, the title compound was obtained.

LC-MS (Method 1): $R_t$=0.64 min; MS (ESIpos): m/z=625 (M+H)$^+$.

Intermediate L100

3-[5-(2-{[2,5-Dioxo-2,5-dihydro-1H-pyrrol-1-yl)acetyl]amino}ethyl)-1,2,4-oxadiazol-3-yl]propanoic acid

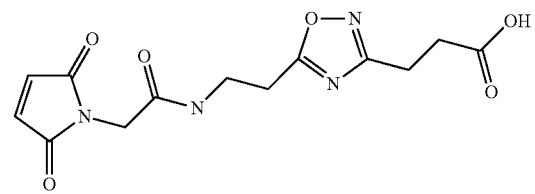 [SMILES: O=C(O)CCc1noc(CCNC(=O)CN2C(=O)C=CC2=O)n1]

To a solution of methyl 3-cyanopropanoate solution (500 mg, 4.42 mmol) in 40 ml of ethanol was added 461 mg (6.60 mmol) of hydroxylamine hydrochloride and 1341.86 mg (13.26 mmol) of triethylamine. The reaction mixture was stirred at 50° C. for 3 h. The mixture was concentrated and the residue was dissolved in ethyl acetate and subsequently washed with water and brine. The organic phase was dried over magnesium sulfate and concentrated. The residue was used without further purification. This gave 400 mg (62% of theory) of the title compound.

To a solution of methyl (4E)-4-{[N-(tert-butoxycarbonyl)-beta-alanyl]amino}-4-(hydroxyimino)butanoate (4.85 g, 33.19 mmol) in 120.0 ml of dioxane was added 6.91 g (36.50 mmol) of N-(tert-butoxycarbonyl)-beta-alanine and 8.22 g (39.82 mmol) of 1,3-dicycloxexylcarbodiimide. The reaction mixture was stirred at room temperature for 3 h. The mixture was concentrated and the residue was dissolved in water and extracted with ethyl acetate. The organic phase was dried over sodium sulfate and concentrated. The residue was purified by flash chromatography. This gave 6.0 g (57% of theory) of the title compound.

A solution of methyl (4E)-4-{[N-(tert-butoxycarbonyl)-beta-alanyl]amino}-4-(hydroxyimino)butanoate (6.0 g, 18.91 mmol) in 100 ml of DMF was stirred at 120° C. for 5 h. Water was added to the mixture and the mixture was extracted with ethyl acetate. The organic phase was dried over sodium sulfate and concentrated. The residue was purified by prep. HPLC. This gave 4 g (71% of theory) of the title compound.

To a solution of 3-(5-{2-[(tert-butoxycarbonyl)amino] ethyl}-1,2,4-oxadiazol-3-yl)propanoic acid (2.0 g, 7.01 mmol) in 30 ml of dichloromethane were added 2.96 g (25.96 mmol) of trifluoroacetic acid. The reaction mixture was stirred at room temperature for 1 h. Water was added to the mixture and the mixture was extracted with dichloromethane. The organic phase was dried over sodium sulfate and concentrated. The residue was used without further purification. This gave 1.50 g (72% of theory) of the title compound.

To a solution of 3-[5-(2-aminoethyl)-1,2,4-oxadiazol-3-yl]propanoic acid (1.5 g, 5.01 mmol) in 25 ml of DMF were added 1.30 g (5.52 mmol) of 1-[2-(2,5-dioxopyrrolidin-1-yl)-2-oxoethyl]-1H-pyrrole-2,5-dione and 1.52 g (15.04 mmol) of triethylamine. The reaction mixture was stirred at room temperature for 1 h. Water was added to the mixture and the mixture was extracted with dichloromethane. The organic phase was dried over sodium sulfate and concentrated. The residue was purified by prep. HPLC. This gave 774 mg (47% of theory) of the title compound.

$^1$H-NMR (300 MHz, DMSO-d$_6$): δ [ppm]=2.67 (t, 2H), 2.91 (t, 2H), 3.03 (t, 2H), 3.46 (q, 2H), 4.28 (s, 2H), 7.01 (s, 2H), 8.37 (t, 1H), 12.28 (bs, 1H).

Intermediate L123

Tert-Butyl [1-fluoro-4-oxobutan-2-yl]carbamate

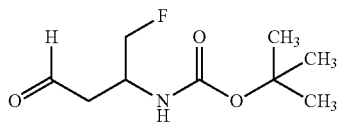

Ethyl 3-[(tert-butoxycarbonyl)amino]-4-fluorobutanoate (150 mg, 602 µmol) (Synth. Com., 1985, 15(5), 377) was initially charged in 12.0 ml of DCM under argon. The reaction mixture was cooled to −78° C., diisobutylaluminium hydride 1M in toluene (1.2 ml, 1.0 M, 1.2 mmol) was added and the mixture stirred for 2 hours. The mixture was carefully quenched with methanol, stirred for 10 minutes and diluted with ethyl acetate. The organic phase was extracted three times with sat. potassium sodium tartrate solution. The organic phase was washed once with sat. NaCl solution and dried over magnesium sulfate. The solvent was evaporated under vacuum and the residue dried under high vacuum. This gave 86.1 mg (67% of theory) of the title compound.

$^1$H-NMR (400 MHz, DMSO-d6) δ[ppm]: 1.37 (s, 9H), 2.58 (m, 2H), 4.18 (m, 1H), 4.31 (dd, 2H), 7.05 (d, 1H), 9.60 (s, 1H)

Intermediate L124

Tert-Butyl N-{(2R)-2-amino-3-oxo-3-[2-(trimethylsilyl)ethoxy]propyl}-N$^2$-(tert-butoxycarbonyl)-L-asparaginate

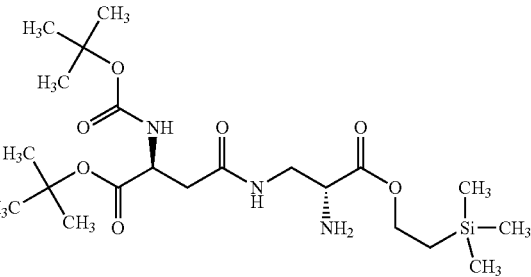

4.0 g (13.8 mmol) of Boc-Asp-OtBu and 1.8 g (15.2 mmol) of N-hydroxysuccinimide were dissolved in 100 mL of ethyl acetate and 3.1 g (15.2 mmol) of 1,3-dicyclohexylcarbodiimide were added at 0° C. The reaction mixture was stirred at 0° C. for 2 hours and then stirred overnight at RT. The reaction mixture was then filtered and evaporated under vacuum. This gave 4.1 g (77% of theory) of the compound-tert-Butyl 4-(2,5-dioxopyrrolidin-1-yl)-N-(tert-butoxycarbonyl)-L-aspartate.

3-Amino-N-[(benzyloxy)carbonyl]-D-alanine (2.53 g, 10.6 mmol) was dissolved in 30 mL of DMF and N,N-diisopropylethylamine (2.74 g, 21.2 mmol) and 1-tert-butyl 4-(2,5-dioxopyrrolidin-1-yl)-N-(tert-butoxycarbonyl)-L-aspartate (4.10 g, 10.6 mmol) were added. The reaction mixture was stirred overnight at RT and evaporated under vacuum. This gave 4.9 g (90% of theory) of the compound (2R)-2-{[(benzyloxy)carbonyl]amino}-3-({(3S)-4-tert-butoxy-3-[(tert-butoxycarbonyl)amino]-4-oxobutanoyl}amino)propanoic acid.

(2R)-2-{[(Benzyloxy)carbonyl]amino}-3-({(3S)-4-tert-butoxy-3-[(tert-butoxycarbonyl)amino]-4-oxobutanoyl}amino)propanoic acid (4.90 g, 9.62 mmol) was dissolved in 100 ml of acetonitrile and pyridine (1.6 ml, 19 mmol), 2-(trimethylsilyl)ethanol (1.7 ml, 12 mmol) and dicyclohexylcarbodiimide (2.38 g, 11.5 mmol) were added at RT. The reaction mixture was stirred at 0° C. for 1 hour and then stirred overnight at RT. The reaction mixture was then filtered and evaporated under vacuum. The residue was purified by prep. RP-HPLC. The solvents were evaporated under vacuum and the residue dried under high vacuum. This gave 3.9 g (66% of theory) of the compound tert-butyl N-{(2R)-2-{[(benzyloxy)carbonyl]amino}-3-oxo-3-[2-(trimethylsilyl)ethoxy]propyl}-N2-(tert-butoxycarbonyl)-L-asparaginate. tert-Butyl N-{(2R)-2-{[(benzyloxy)carbonyl]amino}-3-oxo-3-[2-(trimethylsilyl)ethoxy]propyl}-N$^2$-(tert-butoxycarbonyl)-L-asparaginate (3.80 g, 6.23 mmol) was dissolved in 120 ml of methanol and 380 mg of palladium on carbon (10%) were added. The reaction mixture was hydrogenated with hydrogen at RT and standard pressure for 2 hours and then filtered. The solvent was removed under vacuum. This gave 2.9 g (84% of theory) of the title compound.

$^1$H-NMR (400 MHz, DMSO-$d_6$): δ [ppm]=0.04 (s, 9H), 0.97 (m, 2H), 1.38 (s, 9H), 1.39 (s, 9H), 1.89 (bs, 2H), 2.43 (m, 1H), 3.18 (m, 3H), 3.38 (m, 1H), 4.11 (m, 3H), 6.93 (d, 1H), 7.91 (bt, 1H)

Intermediate L125

Trifluoroacetic acid—tert-butyl N-(2-aminoethyl)-N$^2$-(bromoacetyl)-D-alpha-glutaminate (1:1)

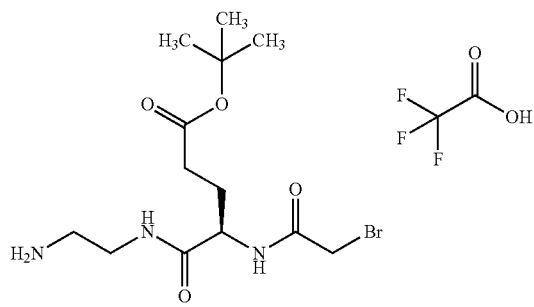 [SMILES: CC(C)(C)OC(=O)CC[C@@H](NC(=O)CBr)C(=O)NCCN ; O=C(O)C(F)(F)F]

This intermediate was prepared by classical methods of peptide chemistry, starting from (2R)-2-{[(benzyloxy)carbonyl]amino}-5-tert-butoxy-5-oxopentanoic acid and tert-butyl (2-aminoethyl)carbamate.

LC-MS (Method 1): $R_t$=0.49 min; MS (ESIpos): m/z=366 and 368 (M+H)$^+$.

Intermediate F104

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{[(2,5-dioxo-2,5-dihydro-1H-pyrrol-1-yl)acetyl]amino}ethyl)butanamide (1:1)

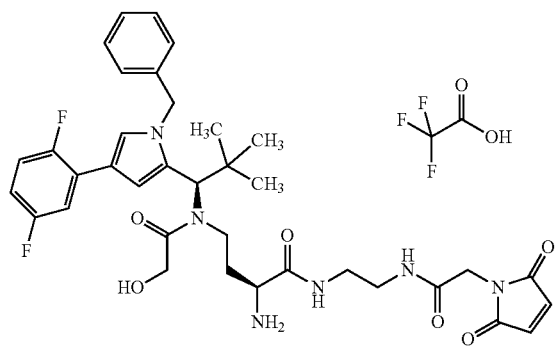 [SMILES: CC(C)(C)[C@H](c1cc(-c2cc(F)ccc2F)cn1Cc1ccccc1)N(CC[C@H](N)C(=O)NCCNC(=O)CN1C(=O)C=CC1=O)C(=O)CO ; O=C(O)C(F)(F)F]

10 mg (0.014 mmol) of Intermediate C53 were dissolved in 3.3 ml of DMF, and 8.5 mg (0.027 mmol) of Intermediate L1, 7.8 mg (0.02 mmol) of HATU and 12 µl of N,N-diisopropylethylamine were added. The reaction was stirred at RT for 15 min and then concentrated. The residue was purified by preparative HPLC giving, after lyophilization, 5.6 mg (38% of theory) of the protected intermediate.

LC-MS (Method 1): $R_t$=1.32 min; MS (ESIpos): m/z=915 (M+H)$^+$.

5.6 mg (0.006 mmol) of this intermediate were taken up in 2 ml of DMF, and 69 mg (0.61 mmol) of 1,4-diazabicyclo [2.2.2]octane were added. The reaction was treated in an ultrasonic bath for 2 h. 35 µl of acetic acid were then added and the reaction was concentrated under high vacuum. The residue was purified by preparative HPLC. This gave 2.4 mg (48% of theory) of the title compound.

LC-MS (Method 1): $R_t$=0.84 min; MS (EIpos): m/z=693 [M+H]$^+$.

HPLC (Method 11): $R_t$=1.91 min;

Alternatively, the title compound was also prepared from Intermediate C58. 15 mg (0.023 mmol) of Intermediate C58 were initially reacted with 11 mg (0.036 mmol) of Intermediate L1 in the presence of 13 mg (0.034 mmol) of HATU and 10 µl of N,N-diisopropylethylamine. After 60 min of stirring at RT, the mixture was concentrated and the residue was purified by preparative HPLC. This gave 12.3 mg (63% of theory) of the protected intermediate.

LC-MS (Method 1): $R_t$=1.3 min; MS (EIpos): m/z=837 [M+H]$^+$.

In the second step, this intermediate was dissolved in 3 ml of 2,2,2-trifluoroethanol. 12 mg (0.088 mmol) of zinc chloride were added, and the reaction was stirred at 50° C. for 2 h. 26 mg (0.088 mmol) of ethylenediamine-N,N,N',N'-tetraacetic acid and 2 ml of a 0.1% strength aqueous trifluoroacetic acid solution were then added. The reaction was purified by preparative HPLC. Concentration of the appropriate fractions and lyophilization of the residue from acetonitrile/water gave 8.1 mg (68% of theory) of the title compound.

LC-MS (Method 1): $R_t$=0.89 min; MS (ESIpos): m/z=693 (M+H)$^+$.

Intermediate F119

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-{2-[(bromoacetyl)amino]ethyl}butanamide (1:1)

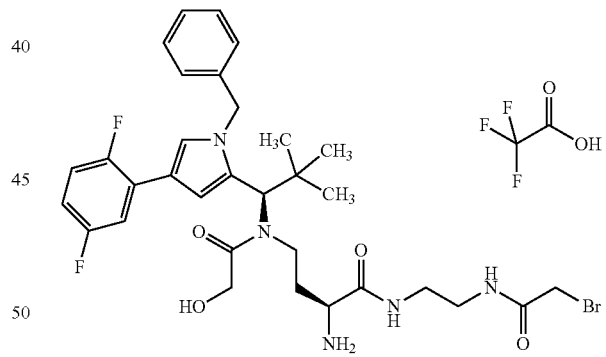

29 mg (0.044 mmol) of Intermediate C58 were taken up in 3.4 ml of DMF, and 36 mg (0.087 mmol) of Intermediate L52, 25 mg (0.065 mmol) of HATU and 19 µl of N,N-diisopropylethylamine were added. After 60 min of stirring at RT, the mixture was concentrated and the residue was purified by preparative HPLC. This gave 26.4 mg (73% of theory) of the intermediate.

LC-MS (Method 1): $R_t$=1.34 min; MS (ESIpos): m/z=820 and 822 (M+H)$^+$.

This intermediate was dissolved in 3 ml of 2,2,2-trifluoroethanol. 6.5 mg (0.048 mmol) of zinc chloride were added, and the reaction was stirred at 50° C. for 4 h. 13.9 mg (0.048 mmol) of ethylenediamine-N,N,N',N'-tetraacetic acid and 2 ml of a 0.1% strength aqueous trifluoroacetic acid solution were added. The reaction was purified by preparative HPLC.

Concentration of the appropriate fractions and lyophilization of the residue from acetonitrile/water gave 14.4 mg (58% of theory) of the title compound.

LC-MS (Method 1): $R_t$=0.88 min; MS (ESIpos): m/z=676 and 678 (M+H)$^+$.

Intermediate F127

Trifluoroacetic acid/(2S)-2-amino-4-({(1R)-1-[1-benzyl-4-(2,5-difluorophenyl)-1H-pyrrol-2-yl]-2,2-dimethylpropyl}[(2S)-2-methoxypropanoyl]amino)-N-(2-{[(2,5-dioxo-2,5-dihydro-1H-pyrrol-1-yl)acetyl]amino}ethyl)butanamide (1:1)

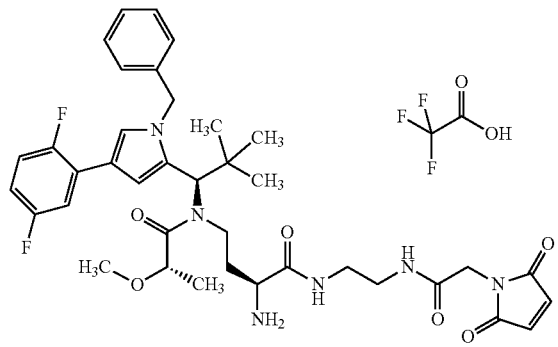 [SMILES: CO[C@@H](C)C(=O)N(CC[C@H](N)C(=O)NCCNC(=O)CN1C(=O)C=CC1=O)[C@@H](c1cc(-c2cc(F)ccc2F)cn1Cc1ccccc1)C(C)(C)C ; O=C(O)C(F)(F)F]

12 mg (0.015 mmol) of Intermediate C59 were dissolved in 2.4 ml of DMF, and 14.6 mg (0.046 mmol) of Intermediate L1, 6 mg (0.031 mmol) of 1-(3-dimethylaminopropyl)-3-ethylcarbodiimide hydrochloride, 5.9 mg (0.039 mmol) of 1-hydroxy-1H-benzotriazole hydrate and 8 µl of N,N-diisopropylethylamine were added. After 1 h of stirring at RT, the mixture was concentrated and the residue was purified by preparative HPLC. This gave 11 mg (70% of theory) of this intermediate.

LC-MS (Method 1): $R_t$=1.34 min; MS (ESIpos): m/z=942 (M+H)$^+$.

11 mg (0.011 mmol) of this intermediate were taken up in 2 ml of DMF, and 123 mg (1.1 mmol) of 1,4-diazabicyclo[2.2.2]octane were added. The reaction was treated in an ultrasonic bath for 2 h. 63 µl of acetic acid were then added and the reaction was concentrated under high vacuum. The residue was purified by preparative HPLC. This gave 2 mg (22% of theory) of the title compound.

LC-MS (Method 1): $R_t$=0.89 min; MS (EIpos): m/z=721 [M+H]$^+$.

HPLC (Method 11): $R_t$=1.95 min;

Intermediate F153

Trifluoroacetic acid/(2S)-2-amino-4-({(1R)-1-[1-benzyl-4-(2,5-difluorophenyl)-1H-pyrrol-2-yl]-2,2-dimethylpropyl}[(2S)-2-hydroxypropanoyl]amino)-N-(2-{[(2,5-dioxo-2,5-dihydro-1H-pyrrol-1-yl)acetyl]amino}ethyl)butanamide (1:1)

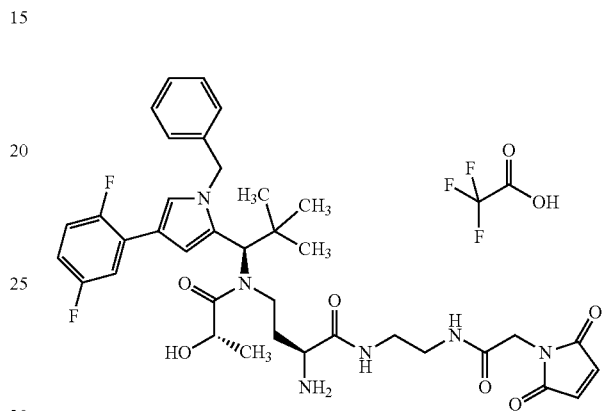

The synthesis was carried out analogously to Intermediate F104 from Intermediate C60.

LC-MS (Method 1): $R_t$=1.1 min; MS (ESIpos): m/z=707 (M+H)$^+$.

Intermediate F155

N$^6$—(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-N$^2$—{N-[6-(2,5-dioxo-2,5-dihydro-1H-pyrrol-1-yl)hexanoyl]-L-valyl-L-alanyl}-L-lysine/trifluoroacetic acid (1:1)

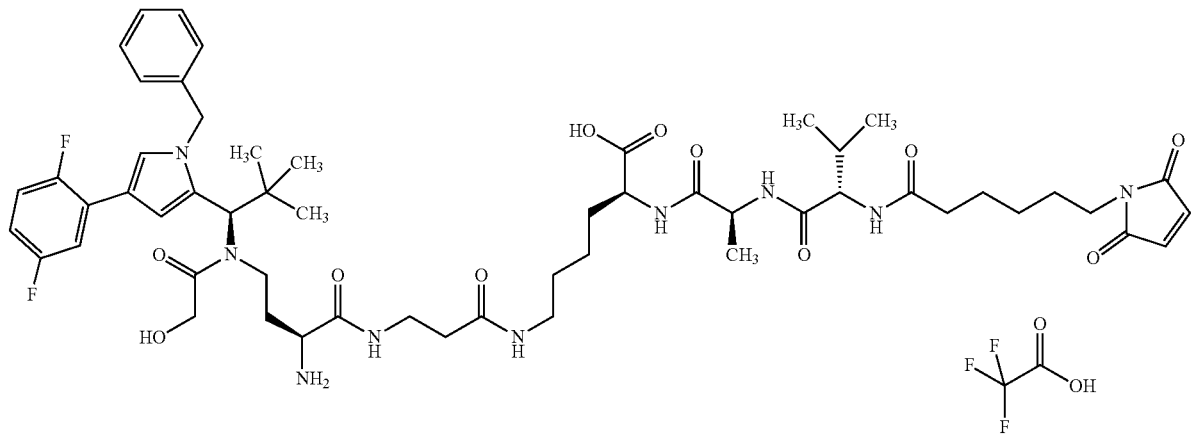 [SMILES: CC(C)[C@H](NC(=O)CCCCCN1C(=O)C=CC1=O)C(=O)N[C@@H](C)C(=O)N[C@@H](CCCCNC(=O)CCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The title compound was prepared by coupling of 14 mg (0.019 mmol) of Intermediate C61 with 15 mg (0.021 mmol) of Intermediate L61 in the presence of 8.7 mg (0.023 mmol) of HATU and 17 µl of N,N-diisopropylethylamine and subsequent deprotection with zinc chloride in trifluoroethanol as described for Intermediate F119. Purification by preparative HPLC gave 13 mg (59% of theory over 2 steps) of the title compound.

LC-MS (Method 1): $R_t$=0.86 min; MS (ESIpos): m/z=1076 (M+H)$^+$.

Intermediate F173

N-[6-(2,5-Dioxo-2,5-dihydro-1H-pyrrol-1-yl)hexanoyl]-L-valyl-L-alanyl-N-[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-L-glutamine/trifluoroacetic acid (1:1)

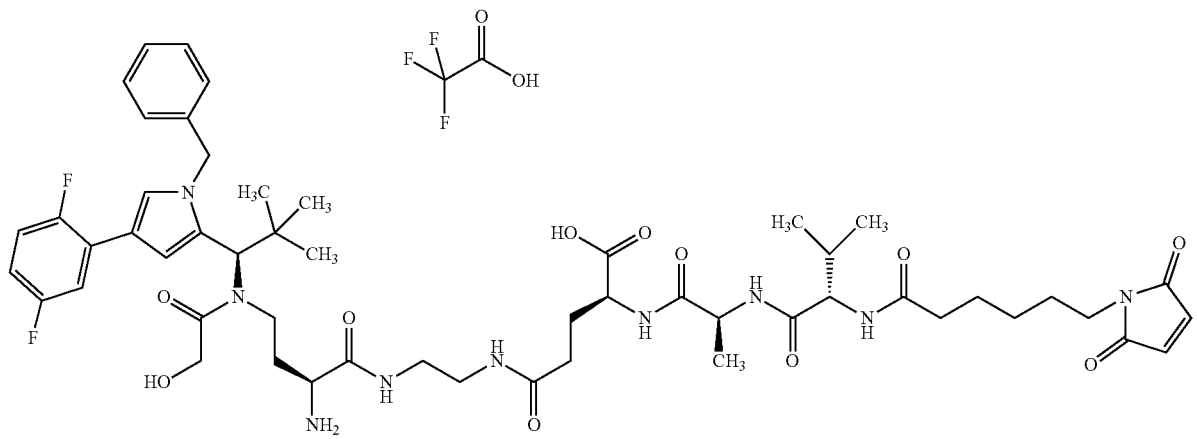 [SMILES: CC(C)[C@H](NC(=O)CCCCCN1C(=O)C=CC1=O)C(=O)N[C@@H](C)C(=O)N[C@@H](CCC(=O)NCCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The title compound was prepared from 15 mg (0.018 mmol) of Intermediate C64 by coupling with 12 mg (0.02 mmol) of Intermediate L63 in the presence of 7.7 mg (0.02 mmol) of HATU and 16 µl of N,N-diisopropylethylamine and subsequent deprotection with zinc chloride in trifluoroethanol as described for Intermediate F119. Purification by preparative HPLC gave 12 mg (58% of theory over 2 steps) of the title compound.

LC-MS (Method 1): $R_t$=0.91 min; MS (EIpos): m/z=1048 [M+H]$^+$.

Intermediate F178

Trifluoroacetic acid/(1R,2S)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-N-{2-[(bromoacetyl)amino]ethyl}cyclopentanecarboxamide (1:1)

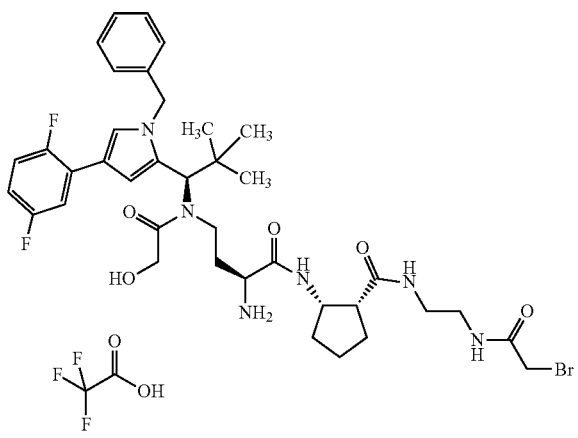 [SMILES: CC(C)(C)[C@H](c1cc(-c2cc(F)ccc2F)cn1Cc1ccccc1)N(CC[C@H](N)C(=O)N[C@H]1CCC[C@H]1C(=O)NCCNC(=O)CBr)C(=O)CO ; O=C(O)C(F)(F)F]

The title compound was prepared analogously to Intermediate F177 using, instead of Intermediate L1, the Intermediate L52.

LC-MS (Method 1): $R_t$=0.89 min; MS (EIpos): m/z=787 and 789 [M+H]$^+$.

Intermediate F180

N-[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-N2-[(2,5-dioxo-2,5-dihydro-1H-pyrrol-1-yl)acetyl]-L-glutamine/trifluoroacetic acid (1:1)

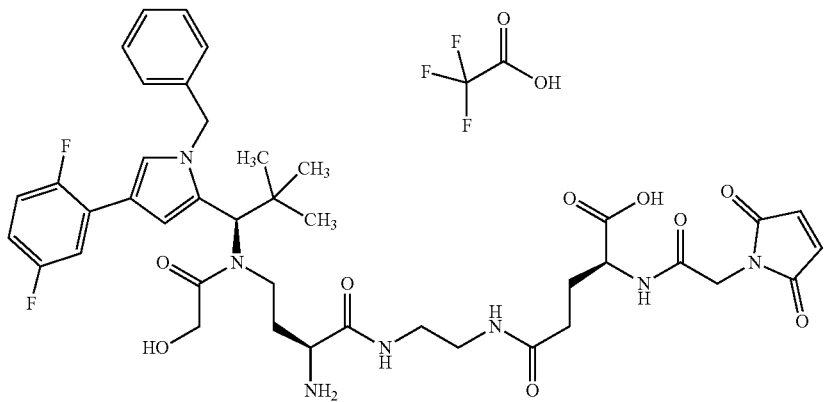 [SMILES: CC(C)(C)[C@H](c1cc(-c2cc(F)ccc2F)cn1Cc1ccccc1)N(CC[C@H](N)C(=O)NCCNC(=O)CC[C@H](NC(=O)CN1C(=O)C=CC1=O)C(=O)O)C(=O)CO ; O=C(O)C(F)(F)F]

The title compound was prepared by coupling of 9.6 mg (0.012 mmol) of Intermediate C64 with 5 mg (0.013 mmol) of Intermediate L64 in the presence of 7 mg (0.018 mmol) of HATU and 6 µl of N,N-diisopropylethylamine and subsequent deprotection with zinc chloride in trifluoroethanol as described for Intermediate F119. Purification by preparative HPLC gave 3.1 mg (28% of theory over 2 steps) of the title compound.

LC-MS (Method 1): $R_t$=0.85 min; MS (EIpos): m/z=822 [M+H]$^+$.

Intermediate F192

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[(2,5-dioxo-2,5-dihydro-1H-pyrrol-1-yl)acetyl]amino}-L-alanine/trifluoroacetic acid (1:1)

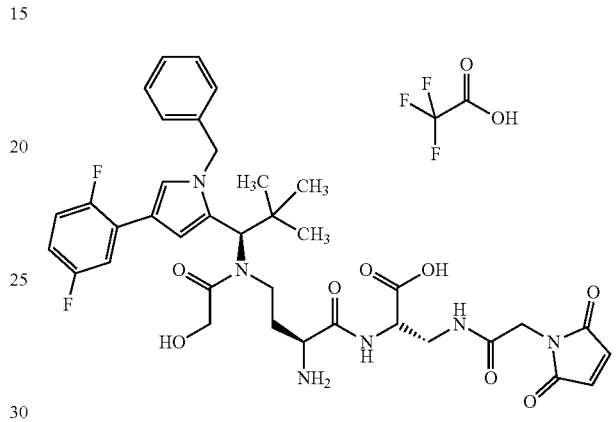

60 mg (0.091 mmol) of Intermediate C58 were taken up in 8 ml of DMF and coupled with 45 mg (0.100 mmol) of Intermediate L65 in the presence of 42 mg (0.11 mmol) of HATU and 64 µl of N,N-diisopropylethylamine. After purification by preparative HPLC, the intermediate was taken up in 10 ml of ethanol and hydrogenated over 10% palladium on activated carbon at RT under hydrogen standard pressure for 45 min. The catalyst was then filtered off, the solvent was removed under reduced pressure and the product was purified by preparative HPLC. Lyophilization from acetonitrile/water 1:1 gave 24.5 mg (31% of theory over 2 steps) of 2-(trimethylsilyl)ethyl 3-amino-N-[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-L-alaninate.

LC-MS (Method 1): $R_t$=1.17 min; MS (EIpos): m/z=844 [M+H]$^+$.

The title compound was then prepared by coupling of 10 mg (0.012 mmol) of this intermediate with 2 mg (0.013 mmol) of commercially available (2,5-dioxo-2,5-dihydro-1H-pyrrol-1-yl)acetic acid intermediate in the presence of 5.4 mg (0.014 mmol) of HATU and 8 μl of N,N-diisopropylethylamine and subsequent deprotection with zinc chloride in trifluoroethanol as described for Intermediate F119. Purification by preparative HPLC gave 3.5 mg (33% of theory over 2 steps) of the title compound.

LC-MS (Method 1): $R_t$=0.81 min; MS (ESIpos): m/z=737 (M+H)$^+$.

Intermediate F193

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[(2,5-dioxo-2,5-dihydro-1H-pyrrol-1-yl)acetyl]amino}-D-alanine/trifluoroacetic acid (1:1)

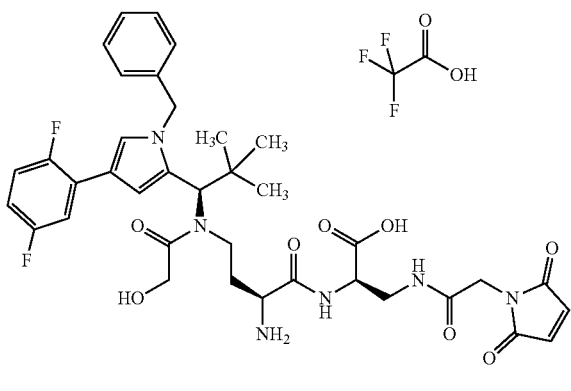 [SMILES: CC(C)(C)[C@H](c1cc(-c2cc(F)ccc2F)cn1Cc1ccccc1)N(CC[C@H](N)C(=O)N[C@H](CNC(=O)CN1C(=O)C=CC1=O)C(=O)O)C(=O)CO ; O=C(O)C(F)(F)F]

The synthesis of the title compound was carried out analogously to Intermediate F192 from 3-{[(benzyloxy)carbonyl]amino}-N-(tert-butoxycarbonyl)-D-alanine/N-cyclohexylcyclohexanamine (1:1).

LC-MS (Method 1): $R_t$=0.87 min; MS (ESIpos): m/z=737 (M+H)$^+$.

Intermediate F194

N-{5-[(2,5-Dioxopyrrolidin-1-yl)oxy]-5-oxopentanoyl}-L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide

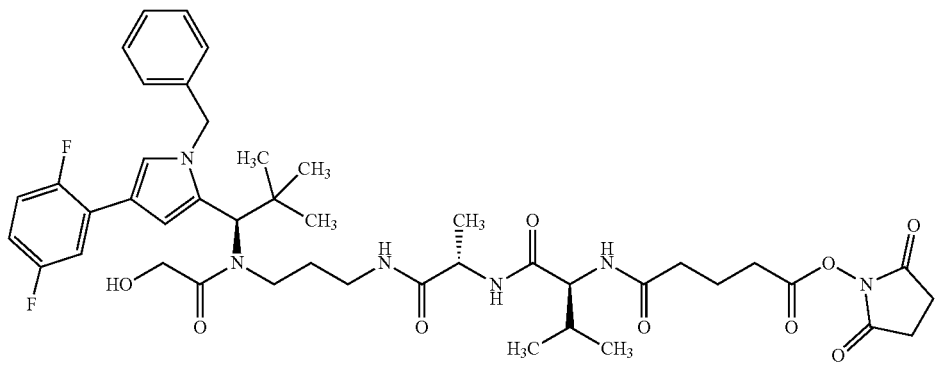 [SMILES: CC(C)[C@H](NC(=O)CCCC(=O)ON1C(=O)CCC1=O)C(=O)N[C@@H](C)C(=O)NCCCN(C(=O)CO)[C@@H](c1cc(-c2cc(F)ccc2F)cn1Cc1ccccc1)C(C)(C)C]

The title compound was prepared from Example M9 first by coupling with N-[(benzyloxy)carbonyl]-L-valyl-L-alanine in the presence of HATU and N,N-diisopropylethylamine. In the next step, the Z protective group was removed by hydrogenating for 1 hour over 10% palladium on activated carbon at RT under hydrogen standard pressure and then converting the deprotected intermediate by reaction with 1,1'-[(1,5-dioxopentane-1,5-diyl)bis(oxy)]dipyrrolidine-2,5-dione into the title compound.

LC-MS (Method 1): $R_t$=1.19 min; MS (ESIpos): m/z=851 [M+H]$^+$.

Intermediate F207

N⁶—(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-N²—{N-[(2,5-dioxo-2,5-dihydro-1H-pyrrol-1-yl)acetyl]-L-valyl-L-alanyl}-L-lysine/trifluoroacetic acid (1:1)

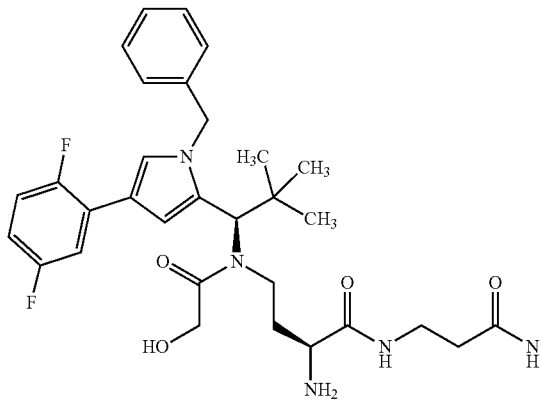
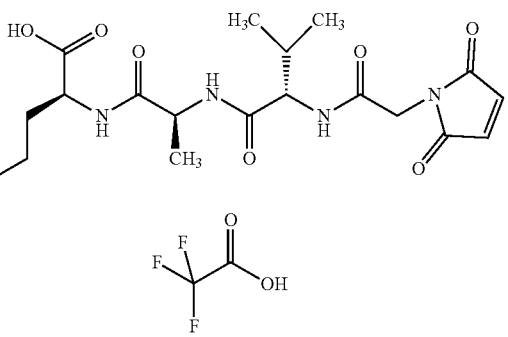

The title compound was prepared analogously to Intermediate F155.

LC-MS (Method 1): $R_t$=0.81 min; MS (ESIpos): m/z=1020 (M+H)⁺.

Intermediate F213

Trifluoroacetic acid/3-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)-N-(2-{[(2,5-dioxo-2,5-dihydro-1H-pyrrol-1-yl)acetyl]amino}ethyl)propanamide (1:1)

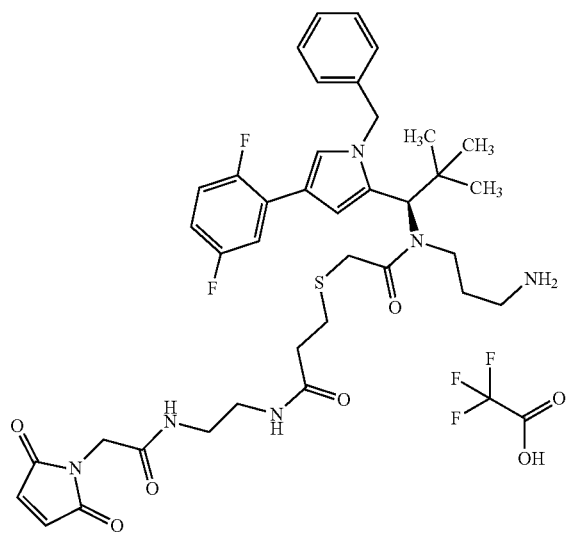

27.5 mg (0.04 mmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged together with 15.9 mg (0.05 mmol) of trifluoroacetic acid/N-(2-aminoethyl)-2-(2,5-dioxo-2,5-dihydro-1H-pyrrol-1-yl)acetamide (1:1) (Intermediate L1) in 1.8 ml of acetonitrile. 32.4 mg (0.31 mmol) of N,N-diisopropylethylamine were then added, and 32.4 mg (0.05 mmol) of T3P (50% in ethyl acetate) were added dropwise. The reaction mixture was stirred at RT overnight. The reaction mixture was purified directly by preparative RP-HPLC (column: Reprosil 125×30; 10μ, flow rate: 50 ml/min, MeCN/water). The solvents were evaporated under reduced pressure and the residue was dried under high vacuum. This gave 11.9 mg (35% of theory) of the compound 2-(trimethylsilyl)ethyl [13-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,7,12-trioxo-10-thia-3,6,13-triazahexadecan-16-yl]carbamate.

LC-MS (Method 1): $R_t$=1.39 min; MS (ESIpos): m/z=881 (M+H)⁺.

11.9 mg (0.01 mol) of 2-(trimethylsilyl)ethyl [13-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,7,12-trioxo-10-thia-3,6,13-triazahexadecan-16-yl]carbamate were dissolved in 1.0 ml of trifluoroethanol, and 5.5 mg (0.04 mmol) of zinc dichloride were added. The reaction mixture was stirred at 50° C. overnight. 11.8 mg (0.04 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 7.4 mg (60% of theory) of the title compound.

LC-MS (Method 5): $R_t$=2.75 min; MS (ESIpos): m/z=737 (M+H)⁺.

Intermediate F216

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]-L-cysteinyl-beta-alanine/trifluoroacetic acid (1:1)

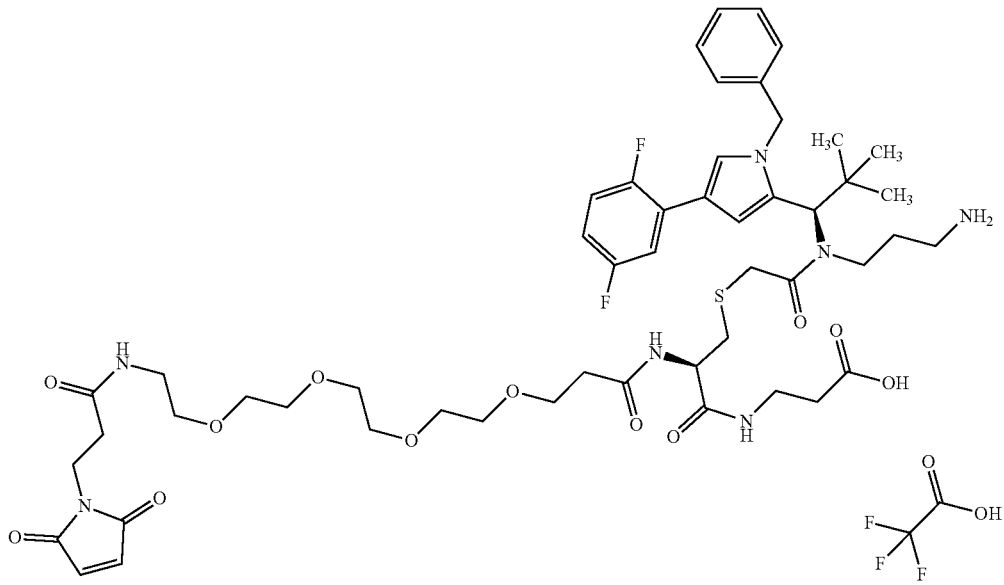 [SMILES: CC(C)(C)[C@H](c1cc(-c2cc(F)ccc2F)cn1Cc1ccccc1)N(CCCN)C(=O)CSC[C@H](NC(=O)CCOCCOCCOCCOCCNC(=O)CCN1C(=O)C=CC1=O)C(=O)NCCC(=O)O ; O=C(O)C(F)(F)F]

Under argon, 30.2 mg (0.06 mmol) of N,N'-bis[(benzyloxy)carbonyl]-L-cysteine were initially charged in 2.0 ml of water and 2.0 ml of isopropanol, and 56.7 mg (0.20 mmol) of TCEP were added. The reaction mixture was stirred at RT for 30 min. 50.0 mg (0.08 mmol) of 2-(trimethylsilyl)ethyl {3-[{(1R)-1-[1-benzyl-4-(2,5-difluorophenyl)-1H-pyrrol-2-yl]-2,2-dimethyl-propyl}(chloroacetyl)amino]propyl}carbamate (Intermediate C70), dissolved in 2.0 ml of isopropanol, and 122.2 mg (0.48 mmol) of 1,8-diazabicyclo[5.4.0]undec-7-ene were then added, and the reaction mixture was stirred at 50° C. for 7 h. Another 122.2 mg (0.48 mmol) of 1,8-diazabicyclo[5.4.0]undec-7-ene were then added, and the reaction mixture was stirred at 50° C. for 1 h. The mixture was diluted with ethyl acetate and the organic phase was extracted with water and saturated sodium bicarbonate solution and washed with saturated NaCl solution. The organic phase was dried over magnesium sulphate and the solvent was evaporated under reduced pressure. The residue was purified by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 43.1 mg (64% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteine.

LC-MS (Method 1): $R_t$=1.46 min; MS (ESIpos): m/z=851 (M+H)$^+$.

16.5 mg (0.05 mmol) of 4-methylbenzenesulphonic acid/benzyl beta-alaninate (1:1) were initially charged together with 14.0 mg (0.11 mmol) of N,N-diisopropylethylamine in 1.5 ml of acetonitrile. The reaction mixture was stirred at RT for 3 min, and 30.8 mg (0.04 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteine dissolved in 1.5 ml of acetonitrile, 23.4 mg (0.18 mmol) of N,N-diisopropylethylamine and 29.9 mg (0.05 mmol) of T3P (50% in ethyl acetate) were then added. The reaction mixture was stirred at RT overnight. Water was added, and the reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. The compound obtained was benzyl S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteinyl-beta-alaninate.

LC-MS (Method 1): $R_t$=1.59 min; MS (ESIpos): m/z=1012 (M+H)$^+$.

43.8 mg (43.3 µmol) of benzyl S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteinyl-beta-alaninate were dissolved in 8.0 ml of ethanol, 4.4 mg of palladium on activated carbon (10%) were added and the mixture was hydrogenated at RT and standard pressure overnight. The reaction mixture was filtered through a cardboard filter and the filter cake was washed with ethanol. The solvent was evaporated under reduced pressure. Two more times, the residue was treated as just described. The residue was purified by preparative RP-HPLC (column:

Reprosil 250×30; 10μ, flow rate: 50 ml/min, MeCN/water, 0.1% TFA). The solvents were evaporated under reduced pressure and the residue was dried under high vacuum. This gave 14.5 mg (37% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl-beta-alanine/trifluoroacetic acid (1:1).

LC-MS (Method 1): $R_t$=1.08 min; MS (ESIpos): m/z=788 (M+H)$^+$.

14.5 mg (16.1 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl-beta-alanine/trifluoroacetic acid (1:1) were initially charged together with 9.1 mg (17.7 μmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide in 1.0 ml of DMF, and 4.9 mg (48.2 μmol) of 4-methylmorpholine were added. The reaction mixture was stirred at RT overnight, and 3.4 mg (0.06 mmol) of acetic acid were then added. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 4.9 mg (50% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl-beta-alanine/trifluoroacetic acid (1:1).

LC-MS (Method 1): $R_t$=1.28 min; MS (ESIpos): m/z=1186 (M+H)$^+$.

14.1 mg (11.9 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[19-(2,5-dioxo-2,5-dihydro-1H-pyrrol-1-yl)-17-oxo-4,7,10,13-tetraoxa-16-azanonadecan-1-oyl]-L-cysteinyl-beta-alanine/trifluoroacetic acid (1:1) were dissolved in 1.5 ml of trifluoroethanol, and 9.7 mg (71.3 μmol) of zinc dichloride were added. The reaction mixture was stirred at 50° C. for 3 h. Another 9.7 mg (71.3 μmol) of zinc dichloride were added and the reaction mixture was stirred at 50° C. for 3 h. Another 9.7 mg (71.3 μmol) of zinc dichloride were added and the reaction mixture was stirred at 70° C. for 4 h. 20.8 mg (0.07 mmol) of ethylenediamine-N,N,N',N'-tetraacetic acid were added and the reaction mixture was stirred for 10 min, and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was lyophilized. This gave 6.2 mg (44% of theory) of the title compound.

LC-MS (Method 1): $R_t$=0.82 min; MS (ESIpos): m/z=1042 (M+H)$^+$.

Intermediate F217

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-[(2,5-dioxo-2,5-dihydro-1H-pyrrol-1-yl)acetyl]-L-cysteine/trifluoroacetic acid (1:1)

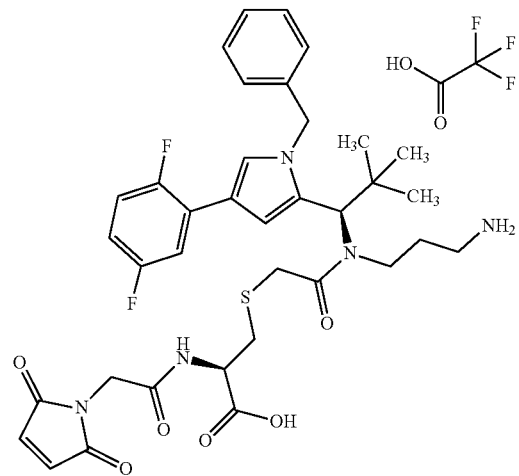

Under argon, 7.5 mg (0.05 mmol) of (2,5-dioxo-2,5-dihydro-1H-pyrrol-1-yl)acetic acid were initially charged in 1.5 ml of DMF, and 7.5 mg (0.05 mmol) of HOBt, 15.5 mg (0.05 mmol) of TBTU and 6.2 mg (0.05 mmol) of N,N-diisopropylethylamine were added. The reaction mixture was stirred at RT for 10 min. 40.0 mg (0.05 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71), dissolved in 1.5 ml of DMF, and 18.7 mg (0.14 mmol) of N,N-diisopropylethylamine were then added, and the reaction mixture was stirred at RT overnight. The reaction mixture was purified directly by preparative RP-F1PLC (column: Reprosil 250×30; 10μ, flow rate: 50 ml/min, MeCN/water, 0.1% TFA). The solvents were evaporated under reduced pressure and the residue was dried under high vacuum. This gave 11.2 mg (25% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(2,5-dioxo-2,5-dihydro-1H-pyrrol-1-yl)acetyl]-L-cysteine.

LC-MS (Method 1): $R_t$=1.37 min; MS (ESIpos): m/z=854 (M+H)$^+$.

10.9 mg (12.8 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(2,5-dioxo-2,5-dihydro-1H-pyrrol-1-yl)acetyl]-L-cysteine were dissolved in 2.0 ml of trifluoroethanol, and 10.4 mg (76.6 μmol) zinc dichloride were added. The reaction mixture was stirred at 50° C. for 4 h. 22.4 mg (0.08 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was lyophilized. This gave 7.5 mg (65% of theory) of the title compound.

LC-MS (Method 1): $R_t$=0.92 min; MS (ESIpos): m/z=710 (M+H)$^+$.

Intermediate F241

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{[N-(bromoacetyl)glycyl]amino}ethyl)butanamide (1:1)

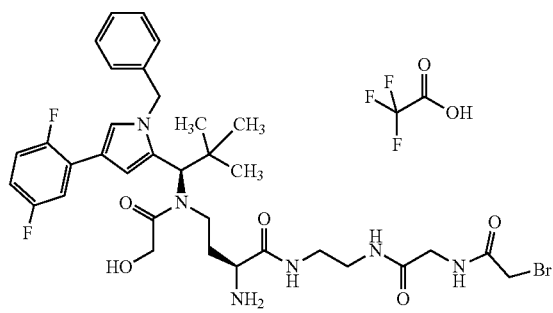 [SMILES: CC(C)(C)[C@H](c1cc(-c2cc(F)ccc2F)cn1Cc1ccccc1)N(CC[C@H](N)C(=O)NCCNC(=O)CNC(=O)CBr)C(=O)CO ; O=C(O)C(F)(F)F]

The title compound was prepared from Intermediate C66 by coupling with commercially available 1-(2-bromoacetoxy)pyrrolidine-2,5-dione and subsequent deblocking with zinc chloride.

LC-MS (Method 1): $R_t$=0.84 min; MS (EIpos): m/z=733 and 735 [M+H]$^+$.

Intermediate F242

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(3-{[(2,5-dioxo-2,5-dihydro-1H-pyrrol-1-yl)acetyl]amino}propyl)butanamide (1:1)

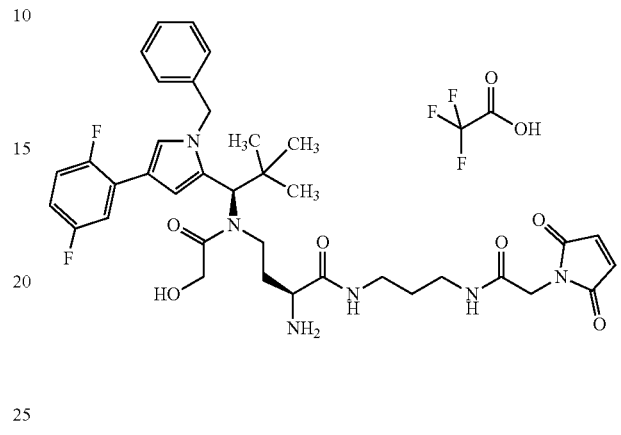

The synthesis of the title compound was carried out analogously to Intermediate F104.

LC-MS (Method 1): $R_t$=0.84 min; MS (ESIpos): m/z=707 (M+H)$^+$.

Intermediate F243

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-[2-(2-{[(2,5-dioxo-2,5-dihydro-1H-pyrrol-1-yl)acetyl]amino}ethoxy)ethyl]butanamide (1:1)

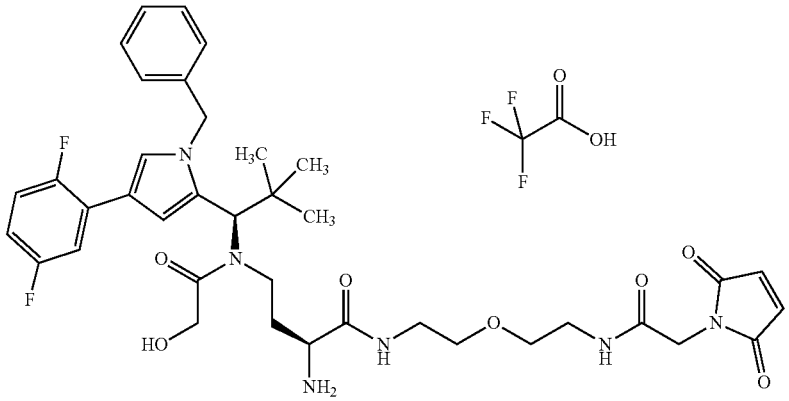 [SMILES: CC(C)(C)[C@H](c1cc(-c2cc(F)ccc2F)cn1Cc1ccccc1)N(CC[C@H](N)C(=O)NCCOCCNC(=O)CN1C(=O)C=CC1=O)C(=O)CO ; O=C(O)C(F)(F)F]

The synthesis of the title compound was carried out analogously to Intermediate F242.

LC-MS (Method 1): $R_t$=0.81 min; MS (ESIpos): m/z=737 (M+H)$^+$.

Intermediate F245

Trifluoroacetic acid/N-{(2S)-2-amino-4-[{(1R)-1-[1-benzyl-4-(2,5-difluorophenyl)-1H-pyrrol-2-yl]-2,2-dimethylpropyl}(glycoloyl)amino]butyl}-N'-(2-{[(2,5-dioxo-2,5-dihydro-1H-pyrrol-1-yl)acetyl]amino}ethyl)succinamide (1:1)

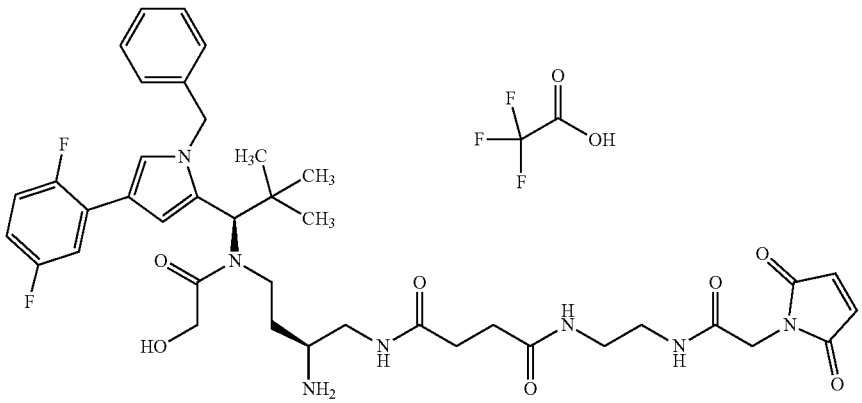 [SMILES: CC(C)(C)[C@H](c1cc(-c2cc(F)ccc2F)cn1Cc1ccccc1)N(CC[C@H](N)CNC(=O)CCC(=O)NCCNC(=O)CN1C(=O)C=CC1=O)C(=O)CO ; O=C(O)C(F)(F)F]

The title compound was prepared by coupling of 10 mg (0.0135 mmol) of Intermediate C65 with 8 mg (0.027 mmol) of Intermediate L1 in 8 ml of DMF in the presence of 15 mg (0.04 mmol) of HATU and 9 μl of N,N-diisopropylethylamine and subsequent deprotection with zinc chloride in trifluoroethanol as described for Intermediate F119. Purification by preparative HPLC gave 8.8 mg (58% of theory over 2 steps) of the title compound.

LC-MS (Method 1): $R_t$=0.84 min; MS (ESIpos): m/z=778 (M+H)$^+$.

Intermediate F247

Trifluoroacetic acid/methyl 4-[(2-{[2-({(2S)-2-amino-4-[{(1R)-1-[1-benzyl-4-(2,5-difluorophenyl)-1H-pyrrol-2-yl]-2,2-dimethyl-propyl}(glycoloyl)amino]butanoyl}amino)ethyl]amino}-2-oxoethyl)amino]-2-bromo-4-oxobutanoate (1:1)

14 mg (0.018 mmol) of Intermediate C66 were dissolved in 14 ml of DCM, and with 10.1 mg (0.037 mmol) of 2-bromo-1-ethylpyridinium tetrafluoroborate (BEP) and, a little at a time, a total of 250 μl of pyridine were added, the pH being kept between 5 and 6. The pH was then adjusted to 4 with acetic acid, the reaction was concentrated and the residue was purified by preparative HPLC. Combination of the appropriate fractions, lyophilization and drying gave 4 mg (21% of theory) of the protected intermediate, which were then deprotected at the amino function with zinc chloride. HPLC purification and lyophilization gave 3 mg (72% of theory) of the title compound as a colourless foam.

LC-MS (Method 1): $R_t$=0.88 min; MS (ESIpos): m/z=805 and 807 (M+H)$^+$.

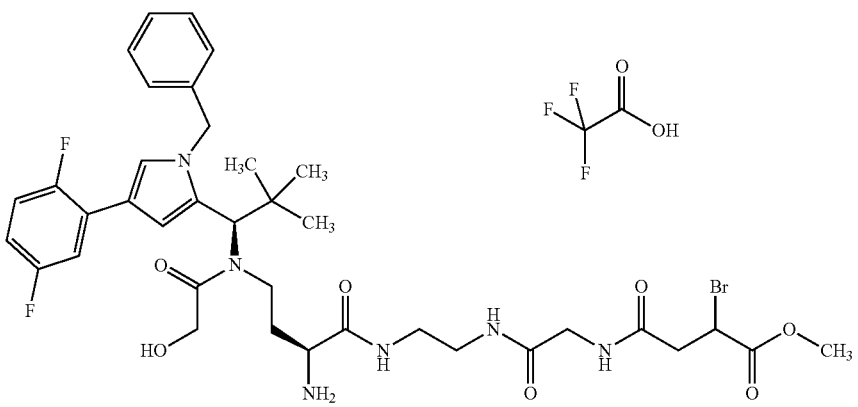 [SMILES: COC(=O)C(Br)CC(=O)NCC(=O)NCCNC(=O)[C@@H](N)CCN(C(=O)CO)[C@@H](c1cc(-c2cc(F)ccc2F)cn1Cc1ccccc1)C(C)(C)C ; O=C(O)C(F)(F)F]

Intermediate F248

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-{2-[2-(2,5-dioxo-2,5-dihydro-1H-pyrrol-1-yl)ethoxy]ethyl}butanamide (1:1)

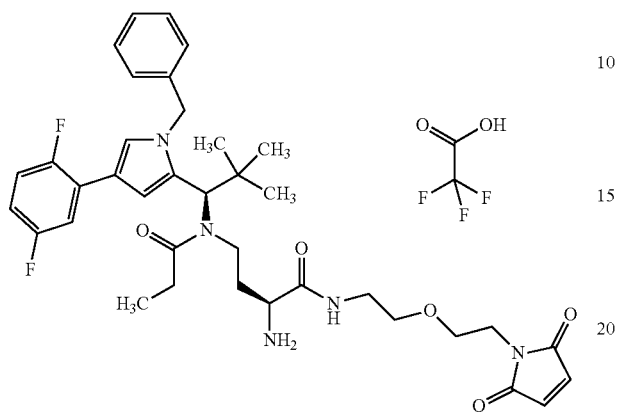

The title compound was prepared by coupling of 10 mg (0.015 mmol) of Intermediate C58 with 5 mg (0.017 mmol) of Intermediate L12 in the presence of HATU and subsequent deprotection with zinc chloride. This gave 6.5 mg (52% of theory over 2 steps) of the title compound.

LC-MS (Method 1): $R_t$=0.91 min; MS (ESIpos): m/z=680 (M+H)$^+$.

Intermediate F254

Trifluoroacetic acid/methyl (3S)-4-[(2-{[2-({(2S)-2-amino-4-[{(1R)-1-[1-benzyl-4-(2,5-difluorophenyl)-1H-pyrrol-2-yl]-2,2-dimethyl-propyl}(glycoloyl)amino]butanoyl}amino)ethyl]amino}-2-oxoethyl)amino]-3-bromo-4-oxobutanoate (1:1)

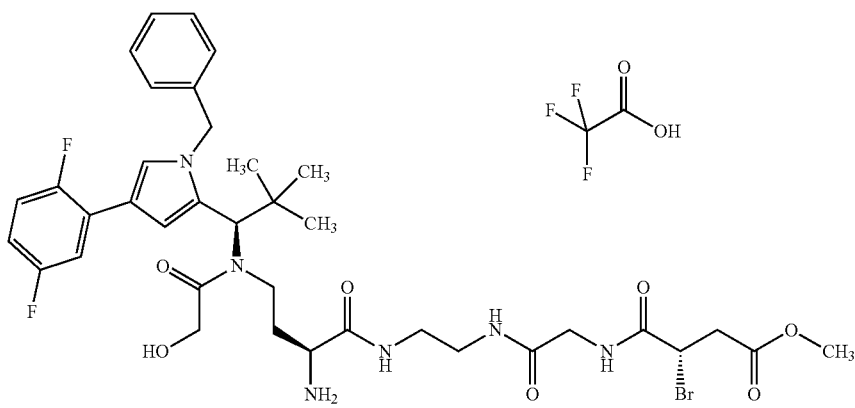 [SMILES: COC(=O)C[C@H](Br)C(=O)NCC(=O)NCCNC(=O)[C@@H](N)CCN(C(=O)CO)[C@@H](c1cc(-c2cc(F)ccc2F)cn1Cc1ccccc1)C(C)(C)C ; O=C(O)C(F)(F)F]

The title compound was prepared analogously to Intermediate 247 by coupling of 15 mg (0.02 mmol) of Intermediate C66 with 21 mg (0.099 mmol) of (2S)-2-bromo-4-methoxy-4-oxobutanoic acid which had been synthesized as described in (J. Org. Chem. 200, 65, 517-522) from (2S)-2-amino-4-methoxy-4-oxobutanoic acid hydrochloride (1:1).

LC-MS (Method 1): $R_t$=0.89 min; MS (ESIpos): m/z=805 and 807 (M+H)$^+$.

Intermediate F255

R/S—(N-[19-(2,5-Dioxo-2,5-dihydro-1H-pyrrol-1-yl)-17-oxo-4,7,10,13-tetraoxa-16-azanonadecan-1-oyl]-L-alpha-glutamyl-S-{2-[(3-aminopropyl){(1R)-1-[1-benzyl-4-(2,5-difluorophenyl)-1H-pyrrol-2-yl]-2,2-dimethylpropyl}amino]-2-oxoethyl})homocysteine/trifluoroacetic acid (1:1)

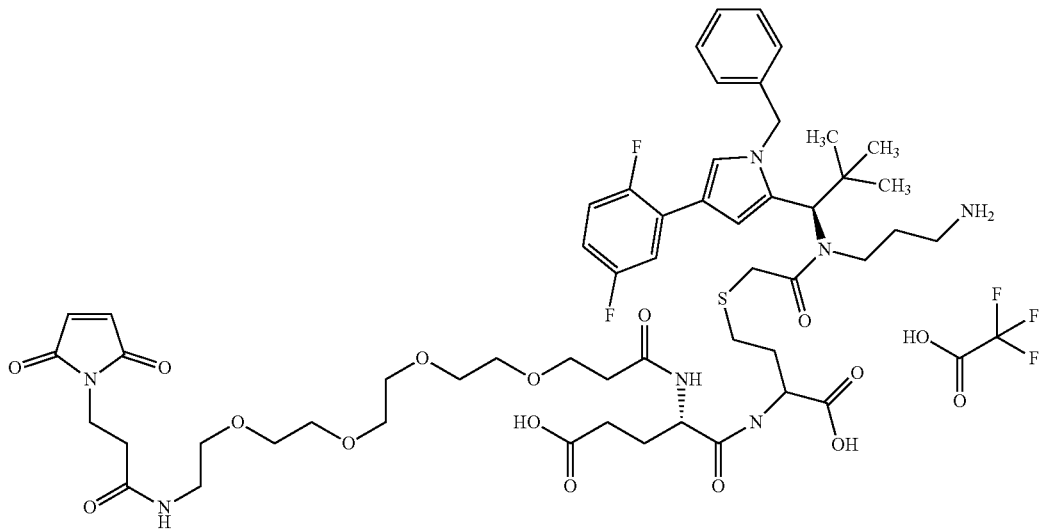 [SMILES: CC(C)(C)[C@H](c1cc(-c2cc(F)ccc2F)cn1Cc1ccccc1)N(CCCN)C(=O)CSCCC(NC(=O)[C@H](CCC(=O)O)NC(=O)CCOCCOCCOCCOCCNC(=O)CCN1C(=O)C=CC1=O)C(=O)O ; O=C(O)C(F)(F)F]

13.1 mg (0.04 mmol) of (2S)-5-(benzyloxy)-2-{[(benzyloxy)carbonyl]amino}-5-oxopentanoic acid were initially charged in 1.0 ml of DMF, and 5.4 mg (0.04 mmol) of HOBt, 11.4 mg (0.04 mmol) of TBTU and 4.6 mg (0.04 mmol) of N,N-diisopropylethylamine were added. The reaction mixture was stirred at RT for 10 min. 30.0 mg (0.04 mmol) of R/S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)homocysteine/trifluoroacetic acid (1:1) (Intermediate C11) dissolved in 12.9 mg (0.1 mmol) of N,N-diisopropylethylamine and 1 ml of DMF were then added. The reaction mixture was stirred at RT overnight. The reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 32 mg (73%) of the compound 4-[2-[[(1R)-1-[1-benzyl-4-(2,5-difluorophenyl)pyrrol-2-yl]-2,2-dimethylpropyl]-[3-(2-trimethylsilylethoxycarbonylamino)propyl]amino]-2-oxoethyl]sulphanyl-2-[[(2S)-5-benzyloxy-2-(benzyloxycarbonylamino)-5-oxo-pentanoyl]amino]butanoic acid.

LC-MS (Method 1): $R_t$=1.53 min; MS (ESIpos): m/z=1084 (M+H)$^+$.

41.4 mg (0.038 mmol) of 4-[2-[[(1R)-1-[1-benzyl-4-(2,5-difluorophenyl)pyrrol-2-yl]-2,2-dimethylpropyl]-[3-(2-trimethylsilylethoxycarbonylamino)propyl]amino]-2-oxoethyl]sulphanyl-2-[[(2S)-5-benzyloxy-2-(benzyloxycarbonylamino)-5-oxo-pentanoyl]amino]butanoic acid was dissolved in 10 ml of ethanol, 4.2 mg of Pd/C were added and the mixture was hydrogenated under standard pressure. The reaction mixture was filtered through a cardboard filter and the filter cake was washed with ethanol. The solvent was evaporated under reduced pressure without heating. The residue was purified by preparative RP-HPLC (column: Reprosil 250×40; 10µ, flow rate: 50 ml/min, MeCN/water, 0.1% TFA). The solvents were evaporated under reduced pressure and the residue was dried under high vacuum. This gave 21.1 mg (56%) of the compound R/S-(L-alpha-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)homocysteine/trifluoroacetic acid (1:1).

LC-MS (Method 1): $R_t$=1.11 min; MS (ESIpos): m/z=860 (M+H)$^+$.

20.4 mg (20.94 µmol) of R/S-(L-alpha-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl))homocysteine/trifluoroacetic acid (1:1) were initially charged together with 11.8 mg (23.04 µmol) of 3-(2,5-dioxo-2,5-dihydro-1H-pyrrol-1-yl)-N-{15-[(2,5-dioxopyrrolidin-1-yl)oxy]-15-oxo-3,6,9,12-tetraoxapentadec-1-yl}propanamide in 1.0 ml of DMF, and 4.2 mg (41.88 µmol) of 4-methylmorpholine were added. The reaction mixture was stirred at RT overnight, and 3.1 mg (0.05 mmol) of acetic acid were then added. The reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 9.5 mg (36%) of the compound R/S—(N-[19-(2,5-dioxo-2,5-dihydro-1H-pyrrol-1-yl)-17-oxo-4,7,10,13-tetraoxa-16-azanonadecan-1-oyl]-L-alpha-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl))homocysteine.

LC-MS (Method 1): $R_t$=1.66 min; MS (ESIpos): m/z=1259 (M+H)$^+$.

9.4 mg (7.47 μmol) of R/S—(N-[19-(2,5-dioxo-2,5-di-hydro-1H-pyrrol-1-yl)-17-oxo-4,7,10,13-tetraoxa-16-azanonadecan-1-oyl]-L-alpha-glutamyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl))homocysteine were dissolved in 1.5 ml of trifluoroethanol, and 6.1 mg (44.81 μmol) of zinc dichloride were added. The reaction mixture was stirred at 50° C. for 3 h. 13.1 mg (0.05 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 6.9 mg (75%) of the title compound.

LC-MS (Method 1): $R_t$=0.87 min; MS (ESIpos): m/z=1114 (M+H)$^+$.

Intermediate F256

Trifluoroacetic acid/N-{(2S)-2-amino-4-[{(1R)-1-[1-benzyl-4-(2,5-difluorophenyl)-1H-pyrrol-2-yl]-2,2-dimethylpropyl}(glycoloyl)amino]butyl}-N'-[2-(2-{[(2,5-dioxo-2,5-dihydro-1H-pyrrol-1-yl)acetyl]amino}ethoxy)ethyl]succinamide (1:1)

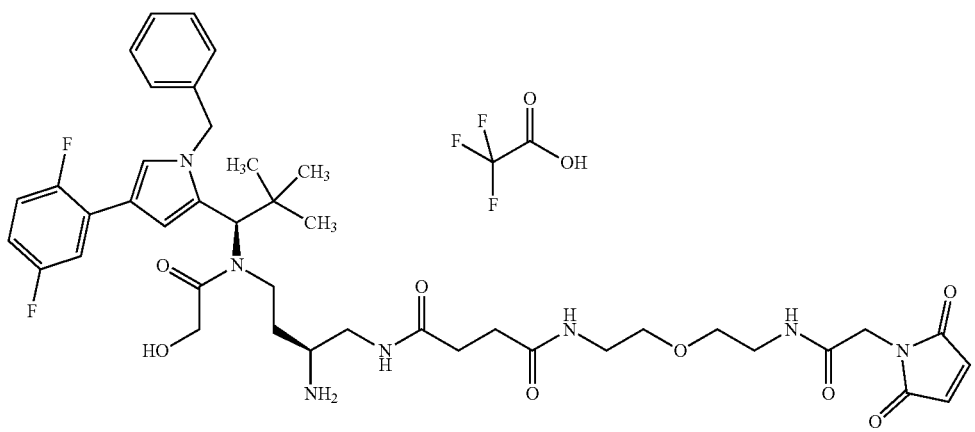 [SMILES: CC(C)(C)[C@H](c1cc(-c2cc(F)ccc2F)cn1Cc1ccccc1)N(CC[C@H](N)CNC(=O)CCC(=O)NCCOCCNC(=O)CN1C(=O)C=CC1=O)C(=O)CO ; O=C(O)C(F)(F)F]

The title compound was prepared by coupling of 10 mg (0.014 mmol) of Intermediate C65 and 9.6 mg (0.027 mmol) of trifluoroacetic acid/N-[2-(2-aminoethoxy)ethyl]-2-(2,5-dioxo-2,5-dihydro-1H-pyrrol-1-yl)acetamide (1:1) in the presence of HATU and N,N-diisopropylethylamine and subsequent deprotection with zinc chloride in trifluoroethanol as described for Intermediate F119. Purification by preparative HPLC gave 8 mg (64% of theory over 2 steps) of the title compound.

LC-MS (Method 1): $R_t$=0.84 min; MS (ESIpos): m/z=822 (M+H)$^+$.

Intermediate F257

R-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-[18-(2,5-dioxo-2,5-dihydro-1H-pyrrol-1-yl)-17-oxo-4,7,10,13-tetraoxa-16-azaoctadecan-1-oyl]-L-cysteine/trifluoroacetic acid (1:1)

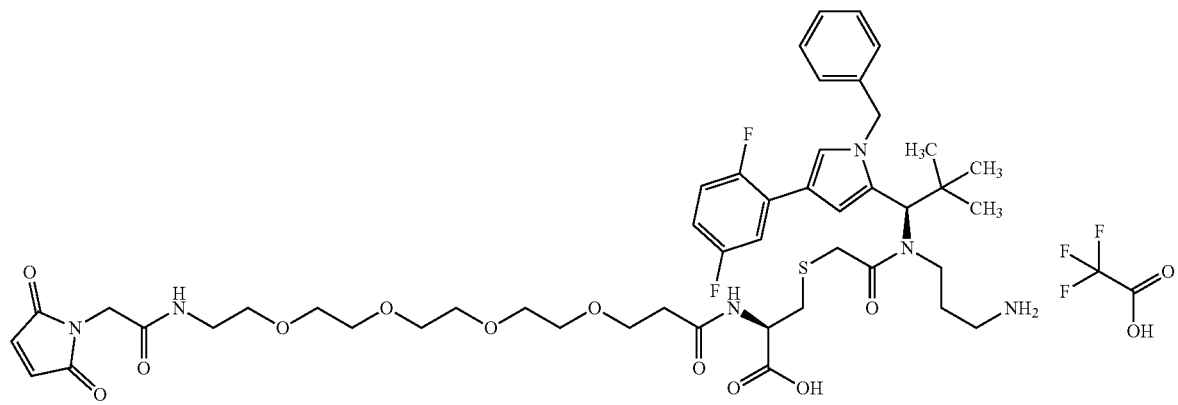

50.0 mg (0.06 mmol) of R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) and 29 mg (0.07 mmol) of 3-[2-[2-[2-[2-[[2-(2,5-dioxopyrrol-1-yl)acetyl]amino]ethoxy]ethoxy]ethoxy]ethoxy]propanoic acid (Intermediate L74) were dissolved in 3.0 ml of DMF, and 27.3 mg (0.07 mmol) of HATU and 23.3 mg (0.18 mmol) of N,N-diisopropylethylamine were added. The reaction mixture was stirred at RT for 2 hours. The reaction mixture was purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 17.4 mg (26%) of the compound R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[18-(2,5-dioxo-2,5-dihydro-1H-pyrrol-1-yl)-17-oxo-4,7,10,13-tetraoxa-16-azaoctadecan-1-oyl]-L-cysteine.

LC-MS (Method 6): $R_t$=1.34 min; MS (ESIpos): m/z=1101 (M+H)$^+$.

17 mg (0.02 mmol) of R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[18-(2,5-dioxo-2,5-dihydro-1H-pyrrol-1-yl)-17-oxo-4,7,10,13-tetraoxa-16-azaoctadecan-1-oyl]-L-cysteine were dissolved in 1.0 ml of trifluoroethanol, and 6.3 mg (0.05 mmol) of zinc dichloride were added. The reaction mixture was stirred at 50° C. overnight. 13.5 mg (0.05 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 7.6 mg (46%) of the title compound.

LC-MS (Method 1): $R_t$=0.91 min; MS (ESIpos): m/z=957 (M+H)$^+$.

Intermediate F258

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-[3-{2-[(bromoacetyl)amino]ethyl}amino)-3-oxopropyl]butanamide (1:1)

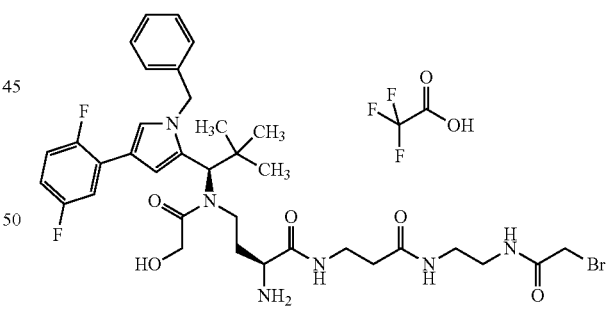

The title compound was prepared by coupling of Intermediate C58 with trifluoroacetic acid/benzyl [2-(beta-alanylamino)ethyl]carbamate (1:1) using HATU, subsequent hydrogenolysis, followed by coupling with 1-(2-bromoacetoxy)pyrrolidine-2,5-dione and finally by deprotection with zinc chloride.

LC-MS (Method 1): $R_t$=0.86 min; MS (ESIpos): m/z=747 and 749 (M+F1)$^+$.

Intermediate F259

N-{(2S)-2-Amino-4-[{(1R)-1-[1-benzyl-4-(2,5-difluorophenyl)-1H-pyrrol-2-yl]-2,2-dimethyl propyl}(glycoloyl)amino]butanoyl}-3-{[N-(bromacetyl)glycyl]amino}-D-alanine/trifluoroacetic acid (1:1)

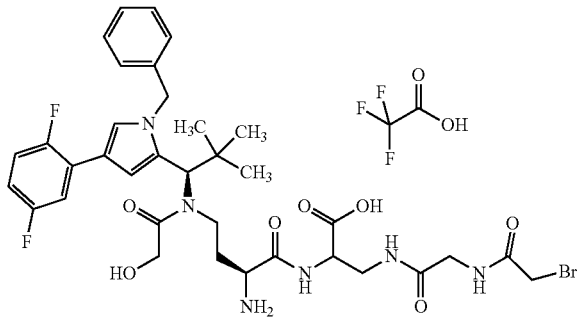 [SMILES: CC(C)(C)[C@H](c1cc(-c2cc(F)ccc2F)cn1Cc1ccccc1)N(CC[C@H](N)C(=O)NC(CNC(=O)CNC(=O)CBr)C(=O)O)C(=O)CO ; O=C(O)C(F)(F)F]

75 mg (0.114 mmol) of Intermediate C58 were taken up in 12.5 ml of DMF and coupled with 78 mg (0.171 mmol) of Intermediate L75 in the presence of 65 mg (0.11 mmol) of HATU and 79 µl of N,N-diisopropylethylamine. After purification by preparative HPLC, the intermediate was taken up in 20 ml of ethanol and hydrogenated over 10% palladium on activated carbon at RT under hydrogen standard pressure for 1 h. The catalyst was then filtered off, the solvent was removed under reduced pressure and the product was purified by preparative HPLC. Lyophilization from acetonitrile/water 1:1 gave 63 mg (64% of theory over 2 steps) of 2-(trimethylsilyl)ethyl 3-amino-N-[(2S)-4-[{(1R)-1-[1-benzyl-4-(2,5-difluorophenyl)-1H-pyrrol-2-yl]-2,2-dimethylpropyl}(glycoloyl)amino]-2-({[2-(trimethylsilyl)ethoxy]carbonyl}amino)butanoyl]-D-alaninate.

LC-MS (Method 1): $R_t$=1.16 min; MS (EIpos): m/z=844 [M+H]$^+$.

40 mg (0.047 mmol) of this intermediate were then coupled as described above with N-[(benzyloxy)carbonyl]glycine in the presence of HATU and then once more hydrogenolytically deprotected.

The title compound was then prepared by coupling of 10 mg (0.012 mmol) of this intermediate with 7.7 mg (0.032 mmol) of commercially available 1-(2-bromoacetoxy)pyrrolidine-2,5-dione in the presence of 4 µl of N,N-diisopropylethylamine and subsequent deprotection with zinc chloride in trifluoroethanol as described for Intermediate F119. Purification by preparative HPLC gave 1.3 mg of the title compound.

LC-MS (Method 1): $R_t$=0.83 min; MS (ESIpos): m/z=111 and 779 (M+H)$^+$.

Intermediate F261

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(2-{2-[(bromoacetyl)amino]ethoxy}ethyl)butanamide (1:1)

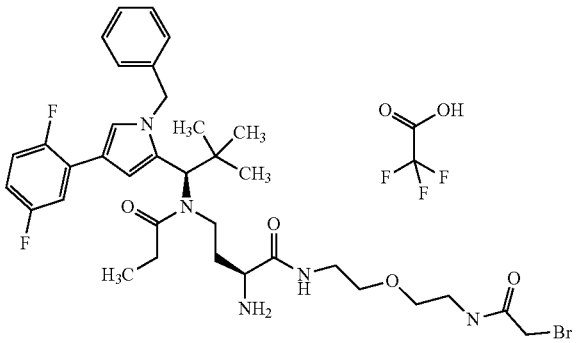 [SMILES: CCC(=O)N(CC[C@H](N)C(=O)NCCOCCNC(=O)CBr)[C@@H](c1cc(-c2cc(F)ccc2F)cn1Cc1ccccc1)C(C)(C)C ; O=C(O)C(F)(F)F]

The title compound was prepared by coupling of 20 mg (0.03 mmol) of Intermediate C58 with 25.8 mg (0.061 mmol) of Intermediate L77 in the presence of HATU and subsequent deprotection with zinc chloride. This gave 11.9 mg (47% of theory over 2 steps) of the title compound.

LC-MS (Method 1): $R_t$=0.84 min; MS (ESIpos): m/z=722 and 720 (M+H)$^+$.

Intermediate F262

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-{3-[2-(2-{[3-(2,5-dioxo-2,5-dihydro-1H-pyrrol-1-yl)propanoyl]amino}ethoxy)ethoxy]propanoyl}-L-cysteine/trifluoroacetic acid (1:1)

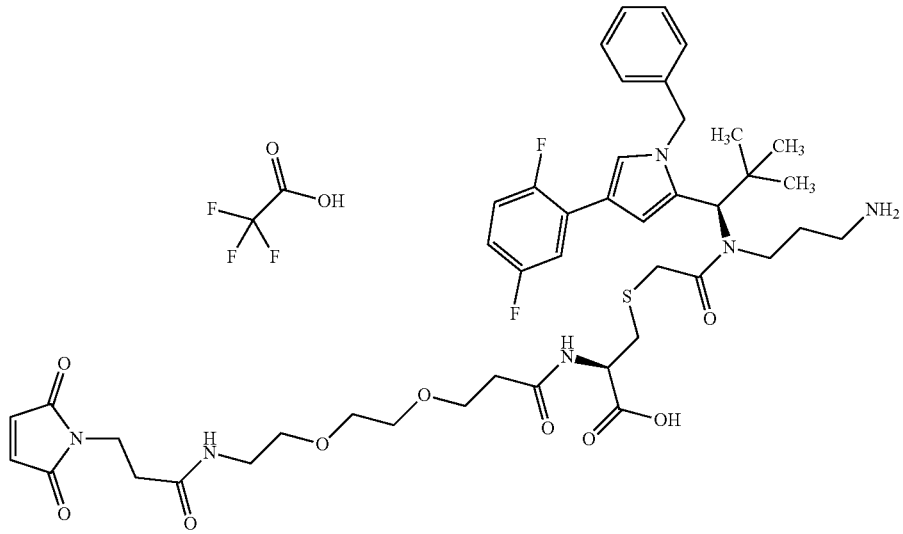 [SMILES: CC(C)(C)[C@H](c1cc(-c2cc(F)ccc2F)cn1Cc1ccccc1)N(CCCN)C(=O)CSC[C@H](NC(=O)CCOCCOCCNC(=O)CCN1C(=O)C=CC1=O)C(=O)O ; O=C(O)C(F)(F)F]

30 mg (36 µmol) of S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cysteine/trifluoroacetic acid (1:1) (Intermediate C71) together with 16.9 mg (40 µmol) of 3-(2,5-dioxo-2,5-dihydro-1H-pyrrol-1-yl)-N-[2-(2-{3-[(2,5-dioxopyrrolidin-1-yl)oxy]-3-oxopropoxy}ethoxy)ethyl]propanamide were initially charged in 1.5 ml of DMF, and 10.9 mg (108 µmol) of 4-methylmorpholine were added. The reaction mixture was stirred at RT overnight, and 7.58 mg (0.13 mmol) of acetic acid were then added. The reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 33.4 mg (80% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-{3-[2-(2-{[3-(2,5-dioxo-2,5-dihydro-1H-pyrrol-1-yl)propanoyl]amino}ethoxy)ethoxy]propanoyl}-L-cysteine.

LC-MS (Method 1): $R_t$=1.34 min; MS (ESIpos): m/z=1027 (M+H)$^+$.

32.8 mg (32 µmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-{3-[2-(2-{[3-(2,5-dioxo-2,5-dihydro-1H-pyrrol-1-yl)propanoyl]amino}ethoxy)ethoxy]propanoyl}-L-cysteine were dissolved in 3.0 ml of trifluoroethanol, and 26.1 mg (192 µmol) of zinc dichloride were added. The reaction mixture was stirred at 50° C. for 2 h. 56.0 mg (0.192 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10µ, flow rate: 50 ml/min, MeCN/water, 0.1% TFA). The solvents were evaporated under reduced pressure and the residue was lyophilized. This gave 22.9 mg (71% of theory) of the title compound.

LC-MS (Method 1): $R_t$=0.88 min; MS (ESIpos): m/z=883 (M+H)$^+$.

Intermediate F263

N-[(2,5-Dioxo-2,5-dihydro-1H-pyrrol-1-yl)acetyl]-beta-alanyl-S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cysteine/trifluoroacetic acid (1:1)

30.0 mg (0.036 mmol) of R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) and 9.8 mg (0.04 mmol) of N-[(2,5-dioxo-2,5-dihydro-1H-pyrrol-1-yl)acetyl]-beta-alanine (Intermediate L78) were dissolved in 1.0 ml of DMF, and 16.4 mg (0.04 mmol) of HATU and 14.0 mg (0.11 mmol) of N,N-diisopropylethylamine were added. The reaction mixture was stirred at RT for 2 hours. The reaction mixture was purified directly by preparative RP-HPLC (column: Reprosil 125×30; 10µ, flow rate: 50 ml/min, MeCN/water/0.1% TFA). The solvents were evaporated under reduced pressure and the residue was dried under high vacuum. This gave 4.2 mg (13%) of the compound N-[(2,5-dioxo-2,5-dihydro-1H-pyrrol-1-yl)acetyl]-beta-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine.

LC-MS (Method 6): $R_t$=1.31 min; MS (ESIpos): m/z=925 (M+H)$^+$.

11.3 mg (0.011 mmol) of N-[(2,5-dioxo-2,5-dihydro-1H-pyrrol-1-yl)acetyl]-beta-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine were dissolved in 2.0 ml of trifluoroethanol, and 5.0 mg (0.04 mmol) of zinc dichloride were added. The reaction mixture was stirred at 50° C. for 2 hours. 10.7 mg (0.04 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 4.4 mg (40%) of the title compound.

LC-MS (Method 1): $R_t$=0.91 min; MS (ESIpos): m/z=781 (M+H)$^+$.

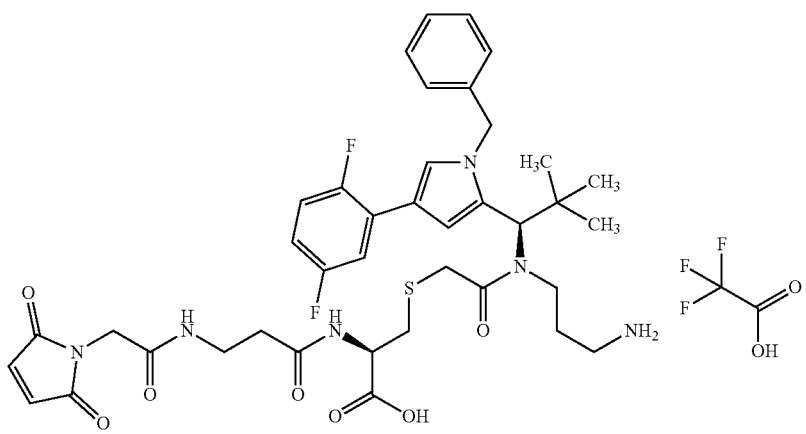

Intermediate F264

N-[6-(2,5-Dioxo-2,5-dihydro-1H-pyrrol-1-yl)hexanoyl]-beta-alanyl-S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cysteine/trifluoroacetic acid (1:1)

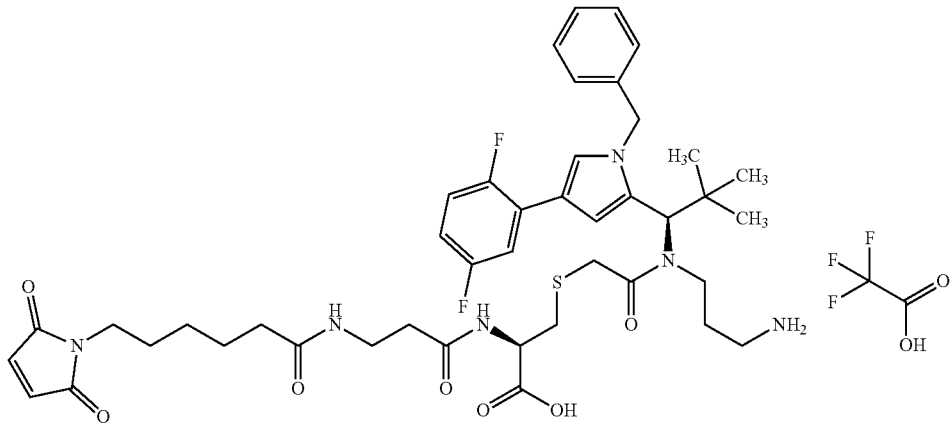

30.0 mg (0.036 mmol) of R-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) and 12.2 mg (0.04 mmol) of N-[6-(2,5-dioxo-2,5-dihydro-1H-pyrrol-1-yl)hexanoyl]-beta-alanine (Intermediate L79) were dissolved in 1.0 ml of DMF, and 16.4 mg (0.04 mmol) of HATU and 14.0 mg (0.11 mmol) of N,N-diisopropylethylamine were added. The reaction mixture was stirred at RT for 2 hours. The reaction mixture was purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 8.9 mg (24%) of the compound N-[6-(2,5-dioxo-2,5-dihydro-1H-pyrrol-1-yl)hexanoyl]-beta-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine.

LC-MS (Method 6): $R_t$=1.38 min; MS (ESIpos): m/z=981 (M+H)$^+$.

15.3 mg (0.015 mmol) of N-[6-(2,5-dioxo-2,5-dihydro-1H-pyrrol-1-yl)hexanoyl]-beta-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine were dissolved in 2.0 ml of trifluoroethanol, and 6.3 mg (0.045 mmol) of zinc dichloride were added. The reaction mixture was stirred at 50° C. for 2 hours. 13.5 mg (0.045 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 9.1 mg (62%) of the title compound.

LC-MS (Method 1): $R_t$=0.92 min; MS (ESIpos): m/z=837 (M+H)$^+$.

Intermediate F26S

Trifluoroacetic acid/N-(3-aminopropyl)-N-{(1R)-1-[1-benzyl-4-(2,5-difluorophenyl)-1H-pyrrol-2-yl]-2,2-dimethylpropyl}-22-(2,5-dioxo-2,5-dihydro-1H-pyrrol-1-yl)-6,17-dioxo-10,13-dioxa-3-thia-7,16-diazadocosane-1-amide (1:1)

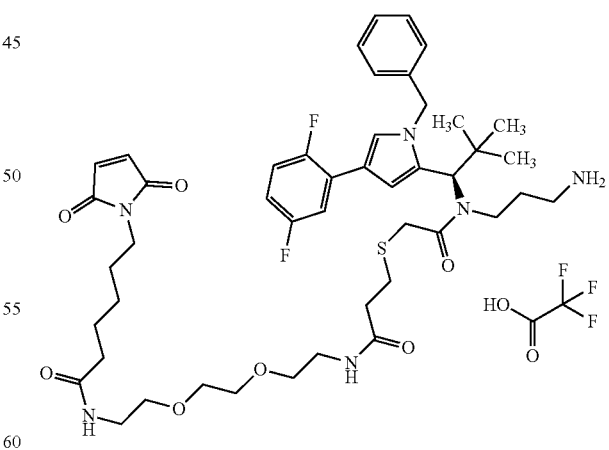

30.0 mg (42.7 μmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) and 25.3 mg (55.6 μmol) of trifluoroacetic acid/N-{2-[2-(2-aminoethoxy)ethoxy]ethyl}-6-(2,5-dioxo-2,5-dihydro-1H-pyrrol-1-yl)

hexanamide (1:1) (Intermediate L82) were initially charged in 1.9 ml of acetonitrile, and 60 µl (340 µmol) of N,N-diisopropylethylamine and 33 µl (56 µmol) of 2,4,6-tripropyl-1,3,5,2,4,6-trioxatriphosphinane 2,4,6-trioxide 50% in ethyl acetate were added. The reaction mixture was stirred at RT overnight. Water (2.0 ml) was added, and purification was carried out directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 26.7 mg (60% of theory) of the compound 2-(trimethylsilyl)ethyl [4-{(1R)-1-[1-benzyl-4-(2,5-difluorophenyl)-1H-pyrrol-2-yl]-2,2-dimethylpropyl}-26-(2,5-dioxo-2,5-dihydro-1H-pyrrol-1-yl)-5,10,21-trioxo-14,17-dioxa-7-thia-4,11,20-triazahexacos-1-yl]carbamate.

LC-MS (Method 1): $R_t$=1.40 min; MS (ESIpos): m/z=1025 (M+H)$^+$. 25.3 mg (24.7 µmol) of 2-(trimethylsilyl)ethyl [4-{(1R)-1-[1-benzyl-4-(2,5-difluorophenyl)-1H-pyrrol-2-yl]-2,2-dimethylpropyl}-26-(2,5-dioxo-2,5-dihydro-1H-pyrrol-1-yl)-5,10,21-trioxo-14,17-dioxa-7-thia-4,11,20-triazahexacos-1-yl]carbamate were dissolved in 2.0 ml of trifluoroethanol, and 20.2 mg (148 µmol) of zinc dichloride were added. The reaction mixture was stirred at 50° C. for 1 h. 43.3 mg (148 µmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 23.4 mg (95% of theory) of the title compound.

LC-MS (Method 1): $R_t$=0.89 min; MS (ESIpos): m/z=881 (M+H)$^+$.

Intermediate F266

Trifluoroacetic acid/N-(3-aminopropyl)-N-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,13-dioxo-6,9-dioxa-16-thia-3,12-diazaoctadecan-18-amide (1:1)

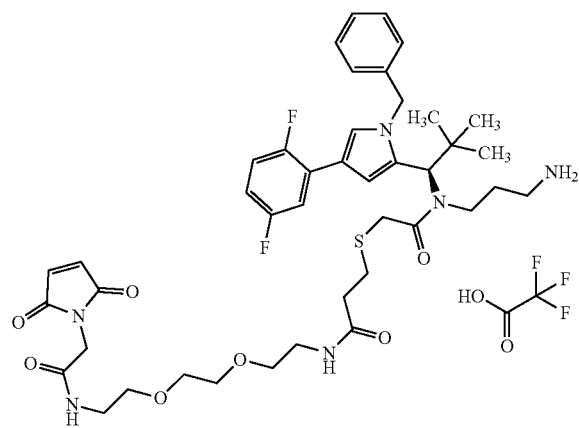 [SMILES: CC(C)(C)[C@H](c1cc(-c2cc(F)ccc2F)cn1Cc1ccccc1)N(CCCN)C(=O)CSCCC(=O)NCCOCCOCCNC(=O)CN1C(=O)C=CC1=O ; O=C(O)C(F)(F)F]

30.0 mg (0.043 mmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged together with 22.2 mg (0.056 mmol) of trifluoroacetic acid/N-{2-[2-(2-aminoethoxy)ethoxy]ethyl}-2-(2,5-dioxo-2,5-dihydro-1H-pyrrol-1-yl)acetamide (1:1) (Intermediate L83) in 1.9 ml of acetonitrile. 60 µl (0.34 mmol) of N,N-diisopropylethylamine were then added, and 33 µl (0.056 mmol) of T3P (50% in ethyl acetate) were added dropwise. The reaction mixture was stirred at RT overnight. Water (2.0 ml) was added. The reaction mixture was purified directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 20.5 mg (49% of theory) of the compound 2-(trimethylsilyl)ethyl [19-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,13,18-trioxo-6,9-dioxa-16-thia-3,12,19-triazadocosan-22-yl]carbamate.

LC-MS (Method 1): $R_t$=1.38 min; MS (ESIpos): m/z=969 (M+H)$^+$.

19.1 mg (19.7 µmol) of 2-(trimethylsilyl)ethyl [19-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,13,18-trioxo-6,9-dioxa-16-thia-3,12,19-triazadocosan-22-yl]carbamate were dissolved in 2.0 ml of trifluoroethanol, and 16.1 mg (118 µmol) of zinc dichloride were added. The reaction mixture was stirred at 50° C. for 1 h. 34.6 mg (118 µmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 13.9 mg (75% of theory) of the title compound.

LC-MS (Method 1): $R_t$=0.86 min; MS (ESIpos): m/z=825 (M+H)$^+$.

Intermediate F267

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-[1-(2,5-dioxo-2,5-dihydro-1H-pyrrol-1-yl)-2,18-dioxo-6,9,12,15-tetraoxa-3-azaoctadecan-18-yl]-L-cysteinyl-beta-alanine/trifluoroacetic acid (1:1)

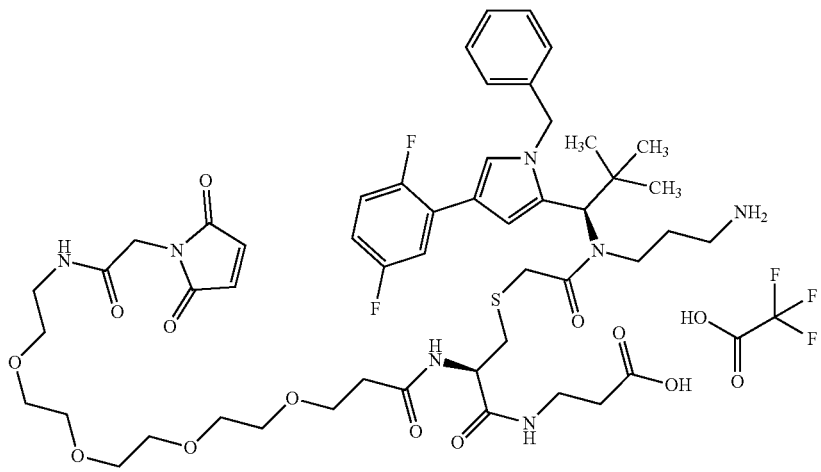 [SMILES: CC(C)(C)[C@H](c1cc(-c2cc(F)ccc2F)cn1Cc1ccccc1)N(CCCN)C(=O)CSC[C@H](NC(=O)CCOCCOCCOCCOCCNC(=O)CN1C(=O)C=CC1=O)C(=O)NCCC(=O)O ; O=C(O)C(F)(F)F]

Under argon, 13.4 mg (33.3 μmol) of 1-(2,5-dioxo-2,5-dihydro-1H-pyrrol-1-yl)-2-oxo-6,9,12,15-tetraoxa-3-azaoctadecan-18-oic acid (Intermediate L74) were initially charged in 1.0 ml of DMF, and 9.3 μl (54.4 μmol) of N,N-diisopropylethylamine and 12.6 mg (33.3 μmol) of HATU were added. The reaction mixture was stirred at RT for 10 min. 25.0 mg (27.7 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl-beta-alanine/trifluoroacetic acid (1:1) (see synthesis of Intermediate F216) dissolved in 4.7 μl (27.7 μmol) of N,N-diisopropylethylamine and 1.0 ml of DMF were then added. The reaction mixture was stirred at RT for 90 minutes. The reaction mixture was purified directly by preparative RP-F1PLC (column: Reprosil 250×30; 10μ, flow rate: 50 ml/min, MeCN/water, 0.1% TFA). The solvents were evaporated under reduced pressure and the residue was dried under high vacuum. This gave 6.90 mg (19% of theory) of the compound S-(11 —{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[1-(2,5-dioxo-2,5-dihydro-1H-pyrrol-1-yl)-2,18-dioxo-6,9,12,15-tetraoxa-3-azaoctadecan-18-yl]-L-cysteinyl-beta-alanine.

LC-MS (Method 5): $R_t$=4.44 min; MS (ESIpos): m/z=1172 (M+H)$^+$.

6.70 mg (5.71 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[1-(2,5-dioxo-2,5-dihydro-1H-pyrrol-1-yl)-2,18-dioxo-6,9,12,15-tetraoxa-3-azaoctadecan-18-yl]-L-cysteinyl-beta-alanine were dissolved in 1.0 ml of trifluoroethanol, and 4.67 mg (34.3 μmol) of zinc dichloride were added. The reaction mixture was stirred at 50° C. for 1 h. 10 mg (34.3 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 4.4 mg (67% of theory) of the title compound.

LC-MS (Method 1): $R_t$=0.85 min; MS (ESIpos): m/z=1028 (M+H)$^+$.

Intermediate F268

Trifluoroacetic acid/N-(3-aminopropyl)-N-{(1R)-1-[1-benzyl-4-(2,5-difluorophenyl)-1H-pyrrol-2-yl]-2,2-dimethylpropyl}-28-(2,5-dioxo-2,5-dihydro-1H-pyrrol-1-yl)-6,23-dioxo-10,13,16,19-tetraoxa-3-thia-7,22-diazaoctacosane-1-amide (1:1)

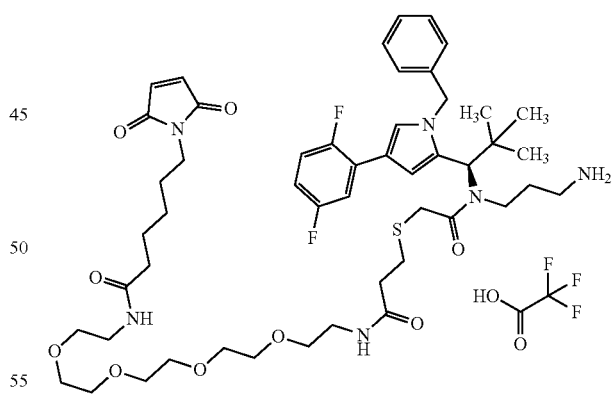

30.0 mg (0.043 mmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silaheptadecan-17-oic acid (Intermediate C69) were initially charged together with 30.2 mg (0.056 mmol) of trifluoroacetic acid/N-(14-amino-3,6,9,12-tetraoxatetradec-1-yl)-6-(2,5-dioxo-2,5-dihydro-1H-pyrrol-1-yl)hexanamide (1:1) (Intermediate L84) in 2.0 ml of acetonitrile. 60 μl (0.34 mmol) of N,N-diisopropylethylamine were then added, and 33 μl (0.056 mmol) of T3P (50% in ethyl acetate) were added dropwise.

The reaction mixture was stirred at RT overnight. Water (2.0 ml) was added. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 27.9 mg (59% of theory) of the compound 2-(trimethylsilyl)ethyl [4-{(1R)-1-[1-benzyl-4-(2,5-difluorophenyl)-1H-pyrrol-2-yl]-2,2-dimethylpropyl}-32-(2,5-dioxo-2,5-dihydro-1H-pyrrol-1-yl)-5,10,27-trioxo-14,17,20,23-tetraoxa-7-thia-4,11,26-triazadotriacont-1-yl]carbamate.

LC-MS (Method 1): $R_t$=1.41 min; MS (ESIpos): m/z=1114 (M+H)$^+$.

25.6 mg (23.0 μmol) of 2-(trimethylsilyl)ethyl [4-{(1R)-1-[1-benzyl-4-(2,5-difluorophenyl)-1H-pyrrol-2-yl]-2,2-dimethylpropyl}-32-(2,5-dioxo-2,5-dihydro-1H-pyrrol-1-yl)-5,10,27-trioxotrioxo-14,17,20,23-tetraoxa-7-thia-4,11,26-triazadotriacont-1-yl]carbamate were dissolved in 2.5 ml of trifluoroethanol, and 18.8 mg (138 μmol) of zinc dichloride were added. The reaction mixture was stirred at 50° C. for 1 h. 40.3 mg (138 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 22.2 mg (88% of theory) of the title compound.

LC-MS (Method 1): $R_t$=0.94 min; MS (ESIpos): m/z=969 (M+H)$^+$.

Intermediate F269

4-{[(8R,14R)-13-(3-Aminopropyl)-14-[1-benzyl-4-(2,5-difluorophenyl)-1H-pyrrol-2-yl]-1-(2,5-dioxo-2,5-dihydro-1H-pyrrol-1-yl)-15,15-dimethyl-2,7,12-trioxo-10-thia-3,6,13-triazahexadecan-8-yl]amino}-4-oxobutanoic acid/trifluoroacetic acid (1:1)

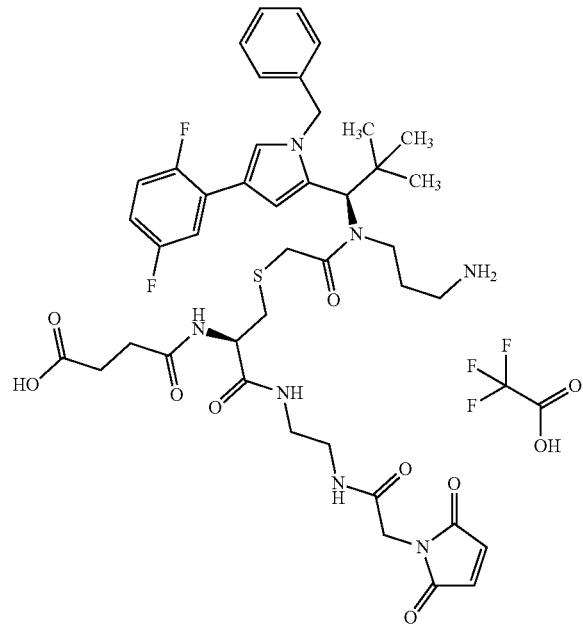 [SMILES: CC(C)(C)[C@H](c1cc(-c2cc(F)ccc2F)cn1Cc1ccccc1)N(CCCN)C(=O)CSC[C@H](NC(=O)CCC(=O)O)C(=O)NCCNC(=O)CN1C(=O)C=CC1=O ; O=C(O)C(F)(F)F]

17.0 mg (0.0195 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine (Intermediate C77) were initially charged together with 4.99 mg (0.0253 mmol) of N-(2-aminoethyl)-2-(2,5-dioxo-2,5-dihydro-1H-pyrrol-1-yl)acetamide (Intermediate L1) in 1.0 ml of acetonitrile. 27 μl (0.16 mmol) of N,N-diisopropylethylamine were then added, and 15 μl (0.025 mmol) of T3P (50% in ethyl acetate) were added dropwise. The reaction mixture was stirred at RT overnight. Water (2.0 ml) was added. The reaction mixture was purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 9.5 mg (46% of theory) of the compound tert-butyl 4-{[(16R)-11-{(1R)-1-[1-benzyl-4-(2,5-difluorophenyl)-1H-pyrrol-2-yl]-2,2-dimethylpropyl}-23-(2,5-dioxo-2,5-dihydro-1H-pyrrol-1-yl)-2,2-dimethyl-6,12,17,22-tetraoxo-5-oxa-14-thia-7,11,18,21-tetraaza-2-silatricosan-16-yl]amino}-4-oxobutanoate.

LC-MS (Method 1): $R_t$=1.47 min; MS (ESIpos): m/z=1052 (M+H)$^+$.

8.3 mg (7.89 μmol) of tert-butyl 4-{[(16R)-11-{(1R)-1-[1-benzyl-4-(2,5-difluorophenyl)-1H-pyrrol-2-yl]-2,2-dimethylpropyl}-23-(2,5-dioxo-2,5-dihydro-1H-pyrrol-1-yl)-2,2-dimethyl-6,12,17,22-tetraoxo-5-oxa-14-thia-7,11,18,21-tetraaza-2-silatricosan-16-yl]amino}-4-oxobutanoate were dissolved in 1.0 ml of trifluoroethanol, and 6.45 mg (47.3 μmol) of zinc dichloride were added. The reaction mixture was stirred at 50° C. for 6 h. 6.45 mg (47.3 μmol) of zinc dichloride were added and the reaction mixture was stirred at 50° C. overnight. 27.7 mg (94.6 μmol) of ethylenediamine-N,N,N',N'-tetraacetic acid were added and the reaction mixture was stirred for 10 min, and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 1.10 mg (14% of theory) of the title compound.

LC-MS (Method 1): $R_t$=0.89 min; MS (ESIpos): m/z=852 (M+H)$^+$.

Intermediate F270

Trifluoroacetic acid/N-(3-aminopropyl)-N-{(1R)-1-[1-benzyl-4-(2,5-difluorophenyl)-1H-pyrrol-2-yl]-2,2-dimethylpropyl}-N'-(2-{[(2,5-dioxo-2,5-dihydro-1H-pyrrol-1-yl)acetyl]amino}ethyl)succinamide (1:1)

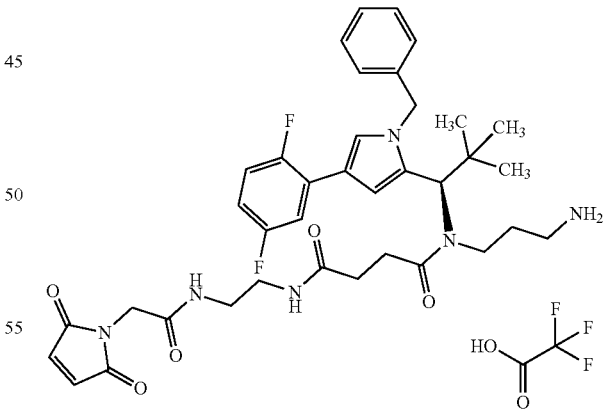

Under argon, 15.0 mg (22.9 μmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecan-15-oic acid (Intermediate C78) were initially charged in 1.0 ml of DMF, and 8.0 μl (45.8 μmol) of N,N-diisopropylethylamine and 10.4 mg (27.4 μmol) of HATU were added. The reaction mixture was stirred at RT for 10 min. 8.54 mg (27.4 μmol) of trifluoroacetic acid/N-

(2-aminoethyl)-2-(2,5-dioxo-2,5-dihydro-1H-pyrrol-1-yl)acetamide (1:1) (Intermediate L1) dissolved in 4.0 µl (22.9 µmol) of N,N-diisopropylethylamine and 1.0 ml of DMF were then added. The reaction mixture was stirred at RT for 1 h. The reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 14.7 mg (77% of theory) of the compound 2-(trimethylsilyl)ethyl [3-({(1R)-1-[1-benzyl-4-(2,5-difluorophenyl)-1H-pyrrol-2-yl]-2,2-dimethylpropyl}{4-[(2-{[(2,5-dioxo-2,5-dihydro-1H-pyrrol-1-yl)acetyl]amino}ethyl)amino]-4-oxobutanoyl}amino)propyl]carbamate.

LC-MS (Method 5): $R_t$=1.33 min; MS (ESIpos): m/z=835 (M+H)$^+$.

13.2 mg (15.8 µmol) of 2-(trimethylsilyl)ethyl [3-({(1R)-1-[1-benzyl-4-(2,5-difluorophenyl)-1H-pyrrol-2-yl]-2,2-dimethylpropyl}{4-[(2-{[(2,5-dioxo-2,5-dihydro-1H-pyrrol-1-yl)acetyl]amino}ethyl)amino]-4-oxobutanoyl}amino)propyl]carbamate were dissolved in 2.0 ml of trifluoroethanol, and 12.9 mg (94.8 µmol) of zinc dichloride were added. The reaction mixture was stirred at 50° C. for 1 h. 27.7 mg (94.6 µmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 10.9 mg (83% of theory) of the title compound.

LC-MS (Method 1): $R_t$=0.83 min; MS (ESIpos): m/z=691 (M+H)$^+$.

Intermediate F271

4-{[(20R,26R)-25-(3-Aminopropyl)-26-[1-benzyl-4-(2,5-difluorophenyl)-1H-pyrrol-2-yl]-1-(2,5-dioxo-2,5-dihydro-1H-pyrrol-1-yl)-27,27-dimethyl-2,19,24-trioxo-6,9,12,15-tetraoxa-22-thia-3,18,25-triazaoctacosan-20-yl]amino}-4-oxobutanoic acid/trifluoroacetic acid (1:1)

Under argon, 19.4 mg (22.2 µmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine (Intermediate C77) were initially charged in 2.0 ml of DMF, and 21.7 mg (44.4 µmol) of trifluoroacetic acid/N-(14-amino-3,6,9,12-tetraoxatetradec-1-yl)-2-(2,5-dioxo-2,5-dihydro-1H-pyrrol-1-yl)acetamide (1:1) (Intermediate L74), 12 µl (67 µmol) of N,N-diisopropylethylamine and 16.9 mg (44.4 µmol) of HATU were added. The reaction mixture was stirred at RT for 1 h. The reaction mixture was purified directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 18.1 mg (66% of theory) of the compound tert-butyl 4-{[(16R)-11-{(1R)-1-[1-benzyl-4-(2,5-difluorophenyl)-1H-pyrrol-2-yl]-2,2-dimethylpropyl}-35-(2,5-dioxo-2,5-dihydro-1H-pyrrol-1-yl)-2,2-dimethyl-6,12,17,34-tetraoxo-5,21,24,27,30-pentaoxa-14-thia-7,11,18,33-tetraaza-2-silapentatriacontan-16-yl]amino}-4-oxobutanoate.

LC-MS (Method 4): $R_t$=1.79 min; MS (ESIpos): m/z=1250 (M+Na)$^+$.

18.1 mg (14.7 µmol) of tert-butyl 4-{[(16R)-11-{(1R)-1-[1-benzyl-4-(2,5-difluorophenyl)-1H-pyrrol-2-yl]-2,2-dimethylpropyl}-35-(2,5-dioxo-2,5-dihydro-1H-pyrrol-1-yl)-2,2-dimethyl-6,12,17,34-tetraoxo-5,21,24,27,30-pentaoxa-14-thia-7,11,18,33-tetraaza-2-silapentatriacontan-16-yl]amino}-4-oxobutanoate were dissolved in 2.0 ml of trifluoroethanol, and 12.0 mg (88.4 µmol) of zinc dichloride were added. The reaction mixture was stirred at 50° C. for 4 h. 25.8 mg (88.4 µmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 12.3 mg (73% of theory) of the title compound. LC-MS (Method 1): $R_t$=0.87 min; MS (ESIpos): m/z=1028 (M+H)$^+$.

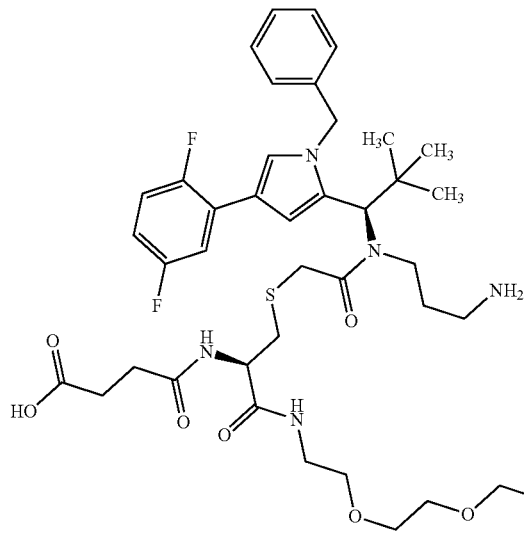
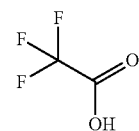
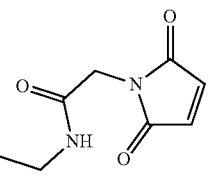

Intermediate F272

Trifluoroacetic acid/N-(3-aminopropyl)-N-{(1R)-1-[1-benzyl-4-(2,5-difluorophenyl)-1H-pyrrol-2-yl]-2,2-dimethylpropyl}-N'-[17-(2,5-dioxo-2,5-dihydro-1H-pyrrol-1-yl)-16-oxo-3,6,9,12-tetraoxa-15-azaheptadec-1-yl]succinamide (1:1)

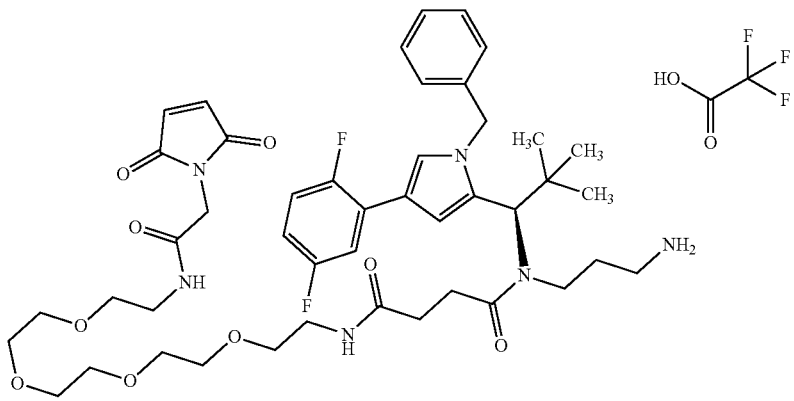 [SMILES: CC(C)(C)[C@H](c1cc(-c2cc(F)ccc2F)cn1Cc1ccccc1)N(CCCN)C(=O)CCC(=O)NCCOCCOCCOCCOCCNC(=O)CN1C(=O)C=CC1=O ; O=C(O)C(F)(F)F]

Under argon, 15.0 mg (22.9 μmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silapentadecan-15-oic acid (Intermediate C78) were initially charged in 1.0 ml of DMF, and 8.0 μl (45.8 μmol) of N,N-diisopropylethylamine and 10.4 mg (27.4 μmol) of HATU were added. The reaction mixture was stirred at RT for 10 min. 13.4 mg (27.4 μmol) of trifluoroacetic acid/N-(14-amino-3,6,9,12-tetraoxatetradec-1-yl)-2-(2,5-dioxo-2,5-dihydro-1H-pyrrol-1-yl)acetamide (1:1) (Intermediate L85) dissolved in 4.0 μl (22.9 μmol) of N,N-diisopropylethylamine and 1.0 ml of DMF were then added. The reaction mixture was stirred at RT for 1 h. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 15.8 mg (68% of theory) of the compound 2-(trimethylsilyl)ethyl [23-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,19,22-trioxo-6,9,12,15-tetraoxa-3,18,23-triazahexacosan-26-yl]carbamate.

LC-MS (Method 1): $R_t$=1.35 min; MS (ESIpos): m/z=1011 (M+H)$^+$.

15.1 mg (14.9 μmol) of 2-(trimethylsilyl)ethyl [23-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,19,22-trioxotrioxo-6,9,12,15-tetraoxa-3,18,23-triazahexacosan-26-yl]carbamate were dissolved in 2.0 ml of trifluoroethanol, and 12.2 mg (89.6 μmol) of zinc dichloride were added. The reaction mixture was stirred at 50° C. for 1 h. 26.2 mg (89.6 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 10.3 mg (70% of theory) of the title compound.

LC-MS (Method 1): $R_t$=0.88 min; MS (ESIpos): m/z=867 (M+H)$^+$.

Intermediate F273

Trifluoroacetic acid/N-(3-aminopropyl)-N-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,19-dioxo-6,9,12,15-tetraoxa-22-thia-3,18-diazatetracosane-24-amide (1:1)

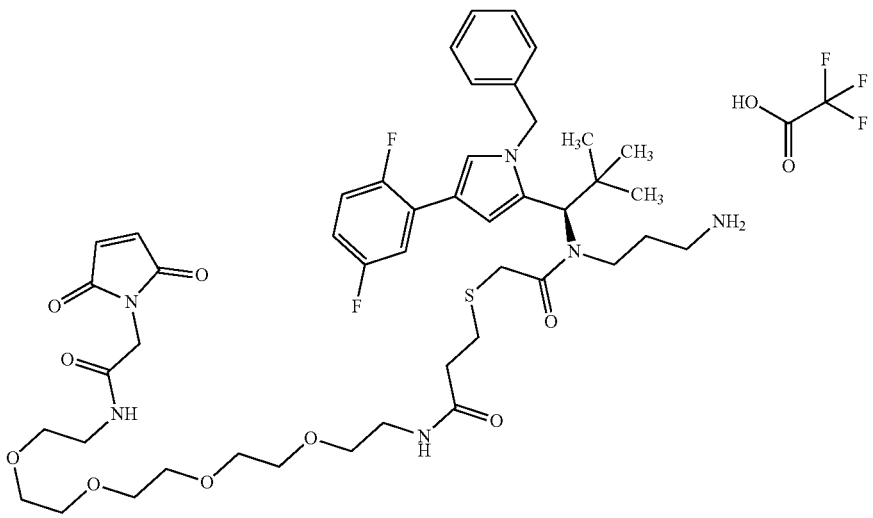 [SMILES: CC(C)(C)[C@H](c1cc(-c2cc(F)ccc2F)cn1Cc1ccccc1)N(CCCN)C(=O)CSCCC(=O)NCCOCCOCCOCCOCCNC(=O)CN1C(=O)C=CC1=O ; O=C(O)C(F)(F)F]

Under argon, 20.0 mg (28.5 µmol) of 11-{(1R)-1-[1-benzyl-4-(2,5-difluorophenyl)-1H-pyrrol-2-yl]-2,2-dimethylpropyl}-2,2-dim ethyl-6,12-dioxo-5-oxa-14-thia-7,11-diaza-2-silaheptadecan-17-oic acid (Intermediate C69) were initially charged in 1.0 ml of DMF, and 10.0 µl (57.0 µmol) of N,N-diisopropylethylamine and 13.0 mg (34.2 µmol) of HATU were added. The reaction mixture was stirred at RT for 10 min. 16.7 mg (34.2 µmol) of trifluoroacetic acid/N-(14-amino-3,6,9,12-tetraoxatetradec-1-yl)-2-(2,5-dioxo-2,5-dihydro-1H-pyrrol-1-yl)acetamide (1:1) (Intermediate L85) dissolved in 5.0 µl (28.5 µmol) of N,N-diisopropylethylamine and 1.0 ml of DMF were then added. The reaction mixture was stirred at RT for 1 h. The reaction mixture was purified directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 18.6 mg (62% of theory) of the compound 2-(trimethylsilyl)ethyl [25-{(1R)-1-[1-benzyl-4-(2,5-difluorophenyl)-1H-pyrrol-2-yl]-2,2-dimethylpropyl}-1-(2, 5-dioxo-2,5-dihydro-1H-pyrrol-1-yl)-2,19,24-trioxo-6,9,12,15-tetraoxa-22-thia-3,18,25-triazaoctacosan-28-yl] carbamate.

LC-MS (Method 1): $R_t$=1.37 min; MS (ESIpos): m/z=1057 (M+H)$^+$.

17.1 mg (16.2 µmol) of 2-(trimethylsilyl)ethyl [25-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-2,19,24-trioxotrioxo-6,9,12,15-tetraoxa-22-thia-3,18,25-triazaoctacosan-28-yl]carbamate were dissolved in 2.0 ml of trifluoroethanol, and 13.2 mg (97.0 µmol) of zinc dichloride were added. The reaction mixture was stirred at 50° C. for 1 h. 28.4 mg (97.0 µmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 250×30; 10µ, flow rate: 50 ml/min, MeCN/water, 0.1% TFA). The solvents were evaporated under reduced pressure and the residue was dried under high vacuum. This gave 9.80 mg (59% of theory) of the title compound.

LC-MS (Method 1): $R_t$=0.88 min; MS (ESIpos): m/z=913 (M+H)$^+$.

Intermediate F274

N-[(2,5-Dioxo-2,5-dihydro-1H-pyrrol-1-yl)acetyl]-L-valyl-L-alanyl-S-{2-[(3-aminopropyl){(1R)-1-[1-benzyl-4-(2,5-difluorophenyl)-1H-pyrrol-2-yl]-2,2-dimethylpropyl}amino]-2-oxoethyl}-L-cysteine/trifluoroacetic acid (1:1)

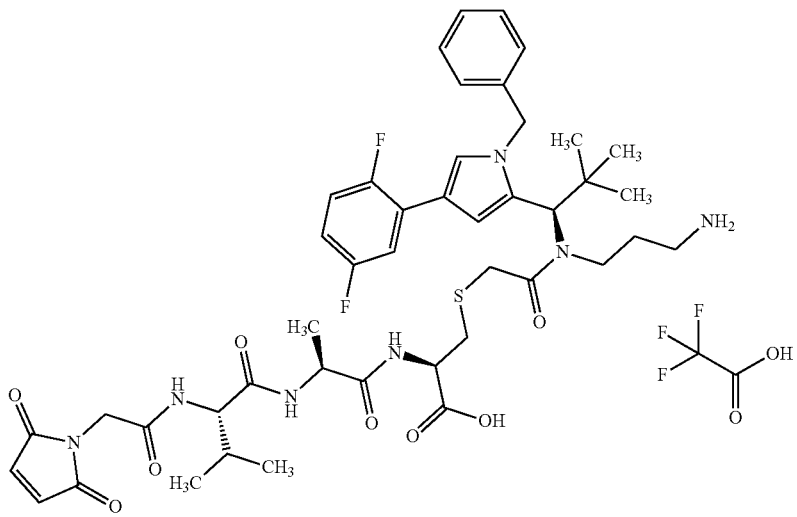 [SMILES: CC(C)[C@H](NC(=O)CN1C(=O)C=CC1=O)C(=O)N[C@@H](C)C(=O)N[C@@H](CSCC(=O)N(CCCN)[C@@H](c1cc(-c2cc(F)ccc2F)cn1Cc1ccccc1)C(C)(C)C)C(=O)O ; O=C(O)C(F)(F)F]

13.9 mg (0.0167 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) were initially charged together with 7.07 mg (0.0217 mmol) of N-[(2,5-dioxo-2,5-dihydro-1H-pyrrol-1-yl)acetyl]-L-valyl-L-alanine (Intermediate L86) in 2.0 ml of acetonitrile. 23 µl (0.13 mmol) of N,N-diisopropylethylamine were then added, and 13 µl (0.022 mmol) of T3P (50% in ethyl acetate) were added dropwise. The reaction mixture was stirred at RT overnight. The reaction mixture was purified directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 3.70 mg (19% of theory) of the compound N-[(2,5-dioxo-2,5-dihydro-1H-pyrrol-1-yl)acetyl]-L-valyl-L-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine.

LC-MS (Method 1): $R_t$=1.34 min; MS (ESIpos): m/z=1024 (M+H)$^+$.

10.6 mg (10.3 µmol) of N-[(2,5-dioxo-2,5-dihydro-1H-pyrrol-1-yl)acetyl]-L-valyl-L-alanyl-S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine were dissolved in 2.0 ml of trifluoroethanol, and 8.46 mg (62.1 µmol) of zinc dichloride were added. The reaction mixture was stirred at 50° C. for 1 h. 18.1 mg (62.1 µmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 5.60 mg (54% of theory) of the title compound.

LC-MS (Method 12): $R_t$=1.69 min; MS (ESIpos): m/z=880 (M+H)$^+$.

Intermediate F275

N-[3-({2-[(3-Aminopropyl){(1R)-1-[1-benzyl-4-(2,5-difluorophenyl)-1H-pyrrol-2-yl]-2,2-dimethylpropyl}amino]-2-oxoethyl}sulphanyl)propanoyl]-N-(2-{[(2,5-dioxo-2,5-dihydro-1H-pyrrol-1-yl)acetyl]amino}ethyl)-L-alpha-glutamine/trifluoroacetic acid (1:1)

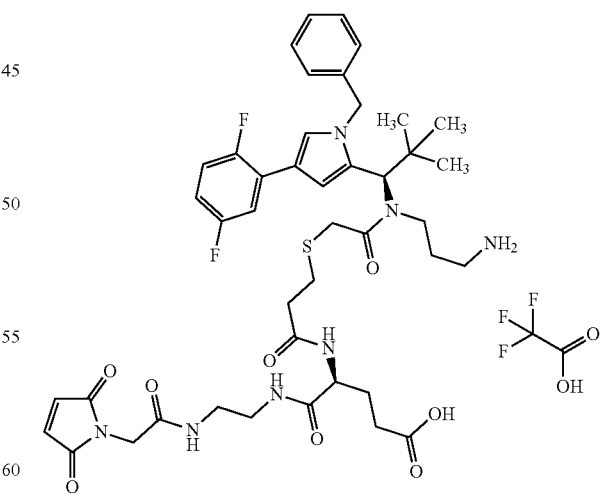

39.0 mg (55.6 µmol) of 11-{(1R)-1-[1-benzyl-4-(2,5-difluorophenyl)-1H-pyrrol-2-yl]-2,2-dimethylpropyl}-2,2-dimethyl-6,12-dioxo-5-oxa-14-thia-7,11-diaza-2-silahepta-decan-17-oic acid (Intermediate C69) were initially charged in 4.0 ml of DMF, 41.6 mg (111 µmol) of 1-benzyl-5-[2-

(trimethylsilyl)ethyl]-L-glutamate hydrochloride (1:1) (Intermediate L89), 29 μl (170 μmol) of N,N-diisopropylethylamine and 42.3 mg (111 μmol) of HATU were added and the mixture was stirred at RT for 1 hour. The reaction mixture was stirred at RT for 1 hour, quenched with acetic acid and purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 53.1 mg (93% of theory) of the compound 1-benzyl-5-[2-(trimethylsilyl)ethyl]-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-L-glutamate.

LC-MS (Method 1): $R_t$=1.71 min; MS (ESIpos): m/z=1021 [M+H]$^+$

Under argon, 7.60 mg (33.9 μmol) of palladium(II) acetate were initially charged in 3.0 ml of dichloromethane, and 14 μl (100 μmol) of triethylamine and 110 μl (680 μmol) of triethylsilane were added. The reaction mixture was stirred at RT for 5 min, and 69.2 mg (67.7 μmol) of 1-benzyl-5-[2-(trimethylsilyl)ethyl]-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-L-glutamate dissolved in 3.0 ml of dichloromethane were added. The reaction mixture was stirred at RT overnight. The reaction mixture was filtered through a cardboard filter and the filter cake was washed with dichloromethane. The solvent was evaporated under reduced pressure. The residue was purified by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 38.4 mg (61% of theory) of the compound (19S)-11-{(1R)-1-[1-benzyl-4-(2,5-difluorophenyl)-1H-pyrrol-2-yl]-2,2-dimethylpropyl}-2,2-dimethyl-6,12,17-trioxo-19-{3-oxo-3-[2-(trimethylsilyl)ethoxy]propyl}-5-oxa-14-thia-7,11,18-triaza-2-silaicosan-20-oic acid.

LC-MS (Method 1): $R_t$=1.53 min; MS (ESIpos): m/z=931 (M+H)$^+$.

10.0 mg (10.7 μmol) of (19S)-11-{(1R)-1-[1-benzyl-4-(2,5-difluorophenyl)-1H-pyrrol-2-yl]-2,2-dimethylpropyl}-2,2-dimethyl-6,12,17-trioxo-19-{3-oxo-3-[2-(trimethylsilyl)ethoxy]propyl}-5-oxa-14-thia-7,11,18-triaza-2-silaicosan-20-oic acid (Intermediate C69) were initially charged in 1.0 ml of DMF, 6.73 mg (21.5 μmol) of N-(2-aminoethyl)-2-(2,5-dioxo-2,5-dihydro-1H-pyrrol-1-yl)acetamide/2,2,2-trifluoroethane-1,1-diol (1:1) (Intermediate L1), 5.6 μl (32 μmol) of N,N-diisopropylethylamine and 8.17 mg (21.5 μmol) of HATU were added and the mixture was stirred at RT for 1 hour. The reaction mixture was stirred at RT for 3 hour, quenched with acetic acid and purified directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 6.90 mg (58% of theory) of the compound 2-(trimethylsilyl)ethyl N2-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-N-(2-{[(2,5-dioxo-2,5-dihydro-1H-pyrrol-1-yl)acetyl]amino}ethyl)-L-alpha-glutaminate.

LC-MS (Method 1): $R_t$=1.57 min; MS (ESIpos): m/z=1110 [M+H]$^+$ 6.90 mg (6.21 μmol) of 2-(trimethylsilyl)ethyl N²-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-N-(2-{[(2,5-dioxo-2,5-dihydro-1H-pyrrol-1-yl)acetyl]amino}ethyl)-L-alpha-glutaminate were dissolved in 2.0 ml of trifluoroethanol, and 5.1 mg (37.2 μmol) zinc dichloride were added. The reaction mixture was stirred at 50° C. for 3 h. 5.1 mg (37.2 μmol) of zinc dichloride were added and the reaction mixture was stirred at 50° C. for 3 h. 5.1 mg (37.2 μmol) of zinc dichloride were added and the reaction mixture was stirred at 50° C. for 3 h. 10.1 mg (74.4 μmol) of zinc dichloride were added and the reaction mixture was stirred at 50° C. overnight and at RT for 72 h. 54.5 mg (186 μmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 2.4 mg (39% of theory) of the title compound.

LC-MS (Method 1): $R_t$=0.86 min; MS (ESIpos): m/z=866 (M+H)$^+$.

Intermediate F276

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-{3-[2-(2-{[(2,5-dioxo-2,5-dihydro-1H-pyrrol-1-yl)acetyl]amino}ethoxy)ethoxy]propanoyl}-L-cysteine/trifluoroacetic acid (1:1)

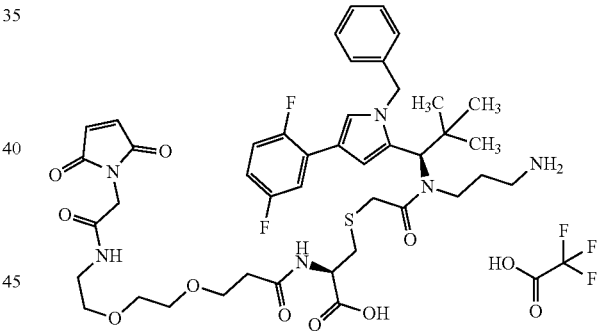

Under argon, 9.08 mg (28.9 μmol) of 3-[2-(2-{[(2,5-Dioxo-2,5-dihydro-1H-pyrrol-1-yl)acetyl]amino}ethoxy)ethoxy]propanoic acid (Intermediate L87) were initially charged in 1.0 ml of DMF, and 8.33 μl (48.2 μmol) of N,N-diisopropylethylamine and 11.0 mg (28.9 μmol) of HATU were added. The reaction mixture was stirred at RT for 10 min. 20.0 mg (27.7 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) dissolved in 4.67 μl (24.1 μmol) of N,N-diisopropylethylamine and 1.0 ml of DMF were then added. The reaction mixture was stirred at RT for 1 h. The reaction mixture was purified directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 4.70 mg (19% of theory) of the compound S-(11-{(1R)-1-[1-benzyl-4-(2,5-difluorophenyl)-1H- pyrrol-2-yl]-2,2-dimethylpropyl}-2,2-dimethyl-6,12-dioxo-5-oxa-7,11-diaza-2-silatridecan-13-yl)-N-{3-[2-(2-{[(2,5-dioxo-2,5-dihydro-1H-pyrrol-1-yl)acetyl]amino}ethoxy)ethoxy]propanoyl}-L-cysteine.

LC-MS (Method 12): $R_t$=2.47 min; MS (ESIpos): m/z=1013 (M+H)$^+$. 13.9 mg (13.7 μmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-{3-[2-(2-{[(2,5-dioxo-2,5-dihydro-1H-pyrrol-1-yl)acetyl]amino}ethoxy)ethoxy]propanoyl}-L-cysteine were dissolved in 2.0 ml of trifluoroethanol, and 5.6 mg (41.2 μmol) of zinc dichloride were added. The reaction mixture was stirred at 50° C. for 1 h. 5.6 mg (41.2 μmol) of zinc dichloride were added and the reaction mixture was stirred at 50° C. for 30 minutes. 24.1 mg (82.4 μmol) of ethylenediamine-N,N,N',N'-tetraacetic acid were added and the reaction mixture was stirred for 10 min, and water (0.1% TFA) was then added. Purification was carried out directly by preparative RP-HPLC (column: Reprosil 250×30; 10μ, flow rate: 50 ml/min, MeCN/water, 0.1% TFA). The solvents were evaporated under reduced pressure and the residue was dried under high vacuum. This gave 10.8 mg (80% of theory) of the title compound.

LC-MS (Method 12): $R_t$=1.58 min; MS (ESIpos): m/z=869 (M+H)$^+$.

Intermediate F277

N-[3-({2-[(3-Aminopropyl){(1R)-1-[1-benzyl-4-(2,5-difluorophenyl)-1H-pyrrol-2-yl]-2,2-dimethylpropyl}amino]-2-oxoethyl}sulphanyl)propanoyl]-3-[(bromoacetyl)amino]-D-alanine/trifluoroacetic acid (1:1)

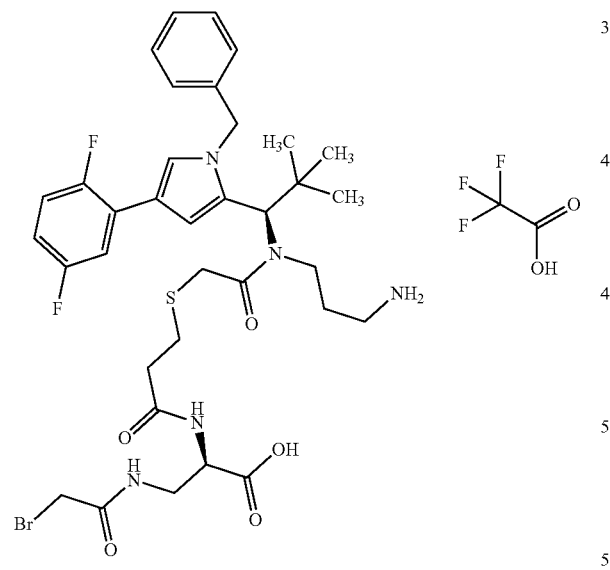

8.90 mg (8.88 μmol) of trifluoroacetic acid/2-(trimethylsilyl)ethyl 3-amino-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-D-alaninate (1:1) (Intermediate C80) and 2.31 mg (9.77 μmol) of 1-(2-bromoacetoxy)pyrrolidine-2,5-dione were dissolved in 1 ml of dimethylformamide, and 2.9 μl (27 μmol) of N-methylmorpholine were added. The reaction mixture was stirred at RT for 1 h. The reaction mixture was purified directly by preparative RP-HPLC (column: Reprosil 125×30; 10μ, flow rate: 50 ml/min, MeCN/water/0.1% TFA). The solvents were evaporated under reduced pressure and the residue was dried under high vacuum. This gave 5.80 mg (65% of theory) of the compound 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-[(bromoacetyl)amino]-D-alaninate.

LC-MS (Method 1): $R_t$=1.57 min; MS (ESIpos): m/z=1008 (M+H)$^+$.

5.80 mg (5.75 μmol) of 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-[(bromoacetyl)amino]-D-alaninate were dissolved in 2.0 ml of trifluoroethanol, and 4.70 mg (34.5 μmol) of zinc dichloride were added. The reaction mixture was stirred at 50° C. for 3 h. 4.70 mg (34.5 μmol) of zinc dichloride were added and the reaction mixture was stirred at 50° C. for 5 h. 20.2 mg (69.0 μmol) of ethylenediamine-N,N,N',N'-tetraacetic acid were added and the reaction mixture was stirred for 10 min, and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 1.70 mg (34% of theory) of the title compound.

LC-MS (Method 1): $R_t$=0.90 min; MS (ESIpos): m/z=764 (M+H)$^+$.

Intermediate F278

N-[3-({2-[(3-Aminopropyl){(1R)-1-[1-benzyl-4-(2,5-difluorophenyl)-1H-pyrrol-2-yl]-2,2-dimethylpropyl}amino]-2-oxoethyl}sulphanyl)propanoyl]-3-{[(2,5-dioxo-2,5-dihydro-1H-pyrrol-1-yl)acetyl]amino}-D-alanine/trifluoroacetic acid (1:1)

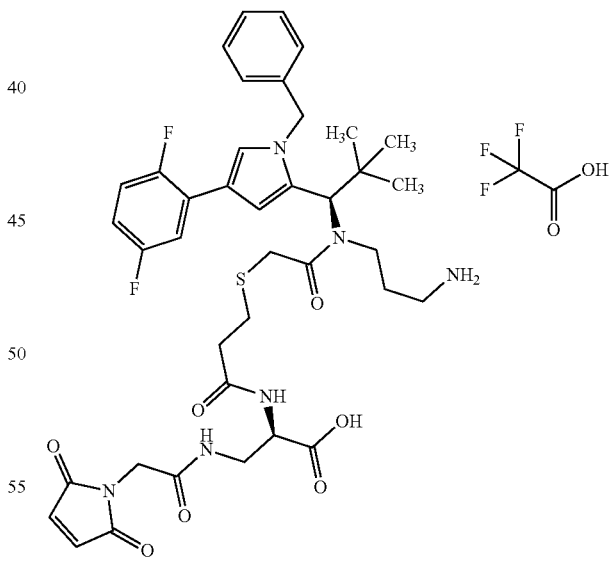

10.0 mg (9.98 μmol) of trifluoroacetic acid/2-(trimethylsilyl)ethyl 3-amino-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-D-alaninate (1:1) (Intermediate C80) and 2.77 mg (11.0 μmol) of 1-{2-[(2,5-dioxopyrrolidin-1-yl)oxy]-2-oxoethyl}-1H-pyrrole-2,5-dione were dissolved in 1 ml of dimethylformamide, and 3.3 μl (30 μmol) of N-methylmorpholine were added. The reaction mixture was stirred at RT overnight. 2.0 µl (35 µmol) of acetic acid were added, and the reaction mixture was purified directly by preparative RP-HPLC (column. Reprosil 125×30, 10µ, flow rate: 50 ml/min, MeCN/water/0.1% TFA). The solvents were evaporated under reduced pressure and the residue was dried under high vacuum. This gave 5.50 mg (54% of theory) of the compound 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-{[(2,5-dioxo-2,5-dihydro-1H-pyrrol-1-yl)acetyl]amino}-D-alaninate.

LC-MS (Method 1): $R_t$=1.51 min; MS (ESIpos): m/z=1024 (M+H)$^+$.

5.50 mg (5.36 µmol) of 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-{[(2,5-dioxo-2,5-dihydro-1H-pyrrol-1-yl)acetyl]amino}-D-alaninate were dissolved in 1.0 ml of trifluoroethanol, and 4.39 mg (32.2 µmol) of zinc dichloride were added. The reaction mixture was stirred at 50° C. for 1 h. 4.39 mg (32.2 µmol) of zinc dichloride were added and the reaction mixture was stirred at 50° C. for 1 h. 4.39 mg (32.2 µmol) of zinc dichloride were added and the reaction mixture was stirred at 50° C. for 4 h. 28.2 mg (96.5 µmol) of ethylenediamine-N,N,N',N'-tetraacetic acid were added and the reaction mixture was stirred for 10 min, and water (0.1% TFA) was then added. Purification was carried out directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 2.70 mg (56% of theory) of the title compound.

LC-MS (Method 1): $R_t$=0.89 min; MS (ESIpos): m/z=781 (M+H)$^+$.

Intermediate F279

N-[6-(2,5-Dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}[({(2R)-2-carboxy-2-[(3-carboxypropanoyl)amino]ethyl}sulphanyl)acetyl]amino)propyl]-L-alaninamide 12.2 mg (14 µmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine (Intermediate C77) were dissolved in 2.0 ml of trifluoroethanol, and 11.4 mg (83.8 µmol) of zinc dichloride were added. The reaction mixture was stirred at 50° C. for 3 h. 24.5 mg (83.8 µmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10µ, flow rate: 50 ml/min, MeCN/water, 0.1% TFA). The solvents were evaporated under reduced pressure and the residue was dried under high vacuum. This gave 4.60 mg (42% of theory) of the compound 4-{[(1R)-2-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)-1-carboxyethyl]amino}-4-oxobutanoic acid/trifluoroacetic acid (1:1).

LC-MS (Method 1): $R_t$=0.88 min; MS (ESIpos): m/z=673 (M+H)$^+$.

10.0 mg (12.7 µmol) of 4-{[(1R)-2-({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)-1-carboxyethyl]amino}-4-oxobutanoic acid/trifluoroacetic acid (1:1) and 7.41 mg (12.7 µmol) of 2,5-dioxopyrrolidin-1-yl N-[6-(2,5-dioxo-2,5-dihydro-1H-pyrrol-1-yl)hexanoyl]-L-valyl-L-alaninate (Intermediate L88) were dissolved in 1.5 ml of dimethylformamide, and 4.4 µl (25 µmol) of N,N-diisopropylethylamine were added. The reaction mixture was stirred at RT for 2 h. 2.0 µl (35 µmol) of acetic acid were added, and the reaction mixture was purified directly by preparative RP-HPLC (column: Reprosil 250×30; 10µ, flow rate: 50 ml/min, MeCN/water/0.1% TFA). The solvents were evaporated under reduced pressure and the residue was dried under high vacuum. This gave 5.20 mg (39% of theory) of the title compound.

LC-MS (Method 1): $R_t$=1.11 min; MS (ESIpos): m/z=1036 (M+H)$^+$.

Intermediate F280

Trifluoroacetic acid/N-[2-({(2S)-2-amino-4-[{(1R)-1-[1-benzyl-4-(2,5-difluorophenyl)-1H-pyrrol-2-yl]-2,2-dimeth-

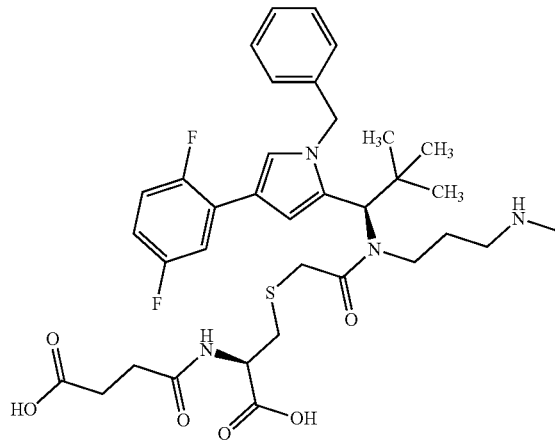
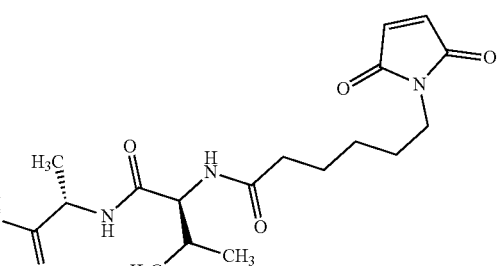

ylpropyl}(glycoloyl)amino]butanoyl}amino)ethyl]-3-(2,5-dioxo-2,5-dihydro-1H-pyrrol-1-yl)benzamide (1:1)

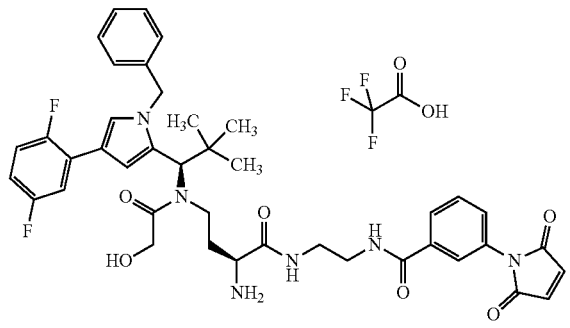 [SMILES: CC(C)(C)[C@H](c1cc(-c2cc(F)ccc2F)cn1Cc1ccccc1)N(CC[C@H](N)C(=O)NCCNC(=O)c1cccc(N2C(=O)C=CC2=O)c1)C(=O)CO ; O=C(O)C(F)(F)F]

The title compound was prepared from Intermediate C64 by coupling with commercially available 1-(3-{[[(2,5-dioxopyrrolidin-1-yl)oxy]carbonyl}phenyl)-1H-pyrrole-2,5-dione and subsequent deprotection with zinc chloride.

LC-MS (Method 1): $R_t$=0.88 min; MS (ESIpos): m/z=755 (M+H)$^+$.

Intermediate F281

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[N-(bromoacetyl)-beta-alanyl]amino}-D-alanine/trifluoroacetic acid (1:1)

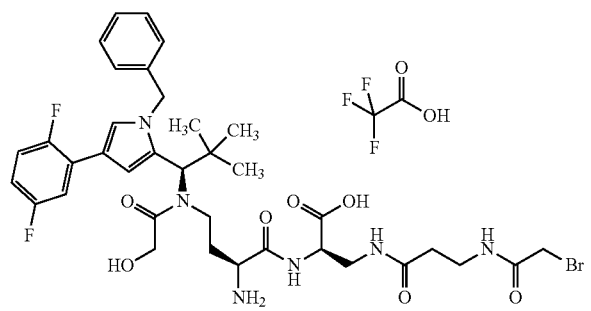 [SMILES: CC(C)(C)[C@H](c1cc(-c2cc(F)ccc2F)cn1Cc1ccccc1)N(CC[C@H](N)C(=O)N[C@H](CNC(=O)CCNC(=O)CBr)C(=O)O)C(=O)CO ; O=C(O)C(F)(F)F]

First, the modified amino acid building blocks N-(bromoacetyl)-beta-alanine and 2-(trimethylsilyl)ethyl-3-amino-N-(tert-butoxycarbonyl)-D-alaninate were prepared by classical methods of peptide chemistry. These were then coupled in the presence of HATU and morpholine. The tert-butoxycarbonyl protective group was then removed using 10% strength trifluoroacetic acid in dichloromethane, giving the intermediate 2-(trimethylsilyl)ethyl 3-{[N-(bromoacetyl)-beta-alanyl]amino}-D-alaninate.

Finally, the title compound was prepared by coupling this intermediate with intermediate C58 in the presence of HATU and 4-methylmorpholine, followed by deprotection with zinc chloride.

LC-MS (Method 1): $R_t$=0.87 min; MS (ESIpos): m/z=791 and 793 (M+H)$^+$.

Intermediate F282

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-(3-{[N-(bromoacetyl)glycyl]amino}propyl)butanamide (1:1)

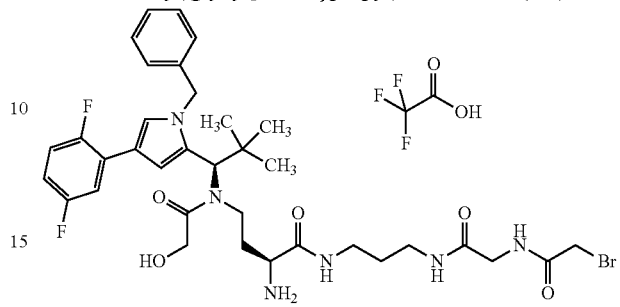

First, the intermediate trifluoroacetic acid/N-(3-aminopropyl)-N2-(bromoacetyl)glycinamide (1:1) was prepared from tert-butyl glycinate and bromoacetic anhydride by classical methods of peptide chemistry.

Finally, the title compound was prepared by coupling this intermediate with intermediate C58 in the presence of HATU and 4-methylmorpholine, followed by deprotection with zinc chloride.

LC-MS (Method 1): $R_t$=0.83 min; MS (ESIpos): m/z=747 and 749 (M+H)$^+$.

Intermediate F283

N-[(2R)-2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)-2-carboxyethyl]-N$^2$-(bromoacetyl)-L-alpha-asparagine/trifluoroacetic acid (1:1)

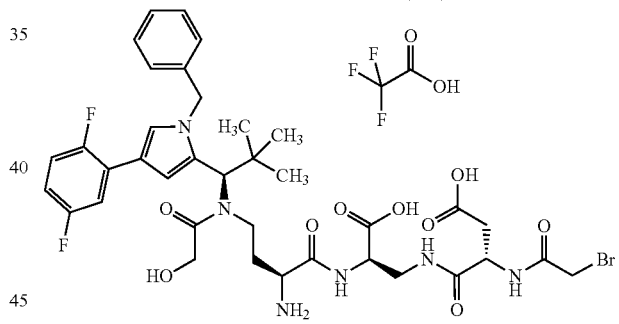

First, the modified amino acid building block (2S)-2-[(bromoacetyl)amino]-4-oxo-4-[2-(trimethylsilyl)ethoxy]butanoic acid and bromoacetic anhydride was prepared from (2S)-2-amino-4-oxo-4-[2-(trimethylsilyl)ethoxy]butanoic acid and bromoacetic anhydride and the amino acid building block 2-(trimethylsilyl)ethyl-3-amino-N-(tert-butoxycarbonyl)-D-alaninate was prepared from commercially available 3-{[(benzyloxy)carbonyl]amino}-N-(tert-butoxycarbonyl)-D-alanine/N-cyclohexylcyclohexanamine (1:1). Both building blocks were coupled in the presence of HATU and morpholine and the tert-butoxycarbonyl protective group was then removed using 5% strength trifluoroacetic acid in dichloromethane, giving the silylethyl ester protective groups and thus the intermediate trifluoroacetic acid/2-(trimethylsilyl)ethyl-N-{(2R)-2-amino-3-oxo-3-[2-(trimethylsilyl)ethoxy]propyl}-N2-(bromoacetyl)-L-alpha-asparaginate (1:1). Finally, the title compound was prepared by coupling this intermediate with intermediate C58 in the presence of HATU and 4-methylmorpholine, followed by deprotection with zinc chloride.

LC-MS (Method 1): $R_t$=0.84 min; MS (ESIpos): m/z=835 and 837 (M+H)$^+$.

Intermediate F284

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[1-(2,5-dioxo-2,5-dihydro-1H-pyrrol-1-yl)-2,18-dioxo-6,9,12,15-tetraoxa-3-azaoctadecan-18-yl]amino}-D-alanine/trifluoroacetic acid (1:1)

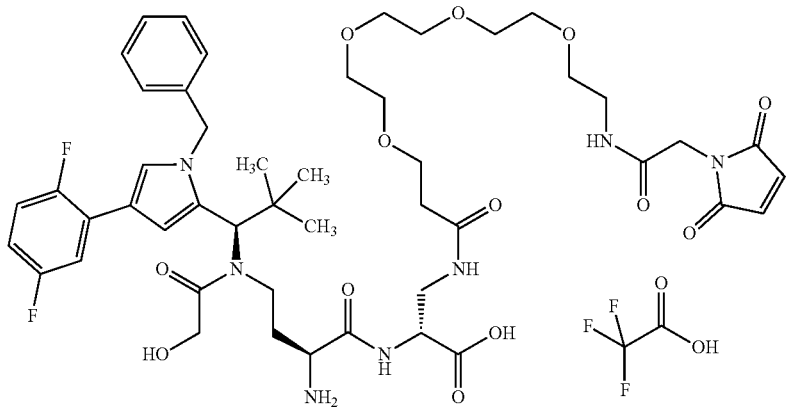

First, intermediate L80 was coupled with commercially available (2,5-dioxo-2,5-dihydro-1H-pyrrol-1-yl)acetic acid in the presence of HATU and N,N-diisopropylethylamine, and the tert-butoxycarbonyl protective group was then removed using 16% strength trifluoroacetic acid in dichloromethane, giving the silylethyl ester protective group.

Finally, the title compound was prepared by coupling this intermediate with intermediate C58 in the presence of HATU and N,N-diisopropylethylamine, followed by deprotection with zinc chloride.

LC-MS (Method 12): $R_t$=1.46 min; MS (ESIpos): m/z=984.45 (M+H)$^+$.

Intermediate F285

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-[(18-bromo-17-oxo-4,7,10,13-tetraoxa-16-azaoctadecan-1-oyl)amino]-D-alanine/trifluoroacetic acid (1:1)

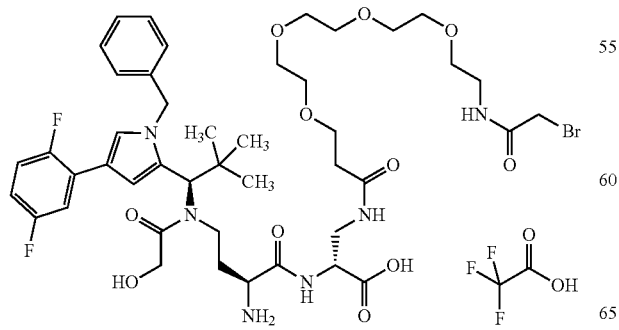

First, intermediate L80 was coupled with commercially available bromoacetic anhydride, and the tert-butoxycarbonyl protective group was then removed using 20% strength trifluoroacetic acid in dichloromethane, giving the silylethyl ester protective group.

Finally, the title compound was prepared by coupling this intermediate with intermediate C58 in the presence of HATU and N,N-diisopropylethylamine, followed by deprotection with zinc chloride.

LC-MS (Method 1): $R_t$=0.85 min; MS (ESIpos): m/z=967 and 969 (M+H)$^+$.

Intermediate F286

1-[(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[(2,5-dioxo-2,5-dihydro-1H-pyrrol-1-yl) acetyl]amino}-D-alanyl) amino]-3,6,9,12-tetraoxapentadecan-15-oic acid/ trifluoroacetic acid (1:1)

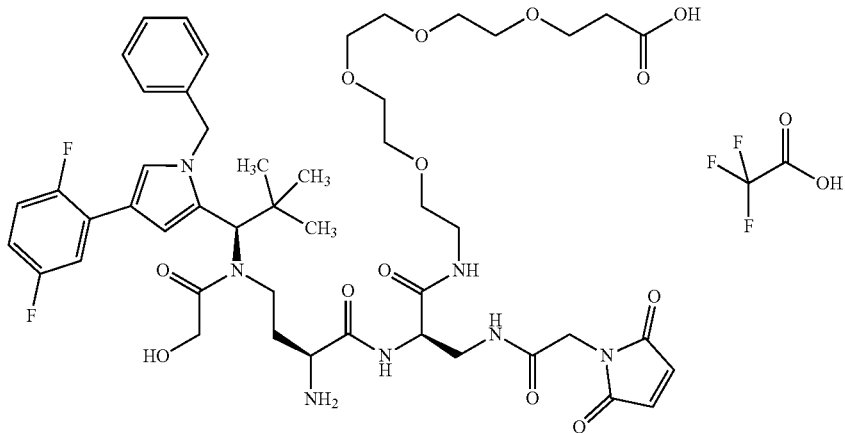 [SMILES: CC(C)(C)[C@H](c1cc(-c2cc(F)ccc2F)cn1Cc1ccccc1)N(CC[C@H](N)C(=O)N[C@H](CNC(=O)CN1C(=O)C=CC1=O)C(=O)NCCOCCOCCOCCOCCC(=O)O)C(=O)CO ; O=C(O)C(F)(F)F]

First, intermediate L91 was coupled with (2,5-dioxo-2,5-dihydro-1H-pyrrol-1-yl)acetic acid in the presence of HATU and N,N-diisopropylethylamine, and the Boc protective group was then removed using 12.5% strength TFA in DCM. The resulting intermediate was coupled with intermediate C58 in the presence of HATU and N,N-diisopropylethylamine and then converted into the title compound by deprotection with zinc chloride.

LC-MS (Method 1): $R_t$=0.84 min; MS (ESIpos): m/z=984 (M+H)$^+$.

Intermediate F288

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-({N-[(2,5-dioxo-2,5-dihydro-1H-pyrrol-1-yl)acetyl]-L-seryl}amino)-D-alanine/trifluoroacetic acid (1:1)

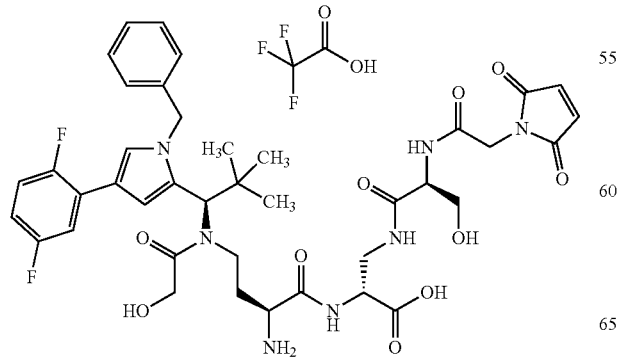

35 mg (39 µmol) of intermediate C74 were coupled in the presence of HATU and N,N-diisopropyethylamine with N-[(2,5-dioxo-2,5-dihydro-1H-pyrrol-1-yl)acetyl]-L-serine which had been prepared beforehand from tert-butyl O-tert-butyl-L-serinate and (2,5-dioxo-2,5-dihydro-1H-pyrrol-1-yl)acetic acid. Deprotection with zinc chloride and purification by HPLC gave 14 mg (38% of theory) of the title compound.

LC-MS (Method 12): $R_t$=1.43 min; MS (ESIpos): m/z=824.34 (M+H)$^+$.

Intermediate F289

$N^2$-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-$N^6$-[(2,5-dioxo-2,5-dihydro-1H-pyrrol-1-yl)acetyl]-D-lysine/ trifluoroacetate (1:1)

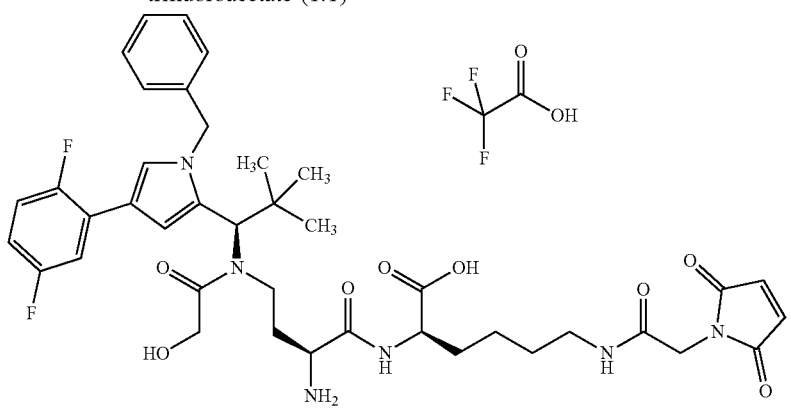

First, trifluoroacetic acid/2-(trimethylsilyl)ethyl-$N^6$-[(2,5-dioxo-2,5-dihydro-1H-pyrrol-1-yl)acetyl]-D-lysinate (1:1) was prepared by classical methods of peptide chemistry from $N^6$-[(benzyloxy)carbonyl]-$N^2$-(tert-butoxycarbonyl)-D-lysine. 12.5 mg (25 µmol) of this intermediate were then coupled in the presence of HATU and 4-methylmorpholine with 15 mg (23 µmol) of Intermediate C58. Deprotection with zinc chloride and purification by HPLC gave 14 mg (53% of theory) of the title compound.

LC-MS (Method 1): $R_t$=0.83 min; MS (ESIpos): m/z=779 (M+H)$^+$.

Intermediate F290

$N^2$—{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-$N^6$-(bromoacetyl)-D-lysine/trifluoroacetic acid (1:1)

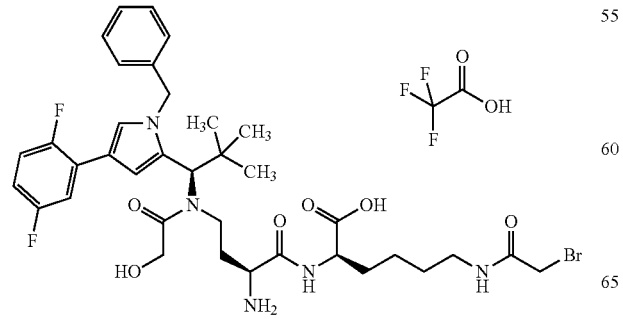

First, trifluoroacetic acid/2-(trimethylsilyl)ethyl-N6-(bromoacetyl)-D-lysinate (1:1) was prepared by classical methods of peptide chemistry from $N^6$-[(benzyloxy)carbonyl]-$N^2$-(tert-butoxycarbonyl)-D-lysine.

12 mg (25 µmol) of this intermediate were then coupled in the presence of HATU and 4-methylmorpholine with 15 mg (23 µmol) of Intermediate C58. Deprotection with zinc chloride and purification by HPLC gave 7 mg (36% of theory) of the title compound.

LC-MS (Method 1): $R_t$=0.86 min; MS (ESIpos): m/z=762 and 764 (M+H)⁺.

Intermediate F291

N-[(2,5-Dioxo-2,5-dihydro-1H-pyrrol-1-yl)acetyl]-L-valyl-N-{3-[{(1R)-1-[1-benzyl-4-(2,5-difluorophenyl)-1H-pyrrol-2-yl]-2,2-dimethylpropyl}(glycoloyl)amino]propyl}-L-alaninamide

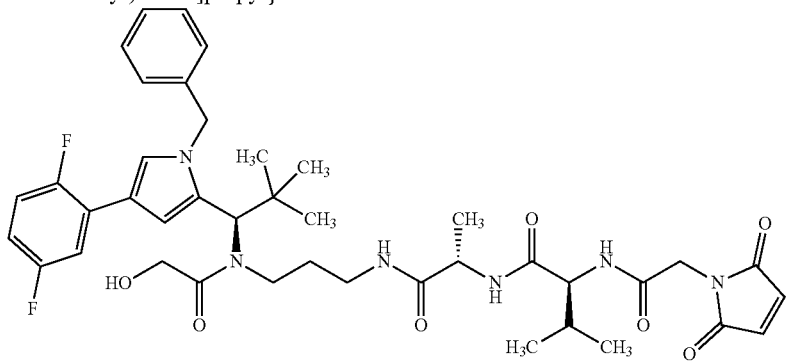

The title compound was prepared from Example M9 first by coupling with N-[(benzyloxy)carbonyl]-L-valyl-L-alanine in the presence of HATU and N,N-diisopropylethylamine. In the next step, the Z protective group was removed by hydrogenating for 1 hour over 10% palladium on activated carbon at RT under hydrogen standard pressure and then converting the deprotected intermediate into the title compound by coupling with (2,5-dioxo-2,5-dihydro-1H-pyrrol-1-yl)acetic acid in the presence of HATU and N,N-diisopropylethylamine.

LC-MS (Method 1): $R_t$=1.21 min; MS (ESIpos): m/z=777 (M+H)⁺.

Intermediate F293

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-3-{[(2,5-dioxo-2,5-dihydro-1H-pyrrol-1-yl)benzoyl]amino}-D-alanine/trifluoroacetic acid (1:1)

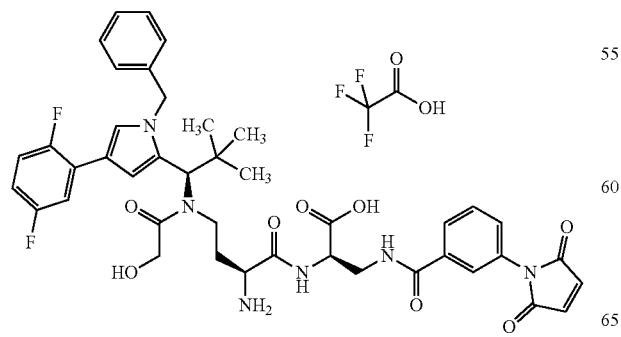

35 mg (39 μmol) of Intermediate C74 were dissolved in 4 ml of DMF and, in the presence of N,N-diisopropylethylamine, coupled with 13.5 mg (43 μmol) of commercially available 1-(3-{[(2,5-dioxopyrrolidin-1-yl)oxy]carbonyl}phenyl)-1H-pyrrole-2,5-dione. Deprotection with zinc chloride and purification by F1PLC gave 12 mg (34% of theory) of the title compound.

LC-MS (Method 12): $R_t$=0.93 min; MS (ESIpos): m/z=799 (M+H)$^+$.

Intermediate F294

N-{5-[(2,5-Dioxopyrrolidin-1-yl)oxy]-5-oxopentanoyl}-L-valyl-N-{(1S)-3-[{(1R)-1-[1-benzyl-4-(2,5-difluorophenyl)-1H-pyrrol-2-yl]-2,2-dimethylpropyl}(glycoloyl)amino]-1-carboxypropyl}-L-alaninamide

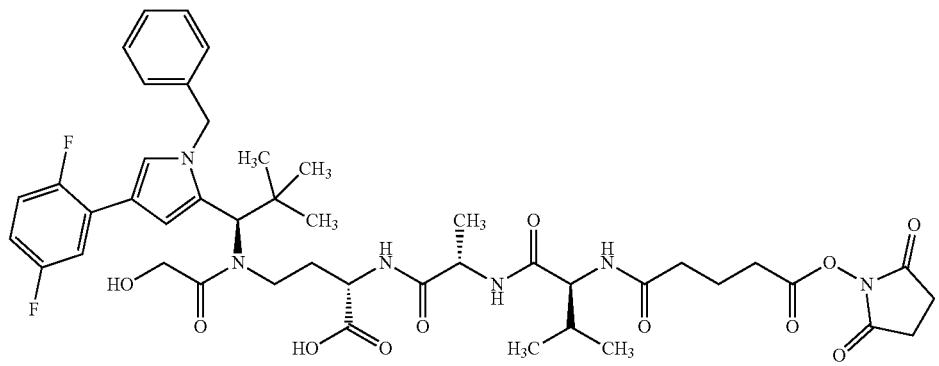 [SMILES: CC(C)[C@H](NC(=O)CCCC(=O)ON1C(=O)CCC1=O)C(=O)N[C@@H](C)C(=O)N[C@@H](CCN(C(=O)CO)[C@@H](c1cc(-c2cc(F)ccc2F)cn1Cc1ccccc1)C(C)(C)C)C(=O)O]

41 mg (0.05 mmol) of Intermediate C76 dissolved in 12 ml of methanol were hydrogenated over 10 mg of 10% palladium on activated carbon at RT for 1 h under hydrogen standard pressure. The catalyst was then filtered off and the solvent was removed under reduced pressure. This gave 32 mg (92% of theory) of the deprotected intermediate.

15 mg (0.022 mmol) of this intermediate were dissolved in DMF, and 13 mg (0.039 mmol) of 1,1'-[(1,5-dioxopentan-1,5-diyl)bis(oxy)]dipyrrolidine-2,5-dione and 7 μl of N,N-diisopropylethylamine were added. After 1 h of stirring at RT, the reaction was concentrated and the residue was purified by HPLC. This gave 9 mg (45% of theory) of the title compound.

LC-MS (Method 1): $R_t$=1.08 min; MS (ESIpos): m/z=895 (M+H)$^+$.

Intermediate F295

N-[(2,5-Dioxo-2,5-dihydro-1H-pyrrol-1-yl)acetyl]-L-valyl-N-{(1S)-3-[{(1R)-1-[1-benzyl-4-(2,5-difluorophenyl)-1H-pyrrol-2-yl]-2,2-dimethylpropyl}(glycoloyl)amino]-1-carboxypropyl}-L-alaninamide

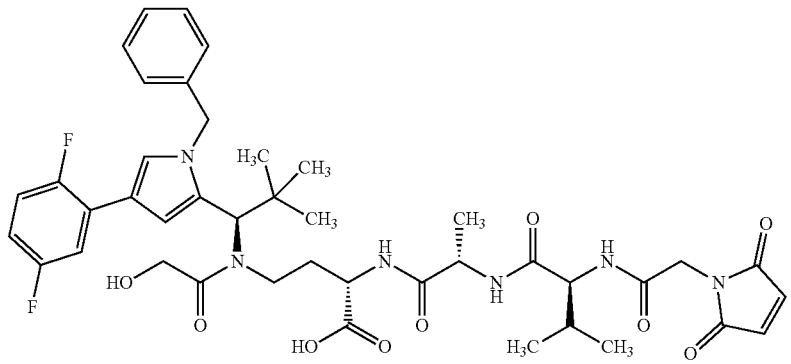 [SMILES: CC(C)[C@H](NC(=O)CN1C(=O)C=CC1=O)C(=O)N[C@@H](C)C(=O)N[C@@H](CCN(C(=O)CO)[C@@H](c1cc(-c2cc(F)ccc2F)cn1Cc1ccccc1)C(C)(C)C)C(=O)O]

41 mg (0.05 mmol) of Intermediate C76 dissolved in 12 ml of methanol were hydrogenated over 10 mg of 10% palladium on activated carbon at RT for 1 h under hydrogen standard pressure. The catalyst was then filtered off and the solvent was removed under reduced pressure. This gave 32 mg (92% of theory) of the deprotected intermediate.

15 mg (0.022 mmol) of this intermediate were dissolved in 4 ml of DMF, and 10 mg (0.039 mmol) of 1-{2-[(2,5-dioxopyrrolidin-1-yl)oxy]-2-oxoethyl}-1H-pyrrole-2,5-dione and 7 µl of N,N-diisopropylethylamine were added. After 2 h of stirring at RT, the reaction was concentrated and the residue was purified by HPLC. This gave 10 mg (56% of theory) of the title compound.

LC-MS (Method 1): $R_t$=1.08 min; MS (ESIpos): m/z=821 (M+H)$^+$.

Intermediate F296

Trifluoroacetic acid/(2S)-2-amino-4-[{(1R)-1-[1-benzyl-4-(2,5-difluorophenyl)-1H-pyrrol-2-yl]-2,2-dimethylpropyl}(glycoloyl)amino]-N-{2-[(2-{[(2,5-dioxo-2,5-dihydro-1H-pyrrol-1-yl)acetyl]amino}ethyl)sulphonyl]ethyl}butanamide (1:1)

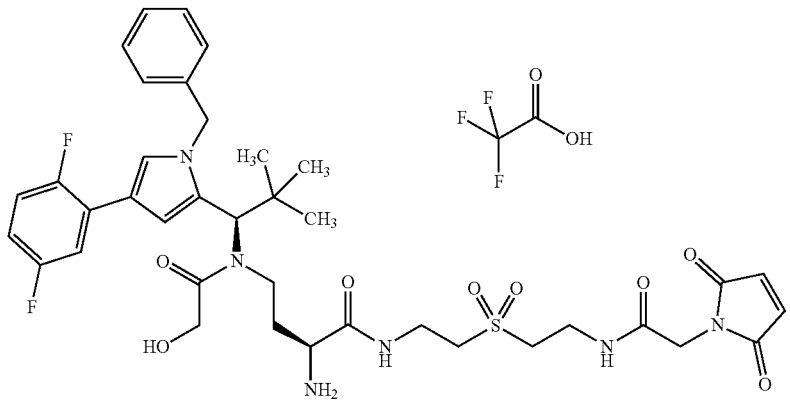 [SMILES: CC(C)(C)[C@H](c1cc(-c2cc(F)ccc2F)cn1Cc1ccccc1)N(CC[C@H](N)C(=O)NCCS(=O)(=O)CCNC(=O)CN1C(=O)C=CC1=O)C(=O)CO ; O=C(O)C(F)(F)F]

The title compound was prepared from Intermediate L81 by coupling with Intermediate C58 in the presence of HATU and N,N-diisopropylethylamine. In the next step, the Z protective group was removed by hydrogenation over 10% palladium on activated carbon in DCM/methanol 1:1 at RT under hydrogen standard pressure for 30 min. The deprotected intermediate was then converted by coupling with (2,5-dioxo-2,5-dihydro-1H-pyrrol-1-yl)acetic acid in the presence of HATU and N,N-diisopropylethylamine and finally by deprotection with zinc chloride into the title compound.

LC-MS (Method 1): $R_t$=0.83 min; MS (ESIpos): m/z=785 (M+H)$^+$.

Intermediate F297

S-{2-[{(1R)-1-[1-Benzyl-4-(2,5-difluorophenyl)-1H-pyrrol-2-yl]-2,2-dimethylpropyl}(pyrrolidin-3-ylmethyl)amino]-2-oxoethyl}-N-[6-(2,5-dioxo-2,5-dihydro-1H-pyrrol-1-yl)hexanoyl]-L-cysteine/ trifluoroacetic acid (1:1) (Isomer 1)

Intermediate F298

S-{2-[{(1R)-1-[1-Benzyl-4-(2,5-difluorophenyl)-1H-pyrrol-2-yl]-2,2-dimethylpropyl}(pyrrolidin-3-ylmethyl)amino]-2-oxoethyl}-N-[6-(2,5-dioxo-2,5-dihydro-1H-pyrrol-1-yl)hexanoyl]-L-cysteine/ trifluoroacetic acid (1:1) (Isomer 2)

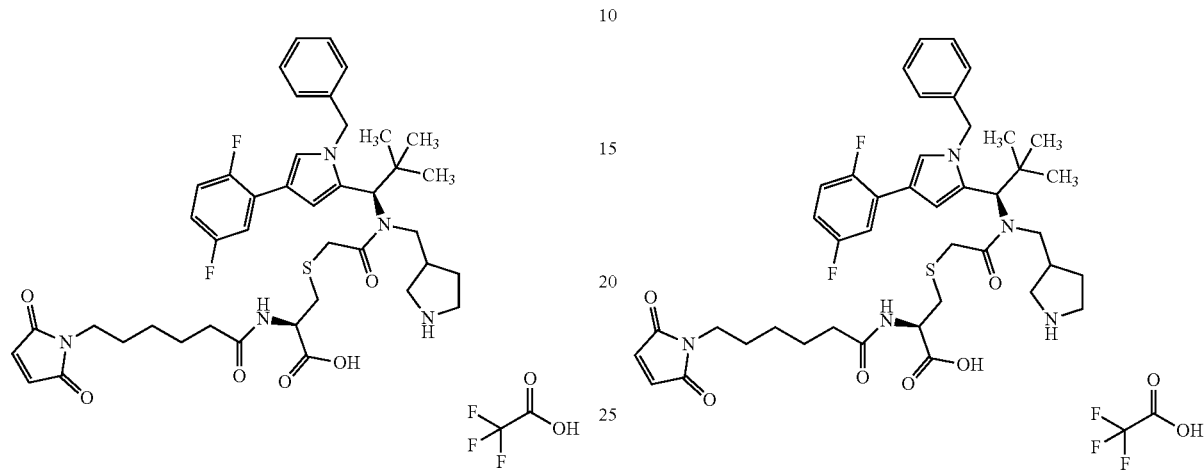

Under argon, 15 mg (0.11 mmol) of zinc chloride were added to a solution of 36 mg (0.03 mmol, 68% pure) of S-[2-({(1R)-1-[1-benzyl-4-(2,5-difluorophenyl)-1H-pyrrol-2-yl]-2,2-dimethyl-propyl} {[1-(tert-butoxycarbonyl)pyrrolidin-3-yl]methyl}amino)-2-oxoethyl]-N-[6-(2,5-dioxo-2,5-dihydro-1H-pyrrol-1-yl)hexanoyl]-L-cysteine (Intermediate C92) in 0.74 ml of 2,2,2-trifluoroethanol, and the reaction mixture was stirred at 50° C. for 7 h. 32 mg (0.11 mmol) of EDTA were then added and the mixture was stirred for 15 minutes. Ethyl acetate was added to the reaction mixture and the organic phase was washed repeatedly with water and with saturated NaCl solution. The organic phase was dried over magnesium sulphate and the solvent was evaporated under reduced pressure. The residue was purified by preparative HPLC. This gave 6.4 mg (25% of theory) of the title compound.

LC-MS (Method 1): $R_t$=0.95 min; MS (ESIpos): m/z=792 (M+H-CF$_3$CO$_2$H)$^+$.

Under argon, 19 mg (0.14 mmol) of zinc chloride were added to a solution of 45 mg (0.04 mmol, 71% pure) of S-[2-({(1R)-1-[1-benzyl-4-(2,5-difluorophenyl)-1H-pyrrol-2-yl]-2,2-dimethyl-propyl} {[1-(tert-butoxycarbonyl)pyrrolidin-3-yl]methyl}amino)-2-oxoethyl]-N-[6-(2,5-dioxo-2,5-dihydro-1H-pyrrol-1-yl)hexanoyl]-L-cysteine (Intermediate C96) in 0.94 ml of 2,2,2-trifluoro-ethanol, and the reaction mixture was stirred at 50° C. for 3 h. 42 mg (0.14 mmol) of EDTA were then added, and the mixture was stirred for 15 minutes. Ethyl acetate was added to the reaction mixture and the organic phase was washed repeatedly with water and with saturated NaCl solution. The organic phase was dried over magnesium sulphate and the solvent was evaporated under reduced pressure. The residue was purified by preparative HPLC. This gave 5.7 mg (18% of theory) of the title compound.

LC-MS (Method 1): $R_t$=0.96 min; MS (ESIpos): m/z=791 (M+H-CF$_3$CO$_2$H)$^+$.

423

Intermediate F299

S-(2-{(3-Aminopropyl)[(R)-[1-benzyl-4-(2,5-difluorophenyl)-1H-pyrrol-2-yl](cyclohexyl)methyl]amino}-2-oxoethyl)-N-[6-(2,5-dioxo-2,5-dihydro-1H-pyrrol-1-yl)hexanoyl]-L-cysteine/trifluoroacetic acid (1:1)

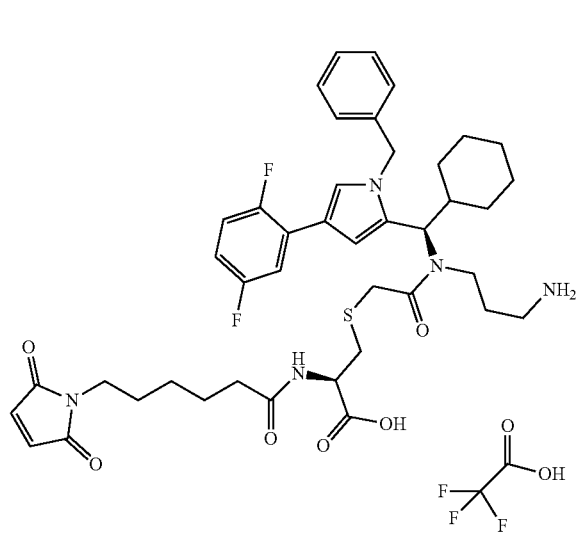 [SMILES: NCCCN(C(=O)CSC[C@H](NC(=O)CCCCCN1C(=O)C=CC1=O)C(=O)O)[C@@H](c1cc(-c2cc(F)ccc2F)cn1Cc1ccccc1)C1CCCCC1 ; O=C(O)C(F)(F)F]

76.8 mg (0.57 mmol) of zinc chloride were added to a solution of 88.0 mg (0.09 mmol) of S-{11-[(R)-[1-benzyl-4-(2,5-difluorophenyl)-1H-pyrrol-2-yl](cyclohexyl)methyl]-2,2-dimethyl-6,12-dioxo-5-oxa-7,11-diaza-2-silatridecan-13-yl}-N-[6-(2,5-dioxo-2,5-dihydro-1H-pyrrol-1-yl)hexanoyl]-L-cysteine (Intermediate C85) in 1.88 ml of 2,2,2-trifluoroethanol, and the reaction mixture was stirred at 50° C. for 3 h. 164.6 mg (0.57 mmol) of EDTA were then added, and the mixture was stirred for 15 minutes. Ethyl acetate was added to the reaction mixture, and the organic phase was washed repeatedly with water and with saturated NaCl solution. The organic phase was dried over sodium sulphate and the solvent was evaporated under reduced pressure. The residue was purified by preparative HPLC. This gave 31 mg (35% of theory) of the title compound.

LC-MS (Method 12): $R_t$=1.82 min; MS (ESIpos): m/z=792 (M+H)$^+$.

424

Intermediate F300

(2S)-2-Amino-4-[{(1R)-1-[1-benzyl-4-(2,5-difluorophenyl)-1H-pyrrol-2-yl]-2,2-dimethylpropyl}(glycoloyl)amino]-N-(2-{[(2R)-2-(2,5-dioxo-2,5-dihydro-1H-pyrrol-1-yl)propanoyl]amino}ethyl)butanamide

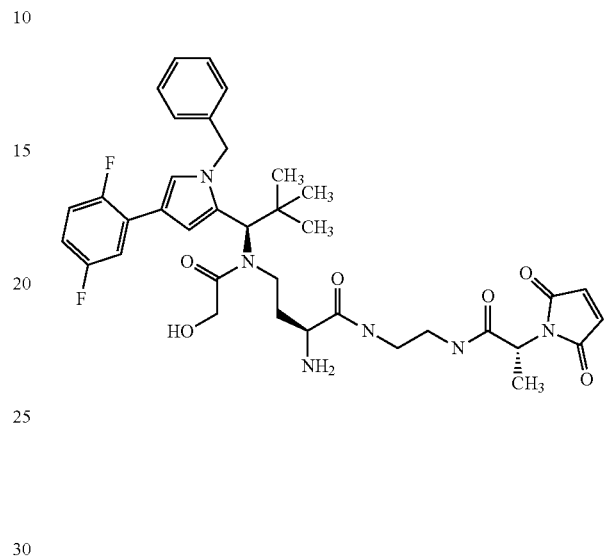

Under argon, 11 mg (0.08 mmol) of zinc chloride were added to a solution of 7 mg (0.08 mmol) of 2-(trimethylsilyl)ethyl-{(2S)-4-[{(1R)-1-[1-benzyl-4-(2,5-difluorophenyl)-1H-pyrrol-2-yl]-2,2-dimethylpropyl}(glycoloyl)amino]-1-[(2-{[(2R)-2-(2,5-dioxo-2,5-dihydro-1H-pyrrol-1-yl)propanoyl]amino}ethyl)amino]-1-oxobutan-2-yl}carbamate (Intermediate 100) in 0.2 ml of 2,2,2-trifluoroethanol and the reaction mixture was stirred at 50° C. for 8 h. 14 mg (0.05 mmol) of EDTA were then added, and the mixture was stirred for 15 minutes. Ethyl acetate was added to the reaction mixture and the organic phase was washed repeatedly with water and with saturated NaCl solution. The organic phase was dried over magnesium sulphate and the solvent was evaporated under reduced pressure. The residue was purified by preparative HPLC. This gave 1.6 mg (27% of theory) of the title compound.

LC-MS (Method 1): $R_t$=0.88 min; MS (ESIpos): m/z=707 (M+H-CF$_3$CO$_2$H)$^+$.

Intermediate F302

S-{2-[{(1R)-1-[1-Benzyl-4-(2,5-difluorophenyl)-1H-pyrrol-2-yl]-2,2-dimethylpropyl}(pyrrolidin-3-ylmethyl)amino]-2-oxoethyl}-N-[(2,5-dioxo-2,5-dihydro-1H-pyrrol-1-yl)acetyl]-L-cysteine trifluoroacetate (1:1) (Isomer 1)

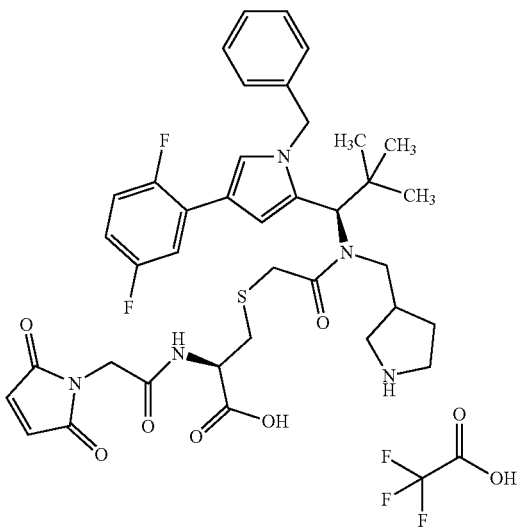

Under argon, 31.7 mg (0.23 mmol) of zinc chloride were added to a mixture of 56.9 mg (58.2 mmol, 85% pure) of S-[2-({(1R)-1-[1-benzyl-4-(2,5-difluorophenyl)-1H-pyrrol-2-yl]-2,2-dimethylpropyl}{[(1-(tert-butoxycarbonyl)pyrrolidin-3-yl]methyl}amino)-2-oxoethyl]-N-[(2,5-di oxo-2,5-dihydro-1H-pyrrol-1-yl)acetyl]-L-cysteine (Intermediate C99) in 1.4 ml of 2,2,2-trifluoroethanol, and the reaction mixture was stirred at 50° C. for 3 h. 68.0 mg (0.23 mmol) of EDTA were then added, and the mixture was stirred for 15 minutes. Ethyl acetate was added to the reaction mixture and the organic phase was washed repeatedly with water and with saturated NaCl solution. The organic phase was dried over magnesium sulphate and the solvent was evaporated under reduced pressure. The residue was purified by preparative HPLC. This gave 7 mg (13% of theory) of the title compound.

LC-MS (Method 1): $R_t$=0.91 min; MS (ESIpos): m/z=736 $(M+H-CF_3CO_2H)^+$.

Intermediate F304

N-(2-{[3-({2-[{(1R)-1-[1-Benzyl-4-(2,5-difluorophenyl)-1H-pyrrol-2-yl]-2,2-dimethyl-propyl}(pyrrolidin-3-ylmethyl)amino]-2-oxoethyl}sulphanyl) propanoyl]amino}ethyl)-6-(2,5-dioxo-2,5-dihydro-1H-pyrrol-1-yl)hexanamide/trifluoroacetic acid (1:1) (Isomer 2)

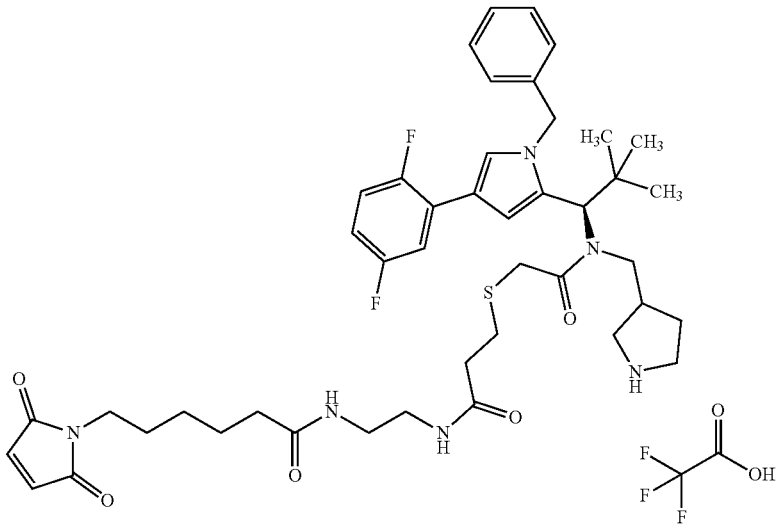 [SMILES: CC(C)(C)[C@H](c1cc(-c2cc(F)ccc2F)cn1Cc1ccccc1)N(CC1CCNC1)C(=O)CSCCC(=O)NCCNC(=O)CCCCCN1C(=O)C=CC1=O ; O=C(O)C(F)(F)F]

13.2 mg (0.10 mmol) of zinc chloride were added to a solution of 22.3 mg (0.02 mmol) of tert-butyl 3-[2-{(1R)-1-[1-benzyl-4-(2,5-difluorophenyl)-1H-pyrrol-2-yl]-2,2-dimethylpropyl}-18-(2,5-dioxo-2,5-dihydro-1H-pyrrol-1-yl)-3,8,13-trioxo-5-thia-2,9,12-triazaoctadec-1-yl]pyrrolidine-1-carboxylate (Intermediate 105) in 0.64 ml of 2,2,2-trifluoroethanol, and the reaction mixture was stirred at 50° C. for 8 h. 28.36 mg (0.10 mmol) of EDTA were then added, and the mixture was stirred for 15 minutes. Ethyl acetate was added to the reaction mixture and the organic phase was washed repeatedly with water and with saturated NaCl solution. The organic phase was dried over magnesium sulphate and the solvent was evaporated under reduced pressure. The residue was purified by preparative RP-HPLC (column: Reprosil 250×30; 10μ, flow rate: 50 ml/mm, MeCN/water, 0.1% TFA). This gave 5 mg (23% of theory) of the title compound.

LC-MS (Method 5): R. 3.05 min; MS (ESIpos): m/z=819 $(M+H-CF_3C02H)^+$.

Intermediate F305

N-{(1R)-1-[1-Benzyl-4-(2,5-difluorophenyl)-1H-pyrrol-2-yl]-2,2-dimethylpropyl}-22-(2,5-dioxo-2,5-dihydro-1H-pyrrol-1-yl)-6,17-dioxo-N-(pyrrolidin-3-ylmethyl)-10,13-dioxa-3-thia-7,16-diazadocosan-1-amide (1:1) trifluoroacetic acid (Isomer 2)

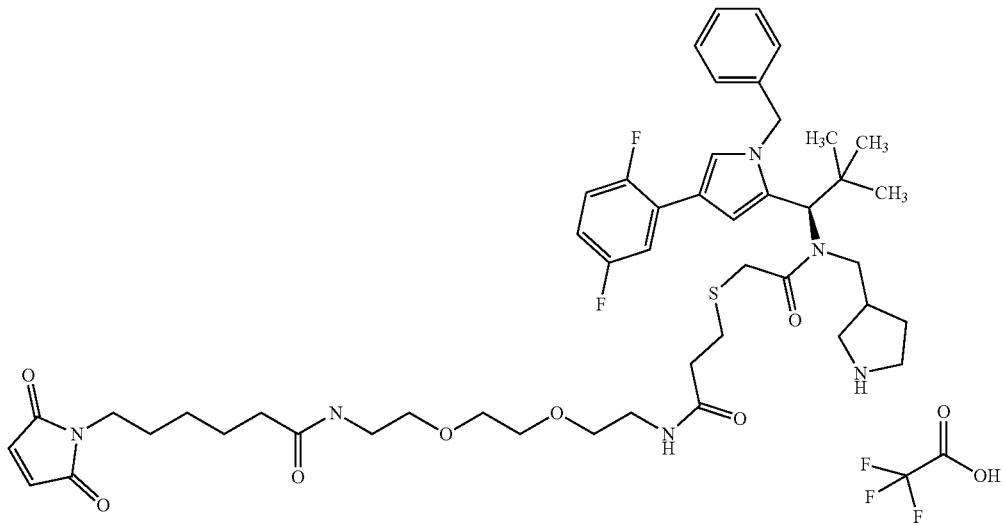 [SMILES: CC(C)(C)[C@H](c1cc(-c2cc(F)ccc2F)cn1Cc1ccccc1)N(CC1CCNC1)C(=O)CSCCC(=O)NCCOCCOCCNC(=O)CCCCCN1C(=O)C=CC1=O ; O=C(O)C(F)(F)F]

To a solution of 24.80 mg (0.02 mmol) of tert-butyl 3-[2-{(1R)-1-[1-benzyl-4-(2,5-difluorophenyl)-1H-pyrrol-2-yl]-2,2-dimethylpropyl}-24-(2,5-dioxo-2,5-dihydro-1H-pyrrol-1-yl)-3,8,19-trioxo-12,15-dioxa-5-thia-2,9,18-triazatetracos-1-yl]pyrrolidine-1-carboxylate (intermediate C99) in 0.65 ml of 2,2,2-trifluoroethanol was added 13.42 mg (0.10 mmol) of zinc chloride and the reaction mixture was stirred at 50° C. for 8 h. Subsequently, 28.78 mg (0.10 mmol) of EDTA were added and the mixture was stirred for 15 minutes. Ethyl acetate was added to the reaction mixture and the org. phase was washed repeatedly with water and sat. NaCl solution. The organic phase was dried over magnesium sulfate and the solvent evaporated under vacuum. The residue was purified by preparative HPLC. This gave 10 mg (44% of theory) of the title compound.

LC-MS (Method 5): $R_t$=3.11 min; MS (ESIpos): m/z=907 $(M+H-CF_3CO_2H)^+$.

Intermediate F306

$N^6$—(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-$N^2$—{N-[(2,5-dioxo-2,5-dihydro-1H-pyrrol-1-yl)acetyl]-L-valyl-L-alanyl-beta-alanyl}-L-lysine-trifluoroacetic acid (1:1)

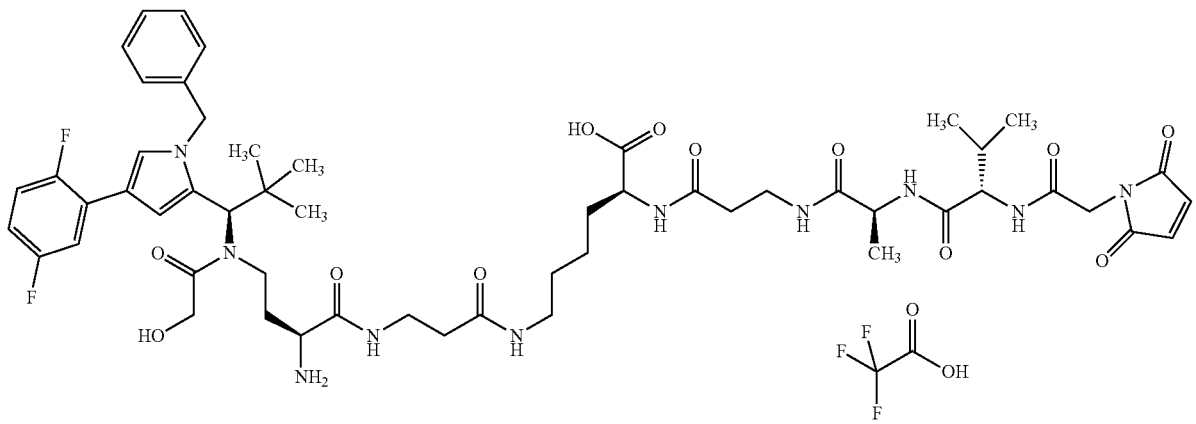 [SMILES: CC(C)[C@H](NC(=O)CN1C(=O)C=CC1=O)C(=O)N[C@@H](C)C(=O)NCCC(=O)N[C@@H](CCCCNC(=O)CCNC(=O)[C@@H](N)CCN(C(=O)CO)[C@@H](c1cc(-c2cc(F)ccc2F)cn1Cc1ccccc1)C(C)(C)C)C(=O)O ; O=C(O)C(F)(F)F]

The title compound was prepared by coupling of 24 mg (0.029 mmol) of the intermediate C61 with 30 mg (0.035 mmol) of intermediate L99 in the presence of 16.7 mg (0.044 mmol) of HATU and 15 µl of N,N-diisopropylethylamine and subsequent deprotection using zinc chloride in trifluoroethanol as described for intermediate F119. After purification by preparative HPLC, 19 mg (52% of theory over 2 stages) of the title compound were obtained.

LC-MS (Method 1): $R_t$=0.84 min; MS (ESIpos): m/z=1091 (M+H)$^+$.

Intermediate F307

N-[6-(2,5-Dioxo-2,5-dihydro-1H-pyrrol-1-yl)hexanoyl]-L-valyl-L-alanyl-S-{(5R,14R)-13-(3-aminopropyl)-14-[1-benzyl-4-(2,5-difluorophenyl)-1H-pyrrol-2-yl]-5-carboxy-15,15-dimethyl-2,7,12-trioxo-10-thia-3,6,13-triazahexadec-1-yl}-L-cysteine-trifluoroacetic acid (1:1)

dimethyl-6,12,17-trioxo-5-oxa-14-thia-7,11-diaza-2-silaheptadecan-17-yl)-3-[(bromoacetyl)amino]-D-alaninate (31.9 mg, 31.6 µmol) and L-cysteine (7.66 mg, 63.2 µmol) were dissolved in 3.0 ml of DMF and stirred overnight at RT. The reaction mixture was immediately purified by prep. RP-HPLC (column: Reprosil 250×30; 10µ, flow: 50 mL/min, MeCN/water/0.1% TFA). The solvents were evaporated under vacuum and the residue dried under high vacuum. This gave 28.1 mg (76% of theory) of the compound S-[(19R)-11-{(1R)-1-[1-benzyl-4-(2,5-difluorophenyl)-1H-pyrrol-2-yl]-2,2-dimethylpropyl}-2,2-dimethyl-6,12,17,22-tetraoxo-19-{[2-(trimethylsilyl)ethoxy]carbonyl}-5-oxa-14-thia-7,11,18,21-tetraaza-2-silatricosan-23-yl]-L-cysteine-trifluoroacetic acid (1:1).

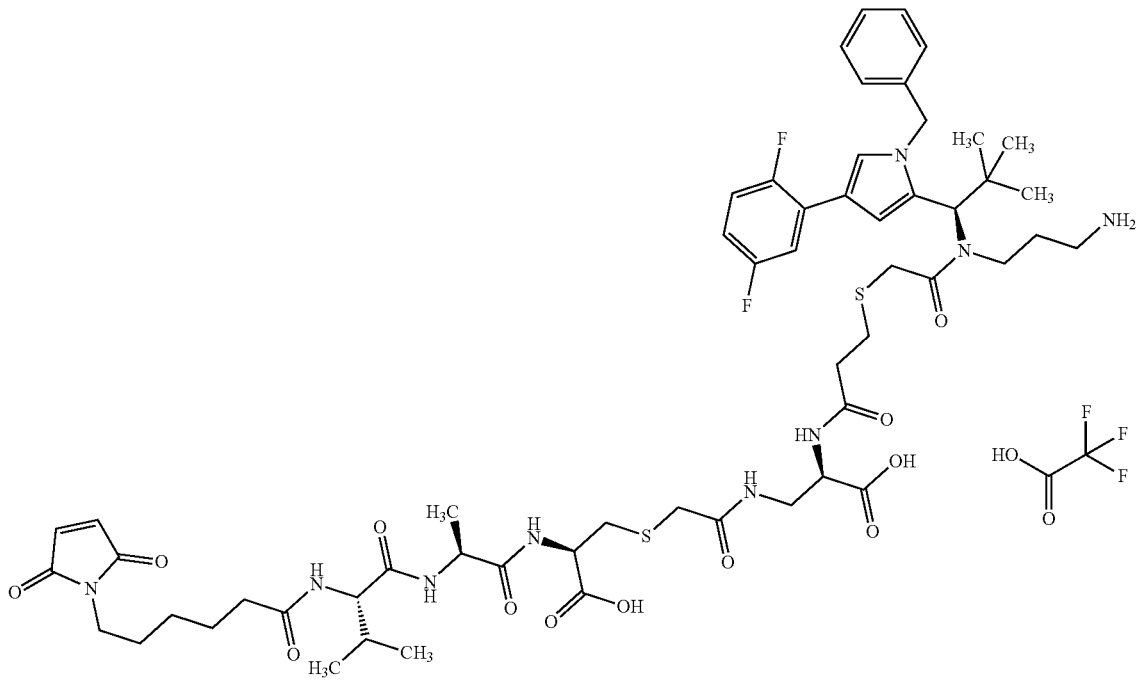 [SMILES: CC(C)[C@H](NC(=O)CCCCCN1C(=O)C=CC1=O)C(=O)N[C@@H](C)C(=O)N[C@@H](CSCC(=O)NC[C@@H](NC(=O)CCSCC(=O)N(CCCN)[C@@H](c1cc(-c2cc(F)ccc2F)cn1Cc1ccccc1)C(C)(C)C)C(=O)O)C(=O)O ; O=C(O)C(F)(F)F]

8.90 mg (8.88 µmol) of trifluoroacetic acid 2-(trimethylsilyl)ethyl 3-amino-N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-D-alaninate (1:1) (intermediate C80) and 2.31 mg (9.77 µmol) of 1-(2-bromoacetoxy)pyrrolidine-2,5-dione were dissolved in 1 ml of dimethylformamide and 2.9 µl (27 µmol) of N-methylmorpholine were added. The reaction mixture was stirred at RT for 1 h. The reaction mixture was immediately purified by prep. RP-HPLC (column: Reprosil 125×30; 10µ, flow: 50 mL/min, MeCN/water/0.1% TFA). The solvents were evaporated under vacuum and the residue dried under high vacuum. This gave 5.80 mg (65/o of theory) of the compound 2-(trimethylsilyl)ethyl N-(11-{(1R)-1-[1-benzyl-4-(2,5-difluorophenyl)-1H-pyrrol-2-yl]-2,2-dimethylpropyl}-2,2-dimethyl-6,12,17-trioxo-5-oxa-14-thia-7,11-diaza-2-silaheptadecan-17-yl)-3-[(bromoacetyl)amino]-D-alaninate.

LC-MS (Method 1): $R_t$=1.57 min; MS (ESIpos): m/z=1008 (M+H)$^+$.

2-(Trimethylsilyl)ethyl N-(11-{(1R)-1-[1-benzyl-4-(2,5-difluorophenyl)-1H-pyrrol-2-yl]-2,2-dimethylpropyl}-2,2-

LC-MS (Method 12): $R_t$=2.52 min; MS (ESIpos): m/z=1049 [M+H]$^+$

S-[(19R)-11-{(1R)-1-[1-Benzyl-4-(2,5-difluorophenyl)-1H-pyrrol-2-yl]-2,2-dimethylpropyl}-2,2-dimethyl-6,12,17,22-tetraoxo-19-{[2-(trimethylsilyl)ethoxy]carbonyl}-5-oxa-14-thia-7,11,18,21-tetraaza-2-silatricosan-23-yl]-L-cysteine-trifluoroacetic acid (1:1) (13.5 mg, 11.6 µmol) was dissolved in 1.0 ml of DMF, 2,5-dioxopyrrolidin-1-yl N-[6-(2,5-dioxo-2,5-dihydro-1H-pyrrol-1-yl)hexanoyl]-L-valyl-L-alaninate (6.76 mg, 11.6 µmol) (intermediate L88) and N,N-diisopropylethylamine (4.0 µl, 23 µmol) were added and the mixture was stirred at RT for 1 h. The reaction mixture was immediately purified by prep. RP-HPLC (column: Reprosil 250×30; 10µ, flow: 50 mL/min, MeCN/water/ 0.1% TFA). The solvents were evaporated under vacuum and the residue dried under high vacuum. This gave 11.1 mg (68% of theory) of the compound N-[6-(2,5-dioxo-2,5-dihydro-1H-pyrrol-1-yl)hexanoyl]-L-valyl-L-alanyl-S-[(19R)-11-{(1R)-1-[1-benzyl-4-(2,5-difluorophenyl)-1H-pyrrol-2-yl]-2,2-dimethylpropyl}-2,2-dimethyl-6,12,17,22-tetraoxo-19-{[2-(trimethylsilyl)ethoxy]carbonyl}-5-oxa-14-thia-7,11,18,21-tetraaza-2-silatricosan-23-yl]-L-cysteine.

LC-MS (Method 14): $R_t$=7.38 min; MS (ESIpos): m/z=1412 [M+H]$^+$

N-[6-(2,5-Dioxo-2,5-dihydro-1H-pyrrol-1-yl)hexanoyl]-L-valyl-L-alanyl-S-[(19R)-11-{(1R)-1-[1-benzyl-4-(2,5-difluorophenyl)-1H-pyrrol-2-yl]-2,2-dimethylpropyl}-2,2-dimethyl-6,12,17,22-tetraoxo-19-{[2-(trimethylsilyl)ethoxy]carbonyl}-5-oxa-14-thia-7,11,18,21-tetraaza-2-silatricosan-23-yl]-L-cysteine (9.40 mg, 6.65 µmol) was dissolved in 2.0 ml of trifluoroethanol and zinc dichloride (5.44 mg, 39.9 µmol) was added. The reaction mixture was stirred at 50° C. for 1 h. Zinc dichloride (5.44 mg, 39.9 µmol) was added and the reaction mixture stirred at 50° C. for 1 h. Ethylenediamine-N,N,N',N'-tetraacetic acid (23.4 mg, 79.8 µmol) was added to the reaction mixture, stirred for 10 min and then water (0.1% TFA) was added. Purification was carried out immediately by prep. RP-HPLC (column: Reprosil 250×30; 10µ, flow: 50 mL/mm, MeCN/water, 0.1% TFA). The solvents were evaporated under vacuum and the residue dried under high vacuum. This gave 5.60 mg (66% of theory) of the title compound.

LC-MS (Method 1): $R_t$=0.93 min; MS (ESIpos): m/z=1168 (M+H)$^+$.

Intermediate F308

N-[6-(2,5-Dioxo-2,5-dihydro-1H-pyrrol-1-yl)hexanoyl]-L-valyl-N-[(12R,19R)-19-amino-4-{(1R)-1-[1-benzyl-4-(2,5-difluorophenyl)-1H-pyrrol-2-yl]-2,2-dimethylpropyl}-12,19-dicarboxy-5,10,15-trioxo-7,17-dithia-4,11,14-triazanonadec-1-yl]-L-alaninamide-trifluoroacetic acid (1:1)

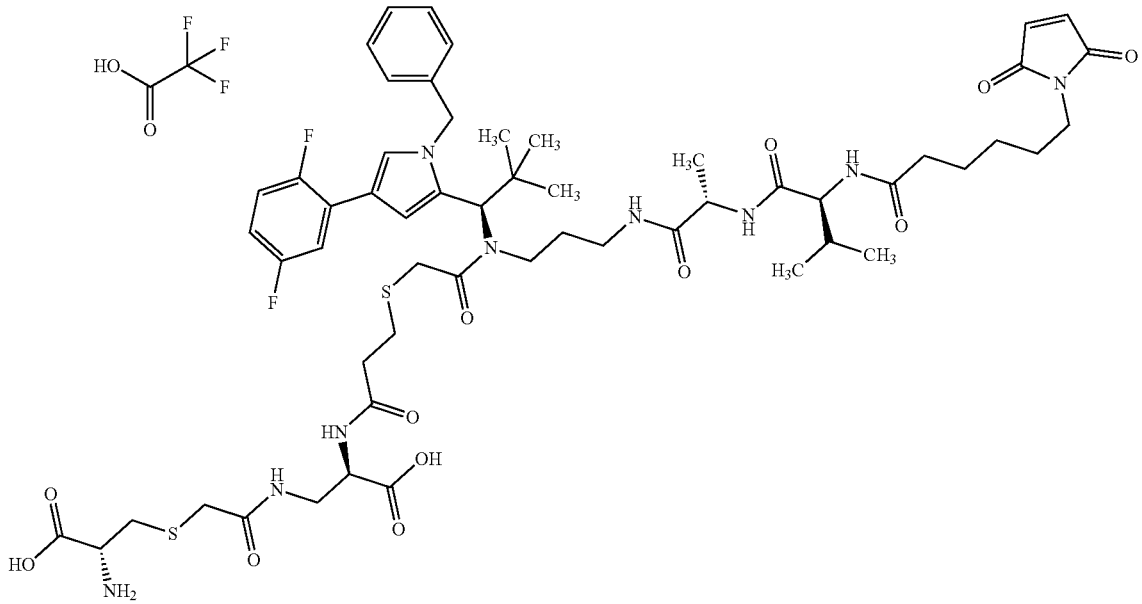 [SMILES: CC(C)[C@H](NC(=O)CCCCCN1C(=O)C=CC1=O)C(=O)N[C@@H](C)C(=O)NCCCN(C(=O)CSCCC(=O)N[C@H](CNC(=O)CSC[C@H](N)C(=O)O)C(=O)O)[C@@H](c1cc(-c2cc(F)ccc2F)cn1Cc1ccccc1)C(C)(C)C ; O=C(O)C(F)(F)F]

N-[3-({2-[(3-Aminopropyl){(1R)-1-[1-benzyl-4-(2,5-difluorophenyl)-1H-pyrrol-2-yl]-2,2-dimethylpropyl}amino]-2-oxoethyl}sulfanyl)propanoyl]-3-[(bromoacetyl)amino]-D-alanine-trifluoroacetic acid (1:1) (12.7 mg, 14.5 µmol) and N-{[2-(trimethylsilyl)ethoxy]carbonyl}-L-cysteine (3.84 mg, 14.5 µmol) were dissolved in 1.5 ml of DMF and stirred overnight at RT. N,N-Diisopropylethylamine (2.5 µl, 14 µmol) was then added. The reaction mixture was stirred at RT for 3 h and water (0.1% TFA) was then added. Purification was immediately carried out by prep. RP-HPLC (column: Reprosil 250×30; 10µ, flow: 50 mL/min, MeCN/water, 0.1% TFA). The solvents were evaporated under vacuum and the residue dried under high vacuum. This gave 7.40 mg (48% of theory) of the compound S-{(5R,14R)-13-(3-aminopropyl)-14-[1-benzyl-4-(2,5-difluorophenyl)-1H-pyrrol-2-yl]-5-carboxy-15,15-dimethyl-2,7,12-trioxo-10-thia-3,6,13-triazahexadec-1-yl}-N-{[2-(trimethylsilyl)ethoxy]carbonyl}-L-cysteine-trifluoroacetic acid (1:1).

LC-MS (Method 1): $R_t$=1.03 min; MS (ESIpos): m/z=949 [M+H]$^+$

S-{(5R,14R)-13-(3-Aminopropyl)-14-[1-benzyl-4-(2,5-difluorophenyl)-1H-pyrrol-2-yl]-5-carboxy-15,15-dimethyl-2,7,12-trioxo-10-thia-3,6,13-triazahexadec-1-yl}-N-{[2-(trimethylsilyl)ethoxy]carbonyl}-L-cysteine-trifluoroacetic acid (1:1) (7.50 mg, 7.05 µmol) was dissolved in 1.0 ml of DMF and 2,5-dioxopyrrolidin-1-yl N-[6-(2,5-dioxo-2,5-dihydro-1H-pyrrol-1-yl)hexanoyl]-L-valyl-L-alaninate (4.11 mg, 82% purity, 7.05 µmol) (intermediate L88) and N,N-diisopropylethylamine (2.5 µl, 14 µmol) were added. The reaction mixture was stirred at RT for 1 h and then immediately purified by prep. RP-HPLC (column: Reprosil 250×30; 10µ, flow. 50 mL/min, MeCN/water/0.1% TFA). The solvents were evaporated under vacuum and the residue was dried under high vacuum. This gave 4.30 mg (46%) of the compound N-[6-(2,5-dioxo-2,5-dihydro-1H-pyrrol-1-yl)hexanoyl]-L-valyl-N-[(8R,15R)-23-{(1R)-1-[1-benzyl-4-(2,5-difluorophenyl)-1H-pyrrol-2-yl]-2,2-dimethylpropyl}-8,15-dicarboxy-2,2-dimethyl-6,12,17,22-tetraoxo-5-oxa-10,20-dithia-7,13,16,23-tetraaza-2-silahexacosan-26-yl]-L-alaninamide.

LC-MS (Method 14): $R_t$=6.47 min; MS (ESIpos): m/z=1312 [M+H]$^+$

N-[6-(2,5-Dioxo-2,5-dihydro-1H-pyrrol-1-yl)hexanoyl]-L-valyl-N-[(8R,15R)-23-{(1R)-1-[1-benzyl-4-(2,5-difluorophenyl)-1H-pyrrol-2-yl]-2,2-dimethylpropyl}-8,15-dicarboxy-2,2-dimethyl-6,12,17,22-tetraoxo-5-oxa-10,20-dithia-7,13,16,23-tetraaza-2-silahexacosan-26-yl]-L-alaninamide (4.00 mg, 3.05 µmol) was dissolved in 1.0 ml of trifluoroethanol and zinc dichloride (2.49 mg, 18.3 µmol) was added.

The reaction mixture was stirred at 50° C. for 1 h and ethylenediamine-N,N,N',N'-tetraacetic acid (5.34 mg, 18.3 µmol) was then added, stirred for 10 min and water (0.1% TFA) was then added. Purification was immediately carried out by prep. RP-HPLC (column: Reprosil 250×30; 10µ, flow: 50 mL/min, MeCN/water, 0.1% TFA). The solvents were evaporated under vacuum and the residue dried under high vacuum. This gave 2.50 mg (64% of theory) of the title compound.

LC-MS (Method 1): $R_t$=LOO min; MS (ESIpos): m/z=1168 [M+H]$^+$

Intermediate F309

4-{[(11R,17R)-16-(3-Aminopropyl)-17-[1-benzyl-4-(2,5-difluorophenyl)-1H-pyrrol-2-yl]-1-(2,5-dioxo-2,5-dihydro-1H-pyrrol-1-yl)-18,18-dimethyl-6,6-dioxido-2,10,15-trioxo-6lambda$^6$,13-dithia-3,9,16-triazanonadecan-11-yl]amino}-4-oxobutanoic acid-trifluoroacetic acid (1:1)

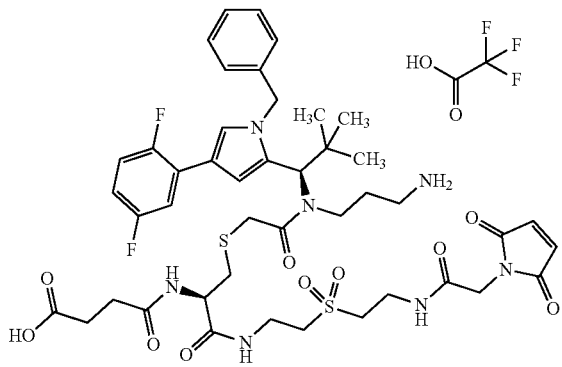 [SMILES: CC(C)(C)[C@H](c1cc(-c2cc(F)ccc2F)cn1Cc1ccccc1)N(CCCN)C(=O)CSC[C@H](NC(=O)CCC(=O)O)C(=O)NCCS(=O)(=O)CCNC(=O)CN1C(=O)C=CC1=O ; O=C(O)C(F)(F)F]

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine (50.0 mg, 57.3 µmol) (intermediate C77) and trifluoroacetic acid-benzyl {2-[(2-aminoethyl)sulfonyl]ethyl}carbamate (1:1) (27.5 mg, 68.7 µmol) (intermediate L81) were initially charged in 4.0 ml of DMF, and HATU (26.1 mg, 68.7 µmol) and N,N-diisopropylethylamine: (30 µl, 170 µmol) were added. The reaction mixture was stirred at RT for 10 min and then purified immediately by prep. RP-HPLC (column: Reprosil 250×30; 10µ, flow: 50 mL/min, MeCN/water/0.1% TFA). The solvents were evaporated under vacuum and the residue dried under high vacuum. This gave 53.9 mg (81%) of the compound tert-butyl 4-{[(12R)-17-{(1R)-1-[1-benzyl-4-(2,5-difluorophenyl)-1H-pyrrol-2-yl]-2,2-dim ethylpropyl}-26,26-dimethyl-7,7-dioxido-3,11,16,22-tetraoxo-1-phenyl-2,23-dioxa-7lambda$^6$,14-dithia-4,10,17,21-tetraaza-26-silaheptacosan-12-yl]amino}-4-oxobutanoate.

LC-MS (Method 1): $R_t$=1.54 min; MS (ESIpos): m/z=1141 [M+H]$^+$

Under argon, palladium(II) acetate (5.12 mg, 22.8 µmol) was initially charged in 3.0 ml of DCM, triethylamine (9.5 µl, 68 µmol) and triethylsilane (73 µl, 460 µmol) were added and the mixture was stirred for 5 min. tert-Butyl 4-{[(12R)-17-{(1R)-1-[1-benzyl-4-(2,5-difluorophenyl)-1H-pyrrol-2-yl]-2,2-dimethylpropyl}-26,26-dimethyl-7,7-dioxido-3,11,16,22-tetraoxo-1-phenyl-2,23-dioxa-7lambda$^6$,14-dithia-4,10,17,21-tetraaza-26-silaheptacosan-12-yl]amino}-4-oxobutanoate (52.1 mg, 45.6 µmol) in 2.0 ml DCM was then added. The reaction mixture was stirred overnight at RT and 2.0 ml of water were added. The solvents were evaporated under vacuum. Acetonitrile was added to the residue, the residue was filtered and purified by prep. RP-HPLC (column: Reprosil 125×30; 10µ, flow: 50 mL/min, MeCN/water/0.1% TFA). The solvents were evaporated under vacuum and the residue dried under high vacuum. This gave 43.4 mg (85%) of the compound trifluoroacetic acid-tert-butyl 4-{[(16R)-23-amino-11-{(1R)-1-[1-benzyl-4-(2,5-difluorophenyl)-1H-pyrrol-2-yl]-2,2-dimethylpropyl}-2,2-dimethyl-21,21-dioxido-6,12,17-trioxo-5-oxa-14,21lambda$^6$-dithia-7,11,18-triaza-2-silatricosan-16-yl]amino}-4-oxobutanoate (1:1).

LC-MS (Method 1): $R_t$=1.21 min; MS (ESIpos): m/z=1007 [M+H]$^+$

Trifluoroacetic acid-tert-butyl 4-{[(16R)-23-amino-11-{(1R)-1-[1-benzyl-4-(2,5-difluorophenyl)-1H-pyrrol-2-yl]-2,2-dimethylpropyl}-2,2-dimethyl-21,21-dioxido-6,12,17-trioxo-5-oxa-14,21lambda$^6$-dithia-7,11,18-triaza-2-silatricosan-16-yl]amino}-4-oxobutanoate (1:1) (20.0 mg, 17.8 µmol) and (2,5-dioxo-2,5-dihydro-1H-pyrrol-1-yl)acetic acid (3.32 mg, 21.4 µmol) were initially charged in 2.0 ml of DMF and HATU (8.14 mg, 21.4 µmol) and N,N-diisopropylethylamine (9.3 µl, 54 µmol) were added.

The reaction mixture was stirred at RT for 10 min. The reaction mixture was purified immediately by prep. RP-HPLC (column: Reprosil 250×30; 10µ, flow: 50 mL/min, MeCN/water/0.1% TFA). The solvents were evaporated under vacuum and the residue dried under high vacuum. This gave 17.4 mg (85%) of the compound tert-butyl 4-{[(16R)-11-{(1R)-1-[1-benzyl-4-(2,5-difluorophenyl)-1H-pyrrol-2-yl]-2,2-dimethylpropyl}-26-(2,5-dioxo-2,5-dihydro-1H-pyrrol-1-yl)-2,2-dimethyl-21,21-dioxido-6,12,17,25-tetraoxo-5-oxa-14,21lambda$^6$-dithia-7,11,18,24-tetraaza-2-silahexacosan-16-yl]amino}-4-oxobutanoate.

LC-MS (Method 1): $R_t$=L46 min; MS (ESIpos): m/z=1144 [M+H]$^+$ tert-Butyl 4-{[(16R)-11-{(1R)-1-[1-benzyl-4-(2,5-difluorophenyl)-1H-pyrrol-2-yl]-2,2-dimethylpropyl}-26-(2,5-dioxo-2,5-dihydro-1H-pyrrol-1-yl)-2,2-dimethyl-21,21-dioxido-6,12,17,25-tetraoxo-5-oxa-14,21lambda$^6$-dithia-7,11,18,24-tetraaza-2-silahexacosan-16-yl]amino}-4-oxobutanoate (15.9 mg, 13.9 µmol) was dissolved in 2.0 ml of trifluoroethanol and zinc dichloride (11.4 mg, 83.4 µmol) was added. The reaction mixture was stirred at 50° C. for 1 h. Zinc dichloride (11.4 mg, 83.4 µmol) was added and the reaction mixture was stirred at 50° C. for 1 h. Zinc dichloride (11.4 mg, 83.4 µmol) was added and the reaction mixture stirred at 50° C. for 1 h. Ethylenediamine-N,N,N',N'-tetraacetic acid (73.2 mg, 250 µmol) was added to the reaction mixture, the mixture was stirred for 10 min and water (0.1% TFA) was then added. Purification was carried out immediately by prep. RP-HPLC (column: Reprosil 250×30; 10µ, flow. 50 mL/min, MeCN/water, 0.1% TFA). The solvents were evaporated under vacuum and the residue dried under high vacuum. This gave 10 mg (68% of theory) of the title compound.

LC-MS (Method 12): $R_t$=1.45 min; MS (ESIpos): m/z=944 [M+H]$^+$

Intermediate F310

Trifluoroacetic acid-N-[(8R,14R)-13-(3-aminopropyl)-14-[1-benzyl-4-(2,5-difluorophenyl)-1H-pyrrol-2-yl]-1-(2,5-dioxo-2,5-dihydro-1H-pyrrol-1-yl)-15,15-dimethyl-2,7,12-trioxo-10-thia-3,6,13-triazahexadecan-8-yl]-2,5,8,11-tetraoxatetradecan-14-amide (1:1)

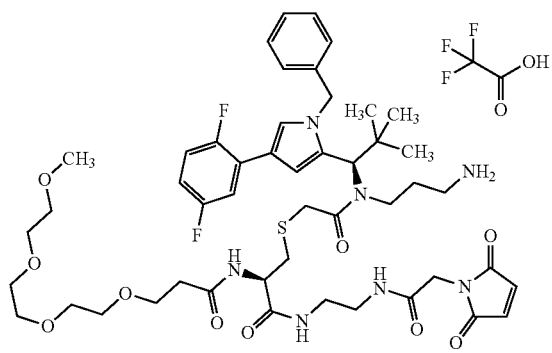 [SMILES: COCCOCCOCCOCCC(=O)N[C@@H](CSCC(=O)N(CCCN)[C@@H](c1cc(-c2cc(F)ccc2F)cn1Cc1ccccc1)C(C)(C)C)C(=O)NCCNC(=O)CN1C(=O)C=CC1=O ; O=C(O)C(F)(F)F]

S-(11-{(1R)-1-[1-Benzyl-4-(2,5-difluorophenyl)-1H-pyrrolo-2-yl]-2,2-dimethylpropyl}-2,2-dimethyl-6,12-dioxo-5-oxa-7,11-diaza-2-silatridecan-13-yl)-L-cysteine-trifluoroacteic add (1:1) (100 mg, 120 µmol) (intermediate C70) and 1-[(14-oxo-2,5,8,11-tetraoxatetradecan-14-yl)oxy]pyrrolidine-2,5-dione (44.1 mg, 132 µmol) were initially charged in 3.0 ml of DMF and 4-methylmorpholine (40 µl, 360 µmol) was added. The reaction mixture was stirred overnight at RT, quenched with acetic acid (420 µmol) and purified immediately by prep. RP-HPLC (column: Reprosil 125×30; 10µ, flow: 50 mL/min, MeCN/water/0.1% TFA). The solvents were evaporated under vacuum and the residue was dried under high vacuum. This gave 69.4 mg (62% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(14-oxo-2,5,8,11-tetraoxatetradecan-14-yl)-L-cysteine.

LC-MS (Method 12): $R_t$=2.61 min; MS (ESIneg): m/z=933 [M−H]⁻

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(14-oxo-2,5,8,11-tetraoxatetradecan-14-yl)-L-cysteine (27.0 mg, 28.9 µmol) was initially charged in 2.0 ml of DMF and N-(2-aminoethyl)-2-(2,5-dioxo-2,5-dihydro-1H-pyrrol-1-yl)acetamide (11.4 mg, 57.7 µmol) (intermediate L1), N,N-diisopropylethylamine (15 µl, 87 µmol) and HATU (22.0 mg, 57.7 µmol) were added. The reaction mixture was stirred at RT for 3 h and purified immediately by prep. RP-HPLC (column: Reprosil 250×30; 10µ, flow: 50 mL/min, MeCN/water/0.1% TFA). The solvents were evaporated under vacuum and the residue dried under high vacuum. This gave 13.7 mg (43% of theory) of the compound 2-(trimethylsilyl)ethyl {(16R)-21-{(1R)-1-[1-benzyl-4-(2,5-difluorophenyl)-1H-pyrrol-2-yl]-2,2-dimethylpropyl}-16-[(2-{[(2,5-dioxo-2,5-dihydro-1H-pyrrol-1-yl)acetyl]amino}ethyl)carbamoyl]-14,20-dioxo-2,5,8,11-tetraoxa-18-thia-15,21-diazatetracosan-24-yl}carbamate.

LC-MS (Method 12): $R_t$=2.54 min; MS (ESIpos): m/z=1114 [M+H]⁺

2-(Trimethylsilyl)ethyl {(16R)-21-{(1R)-1-[1-benzyl-4-(2,5-difluorophenyl)-1H-pyrrol-2-yl]-2,2-dimethylpropyl}-16-[(2-{[(2,5-dioxo-2,5-dihydro-1H-pyrrol-1-yl)acetyl]amino}ethyl)carbamoyl]-14,20-dioxo-2,5,8,11-tetraoxa-18-thia-15,21-diazatetracosan-24-yl}carbamate (13.7 mg, 12.3 µmol) was dissolved in 2.0 ml of trifluoroethanol and zinc dichloride (10.1 mg, 73.8 µmol) was added. The reaction mixture was stirred at 50° C. for 4 h. Ethylenediamine-N,N,N',N'-tetraacetic acid (21.6 mg, 73.8 µmol) was added to the reaction mixture, the mixture was stirred for 10 mm and then water (0.1% TFA) was added. The purification was carried out immediately by prep. RP-HPLC (column: Reprosil 250×30; 10µ, flow: 50 mL/min, MeCN/water, 0.1% TFA). The solvents were evaporated under vacuum and the residue dried under high vacuum. This gave 7.30 mg (47% of theory) of the title compound.

LC-MS (Method 1): $R_t$=1.01 min; MS (ESIpos): m/z=970 [M+H]⁺

Intermediate F311

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-N-[1-(2,5-dioxo-2,5-dihydro-1H-pyrrol-1-yl)-2,30-dioxo-6,9,12,15,18,21,24,27-octaoxa-3-azatriacontan-30-yl]-L-cysteine-trifluoroacetic acid (1:1)

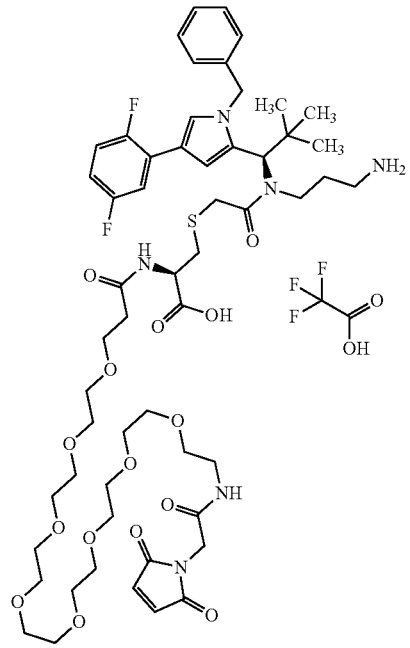 [SMILES: CC(C)(C)[C@H](c1cc(-c2cc(F)ccc2F)cn1Cc1ccccc1)N(CCCN)C(=O)CSC[C@H](NC(=O)CCOCCOCCOCCOCCOCCOCCOCCOCCNC(=O)CN1C(=O)C=CC1=O)C(=O)O ; O=C(O)C(F)(F)F]

1-(2,5-Dioxo-2,5-dihydro-1H-pyrrol-1-yl)-2-oxo-6,9,12,15,18,21,24,27-octaoxa-3-azatriacontan-30-oic acid (10.8 mg, 18.7 µmol) (intermediate L97) was initially charged in 1.0 ml of DMF, N,N-diisopropylethylamine (5.4 µl, 31.2 µmol) and HATU (7.10 mg, 18.7 µmol) were added and the mixture stirred for 10 min. Next, S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine trifluoroacetic acid (1:1) (12.9 mg, 15.6 µmol) (intermediate C71), dissolved in 1.0 ml of DMF and N,N-diisopropylethylamine (2.7 µl, 15.6 µmol), was added. The reaction mixture was stirred at RT for 2 h and then purified immediately by prep. RP-HPLC (column: Reprosil 125×30; 10µ, flow: 50 mL/min, MeCN/water/0.1%

TFA). The solvents were evaporated under vacuum and the rescue dried under high vacuum. This gave 3.5 mg (18%) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[1-(2,5-dioxo-2,5-dihydro-1H-pyrrol-1-yl)-2,30-dioxo-6,9,12,15,18,21,24,27-octaoxa-3-azatriacontan-30-yl]-L-cysteine.

LC-MS (Method 1): $R_t$=1.30 min; MS (ESIneg): m/z=1276 [M−H]⁻

S-(11-{(1R)-1-[1-Benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[1-(2,5-dioxo-2,5-dihydro-1H-pyrrol-1-yl)-2,30-dioxo-6,9,12,15,18,21,24,27-octaoxa-3-azatriacontan-30-yl]-L-cysteine (3.50 mg, 2.74 μmol) was dissolved in 1.0 ml of trifluoroethanol and zinc dichloride (6.25 mg, 16.4 μmol) was added. The reaction mixture was stirred at 50° C. for 4 h. Ethylenediamine-N,N,N',N'-tetraacetic acid (47 μl, 16 μmol) was added to the reaction mixture, the mixture was stirred for 10 minutes and then water (0.1% TFA) was added. Purification was carried out immediately by prep. RP-HPLC (column: Reprosil 125×30; 10μ, flow: 50 mL/min, MeCN/water, 0.1% TFA). The solvents were evaporated under vacuum and the residue dried under high vacuum. This gave 2.0 mg (59% of theory) of the title compound.

LC-MS (Method 1): $R_t$=0.94 min; MS (ESIpos): m/z=1133 (M+H)⁺.

Intermediate F312

N-[(2,5-Dioxo-2,5-dihydro-1H-pyrrol-1-yl)acetyl]-L-valyl-N-[(2S)-4-[{(1R)-1-[1-benzyl-4-(2,5-difluorophenyl)-1H-pyrrol-2-yl]-2,2-dimethylpropyl}(glycoloyl)amino]-1-{[2-(L-gamma-glutamylamino)ethyl]amino}-1-oxobutan-2-yl]-L-alaninamide-trifluoroacetic acid (1.1)

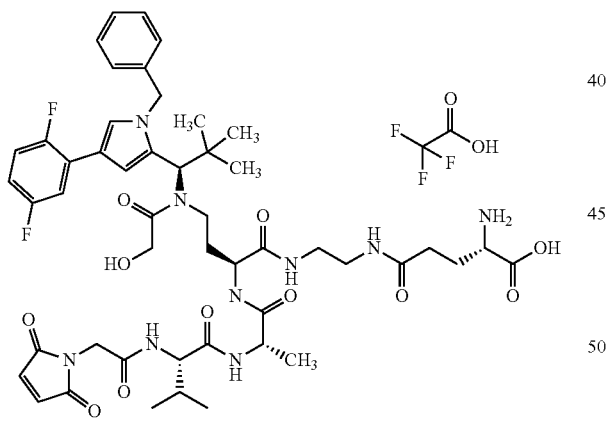

The title compound was prepared from intermediate C103 by coupling with N-[(benzyloxy)carbonyl]-L-valyl-L-alanine in the presence of HATU and N,N-diisopropylethylamine. In the next step, the Z protecting group was removed by hydrogenation for one hour over 10% palladium on active carbon in DCM/methanol 1:1 at RT under standard hydrogen pressure. The deprotected intermediate was subsequently converted to the title compound by coupling with (2,5-dioxo-2,5-dihydro-1H-pyrrol-1-yl)acetic acid in the presence of HATU and N,N-diisopropylethylamine and finally by deprotection using zinc chloride and purification by preparative HPLC.

LC-MS (Method 1): Rt=0.9 min; MS (ESIpos): m/z=992 (M+H)⁺.

Intermediate F313

S-[2-({(1R)-1-[1-Benzyl-4-(2,5-difluorophenyl)-1H-pyrrol-2-yl]-2,2-dimethylpropyl}{[(3R,4R)-4-fluoropyrrolidin-3-yl]methyl}amino)-2-oxoethyl]-N-[1-(2,5-dioxo-2,5-dihydro-1H-pyrrol-1-yl)-2,18-dioxo-6,9,12,15-tetraoxa-3-azaoctadecan-18-yl]-L-cysteine-trifluoroacetic acid (1:1)

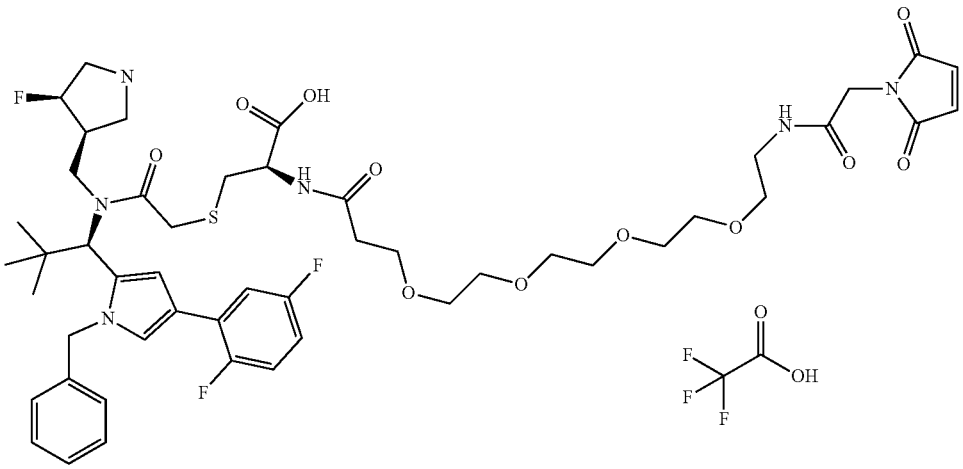 [SMILES: CC(C)(C)[C@H](c1cc(-c2cc(F)ccc2F)cn1Cc1ccccc1)N(C[C@@H]1CNC[C@@H]1F)C(=O)CSC[C@H](NC(=O)CCOCCOCCOCCOCCNC(=O)CN1C(=O)C=CC1=O)C(=O)O ; O=C(O)C(F)(F)F]

To a solution of 55.0 mg (0.14 mmol) of 1-(2,5-dioxo-2,5-dihydro-1H-pyrrol-1-yl)-2-oxo-6,9,12,15-tetraoxa-3-azaoctadecan-18-oic acid in 2.60 ml of DMF under argon were added 16.9 mg (0.13 mmol) of N,N-diisopropylethylamine and 50.0 mg (0.13 mmol) of HATU. The reaction mixture was stirred at RT for 10 minutes. Subsequently, a solution of 40.0 mg (0.05 mmol) of S-[2-({(1R)-1-[1-benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]-L-cysteine (intermediate C107) was added and the mixture stirred overnight at RT. Water was added to the mixture and the mixture extracted with dichloromethane. The organic phase was dried over magnesium sulfate and the solvent was evaporated under vacuum and the residue dried under high vacuum. The residue was purified by prep. HPLC. This gave 10 mg (13% of theory, purity 82%) of the title compound.

LC-MS (Method 1): $R_t$=1.36 min; MS (ESIpos): m/z=1145 (M+H)$^+$.

4.3 mg (0.03 mmol) of zinc chloride was added to a solution of 10.9 mg (7.8 mmol, 82% purity) of S-[2-({(1R)-1-[1-benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]-N-[1-(2,5-dioxo-2,5-dihydro-1H-pyrrol-1-yl)-2,18-dioxo-6,9,12,15-tetraoxa-3-azaoctadecan-18-yl]-L-cysteine in 0.85 ml of 2,2,2-trifluoroethanol and the reaction mixture was stirred at 50° C. for 2.5 h. Subsequently, 9.1 mg (0.03 mmol) of EDTA were added and the mixture was stirred for 15 minutes. The reaction mixture was purified by prep. HPLC. This gave 2.3 mg (26% of theory) of the title compound.

LC-MS (Method 1): $R_t$ 0.89 min; MS (ESIpos): m/z=781 (M+H-CF$_3$CO$_2$H)$^+$.

Intermediate F314

Trifluoroacetic acid-3-{[2-({(1R)-1-[1-benzyl-4-(2,5-difluorophenyl)-1H-pyrrol-2-yl]-2,2-dimethylpropyl}{[(3S,4R)-4-fluoropyrrolidin-3-yl]methyl}amino)-2-oxoethyl]sulfanyl}-N-(2-{[(2,5-dioxo-2,5-dihydro-1H-pyrrol-1-yl)acetyl]amino}ethyl)propanamide

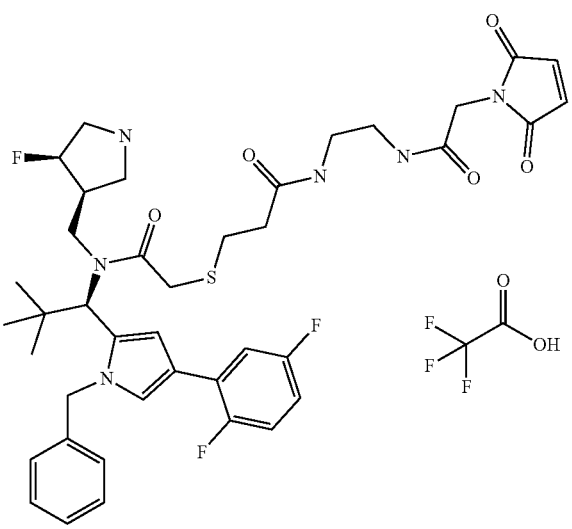 [SMILES: CC(C)(C)[C@H](c1cc(-c2cc(F)ccc2F)cn1Cc1ccccc1)N(C[C@@H]1CNC[C@@H]1F)C(=O)CSCCC(=O)NCCNC(=O)CN1C(=O)C=CC1=O ; O=C(O)C(F)(F)F]

To a solution of 50.0 mg (0.04 mmol) of 3-{[2-({(1R)-1-[1-benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]sulfanyl}propanoic acid (intermediate 106) in 3.14 ml of DMF under argon were added 16.89 mg (0.13 mmol) of N,N-diisopropylethylamine and 33.13 mg (0.087 mmol) of HATU. The reaction mixture was stirred at RT for 10 minutes. Subsequently, a solution of 27.29 mg (0.09 mmol) of N-(2-aminoethyl)-2-(2,5-dioxo-2,5-dihydro-1H-pyrrol-1-yl)acetamide (1:1)trifluoroacetic acid (intermediate L1) was added and the mixture stirred at RT for 15 minutes. Water was added to the mixture and the mixture extracted with dichloromethane. The organic phase was dried over magnesium sulfate and the solvent evaporated under vacuum and the residue dried under high vacuum. The residue was purified by prep. HPLC. This gave 41 mg (68% of theory, purity 66%) of the title compound.

LC-MS (Method 12): $R_t$=2.55 min; MS (ESIneg): m/z=959 (M−H+Na)⁻.

24.7 mg (0.18 mmol) of zinc chloride were added to a solution of 41.1 mg (0.03 mmol, purity 66%) of 2-(trimethylsilyl)ethyl (3R,4R)-3-[2-{(1R)-1-[1-benzyl-4-(2,5-difluorophenyl)-1H-pyrrol-2-yl]-2,2-dimethylpropyl}-14-(2,5-dioxo-2,5-dihydro-1H-pyrrol-1-yl)-3,8,13-trioxo-5-thia-2,9,12-triazatetradec-1-yl]-4-fluoropyrrolidine-1-carboxylate in 2.54 ml of 2,2,2-trifluoroethanol and the reaction mixture was stirred at 50° C. for 2.5 h. Subsequently, 53.0 mg (0.18 mmol) of EDTA were added and the mixture was stirred for 15 minutes. The reaction mixture was purified by prep. HPLC. This gave 10 mg (36% of theory) of the title compound.

LC-MS (Method 1): R. 0.89 min; MS (ESIpos): m/z=781 (M+H-CF₃CO₂H)⁺.

Intermediate F315

S-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-N-{3-[5-(2-{[(2,5-dioxo-2,5-dihydro-1H-pyrrol-1-yl)acetyl]amino}ethyl)-1,2,4-oxadiazol-3-yl]propanoyl}-L-cysteine To a solution of 50.0 mg (0.07 mmol) of 3-[5-(2-{[(2,5-dioxo-2,5-dihydro-1H-pyrrol-1-yl)acetyl]amino}ethyl)-1,2,4-oxadiazol-3-yl]propanoic acid (intermediate L100) in 3.5 ml of DMF under argon were added 18.02 mg (0.14 mmol) of N,N-diisopropylethylamine and 31.82 mg (0.09 mmol) of HATU. The reaction mixture was stirred at RT for 10 minutes. Subsequently, a solution of 50.0 mg (0.07 mmol) of N-(2-aminoethyl)-6-(2,5-dioxo-2,5-dihydro-1H-pyrrol-1-yl)hexanamide acetate (1:1) (intermediate C107) was added and the mixture stirred at RT for 2 h. Water was added to the mixture and the mixture extracted with dichloromethane. The organic phase was dried over magnesium sulfate and the solvent evaporated under vacuum and the residue dried under high vacuum. The residue was further used without purification. This gave 49 mg (21% of theory, purity 31%) of the title compound.

LC-MS (Method 1): $R_t$=1.30 min; MS (ESIpos): m/z=1022 (M+H)⁺.

8.0 mg (0.06 mmol) of zinc chloride were added to a solution of 49.0 mg (0.015 mmol, 31% purity) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-{3-[5-(2-{[(2,5-dioxo-2,5-dihydro-1H-pyrrol-1-yl)acetyl]amino}ethyl)-1,2,4-oxadiazol-3-yl]propanoyl}-L-cysteine in 0.5 ml of 2,2,2-trifluoroethanol and the reaction mixture was stirred at 50° C. for 2 h. Subsequently, 17.2 mg (0.06 mmol) of EDTA were added and the mixture was stirred for 15 minutes. The reaction mixture was purified by prep. HPLC. This gave 3 mg (21% of theory) of the title compound.

LC-MS (Method 1): $R_t$=0.91 min; MS (ESIpos): m/z=877 (M+H-CF₃CO₂H)⁺.

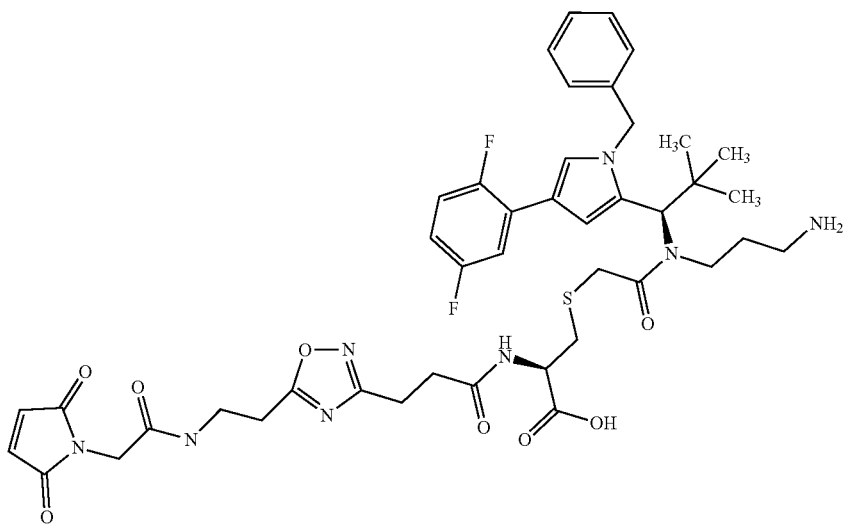 [SMILES: CC(C)(C)[C@H](c1cc(-c2cc(F)ccc2F)cn1Cc1ccccc1)N(CCCN)C(=O)CSC[C@H](NC(=O)CCc1noc(CCNC(=O)CN2C(=O)C=CC2=O)n1)C(=O)O]

Intermediate F316

Trifluoroacetic acid-N-{2-[(3-{[2-({(1R)-1-[1-benzyl-4-(2,5-difluorophenyl)-1H-pyrrol-2-yl]-2,2-dimethylpropyl}{[(3S,4R)-4-fluoropyrrolidin-3-yl]methyl}amino)-2-oxoethyl]sulfanyl}propanoyl)amino]ethyl}-6-(2,5-dioxo-2,5-dihydro-1H-pyrrol-1-yl)hexan amide (1:1)

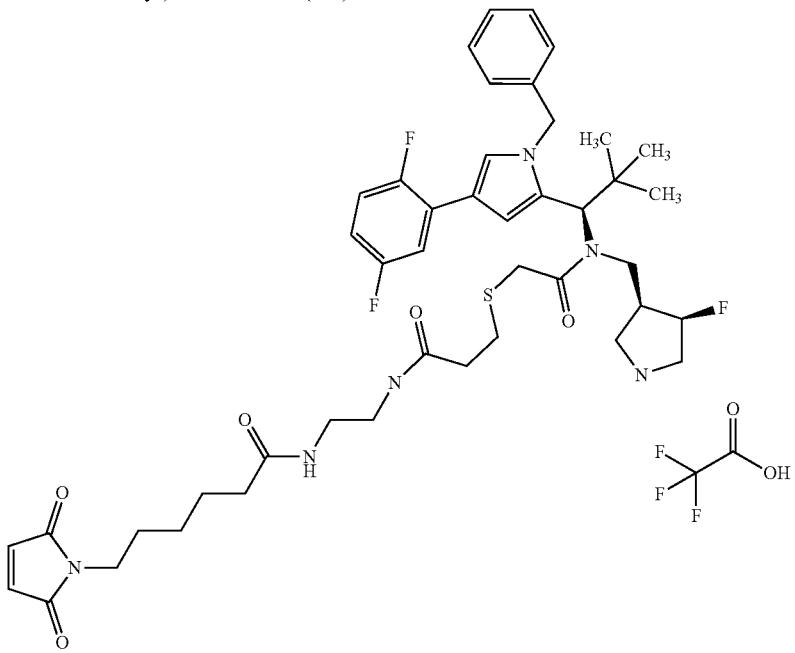

To a solution of 50.0 mg (0.04 mmol, 65% purity) of 3-{[2-({(1R)-1-[1-benzyl-4-(2,5-difluorophenyl)-1H-pyrrol-2-yl]-2,2-dimethylpropyl}{[(3R,4R)-4-fluoro-1-{[2-(trimethylsilyl)ethoxy]carbonyl}pyrrolidin-3-yl]methyl}amino)-2-oxoethyl]sulfanyl}propanoic acid (intermediate 106) in 3.0 ml of DMF under argon were added 16.89 mg (0.13 mmol) of N,N-diisopropylethylamine and 33.13 mg (0.087 mmol) of HATU. The reaction mixture was stirred at RT for 10 minutes. Subsequently, a solution of 37.2 mg (0.09 mmol, purity 70%) of N-(2-aminoethyl)-6-(2,5-dioxo-2,5-dihydro-1H-pyrrol-1-yl)hexanamide acetate (1:1) (intermediate L73) was added and the mixture stirred at RT for 7 minutes. Water was added to the mixture and the mixture extracted with dichloromethane. The organic phase was dried over magnesium sulfate and the solvent evaporated under vacuum and the residue dried under high vacuum. The residue was further used without purification. This gave 57 mg (77% of theory, purity 59%) of the title compound.

LC-MS (Method 12): $R_t$=2.60 min; MS (ESIpos): m/z=981 (M+H)$^+$.

36.0 mg (0.27 mmol) of zinc chloride were added to a solution of 56.0 mg (0.03 mmol, 59% purity) of 2-(trimethylsilyl)ethyl (3R,4R)-3-[2-{(1R)-1-[1-benzyl-4-(2,5-difluorophenyl)-1H-pyrrol-2-yl]-2,2-dimethylpropyl}-18-(2,5-dioxo-2,5-dihydro-1H-pyrrol-1-yl)-3,8,13-trioxo-5-thia-2,9,12-triazaoctadec-1-yl]-4-fluoropyrrolidine-1-carboxylate in 2.8 ml of 2,2,2-trifluoroethanol and the reaction mixture was stirred at 50° C. for 2 h. Subsequently, 78.3 mg (0.27 mmol) of EDTA were added and the mixture was stirred for 15 minutes. The reaction mixture was purified by prep. HPLC. This gave 16 mg (44% of theory, 85% purity) of the title compound.

LC-MS (Method 1): $R_t$=0.89 min; MS (ESIpos): m/z=837 (M+H-AcOH)$^+$.

Intermediate F317

1—[(S-{2-[(3-Aminopropyl) {(1R)-1-[1-benzyl-4-(2,5-difluorophenyl)-1H-pyrrol-2-yl]-2,2-dimethylpropyl}amino]-2-oxoethyl}-N-[1-(2,5-dioxo-2,5-dihydro-1H-pyrrol-1-yl)-2,18-dioxo-6,9,12,15-tetraoxa-3-azaoctadecan-18-yl]-L-cysteinyl)amino]-3,6,9,12-tetraoxapentadecan-15-mc acid-trifluoroacetic acid (1:1)

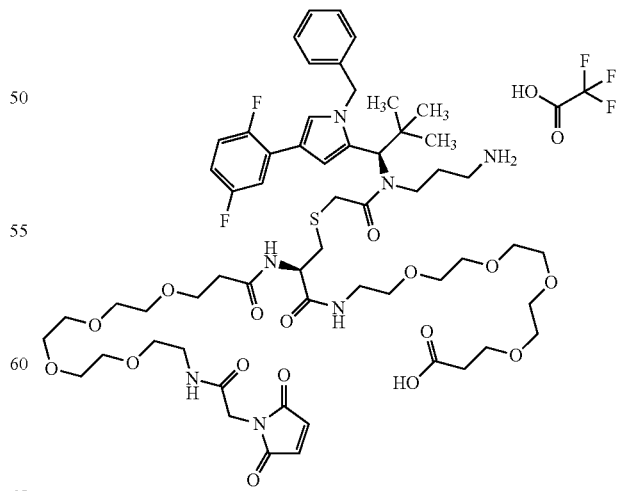

Under argon, 30.2 mg (0.06 mmol) of N,N'-bis[(benzyloxy)carbonyl]-L-cysteine were initially charged in 2.0 mL of water and 2.0 mL of isopropanol and 56.7 mg (0.20 mmol) of TCEP were added. The reaction mixture was stirred at RT for 30 minutes. 50.0 mg (0.08 mmol) of 2-(trimethylsilyl)ethyl {3-[{(1R)-1-[1-benzyl-4-(2,5-difluorophenyl)-1H-pyrrol-2-yl]-2,2-dimethylpropyl}(chloroacetyl)amino]propyl}carbamate (intermediate C70) dissolved in 2.0 mL of isopropanol and 122.2 mg (0.48 mmol) of 1,8-diazabicyclo(5.4.0)undec-7-ene were then added and the reaction mixture was stirred at 50° C. for 7 h. 122.2 mg (0.48 mmol) of 1,8-diazabicyclo(5.4.0)undec-7-ene were again added and the reaction mixture stirred at 50° C. for 1 h. The mixture was diluted with ethyl acetate and the organic phase extracted with water and sat. sodium hydrogen carbonate solution and washed with sat. NaCl solution. The organic phase was dried over magnesium sulfate and the solvent evaporated under vacuum. The residue was purified by prep. RP-HPLC (column: Reprosil 250×30; 10µ, flow: 50 mL/min, MeCN/water, 0.1% TFA). The solvents were evaporated under vacuum and the residue dried under high vacuum. This gave 43.1 mg (64% of theory) of the compound S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteine.

LC-MS (Method 1): $R_t$=1.46 min; MS (ESIpos): m/z=851 (M+H)$^+$.

Under argon, S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteine (50.0 mg, 59 µmol) was dissolved in 1.0 ml DMF and N,N-diisopropylethylamine (20.5 µl, 117 µmol) and HATU (26.8 mg, 70 µmol) were added. The reaction mixture was stirred for 10 min. tert-Butyl 1-amino-3,6,9,12-tetraoxapentadecan-15-oate (22.6 mg, 70 µmol) was then added. The reaction mixture was stirred for 1 hour and then purified immediately by prep. RP-HPLC (column: Reprosil 250×30; 10µ, flow: 50 mL/min, MeCN/water). The solvents were evaporated under vacuum and the residue dried under high vacuum. This gave 59.3 mg (87.5% of theory) of the compound tert-butyl 1-({S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteinyl}amino)-3,6,9,12-tetraoxapentadecan-15-oate.

LC-MS (Method 12): Rt=2.97 min; MS (ESIpos): m/z=1154 [M+H]+

Palladium(II) acetate (6.74 mg, 30.0 µmol) was initially charged in 3.0 ml of dichloromethane under argon and triethylamine (13 µl, 90 µmol) and triethylsilane (96 µl, 600 µmol) were added. The reaction mixture was stirred for 5 min and then tert-butyl-1-({S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[(benzyloxy)carbonyl]-L-cysteinyl}amino)-3,6,9,12-tetraoxapentadecan-15-oate (69.3 mg, 60.0 µmol) in 1.0 ml of dichloromethane was added. The reaction mixture was stirred at RT for 2 hours and then triethylsilane (48 µl, 300 µmol) was added. The reaction mixture was stirred at RT for 2 hours and 2.0 ml of water (0.1% TFA) were added. The solvent was evaporated under vacuum without heating. The residue was taken up in acetonitrile, filtered through a syringe filter and purified by prep. RP-HPLC (column: Reprosil 250×30; 10µ, flow. 50 mL/min, MeCN/water, 0.1% TFA). The solvents were evaporated under vacuum and the residue dried under high vacuum. This gave 65.9 mg (97% of theory) of the compound trifluoroacetic acid tert-butyl-1 {[S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl]amino}-3,6,9,12-tetraoxapentadecan-15-oate (1:1).

LC-MS (Method 1): $R_t$=1.22 min; MS (ESIpos): m/z=1020 [M+H]$^+$ 1-(2,5-Dioxo-2,5-dihydro-1H-pyrrol-1-yl)-2-oxo-6,9,12,15-tetraoxa-3-azaoctadecan-18-oic acid (4.26 mg, 10.6 µmol) was initially charged in 1.0 ml of DMF under argon and N,N-diisopropylethylamine (3.2 µl, 18 µmol) and HATU (4.02 mg, 10.6 µmol) were added. The reaction mixture was stirred for 10 min and then trifluoroacetic acid tert-butyl 1-{[S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteinyl]amino}-3,6,9,12-tetraoxapentadecan-15-oate (1:1) (10.0 mg, 8.82 µmol) dissolved in 1.0 ml of DMF and N,N-diisopropylethylamine (1.5 µl, 8.8 µmol) were added. The reaction mixture was stirred for 1 hour at RT and purified immediately by prep. RP-HPLC (column: Reprosil 250×30; 10µ, flow: 50 mL/min, MeCN/water, 0.1% TFA). The solvents were evaporated under vacuum and the residue dried under high vacuum. This gave 10.9 mg (93% of theory) of the compound tert-butyl 1-({S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(1-(2,5-dioxo-2,5-dihydro-1H-pyrrol-1-yl)-2,18-dioxo-6,9,12,15-tetraoxa-3-azaoctadecan-18-yl]-L-cysteinyl}amino)-3,6,9,12-tetraoxapentadecan-15-oate.

LC-MS (Method 1): $R_t$=1.44 min; MS (ESIpos): m/z=1404 [M+H]$^+$ tert-Butyl 1-((S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[1-(2,5-dioxo-2,5-dihydro-1H-pyrrol-1-yl)-2,18-dioxo-6,9,12,15-tetraoxa-3-azaoctadecan-18-yl]-L-cysteinyl}amino)-3,6,9,12-tetraoxapentadecan-15-oate (8.20 mg, 5.84 µmol) was dissolved in 2.0 trifluoroethanol and zinc chloride (4.77 mg, 35.0 µmol) was added. The reaction mixture was stirred at 50° C. for 1 h.

Zinc chloride (4.77 mg, 35.0 µmol) was added and the reaction mixture was stirred at 50° C. for 1 h. Ethylenediamine-N,N,N',N'-tetraacetic acid (10.2 mg, 35.0 µmol) was added to the reaction mixture, the mixture stirred for 10 min and then water (0.1% TFA) was added. Purification was carried out immediately by prep. RP-HPLC (column: Reprosil 250×30; 10µ, flow: 50 mL/min, MeCN/water, 0.1% TFA). The solvents were evaporated under vacuum and the residue dried under high vacuum. This gave 4.1 mg (53% of theory) of the title compound.

LC-MS (Method 1): $R_t$=0.90 min; MS (ESIpos): m/z=1204 [M+H]$^+$

Intermediate F318

Trifluoroacetic acid 3-{[2-([3-amino-4-fluorobutyl]{(1R)-1-[1-benzyl-4-(2,5-difluorophenyl)-1H-pyrrol-2-yl]-2,2-dimethylpropyl}amino)-2-oxoethyl]sulfanyl}-N-(2-{[(2,5-dioxo-2,5-dihydro-1H-pyrrol-1-yl)acetyl]amino}ethyl)propanamide (1:1)

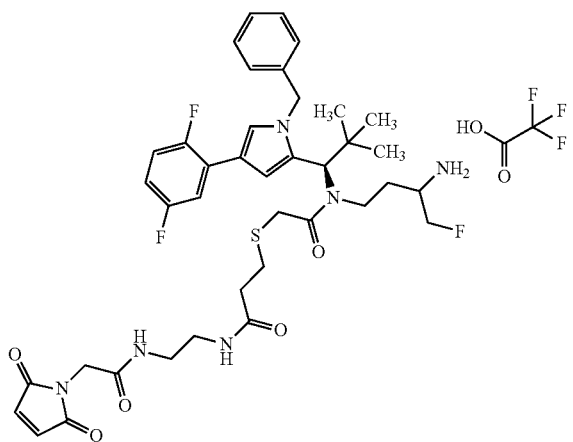 [SMILES: CC(C)(C)[C@H](c1cc(-c2cc(F)ccc2F)cn1Cc1ccccc1)N(CCC(N)CF)C(=O)CSCCC(=O)NCCNC(=O)CN1C(=O)C=CC1=O ; O=C(O)C(F)(F)F]

(1R)-1-[1-Benzyl-4-(2,5-difluorophenyl)-1H-pyrrol-2-yl]-2,2-dimethylpropan-1-amine (124 mg, 350 µmol) (intermediate C52) was initially charged in 5.0 ml of dichloromethane and sodium triacetoxyborohydride (104 mg, 491 µmol) and acetic acid (23 µl, 400 µmol) were added. The reaction mixture was stirred at RT for 5 min and then tert-butyl [1-fluoro-4-oxobutan-2-yl]carbamate (82.7 mg, 403 µmol) (intermediate L123) dissolved in 3.0 ml of dichloromethane was added. The reaction mixture was stirred overnight at RT and ethyl acetate was then added. The mixture was washed twice with saturated sodium hydrogen carbonate solution and then with saturated sodium chloride solution. The organic phase was dried over magnesium sulfate and subsequently concentrated. The residue was purified by column chromatography on Biotage/Isolera (SNAP 25 g) with cyclohexane/ethyl acetate 95:5 as eluent. The solvents were evaporated under vacuum and the residue dried under high vacuum. This gave 146 mg (77% of theory) of the compound tert-butyl [4-({(1R)-1-[1-benzyl-4-(2,5-difluorophenyl)-1H-pyrrol-2-yl]-2,2-dimethylpropyl}amino)-1-fluorobutan-2-yl]carbamate.

LC-MS (Method 13): $R_t$=2.57 min; MS (ESIneg): m/z=588 [M+CHOOH-H]$^-$ tert-Butyl [4-({(1R)-1-[1-benzyl-4-(2,5-difluorophenyl)-1H-pyrrol-2-yl]-2,2-dimethylpropyl}amino)-1-fluorobutan-2-yl]carbamate (100 mg, 184 µmol) was dissolved in 6.0 ml of DCM and triethylamine (85 µl, 610 µmol) and chloroacetyl chloride (47 µl, 590 µmol) were added at 0° C. The reaction mixture was stirred overnight at RT. The solvent was evaporated under vacuum. The residue was taken up in acetonitrile/water and purified by prep. RP-HPLC (column: Reprosil 250×30; 10µ, flow: 50 mL/min, MeCN/water, 0.1% TFA). The solvents were evaporated under vacuum and the residue dried under high vacuum. This gave 80 mg (70% of theory) of the compound tert-Butyl {4-[{(1R)-1-[1-benzyl-4-(2,5-difluorophenyl)-1H-pyrrol-2-yl]-2,2-dimethylpropyl}(chloroacetyl)amino]-1-fluorobutan-2-yl}carbamate.

LC-MS (Method 12): $R_t$=2.67 min; MS (ESIneg): m/z=664 [M-H+COOH]$^-$ tert-Butyl {4-[{(1R)-1-[1-benzyl-4-(2,5-difluorophenyl)-1H-pyrrol-2-yl]-2,2-dimethylpropyl}(chloroacetyl)amino]-1-fluorobutan-2-yl}carbamate (79.2 mg, 128 µmol) and 3-sulfanylpropanoic acid (12 µl, 140 µmol) were initially charged in 3.0 ml of methanol with a drop of water. Potassium carbonate (61.8 mg, 447 µmol) was added to the reaction mixture and stirred at 50° C. for 4 h. Ethyl acetate was added to the mixture and the mixture washed repeatedly with water. The organic phase was washed with saturated sodium chloride solution, dried over magnesium sulfate and subsequently concentrated. The residue was purified by prep. RP-HPLC (column: Reprosil 250×30; 10µ, flow: 50 mL/min, MeCN/water, 0.1% TFA). The solvents were evaporated under vacuum and the residue dried under high vacuum. This gave 68.6 mg (78% of theory) of the compound 9-{(1R)-1-[1-benzyl-4-(2,5-difluorophenyl)-1H-pyrrol-2-yl]-2,2-dimethylpropyl}-6-(fluoromethyl)-2,2-dimethyl-4,10-dioxo-3-oxa-12-thia-5,9-diazapentadecan-15-oic acid.

LC-MS Method 12): $R_t$=2.46 min; MS (ESIneg): m/z=688 [M-H]

9-{(1R)-1-[1-Benzyl-4-(2,5-difluorophenyl)-1H-pyrrol-2-yl]-2,2-dimethylpropyl}-6-(fluoromethyl)-2,2-dimethyl-4,10-dioxo-3-oxa-12-thia-5,9-diazapentadecan-15-oic acid (15.0 mg, 21.7 µmol) and trifluoroacetic acid N-(2-aminoethyl)-2-(2,5-dioxo-2,5-dihydro-1H-pyrrol-1-yl)acetamide (1:1) (8.12 mg, 26.1 µmol) (intermediate L1) were initially charged in 1.6 ml of DMF. To the reaction mixture were added HATU (9.92 mg, 26.1 µmol) and N,N-diisopropylethylamine (11 µl, 65 µmol) and the mixture was stirred at RT for 5 min. Water (0.1% TFA) was added to the reaction mixture and the mixture immediately purified by prep. RP-HPLC (column: Reprosil 250×30; 10µ, flow: 50 mL/min, MeCN/water). The solvents were evaporated under vacuum and the residue dried under high vacuum. This gave 18.6 mg (98% of theory) of compound tert-Butyl [13-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-17-fluoro-2,7,12-trioxo-10-thia-3,6,13-triazaheptadecan-16-yl]carbamate.

LC-MS (Method 12): $R_t$=2.36 min; MS (ESIpos): m/z=869 [M+H]$^+$ tert-Butyl [13-{(1R)-1-[1-benzyl-4-(2,5-difluorophenyl)-1H-pyrrol-2-yl]-2,2-dimethylpropyl}-1-(2,5-dioxo-2,5-dihydro-1H-pyrrol-1-yl)-17-fluoro-2,7,12-trioxo-10-thia-3,6,13-triazaheptadecan-16-yl]carbamate (17.0 mg, 19.6 µmol) was dissolved in 2.0 ml of trifluoroethanol. Zinc chloride (16.0 mg, 117 µmol) was added to the reaction mixture and stirred at 50° C. for 1 hour. Zinc chloride (16.0 mg, 117 µmol) was once again added to the reaction mixture and stirred at 50° C. for 1 hour. Ethylenediamine-N,N,N',N'-tetraacetic acid (68.6 mg, 234 µmol) was added to the mixture, then water (0.1% TFA) was added and the mixture subsequently concentrated under vacuum. The residue was purified by prep. RP-HPLC (column: Reprosil 250×30; 10µ, flow. 50 mL/min, MeCN/water, 0.1% TFA). The solvents were evaporated under vacuum and the residue taken up in a little water and lyophilised. This gave 10.7 mg (60% of theory) of the title compound.

LC-MS (Method 14): $R_t$=5.51 min; MS (ESIpos): m/z=769 [M+H]$^+$

Intermediate F319

N-(3-{[2-({(1R)-1-[1-Benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulfanyl}propanoyl)-beta-alanyl-L-aspartic acid

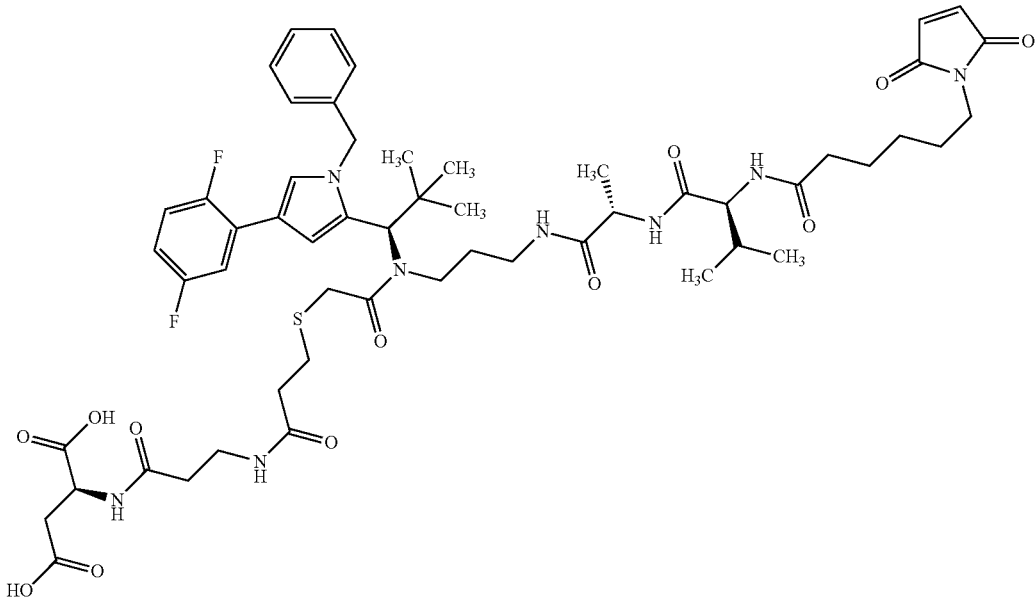 [SMILES: CC(C)[C@H](NC(=O)CCCCCN1C(=O)C=CC1=O)C(=O)N[C@@H](C)C(=O)NCCCN(C(=O)CSCCC(=O)NCCC(=O)N[C@@H](CC(=O)O)C(=O)O)[C@@H](c1cc(-c2cc(F)ccc2F)cn1Cc1ccccc1)C(C)(C)C]

N-[6-(2,5-Dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}[({3-[(2-carboxyethyl)amino]-3-oxopropyl}sulfanyl)acetyl]amino)propyl]-L-alaninamide (9.80 mg, 9.88 µmol) (intermediate C116) and di-tert-Butyl L-aspartate hydrochloride (1:1) (3.34 mg, 11.9 µmol) were initially charged in 1.0 ml DMF under argon and HATU (4.51 mg, 11.9 µmol) and N,N-diisopropylethylamine (5.2 µl, 30 µmol) were added. The reaction mixture was stirred at RT for 10 min and purified immediately by prep. RP-HPLC (column: Reprosil 250×30; 10 g, flow: 50 mL/min, MeCN/water, 0.1% TFA). The solvents were evaporated under vacuum and the residue dried under high vacuum. This gave 10.5 mg (87% of theory) of the compound di-tert-Butyl N-(3-{[2-({(1R)-1-[1-benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulfanyl}propanoyl)-beta-alanyl-L-aspartate.

LC-MS (Method 1): $R_t$=1.33 min; MS (ESIpos): m/z=1219 [M+H]$^+$

Di-tert-Butyl N-(3-{[2-({(1R)-1-[1-benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulfanyl}propanoyl)-beta-alanyl-L-aspartate (9.70 mg, 7.95 µmol) was dissolved in 1.5 ml of trifluoroethanol. Zinc chloride (6.50 mg, 47.7 µmol) was added to the reaction mixture and stirred at 50° C. for 1 hour. Zinc chloride (6.50 mg, 47.7 µmol) was once again added to the reaction mixture and stirred at 50° C. for 1 hour. Ethylenediamine-N,N,N',N'-tetraacetic acid (27.9 mg, 55.4 µmol) was added to the mixture, then water (0.1% TFA) was added and the mixture subsequently concentrated under vacuum. The residue was purified by prep. RP-HPLC (column: Reprosil 250×30; 10µ, flow: 50 mL/min, MeCN/water, 0.1% TFA). The solvents were evaporated under vacuum and the residue taken up in a little water and lyophilised. This gave 4.10 mg (47% of theory) of the title compound.

LC-MS (Method 1): $R_t$=1.07 min; MS (ESIpos): m/z=1107 [M+H]$^+$

Intermediate F320

N-[6-(2,5-Dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}{[(3-{[(1S)-1,3-dicarboxypropyl]amino}-3-oxopropyl)sulfanyl]acetyl}amino)propyl]-L-alaninamide

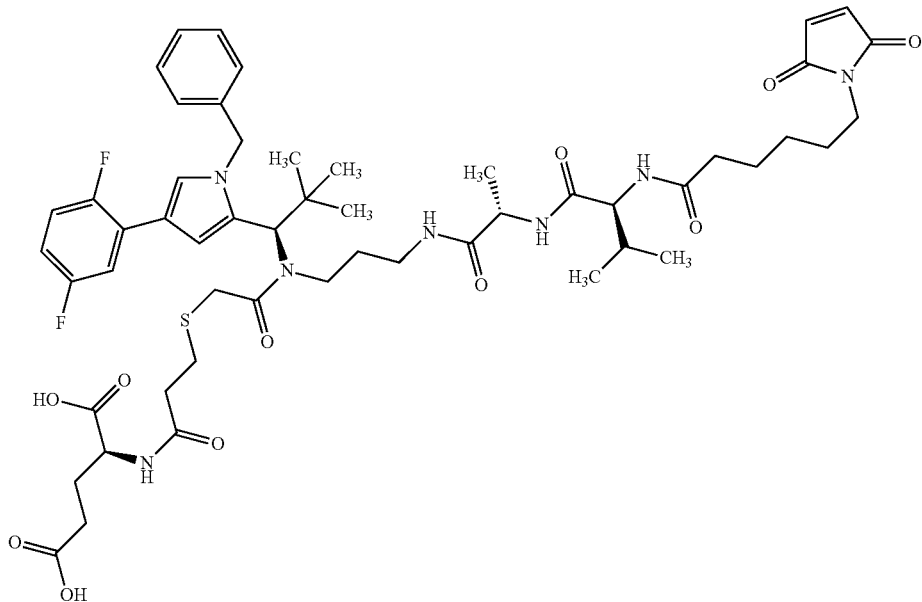 [SMILES: CC(C)[C@H](NC(=O)CCCCCN1C(=O)C=CC1=O)C(=O)N[C@@H](C)C(=O)NCCCN(C(=O)CSCCC(=O)N[C@@H](CCC(=O)O)C(=O)O)[C@@H](c1cc(-c2cc(F)ccc2F)cn1Cc1ccccc1)C(C)(C)C]

N-[6-(2,5-Dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}{[(2-carboxyethyl)sulfanyl]acetyl}amino)propyl]-L-alaninamide (20.0 mg, 21.7 µmol) (intermediate C115) and di-tert-Butyl L-glutamate hydrochloride (1:1) (7.71 mg, 26.1 µmol) were initially charged in 2.0 ml of DMF under argon und HATU (9.91 mg, 26.1 µmol) and N,N-diisopropylethylamine (11 µl, 65 µmol) were added. The reaction mixture was stirred at RT for 10 min and then purified immediately by prep. RP-HPLC (column: Reprosil 250×30; 10µ, flow: 50 mL/min, MeCN/water, 0.1% TFA). The solvents were evaporated under vacuum and the residue dried under high vacuum. This gave 16.4 mg (65% of theory) of the compound di-tert-Butyl (2S)-2-{[(13 S, 16S)-7-{(1R)-1-[1-benzyl-4-(2,5-difluorophenyl)-1H-pyrrol-2-yl]-2,2-dimethylpropyl}-23-(2,5-dioxo-2,5-dihydro-1H-pyrrol-1-yl)-16-isopropyl-13-methyl-6,12,15,18-tetraoxo-4-thia-7,11,14,17-tetraazatricosan-1-oyl]amino}pentanedioate.

LC-MS (Method 1): $R_t$=1.40 min; MS (ESIpos): m/z=1162 [M+H]$^+$

Di-tert-Butyl (2S)-2-{[(13S,16S)-7-{(1R)-1-[1-benzyl-4-(2,5-difluorophenyl)-1H-pyrrol-2-yl]-2,2-dimethylpropyl}-23-(2,5-dioxo-2,5-dihydro-1H-pyrrol-1-yl)-16-isopropyl-13-methyl-6,12,15,18-tetraoxo-4-thia-7,11,14,17-tetraazatricosan-1-oyl]amino}pentanedioate (14.7 mg, 12.6 µmol) was dissolved in 1.5 ml of trifluoroethanol. Zinc chloride (10.3 mg, 75.9 µmol) was added to the reaction mixture and stirred at 50° C. for 1 hour. Zinc chloride (10.3 mg, 75.9 µmol) was once again added to the reaction mixture and stirred at 50° C. for 1 hour. Ethylenediamine-N,N,N',''N-tetraacetic acid (44.4 mg, 152 µmol) was added to the mixture, then water (0.1% TFA) was added and the mixture subsequently concentrated under vacuum. The residue was purified by prep. RP-HPLC (column: Reprosil 250×30; 10µ, flow: 50 mL/min, MeCN/water, 0.1% TFA). The solvents were evaporated under vacuum and the residue taken up in a little water and lyophilised. This gave 6.0 mg (45% of theory) of the title compound.

LC-MS (Method 1): $R_t$=1.10 min; MS (ESIneg): m/z=1048 [M−H]

Intermediate F321

N-(3-{[2-({(1R)-1-[1-Benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulfanyl}propanoyl)-beta-alanyl-D-glutamic acid

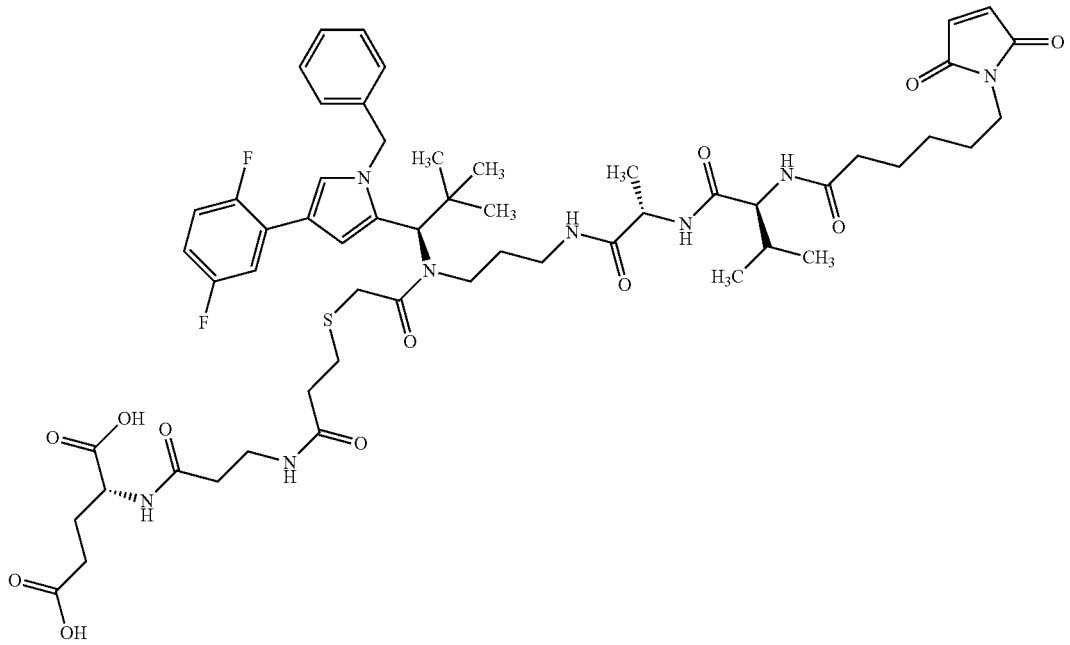 [SMILES: CC(C)[C@H](NC(=O)CCCCCN1C(=O)C=CC1=O)C(=O)N[C@@H](C)C(=O)NCCCN(C(=O)CSCCC(=O)NCCC(=O)N[C@H](CCC(=O)O)C(=O)O)[C@@H](c1cc(-c2cc(F)ccc2F)cn1Cc1ccccc1)C(C)(C)C]

N-[6-(2,5-Dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}[({3-[(2-carboxyethyl)amino]-3-oxopropyl}sulfanyl)acetyl]amino)propyl]-L-alaninamide (9.80 mg, 9.88 µmol) (intermediate C116) and di-tert-Butyl D-glutamate hydrochloride (1:1) (3.51 mg, 11.9 µmol) were initially charged in 1.0 ml of DMF under argon and HATU (4.51 mg, 11.9 µmol) and N,N-diisopropylethylamine (5.2 µl, 30 µmol) were added. The reaction mixture was stirred at RT for 10 min and purified immediately by prep. RP-HPLC (column: Reprosil 250×30; 10µ, flow: 50 mL/min, MeCN/water, 0.1% TFA). The solvents were evaporated under vacuum and the residue dried under high vacuum. This gave 11.7 mg (96% of theory) of the compound di-tert-Butyl N-(3-{[2-({(1R)-1-[1-benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulfanyl}propanoyl)-beta-alanyl-D-glutamate.

LC-MS (Method 1): $R_t$=1.34 min; MS (ESIpos): m/z=1233 [M+H]

Di-tert-Butyl N-(3-{[2-({(1R)-1-[1-benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulfanyl}propanoyl)-beta-alanyl-D-glutamate (11.5 mg, 9.32 µmol) was dissolved in 1.5 ml of trifluoroethanol. (7.62 mg, 55.9 µmol) was added to the reaction mixture and stirred at 50° C. for 1 h. Zinc chloride (7.62 mg, 55.9 µmol) was once again added to the reaction mixture and stirred at 50° C. for 1 h. Ethylenediamine-N,N,N',N'-tetraacetic acid (32.6 mg, 112 µmol) was added to the mixture, then water (0.1% TFA) was added and the mixture subsequently concentrated under vacuum. The residue was purified by prep. RP-HPLC (column: Reprosil 250×30; 10µ, flow: 50 mL/min, MeCN/water, 0.1% TFA). The solvents were evaporated under vacuum and the residue taken up in a little water and lyophilized. This gave 6.5 mg (62% of theory) of the title compound.

LC-MS (Method 1): $R_t$=1.07 min; MS (ESIpos): m/z=1121 [M+H]$^+$

Intermediate F322

N-(3-{[2-({(1R)-1-[1-Benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulfanyl}propanoyl)-beta-alanyl-L-glutamic acid

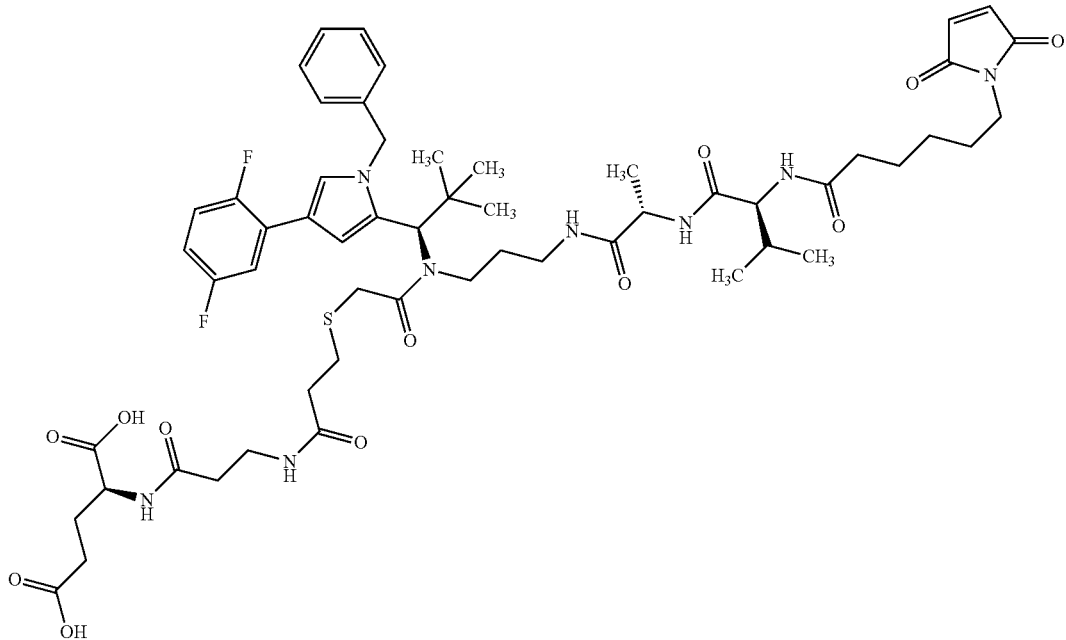 [SMILES: CC(C)[C@H](NC(=O)CCCCCN1C(=O)C=CC1=O)C(=O)N[C@@H](C)C(=O)NCCCN(C(=O)CSCCC(=O)NCCC(=O)N[C@@H](CCC(=O)O)C(=O)O)[C@@H](c1cc(-c2cc(F)ccc2F)cn1Cc1ccccc1)C(C)(C)C]

N-[6-(2,5-Dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}[({3-[(2-carboxyethyl)amino]-3-oxopropyl}sulfanyl)acetyl]amino)propyl]-L-alaninamide (9.80 mg, 9.88 µmol) (intermediate C116) and di-tert-Butyl L-glutamate hydrochloride (1:1) (3.51 mg, 11.9 µmol) were initially charged in 1.0 ml of DMF under argon and HATU (4.51 mg, 11.9 µmol) and N,N-diisopropylethylamine (5.2 µl, 30 µmol) were added. The reaction mixture was stirred at RT for 10 min and purified immediately by prep. RP-HPLC (column: Reprosil 250×30; 10µ, flow. 50 mL/min, MeCN/water, 0.1% TFA). The solvents were evaporated under vacuum and the residue dried under high vacuum. This gave 11.3 mg (93% of theory) of the compound di-tert-Butyl N-(3-{[2-({(1R)-1-[1-benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulfanyl}propanoyl)-beta-alanyl-L-glutamate.

LC-MS (Method 1): $R_t$=1.34 min; MS (ESIpos): m/z=1233 [M+H]$^+$

Di-tert-Butyl N-(3-{[2-({(1R)-1-[1-benzyl-4-(2,5-difluorophenyl)-1H-pyrrol-2-yl]-2,2-dimethylpropyl}[3-({N-[6-(2,5-dioxo-2,5-dihydro-1H-pyrrol-1-yl)hexanoyl]-L-valyl-L-alanyl}amino)propyl]amino)-2-oxoethyl]sulfanyl}propanoyl)-beta-alanyl-L-glutamate (11.0 mg, 8.92 µmol) was dissolved in 1.5 ml of trifluoroethanol. Zinc chloride (7.29 mg, 53.5 µmol) was added to the reaction mixture and stirred at 50° C. for 1 h. Zinc chloride (7.29 mg, 53.5 µmol) was once again added to the reaction mixture and stirred at 50° C. for 1 h. Ethylenediamine-N,N,N',N'-tetraacetic acid (31.2 mg, 107 µmol) was added to the mixture, then water (0.1% TFA) was added and subsequently the mixture was concentrated under vacuum. The residue was purified by prep. RP-HPLC (column: Reprosil 250×30; 10µ, flow: 50 mL/min, MeCN/water, 0.1% TFA). The solvents were evaporated under vacuum and the residue taken up in a little water and lyophilized. This gave 5.10 mg (51% of theory) of the title compound.

LC-MS (Method 1): $R_t$=1.07 min; MS (ESIpos): m/z=1121 [M+H]$^+$

Intermediate F323

N-[6-(2,5-Dioxo-2,5-dihydro-1H-pyrrol-1-yl)hexanoyl]-L-valyl-N-[3-({[(3-{[(1R)-2-(L-beta-asparagylamino)-1-carboxyethyl]amino}-3-oxopropyl)sulfanyl]acetyl}{(1R)-1-[1-benzyl-4-(2,5-difluorophenyl)-1H-pyrrol-2-yl]-2,2-dimethylpropyl}amino)propyl]-L-alaninamide trifluoroacteic acid (1:1)

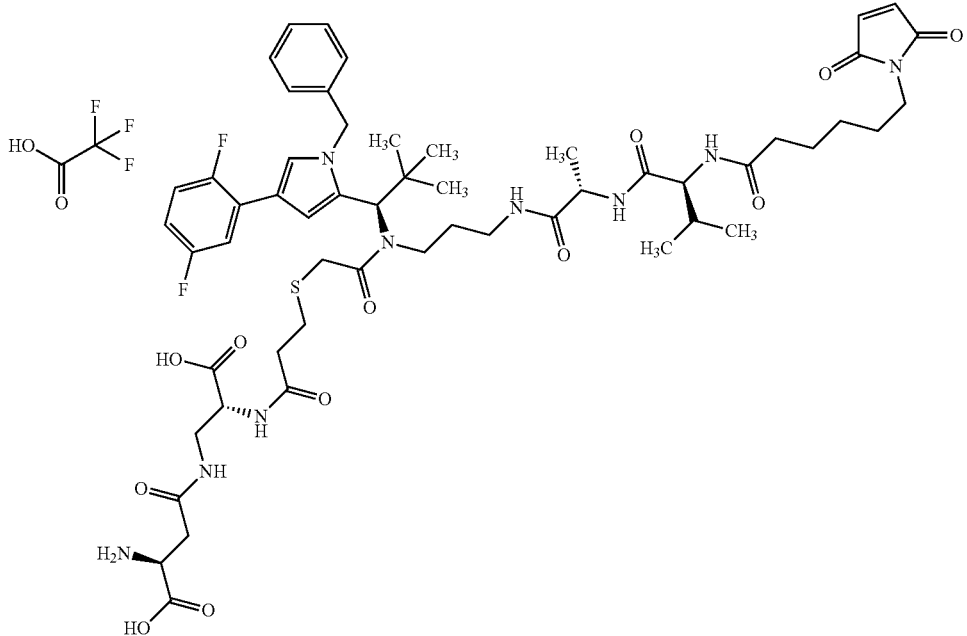

N-[6-(2,5-Dioxo-2,5-dihydro-1H-pyrrol-1-yl)hexanoyl]-L-valyl-N-[3-({(1R)-1-[1-benzyl-4-(2,5-difluorophenyl)-1H-pyrrol-2-yl]-2,2-dimethylpropyl}{[(2-carboxyethyl)sulfanyl]acetyl}amino)propyl]-L-alaninamide (10.0 mg, 7.05 μmol) (intermediate C115) and tert-Butyl N-{(2R)-2-amino-3-oxo-3-[2-(trimethylsilyl)ethoxy]propyl}-N -(tert-butoxycarbonyl)-L-asparaginate (4.02 mg, 8.46 μmol) (intermediate L124) were initially charged in 2.0 ml of DMF under argon and HATU (3.22 mg, 8.46 μmol) and N,N-diisopropylethylamine (3.7 μl, 21 μmol) were added. The reaction mixture was stirred at RT for 10 min and purified immediately by prep. RP-HPLC (column: Reprosil 250×30; 10μ, flow: 50 mL/mm, MeCN/water, 0.1% TFA). The solvents were evaporated under vacuum and the residue taken up in a little water and lyophilised. This gave 4.3 mg (32% of theory) of the compound 6-tert-Butyl 11-[2-(trimethylsilyl)ethyl]-(6S,11R,25S,28S)-19-{(1R)-1-[1-benzyl-4-(2,5-difluorophenyl)-1H-pyrrol-2-yl]-2,2-dimethylpropyl}-35-(2,5-dioxo-2,5-dihydro-1H-pyrrol-1-yl)-28-isopropyl-2,2,25-trimethyl-4,8,13,18,24,27,30-heptaoxo-3-oxa-16-thia-5,9,12,19,23,26,29-heptaazapentatriacontane-6,11-dicarboxylate.

LC-MS (Method 5): $R_t$=5.32 min; MS (ESIpos): m/z=1379 [M+H]$^+$ 6-tert-Butyl 11-[2-(trimethylsilyl)ethyl]-(6S,11R,25S,28S)-19-{(1R)-1-[1-benzyl-4-(2,5-difluorophenyl)-1H-pyrrol-2-yl]-2,2-dimethylpropyl}-35-(2,5-dioxo-2,5-dihydro-1H-pyrrol-1-yl)-28-isopropyl-2,2,25-trimethyl-4,8,13,18,24,27,30-heptaoxo-3-oxa-16-thia-5,9,12,19,23,26,29-heptaazapentatriacontane-6,11-dicarboxylate (4.10 mg, 73% purity, 2.17 μmol) was dissolved in 2.0 ml of trifluoroethanol. Zinc chloride (1.77 mg, 13.0 μmol) was added to the reaction mixture and stirred at 50° C. for 1 h. Zinc chloride (1.77 mg, 13.0 μmol) was added five more times to the reaction mixture and stirred at 50° C. for 1 h. Ethylenediamine-N,N,N',N'-tetraacetic acid (22.0 mg, 78 μmol) was added to the mixture and then water (0.1% TFA) was added and subsequently the mixture was concentrated under vacuum. The residue was purified by prep. RP-HPLC (column: Reprosil 250×30; 10μ, flow. 50 mL/min, MeCN/water, 0.1% TFA). The solvents were evaporated under vacuum and the residue was taken up in a little water and lyophilised. This gave 2.1 mg (69% of theory) of the title compound.

LC-MS (Method 1): $R_t$=0.98 min; MS (ESIpos): m/z=1122 [M+H]$^+$

Intermediate F324

S-[2-({(1R)-1-[1-Benzyl-4-(2,5-difluorophenyl)-1H-pyrrol-2-yl]-2,2-dimethylpropyl}[pyrrolidin-3-ylmethyl]amino)-2-oxoethyl]-N-[1-(2,5-dioxo-2,5-dihydro-1H-pyrrol-1-yl)-2,18-dioxo-6,9,12,15-tetraoxa-3-azaoctadecan-18-yl]-L-cysteine-trifluoroacetic acid (1:1) (Isomer 1)

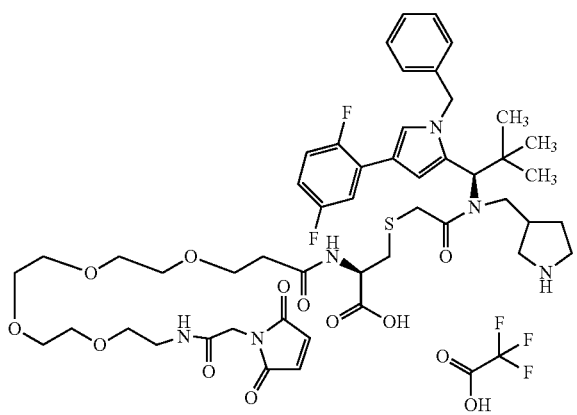 [SMILES: CC(C)(C)[C@H](c1cc(-c2cc(F)ccc2F)cn1Cc1ccccc1)N(CC1CCNC1)C(=O)CSC[C@H](NC(=O)CCOCCOCCOCCOCCNC(=O)CN1C(=O)C=CC1=O)C(=O)O ; O=C(O)C(F)(F)F]

1-(2,5-Dioxo-2,5-dihydro-1H-pyrrol-1-yl)-2-oxo-6,9,12,15-tetraoxa-3-azaoctadecan-18-oic acid (99.6 mg, 247 µmol) (intermediate L74) was initially charged in 1.4 ml of DMF under argon and HATU (90.4 mg, 238 µmol) and N,N-diisopropylethylamine (41 µl, 240 µmol) were added. The reaction mixture was stirred at RT for 10 min and S-[2-({(1R)-1-[1-benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-L-cysteine (70.0 mg, 95.2 µmol) (intermediate C90) dissolved in 1.4 ml of DMF was added. The reaction mixture was stirred overnight at RT and purified immediately by prep. RP-HPLC (column: Reprosil 250×30; 10µ, flow: 50 mL/min, MeCN/water, 0.1% TFA). The solvents were evaporated under vacuum and the residue was taken up in a little water and lyophilized. This gave 19.0 mg (18.4% of theory) of the compound S-[2-({(1R)-1-[1-benzyl-4-(2,5-difluorophenyl)-1H-pyrrol-2-yl]-2,2-dimethylpropyl}{[(3R)-1-(tert-butoxycarbonyl)pyrrolidin-3-yl]methyl}amino)-2-oxoethyl]-N-[1-(2,5-dioxo-2,5-dihydro-1H-pyrrol-1-yl)-2,18-dioxo-6,9,12,15-tetraoxa-3-azaoctadecan-18-yl]-L-cysteine.

LC-MS (Method 12): $R_t$=2.29 min; MS (ESIpos): m/z=1082 [M+H]$^+$

S-[2-({(1R)-1-[1-Benzyl-4-(2,5-difluorophenyl)-1H-pyrrol-2-yl]-2,2-dimethylpropyl}{[1-(tert-butoxycarbonyl)pyrrolidin-3-yl]methyl}amino)-2-oxoethyl]-N-[1-(2,5-dioxo-2,5-dihydro-1H-pyrrol-1-yl)-2,18-dioxo-6,9,12,15-tetraoxa-3-azaoctadecan-18-yl]-L-cysteine (17.0 mg, 15.7 µmol) was dissolved in 2.0 ml of trifluoroethanol. Zinc chloride (8.56 mg, 62.8 µmol) was added to the reaction mixture and stirred at 50° C. for 1 h. Zinc chloride (8.56 mg, 62.8 µmol) was added once again to the reaction mixture and stirred at 50° C. for 2 h. Ethylenediamine-N,N,N',N'-tetraacetic acid (36.7 mg, 126 µmol) was added to the mixture, then water (0.1% TFA) was added and subsequently the mixture was concentrated under vacuum. The residue was purified by prep. RP-HPLC (column: Reprosil 250×30; 10µ, flow: 50 mL/min, MeCN/water, 0.1% TFA). The solvents were evaporated under vacuum and the residue dried under high vacuum. This gave 3.90 mg (22% of theory) of the title compound.

LC-MS (Method 1): $R_t$=0.89 min; MS (ESIpos): m/z=983 [M+H]$^+$

Intermediate F325

N-[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-N$^2$-[(2,5-dioxo-2,5-dihydro-1H-pyrrol-1-yl)acetyl]-D-alpha-glutamine-trifluoroacetic acid (1:1)

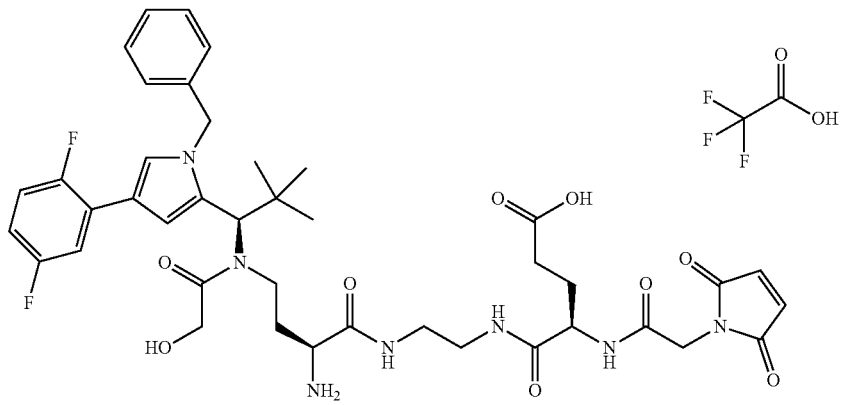 [SMILES: CC(C)(C)[C@H](c1cc(-c2cc(F)ccc2F)cn1Cc1ccccc1)N(CC[C@H](N)C(=O)NCCNC(=O)[C@@H](CCC(=O)O)NC(=O)CN1C(=O)C=CC1=O)C(=O)CO ; O=C(O)C(F)(F)F]

30 mg (0.046 mmol) of intermediate C58 were coupled with 29 mg (0.055 mmol) of trifluoroacetic acid-benzyl N-(2-aminoethyl)-N2-[(benzyloxy)carbonyl]-D-alpha-glutaminate (1:1) in the presence of 1.5 equiv. of HATU and 3 equiv. of N,N-diisopropylethylamine. After purification by preparative HPLC, 39.5 mg (82% of theory) of the protected intermediate were obtained. The benzyl ester groups were firstly cleaved off from this intermediate by hydrogenolysis. In two further steps, the subsequent coupling with 1-{2-[(2,5-dioxopyrrolidin-1-yl)oxy]-2-oxoethyl}-1H-pyrrole-2,5-dione in DMF in the presence of 3 equiv. of N,N-diisopropylethylamine and cleavage of the Teoc protecting group with zinc chloride in trifluoroethanol as in intermediate F119 then led to the title compound.

LC-MS (Method 12): $R_f$=1.44 min; MS (ESIpos): m/z=822 (M+H)$^+$.

Intermediate F326

N-[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-N$^2$-(bromoacetyl)-D-alpha-glutamine-trifluoroacetic acid (1:1)

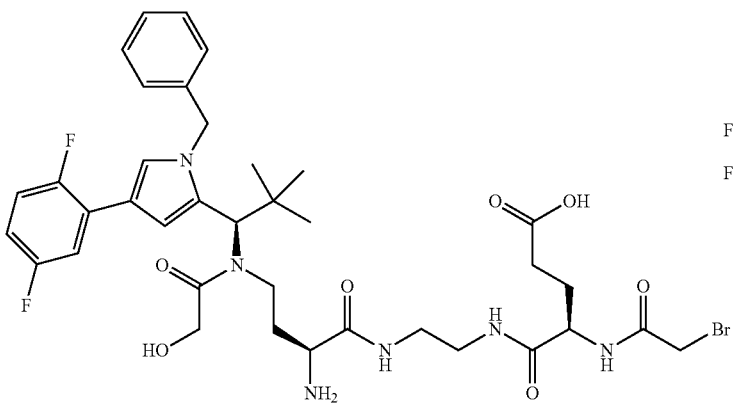
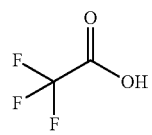

43 mg (0.066 mmol) of intermediate C58 were coupled with 57 mg (0.077 mmol) of intermediate L125 in the presence of 1.5 equiv. of HATU and 4 equiv. of 4-methylmorpholine. After purification by preparative HPLC, 27 mg (34% of theory) of the protected intermediate were obtained. This was subsequently converted to the title compound with zinc chloride in trifluoroethanol as described in intermediate F119.

LC-MS (Method 1): $R_f$=0.83 min; MS (ESIpos): m/z=805 and 807 (M+H)$^+$.

B: Preparation of Antibody Drug Conjugates (ADC)

B-1. General Process for Generating Anti-B7H3 Antibodies

The anti-B7H3 antibodies were generated by the screening of a phage display library on cells expressing recombinant murine B7H3 and human B7H3. The antibodies obtained in this manner were reformatted into human IgG1 format and used for the Working examples described here.

B-2. General Process for Expressing Anti-B7H3 Antibodies in Mammalian Cells

The antibodies, for example TPP-3803 and TPP-5706, were produced in transient cultures of mammalian cells, as described by Tom et al., Chapter 12 in Methods Express: Expression Systems, edited by Micheal R. Dyson and Yves Durocher, Scion Publishing Ltd, 2007 (see AK-Example 1).

B-3. General Process for Purifying Antibodies from Cell Supernatants

The antibodies, for example TPP-3803 and TPP-5706, were obtained from the cell culture supernatants. The cell supernatants were clarified by centrifugation of cells. The cell supernatant was then purified by affinity chromatography on a MabSelect Sure (GE Healthcare) chromatography column. To this end, the column was equilibrated in DPBS pH 7.4 (Sigma/Aldrich), the cell supernatant was applied and the column was washed with about 10 column volumes of DPBS pH 7.4+500 mM sodium chloride. The antibodies were eluted in 50 mM sodium acetate pH 3.5+500 mM sodium chloride and then purified further by gel filtration chromatography on a Superdex 200 column (GE Healthcare) in DPBS pH 7.4.

B-4. General Process for Coupling to Cysteine Side Chains

The following anti-B7H3 antibodies were used for the coupling reactions:

| |
|---|
| TPP-6497 |
| TPP-6499 |

| -continued |
|---|
| TPP-6501 |
| TPP-6502 |
| TPP-6515 |
| TPP-7611 |
| TPP-8322 |
| TPP-8382 |
| TPP-8564 |
| TPP-8565 |
| TPP-8567 |
| TPP-8568 |

The coupling reactions were usually carried out under argon.

Process A:

Between 2 and 5 equivalents of tris(2-carboxyethyl)phosphine hydrochloride (TCEP), dissolved in PBS buffer, were added to a solution of the appropriate antibody in PBS buffer in the concentration range between 1 mg/ml and 20 mg/ml, preferably in the range of about 5 mg/ml to 15 mg/ml, and the mixture was stirred at RT for 30 min to 1 h. Subsequently, depending on the intended loading, from 2 to 12 equivalents, preferably about 5-10 equivalents of the maleinimide precursor compound or halide precursor compound to be coupled were added as a solution in DMSO. Here, the amount of DMSO should not exceed 10% of the total volume. The reaction was stirred in the case of maleinimide precursors for 60-240 min at RT and in the case of halide precursors between 8 and 24 h at RT and then applied to PBS-equilibrated PD 10 columns (Sephadex® G-25, GE Healthcare) and eluted with PBS buffer. Generally, unless indicated otherwise, 5 mg of the antibody in question in PBS buffer were used for the reduction and the subsequent coupling. Purification on the PD10 column thus in each case afforded solutions of the respective ADCs in 3.5 ml PBS buffer. The sample was then concentrated by ultracentrifugation and optionally rediluted with PBS buffer. If required, for better removal of low-molecular weight components, concentration by ultrafiltration was repeated after redilution with PBS buffer. For biological tests, if required, the concentrations of the final ADC samples were optionally adjusted to the range of 0.5-15 mg/ml by redilution. The respective protein concentrations, stated in the working examples, of the ADC solutions were determined. Furthermore, antibody loading (drug/mAb ratio) was determined using the methods described under B-7.

The ADCs produced by this process may also be present to a lesser or higher degree in the form of the hydrolysed open-chain succinamides attached to the antibodies.

In particular the KSP-1-ADCs attached though the linker substructure

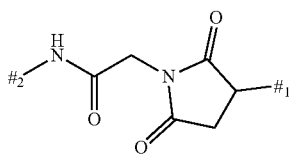

to thiol groups of the antibodies may optionally also be prepared in a targeted manner by rebuffering after the coupling and stirring at pH 8 for about 20-24 h according to Scheme 28 via the ADCs attached via open-chain succinamides.

1 represents the sulphur bridge to the antibody, and #2 the point of attachment to the modified KSP inhibitor Such ADCs where the linker is attached to the antibodies through hydrolysed open-chain succinamides may optionally also be prepared in a targeted manner by an exemplary procedure as follows:

Small Scale Coupling:

To a solution of 2-5 mg of the relevant antibody in PBS buffer in the concentration range from 1 mg/mL to 20 mg/mL, preferably in the range from about 5 mg/ml to 15 mg/ml, were added between 2 and 5 equivalents of tris(2-carboxyethyl)phosphine hydrochloride (TCEP) dissolved in PBS buffer, and the mixture stirred at RT for 30 min to 1 h. For this purpose, the solution of the antibody used in each case can be used at the concentration specified in the working examples, or optionally can also be diluted with PBS buffer to about half the specified starting concentration, in order to reach the preferred concentration range. Subsequently, depending on the desired loading, between 2 and 12 equivalents, preferably about 5-10 equivalents of the maleimide precursor compound to be coupled were added as a solution in DMSO. In this case, the amount of DMSO should not exceed 10% of the total volume. The mixture was stirred at RT for 60-240 min and then diluted to a volume of 3-7 ml with PBS buffer, which had been previously adjusted to pH 8, and stirred overnight at RT under argon. This solution was then applied to a PD 10 column (Sephadex® G-25, GE Healthcare) equilibrated to pH 7.2 with PBS buffer and eluted with PBS buffer pH7.2. This was subsequently concentrated by ultracentrifugation and redilution with PBS buffer (pH 7.2).

Medium Scale Coupling:

Under argon, a solution of 0.344 mg TCEP in 100 µl of PBS buffer was added to 60 mg of the antibody in question in 5 ml of PBS buffer (c~12 mg/ml). The reaction was stirred at RT for 30 min, and 0.003 mmol of a maleinimide precursor compound dissolved in 600 µl of DMSO was then added. After a further 1.5 h-2 h of stirring at RT, the reaction was diluted with 1075 ml PBS buffer which had been adjusted to pH 8 beforehand.

This solution was then applied to PD 10 columns (Sephadex® G-25, GE Healthcare) which had been equilibrated with PBS buffer pH 8 and was eluted with PBS buffer pH 8. The eluate was diluted with PBS buffer pH 8 to a total volume of 14 ml. This solution was stirred at RT under argon overnight. Buffering was then optionally carried out further to pH 7.2. The ADC solution was concentrated by ultracentrifugation, rediluted with PBS buffer (pH 7.2) and then optionally concentrated again to a concentration of approximately 10 mg/ml.

Other potentially hydrolysis-sensitive thianylsuccinimide bridges to the antibody in the working examples contain the following linker substructures, where #1 represents the thioether linkage to the antibody and #2 the point of attachment to the modified KSP inhibitor:

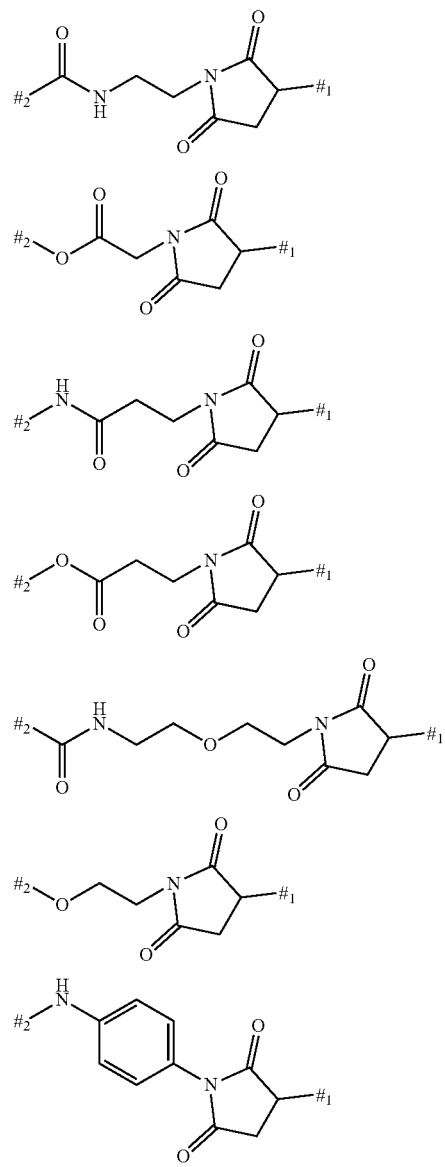

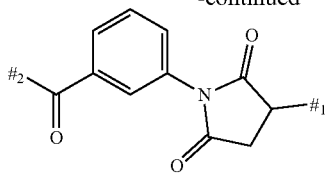

These linker substructures represent the linking unit to the antibody and have (in addition to the linker composition) a significant effect on the structure and the profile of the metabolites formed m the tumour cells.

In the structural formulae shown, AK has the meaning

AK=anti-B7H3 AK (partially reduced)-S§¹ where
§¹> represents the linkage to the succinimide group or to any isomeric hydrolysed open-chain succinamides or the alkylene radical resulting therefrom,
and
S represents the sulphur atom of a cysteine residue of the partially reduced antibody.

B-5. General Process for Coupling to Lysine Side Chains

The following anti-B7H3 antibody was used for the coupling reactions:

---
TPP-6502
---

The coupling reactions were usually carried out under argon.

From 2 to 8 equivalents of the precursor compound to be coupled were added as a solution in DMSO to a solution of the antibody in question in PBS buffer in a concentration range between 1 mg/ml and 20 mg/ml, preferably about 10 mg/ml, depending on the intended loading. After 30 min to 6 h of stirring at RT, the same amount of precursor compound in DMSO was added again. Here, the amount of DMSO should not exceed 10% of the total volume. After a further 30 min to 6 h of stirring at RT, the reaction was applied to PD 10 columns (Sephadex® G-25, GE Healthcare) equilibrated with PBS and eluted with PBS buffer. Generally, unless indicated otherwise, 5 mg of the antibody in question in PBS buffer were used for the reduction and the subsequent coupling. Purification on the PD 10 column thus in each case afforded solutions of the respective ADCs in 3.5 ml PBS buffer. The sample was then concentrated by ultracentrifugation and optionally rediluted with PBS buffer. If required, for better removal of low-molecular weight components, concentration by ultrafiltration was repeated after redilution with PBS buffer. For biological tests, if required, the concentrations of the final ADC samples were optionally adjusted to the range of 0.5-15 mg/ml by redilution.

The respective protein concentrations, stated in the working examples, of the ADC solutions were determined. Furthermore, antibody loading (drug/mAb ratio) was determined using the methods described under B-7.

In the structural formulae shown, $AK_2$ has the meaning $AK_2$=anti-B7H3 AK-NH§² where
§² represents the linkage to the carbonyl group
and
NH represents the side-chain amino group of a lysine residue of the antibody.

B-6a. General Process for Preparing Closed Succinimide-Cysteine Adducts:

In an exemplary embodiment, 10 μmol of the maleinimide precursor compounds described above were taken up in 3-5 ml of DMF, and 2.1 mg (20 μmol) of L-cysteine were added. The reaction mixture was stirred at RT for 2 h to 24 h, then concentrated under reduced pressure and then purified by preparative HPLC.

B-6aa. General Process for Preparing Isomeric Open Succinamide-Cysteine Adducts:

In an exemplary embodiment, 68 μmol of the maleinimide precursor compounds described above were taken up in 15 ml of DMF, and with 36 mg (136 μmol) of N-{[2-(trimethylsilyl)ethoxy]carbonyl}-L-cysteine were added. The reaction mixture was stirred at RT for ~20 h, then concentrated under reduced pressure and then purified by preparative HPLC. The appropriate fractions were combined and the solvents were evaporated under reduced pressure, and the residue was then dissolved in 15 ml of THF/water 1:1. 131 μl of a 2M aqueous lithium hydroxide solution were added and the reaction was stirred at RT for 1 h. The reaction was then neutralized with a 1M hydrochloric acid, the solvent was evaporated under reduced pressure and the residue was purified by preparative HPLC. This gave ~50% of theory of the regioisomeric protected intermediates as a colourless foam.

In the last step, 0.023 mmol of these regioisomeric hydrolysis products were dissolved in 3 ml of 2,2,2-trifluoroethanol. 12.5 mg (0.092 mmol) of zinc chloride were added, and the reaction was stirred at 50° C. for 4 h. 27 mg (0.092 mmol) of ethylenediamine-N,N,N',N'-tetraacetic acid were then added, and the solvent was evaporated under reduced pressure. The residue was purified by preparative HPLC. Concentration of the appropriate fractions and lyophilizahon of the residue from acetonitrile/water gave the hydrolysed open sulphanylsuccinamides as a regioisomer mixture.

Further Purification and Characterization of the Conjugates According to the Invention After the reaction, in some instances the reaction mixture was concentrated, for example by ultrafiltration, and then desalted and purified by chromatography, for example using a Sephadex®G-25 column. Elution was carried out, for example, with phosphate-buffered saline (PBS). The solution was then sterile filtered and frozen. Alternatively, the conjugate can be lyophilized.

B-7. Determination of the Antibody, the Toxophor Loading and the Proportion of Open Cysteine Adducts For protein identification in addition to molecular weight determination after deglycosylation and/or denaturing, a tryptic digestion was carried out which, after denaturing, reduction and derivatization, confirms the identity of the protein via the tryptic peptides found.

The toxophor loading of the PBS buffer solutions obtained of the conjugates described in the working examples was determined as follows:

Determination of toxophor loading of lysine-linked ADCs was carried out by mass spectrometric determination of the molecular weights of the individual conjugate species. Here, the antibody conjugates were first deglycosylated with PNGaseF, and the sample was acidified and, after HPLC separation/desalting, analysed by mass spectrometry using ESI-MicroTofq (Bruker Daltomk). All spectra over the signal in the TIC (Total Ion Chromatogram) were added and the molecular weight of the different conjugate species was calculated based on MaxEnt deconvolution. The DAR (=drug/antibody ratio) was then calculated after signal integration of the different species.

The toxophor loading of cysteine-linked conjugates was determined by reversed-phase chromatography of the reduced and denatured ADCs. Guanidinium hydrochloride (GuHCl) (28.6 mg) and a solution of DL-dithiothreitol (DTT) (500 mM, 3 μl) were added to the ADC solution (1 mg/ml, 50 μl). The mixture was incubated at 55° C. for one hour and analysed by HPLC.

HPLC analysis was carried out on an Agilent 1260 HPLC system with detection at 220 nm. A Polymer Laboratories PLRP-S polymeric reversed-phase column (catalogue number PL 1912-3802) (2.1 ×150 mm, 8 μm particle size, 1000 Å) was used at a flow rate of 1 ml/min with the following gradient: 0 min, 25% B; 3 min, 25% B; 28 min, 50% B. Mobile phase A consisted of 0.05% trifluoroacetic acid (TFA) in water, mobile phase B of 0.05% trifluoroacetic acid in acetonitrile.

The detected peaks were assigned by retention time comparison with the light chain (L0) and the heavy chain (H0) of the non-conjugated antibody. Peaks detected exclusively in the conjugated sample were assigned to the light chain with one toxophor (L1) and the heavy chains with one, two and three toxophors (H1, H2, H3).

Average loading of the antibody with toxophors was calculated from the peak areas determined by integration as double the sum of HC load and LC load, where LC load is calculated from the sum of the toxophor number-average weighed integration results of all LC peaks divided by the sum of the singly weighed integration results of all LC peaks, and where the HC-load is calculated from the sum of the toxophor number-average weighed integration results of all HC peaks divided by the sum of the singly weighed integration results of all HC peaks. In individual cases, it may not be possible to determine the toxophor load accurately owing to co-elutions of some peaks.

In the cases where light and heavy chains could not be separated sufficiently by HPLC, determination of toxophor loading of cysteine-linked conjugates was carried out by mass spectrometric determination of the molecular weights of the individual conjugate species at light and heavy chain.

Guanidinium hydrochloride (GuHCl) (28.6 mg) and a solution of DL-dithiothreitol (DTT) (500 mM, 3 μl) were added to the ADC solution (1 mg/ml, 50 μl). The mixture was incubated for one hour at 55° C., and analysed by mass spectrometry after online desalting using ESI-MicroTof$_Q$ (Bruker Daltonik).

For the DAR determination, all spectra were added over the signal in the TIC (Total Ion Chromatogram), and the molecular weight of the different conjugate species at light and heavy chain was calculated based on MaxEnt deconvolution. Average loading of the antibody with toxophors was calculated from the peak areas determined by integration as double the sum of HC load and LC load, where LC load is calculated from the sum of the toxophor number-average weighed integration results of all LC peaks divided by the sum of the singly weighed integration results of all LC peaks, and where the HC-load is calculated from the sum of the toxophor number-average weighed integration results of all HC peaks divided by the sum of the singly weighed integration results of all HC peaks.

To determine the proportion of the open cysteine adduct, the molecular weight area ratio of closed to open cysteine adduct (molecular weight delta 18 Dalton) of all singly conjugated light and heavy chain variants was determined. The mean of all variants yielded the proportion of the open cysteine adduct.

B-8. Checking the Antigen-Binding of the ADC

The capability of the binder of binding to the target molecule was checked after coupling had taken place. The person skilled in the art is familiar with multifarious methods which can be used for this purpose; for example, the affinity of the conjugate can be checked using ELISA technology or surface plasmon resonance analysis (BIAcore™ measurement). The conjugate concentration can be measured by the person skilled in the art using customary methods, for example for antibody conjugates by protein determination, (see also Doronina et al.; Nature Biotechnol. 2003, 21.778-784 and Poison et al., Blood 2007; 1102:616-623).

Metabolite Embodiments

Example M1

S-[1-(2-{[2-({(2S)-2-Amino-4-[{(1R)-1-[1-benzyl-4-(2,5-difluorophenyl)-1H-pyrrol-2-yl]-2,2-dimethyl-propyl}(glycoloyl)amino]butanoyl}amino)ethyl]amino}-2-oxoethyl)-2,5-dioxopyrrolidin-3-yl]-L-cysteine/trifluoroacetic acid (1:1)

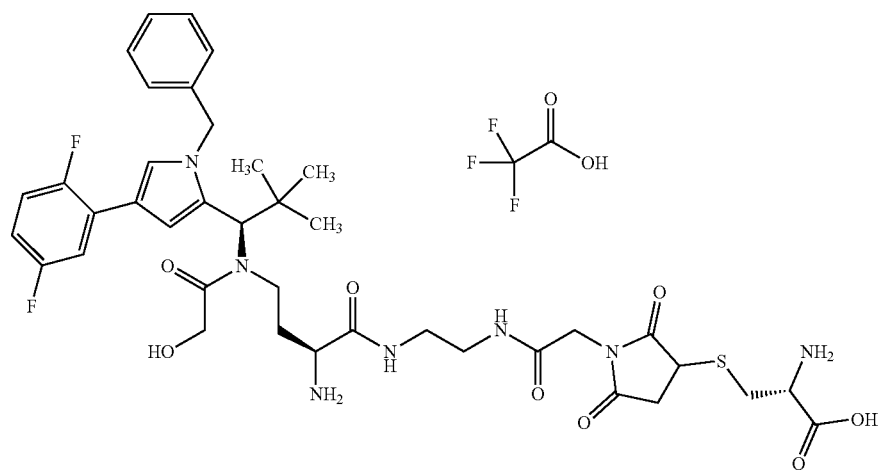 [SMILES: CC(C)(C)[C@H](c1cc(-c2cc(F)ccc2F)cn1Cc1ccccc1)N(CC[C@H](N)C(=O)NCCNC(=O)CN1C(=O)CC(SC[C@H](N)C(=O)O)C1=O)C(=O)CO ; O=C(O)C(F)(F)F]

1.8 mg (2 µmol) of Intermediate F104 were taken up in 1 ml of DMF, and 2.7 mg (22 µmol) of L-cysteine were added. The reaction mixture was stirred at RT for 20 h, then concentrated under reduced pressure and then purified by preparative HPLC. 0.6 mg (26% of theory) of the title compound remained as a colourless foam.

LC-MS (Method 1): $R_t$=0.80 min; MS (EIpos): m/z=814 [M+H]$^+$.

Example M2

4-[(2-{[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-{[(2R)-2-amino-2-carboxyethyl]sulphanyl}-4-oxobutanoic acid/trifluoroacetic acid (1:1) and 4-[(2-{[2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-2-{[(2R)-2-amino-2-carboxyethyl]sulphanyl}-4-oxobutanoic acid/trifluoroacetic acid (1:1)

First, L-cysteine was converted with 1-({[2-(trimethylsilyl)ethoxy]carbonyl}oxy)pyrrolidine-2,5-dione in DMF in the presence of MA-diisopropylethylamine into N-{[2-(trimethylsilyl)ethoxy]carbonyl}-L-cysteine.

406 mg (1.53 mmol) of N-{[2-(trimethylsilyl)ethoxy]carbonyl}-L-cysteine were dissolved in 10 ml of DMF, 157.5 mg (1.606 mmol) of maleic anhydride were added and the reaction was stirred at RT for 1 hour. 7.5 mg (0.01 mmol) of intermediate C66 were added to 130 µl of this solution, and the reaction was stirred at RT for 5 min. The mixture was then concentrated under reduced pressure, and the residue was purified by preparative HPLC. The solvent was evaporated under reduced pressure and the residue was dried under high vacuum. This gave 10 mg (89%) of the protected intermediate; it was not possible to separate the regioisomers neither by HPLC nor by LC-MS.

LC-MS (Method 1): $R_t$=1.38 min; MS (EIpos): m/z=1120 [M+H]$^+$.

In the last step, the 10 mg of this intermediate were dissolved in 2 ml of 2,2,2-trifluoroethanol. 12 mg (0.088 mmol) of zinc chloride were added, and the reaction was stirred at 50° C. for 30 min. 26 mg (0.088 mmol) of ethylenediamine-N,N,N',N'-tetraacetic acid were then

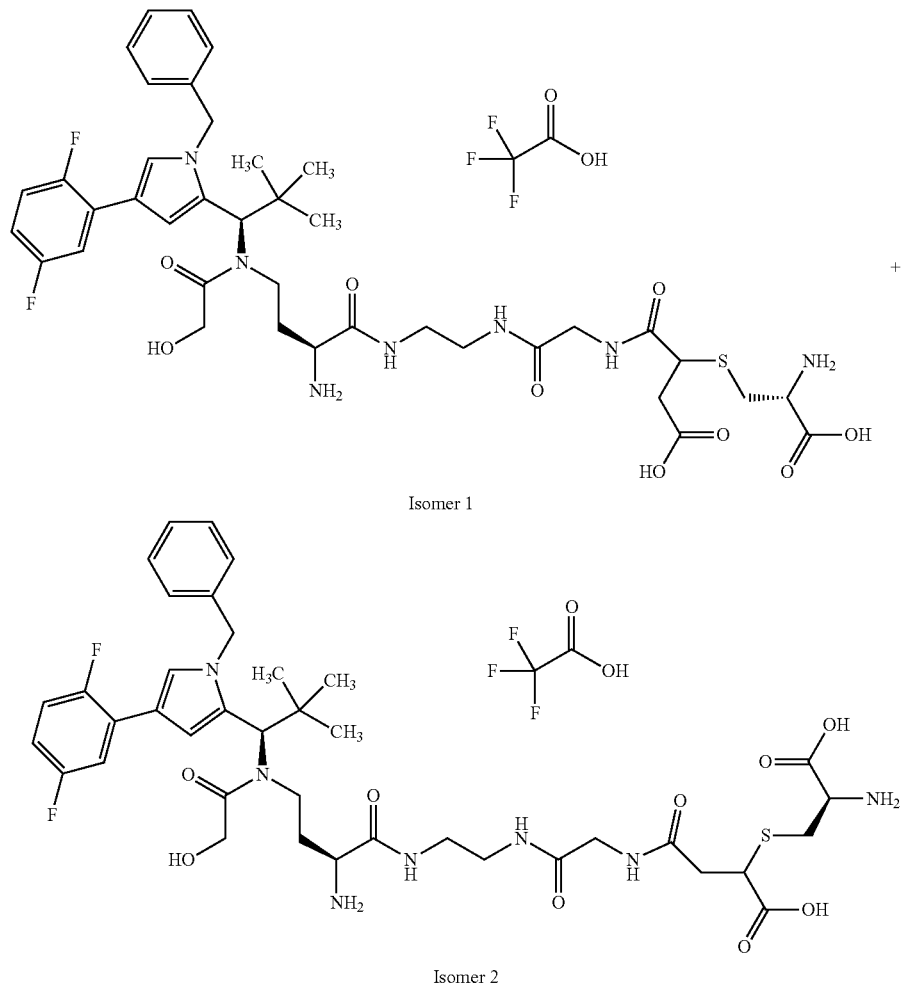

Isomer 1

Isomer 2

LC-MS (Method 1): $R_t$=0.80 min; MS (EIpos): m/z=814 [M+H]$^+$.

added, and the solvent was evaporated under reduced pressure. The residue was purified by preparative HPLC. Concentration of the appropriate fractions and lyophilization of the residue from acetonitrile/water gave 8.3 mg (99% of theory) of the title compound as a regioisomer mixture in a ratio of 87:13.

LC-MS (Method 5): $R_t$=2.3 min and 2.43 min; MS (ESIpos): m/z=832 (M+H)$^+$.

$^1$H-NMR main regioisomer: (500 MHz, DMSO-d$_6$): δ=8.7 (m, 1H), 8.5 (m, 2H), 8.1 (m, 1H), 7.6 (m, 1H), 7.5 (s, 1H) 7.4-7.15 (m, 6H), 6.9-7.0 (m, 1H), 6.85 (s, 1H), 5.61 (s, 1H), 4.9 and 5.2 (2d, 2H), 4.26 and 4.06 (2d, 2H), 3.5-3.8 (m, 5H), 3.0-3.4 (m, 5H), 2.75-3.0 (m, 3H), 2.58 and 2.57 (dd, 1H), 0.77 and 1,5 (2m, 2H), 0.81 (s, 9H).

Alternatively, the regioisomeric title compounds were prepared as follows:

To this end, first L-cysteine was converted with 1-({[2-(trimethyl-silyl)ethoxy]carbonyl}oxy)pyrrolidine-2,5-dione in DMF in the presence of A/A-diisopropyl-ethylamine into N-{[2-(trimethylsilyl)ethoxy]carbonyl}-L-cysteine. 55 mg (0.068 mmol) of Intermediate F104 and 36 mg (0.136 mmol) of N-{[2-(trimethylsilyl) ethoxy]carbonyl}-L-cysteine were dissolved in 15 ml of DMF, and the mixture was stirred at RT for 20 h. The mixture was then concentrated and the residue was purified by preparative HPLC. The appropriate fractions were combined and the solvents were evaporated under reduced pressure, and the residue was then dissolved in 15 ml of THF/water 1:1. 131 μl of a 2M aqueous lithium hydroxide solution were added and the reaction was stirred at RT for 1 h. The reaction was then neutralized with a 1M hydrochloric acid, the solvent was evaporated under reduced pressure and the residue was purified by preparative HPLC. This gave 37 mg (50% of theory) of the regioisomeric protected intermediates as a colourless foam.

LC-MS (Method 5): $R_t$=3.33 min and 3.36 min; MS (ESIpos): m/z=976 (M+H)$^+$.

In the last step, 25 mg (0.023 mmol) of this intermediate were dissolved in 3 ml of 2,2,2-trifluoroethanol. 12.5 mg (0.092 mmol) of zinc chloride were added, and the reaction was stirred at 50° C. for 4 h. 27 mg (0.092 mmol) of ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave 18.5 mg (85% of theory) of the title compound as a regioisomer mixture in a ratio of 21:79.

LC-MS (Method 5): $R_t$=2.37 min and 3.44 min; MS (ESIpos): m/z=832 (M+H)$^+$.

Example M3

4-[(2-{[(2R)-2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)-2-carboxyethyl]amino}-2-oxoethyl)amino]-3-{[(2R)-2-amino-2-carboxyethyl]sulphanyl}-4-oxobutanoic acid/trifluoroacetic acid (1:1) and 4-[(2-{[(2R)-2-({(2S)-2-amino-4-[{(1R)-1-[1-benzyl-4-(2,5-difluorophenyl)-1H-pyrrol-2-yl]-2,2-dimethylpropyl}(glycoloyl)amino]butanoyl}amino)-2-carboxyethyl]amino}-2-oxoethyl)amino]-2-{[(2R)-2-amino-2-carboxyethyl]sulphanyl}-4-oxobutanoic acid/trifluoroacetic acid (1:1)

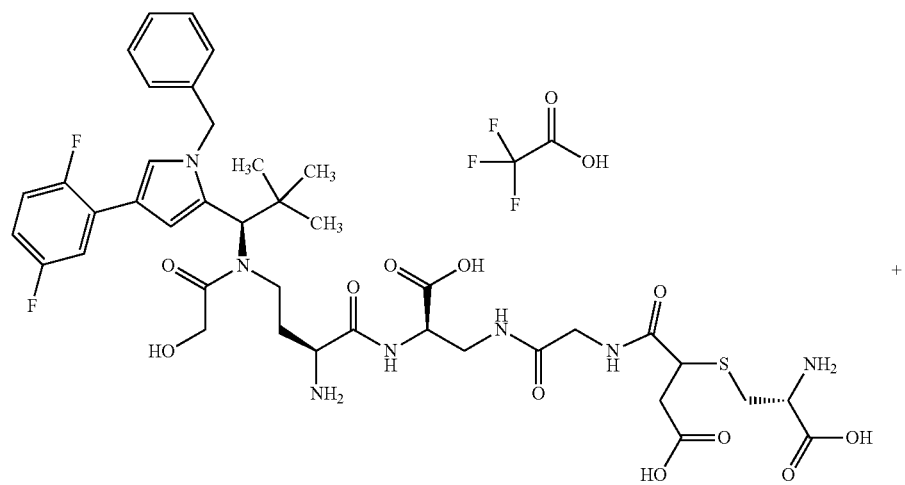

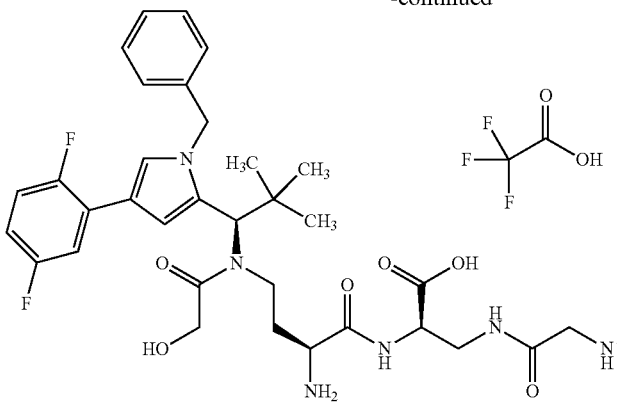

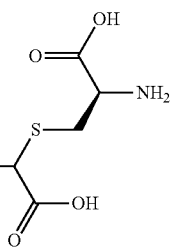

First, L-cysteine was converted with 1-({[2-(trimethylsilyl)ethoxy]carbonyl}oxy)pyrrolidine-2,5-dione in DMF in the presence of N,N'-diisopropylethylamine into N-{[2-(trimethylsilyl)ethoxy]carbonyl}-L-cysteine.

11 mg (0.013 mmol) of Intermediate F193 and 8 mg (0.016 mmol) of N-{[2-(trimethylsilyl) ethoxy]carbonyl}-L-cysteine were dissolved in 3 ml of DMF, and the mixture was stirred at RT for 20 h. The mixture was then concentrated and the residue was purified by preparative HPLC.

The appropriate fractions were combined and the solvents were evaporated under reduced pressure, and the residue was then dissolved in 2 ml of THF/water 1:1. 19 μl of a 2M aqueous lithium hydroxide solution were added and the reaction was stirred at RT for 1 h. Another 19 μl of the 2M aqueous lithium hydroxide solution were then added and the reaction was stirred at RT overnight. The mixture was then neutralized with a 1M hydrochloric acid, the solvent was evaporated under reduced pressure and the residue was purified by preparative HPLC. This gave 4.1 mg (38% of theory) of the regioisomeric protected intermediates as a colourless foam.

LC-MS (Method 1): $R_t$=1.03 min (breit); MS (ESIpos): m/z=1020 (M+H)$^+$.

In the last step, 4.1 mg (0.004 mmol) of this intermediate were dissolved in 3 ml of 2,2,2-trifluoroethanol. 3 mg (0.022 mmol) of zinc chloride were added, and the reaction was stirred at 50° C. for 1 h. 6 mg (0.022 mmol) of ethylenediamine-N,N,N',N'-tetraacetic acid and 2 ml of a 0.1% strength aqueous trifluoroacetic acid were then added, and the solvent was evaporated under reduced pressure. The residue was purified by preparative HPLC. Concentration of the appropriate fractions and lyophilization of the residue from acetonitrile/water gave 5 mg (quant.) of the title compound as a regioisomer mixture in a ratio of 20:80.

LC-MS (Method 1): $R_t$=0.78 min (breit); MS (ESIpos): m/z=876 (M+H)$^+$.

LC-MS (Method 5): $R_t$=2.36 min and 2.39 min; MS (ESIpos): m/z=876 (M+H)$^+$.

Example M4

S-(1-{2-[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethoxy]ethyl}-2,5-dioxopyrrolidin-3-yl)-L-cysteine/trifluoroacetic acid (1:1)

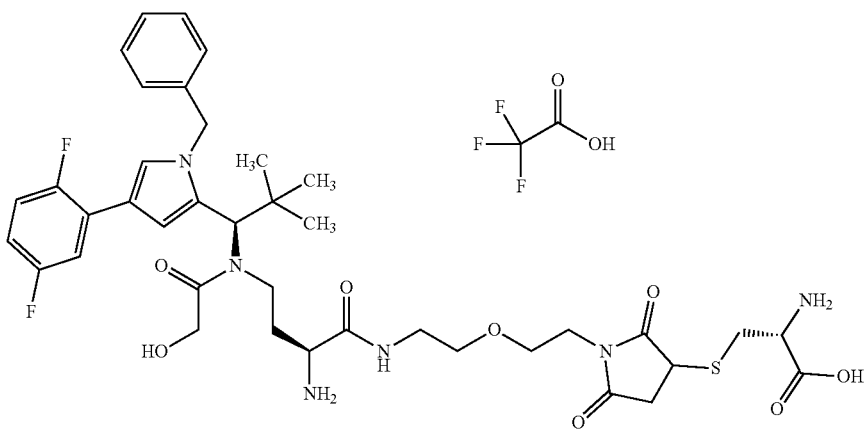 [SMILES: CC(C)(C)[C@H](c1cc(-c2cc(F)ccc2F)cn1Cc1ccccc1)N(CC[C@H](N)C(=O)NCCOCCN1C(=O)CC(SC[C@H](N)C(=O)O)C1=O)C(=O)CO ; O=C(O)C(F)(F)F]

3 mg (4 μmol) of Intermediate F248 were taken up in 2 ml of DMF, and 0.9 mg (8 μmol) of L-cysteine were added. The reaction mixture was stirred at RT for 18 h and then concentrated under reduced pressure. The residue was purified by preparative HPLC. The appropriate fractions were concentrated, giving, after lyophilization of the residue from acetonitrile/water, 1.1 mg (32% of theory) of the title compound as a white solid.

LC-MS (Method 1): $R_t$=0.78 min; MS (EIpos): m/z=801 [M+H]$^+$.

Example M5

(3R,7S)-7-Amino-17-{[(2R)-2-amino-2-carboxy-ethyl]sulphanyl}-3-[1-benzyl-4-(2,5-difluorophenyl)-1H-pyrrol-2-yl]-4-glycoloyl-2,2-dimethyl-8,16-dioxo-12-oxa-4,9,15-triazanonadecan-19-oic acid/ trifluoroacetic acid (1:1) and (3R,7S)-7-amino-18-{[(2R)-2-amino-2-carboxyethyl]sulphanyl}-3-[1-benzyl-4-(2,5-difluorophenyl)-1H-pyrrol-2-yl]-4-glycoloyl-2,2-dimethyl-8,16-dioxo-12-oxa-4,9,15-triazanonadecan-19-oic acid/trifluoroacetic acid (1:1)

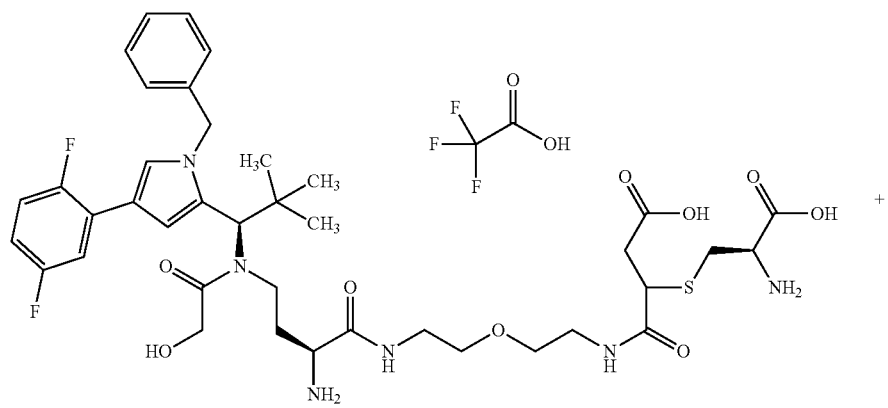

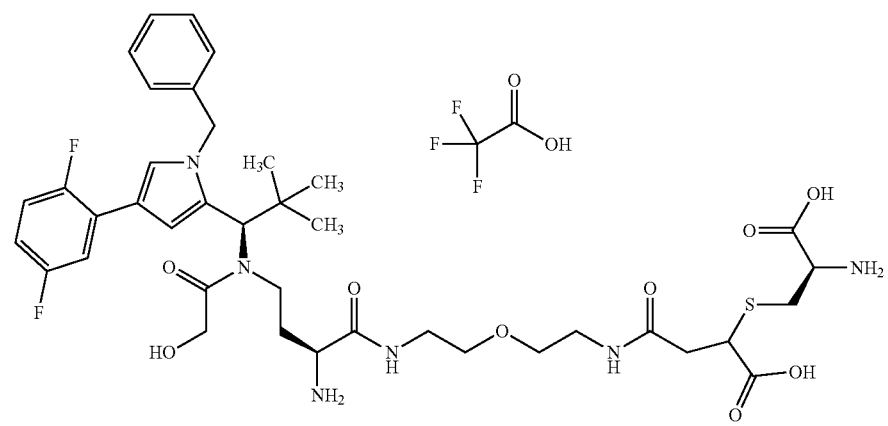

8 mg (0.010 mmol) of the protected intermediate of Intermediate F248 and 5.1 mg (0.02 mmol) of N-{[2-(trimethylsilyl)ethoxy]carbonyl}-L-cysteine were dissolved in 3 ml of DMF, and the mixture was stirred at RT for 18 h and then treated in an ultrasonic bath for 2 h. The mixture was then concentrated and the residue was purified by preparative HPLC. The appropriate fractions were combined and the solvents were evaporated under reduced pressure, and the residue was then dissolved in 2 ml of THF/water 1:1. 15 µl of a 2M aqueous lithium hydroxide solution were added and the reaction was stirred at RT for 15 min. The reaction was then adjusted to a pH of ~3 with a 1M hydrochloric acid, diluted with 20 ml of sodium chloride solution and extracted twice with 20 ml of ethyl acetate. The organic phase was dried over magnesium sulphate and concentrated, and the residue was lyophilized from acetonitrile/water. This gave 8.4 mg (78% of theory over 2 steps) of the regioisomeric protected intermediates as a colourless foam.

LC-MS (Method 1): $R_f$=1.44 min and 3.43 min; MS (ESIpos): m/z=1107 (M+H).

In the last step, 8 mg (0.007 mmol) of this intermediate were dissolved in 5 ml of 2,2,2-trifluoroethanol. 9.8 mg (0.072 mmol) of zinc chloride were added, and the reaction was stirred at 50° C. for 1.5 h. Ethylenediamine-N,N,N',N'-tetraacetic acid were then added, and the solvent was evaporated under reduced pressure. The residue was purified by preparative HPLC. Concentration of the appropriate fractions and lyophilization of the residue from acetonitrile/water gave 4 mg (59% of theory) of the title compound as a regioisomer mixture in a ratio of 31:67.

LC-MS (Method 1): $R_f$=0.79 min and 0.81 min; MS (ESIpos): m/z=819 (M+H)$^+$.

Example M6

2-{[(2R)-2-Amino-2-carboxyethyl]sulphanyl}-4-({(14R)-13-(3-aminopropyl)-14-[1-benzyl-4-(2,5-difluorophenyl)-1H-pyrrol-2-yl]-15,15-dimethyl-2,7,12-trioxo-10-thia-3,6,13-triazahexadec-1-yl}amino)-4-oxobutanoic acid/trifluoroacetic acid (1:2) and 3-{[(2R)-2-amino-2-carboxyethyl]sulphanyl}-4-({(14R)-13-(3-aminopropyl)-14-[1-benzyl-4-(2,5-difluorophenyl)-1H-pyrrol-2-yl]-15,15-dimethyl-2,7,12-trioxo-10-thia-3,6,13-triazahexadec-1-yl}amino)-4-oxobutanoic acid/trifluoroacetic acid (1:2)

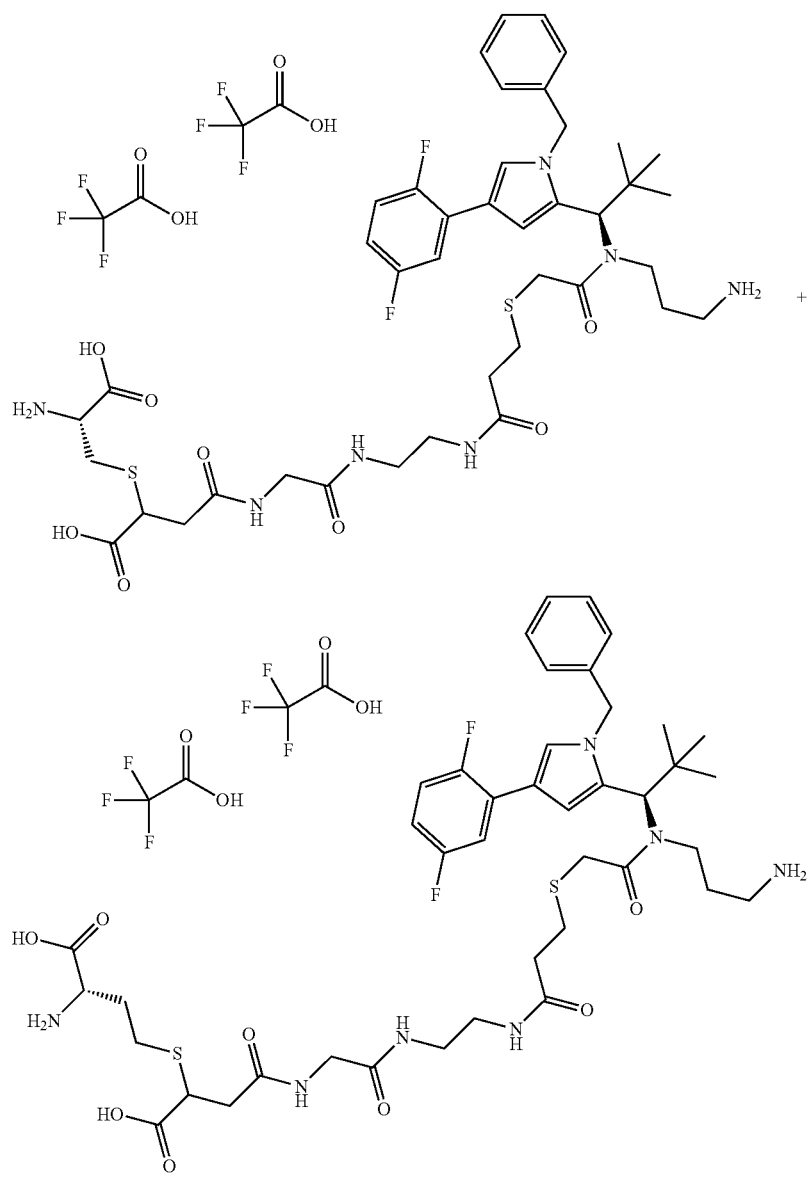

18 mg (0.021 mmol) of Intermediate F213 and 11.2 mg (0.04 mmol) of N-{[2-(trimethylsilyl) ethoxy]carbonyl}-L-cysteine were dissolved in 2 ml of DMF, and the mixture was stirred at RT for 18 h. The reaction mixture was concentrated under reduced pressure. The residue (21.2 mg) was dissolved in 3 ml of THF/water 1:1. 0.04 ml of a 2M aqueous lithium hydroxide solution were added and the reaction was stirred at RT for 3 hours. 0.02 ml of a 2M aqueous lithium hydroxide solution were added and the reaction was stirred at RT for 1 hour. The reaction was then adjusted to a pH of ~7 using 7.2 mg (0.12 mmol) of acetic acid. The reaction mixture was purified directly by preparative RP-HPLC (column: Reprosil 125×30; 10μ, flow rate: 50 ml/min, MeCN/water; 0.1% TFA). The solvents were evaporated under reduced pressure and the residue was dried under high vacuum. This gave 13 mg (57% over 2 steps) of the regioisomeric protected intermediates.

LC-MS (Method 1): $R_t$=1.03 min; MS (ESIpos): m/z=1020 (M+H)$^+$.

In the last step, 13 mg (0.01 mmol) of this intermediate were dissolved in 2 ml of 2,2,2-trifluoroethanol. 6.2 mg (0.05 mmol) of zinc chloride were added, and the reaction was stirred at 50° C. for 7 h. 13.3 mg (0.05 mmol) of ethylenediamine-N,N,N',N'-tetraacetic acid were then added, and the product was purified by preparative HPLC. Concentration of the appropriate fractions and lyophilization of the residue from acetonitrile/water gave 10.3 mg (81.4%) of the title compound as a regioisomer mixture.

LC-MS (Method 1): $R_t$=1.03 min; MS (ESIpos): m/z=875 (M+H)$^+$.

Example M7

S-(2-{[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)-L-cysteine/trifluoroacetic acid (1:1)

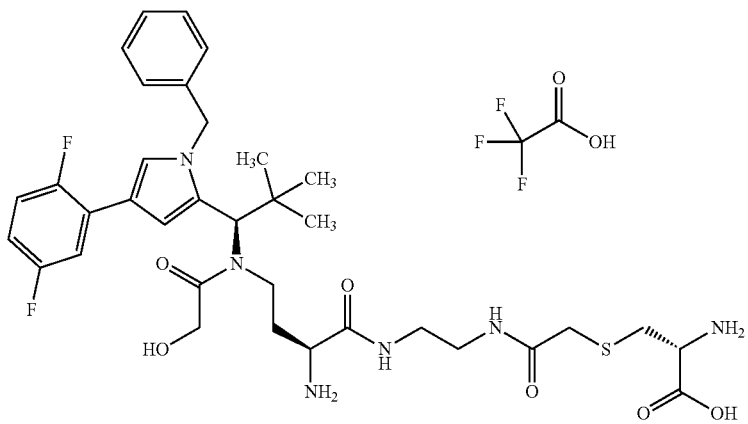 [SMILES: CC(C)(C)[C@H](c1cc(-c2cc(F)ccc2F)cn1Cc1ccccc1)N(CC[C@H](N)C(=O)NCCNC(=O)CSC[C@H](N)C(=O)O)C(=O)CO ; O=C(O)C(F)(F)F]

6 mg (8 μmol) of Intermediate F119 were taken up in 3 ml of DMF, and 1.8 mg (15 μmol) of L-cysteine were added. The reaction mixture was stirred at RT for 6 h and then allowed to stand at RT for 3 days. The reaction was then concentrated under reduced pressure, and the product was purified by preparative HPLC.

LC-MS (Method 1): $R_t$=0.81 min; MS (ESIpos): m/z=717 (M+H)$^+$.

Example M8

(3R)-6-{(11S,15R)-11-Amino-15-[1-benzyl-4-(2,5-difluorophenyl)-1H-pyrrol-2-yl]-14-glycoloyl-16,16-dimethyl-2,5,10-trioxo-3,6,9,14-tetraazaheptadec-1-yl}-5-oxothiomorpholine-3-carboxylic acid/trifluoroacetic acid (1:1)

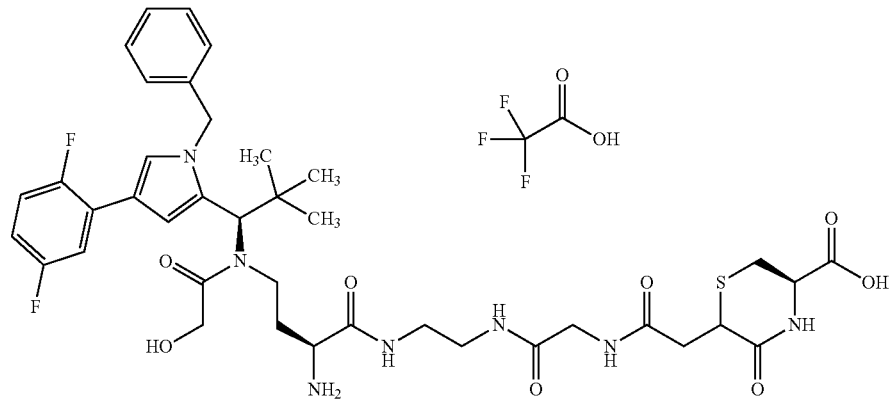

4 mg (0.004 mmol) of the compound from Example 135 were dissolved in 4 ml of THF/water, and 48 μl of a 2-molar aqueous lithium hydroxide solution were added. The reaction was stirred at RT for 1 h and then concentrated and purified by preparative HPLC. Combination, concentration and lyophilization of the appropriate fractions from acetonitrile/water gave 2.4 mg (60% of theory) of the title compound.

LC-MS (Method 1): $R_t$=0.86 min; MS (EIpos): m/z=814 $[M+H]^+$.

Example M9

N-(3-Aminopropyl)-N-{(1R)-1-[1-benzyl-4-(2,5-difluorophenyl)-1H-pyrrol-2-yl]-2,2-dimethylpropyl}-2-hydroxyacetamide

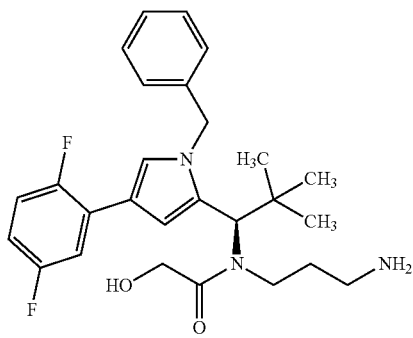 [SMILES: CC(C)(C)[C@H](c1cc(-c2cc(F)ccc2F)cn1Cc1ccccc1)N(CCCN)C(=O)CO]

150.0 mg (0.42 mmol) of (1R)-1-[1-benzyl-4-(2,5-difluorophenyl)-1H-pyrrol-2-yl]-2,2-dimethylpropan-1-amine (Intermediate C52) were initially charged in 2.0 ml of dichloromethane, and 29.2 mg (0.49 mmol) of HOAc and 125.6 mg (0.59 mmol) of sodium triacetoxyborohydride were added and the mixture was stirred at RT for 5 min. 98.9 mg (0.49 mmol) of 3-(1,3-dioxo-1,3-dihydro-2H-isoindol-2-yl)propanal were added. The reaction mixture was stirred at RT overnight. The reaction mixture was diluted with ethyl acetate and the organic phase was washed twice with saturated sodium carbonate solution and once with saturated NaCl solution. After drying over magnesium sulphate, the solvent was evaporated under reduced pressure and the residue was purified on silica gel (mobile phase: dichloromethane/methanol 100:1). The solvents were evaporated under reduced pressure and the residue was dried under high vacuum. This gave 188.6 mg (74%) of the compound 2-[3-({(1R)-1-[1-benzyl-4-(2,5-difluorophenyl)-1H-pyrrol-2-yl]-2,2-dimethylpropyl}amino)propyl]-1H-isoindole-1,3(2H)-dione.

LC-MS (Method 1): $R_t$=1.00 min; MS (ESIpos): m/z=541 $[M+H]^+$.

171.2 mg (0.32 mmol) of 2-[3-({(1R)-1-[1-benzyl-4-(2,5-difluorophenyl)-1H-pyrrol-2-yl]-2,2-dimethylpropyl}amino)propyl]-1H-isoindole-1,3(2H)-dione were initially charged in 5.0 ml of dichloromethane, and 73.6 mg (0.73 mmol) of triethylamine were added. At 0° C. 94.9 mg (0.70 mmol) of acetoxyacetyl chloride were added, and the reaction mixture was stirred at RT overnight. The reaction mixture was diluted with ethyl acetate and the organic phase was washed twice with saturated sodium bicarbonate solution and once with sat. NaCl solution. After drying over magnesium sulphate, the solvent was evaporated under reduced pressure and the residue was purified using Biotage Isolera (silica gel, column 10 g SNAP, flow rate 12 ml/min, ethyl acetate/cyclohexane 1:3). The solvents were evaporated under reduced pressure and the residue was dried under high vacuum. This gave 159.0 mg (77%) of the compound 2-({(1R)-1-[1-benzyl-4-(2,5-difluorophenyl)-1H-pyrrol-2-yl]-2,2-dimethylpropyl}[3-(1,3-dioxo-1,3-dihydro-2H-isoindol-2-yl)propyl]amino)-2-oxoethyl acetate.

LC-MS (Method 1): $R_t$=1.35 min; MS (ESIpos): m/z=642 $[M+H]^+$.

147.2 mg (0.23 mmol) of 2-({(1R)-1-[1-benzyl-4-(2,5-difluorophenyl)-1H-pyrrol-2-yl]-2,2-dimethylpropyl}[3-(1,3-dioxo-1,3-dihydro-2H-isoindol-2-yl)propyl]amino)-2-oxoethyl acetate were initially charged in 4.0 ml of ethanol, and 356.2 mg (4.59 mmol) of methanamine (40% in water) were added. The reaction mixture was stirred at 50° C. overnight. The solvent was evaporated under reduced pressure and the residue co-distilled three times with toluene. The residue was purified on silica gel (mobile phase: dichloromethane/methanol=10:1). The solvents were evaporated under reduced pressure and the residue was dried under high vacuum. This gave 67.4 mg (63%) of the title compound.

LC-MS (Method 1): Rt=0.91 min; MS (ESIpos): m/z=470 $[M+H]^+$.

Example M10

(2R,28R)-28-Amino-2-[({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)methyl]-25-(carboxymethyl)-4,20,24-trioxo-7,10,13,16-tetraoxa-26-thia-3,19,23-triazanonacosan-1,29-dioic acid/trifluoroacetic acid (1:2) and (1R,28R,34R)-1-amino-33-(3-aminopropyl)-34-[1-benzyl-4-(2,5-difluorophenyl)-1H-pyrrol-2-yl]-35,35-dimethyl-6,10,26,32-tetraoxo-14,17,20,23-tetraoxa-3,30-dithia-7,11,27,33-tetraazahexatriacontane-1,4,28-tricarboxylic acid/trifluoroacetic acid (1:2)

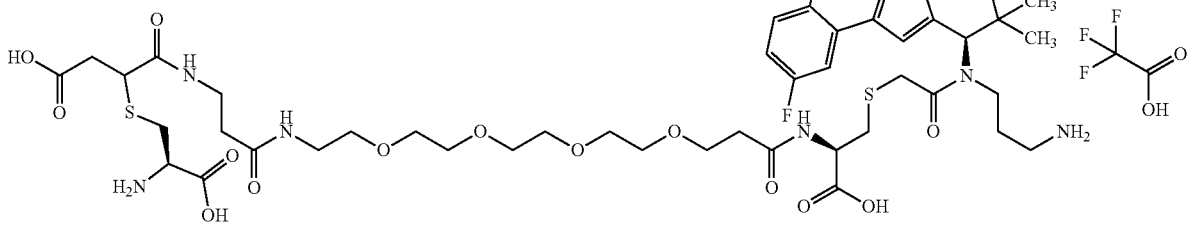

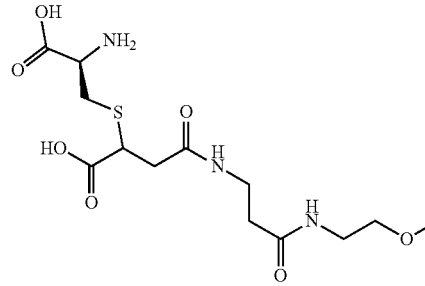
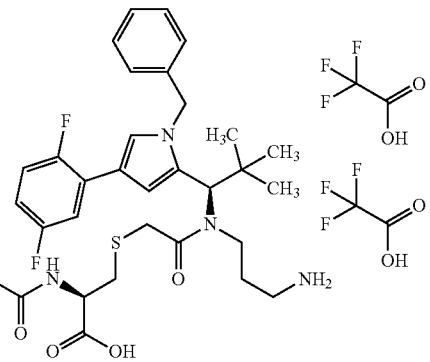

20 mg (0.018 mmol) of R-{2-[(3-aminopropyl){(1R)-1-[1-benzyl-4-(2,5-difluorophenyl)-1H-pyrrol-2-yl]-2,2-dimethylpropyl}amino]-2-oxoethyl}-N-[19-(2,5-dioxo-2,5-dihydro-1H-pyrrol-1-yl)-17-oxo-4,7,10,13-tetraoxa-16-azanonadecan-1-oyl]-L-cysteine/trifluoroacetic acid (1:1) (Intermediate F209) and 9.78 mg (0.036 mmol) of N-{[2-(trimethylsilyl)ethoxy]carbonyl}-L-cysteine were dissolved in 2 ml of DMF, and the mixture was stirred at RT for 18 h. The reaction mixture was concentrated under reduced pressure. The residue (47.7 mg) was dissolved in 3 ml of THF/water 1:1. 0.08 ml of a 2M aqueous lithium hydroxide solution were added and the reaction was stirred at RT for 1 hour. The reaction was then adjusted to a pH of ~7 using 9.26 mg (0.15 mmol) of acetic acid. The reaction mixture was purified directly by preparative RP-HPLC (column: Reprosil 125×30; 10μ, flow rate: 50 ml/min, MeCN/water; 0.1% TFA). The solvents were evaporated under reduced pressure and the residue was dried under high vacuum. This gave 15.3 mg (29% over 2 steps) of the regioisomeric protected intermediates.

LC-MS (Method 6): $R_t$=12.26 min and 12.30 min; MS (ESIpos): m/z=1254 (M+H)$^+$.

In the last step, 15.3 mg (0.01 mmol) of this intermediate were dissolved in 2 ml of 2,2,2-trifluoroethanol. 6.1 mg (0.05 mmol) of zinc chloride were added, and the reaction was stirred at 50° C. for 2 h. 13.1 mg (0.05 mmol) of ethylenediamine-N,N,N',N'-tetraacetic acid were then added, and the product was purified by preparative HPLC. Concentration of the appropriate fractions and lyophilization of the residue from acetonitrile/water gave 11.9 mg (79.5%) of the title compound as a regioisomer mixture.

LC-MS (Method 1): $R_t$=0.85 min; MS (ESIpos): m/z=1110 (M+H)$^+$.

Example M11

S-{2-[(3-Aminopropyl){(1R)-1-[1-benzyl-4-(2,5-difluorophenyl)-1H-pyrrol-2-yl]-2,2-dimethylpropyl}amino]-2-oxoethyl}-L-cysteine/trifluoroacetic acid (1:2)

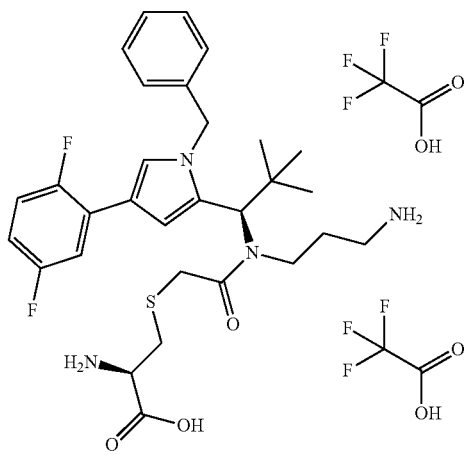 [SMILES: CC(C)(C)[C@H](c1cc(-c2cc(F)ccc2F)cn1Cc1ccccc1)N(CCCN)C(=O)CSC[C@H](N)C(=O)O ; O=C(O)C(F)(F)F ; O=C(O)C(F)(F)F]

15.0 mg (0.018 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-L-cysteine/trifluoroacetic acid (1:1) (Intermediate C71) were dissolved in 1.0 ml of trifluoroethanol, and 7.4 mg (0.054 mmol) of zinc dichloride were added. The reaction mixture was stirred at 50° C. overnight. 15.8 mg (0.054 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125× 30; 10μ, flow rate: 50 ml/min, MeCN/water, 0.1% TFA). The solvents were evaporated under reduced pressure and the residue was dried under high vacuum. This gave 11.1 mg (77%) of the title compound.

LC-MS (Method 1): $R_t$=0.83 min; MS (ESIpos): m/z=573 (M+H)$^+$.

Example M12

4-{[(1R)-2-({2-[(3-Aminopropyl) {(1R)-1-[1-ben-zyl-4-(2,5-difluorophenyl)-1H-pyrrol-2-yl]-2,2-dimethylpropyl}amino]-2-oxoethyl}sulphanyl)-1-carboxyethyl]amino}-4-oxobutanoic acid/trifluoroacetic acid (1:1)

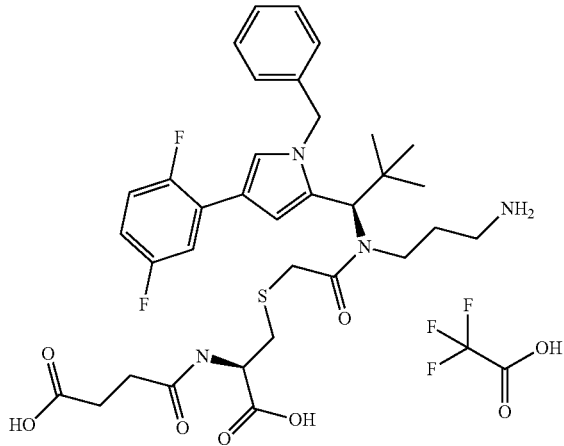 [SMILES: CC(C)(C)[C@H](c1cc(-c2cc(F)ccc2F)cn1Cc1ccccc1)N(CCCN)C(=O)CSC[C@H](NC(=O)CCC(=O)O)C(=O)O ; O=C(O)C(F)(F)F]

12.2 mg (0.014 mmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-(4-tert-butoxy-4-oxobutanoyl)-L-cysteine (Intermediate C77) were dissolved in 2.0 ml of trifluoroethanol, and 11.4 mg (0.084 mmol) of zinc dichloride were added. The reaction mixture was stirred at 50° C. for 3 h. 24.5 mg (0.084 mmol) of ethylenediamine-N,N,N',N'-tetraacetic acid were added, the reaction mixture was stirred for 10 min and water (0.1% TFA) was then added. Purification was carried out directly by preparative RP-HPLC (column: Reprosil 125×30; 10μ, flow rate: 50 ml/min, MeCN/water, 0.1% TFA). The solvents were evaporated under reduced pressure and the residue was dried under high vacuum. This gave 4.6 mg (42%) of the title compound.

LC-MS (Method 1): $R_t$=0.88 min; MS (ESIpos): m/z=673 (M+H)$^+$.

Example M13

4-[(2-{[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-2-{[(2R)-2-amino-2-carboxyethyl]sulphanyl}-4-oxobutanoic acid/trifluoroacetic acid (1:1) Regioisomer 1, Epimer 1 (2R) or (2S)

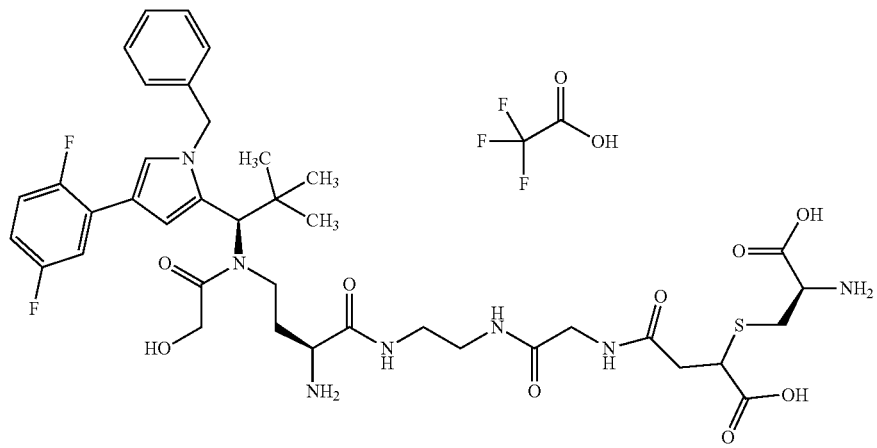 [SMILES: CC(C)(C)[C@H](c1cc(-c2cc(F)ccc2F)cn1Cc1ccccc1)N(CC[C@H](N)C(=O)NCCNC(=O)CNC(=O)CC(SC[C@H](N)C(=O)O)C(=O)O)C(=O)CO ; O=C(O)C(F)(F)F]

LC-MS (Method 5): $R_t$=2.44 min; MS (ESIpos): m/z=832 [M+H]$^+$.

First, methyl L-cysteinate hydrochloride (1:1) was converted with 1-({[2-(trimethylsilyl)ethoxy]carbonyl}oxy)pyrrolidine-2,5-dione in DMF in the presence of N,N-diisopropylethylamine into methyl N-{[2-(trimethylsilyl)ethoxy]carbonyl}-L-cysteinate. 408 mg (1.93 mmol) of commercially available 3-bromo-4-methoxy-4-oxobutanoic acid and 180 mg (0.644 mmol) of methyl N-{[2-(trimethylsilyl)ethoxy]carbonyl}-L-cysteinate were dissolved in 8 ml of DMF, and 147 mg (0.97 mmol) of 1,8-diazabicyclo[5.4.0]undec-7-ene were added. After 18 h of stirring at RT, another 136 mg (0.64 mmol) of 3-bromo-4-methoxy-4-oxobutanoic acid and 147 mg (0.97 mmol) of 1,8-diazabicyclo[5.4.0]undec-7-ene were added, and the mixture was stirred at RT for a further 12 h and then concentrated under reduced pressure. The residue was purified by preparative HPLC. Combination of the appropriate fractions and evaporation of the solvents under reduced pressure gave 151 mg (57% of theory) of 4-methoxy-3-{[(2R)-3-methoxy-3-oxo-2-({[2-(trimethylsilyl)ethoxy]carbonyl}amino)propyl]sulphanyl}-4-oxobutanoic acid.

LC-MS (Method 12): $R_t$=1.74 min; MS (ESIneg): m/z=408 (M–H)$^-$.

Of this intermediate, 145 mg were separated by supercritical fluid chromatography via chiral columns into the individual diastereomers (SFC; column: DAICEL, AD-H 5u 250×20 mm; flow rate: 80 ml/min; method: AD-25% ETOH-80 ml; pressure: 100 bar; wavelength: 210 nM), giving 63 mg (43%) of Epimer 1 and 58 mg (40%) of Epimer 2.

Epimer 1 was characterized as follows:
LC-MS (Method 5): $R_t$=2.94 min; MS (ESIneg): m/z=408 (M–H)$^-$.
$^1$H-NMR: (400 MHz, DMSO-d$_6$): δ=7.57 (d, 1H), 4.24 (m, 1H), 4.05 (t, 2H), 3.67 (t, 1H), 3.65 (s, 3H), 3.62 (s, 3H), 3.05 (dd, 1H), 2.70-2.88 (m, 2H), 2.59 (dd, 1H), 0.93 (t, 2H), 0.02 (s, 9H).

Epimer 2 was characterized as follows:
LC-MS (Method 5): $R_t$=2.95 min; MS (ESIneg): m/z=408 (M–H)$^-$.
$^1$H-NMR: (400 MHz, DMSO-d$_6$): δ=7.58 (d, 1H), 4.16-4.23 (m, 1H), 4.05 (t, 2H), 3.67 (dd, 1H), 3.65 (s, 3H), 3.64 (s, 3H), 3.04 (dd, 1H), 2.88 (dd, 1H), 2.77 (dd, 1H), 2.61 (dd, 1H), 0.92 (t, 2H), 0.02 (s, 9H).

32.5 mg (0.079 mmol) of Epimer 1 were coupled in the presence of 30 mg (0.079 mmol) of HATU and 13.4 mg (0.132 mmol) of 4-methylmorpholine with 50 mg (0.066 mmol) of Intermediate C66, giving, after HPLC purification, 43 mg (57% of theory) of the fully protected intermediate methyl 4-{[(8S)-8-{2-[{(1R)-1-[1-benzyl-4-(2,5-difluorophenyl)-1H-pyrrol-2-yl]-2,2-dimethylpropyl}(glycoloyl)amino]ethyl}-2,2-dimethyl-6,9,14-trioxo-5-oxa-7,10,13-triaza-2-silapentadecan-15-yl]amino}-2-{[(2R)-3-methoxy-3-oxo-2-({[2-(trimethylsilyl)ethoxy]carbonyl}amino)propyl]sulphanyl}-4-oxobutanoate. 40 mg (0.035 mmol) of this intermediate were then stirred at RT with 0.9 ml of a 2-molar lithium hydroxide solution in 11 ml of methanol for 20 min, resulting in the cleavage of both methyl ester groups. Purification by HPLC gave 12 mg (31% of theory) of the dicarboxylic acid derivative.

LC-MS (Method 5): $R_t$=4.74 min; MS (ESIpos): m/z=1120 [M+H]$^+$.

Finally, 10 mg (0.009 mmol) of this intermediate were completely deprotected with zinc chloride in trifluoroethanol as described above. The residue was purified by preparative HPLC. Concentration of the appropriate fractions and lyophilization of the residue from acetonitrile/water gave 2.6 mg (30% of theory) of the title compound.

LC-MS (Method 5): $R_t$=2.44 min; MS (ESIpos): m/z=832 [M+H]$^+$.

Example M14

4-[(2-{[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-2-{[(2R)-2-amino-2-carboxyethyl]sulphanyl}-4-oxobutanoic acid/trifluoroacetic acid (1:1) Regioisomer 1, Epimer 2 (2R or 2S)

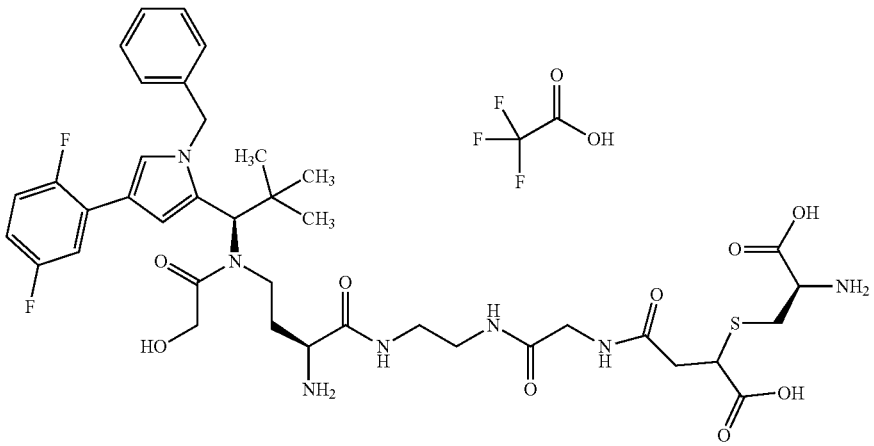 [SMILES: CC(C)(C)[C@H](c1cc(-c2cc(F)ccc2F)cn1Cc1ccccc1)N(CC[C@H](N)C(=O)NCCNC(=O)CNC(=O)CC(SC[C@H](N)C(=O)O)C(=O)O)C(=O)CO ; O=C(O)C(F)(F)F]

LC-MS (Method 5): $R_t$=2.44 min; MS (EIpos): m/z=832 [M+H]$^+$.

The intermediate Epimer 2 described in Example M13 was reacted analogously to the description in Example M13:

32.5 mg (0.079 mmol) of Epimer 2 were coupled in the presence of 30 mg (0.079 mmol) of HATU and 13.4 mg (0.132 mmol) of 4-methylmorpholine with 50 mg (0.066 mmol) of Intermediate C66, giving, after HPLC purification, 43 mg (57% of theory) of the fully protected intermediate methyl 4-{[(8S)-8-{2-[{(1R)-1-[1-benzyl-4-(2,5-difluorophenyl)-1H-pyrrol-2-yl]-2,2-dimethylpropyl}(glycoloyl)amino]ethyl}-2,2-dimethyl-6,9,14-trioxo-5-oxa-7,10,13-triaza-2-silapentadecan-15-yl]amino}-2-{[(2R)-3-methoxy-3-oxo-2-({[2-(trimethylsilyl)ethoxy]carbonyl}amino)propyl]sulphanyl}-4-oxobutanoate.

40 mg (0.035 mmol) of this intermediate were then stirred at RT with 0.9 ml of a 2-molar lithium hydroxide solution in 11 ml of methanol for 20 min, resulting in the cleavage of both methyl ester groups. Purification by HPLC gave 11 mg (28% of theory) of the dicarboxylic acid derivative.

LC-MS (Method 5): $R_t$=4.74 min; MS (ESIpos): m/z=1120 [M+H]$^+$.

Finally, 10 mg (0.009 mmol) of this intermediate were completely deprotected with zinc chloride in trifluoroethanol as described above. The residue was purified by preparative HPLC. Concentration of the appropriate fractions and lyophilization of the residue from acetonitrile/water gave 4.4 mg (52% of theory) of the title compound.

LC-MS (Method 5): $R_t$=2.44 min; MS (ESIpos): m/z=832 [M+H]$^+$.

Example M15

4-[(2-{[2-({(2S)-2-Amino-4-[{(1R)-1-[1-benzyl-4-(2,5-difluorophenyl)-1H-pyrrol-2-yl]-2,2-dimethyl-propyl}(glycoloyl)amino]butanoyl}amino)ethyl]amino}-2-oxoethyl)amino]-3-{[(2R)-2-amino-2-carboxyethyl]sulphanyl}-4-oxobutanoic acid/ trifluoroacetic acid (1.1) Regioisomer 2, Epimer 1 (3R or 3S)

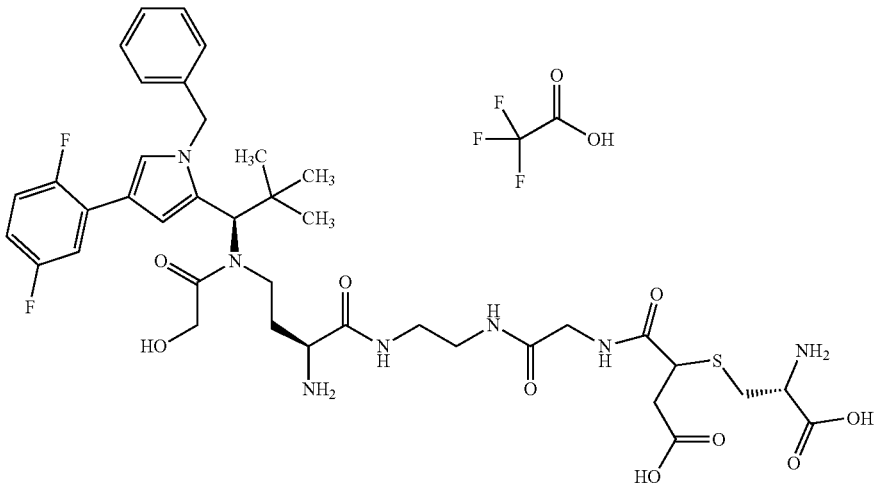 [SMILES: CC(C)(C)[C@H](c1cc(-c2cc(F)ccc2F)cn1Cc1ccccc1)N(CC[C@H](N)C(=O)NCCNC(=O)CNC(=O)C(CC(=O)O)SC[C@H](N)C(=O)O)C(=O)CO ; O=C(O)C(F)(F)F]

742.8 mg (3.3 mmol) of commercially available 2-bromo-4-ethoxy-4-oxobutanoic acid and 802 mg (2.87 mmol) of methyl N-{[2-(trimethylsilyl)ethoxy]carbonyl}-L-cysteinate were dissolved in 32 ml of DMF, and 655.4 mg (4.31 mmol) of 1,8-diazabicyclo[5.4.0]undec-7-ene were added. After 20 h of stirring at RT, the reaction was concentrated under reduced pressure and the residue was purified by preparative HPLC. Combination of the appropriate fractions and evaporation of the solvents under reduced pressure gave 521 mg (43% of theory) of 4-ethoxy-2-{[(2R)-3-methoxy-3-oxo-2-({[2-(trimethylsilyl)ethoxy]carbonyl}amino)propyl]sulphanyl}-4-oxobutanoic acid.

LC-MS (Method 5): $R_t$=3.13 min; MS (ESIpos): m/z=424 (M+H)$^+$.

Of this intermediate, 510 mg were separated by supercritical fluid chromatography via chiral columns into the individual diastereomers (SFC; column: DAICEL, AD-H 5u 250×20 mm; flow rate: 80 ml/min; method: AD-10% ETOH-80 ml; pressure: 100 bar; wavelength: 210 nM), giving 100 mg (20%) of Epimer 1 and 141 mg (28%) of Epimer 2.

Epimer 1 was characterized as follows:
LC-MS (Method 1): $R_t$=0.99 min; MS (ESIneg): m/z=422 (M–H)$^-$.

$^1$H-NMR: (400 MHz, DMSO-ds): δ=7.60 (d, 1H), 4.18-4.26 (m, 1H), 4.01-4.08 (m, 4H), 3.63 (s, 3H), 3.59 (dd, 1H), 3.04 (dd, 1H), 2.92 (dd, 1H), 2.80 (dd, 1H), 2.63 (dd, 1H), 1.17 (t, 3H), 0.92 (t, 2H), 0.02 (s, 9H).

Epimer 2 was characterized as follows:
LC-MS (Method 5): $R_t$=2.95 min; MS (ESIneg): m/z=408 (M–H)$^-$.

LC-MS (Method 5): $R_t$=2.45 min; MS (EIpos): m/z=832 [M+H]$^+$.

$^1$H-NMR: (400 MHz, DMSO-d$_6$): δ=7.56 (d, 1H), 4.21-4.29 (m, 1H), 4.01-4.1 (m, 4H), 3.64 (s, 3H), 3.58 (dd, 1H), 3.08 (dd, 1H), 2.85 (dd, 1H), 2.78 (dd, 1H), 2.60 (dd, 1H), 1.17 (t, 3H), 0.93 (t, 2H), 0.02 (s, 9H). 33.6 mg (0.079 mmol) of Epimer 1 were coupled in the presence of 30 mg (0.079 mmol) of HATU and 13.4 mg (0.132 mmol) of 4-methylmorpholine with 50 mg (0.066 mmol) of Intermediate C66, giving, after HPLC purification, 51 mg (63% of theory) of the fully protected intermediate ethyl 4-{[(8S)-8-{2-[{(1R)-1-[1-benzyl-4-(2,5-difluorophenyl)-1H-pyrrol-2-yl]-2,2-dimethyl-propyl}(glycoloyl)amino]ethyl}-2,2-dimethyl-6,9,14-trioxo-5-oxa-7,10,13-triaza-2-silapentadecan-15-yl]amino}-3-{[(2R)-3-methoxy-3-oxo-2-({[2-(trimethylsilyl)ethoxy]carbonyl}amino)propyl]sulphanyl}-4-oxobutanoate. 49 mg (0.042 mmol) of this intermediate were then stirred at RT with 0.5 ml of a 2-molar lithium hydroxide solution in 12 ml of THF/water 1:1 for 30 min, resulting in the cleavage of both methyl ester groups. Acidification and purification by HPLC gave 11 mg (24% of theory) of the dicarboxylic acid derivative.

LC-MS (Method 5): $R_t$=4.68 min; MS (ESIpos): m/z=1120 [M+H]$^+$.

Finally, 11 mg (0.01 mmol) of this intermediate were completely deprotected with zinc chloride in trifluoroethanol as described above. The residue was purified by preparative HPLC. Concentration of the appropriate fractions and lyophilization of the residue from acetonitrile/water gave 3.7 mg (39% of theory) of the title compound.

LC-MS (Method 5): $R_t$=2.45 min; MS (ESIpos): m/z=832 [M+H]$^+$.

Example M16

4-[(2-{[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]amino}-2-oxoethyl)amino]-3-{[(2R)-2-amino-2-carboxyethyl]sulphanyl}-4-oxobutanoic acid/trifluoroacetic acid (1:1) Regioisomer 2, Epimer 2 (3R or 3S)

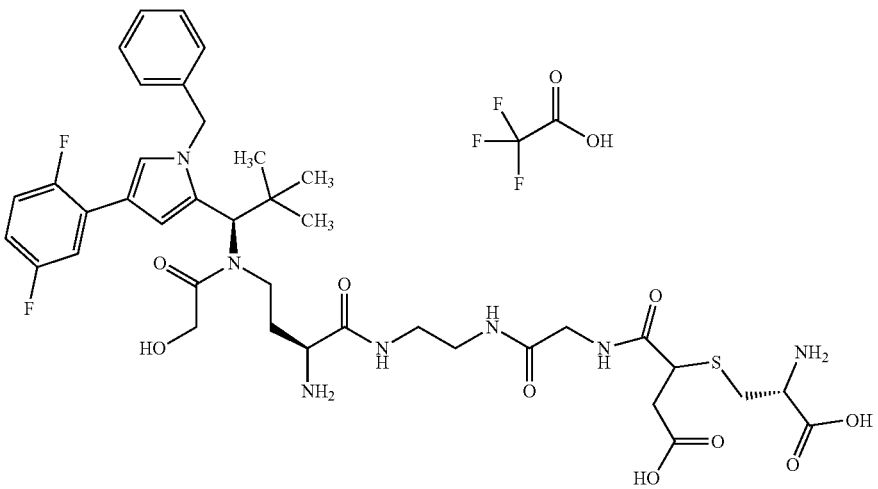 [SMILES: CC(C)(C)[C@H](c1cc(-c2cc(F)ccc2F)cn1Cc1ccccc1)N(CC[C@H](N)C(=O)NCCNC(=O)CNC(=O)C(CC(=O)O)SC[C@H](N)C(=O)O)C(=O)CO ; O=C(O)C(F)(F)F]

LC-MS (Method 5): $R_t$=2.44 min; MS (EIpos): m/z=832 [M+H]⁺.

The intermediate Epimer 2 described in Example M15 was reacted analogously to the description in Example M15:

33.6 mg (0.079 mmol) of Epimer 2 were coupled in the presence of 30 mg (0.079 mmol) of HATU and 13.4 mg (0.132 mmol) of 4-methylmorpholine with 50 mg (0.066 mmol) of Intermediate C66, giving, after HPLC purification, 51 mg (63% of theory) of the folly protected intermediate ethyl 4-{[(8S)-8-{2-[{(1R)-1-[1-benzyl-4-(2,5-difluorophenyl)-1H-pyrrol-2-yl]-2,2-dimethylpropyl}(glycoloyl)amino]ethyl}-2,2-dimethyl-6,9,14-trioxo-5-oxa-7,10,13-triaza-2-silapentadecan-15-yl]amino}-3-{[(2R)-3-methoxy-3-oxo-2-({[2-(trimethylsilyl)ethoxy]carbonyl}amino)propyl]sulphanyl}-4-oxobutanoate. 49 mg (0.042 mmol) of this intermediate were then stirred at RT with 0.5 ml of a 2-molar lithium hydroxide solution in 12 ml of THF/water 1:1 for 30 min, resulting in the cleavage of both methyl ester groups. Acidification and purification by HPLC gave 13.4 mg (28% of theory) of the dicarboxylic acid derivative.

LC-MS (Method 5): $R_t$=4.66 min; MS (ESIpos): m/z=1120 [M+H]⁺.

Finally, 13.4 mg (0.012 mmol) of this intermediate were completely deprotected with zinc chloride in trifluoroethanol as described above. The residue was purified by preparative HPLC. Concentration of the appropriate fractions and lyophilization of the residue from acetonitrile/water gave 7.5 mg (66% of theory) of the title compound.

LC-MS (Method 5): $R_t$=2.44 min; MS (ESIpos): m/z=832 [M+H]⁺.

Example M17

(2S)-2-Amino-4-[{(1R)-1-[1-benzyl-4-(2,5-difluorophenyl)-1H-pyrrol-2-yl]-2,2-dimethylpropyl}(glycoloyl)amino]butanoic acid hydrochloride (1.1)

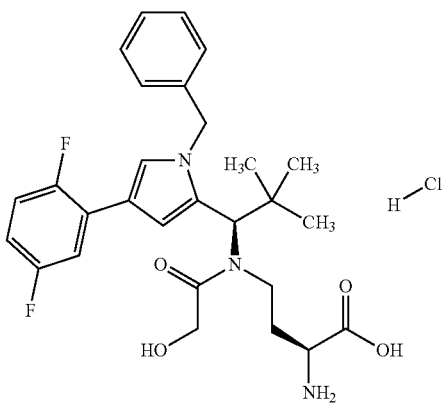 [SMILES: CC(C)(C)[C@H](c1cc(-c2cc(F)ccc2F)cn1Cc1ccccc1)N(CC[C@H](N)C(=O)O)C(=O)CO ; Cl]

150 mg (0.2 mmol) of Intermediate C53 were dissolved in 15 ml of DMF, and 2.29 g (20.39 mmol) of DABCO. The reaction was treated in an ultrasonic bath for 30 min. By addition of 1.17 ml of acetic acid, the reaction was then adjusted to pH 3-4, and the mixture was concentrated under reduced pressure. The residue was purified by preparative HPLC and the appropriate fractions were concentrated at RT under reduced pressure. The residue was taken up in acetonitrile/water (1:1), 5 ml of a 4N hydrochloric acid were added and the mixture was then lyophilized. This gave 81 mg (68% of theory) of the title compound.

LC-MS (Method 5): $R_t$=2.69 min; MS (EIpos): m/z=514 [M+H]⁺.

Example M18

N-[2-({(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}amino)ethyl]-L-glutamine/trifluoroacetic acid (1.1)

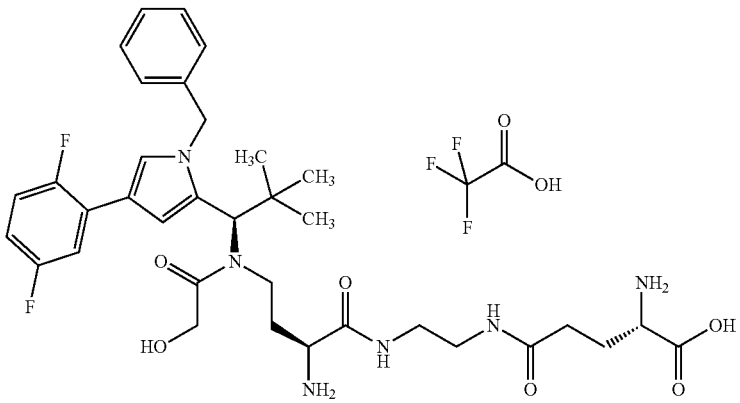 [SMILES: CC(C)(C)[C@H](c1cc(-c2cc(F)ccc2F)cn1Cc1ccccc1)N(CC[C@H](N)C(=O)NCCNC(=O)CC[C@H](N)C(=O)O)C(=O)CO ; O=C(O)C(F)(F)F]

First, trifluoroacetic acid/benzyl N-(2-aminoethyl)-N²-[(benzyloxy)carbonyl]-L-glutaminate (1:1) was prepared using classical methods of peptide chemistry. In the presence of HATU, this intermediate was then coupled with Intermediate C58. Subsequently, first the benzyloxycarbonyl protective group and the benzyl ester were removed by hydrogenolytic cleavage, and then the 2-(trimethylsilyl)ethoxycarbonyl protective group was removed using zinc chloride.

LC-MS (Method 6): $R_t$=1.91 min; MS (EIpos): m/z=685 [M+H]⁺.

Example M19

N⁶—(N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl)-L-lysine/trifluoroacetic acid (1:1)

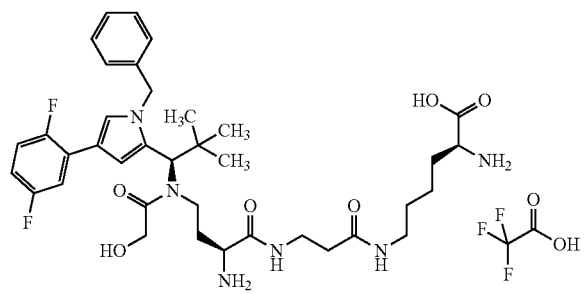 [SMILES: CC(C)(C)[C@H](c1cc(-c2cc(F)ccc2F)cn1Cc1ccccc1)N(CC[C@H](N)C(=O)NCCC(=O)NCCCC[C@H](N)C(=O)O)C(=O)CO ; O=C(O)C(F)(F)F]

Initially, trifluoroacetic acid/2-(trimethylsilyl)ethyl-N2-[(benzyloxy)carbonyl]-L-lysinate (1:1) was prepared using classical protective group operations known in peptide chemistry. In the presence of HATU, this intermediate was then coupled with Intermediate C61. Subsequently, first the 2-(trimethylsilyl)ethoxycarbonyl protective group and the 2-(trimethylsilyl)ethyl ester were cleaved using zinc chloride. Finally, the title compound was obtained by hydrogenolytical cleavage of the benzyloxycarbonyl protective group and purification by preparative HPLC.

HPLC (Method 11): $R_t$=1.65 min;

Example M20

(1R,4R,27R,33R)-1-Amino-32-(3-aminopropyl)-33-[1-benzyl-4-(2,5-difluorophenyl)-1H-pyrrol-2-yl]-34,34-dimethyl-6,9,25,31-tetraoxo-13,16,19,22-tetraoxa-3,29-dithia-7,10,26,32-tetraazapentatriacontane-1,4,27-tricarboxylic acid/trifluoroacetic acid (1:2)

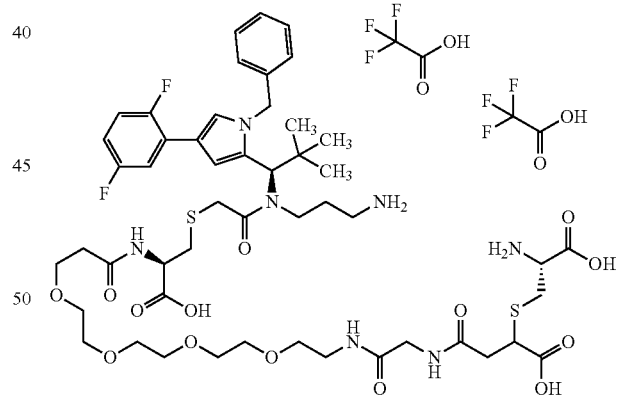

First, methyl L-cysteinate hydrochloride (1:1) was converted with 1-({[2-(trimethyl-silyl)ethoxy]carbonyl}oxy)pyrrolidine-2,5-dione in DMF in the presence of N,N-diisopropyl-ethylamine into methyl N-{[2-(trimethylsilyl)ethoxy]carbonyl}-L-cysteinate. 408 mg (1.93 mmol) of commercially available 3-bromo-4-methoxy-4-oxobutanoic acid and 180 mg (0.644 mmol) of methyl N-{[2-(trimethylsilyl)ethoxy]carbonyl}-L-cysteinate were dissolved m 8 ml of DMF, and 147 mg (0.97 mmol) of 1,8-diazabicyclo[5.4.0]undec-7-ene were added. After 18 h of stirring at RT, another 136 mg (0.64 mmol) of 3-bromo-4-methoxy-4-oxobutanoic acid and 147 mg (0.97 mmol) of 1,8-diazabicyclo[5.4.0]undec-7-ene were added, and the mixture was stirred at RT for a further 12 h and then concentrated under reduced pressure. The residue was purified by preparative HPLC. Combination of the appropriate fractions and evaporation of the solvents under reduced pressure gave 151 mg (57% of theory) of 4-methoxy-3-{[(2R)-3-methoxy-3-oxo-2-({[2-(trimethylsilyl)ethoxy]carbonyl}amino)propyl]sulphanyl}-4-oxobutanoic acid.

LC-MS (Method 12): $R_t$=1.74 min; MS (ESIneg): m/z=408 (M−H)⁻.

3.66 mg (8.93 µmol) of 4-methoxy-3-{[(2R)-3-methoxy-3-oxo-2-({[2-(trimethyl-silyl)ethoxy]carbonyl}amino)propyl]sulphanyl}-4-oxobutanoic acid were coupled in the presence of 3.66 mg (8.93 µmol) of HATU and 1.6 µl (15 µmol) of 4-methylmorpholine with 13.0 mg (7.44 µmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-(glycylamino)-4,7,10,13-tetraoxapentadecan-1-oyl]-L-cysteine/trifluoroacetic acid (1:1) (Intermediate C80), giving, after HPLC purification, 3.9 mg (37% of theory) of the fully protected intermediate S-(11-{(1R)-1-[1-benzyl-4-(2,5-difluorphenyl)-1H-pyrrol-2-yl]-2,2-dimethylpropyl}-2,2-dimethyl-6,12-dioxo-5-oxa-7,11-diaza-2-silatridecan-13-yl)-N-[15-({N-[(8R,11R)-8,11-bis(methoxycarbonyl)-2,2-dimethyl-6,13-dioxo-5-oxa-10-thia-7-aza-2-silatridecan-13-yl]glycyl}amino)-4,7,10,13-tetraoxapentadecan-1-oyl]-L-cysteine. 3.90 mg (2.76 µmol) of this intermediate were then stirred at RT with 35 µl of a 2-molar lithium hydroxide solution in 1.0 ml of THF/water 3:1 for 15 min, resulting in the cleavage of both methyl ester groups. Purification by HPLC gave 3.60 mg (94% of theory) of the dicarboxylic acid derivative.

LC-MS (Method 5): $R_t$=4.83 min; MS (ESIpos): m/z=1385 [M+H]⁺.

Finally, 3.6 mg (2.60 µmol) of this intermediate were completely deprotected with zinc chloride in trifluoroethanol as described above. The residue was purified by preparative HPLC. Concentration of the appropriate fractions and lyophilization of the residue from acetonitrile/water gave 1.92 mg (55% of theory) of the title compound.

LC-MS (Method 5): $R_t$=2.72 min; MS (ESIneg): m/z=1094 [M−H]

Example M21

(2R,24S,27R)-27-Amino-2-[({2-[(3-aminopropyl){(1R)-1-[1-benzyl-4-(2,5-difluorophenyl)-1H-pyrrol-2-yl]-2,2-dimethylpropyl}amino]-2-oxoethyl}sulphanyl)methyl]-24-(carboxymethyl)-4,20,23-trioxo-7,10,13,16-tetraoxa-25-thia-3,19,22-triazaoctacosane-1,28-dioic acid/trifluoroacetic acid (1:2)

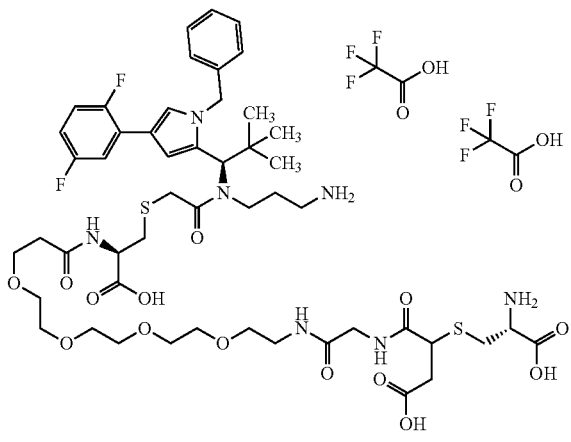 [SMILES: CC(C)(C)[C@H](c1cc(-c2cc(F)ccc2F)cn1Cc1ccccc1)N(CCCN)C(=O)CSC[C@H](NC(=O)CCOCCOCCOCCOCCNC(=O)CNC(=O)C(CC(=O)O)SC[C@H](N)C(=O)O)C(=O)O ; O=C(O)C(F)(F)F ; O=C(O)C(F)(F)F]

742.8 mg (3.3 mmol) of commercially available 2-bromo-4-ethoxy-4-oxobutanoic acid and 802 mg (2.87 mmol) of methyl N-{[2-(trimethylsilyl)ethoxy]carbonyl}-L-cysteinate were dissolved in 32 ml of DMF, and 655.4 mg (4.31 mmol) of 1,8-diazabicyclo[5.4.0]undec-7-ene were added. After 20 h of stirring at RT, the reaction was concentrated under reduced pressure and the residue was purified by preparative HPLC. Combination of the appropriate fractions and evaporation of the solvents under reduced pressure gave 521 mg (43% of theory) of 4-ethoxy-2-{[(2R)-3-methoxy-3-oxo-2-({[2-(trimethylsilyl)ethoxy]carbonyl}amino)propyl]sulphanyl}-4-oxobutanoic acid.

LC-MS (Method 5): $R_t$=3.13 min; MS (ESIpos): m/z=424 (M+H)⁺.

4.36 mg (10.3 µmol) of 4-ethoxy-2-{[(2R)-3-methoxy-3-oxo-2-({[2-(trimethylsilyl)ethoxy]carbonyl}amino)propyl]sulphanyl}-4-oxobutanoic acid were coupled in the presence of 3.92 mg (10.3 µmol) of HATU and 1.9 µl (17 µmol) of 4-methylmorpholine with 15.0 mg (8.59 µmol) of S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-(glycyl-amino)-4,7,10,13-tetraoxapentadecan-1-oyl]-L-cysteine/trifluoroacetic acid (1:1) (Intermediate C80), giving, after HPLC purification, 3.6 mg (26% of theory) of the folly protected intermediate S-(11-{(1R)-1-[1-benzyl-4-(2,5-difluorophenyl)-1H-pyrrol-2-yl]-2,2-dimethylpropyl}-2,2-dimethyl-6,12-dioxo-5-oxa-7,11-diaza-2-silatridecan-13-yl)-N-[15-({N-[(8R,11S)-11-(2-ethoxy-2-oxoethyl)-8-(methoxycarbonyl)-2,2-dimethyl-6,12-dioxo-5-oxa-10-thia-7-aza-2-siladodecan-12-yl]glycyl}amino)-4,7,10,13-tetraoxapentadecan-1-oyl]-L-cysteine. 6.20 mg (2.82 µmol) of this intermediate were then stirred at RT with 35 µl of a 2-molar lithium hydroxide solution in 1.0 ml of THF/water 1:1 for 15 min, resulting in the cleavage of both ester groups. Acidification and purification by HPLC gave 3.60 mg (92% of theory) of the dicarboxylic acid derivative.

LC-MS (Method 5): $R_t$=4.71 min; MS (ESIpos): m/z=1385 [M+H]⁺.

Finally, 3.60 mg (1.69 µmol) of this intermediate were completely deprotected with zinc chloride in trifluoroethanol as described above. The residue was purified by preparative HPLC. Concentration of the appropriate fractions and lyophilization of the residue from acetonitrile/water gave 0.88 mg (39% of theory) of the title compound.

LC-MS (Method 5): $R_t$=2.72 min; MS (ESIneg): m/z=1094 [M−H]

Example M22

(2R,27R)-27-Amino-2-[({2-[(3-aminopropyl) {(1R)-1-[1-benzyl-4-(2,5-difluorophenyl)-1H-pyrrol-2-yl]-2,2-dimethylpropyl}amino]-2-oxoethyl}sulfanyl) methyl]-24-(carboxymethyl)-4,20,23-trioxo-7,10,13,16-tetraoxa-25-thia-3,19,22-triazaoctacosane-1,28-dioic acid-trifluoroacetic acid (1:2) and (1R,27R,33R)-1-amino-32-(3-aminopropyl)-33-[1-benzyl-4-(2,5-difluorophenyl)-1H-pyrrol-2-yl]-34,34-dimethyl-6,9,25,31-tetraoxo-13,16,19,22-tetraoxa-3,29-dithia-7,10,26,32-tetraazapentatriacontane-1,4,27-tricarboxylic acid-trifluoroacetic acid (1.2)

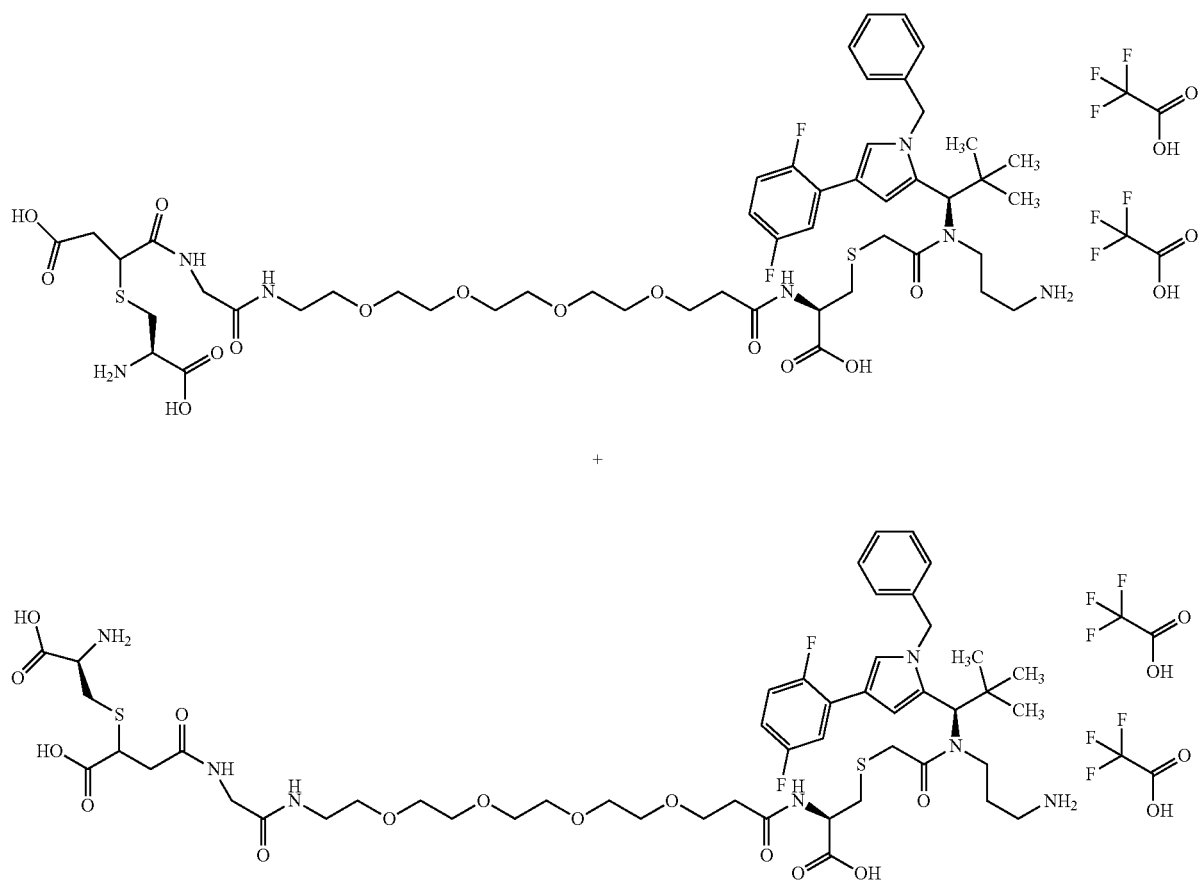

16.5 mg (0.015 mmol) of S-{2-[(3-aminopropyl){(1R)-1-[1-benzyl-4-(2,5-difluorophenyl)-1H-pyrrol-2-yl]-2,2-dimethylpropyl}amino]-2-oxoethyl}-N-[1-(2,5-dioxo-2,5-dihydro-1H-pyrrol-1-yl)-2,18-dioxo-6,9,12,15-tetraoxa-3-azaoctadecan-18-yl]-L-cysteine-trifluoroacetic acid (1:1) (intermediate F257) and 8.18 mg (0.031 mmol) of N-{[2-(trimethylsilyl)ethoxy]carbonyl}-L-cysteine wore dissolved in 2 ml of DMF and the mixture stirred at RT for 18 h. The reaction mixture was evaporated under vacuum. The residue (28.9 mg) was dissolved in 3 mL of THF/water 1:1. 0.046 mL of a 2M aqueous lithium hydroxide solution was added and the mixture stirred at RT for 3 h. Subsequently, the mixture was adjusted to a pH of ~7 with 5.2 μl (0.092 mmol) of acetic acid. The reaction mixture was purified immediately by prep. RP-HPLC (column: Reprosil 125×30; 10μ, flow: 50 mL/min, MeCN/water; 0.1% TFA). The solvents were evaporated under vacuum and the residue dried under high vacuum. 12.1 mg (58% over 2 stages) of the regioisomeric protected intermediates were obtained.

LC-MS (Method 12): $R_t$=1.82 min; MS (ESIpos): m/z=1240 (M+H)$^+$.

In the final step, 12.1 mg (0.009 mmol) of this intermediate were dissolved in 2 mL of 2,2,2-trifluoroethanol. 7.3 mg (0.054 mmol) of zinc chloride were added and the mixture was stirred at 50° C. for 2 h. Subsequently, 15.7 mg (0.054 mmol) of ethylenediamine-N,N,N',N'-tetraacetic acid were added and the solution was purified by preparative HPLC. After concentrating the relevant fractions and lyophilisation of the residue from acetonitrile/water, 6.4 mg (59%) of the title compound was obtained as a regioisomeric mixture.

LC-MS (Method 1): $R_t$=0.86 min; MS (ESIpos): m/z=1096 (M+H)$^+$.

Example M23

N-{(2S)-2-Amino-4-[{(1R)-1-[1-benzyl-4-(2,5-difluorophenyl)-1H-pyrrol-2-yl]-2,2-dimethyl propyl}(glycoloyl)amino]butanoyl}-beta-alanyl-L-glutamic acid-trifluoroacetic acid (1:1)

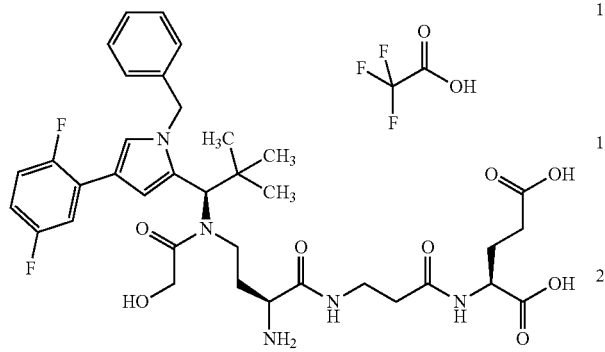

Firstly, di-tert-Butyl L-glutamate hydrochloride (1:1) was coupled with intermediate C61 in the presence of HATU and N,N-diisopropylethylamine. Subsequently, the protected intermediate was taken up in trifluoroethanol and fully deprotected by stirring overnight at 50° C. in the presence of zinc chloride. The work-up was carried out after addition of EDTA by purification by preparative HPLC.

LC-MS (Method 12): $R_t$=1.45 min; MS (ESIpos): m/z=714 [M+H]$^+$.

Example M24

N-{(2S)-2-Amino-4-[{(1R)-1-[1-benzyl-4-(2,5-difluorophenyl)-1H-pyrrol-2-yl]-2,2-dimethylpropyl}(glycoloyl)amino]butanoyl}-beta-alanyl-D-glutamic acid-trifluoroacetic acid

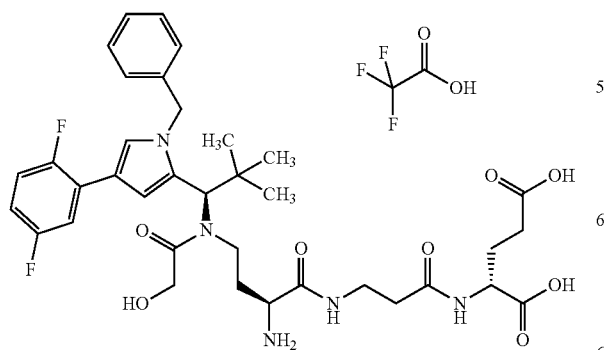

Firstly, di-tert-Butyl D-glutamate hydrochloride (1:1) was coupled with intermediate C61 in the presence of HATU and N,N-diisopropylethylamine. Subsequently, the protected intermediate was taken up in trifluoroethanol and fully deprotected by stirring at 50° C. in the presence of zinc chloride. The work-up was carried out after addition of EDTA by purification by preparative HPLC.

LC-MS (Method 12): $R_t$=1.41 min; MS (ESIpos): m/z=714 [M+H]$^+$.

Example M25

N-{(2S)-2-Amino-4-[{(1R)-1-[1-benzyl-4-(2,5-difluorophenyl)-1H-pyrrol-2-yl]-2,2-dimethyl propyl}(glycoloyl)amino]butanoyl}-L-glutamic acid-trifluoroacetic acid (1:1)

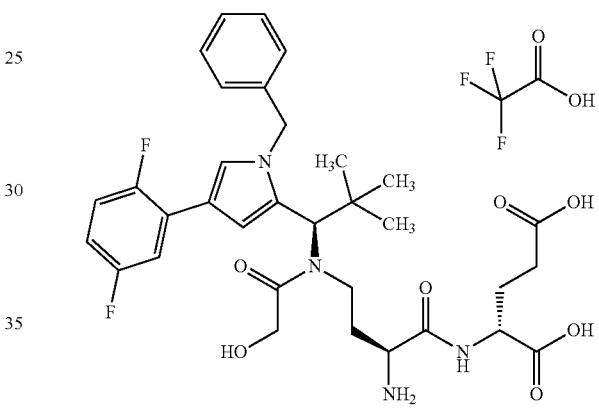

Firstly, di-tert-Butyl L-glutamate hydrochloride (1:1) was coupled with intermediate C61 in the presence of HATU and N,N-diisopropylethylamine. In the next step, the Z protecting group was removed by hydrogenation for 45 minutes over 10% palladium on active carbon in methanol at RT under standard hydrogen pressure. Subsequently, the partially protected intermediate was taken up in trifluoroethanol and fully deprotected by stirring at 50° C. for 7 hours in the presence of zinc chloride. The work-up was carried out after addition of EDTA by purification by preparative HPLC.

LC-MS (Method 12): $R_t$=1.44 min; MS (ESIpos): m/z=643 [M+H]$^+$.

Example M26

4-[(2-{[2-({(2S)-2-Amino-4-[{(1R)-1-[1-benzyl-4-(2,5-difluorophenyl)-1H-pyrrol-2-yl]-2,2-dimethyl-propyl}(glycoloyl)amino]butanoyl}amino)ethyl]amino}-2-oxoethyl)amino]-2-{[(2R)-2-amino-2-carboxyethyl]sulfanyl}-4-oxobutanoic acid-trifluoroacetic acid (1:1) Regioisomer 1, epimeric mixture

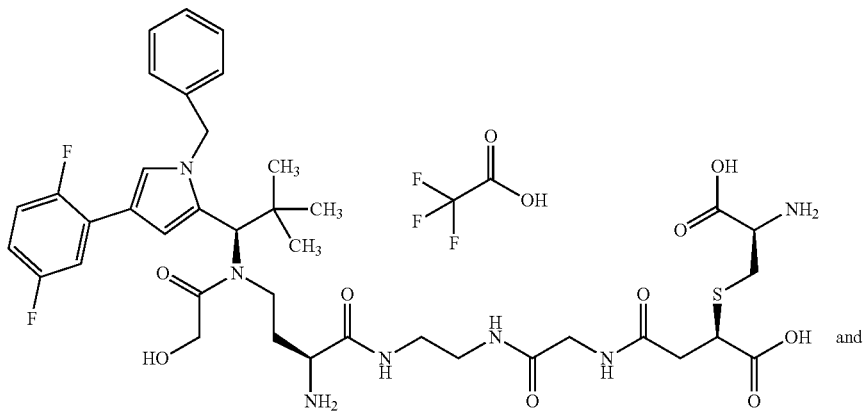

and

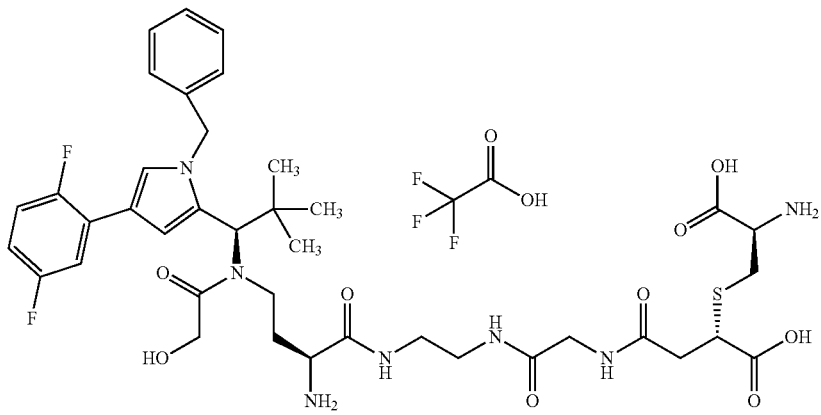

This example describes the epimeric mixture of the compounds of Example 13 and Example 14. The synthesis was carried out analogously to Example 13, in which the separation of the two epimers by supercritical fluid chromatography was omitted and the title compound was prepared as an epimeric mixture.

LC-MS (Method 5): $R_t$=2.43 min; MS (ESIpos): m/z=832 [M+H]$^+$.

Example M27

4-[(2-{[2-({(2S)-2-Amino-4-[{(1R)-1-[1-benzyl-4-(2,5-difluorophenyl)-1H-pyrrol-2-yl]-2,2-dimethyl-propyl}(glycoloyl)amino]butanoyl}amino)ethyl]amino}-2-oxoethyl)amino]-3-{[(2R)-2-amino-2-carboxyethyl]sulfanyl}-4-oxobutanoic acid-trifluoroacetic acid (1:1) Regioisomer 2, epimeric mixture

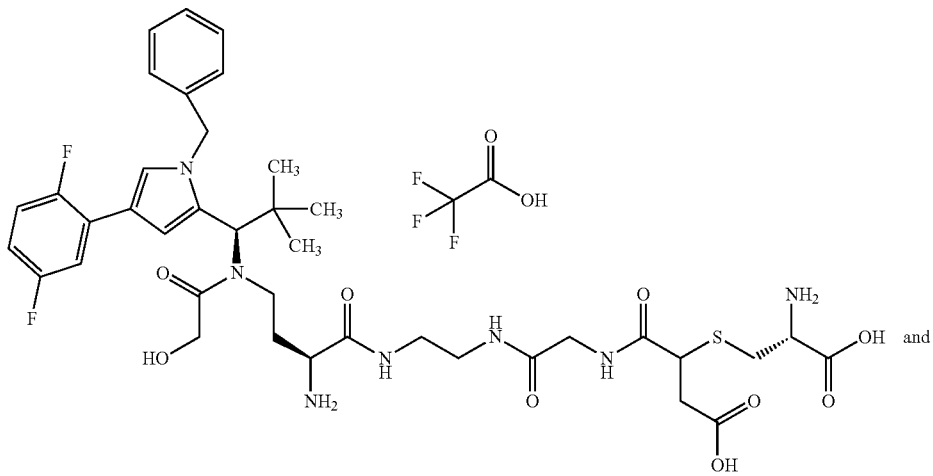

and

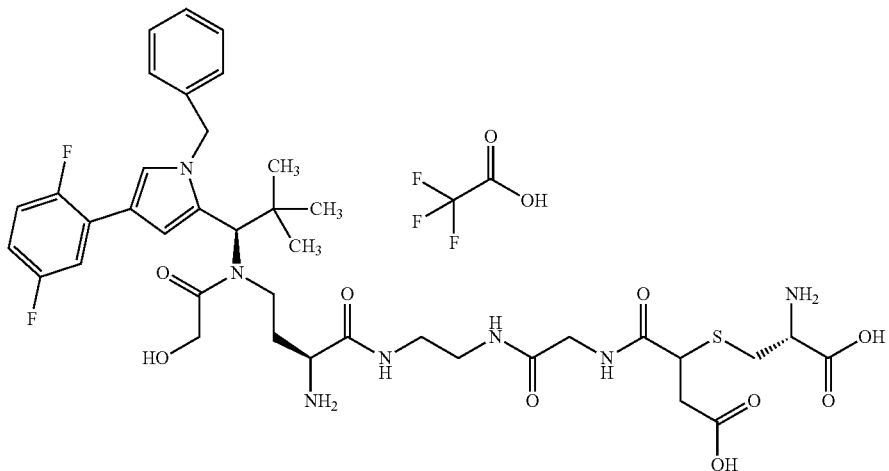

This example describes the epimeric mixture of the compounds of Example 15 and Example 16. The synthesis was carried out analogously to Example 15, in which the separation of the two epimers by supercritical fluid chromatography was omitted and the title compound was prepared as an epimeric mixture.

LC-MS (Method 5): $R_t$=2.45 min; MS (EIpos): m/z=832 [M+H]$^+$.

Working Examples ADCs

The coupling reactions were carried out under argon.

The ADCs shown in the structural formulae of the Working examples, which were coupled to the cystein side chains of the antibodies via maleimide radicals, are, depending on the linker and the coupling procedure, mainly present in the ring-opened or ring-closed forms shown in each case. However, the preparation may comprise a small proportion of the respective other form.

The ADCs shown in the Working examples were in some cases prepared with a plurality of anti-B7H3 antibodies. The antibodies used in each case and the analytical data of the ADCs prepared are summarized in Table 1 at the end of the working examples.

Example 173

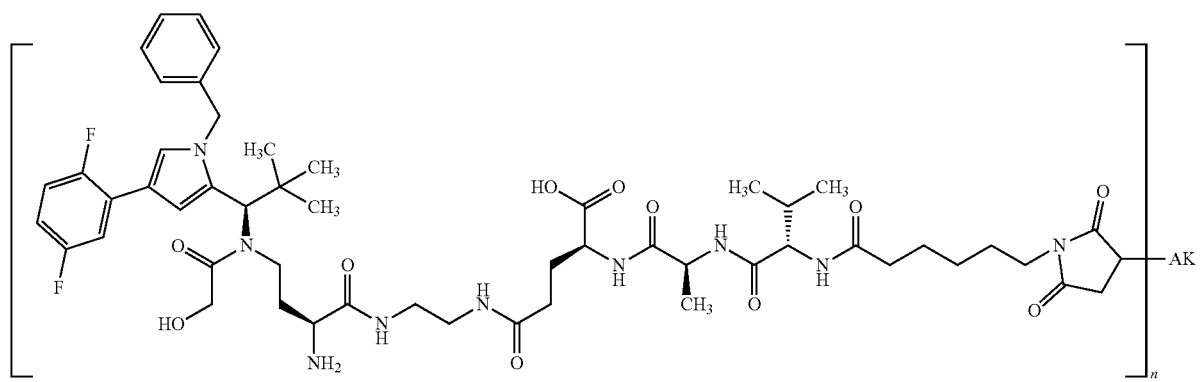

Here, 5 mg of the respective anti-B7H3 antibodies in PBS (c=11.1 mg/ml) were used for coupling with Intermediate F173. After addition of 0.029 mg of TCEP dissolved in 50 μl of PBS buffer, the reaction was stirred at RT for 30 min. Then, 0.31 mg (0.23 μmol) of F173 in 50 μl of DMSO were added, and the reaction was stirred at RT for a further 1.5 h and subsequently purified on Sephadex. Finally, the reaction was concentrated by ultracentrifugation and rediluted with PBS.

Example 194

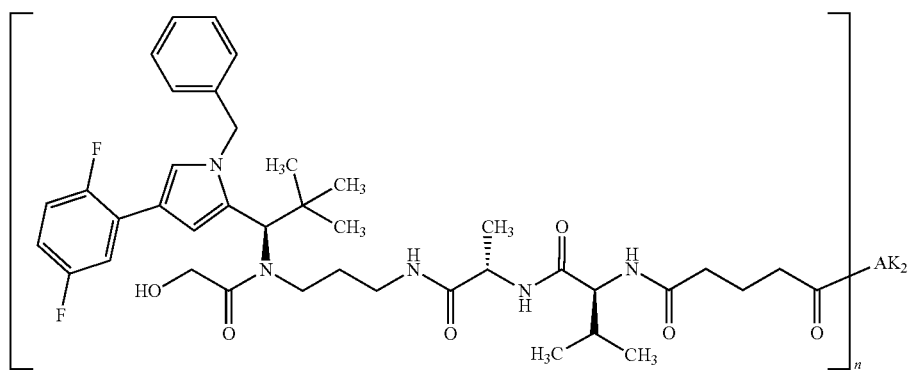

Here, 5 mg of the respective anti-B7H3 antibodies in 450 μl of PBS (c=11.1 mg/ml) were used for coupling with Intermediate F194. First, 5 eq of Intermediate F194 dissolved in 50 μl of DMSO were added, and after 1 h of stirring at RT the same amount was added again and the reaction was stirred at RT for a further hour. The reaction was subsequently purified on a Sephadex column, then concentrated by ultracentrifugation and rediluted with PBS.

507

Example 208

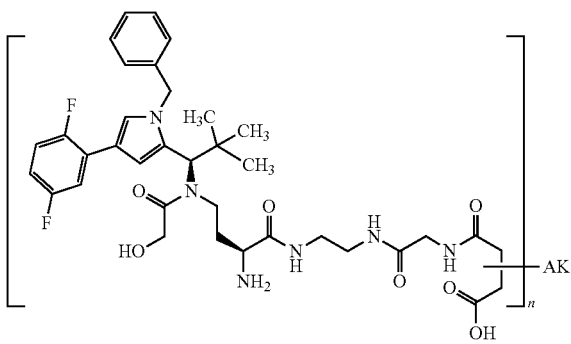

Under argon, a solution of 0.287 mg of TCEP in 50 μl of PBS buffer was added to 5 mg of the respective anti-B7H3 antibodies in 450 μl of PBS (c=11.1 mg/ml). The reaction was stirred at RT for 30 min, and 0.215 mg (0.000267 mmol) of Intermediate F104 dissolved in 50 μl of DMSO were then added. After a further 90 min of stirring at RT, the reaction was diluted with 1950 μl of PBS buffer which had been adjusted to pH 8 beforehand.

This solution was then applied to PD 10 columns (Sephadex® G-25, GE Healthcare) which had been equilibrated with PBS buffer pH 8 and was eluted with PBS buffer pH 8. The eluate was then concentrated by ultracentrifugation and rediluted with PBS buffer (pH 7.2).

508

Example 240

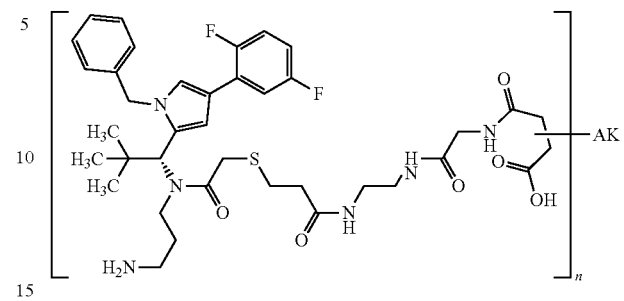

Under argon, a solution of 0.017 mg of TCEP in 30 μl of PBS buffer was added to 3 mg of the respective anti-B7H3 antibodies in 75 μl of PBS (c=39.8 mg/ml). The reaction was diluted with 1335 μl of PBS buffer which had been adjusted to pH 8 beforehand and stirred at RT for 1 h. 0.119 mg (0.00014 mmol) of Intermediate F240 dissolved in 60 μl of DMSO were then added. After a further 90 min of stirring at RT, the reaction was diluted with 1.0 ml of PBS buffer pH 8 and applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form.

Example 257

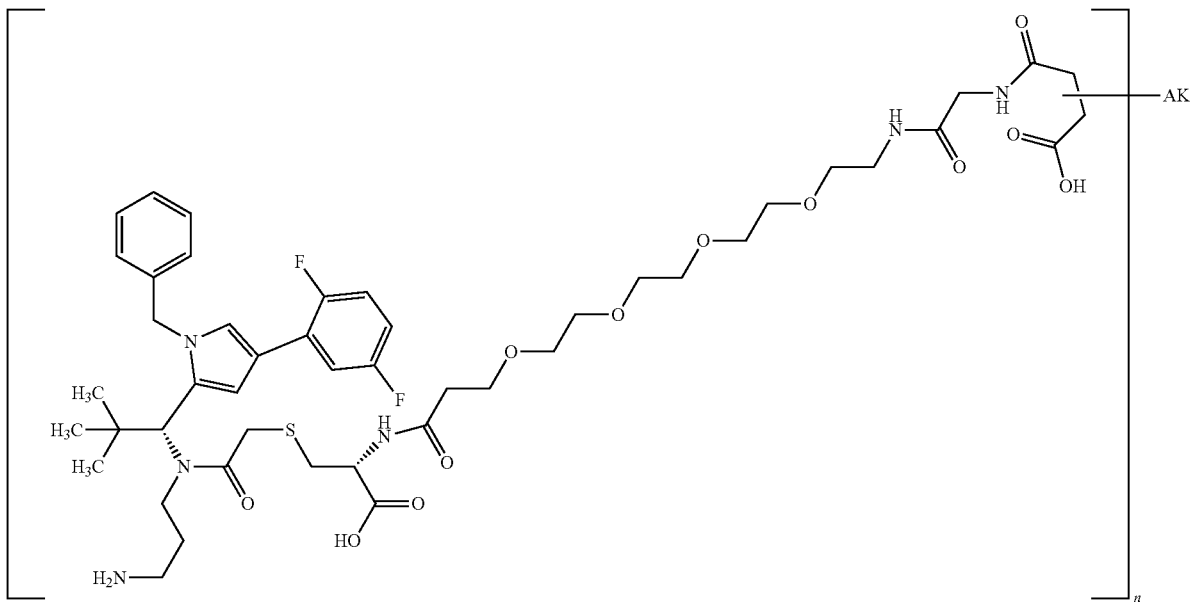

Under argon, a solution of 0.029 mg of TCEP in 50 μl of PBS buffer was added to 5 mg of the respective anti-B7H3 antibodies in 133 μl of PBS (c=44.1 mg/ml). The reaction was diluted with 2237 μl of PBS buffer which had been adjusted to pH 8 beforehand and stirred at RT for 1 h. 0.250 mg (0.00023 mmol) of Intermediate F257 dissolved in 100 μl of DMSO were then added. After a further 90 min of stirring at RT, the reaction was applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form.

A solution of 0.14 mg of TCEP in 0.20 ml of PBS buffer was added under argon to 25 mg of the anti-B7H3 antibodies in question in 2.363 ml of PBS (c=10.58 mg/mL). The mixture was stirred at RT for 30 min and then 0.746 mg (0.00083 mmol) of intermediate F263, dissolved in 200 μl of DMSO, was added. After stirring further at RT for 90 min, the mixture was rebuffered to pH 8 by means of PD-10 columns. The combined eluates were then stirred at RT overnight under argon. This was then rebuffered to a pH of 7.2 using PBS buffer by means of PD-10 columns and the eluate diluted with PBS to a total volume of 15 ml. Subsequently, the eluate was concentrated by ultracentrifugation, rediluted with PBS buffer (pH 7.2) and concentrated again.

Example 263

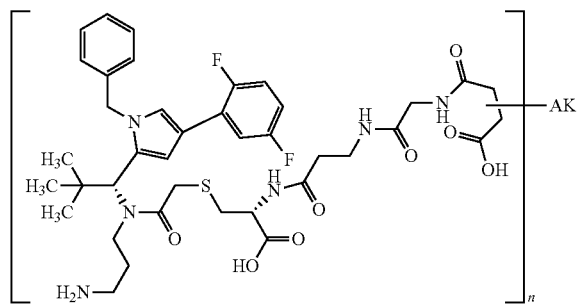

Example 267

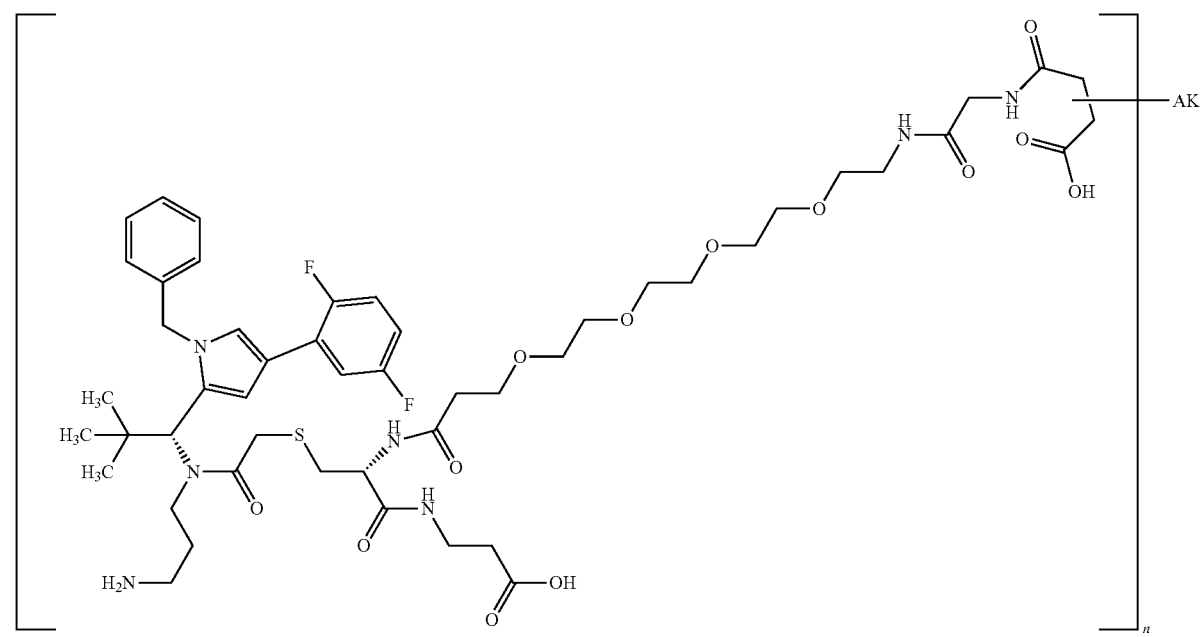

A solution of 0.14 mg of TCEP in 0.20 ml of PBS buffer was added under argon to 25 mg of the anti-B7H3 antibodies in question in 2.363 ml of PBS (c=10.58 mg/mL). The mixture was stirred at RT for 30 min and then 0.952 mg (0.00083 mmol) of intermediate F267, dissolved in 200 µl of DMSO, was added. After stirring further at RT for 90 min, the mixture was rebuffered to pH 8 by means of PD-10 columns. The combined eluates were then stirred at RT overnight under argon. This was then rebuffered to a pH of 7.2 using PBS buffer by means of PD-10 columns and the eluate diluted with PBS to a total volume of 15 ml. Subsequently, the eluate was concentrated by ultracentrifugation, rediluted with PBS buffer (pH 7.2) and concentrated again.

Example 271

Example 274

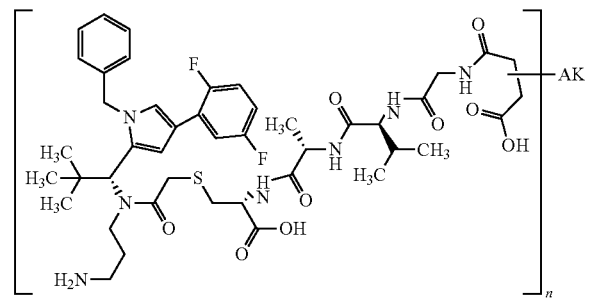

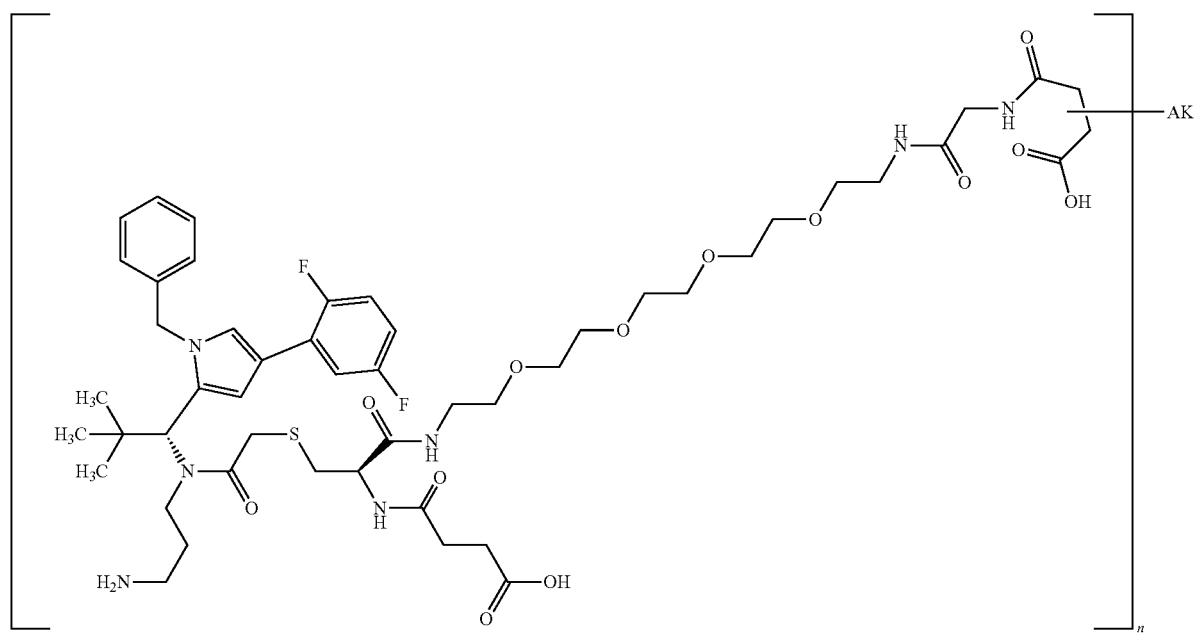

A solution of 0.14 mg of TCEP in 0.20 ml of PBS buffer was added under argon to 25 mg of the anti-B7H3 antibodies in question in 2.363 ml of PBS (c=10.58 mg/mL). The mixture was stirred at RT for 30 min and then 0.761 mg (0.00083 mmol) of intermediate F271, dissolved in 200 µl of DMSO, was added. After stirring further at RT for 90 min, the mixture was rebuffered to pH 8 by means of PD-10 columns. The combined eluates were then stirred at RT overnight under argon. This was then rebuffered to a pH of 7.2 using PBS buffer by means of PD-10 columns and the eluate diluted with PBS to a total volume of 15 ml. Subsequently, the eluate was concentrated by ultracentrifugation, rediluted with PBS buffer (pH 7.2) and concentrated again.

Under argon, a solution of 0.029 mg of TCEP in 50 µl of PBS buffer was added to 2.5 mg of the respective anti-B7H3 antibodies in 132 µl of PBS (c=38.0 mg/ml). The reaction was diluted with 2218 µl of PBS buffer which had been adjusted to pH 8 beforehand and stirred at RT for 1 h. 0.232 mg (0.00023 mmol) of Intermediate F274 dissolved in 100 µl of DMSO were then added. After a further 90 min of stirring at RT, the reaction was applied to PD 10 columns (Sephadex® G-25, GE Healthcare) which had been equilibrated with PBS buffer pH 8 and was eluted with PBS buffer pH 8. The eluate was stirred under argon at RT overnight and then concentrated by ultracentrifugation and rediluted with PBS buffer (pH 7.2). Under these conditions, some of the ADCs may also be present in the ring-closed form.

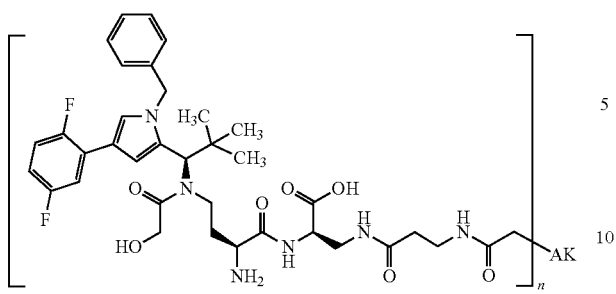

Here, 5 mg of the respective anti-B7H3 antibodies in 510 µl of PBS at pH 7.2 (c-9.8 mg/ml) were used for coupling with Intermediate F281. The reduction time of the antibody in the presence of 0.029 mg of TCEP was 30 min. After addition of 0.22 mg (0.23 µmol) of F281 in 50 µl of DMSO, the reaction was then stirred at RT for 20 h and subsequently purified on Sephadex. The eluate was finally concentrated by ultracentrifugation and rediluted with PBS.

Example 284

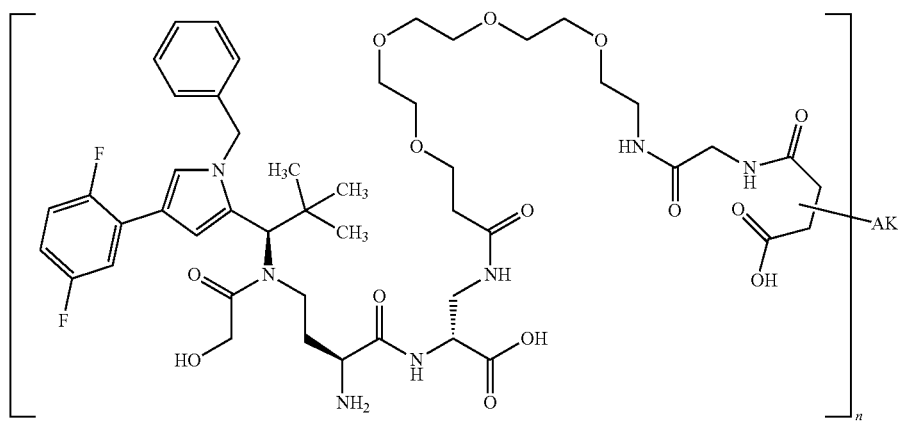

Under argon, a solution of 0.029 mg of TCEP in 50 µl of PBS buffer was added to 5 mg of the respective anti-B7H3 antibodies in 450 µl of PBS (c=11.1 mg/ml), and the mixture was stirred at RT for 30 min. 0.26 mg (0.23 µmol) of Intermediate F284 dissolved in 50 µl of DMSO were then added. After a further 90 min of stirring at RT, the mixture was made up to 2.5 ml with PBS buffer pH 8 and passed through a PD 10 column (Sephadex® G-25, GE Healthcare) equilibrated with PBS buffer pH 8, eluted with PBS buffer pH 8 and then stirred at RT overnight. The eluate was then concentrated by ultracentrifugation and rediluted with PBS buffer (pH 7.2).

Example 296

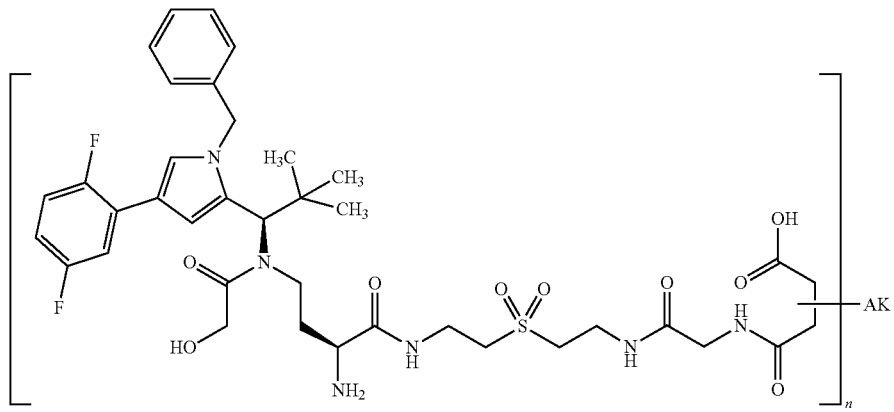

A solution of 0.029 mg of TCEP in 50 μl of PBS buffer was added under argon to 5 mg of the anti-B7H3 antibodies in question in 500 μL ml of PBS (c=10 mg/mL) and the mixture was stirred at RT for 30 min. Then, 0.21 mg (0.23 μmol) of intermediate F296, dissolved in 50 μl of DMSO, was added. After stirring further at RT for 90 min, the mixture was made up to 2.5 ml with PBS buffer pH 8 and applied to a PD 10 column (Sephadex® G-25, GE Healthcare) equilibrated with PBS buffer pH 8, eluted with PBS buffer pH 8 and subsequently stirred at RT overnight. The eluate was then concentrated by ultracentrifugation and rediluted with PBS buffer (pH 7.2).

Example 297

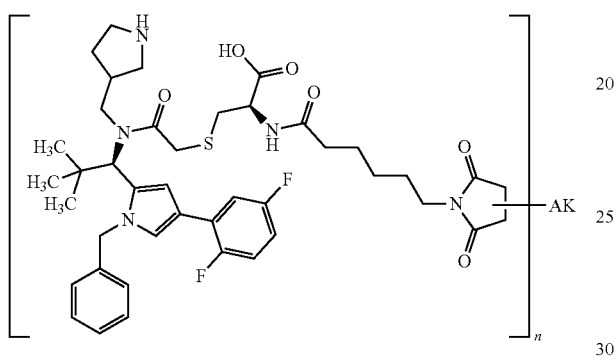

Here, 3 mg of the respective anti-B7H3 antibodies in 270 μl of PBS at pH 7.2 (c-11.1 mg/ml) were used for coupling with Intermediate F297. The reduction time of the antibody in the presence of 0.017 mg of TCEP was 30 min. After addition of 0.13 mg (0.14 μmol) of F297 in 50 μl of DMSO, the reaction was then stirred at RT for 2 h and subsequently purified on Sephadex. The eluate was finally concentrated by ultracentrifugation and rediluted with PBS.

Example 307

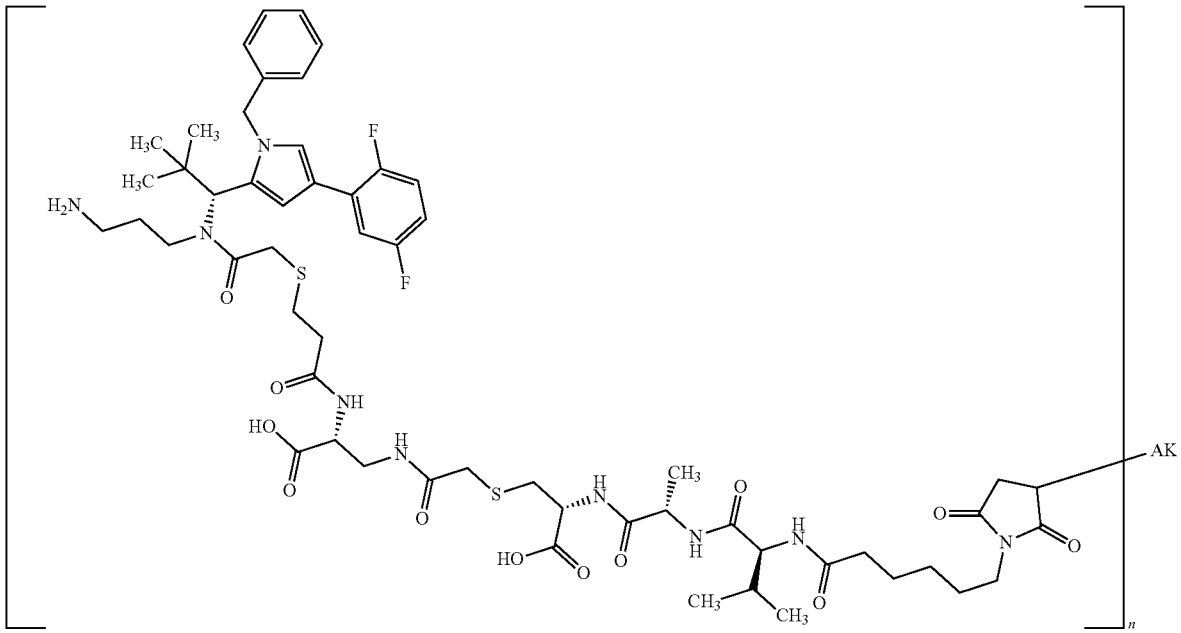

A solution of 0.14 mg of TCEP in 0.20 ml of PBS buffer was added under argon to 25 mg of the anti-B7H3 antibodies in question in 2.363 ml of PBS (c=10.58 mg/mL). The mixture was stirred at RT for 30 min and then 1.07 mg (0.00083 mmol) of intermediate F307, dissolved in 200 µl of DMSO, was added. After stirring further at RT for 90 min, the mixture was purified by means of PD-10 columns and the eluate diluted with PBS to a total volume of 15 ml. Subsequently, the eluate was concentrated by ultracentrifugation, rediluted with PBS buffer (pH 7.2) and concentrated again.

Example 308

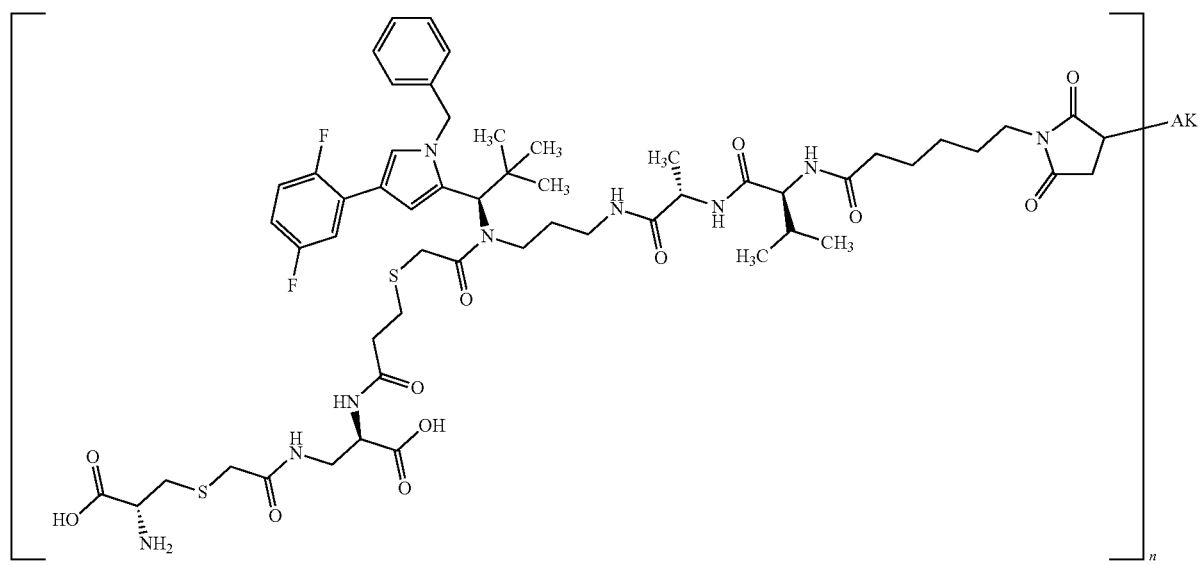

A solution of 0.029 mg of TCEP in 50 µl of PBS buffer was added under argon to 5 mg of the respective anti-B7H3 antibodies in 473 µL ml of PBS (c=10.58 mg/mL). The mixture was diluted with 1877 µl of PBS buffer and stirred at RT for 30 min. 0.256 mg (0.00023 mmol) of intermediate F308 dissolved in 100 µl of DMSO was then added. After stirring a further 90 min at RT, the mixture was purified on PD 10 columns (Sephadex® G-25, GE Healthcare) and subsequently concentrated by ultracentrifugation and rediluted with PBS buffer.

Example 309

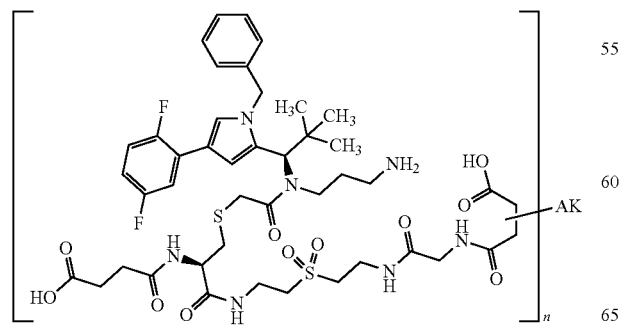

A solution of 0.14 mg of TCEP in 0.20 ml of PBS buffer was added under argon to 25 mg of the anti-B7H3 antibodies in question in 2.363 ml of PBS (c=10.58 mg/mL). The mixture was stirred at RT for 30 min and then 0.705 mg (0.00083 mmol) of intermediate F309, dissolved in 200 µl of DMSO, was added. After stirring further at RT for 90 min, the mixture was rebuffered to pH 8 by means of PD-10 columns. The combined eluates were then stirred at RT overnight under argon. This was then rebuffered to a pH of 7.2 using PBS buffer by means of PD-10 columns and the eluate diluted with PBS to a total volume of 15 ml. Subsequently, the eluate was concentrated by ultracentrifugation and rediluted with PBS buffer (pH 7.2).

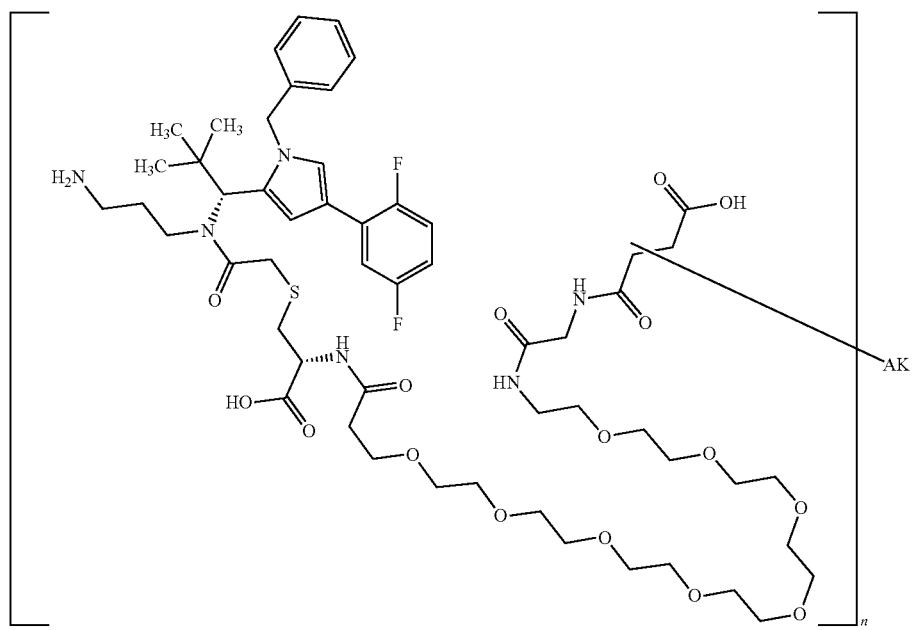

A solution of 0.029 mg of TCEP in 50 µl of PBS buffer was added under argon to 5 mg of the anti-B7H3 antibodies in question in 450 µL ml of PBS (c=11.11 mg/mL). The mixture was stirred at RT for 30 min. Then, 0.291 mg (0.00023 mmol) of intermediate F311, dissolved in 50 µl of DMSO, was added. After stirring further at RT for 90 min, the mixture was diluted with 1950 µl of PBS buffer pH 8 and applied to PD 10 columns (Sephadex® G-25, GE Healthcare) equilibrated with PBS buffer pH 8, and eluted with PBS buffer pH 8. The eluate was stirred at RT under argon overnight and subsequently concentrated by ultracentrifugation and rediluted with PBS buffer (pH 7.2).

Example 314

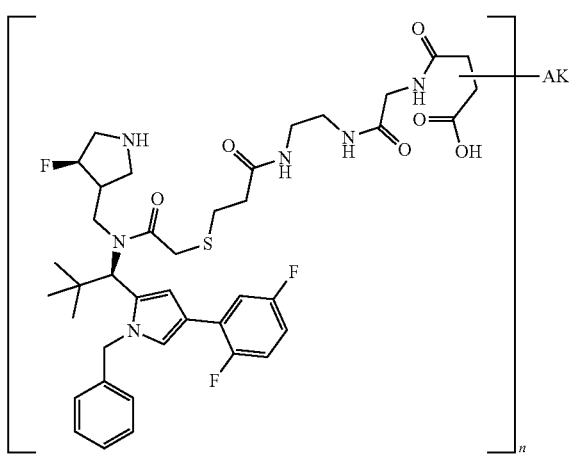

A solution of 0.029 mg of TCEP in 50 μl of PBS buffer was added under argon to 5 mg of the anti-B7H3 antibodies in question in 450 μL ml of PBS (c=11.11 mg/mL). The mixture was stirred at RT for 30 min. Then, 0.209 mg (0.00023 mmol) of intermediate F314, dissolved in 50 μl of DMSO, was added. After stirring further at RT for 90 min, the mixture was diluted with 1950 μl of PBS buffer pH 8 and then applied to PD 10 columns (Sephadex® G-25, GE Healthcare) equilibrated with PBS buffer pH 8, and eluted with PBS buffer pH 8. The eluate was stirred at RT under argon overnight and subsequently concentrated by ultracentrifugation and rediluted with PBS buffer (pH 7.2).

Example 317

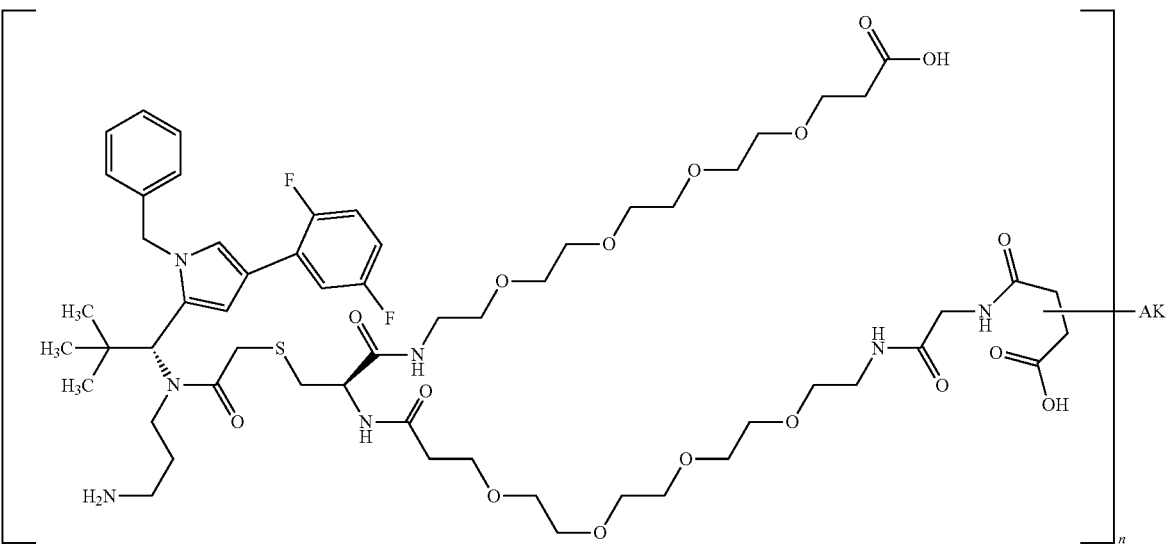

A solution of 0.029 mg of TCEP in 50 μl of PBS buffer was added under argon to 5 mg of the anti-B7H3 antibodies in question in 450 μL ml of PBS (c=11.11 mg/mL). The mixture was stirred at RT for 30 min. Then, 0.308 mg (0.00023 mmol) of intermediate F317, dissolved in 50 μl of DMSO, was added. After stirring further at RT for 90 min, the mixture was diluted with 1950 μl of PBS buffer pH 8 and then applied to PD 10 columns (Sephadex® G-25, GE Healthcare) equilibrated with PBS buffer pH 8, and eluted with PBS buffer pH 8. The eluate was stirred at RT under argon overnight and subsequently concentrated by ultracentrifugation and rediluted with PBS buffer (pH 7.2).

Example 318

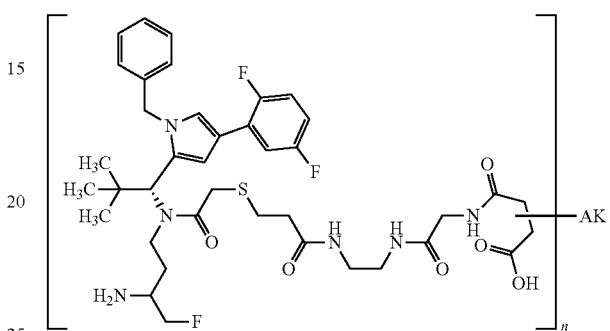

A solution of 0.029 mg of TCEP in 50 μl of PBS buffer was added under argon to 5 mg of the anti-B7H3 antibodies in question in 450 μL ml of PBS (c=11.11 mg/mL). The mixture was stirred at RT for 30 min. Then, 0.206 mg (0.00023 mmol) of intermediate F318, dissolved in 50 μl of DMSO, was added. After stirring further at RT for 90 min, the mixture was diluted with 1950 μl of PBS buffer pH 8 and applied to PD 10 columns (Sephadex® G-25, GE Healthcare) equilibrated with PBS buffer pH 8, and eluted with PBS buffer pH 8. The eluate was stirred at RT under argon overnight and subsequently concentrated by ultracentrifugation and rediluted with PBS buffer (pH 7.2).

Example 319

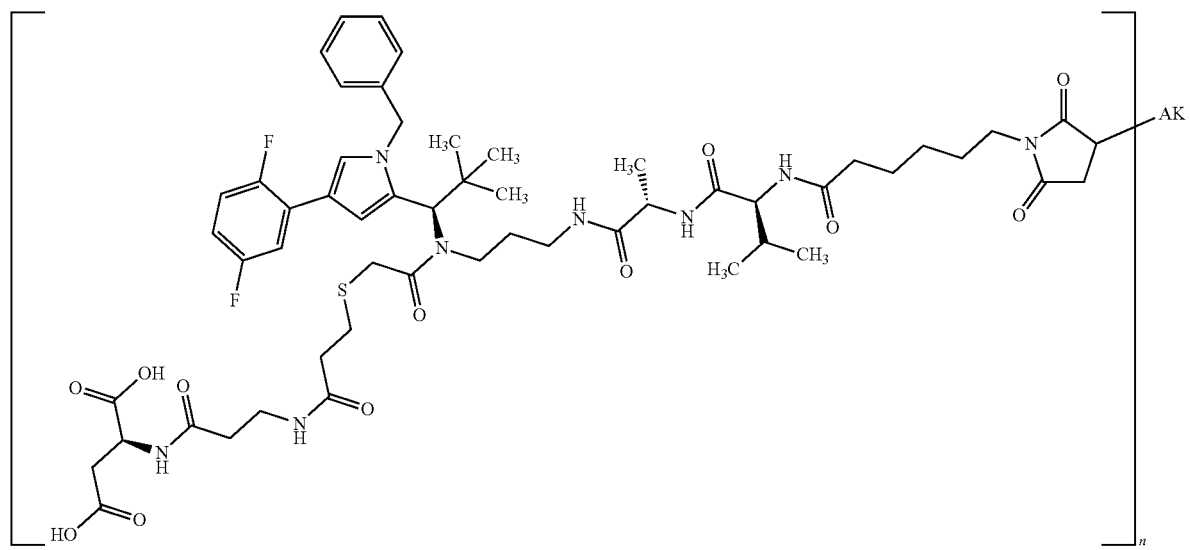

A solution of 0.029 mg of TCEP in 50 µl of PBS buffer was added under argon to 5 mg of the anti-B7H3 antibodies in question in 319 µL ml of PBS (c=15.69 mg/mL). The mixture was diluted with 2031 µl of PBS buffer and stirred at RT for 30 min. Then, 0.258 mg (0.00023 mmol) of intermediate F319, dissolved in 100 µl of DMSO, was added. After stirring further at RT for 90 min, the mixture was purified on PD 10 columns (Sephadex® G-25, GE Healthcare) and subsequently concentrated by ultracentrifugation and rediluted with PBS buffer.

Example 320

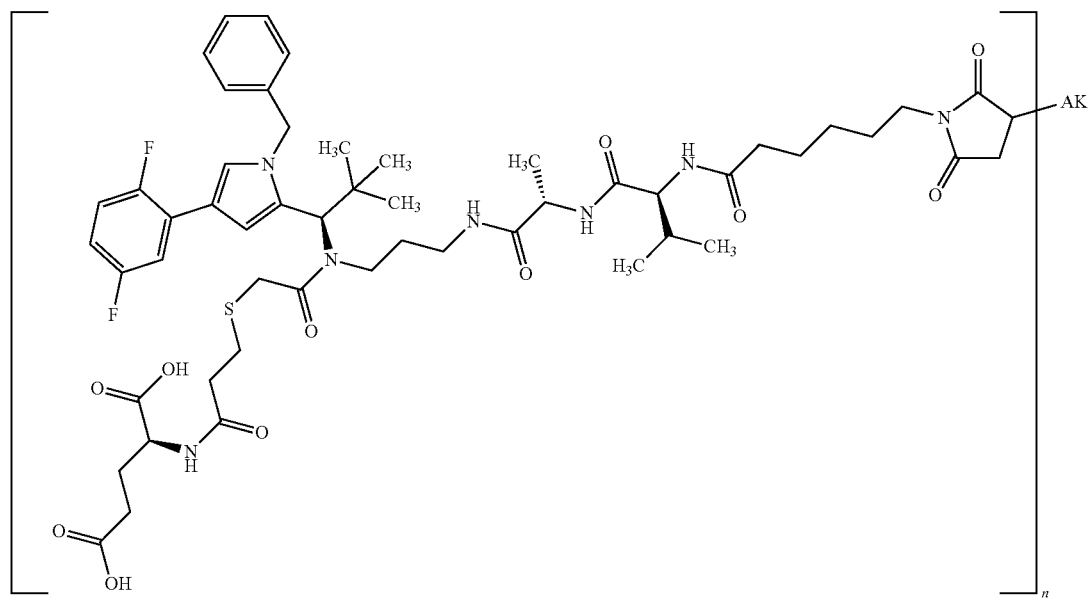

A solution of 0.029 mg of TCEP in 50 μl of PBS buffer was added under argon to 5 mg of the anti-B7H3 antibodies in question in 319 μL ml of PBS (c=15.69 mg/mL). The mixture was diluted with 2031 μl of PBS buffer and stirred at RT for 30 min. Then, 0.245 mg (0.00023 mmol) of intermediate F320, dissolved in 100 μl of DMSO, was added. After stirring further at RT for 90 min, the mixture was purified on PD 10 columns (Sephadex® G-25, GE Healthcare) and subsequently concentrated by ultracentrifugation and rediluted with PBS buffer.

Example 321

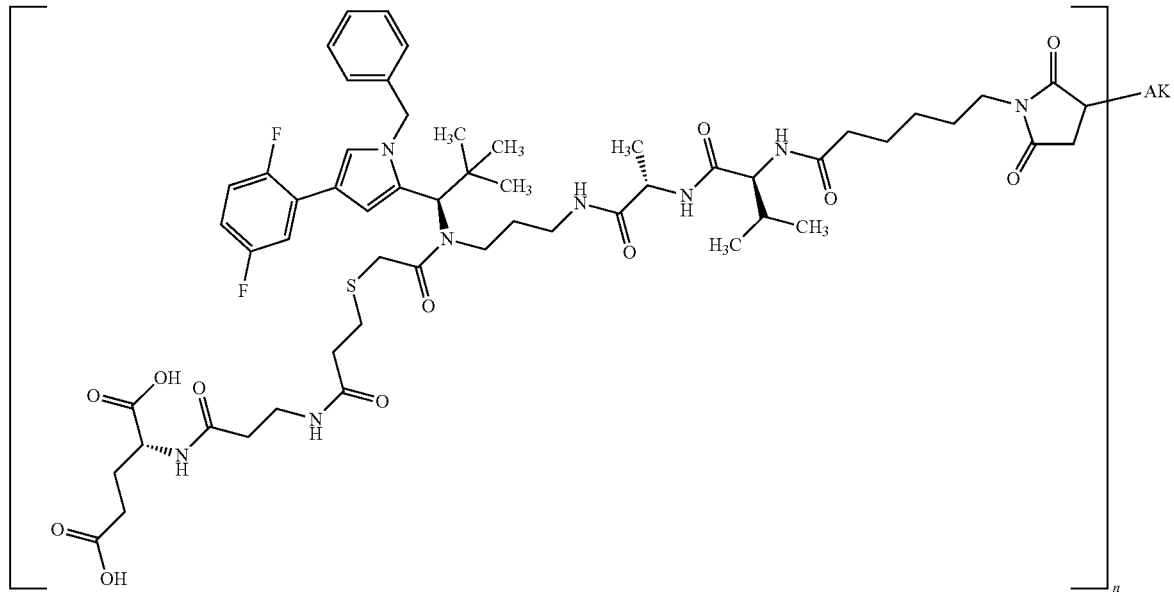

A solution of 0.029 mg of TCEP in 50 μl of PBS buffer was added under argon to 5 mg of the anti-B7H3 antibodies in question in 319 μL ml of PBS (c=15.69 mg/mL). The mixture was diluted with 2031 μl of PBS buffer and stirred at RT for 30 min. Then, 0.262 mg (0.00023 mmol) of intermediate F321, dissolved in 100 μl of DMSO, was added. After stirring further at RT for 90 min, the mixture was purified on PD 10 columns (Sephadex® G-25, GE Healthcare) and subsequently concentrated by ultracentrifugation and rediluted with PBS buffer.

Example 322

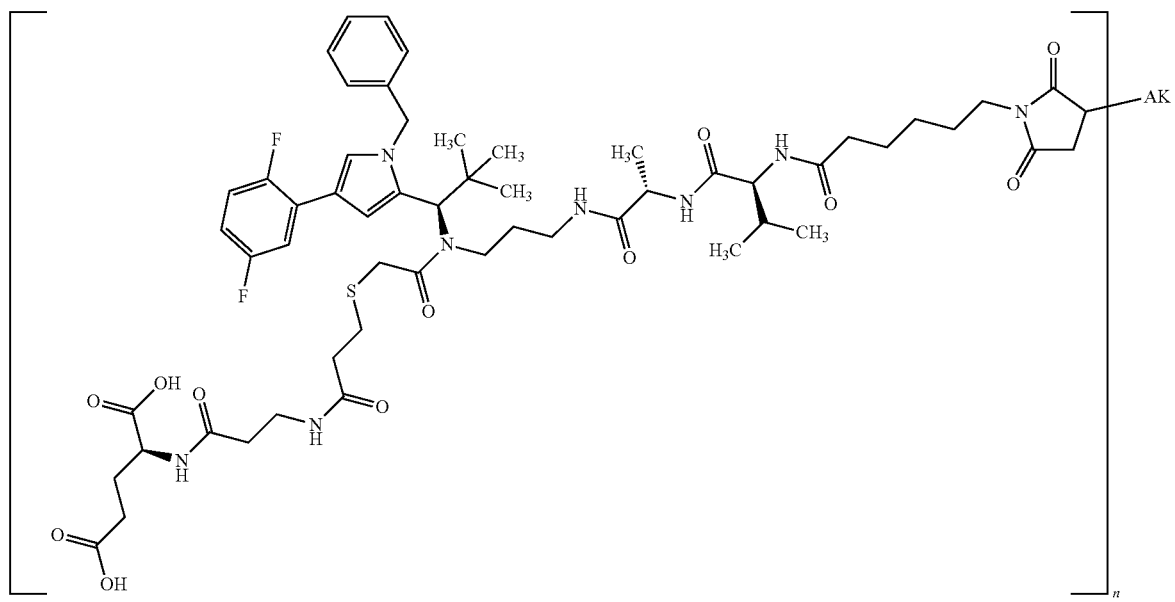

A solution of 0.172 mg of TCEP in 0.30 ml of PBS buffer was added under argon to 30 mg of the anti-B7H3 antibodies in question in 3 ml of PBS (c=10.0 mg/mL). The mixture was stirred at RT for 30 min and then 1.12 mg (0.001 mmol) of intermediate F322, dissolved in 300 µl of DMSO, were added. After stirring further at RT for 90 min, the mixture was purified on PD 10 columns and the eluate diluted with PBS to a total volume of 15 ml. Subsequently, the eluate was concentrated by ultracentrifugation, rediluted with PBS buffer (pH 7.2) and concentrated again.

Example 323

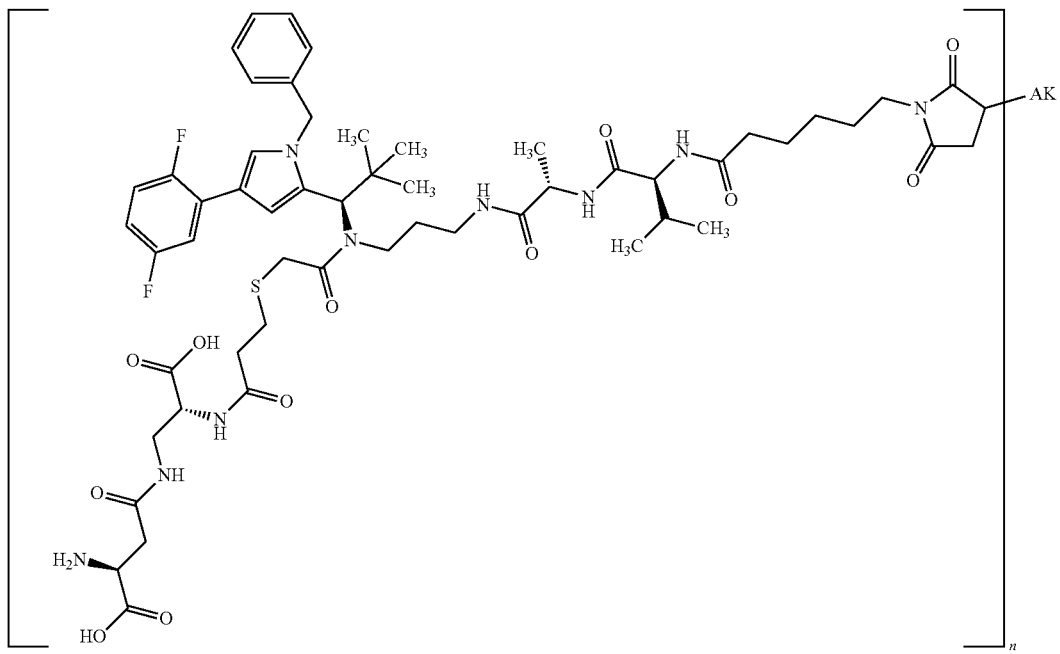

A solution of 0.029 mg of TCEP in 50 µl of PBS buffer was added under argon to 5 mg of the anti-B7H3 antibodies in question in 450 µL ml of PBS (c=11.11 mg/mL). The mixture was stirred at RT for 30 min. Then, 0.328 mg (0.00023 mmol) of intermediate F323, dissolved in 50 µl of DMSO, was added. After stirring further at RT for 90 min, the mixture was diluted with 1950 µl of PBS buffer, then purified on PD 10 columns (Sephadex® G-25, GE Healthcare) and subsequently concentrated by ultracentrifugation and rediluted with PBS buffer.

Example 325

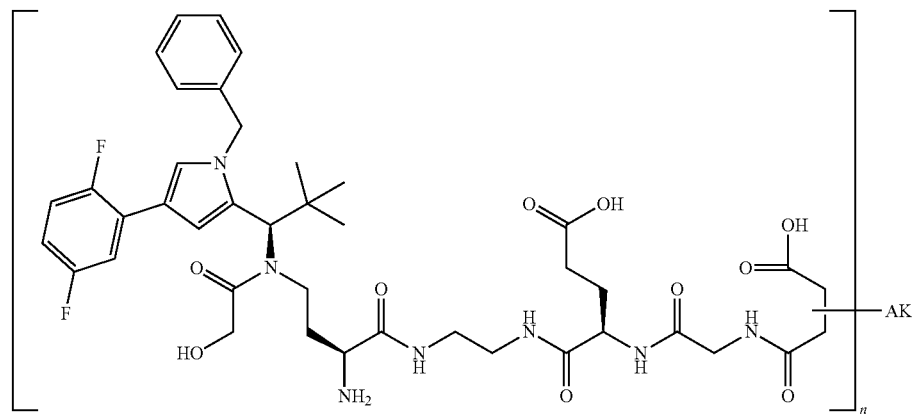

A solution of 0.029 mg of TCEP in 50 µl of PBS buffer was added under argon to 5 mg of the anti-B7H3 antibodies in question in 0.400 ml of PBS (c=12.5 mg/mL). The mixture was stirred at RT for 30 min and then 0.22 mg (0.00023 mmol) of intermediate F325, dissolved in 50 µl of DMSO, was added. After stirring further at RT for 90 min, the mixture was made up to 2.5 ml with PBS buffer pH 8 and applied to a PD 10 column (Sephadex® G-25, GE Healthcare) equilibrated with PBS buffer pH 8, eluted with PBS buffer pH 8 and subsequently stirred at RT overnight under argon. The eluate was then concentrated by ultracentrifugation and rediluted with PBS buffer (pH 7.2).

Example 326

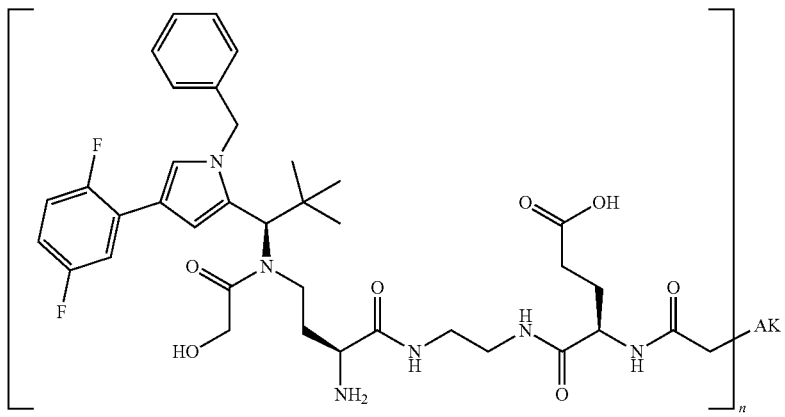

A solution of 0.029 mg of TCEP in 50 µl of PBS buffer was added under argon to 5 mg of the anti-B7H3 antibodies in question in 0.400 ml of PBS (c=12.5 mg/mL), The mixture was stirred at RT for 30 min and then 0.22 mg (0.00023 mmol) of intermediate F326, dissolved in 50 µl of DMSO, was added. The mixture was then stirred overnight at RT under argon, then made up to 2.5 ml with PBS buffer pH 7.2 and applied to a PD 10 column (Sephadex® G-25, GE Healthcare) equilibrated with PBS buffer pH 7.2. Subsequently, the mixture was concentrated by ultracentrifugation and rediluted with PBS buffer (pH 7.2).

TABLE 1

Antibodies used and analytical data of the ADCs from the Working examples:

| Example | mAb used TPP | ADC concentration mg/ml | DAR |
|---|---|---|---|
| 173-6515 | 6515 | 2.12 | 3.5 |
| 194-6502 | 6502 | 1.36 | 1.4 |
| 208-6497 | 6497 | 1.42 | 3.2 |
| 208-6497 | 6497 | 11.7 | 3.9 |
| 208-6499 | 6499 | 1.05 | 2.7 |
| 208-6501 | 6501 | 0.66 | 2.7 |
| 208-6501 | 6501 | 8.36 | 3.3 |
| 208-6502 | 6502 | 1.12 | 2.9 |
| 208-6502 | 6502 | 11.18 | 3.7 |
| 208-6515 | 6515 | 2.05 | 3.6 |
| 208-6575 | 6575 | 12.8 | 4.2 |
| 208-7611 | 7611 | 8.35 | 4.6 |
| 208-8322 | 8322 | 8.35 | 4.0 |
| 208-8382 | 8382 | 11.18 | 4.6 |
| 208-8564 | 8564 | 6.97 | 3.6 |
| 208-8565 | 8565 | 8.77 | 3.9 |
| 208-8567 | 8567 | 1.92 | 3.5 |
| 208-8567 | 8567 | 10.13 | 4.8 |
| 208-8568 | 8568 | 2.34 | 3.2 |
| 240-6497 | 6497 | 0.97 | 2.6 |
| 240-8382 | 8382 | 8.12 | 3.5 |
| 257-6499 | 6499 | 0.99 | 3.1 |
| 257-6497 | 6497 | 7.99 | 3.7 |
| 257-8382 | 8382 | 7.76 | 3.5 |
| 257-8567 | 8567 | 1.77 | 3.6 |
| 263-6497 | 6497 | 8.36 | 3.4 |
| 267-6797 | 6497 | 8.06 | 1.7 |
| 271-6497 | 6497 | 8.53 | 3.1 |
| 274-6499 | 6499 | 0.69 | 3.5 |
| 281-6501 | 6501 | 0.76 | 1.0 |
| 281-8382 | 8382 | 1.95 | 3.1 |
| 281-8567 | 8567 | 1.80 | 3.5 |
| 284-6501 | 6501 | 0.38 | 1.7 |
| 284-8382 | 8382 | 1.89 | 4.2 |
| 284-8567 | 8567 | 2.06 | 4.3 |
| 296-8382 | 8382 | 1.77 | 4.1 |
| 296-8567 | 8567 | 1.91 | 4.1 |
| 297-6501 | 6501 | 0.62 | 2.4 |
| 307-6497 | 6497 | 4.79 | 3.3 |
| 308-6497 | 6497 | 1.41 | 2.6 |
| 309-6497 | 6497 | 8.25 | 3.8 |
| 311-8382 | 8382 | 1.45 | 1.5 |
| 314-8382 | 8382 | 1.33 | 4.2 |
| 318-6497 | 6497 | 1.75 | 1.9 |
| 318-8382 | 8382 | 1.49 | 4.1 |
| 319-8382 | 8382 | 1.89 | 2.8 |
| 320-8382 | 8382 | 1.85 | 2.7 |
| 321-8382 | 8382 | 2.02 | 2.8 |
| 322-8382 | 8382 | 9.45 | 3.5 |
| 323-8382 | 8382 | 2.09 | 4.6 |
| 325-8382 | 8382 | 1.73 | 3.5 |
| 326-8382 | 8382 | 1.95 | 2.6 |

C: Assessment of Biological Efficacy

The biological activity of the compounds according to the invention can be shown in the assays described below:

a. C-1a—Determination of the Cytotoxic Effects of the ADCs Directed Against B7H3

The analysis of the cytotoxic effects of the anti-B7H3 ADCs was carried out with various cell lines:

A498: human renal carcinoma cells, ATCC-CRL-HTB-44, standard medium: RPMI 1640; (Biochrom; # FG 1215, with stable glutamine)+10% FCS (Biochrom; # S0415), B7H3-positive.

MCF-7: human breast cancer cells, standard medium: RPMI 1640; (Biochrom; # F 1275, without phenol red)+E2 (final: 1E-10M; (3-estradiol, Sigma # E2758 or ZK 5018 in CLL)+10% CCS, +2 mUnits/ml insulin (bovine, Biochrom; # K 3510)+L-alanyl-L-glutamine; (final. 2 mM, Biochrom; # K 0302), B7H3-positive.

Caki-2: human renal carcinoma cells, ATCC-HTB-27, standard medium: DMEM/Hams F12 (#FG4815, Biochrom AG)+10% FCS (#F2442, Sigma), B7H3-positive.

Raji: human Burkitt's lymphoma cells, DMSZ-ACC-319, standard medium: RPMI 1640; (Biochrom; # FG 1215, with stable glutamine)+10% FCS (Biochrom; # S0415), B7H3-negative.

NCI-H292: human mucoepidermoid lung carcinoma cells, ATCC-CRL-1848, standard medium. RPMI 1640 (Biochrom; #FG1215, stab, glutamine)+10% FCS (Biochrom; #S0415).

SCC4: human radix linguae carcinoma cells, standard medium: DMEM/Ham's F12; (Biochrom, #FG 4815, with stable glutamine+10% FCS (Biochrom; #S0415), hydrocortisone; (final: 40 ng/ml, Biochrom; # K 3520).

U251: human glioblastoma cells, standard medium: RPMI 1640 (Biochrom; #FG1215, stable glutamine)+10% FCS (Biochrom; #S0415).

The cells were cultivated by the standard method as stated by the American Tissue Culture Collection (ATCC) for the cell lines in question.

CTG Assay

The cells were cultivated according to the standard method using the growth media listed under C-1. The test was carried out by detaching the cells with a solution of trypsin (0.05%) and EDTA (0.02%) in PBS (Biochrom AG #L2143), pelleting, resuspending in culture medium, counting and sowing into a 96-well culture plate with white bottom (Costar #3610) (75 µl/well, the following cell numbers per well: NCI-H292: 2500 cells/well, BxPC3 2500 cells/well) and incubating in an incubator at 37° C. in 5% carbon dioxide. After 24 h, the antibody drug conjugates in 25 µl of culture medium (four-fold concentrated) were added to the cells such that a final concentration of antibody drug conjugates of $3\times10^{-7}$ M to $3\times10^{-11}$ M on the cells was reached (in triplicate). The cells were then incubated in an incubator at 37° C., and 5% carbon dioxide. In a parallel plate, the cell vitality was determined at the start of the drug treatment (day 0) using the Cell Titer Glow (CTG) Luminescent Cell Viability Assay (Promega #G7573 and #G7571). To this end, 100 µl of the substance were added per cell batch, the plates were then covered with aluminium foil, shaken on the plate shaker at 180 rpm for 2 minutes, allowed to stand on the laboratory bench for 8 minutes and then measured using a luminometer (Victor X2, Perkin Elmer). The substrate detects the ATP content in the living cells, generating a luminescence signal of which the height is directly proportional to the vitality of the cells. After 72 h of incubation with the antibody drug conjugates, in these cells, too, the vitality was determines using the Cell Titer Glow Luminescent Cell Viability Assay as described above. From the measured data, the $IC^{50}$ of the growth inhibition in comparison to day 0 was calculated using the DRC (dose response curve) analysis spreadsheet with a 4-parameter fit. The DRC analysis spreadsheet is a Biobook Spreadsheet developed by Bayer Pharma AG and Bayer Business Services on the IDBS E-WorkBook Suite platform (1DBS: ID Business Solutions Ltd., Guildford, UK).

Tables 1a and 1b below list the $IC_{50}$ values of representative working examples for the anti-B7H3 antibodies from this assay:

TABLE 1a

| Example No. | MCF-7 CTG (IC50 M) | A498 CTG (IC 50 M) | Caki-2 CTG (IC50 M) | Raji CTG (IC50 M) |
|---|---|---|---|---|
| M09 | 3E-11 | — | — | 3E-11 |
| 173-6515 | 7.89E-10 | >3.07E-7 | 2.57E-9 | 1.23E-7 |
| 194-6502 | 1.00E-9 | 2.93E-9 | 3.66E-10 | >3.00E-7 |
| 208-6497 | 6.9E-11 | — | — | 1.67E-07 |
| 208-6499 | 1.35E-10 | — | — | >3.0E-7 |
| 208-6501 | 1.61E-10 | <3.0E-11 | — | 1.26E-07 |
| 208-6502 | 3.97E-11 | 6.67E-11 | — | 1.24E-07 |
| 208-6515 | 3.38E-10 | 6.88E-10 | — | 1.14E-07 |
| 240-6497 | 1.04E-10 | >3.00E-7 | >3.00E-7 | 4.57E-8 |
| 257-6499 | 1.13E-10 | 2.47E-10 | <3.00E-11 | 7.28E-8 |

TABLE 1b

| Example No. | U251 CTG (IC50 M) | NCI-H292 CTG (IC50 M) |
|---|---|---|
| 208-isotype control | 7.76E-8 | 1.37E-7 |
| 208-8382 | 3.60E-10 | 1.37E-9 |
| 208-8564 | 1.13E-10 | 1.30E-9 |
| 257-8382 | 8.56E-11 | not tested |
| 208-6497 | 7.68E-11 | not tested |
| 208-6501 | 2.95E-10 | not tested |
| 208-6502 | 9.33E-10 | not tested |
| 208-6515 | 4.10E-10 | not tested |
| 208-7611 | 2.49E-10 | not tested |
| 208-8322 | 6.75E-11 | not tested |
| 208-8564 | 1.13E-10 | 1.30E-09 |
| 208-8565 | 8.38E-11 | not tested |
| 208-8567 | <3.00E-11 | 3.74E-10 |
| 208-8567 | 3.40E-10 | 9.46E-9 |
| 208-8568 | 3.99E-10 | 9.03E-8 |
| 240-6497 | 2.97E-10 | not tested |
| 240-8382 | 2.24E-10 | not tested |
| 257-6497 | 5.58E-11 | not tested |
| 257-6499 | 7.36E-11 | 1.09E-09 |
| 257-8382 | 8.56E-11 | not tested |
| 257-8567 | 4.28E-11 | 2.13E-10 |
| 263-6497 | 4.37E-9 | not tested |
| 267-6497 | 2.84E-8 | not tested |
| 271-6497 | 2.87E-8 | not tested |
| 274-6499 | 1.20E-9 | not tested |
| 281-6501 | 2.99E-8 | not tested |
| 281-8382 | 1.35E-10 | 4.60E-9 |
| 281-8567 | 3.16E-10 | 1.25E-8 |
| 284-6501 | 6.29E-8 | not tested |
| 284-8382 | 1.54E-10 | not tested |
| 284-8567 | 2.46E-10 | not tested |
| 296-8382 | 1.17E-10 | 9.66E-9 |
| 296-8567 | 1.26E-10 | 5.48E-9 |
| 297-6501 | 7.04E-10 | not tested |
| 307-6497 | 4.66E-10 | not tested |
| 308-6497 | 2.16E-7 | not tested |
| 309-6497 | 6.57E-8 | not tested |
| 311-8382 | 2.10E-8 | >3.00E-7 |
| 314-8382 | 1.93E-10 | 1.41E-9 |
| 317-6497 | 1.42E-8 | 1.99E-7 |
| 317-8382 | 1.81E-8 | 2.20E-7 |
| 318-6497 | 4.77E-8 | not tested |
| 318-8382 | 1.17E-9 | 1.28E-8 |
| 319-8382 | 1.44E-9 | not tested |
| 320-8382 | 3.46E-8 | not tested |
| 321-8382 | 3.90E-9 | not tested |
| 322-8382 | 2.31E-10 | 4.85E-10 |
| 323-8382 | 8.02E-10 | 9.55E-8 |

TABLE 1b-continued

| Example No. | U251 CTG (IC50 M) | NCI-H292 CTG (IC50 M) |
| --- | --- | --- |
| 325-8382 | 6.44E−11 | not tested |
| 326-8382 | 6.66E−9 | not tested |

C-1b Determination of the Inhibition of the Kinesin Spindle Protein KSP/Eg5 by Selected Examples The motor domain of the human kinesin spindle protein KSP/Eg5 (tebu-bio/Cytoskeleton Inc, No. 027EG01-XL) was incubated in a concentration of 10 nM with microtubuli (bovine or porcine, tebu-bio/Cytoskeleton Inc) stabilized with 50 μg/ml taxol (Sigma No. T7191-5MG) for 5 min at RT in 15 mM PIPES, pH 6.8 (5 mM $MgCl_2$ and 10 mM DTT, Sigma). The freshly prepared mixture was aliquoted into a 384 MTP (Greiner bio-one REF 781096). The inhibitors to be examined at concentrations of 1.0×10-6 M to 1.0×10-13 M and ATP (final concentration 500 μM, Sigma) were then added. Incubation was at RT for 2 h. ATPase activity was detected by detecting the inorganic phosphate formed using malachite green (Biomol). After addition of the reagent, the assay was incubated at RT for 50 min prior to detection of the absorption at a wavelength of 620 nm. The positive controls used were monastrol (Sigma, M8515-1 mg) and ispinesib (AdooQ Bioscience A10486). The individual data of the dose-activity curve are eight-fold determinations. The $IC_{50}$ values are means of two independent experiments. The 100% control was the sample which had not been treated with inhibitors.

Table 2 below lists the $IC_{50}$ values of representative working examples from the assay described and the corresponding cytotoxicity data (MTT assay).

TABLE 2

| Examples | KSP assay $IC_{50}$ [M] | NCI-H292 $IC_{50}$ [M] MTT assay | KPL4 $IC_{50}$ [M] MTT assay |
| --- | --- | --- | --- |
| M1 | 2.01E−09 | 5.00E−07 | 5.00E−07 |
| M2 | 2.45E−09 | 2.04E−07 | 1.63E−07 |
| M3 | 1.52E−09 | 3.21E−08 | 9.00E−08 |
| M4 | 2.71E−10 | 4.43E−08 | 1.76E−07 |
| M5 | 4.57E−10 | 7.94E−08 | 2.22E−07 |
| M6 | 1.78E−09 | 4.63E−08 | 1.93E−07 |
| M7 | 6.21E−10 | 2.22E−08 | 9.25E−08 |
| M9 | 1.07E−09 | 7.74E−10 | 2.57E−10 |
| M10 | 4.70E−10 | 3.03E−07 | 2.26E−07 |
| M11 | 1.11E−09 | 4.32E−11 | |
| M12 | 4.46E−10 | 3.3E−08 | |
| M13 | 1.50E−09 | 1.52E−07 | 1.69E−07 |
| M14 | 2.16E−09 | 1.74E−07 | 1.82E−07 |
| M15 | 9.64E−10 | 1.33E−07 | 1.69E−07 |
| M16 | 1.48E−09 | 1.43E−07 | 1.95E−07 |
| M17 | 4.17E−09 | 7.35E−09 | |
| M18 | 5.17E−09 | 3.55E−08 | |
| M19 | 2.58E−09 | 1.21E−07 | |
| M20 | 1.50E−09 | 1.49E−07 | 2.13E−07 |
| M21 | 2.31E−09 | | |
| M22 | 8.27E−10 | 2.89E−08 | 1.82E−07 |
| M23 | 1.26E−09 | 5.00E−07 | 5.00E−07 |
| M24 | 2.90E−09 | 1.67E−07 | 5.00E−07 |
| M25 | 2.91E−09 | 5.00E−07 | 5.00E−07 |
| M26 | 9.441E−10 | 6.38E−08 | |
| M27 | 2.03E−09 | 2.76E−07 | |

The activity data reported relate to the working examples described in the present experimental section.

C-2 Internalisation Assay

Internalisation is a key process which enables specific and efficient provision of the cytotoxic payload in antigen-expressing cancer cells via antibody drug conjugates (ADC). This process is monitored via fluorescent labelling of specific B7H3 antibodies and an isotype control antibody. First, the fluorescent dye was conjugated to lysines of the antibody. Conjugation was carried out using a two-fold molar excess of CypHer 5E mono NHS ester (Batch 357392, GE Healthcare) at pH 8.3. After the coupling, the reaction mixture was purified by gel chromatography (Zeba Spin Desalting Columns, 40K, Thermo Scientific, No. 87768; elution buffer: DULBECCO S PBS, Sigma-Aldrich, No. D8537), to eliminate excess dye and to adjust the pH. The protein solution was concentrated using VIVASPIN 500 columns (Sartorius stedim biotec). The dye load of the antibody was determined by spectrophotometric analysis (NanoDrop) and subsequent calculation (D: $P=A_{dye}\varepsilon_{protein}$: $(A_{280}-0.16A_{dye})\varepsilon_{dye}$). The dye load of the B7H3 antibodies examined here and the isotype control were of a comparable order. In cell binding assays, it was confirmed that the coupling did not lead to a change in the affinity of the antibodies.

The labelled antibodies were used in the internalization assays. Prior to the start of this treatment, cells ($2\times10^4$/well) in 100 μl of medium were sown in a 96-MTP (fat, black, clear bottom No 4308776, from Applied Biosystems). After 18 h of incubation at 37° C./5% $CO_2$, the medium was replaced and labelled anti-B7H3 antibodies were added in various concentrations (10, 5, 2.5, 1, 0.1 μg/ml). The same treatment scheme was used for the labelled isotype control (negative control). The chosen incubation times were 0 h, 0.25 h, 0.5 h, 1 h, 1.5 h, 2 h, 3 h, 6 h and 24 h. Fluorescence measurement was carried out using the InCellAnalyzer 1000 (from GE Healthcare). Kinetic evaluation was carried out via measurement of the parameters granule counts/cell and total granule intensity/cell.

After binding to B7H3, B7H3 antibodies were examined for their internalization abfirty. To this end, the B7H3-expressing cell lines (A498, 786-0) were chosen. A target-mediated specific internalization with the B7H3 antibodies was observed (FIG. 2 Example A498 cell line), whereas the isotype control showed no internalization.

C-3 In Vitro Tests for Determining Cell Permeability

The cell permeability of a substance can be investigated by means of in vitro testing in a flux assay using Caco-2 cells [M. D. Troutman and D. R. Thakker, Pharm. Res. 20 (8), 1210-1224 (2003)]. For this purpose, the cells were cultured for 15-16 days on 24-well filter plates. For the determination of permeation, the respective test substance was applied in a HEPES buffer to the cells either apically (A) or basally (B) and incubated for 2 hours. After 0 hours and after 2 hours, samples were taken from the cis and trans compartments. The samples were separated by HPLC (Agilent 1200, Böblingen, Germany) using reverse phase columns. The HPLC system was coupled via a Turbo Ion Spray Interface to a Triple Quadropol mass spectrometer API 4000 (AB SCIEX Deutschland GmbH, Darmstadt, Germany). The permeability was evaluated on the basis of a $P_{app}$ value, which was calculated using the formula published by Schwab et al. [D. Schwab et al., J. Med. Chem. 46, 1716-1725 (2003)]. A substance was classified as actively transported when the ratio of $P_{app}$ (B-A) to $P_{app}$ (A-B) (efflux ratio) was >2 or <0.5.

Of critical importance for toxophores which are released intracellularly is the permeability from B to A [$P_{app}$ (B-A)] and the ratio of $P_{app}$ (B-A) to $P_{app}$ (A-B) (efflux ratio): the lower this permeability, the slower the active and passive transport processes of the substance through the monolayer of Caco-2 cells. If additionally the efflux ratio does not indicate any active transport, the substance may, following intracellular release, remain longer in the cell. Hence, there is also more time available for interaction with the biochemical target (in this case: kinesin spindle protein, KSP/Eg5).

Table 3 below sets out permeability data for representative working examples from this assay:

TABLE 3

| Working Example | $P_{app}$ (B-A) [nm/s] | Efflux ratio |
| --- | --- | --- |
| M1 | 7.8 | 4 |
| M2 | 4.8 | 6.4 |
| M3 | 1.4 | 1.3 |
| M4 | 21.3 | 18.7 |
| M5 | 20.3 | 26.5 |
| M6 | 1.7 | 0.7 |
| M7 | 5.6 | 2.2 |
| M9 | 213 | 16 |
| M11 | 24.3 | 27.7 |
| M12 | 3.3 | 1.8 |
| M13 | 7.1 | 3.6 |
| M14 | 12.7 | 6.6 |
| M15 | 6.4 | 4.4 |
| M16 | 9.0 | 7.0 |
| M17 | 93.6 | 81.5 |
| M18 | 1.6 | 2.9 |
| M19 | 1.9 | 2.9 |
| M21 | 0.5 | 1.5 |
| M22 | 0.9 | 0.9 |
| M23 | 2.8 | 2.0 |
| M24 | 3.9 | 1.0 |
| M25 | 8.1 | 3.6 |
| M26 | 13.0 | 9.6 |
| M27 | 13.2 | 11.9 |

C-4 In Vitro Tests for Determining the Substrate Properties for P-Glycoprotein (P-Gp)

Many tumour cells express transporter proteins for drugs, and this frequently accompanies the development of resistance towards cytostatics. Substances which are not substrates of such transporter proteins, such as P-glycoprotein (P-gp) or BCRP, for example, could therefore exhibit an improved activity profile.

The substrate properties of a substance for P-gp (ABCB1) were determined by means of a flux assay using LLC-PK1 cells which overexpress P-gp (L-MDR1 cells) [A. H. Schinkel et al., *J. Clin. Invest.* 96, 1698-1705 (1995)]. For this purpose, the LLC-PK1 cells or L-MDR1 cells were cultured on 96-well filter plates for 3-4 days. For determination of the permeation, the respective test substance, alone or in the presence of an inhibitor (such as ivermectin or verapamil, for example), was applied in a HEPES buffer to the cells either apically (A) or basally (B) and incubated for 2 hours. After 0 hours and after 2 hours, samples were taken from the cis and trans compartments. The samples were separated by HPLC using reverse phase columns. The HPLC system was coupled via a Turbo Ion Spray Interface to a Triple Quadropol mass spectrometer API 3000 (Applied Biosystems Applera, Darmstadt, Germany). The permeability was evaluated on the basis of a $P_{app}$ value, which was calculated using the formula published by Schwab et al. [D. Schwab et al., *J. Med. Chem.* 46, 1716-1725 (2003)]. A substance was classified as P-gp substrate when the efflux ratio of $P_{app}$ (B-A) to $P_{app}$ (A-B) was >2.

As further criteria for the evaluation of the P-gp substrate properties, the efflux ratios in L-MDR1 and LLC-PK1 cells or the efflux ratio in the presence or absence of an inhibitor may be compared. If these values differ by a factor of more than 2, the substance in question is a P-gp substrate.

C-5 Pharmacokinetics

After i.v. administration of 3-30 mg/kg of various ADCs, the plasma and tumor concentrations of the antibody parts of the ADCs can be measured by ELISA (see section: analytics for quantifying antibodies) and the pharmacokinetic parameters such as clearance (CL), area under the curve (AUC) and half-life ($t_{1/2}$) can be calculated. Analogously, potentially occurring metabolite concentrations of the ADCs in plasma, tumor and tissue can be measured.

Following administration of 5 mg/kg i.v. of the ADC example 208-8382 to male rats, the following parameters could be determined for the ADC:

| Parameter | Example 208-8382 |
| --- | --- |
| AUCnorm (kg × h/L) | 1506 |
| AUC (mg × h/L) | 7532 |
| Cmax, norm (kg/L) | 21 |
| Cmax (mg/L) | 104 |
| CL (mL/h/kg) | 0.66 |
| Vss (L/kg) | 0.1 |
| MRT (h) | 152 |
| T ½ (h) | 119 |

Analytics for Quantifying the Antibodies Used

The antibody part of the ADCs was determined by ligand binding assay (ELISA) as total IgG concentration in plasma samples and tumor lysates. Here, the sandwich ELISA format was used. This ELISA was qualified and validated for the determination in plasma and tumor samples. The ELISA plates were coated with goat anti-human-IgG-Fc antibodies. After incubation with the sample, the plates were washed and incubated with a detector conjugate of monkey anti-human-IgG(H+L) antibody and horseradish peroxidase (HRP). After a further washing step, the HRP substrate OPD was added and the color development monitored via the absorption at 490 nm. Standard samples with known IgG concentration were fitted by means of a 4-parameter equation. Within the lower (LLOQ) and upper (ULOQ) quantification limits, the unknown concentrations were determined by interpolation.

C-6 Efficacy Assay In Vivo

The efficacy of the conjugates according to the invention were tested in vivo, for example, by means of xenograft models. Methods are known from the prior art to those skilled in the art by which the efficacy of the compounds according to the invention can be assayed (see e.g. WO 2005/081711; Poison et al., Cancer Res. 2009 Mar. 15; 69(6):2358-64). For this purpose, for example, a tumor cell line expressing the target molecule of the binder was implanted in rodents (e.g. mice). Subsequently, either a conjugate according to the invention, an isotype antibody control conjugate or a control antibody or isotonic salt solution was administered to the implanted animals. The administration was carried out once or more often. After an incubation time of several days, the tumor size was determined in comparison to the conjugate-treated animals and the control group. The conjugate-treated animals showed a smaller tumor size.

C-6a. Growth Inhibition/Regression of Experimental Tumors in the Mouse

Human tumor cells expressing the antigen for the Antibody Drug Conjugate are inoculated subcutaneously into the flank of immunosuppressed mice, for example NMRi Nude or SCID mice. 1-10 million cells are removed from the cell culture, centrifuged and resuspended in medium or medium/matrigel. The cell suspension is injected under the skin of the mouse.

A tumor grows in place within a few days. The treatment starts after establishment of the tumor, at around a tumor size of 40 mm². In order to investigate the effect on relatively large tumors, the treatment may be initiated only at a tumor size of 50-100 mm.

The treatment with the ADCs is administered intravenously (i.v.) into the tail vein of the mouse. The ADC is administered at a volume of 5 mL/kg.

The treatment schedule is guided by the pharmacokinetics of the antibody. Standard treatment is three times in succession every fourth day. For slowly growing tumours, treatment is once a week. For a rapid assessment, a schedule having a single treatment may also be suitable. Treatment can however be progressed further or a second cycle of three treatment days may follow on at a later time point.

As standard, 8 animals are used per treatment group. In addition to the groups receiving the active substances, a group is treated only with buffer as control group according to the same schedule.

During the course of the experiment, the tumor area is regularly measured in two dimensions (length/width) using a caliper. The tumor area is determined as length×width. The comparison of the average tumor area of the treated group with the control group is stated as T/C area.

If all experimental groups are terminated at the same time at the end of treatment, the tumors can be removed and weighed. The comparison of the average tumor weight of the treated group with the control group is stated as T/C weight.
C-6b. Efficacy in Human Tumor Xenograft Models The respective tumor cells are inoculated subcutaneously in the flank of female NMRI nude mice (Janvier). The antibody drug conjugate is administered intravenously at a tumor size of ~40 mm². Following the treatment, the tumor growth is followed up as appropriate.

The treatment with the anti-B7H3 antibody drug conjugates leads to a distinct and prolonged tumor growth inhibition compared to the control group and the isotype drug conjugates (the lack of efficacy of the latter was demonstrated in previous experiments). Table 8 gives the T/C values, determined via the tumor weights and tumor area calculated after start of treatment on the day of the final measurement of the control group.

TABLE 8

| Example | Tumor Model | Dose | Dosing schedule | T/C area |
|---|---|---|---|---|
| 208-8382 | SCC4 (human radix linguae carcinoma) | 10 mg/kg | Q7dx3 | 0.34 (Day 32, final) |
| 208-8382 | NCI-H292 (human lung carcinoma) | 10 mg/kg | Q7dx3 | 0.33 (Day 24, final) |
| 208-8382 | A498 (human kidney cell carcinoma) | 10 mg/kg | Q7dx3 | 0.43 (Day 53) |
| 208-8564 | | 10 mg/kg | Q7dx3 | 0.36 (Day 53) |
| 208-8382 | U251 (human glioblastoma) | 5 mg/kg | Q7dx3 | 0.32 (Day 34) |
| 257-8382 | | 5 mg/kg | Q7dx3 | 0.42 (Day 34) |

Working Examples of Anti-B7H3 Antibodies

All examples were carried out using standard methods known to the person skilled in the art, unless described here in detail. Routine methods of molecular biology of the examples that follow can be carried out as described in standard laboratory textbooks such as Sambrook et al., Molecular Cloning: a Laboratory Manual, 2. Edition; Cold Spring Harbor Laboratory Press, Cold Spring Harbor, N.Y., 1989.
Binding of Anti-B7H3 Antibodies to Various Human B7 Antigens by Means of ELISA TPP6497, TPP6499, TPP6501, TPP6502 and TPP6515 were synthesized as described above. Binding of the antibodies to human B7H3 and to human B7H2 and B7H4 was characterized using ELISAs. Black 384-well Maxisorp plates (Nunc) were coated with anti-human IgG Fc (Sigma, 12316; 1:440 dilution) in single coating buffer (Candor) for one hour at 37° C. After washing once with PSB, 0.05% Tween, the plate was blocked with 100% Smart Block (Candor) for one hour at 37° C. The antibody to be tested was then attached to the plate (2 μg/ml IgG in PBS, 0.05% Tween, 10% Smart Block; 1 hour, room temperature). After washing three times, the plate was incubated with the antigen in question or with buffer alone (37 ng/ml in PBS, 0.05% Tween, 10% Smart block; B7H2: RnDSystems, 8206-B7; B7H3: RnDSystems, 2318-B3-050/CF; B7H4. RnDSystems, 6576-B7; 1 hour, room temperature). After washing three times, the plate was incubated with an anti-His HRP antibody (Novagen, 71840-3; 1:10000 dilution; 1 hour, room temperature). After washing three times, the plate was incubated with Amplex Red for 30 minutes and then read. The data in Table AK-1 show that TPP6497, TPP6499, TPP6501, TPP6502 and TPP6515 B7H3 bind B7H3, but not B7H2 or B7H4.

TABLE AK-1

Binding of anti-B7H3 antibodies to B7H2, B7H3 and B7H4

| B7 Protein | B7H2 | B7H3 | B7H4 |
|---|---|---|---|
| Quotient signal (B7)/signal (buffer) TPP6497 | <1.5 | 111 | <1.5 |
| Quotient signal (B7)/signal (buffer) TPP6499 | <1.5 | 109 | <1.5 |
| Quotient signal (B7)/signal (buffer) TPP6501 | <1.5 | 118 | <1.5 |
| Quotient signal (B7)/signal (buffer) TPP6502 | <1.5 | 126 | <1.5 |
| Quotient signal (B7)/signal (buffer) TPP6515 | <1.5 | 116 | <1.5 |

By virtue of their specific binding to B7H3, TPP6497, TPP6499, TPP6501, TPP6502 and TPP6515 are suitable candidates for the development of therapeutics for the treatment of diseases and other adverse effects which involve B7H3-expressing cells. According to the invention, it is possible to achieve, by the amino acid substitutions listed below, an even closer similarity of the antibodies mentioned with human germ line sequences: these are, for TPP6497 in the height chain: P33T, G51S, S53N, N54Q, S77T, R80Q, S81A, Q90A, S91A, F92W, F92Y, S94D, K97N, K97S, K98G, K105Q. For TPP6497 in the heavy chain: R30S, S50A, V51I, A58T, L59Y, T97A, R98K. For TPP6499 in the light chain: G25S, Y26S, V29I, G31S, N33Y, N33T, N35Y, G51R, S53N, N54Q, S77T, R80Q, S81A, Q90A, S91A, Y92W, S94D, K106Q. For TPP6499 in the heavy chain: R30S, D31S, F32Y, Y33A, N35S, I37V, S50A, S50Y, A53G, A53S, K56G, K56S, Y57S, Y57T, P114S, P114Y. For TPP6501 in the light chain: R31S, I33Y, I33T, N35Y, S52N, Q90A, T91A, G93D, T94D, G95S, W96L, V97S, F98G, K103Q. For TPP6501 in the heavy chain: G33A, H35S, N101Y, L103Y, L103N, L113T. For TPP6502 in the light chain: G25S, P33Y, P33T, N35Y, G51R, S53N, K54Q, Q90A, S91A, Y92W, S94D, W99V, G103E, K106E. For TPP6502 in the heavy chain: T31S, G33A, H35S, T97A, R98K, L113T. For TPP6515 in the light chain: T33Y, N35Y, D53N, L56P, L57S, Q90A, S91A, Y92W, S94D, W99V, G103E, K106E. For TPP6515 in the heavy chain: G33A, H35S, V40A, T57S, L104Y, L104W, Y107S.

These substitutions further reduce immunogenicity in humans, which is an advantageous property with respect to the development of therapeutics based on the antibodies according to the invention.

Determination of the Binding Affinity of the Antibodies by Surface Plasmon Resonance Surface plasmon resonance (SPR) experiments for quantitative binding analysis were earned out using a Biacore T200 instrument (GE Healthcare Biacore, Inc.). Here, the antibodies to be investigated were fixed with the aid of an anti-human Fc antibody amine-coupled to the sensor chip surface ("Human Antibody Capture Kit", BR-1008-39, GE Healthcare Biacore, Inc."). The amine coupling was carried out according to the manufacturer's instructions using 1-ethyl-3-(3-dimethylaminopropyl) carbodiimide hydrochloride (EDC), N-hydroxysuccinimide (NHS) and ethanolamine HCl pH 8.5 ("Amine Coupling Kit" BR-1000-50, GE Healthcare Biacore, Inc.). For the analyses, Series S Sensor Chips CM5 (GE Healthcare Biacore, Inc.) were used with the running buffer HBS-EP+ (10 mM HEPES pH 7.4, 150 mM NaCl, 3 mM EDTA, 0.05% Surfactant P20). All experimental steps were carried out at 25° C. After fixing of the anti-B7H3 antibodies to be investigated, injections of the extracellular domain of B7H3 (analyte, R&D Systems) were carried out at a concentration of 400 nM, where the sensor surface was regenerated with glycine HCl pH 2.0 after each antigen injection. Before a fresh analyte injection, antibodies were each fixed under identical conditions as before. For all measurements, an upstream flow cell served as reference cell in which only immobilized amine-coupled anti-human Fc antibody was present. For semiquantitative comparison with each other, the sensorgrams obtained were evaluated after double-referencing (subtraction of the reference flow cell signal and a buffer injection) by a global fit based on a 1:1 Langmuir binding model using the Biacore T200 Evaluation Software (GE Healthcare Biacore, Inc.).

TABLE AK-2 recombinant antigens (B7H3) used for affinity comparison

| Nomenclature | Description | Origin | Cat. No (R&D) |
|---|---|---|---|
| TPP-3761 | B7H3 short | human | 1949-B3/CF |
| TPP-3760 | B7H3 long | human | 2318-B3/CF |

TABLE AK-3

Approximate monovalent and apparent $K_D$ values of the anti-B7H3 antibodies determined by SPR with B7H3 short and B7H3 long proteins (TPP-3761 and TPP-3760 as analyte)

| Nomenclature | Approximate monovalent affinity value ($K_D$ in nM) | Approximate apparent affinity value ($K_{Dapp}$ in nM) |
|---|---|---|
| TPP-6497 | 1.0E−06 | 1.2E−08 |
| TPP-8382 | 7.7E−07 | 1.2E−08 |
| TPP-8567 | 8.3E−07 | 1.3E−08 |

TABLE AK-3-continued

Approximate monovalent and apparent $K_D$ values of the anti-B7H3 antibodies determined by SPR with B7H3 short and B7H3 long proteins (TPP-3761 and TPP-3760 as analyte)

| Nomenclature | Approximate monovalent affinity value ($K_D$ in nM) | Approximate apparent affinity value ($K_{Dapp}$ in nM) |
|---|---|---|
| TPP-8322 | 7.5E−07 | 1.0E−08 |
| TPP-8568 | 1.4E−06 | 1.1E−08 |
| TPP-8748 | 1.8E−06 | 9.4E−09 |
| TPP-8750 | 1.2E−06 | 9.5E−09 |

Binding of Anti-B7H3 Antibodies to Various Antigen-Expressing Cancer Cell Lines

The binding of the anti-B7H3 antibodies to various human cancer cell lines (A498, U251, U87 MG) was investigated by flow cytometry. For this purpose, the cells (5×10 cells/well) were incubated in FACS buffer (PBS without Ca/Mg, 3% FCS, Biochrom) with 10 μg/mL primary antibody solution (start concentration) on ice for 30-45 min protected from light. A dose response curve (1:5 dilution) was generated. Following incubation, 200 μL of ice-cold FACS buffer were pipetted in and the cell suspension was centrifuged at 4° C., 400 g for 4 min. The cell pellet was washed with 300 μL of ice-cold FACS buffer prior to resuspending the pellet obtained in 100 μL of FACS buffer and again incubating for 30 min on ice with secondary antibody (monoclonal anti-kappa light chains FITC antibody, Sigma, No. SAB4700605) in a 1:10 dilution. Subsequently, the cells were washed with ice-cold FACS buffer and adjusted to a cell concentration of 0.5×10$^6$ cells/mL before carrying out the flow cytometry using a Guava flow cytometer (Millipore). Propidium iodide (final concentration 1 μg/mL) was used for the live staining. With the aid of the background-corrected geometric mean fluorescence values, the IC50 value of the antibody to be investigated was determined.

TABLE AK-4

FACS Analysis: Binding of the anti-B7H3 antibodies to various cancer cell lines.

| Cell Line | A498 EC50 [M] | U251 MG EC50 [M] | U87 MG EC50 [M] |
|---|---|---|---|
| Source | ATCC No. HTW-44 | CLS No. 300385 | ATCC No. HTB-14 |
| TPP-6497 | 3.10E−10 | | |
| TPP-7611 | 5.99E−10 | 4.85E−10 | |
| TPP-8382 | 1.03E−09 | 1.42E−09 | 2.15E−09 |
| TPP-8564 | 1.39E−09 | 1.61E−09 | 1.71E−09 |
| TPP-8567 | 1.79E−09 | 1.10E−09 | 1.67E−09 |
| TPP-6502 | 1.43E−10 | | |
| TPP-8322 | 1.02E−09 | 8.33-10 | 8.87E−10 |
| TPP-8565 | 9.41E−10 | 8.18E−10 | 8.21E−10 |
| TPP-8568 | 6.75E−10 | 6.20E−10 | 8.18E−10 |
| TPP-8748 | 1.67E−09 | 7.83E−10 | |
| TPP-8750 | 8.55E−10 | 7.07E−10 | |
| TPP-6501 | 1.23E−09 | | |
| TPP-6499 | 8.47E−10 | | |
| TPP-6515 | 6.61E−10 | | |

The invention claimed is:
1. A conjugate of an antibody with one or more drug molecules of the formula below:

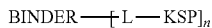

wherein
BINDER is a glycosylated or aglycosylated anti-B7H3 antibody, or an antigen-binding fragment thereof comprising:
  a variable heavy chain comprising the variable CDR1 sequence of the heavy chain, as shown in SEQ ID NO: 2, the variable CDR2 sequence of the heavy chain, as shown in SEQ ID NO: 3, and the variable CDR3 sequence of the heavy chain, as shown in SEQ ID NO: 4, and
  a variable light chain comprising the variable CDR1 sequence of the light chain, as shown in SEQ ID NO: 6, the variable CDR2 sequence of the light chain, as shown in SEQ ID NO: 7, and the variable CDR3 sequence of the light chain, as shown in SEQ ID NO: 8; or
  a variable heavy chain comprising the variable CDR1 sequence of the heavy chain, as shown in SEQ ID NO: 12, the variable CDR2 sequence of the heavy chain, as shown in SEQ ID NO: 13, and the variable CDR3 sequence of the heavy chain, as shown in SEQ ID NO: 14, and
  a variable light chain comprising the variable CDR1 sequence of the light chain, as shown in SEQ ID NO: 16, the variable CDR2 sequence of the light chain, as shown in SEQ ID NO: 17, and the variable CDR3 sequence of the light chain, as shown in SEQ ID NO: 18; or
  a variable heavy chain comprising the variable CDR1 sequence of the heavy chain, as shown in SEQ ID NO: 22, the variable CDR2 sequence of the heavy chain, as shown in SEQ ID NO: 23, and the variable CDR3 sequence of the heavy chain, as shown in SEQ ID NO: 24, and
  a variable light chain comprising the variable CDR1 sequence of the light chain, as shown in SEQ ID NO: 26, the variable CDR2 sequence of the light chain, as shown in SEQ ID NO: 27, and the variable CDR3 sequence of the light chain, as shown in SEQ ID NO: 28; or
  a variable heavy chain comprising the variable CDR1 sequence of the heavy chain, as shown in SEQ ID NO: 32, the variable CDR2 sequence of the heavy chain, as shown in SEQ ID NO: 33, and the variable CDR3 sequence of the heavy chain, as shown in SEQ ID NO: 34, and
  a variable light chain comprising the variable CDR1 sequence of the light chain, as shown in SEQ ID NO: 36, the variable CDR2 sequence of the light chain, as shown in SEQ ID NO: 37, and the variable CDR3 sequence of the light chain, as shown in SEQ ID NO: 38; or
  a variable heavy chain comprising the variable CDR1 sequence of the heavy chain, as shown in SEQ ID NO: 42, the variable CDR2 sequence of the heavy chain, as shown in SEQ ID NO: 43 and the variable CDR3 sequence of the heavy chain, as shown in SEQ ID NO: 44, and
  a variable light chain comprising the variable CDR1 sequence of the light chain, as shown in SEQ ID NO: 46, the variable CDR2 sequence of the light chain, as shown in SEQ ID NO: 47 and the variable CDR3 sequence of the light chain, as shown in SEQ ID NO: 48; or
  a variable heavy chain comprising the variable CDR1 sequence of the heavy chain, as shown in SEQ ID NO: 2, the variable CDR2 sequence of the heavy chain, as shown in SEQ ID NO: 56 and the variable CDR3 sequence of the heavy chain, as shown in SEQ ID NO: 4, and
  a variable light chain comprising the variable CDR1 sequence of the light chain, as shown in SEQ ID NO: 6, the variable CDR2 sequence of the light chain, as shown in SEQ ID NO: 58 and the variable CDR3 sequence of the light chain, as shown in SEQ ID NO: 8;
L is a linker,
n is a number from 1 to 50, and
KSP is a compound of formula (I) below:

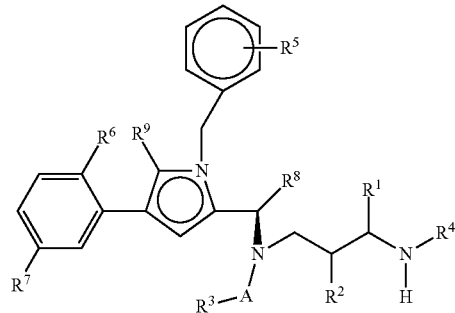

Formula (I)

wherein
$R^1$ is —H, -L-#1, -MOD or —$(CH_2)_{0-3}Z$,
  wherein
  Z is —H, —$NHY^3$, —$OY^3$, —$SY^3$, halogen, —C(=O)—$NY^1Y^2$ or —C(=O)—$OY^3$,
  $Y^1$ and $Y^2$ are independently —H, —$NH_2$, —$(CH_2CH_2O)_{0-3}$—$(CH_2)_{0-3}Z'$ or —$CH(CH_2W)Z'$,
  $Y^3$ is —H or —$(CH_2)_{0-3}Z'$,
  Z' is —H, —$NH_2$, —$SO_3H$, —COOH, —NH—C(=O)—$CH_2$—$CH_2$—$CH(NH_2)COOH$ or —(C=O—NH—$CHY^4)_{1-3}COOH$;
  W is H or OH,
  $Y^4$ is straight-chain or branched $C_{1-6}$ alkyl which is optionally substituted by —NH—C(=O)—$NH_2$, or is aryl or benzyl which are optionally substituted by —$NH_2$;
$R^2$ is H, -MOD, —C(=O)—$CHY^4$—$NHY^5$ or —$(CH_2)_{0-3}Z$,
  wherein
  Z is —H, halogen, —$OY^3$, —$SY^3$, —$NHY^3$, —C(=O)—$NY^1Y^2$ or —C(=O)—$OY^3$,
  $Y^1$ and $Y^2$ are independently —H, —$NH_2$ or —$(CH_2)_{0-3}Z'$,
  $Y^3$ is —H or —$(CH_2)_{0-3}Z'$,
  Z' is —H, —$SO_3H$, —$NH_2$ or —COOH;
  $Y^4$ is straight-chain or branched $C_{1-6}$-alkyl which is optionally substituted by —NH—C(=O)—$NH_2$, or is aryl or benzyl which are optionally substituted by —$NH_2$, and Y⁵ is —H or —C(=O)—CHY⁶—NH₂,
Y⁶ is straight-chain or branched $C_{1-6}$-alkyl;
R⁴ is —H, -L-#1, —SG$_{lys}$-(C=O)$_{0-1}$—R⁴', —C(=O)—CHY⁴—NHY⁵ or —(CH₂)$_{0-3}$Z,
wherein
SG$_{lys}$ is a group cleavable by lysosomal enzymes,
R⁴' R⁴' is a $C_{1-10}$-alkyl, $C_{5-10}$-aryl or $C_{6-10}$-aralkyl, $C_{5-10}$-heteroalkyl, $C_{1-10}$-alkyl-O—$C_{6-10}$-aryl, $C_{5-10}$-heterocycloalkyl, heteroaryl, heteroarylalkyl, heteroarylalkoxy, $C_{1-10}$-alkoxy, $C_{6-10}$-aryloxy or $C_{6-10}$-aralkoxy, $C_{5-10}$-heteroaralkoxy, $C_{1-10}$-alkyl-O—$C_{6-10}$-aryloxy, $C_{5-10}$-heterocycloalkoxy group, which may be substituted once or more than once by —NH₂, —NH-alkyl, —N(alkyl)₂, NH—C(=O)-alkyl, N(alkyl)-C(=O)alkyl, —SO₃H, —SO₂NH₂, —SO₂—N(alkyl)₂, —COOH, —C(=O)NH₂, —C(=O)N(alkyl)₂, or —OH, —H or a group —O$_x$—(CH₂CH₂O)$_v$—R⁴''',
wherein x is 0 or 1,
wherein v is a number from 1 to 20,
wherein R⁴''' is —H, -alkyl, —CH₂—COOH, —CH₂—CH₂—COOH, or —CH₂—CH₂—NH₂;
Z is —H, halogen, —OY³, —SY³, NHY³, —C(=O)—NY¹Y² or —C(=O)—OY³,
Y¹ and Y² are independently —H, —NH₂ or —(CH₂)$_{0-3}$Z',
Y³ is —H or —(CH₂)$_{0-3}$Z',
Z' is —H, —SO₃H, —NH₂ or —COOH;
Y⁴ is straight-chain or branched $C_{1-6}$-alkyl which is optionally substituted by —NH—C(=O)—NH₂, or is aryl or benzyl which are optionally substituted by —NH₂,
Y⁵ is —H or —C(=O)—CHY⁶—NH₂, and
Y⁶ is straight-chain or branched $C_{1-6}$-alkyl;
or
R² and R⁴ taken together form a pyrrolidine ring, wherein the atoms linking R² and R⁴ are of the formula —CH₂—CHR¹¹— or —CHR¹¹—CH₂—;
wherein
R¹¹ is —H, —NH₂, —SO₃H, —COOH, —SH, halogen, $C_{1-4}$-alkyl, $C_{1-4}$-haloalkyl, $C_{1-4}$-alkoxy, hydroxyl-substituted $C_{1-4}$-alkyl, —C(=O)—O—($C_{1-4}$-alkyl) or —OH;
A is —C(=O)—, —S(=O)—, —S(=O)₂—, —S(=O)₂NH— or —CNNH—;
R³ is -L-#1, -MOD or an optionally substituted alkyl, cycloalkyl, aryl, heteroaryl, heteroalkyl, heterocycloalkyl group, which may each be substituted by 1-3 —OH groups, 1-3 halogen atoms, 1-3 halogenated alkyl groups, 1-3 —O-alkyl groups, 1-3 —SH groups, 1-3 —S-alkyl groups, 1-3 —O—C(=O)-alkyl groups, 1-3 —O—C(=O)—NH—alkyl groups, 1-3 —NH—C(=O)-alkyl groups, 1-3 —NH—C(=O)—NH—alkyl groups, 1-3 —S(=O)$_n$-alkyl groups, 1-3 —S(=O)₂NH-alkyl groups, 1-3 —NH-alkyl groups, 1-3 —N(alkyl)₂ groups, 1-3 —NH₂ groups or 1-3 —(CH₂)$_{0-3}$Z groups,
wherein
n is 0, 1 or 2,
Z is —H, halogen, —OY³, —SY³, —NHY³, —C(=O)—NY¹Y² or —C(=O)—OY³,
Y¹ and Y² are independently —H, —NH₂ or —(CH₂)$_{0-3}$Z',
Y³ is —H, —(CH₂)$_{0-3}$—CH(NH—C(=O)—CH₃)Z', —(CH₂)$_{0-3}$—CH(NH₂)Z' or —(CH₂)$_{0-3}$Z',
Z' is —H, —SO₃H, —NH₂ or —COOH, R⁵ is —H, —NH₂, —NO₂, halogen, —CN, CF₃, —OCF₃, —CH₂F, —CH₂F, SH or —(CH₂)$_{0-3}$Z,
wherein
Z is —H, —OY³, —SY³, halogen, —NHY³, —C(=O)—NY¹Y² or —C(=O)—OY³,
Y¹ and Y² are independently —H, —NH₂ or —(CH₂)$_{0-3}$Z',
Y³ is —H or —(CH₂)$_{0-3}$Z',
Z' is —H, —SO₃H, —NH₂ or —COOH;
R⁶ and R⁷ are independently —H, cyano, $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, hydroxy, —NO₂, —NH₂, —COOH or halogen,
R⁸ is $C_{1-10}$-alkyl, fluoro-$C_{1-10}$-alkyl, $C_{2-10}$-alkenyl, fluoro-$C_{2-10}$-alkenyl, $C_{2-10}$-alkynyl, fluoro-$C_{2-10}$-alkynyl, $C_{4-10}$-cycloalkyl, fluoro-$C_{4-10}$-cycloalkyl or —(CH₂)$_{0-2}$—(HZ²), which may be mono- or disubstituted identically or differently by —OH, —COOH or —NH₂, and
wherein
HZ² is a 4- to 7-membered heterocycle having up to two heteroatoms selected from the group consisting of N, O and S,
R⁹ is —H, —F, —CH₃, —CF₃, —CH₂F or —CHF₂;
wherein
one of the substituents R¹, R³ and R⁴ is -L-#1,
L is the linker and #1 is the bond to the antibody,
-MOD is —(NR¹⁰)$_n$-(G1)$_o$-G2-G3,
wherein
R¹⁰ is —H or $C_1$-$C_3$-alkyl;
G1 is —NHC(=O)—, —C(=O)—NH—;
n is 0 or 1;
o is 0 or 1; and
G2 is a straight-chain or branched hydrocarbon chain which has 1 to 10 carbon atoms and which may be interrupted once or more than once by one or more of the groups —O—, —S—, —S(=O)—, S(=O)₂, —NR$^y$—, —NR$^y$C(=O)—, —C(=O)—NR$^y$—, —NR$^y$NR$^y$—, —S(=O)₂—NR$^y$NR$^y$—, —C(=O)—NR$^y$NR$^y$—,
wherein
R$^y$ is —H, phenyl, $C_1$-$C_{10}$-alkyl, $C_2$-$C_{10}$-alkenyl or $C_2$-$C_{10}$-alkynyl, each of which may be mono- or polysubstituted identically or differently by —NH—C(=O)—NH₂, —COOH, —OH, —NH₂, —NH—CN—NH₂, sulfonamide, sulfone, sulfoxide or sulfonic acid,
and/or which may be interrupted one or more times, identically or differently, by —C(=O)—, —CR$^x$=N—O—,
wherein
R$^x$ is —H, $C_1$-$C_3$-alkyl or phenyl, and
wherein
the hydrocarbon chain including a $C_1$-$C_{10}$-alkyl group optionally substituted on the hydrocarbon group as side chain may be substituted by —NH—C(=O)—NH₂, —COOH, —OH, —NH₂, —NH—CN—NH₂, sulfonamide, sulfone, sulfoxide or sulfonic acid,
G3 is —H or —COOH,
or a salt, a solvate, a salt of the solvate or an epimer thereof.
2. The conjugate according to claim 1, wherein A is —C(=O)—.
3. The conjugate according to claim 1, wherein R¹ is —H, -L-#1, —COOH, —C(=O)—NHNH₂, —(CH₂)$_{1-3}$NH₂, —C(=O)—NZ"(CH$_2$)$_{1-3}$NH$_2$ or —C(=O)—NZ"CH$_2$COOH, wherein Z" is —H or —NH$_2$.

4. The conjugate according to claim 1, wherein R$^2$ and R$^4$ are —H, or R$^2$ and R$^4$ taken together form a pyrrolidine ring, wherein the atoms linking R$^2$ and R$^4$ are of the formula —CH$_2$—CHR$^{11}$— or —CHR$^{11}$—CH$_2$—;
wherein R$^{11}$ is —H, —COOH, —F, CH$_3$—, —CH$_2$F, —OCH$_3$, —CH$_2$OH,
—C(=O)—O—(C$_{1-4}$-alkyl) or OH.

5. The conjugate according to claim 1, wherein R$^3$ is -L-#1 or is a phenyl group which may be mono- or polysubstituted by halogen, C$_{1-3}$-alkyl or fluoro-C$_{1-3}$-alkyl, or is a C$_{1-10}$-alkyl group or fluoro-C$_{1-10}$-alkyl group which is optionally substituted by —OY$^4$, —SY$^4$, —O—C(=O)—Y$^4$, —O—C(=O)—NH—Y$^4$, —NH—C(=O)—Y$^4$, —NH—C(=O)—NH—Y$^4$, —S(O)$_n$—Y$^4$, —S(=O)$_2$—NH—Y$^4$, —NH—Y$^4$ or —N(Y$^4$)$_2$,
wherein
n is 0, 1 or 2,
Y$^4$ is —H, phenyl which is optionally mono- or polysubstituted by halogen, C$_{1-3}$ alkyl, or fluoro-C$_{1-3}$-alkyl, or is alkyl which may be substituted by —OH, —COOH, and/or —NH—C(O)—C$_{1-3}$-alkyl.

6. The conjugate according to claim 5, wherein the conjugate has the formula (IIj) below:

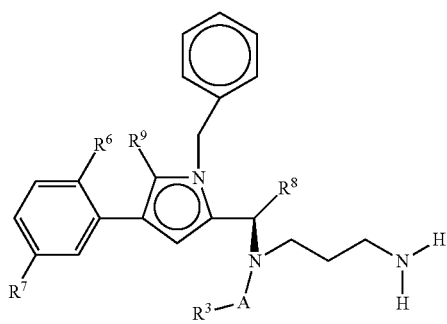

(IIj)

wherein
R$^3$ is -L-#1;
A is —C(=O).

7. The conjugate according to claim 1, wherein the substituent R$^1$ is -L-#1.

8. The conjugate according to claim 7, wherein the conjugate has the formula (IIk):

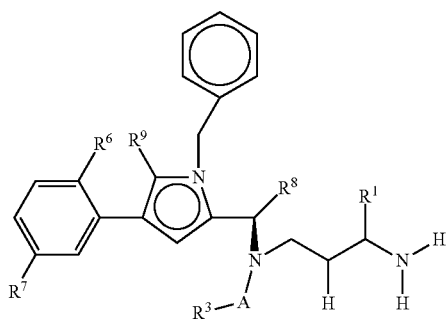

(IIk)

wherein
R$^1$ is -L-#1;
A is —C(=O)— and
R$^3$ is —CH$_2$OH.

9. The conjugate according to claim 1, wherein R$^5$ is —H or —F.

10. The conjugate according to claim 1, wherein R$^6$ and R$^7$ are independently —H, C$_{1-3}$-alkyl, fluoro-C$_{1-3}$-alkyl, C$_{2-4}$-alkenyl, fluoro-C$_{2-4}$-alkenyl, C$_{2-4}$-alkynyl, fluoro-C$_{2-4}$-alkynyl, hydroxy or halogen.

11. The conjugate according to claim 1, wherein R$^8$ is a branched C$_{1-5}$-alkyl group or cyclohexyl.

12. The conjugate according to claim 1, wherein R$^9$ is —H or fluorine.

13. The conjugate according to claim 1, wherein the linker -L- has one of the basic structures (i) to (iv) below:
(i) —(C=O)$_m$-SG1-L1-L2-;
(ii) —(C=O)$_m$-L1-SG-L1-L2-;
(iii) —(C=O)$_m$-L1-L2-;
(iv) —(C=O)$_m$-L1-SG-L2,
wherein m is 0 or 1, SG and SG1 represent in vivo cleavable groups, each L1 is independently an organic group not cleavable in vivo, and L2 is a group configured to couple to the binder.

14. The conjugate according to claim 13, wherein the in vivo cleavable group SG is a 2-8 oligopeptide group, or a disulfide, a hydrazone, an acetal or an aminal and SG1 is a 2-8 oligopeptide group.

15. The conjugate according to claim 1, wherein the linker L is attached to a cysteine side chain or a cysteine residue and has the formula below:

§ —(C(=O)—)$_m$-L1-L2-§ § wherein
m is 0 or 1;
§ is the bond to the active compound molecule, and
§ § is the bond to the antibody, and
-L2- is

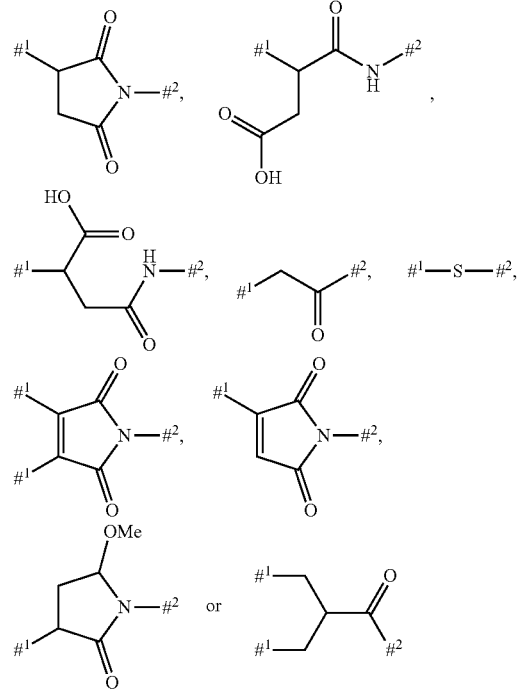

wherein
¹ denotes the point of attachment to the sulfur atom of the antibody,
² denotes the point of attachment to group L¹,
L1 —(NR¹⁰)$_n$-(G1)$_o$-G2-,
wherein
R¹⁰ is —H, —NH$_2$ or C$_1$-C$_3$-alkyl;
G1 is —NH—C(=O)—;
n is 0 or 1;
o is 0 or 1; and
G2 is a straight-chain or branched hydrocarbon chain having 1 to 100 carbon atoms from aryl groups, and/or straight-chain and/or branched alkyl groups, and/or cyclic alkyl groups and which may be interrupted once or more than once, identically or differently, by —O—, —S—, —S(=O)—, S(=O)$_2$—, —NH—, —C(=O)—, —N—CH$_3$—, —NHNH—, —S(=O)$_2$—NHNH—, —NH—C(=O)—, —C(=O)—NH—, —C(=O)—NH—NH— and a 5- to 10-membered aromatic or non-aromatic heterocycle having 1 to 4 identical or different heteroatoms and/or hetero groups selected from the group consisting of N, O and S, —S(=O)— or —S(=O)$_2$—,
wherein
straight-chain or branched hydrocarbon chain may optionally be substituted by —NH—C(=O)—NH$_2$, —COOH, —OH, —NH$_2$, —NH—CNNH, sulfonamide, sulfone, sulfoxide or sulfonic acid,
or is one of the groups below:

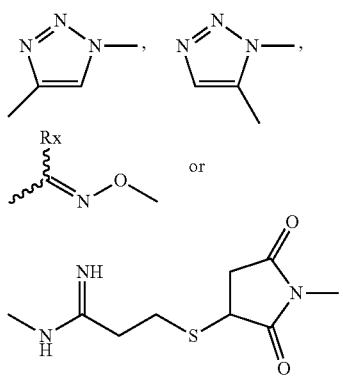

wherein R$^x$ is —H, C$_1$-C$_3$-alkyl or phenyl.

16. The conjugate according to claim 15, wherein L2 is represented by one or both of the formulae below:

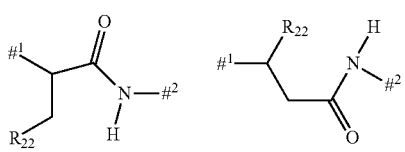

wherein
¹ denotes the point of attachment to the sulfur atom of the binder, #² denotes the point of attachment to group L¹, R²² is —COOH and
more than 80% (based on the total number of bonds of the linker to the binder) of the bonds to the sulfur atom of the binder are present in one of these two structures.

17. The conjugate according to claim 15, wherein L¹ has the formulae below:

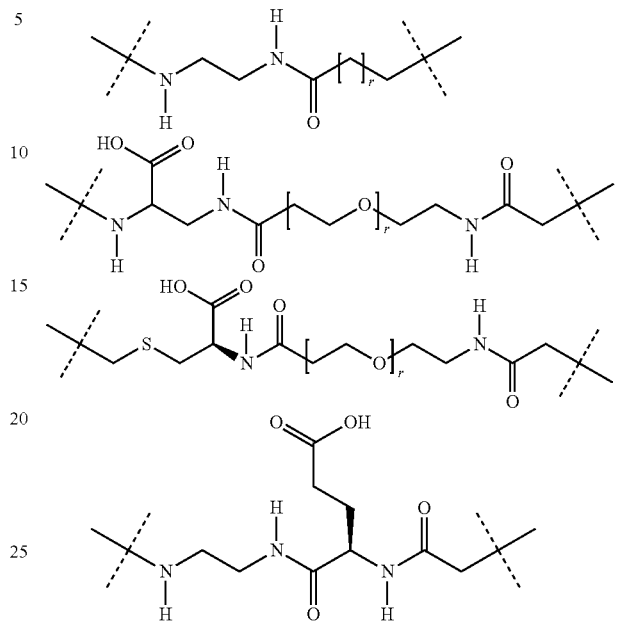

wherein
r is a number from 0 to 8.

18. The conjugate according to claim 1, wherein the linker -L- is attached to a cysteine side chain or a cysteine residue and has the formula below:

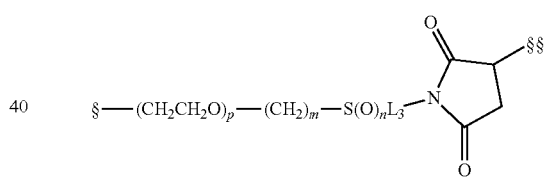

wherein
§ is the bond to the active compound molecule, and
§ § is the bond to the antibody,
m is 0, 1, 2 or 3;
n is 0, 1 or 2;
p is a number from 0 to 20; and
L3 is

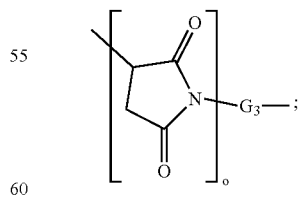

wherein
o is 0 or 1; and
G3 is a straight-chain or branched hydrocarbon chain having 1 to 100 carbon atoms from aryl groups, and/or straight-chain and/or branched alkyl groups, and/or cyclic alkyl groups and which may be interrupted once or more than once, identically or differently, by —O—, —S—, —S(=O)—, S(=O)₂—, —NH—, —C(=O)—, —N—CH₃—, —NHNH—, —S(=O)₂—NHNH—, —NH—C(=O)—, —C(=O)—NH—, —C(=O)—NH—NH— and a 5- to 10-membered aromatic or non-aromatic heterocycle having 1 to 4 identical or different heteroatoms and/or hetero groups selected from the group consisting of N, O and S, —S(=O)— or —S(=O)₂—, wherein the straight-chain or branched hydrocarbon chain may optionally be substituted by —NH—C(=O)—NH₂, —COOH, —OH, —NH₂—, NH—CN—NH₂, sulfonamide, sulfone, sulfoxide or sulfonic acid.

19. The conjugate according to claim 1, wherein the conjugate has one of the formulae below:

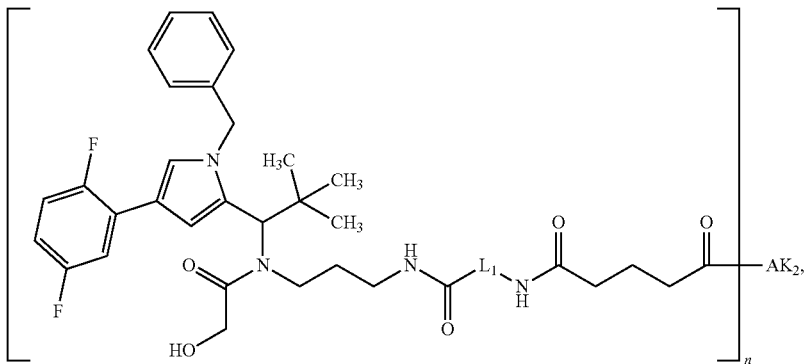

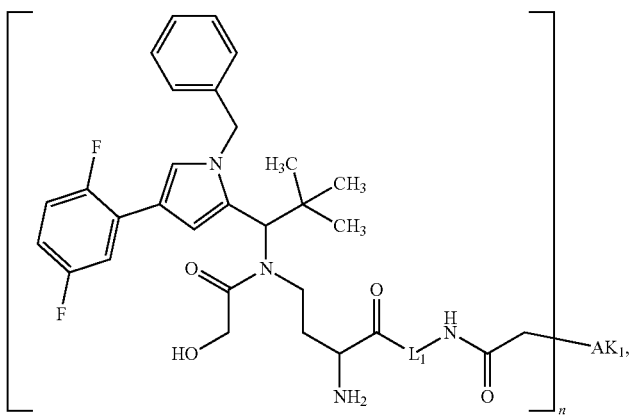

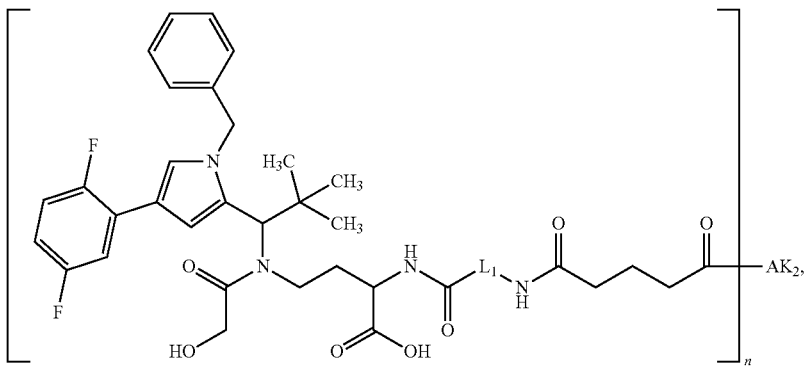

-continued
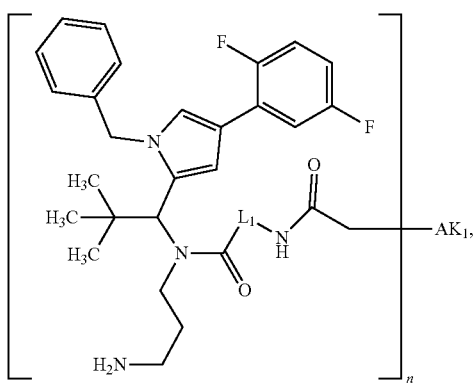
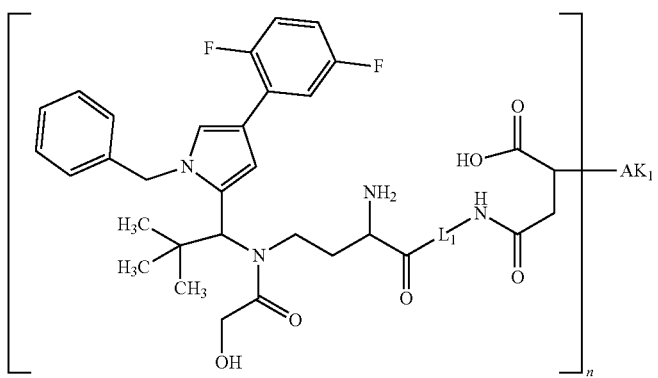
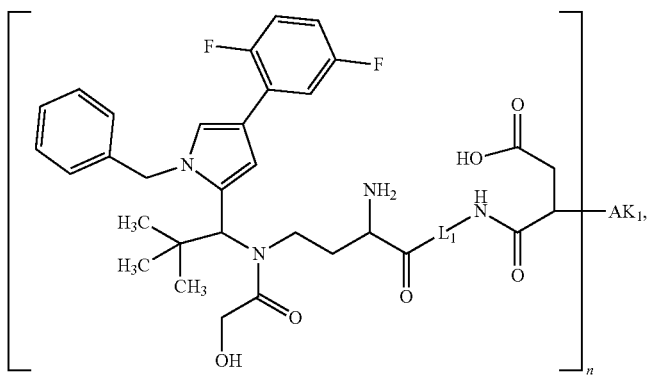
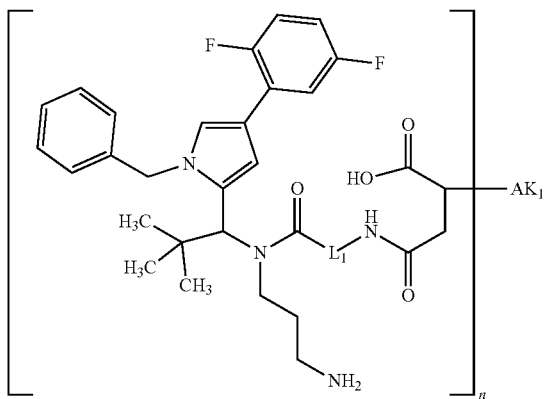

625
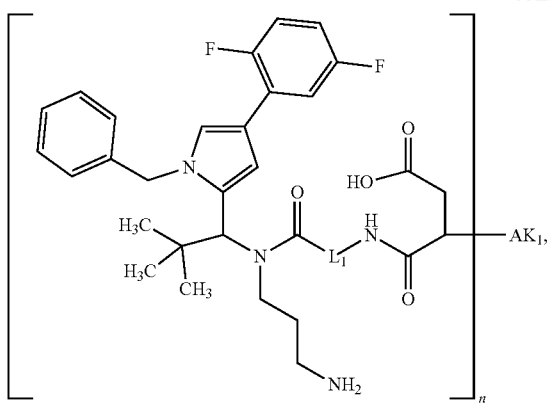
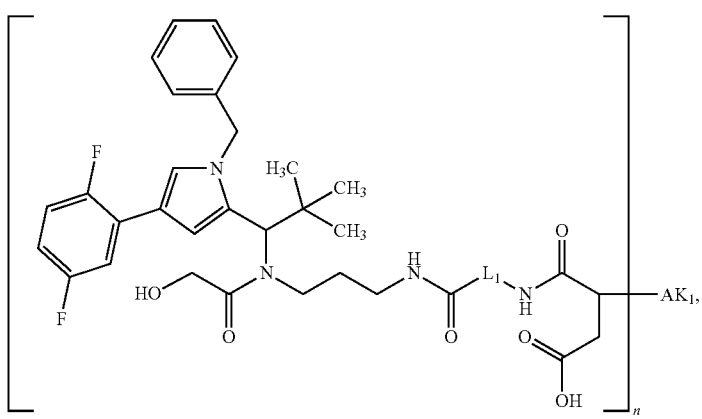
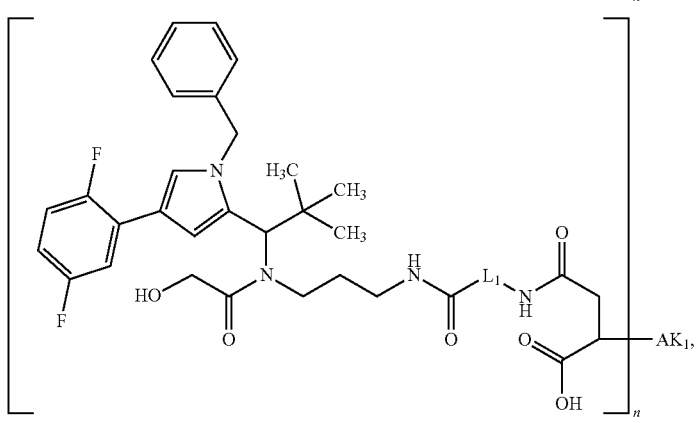
-continued
626
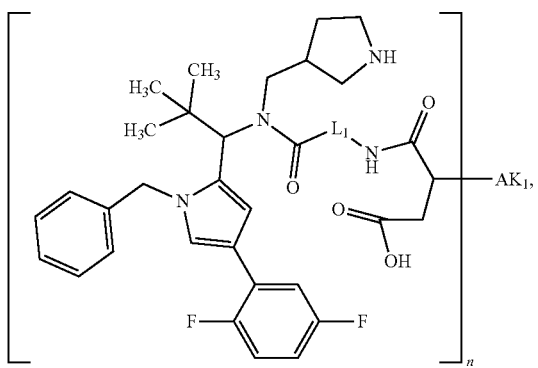 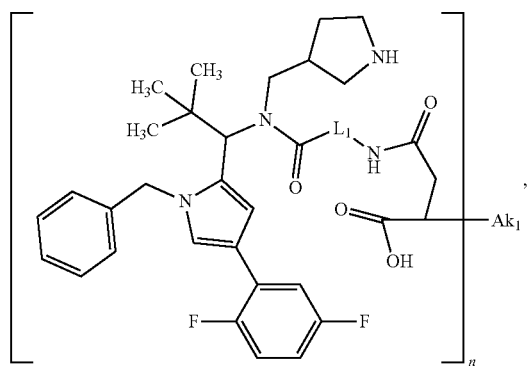

-continued
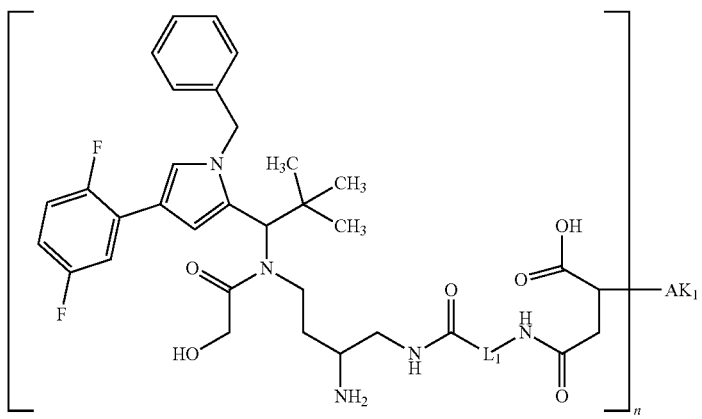
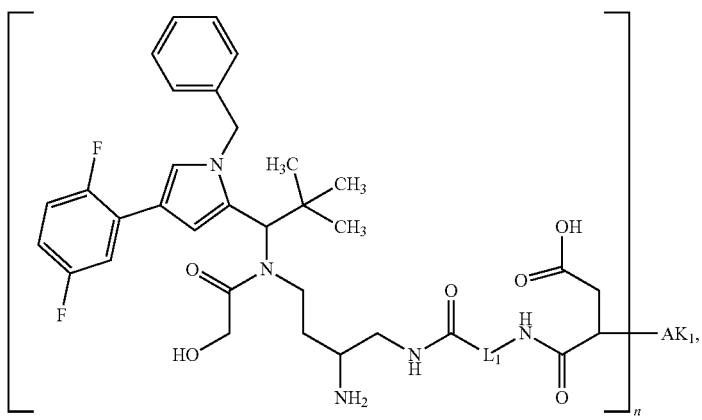
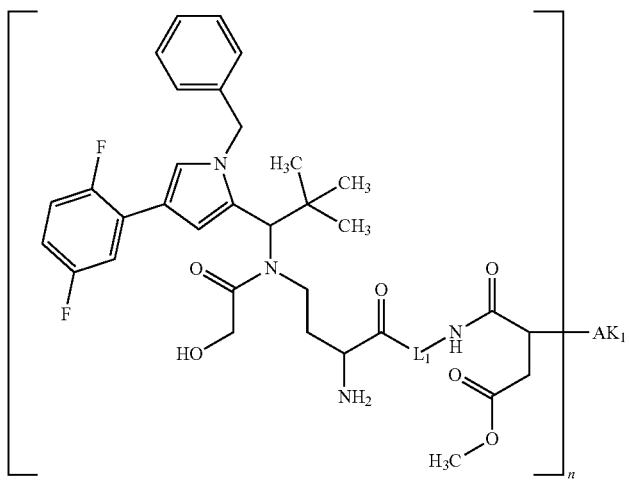

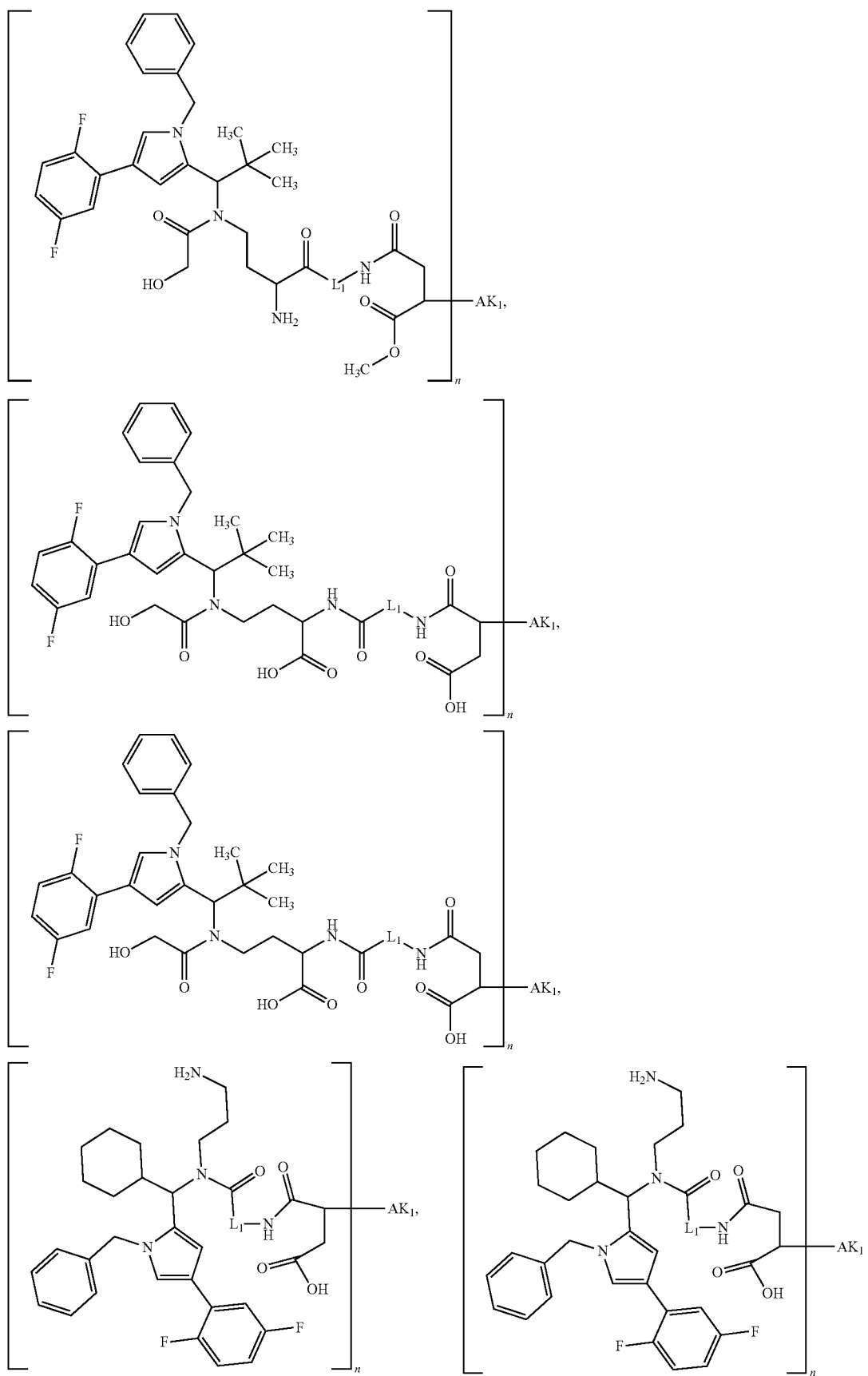

-continued
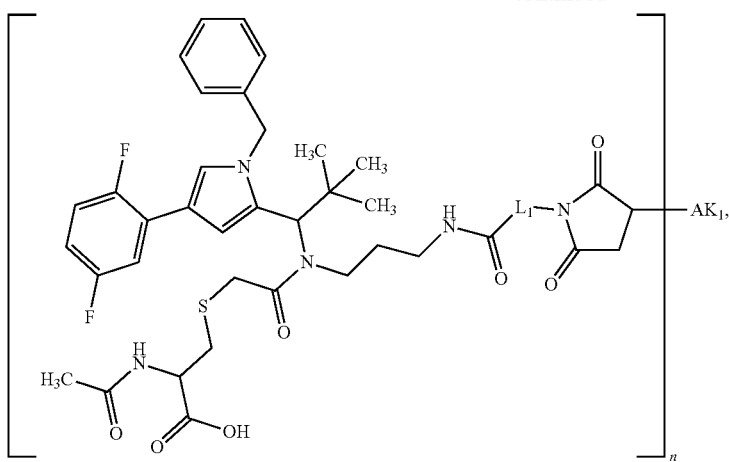
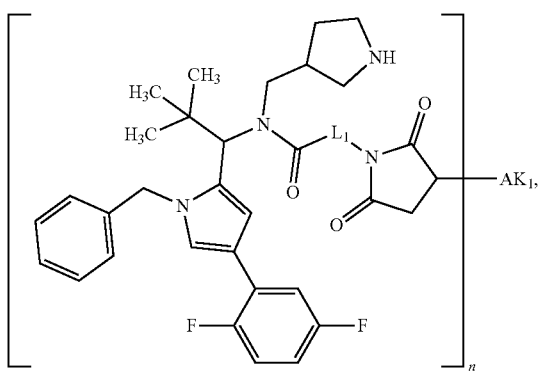
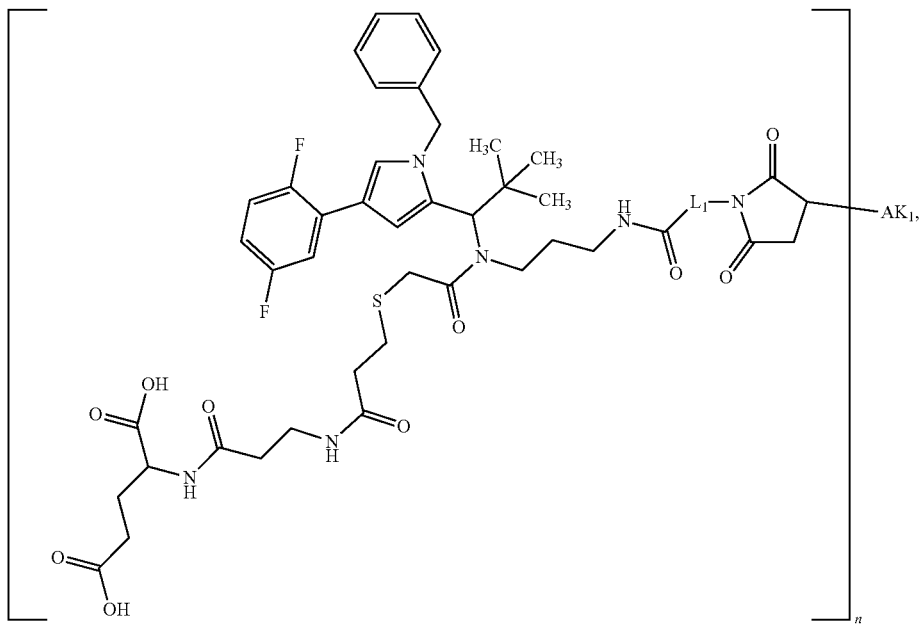

633
634
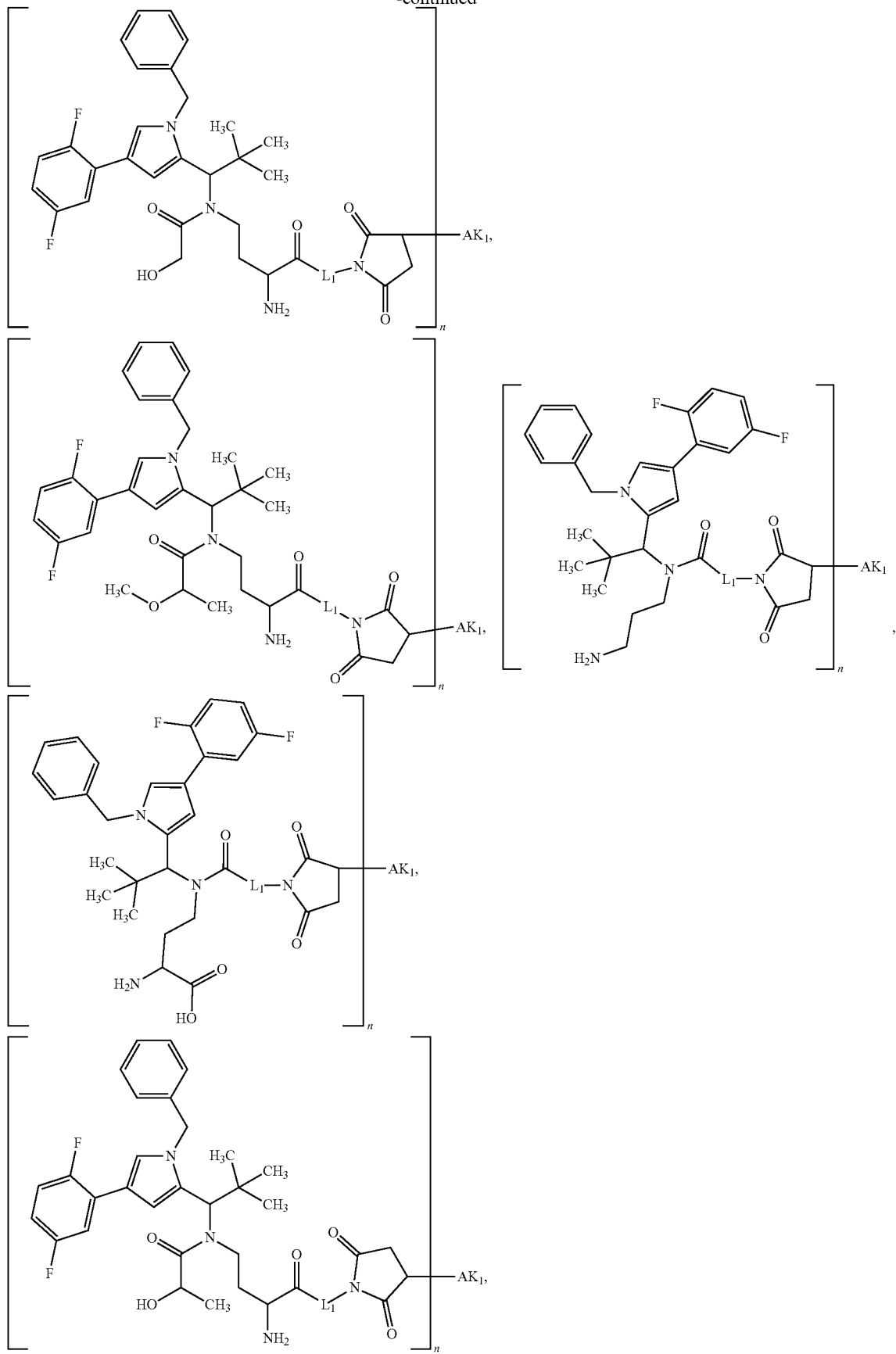

635
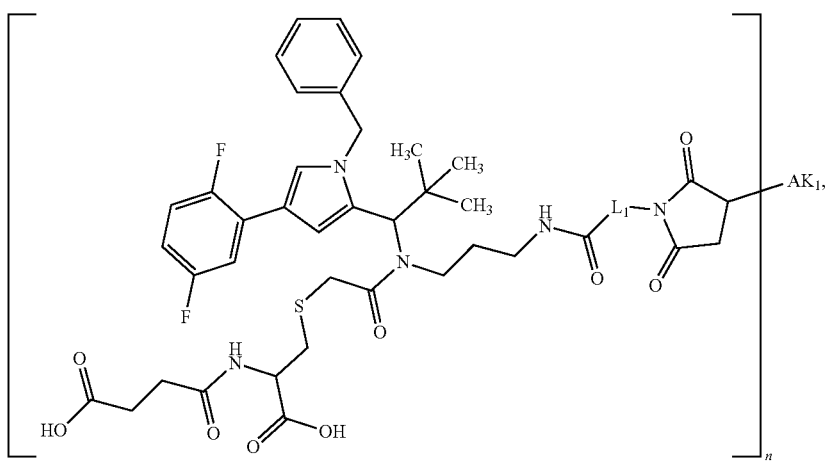
636
-continued
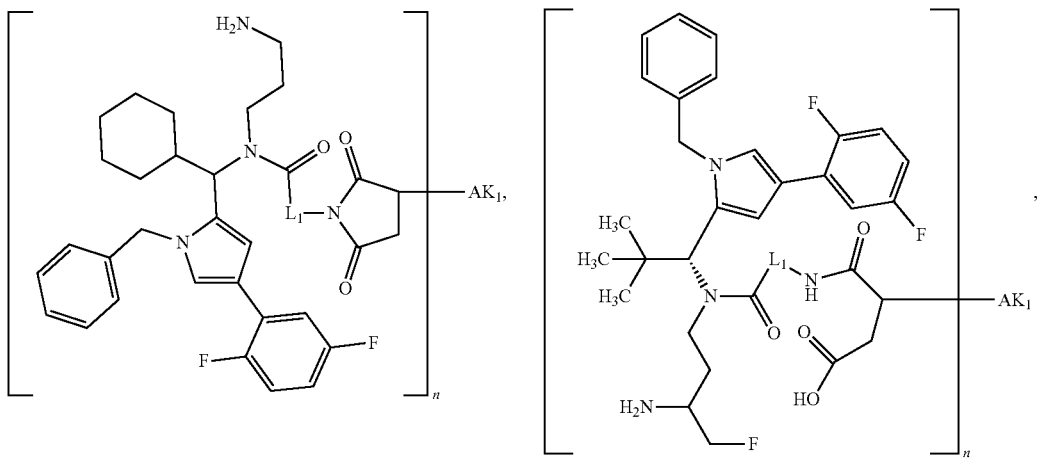
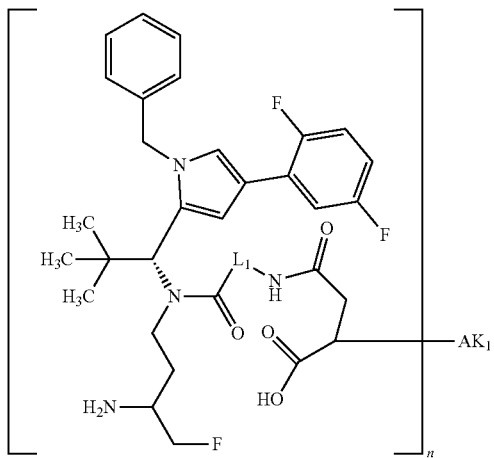

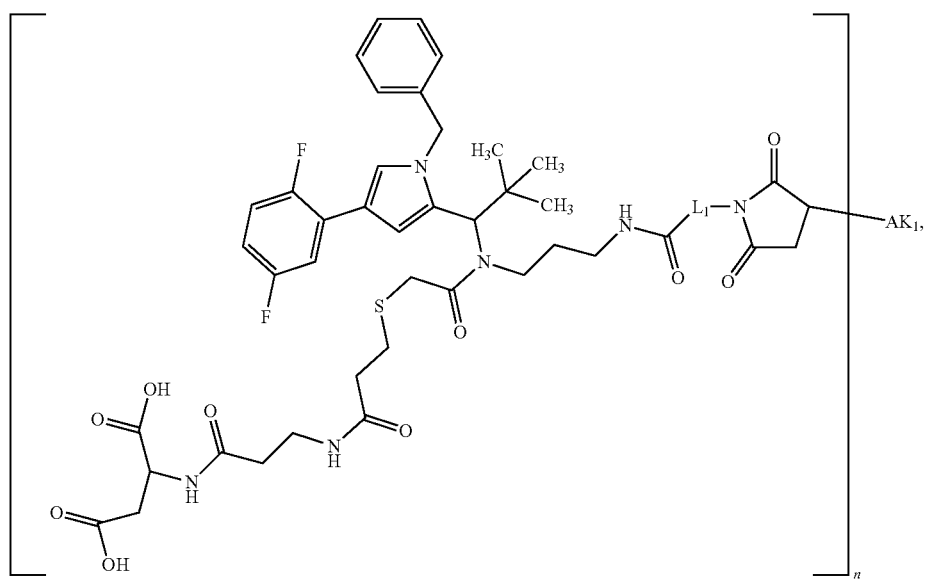
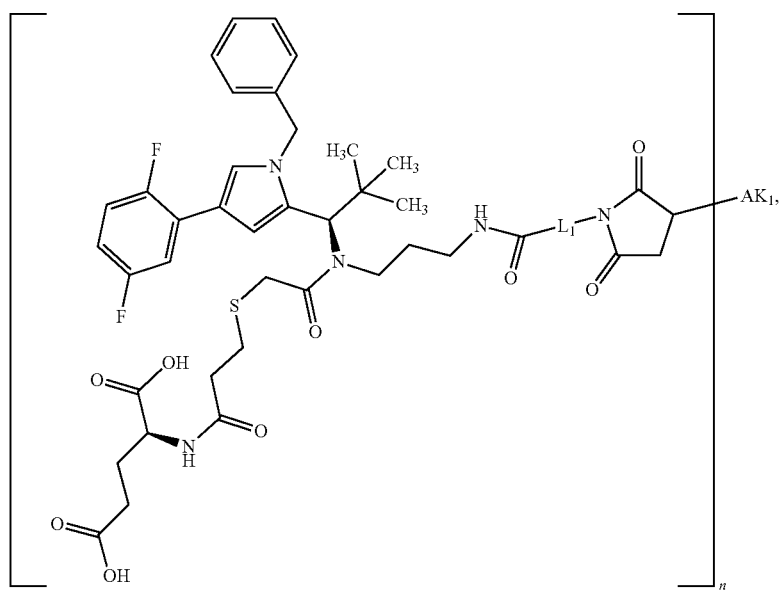

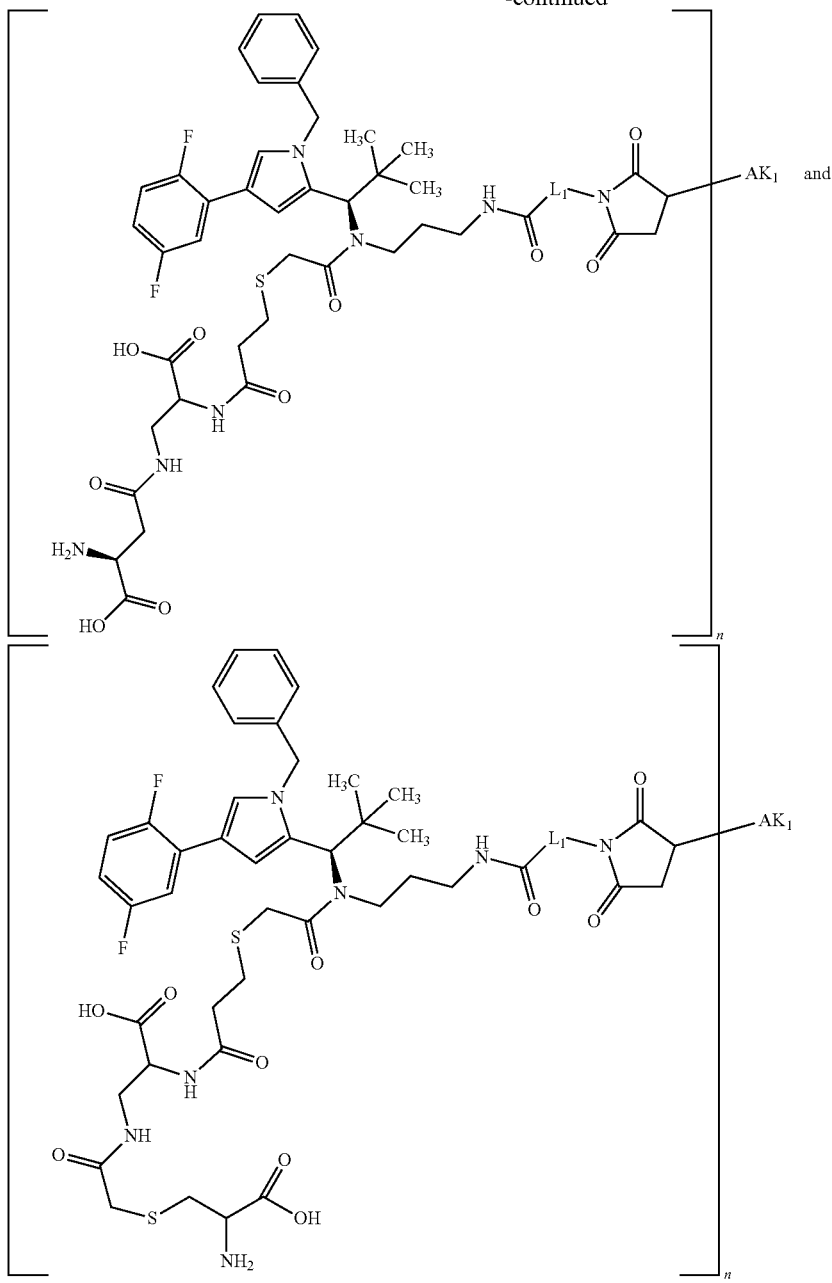

wherein
AK1 is an antibody linked via cysteine and
AK2 is an antibody linked via lysine, which binds to B7H3 and is a chimeric or humanized variant of the antibody TPP-6497,
n is a number from 1 to 20; and
$L_1$ is a straight-chain or branched hydrocarbon chain having 1 to 30 carbon atoms, which may be interrupted once or more than once, identically or differently, by —O—, —S—, —C(=O)—, —S(=O)$_2$—, —NH—, cyclopentyl, piperidinyl, phenyl, wherein the straight-chain or branched hydrocarbon chain may be substituted with —COOH, or —NH$_2$, or a salt, a solvate, a salt of the solvate or an epimer thereof.

20. The conjugate according to claim 19, wherein the linker $L_1$ is the group

§—NH—(CH$_2$)$_2$—§§;  §—NH—(CH$_2$)$_6$—§§;  §—NH—(CH$_2$)$_2$—O—(CH$_2$)$_2$—§§;  §—NH—CH(COOH)—(CH$_2$)$_4$—§§;

§—NH—NH—C(=O)—(CH$_2$)$_5$—§§;  §—NH—(CH$_2$)$_2$—C(=O)—O—(CH$_2$)$_2$—§§;  §—NH—(CH$_2$)$_2$—C(=O)—NH—(CH$_2$)$_2$—§§;

-continued

§—NH—(CH$_2$)$_2$—NH—C(=O)—CH$_2$—§§;   §—NH—(CH$_2$)$_3$—NH—C(=O)—CH$_2$—§§;

§—NH—(CH$_2$)$_2$—NH—C(=O)—(CH$_2$)$_2$—§§;   §—NH—(CH$_2$)$_2$—NH—C(=O)—(CH$_2$)$_5$—§§;

§—NH—(CH$_2$)$_2$—NH—C(=O)—CH(CH$_3$)—§§;   §—NH—(CH$_2$)$_2$—O—(CH$_2$)$_2$—NH—C(=O)—CH$_2$—§§;

§—NH—CH(COOH)—CH$_2$—NH—C(=O)—CH$_2$—§§;   §—NH—CH(COOH)—(CH$_2$)$_2$—NH—C(=O)—CH$_2$—§§;

§—NH—CH(COOH)—(CH$_2$)$_4$—NH—C(=O)—CH$_2$—§§;   §—NH—CH(COOH)—CH$_2$—NH—C(=O)—(CH$_2$)$_2$—§§;

§—NH—(CH$_2$)$_2$—NH—C(=O)—CH(C$_2$H$_4$COOH)—§§;   §—NH—(CH$_2$)$_2$—NH—C(=O)—((CH$_2$)$_2$—O)$_3$—(CH$_2$)$_2$—§§;

§—NH—(CH$_2$)$_2$—S(=O)$_2$—(CH$_2$)$_2$—NH—C(=O)—CH$_2$—§§;

§—NH—(CH$_2$)$_2$—NH—C(=O)—CH$_2$—NH—C(=O)—CH$_2$—§§;

§—NH—(CH$_2$)$_3$—NH—C(=O)—CH$_2$—NH—C(=O)—CH$_2$—§§;

§—NH—CH(COOH)—CH$_2$—NH—C(=O)—CH(CH$_2$COOH)—§§;

§—NH—(CH$_2$)$_2$—NH—C(=O)—CH(C$_2$H$_4$COOH)—NH—C(=O)—CH$_2$—§§;

§—NH—CH(COOH)—CH$_2$—NH—C(=O)—(CH$_2$)$_2$—NH—C(=O)—CH$_2$—§§;

§—NH—(CH$_2$)$_2$—NH—C(=O)—(CH$_2$)$_2$—CH(COOH)—NH—C(=O)—CH$_2$—§§;

§—NH—CH(COOH)—CH$_2$—NH—C(=O)—CH(CH$_2$OH)—NH—C(=O)—CH$_2$—§§;

§—NH—CH[C(=O)—NH—(CH$_2$)$_2$—O)$_4$—(CH$_2$)$_2$COOH]—CH$_2$—NH—C(=O)—CH$_2$—§§;

§—NH—CH(COOH)—CH$_2$—NH—C(=O)—((CH$_2$)$_2$—O)$_4$—(CH$_2$)$_2$—NH—C(=O)—CH$_2$—§§;

§—NH—(CH$_2$)$_4$—CH(COOH)—NH—C(=O)—CH(CH$_3$)—NH—C(=O)—CH(isoC$_3$H$_7$)—§§;

§—NH—(CH$_2$)$_4$—CH(COOH)—NH—C(=O)—CH(CH$_3$)—NH—C(=O)—CH(isoC$_3$H$_7$)—NH—C(=O)—(CH$_2$)$_5$—§§;

§—NH—(CH$_2$)$_2$—C(=O)—NH—(CH$_2$)$_4$—CH(COOH)—NH—C(=O)—CH(CH$_3$)—NH—C(=O)—CH(isoC$_3$H$_7$)—NH—C(=O)—CH$_2$—§§;

§—NH—(CH$_2$)$_2$—C(=O)—NH—(CH$_2$)$_4$—CH(COOH)—NH—C(=O)—CH(CH$_3$)—NH—C(=O)—CH(isoC$_3$H$_7$)—NH—C(=O)—(CH$_2$)$_5$—§§;

§—NH—(CH$_2$)$_4$—CH(COOH)—NH—C(=O)—CH[(CH$_2$)$_3$—NH—C(=O)—NH$_2$]—NH—C(=O)—CH(isoC$_3$H$_7$)—NH—C(=O)—(CH$_2$)$_5$—§§;

§—NH—(CH$_2$)$_2$—NH—C(=O)—(CH$_2$)$_2$—CH(COOH)—NH—C(=O)—CH(CH$_3$)—NH—C(=O)—CH(isoC$_3$H$_7$)—NH—C(=O)—(CH$_2$)$_5$—§§;

§—NH—CH(CH$_3$)—C(=O)—NH—(CH$_2$)$_4$—CH(COOH)—NH—C(=O)—CH(CH$_3$)—NH—C(=O)—CH(isoC$_3$H$_7$)—NH—C(=O)—(CH$_2$)$_5$—§§;

§—NH—(CH$_2$)$_2$—C(=O)—NH—(CH$_2$)$_4$—CH(COOH)—NH—C(=O)—CH[(CH$_2$)$_3$—NH—C(=O)—NH$_2$]—NH—C(=O)—CH(isoC$_3$H$_7$)—NH—C(=O)—(CH$_2$)$_5$—§§;

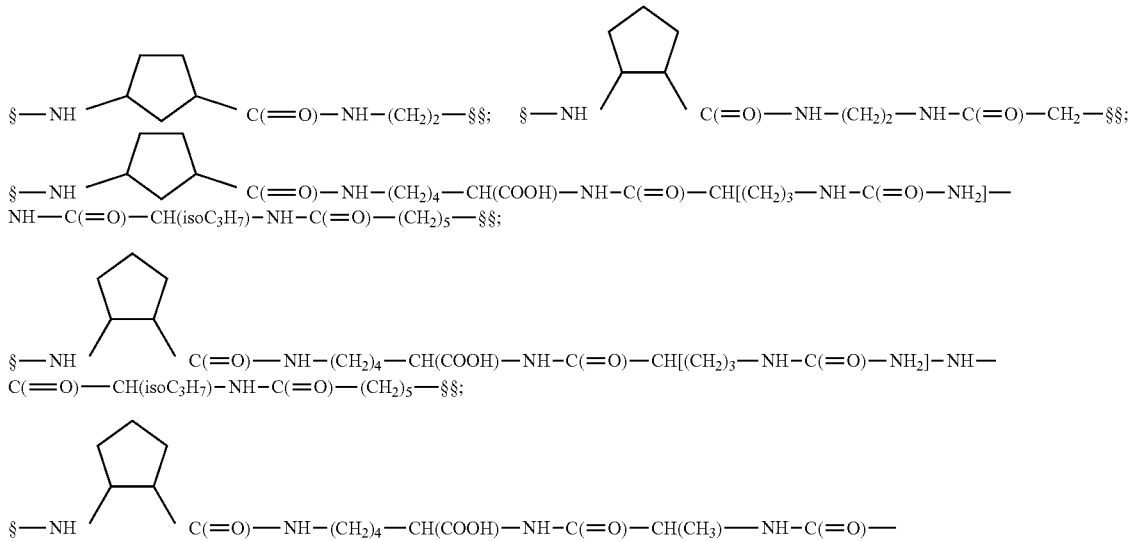

-continued

CH(isoC₃H₇)—NH—C(=O)—(CH₂)₅—§§;

§—NH—(CH₂)₂—C(=O)—NH—CH(isoC₃H₇)—C(=O)—NH—CH[(CH₂)₃—NH—C(=O)—NH₂]—C(=O)—

[4-oxypiperidine-1-yl]—C(=O)—CH₂—§§;

§—NH—(CH₂)₂—C(=O)—NH—CH(isoC₃H₇)—C(=O)—NH—CH(CH₃)—C(=O)—O—[piperidine-4-yl-N]—C(=O)—

[meta-phenylene]—CH₂—§§; §—NH—(CH₂)₂—NH—C(=O)—[meta-phenylene]—§§; §—NH—CH(COOH)—CH₂—NH—C(=O)—[meta-phenylene]—§§;

§—NH—(CH₂)₂—C(=O)—NH—CH(CH₃)—C(=O)—NH—CH[(CH₂)₃—NH—C(=O)—NH₂]—C(=O)—NH—

[para-phenylene]—§§; §—(CH₂)₂—C(=O)—NH—(CH₂)₂—§§; §—(CH₂)₂—C(=O)—NH—(CH₂)₂—NH—C(=O)—CH₂—§§;

§—CH(CH₃)—NH—C(=O)—CH(isoC₃H₇)—§§; §—CH(CH₃)—NH—C(=O)—CH(isoC₃H₇)—NH—C(=O)—CH₂—§§;

§—CH(CH₃)—NH—C(=O)—CH(isoC₃H₇)—NH—C(=O)—(CH₂)₅—§§;

§—(CH₂)₂—C(=O)—NH—((CH₂)₂—O)₄—(CH₂)₂—NH—C(=O)—CH₂—§§;

§—CH(CH₃)—NH—C(=O)—CH(isoC₃H₇)—NH—C(=O)—((CH₂)₂—O)₄—(CH₂)₂—NH—C(=O)—(CH₂)₂— §§;

§—[para-phenylene]—NH—C(=O)—CH(CH₃)—NH—C(=O)—CH(isoC₃H₇)—NH—C(=O)—((CH₂)₂—O)₄—
(CH₂)₂—NH—C(=O)—(CH₂)₂—§§; §—CH₂—S—(CH₂)₂—C(=O)—NH—(CH₂)₂—§§;

§—CH₂—S—(CH₂)₅—C(=O)—NH—(CH₂)₂—§§; §—CH₂—S—CH₂CH(COOH)—NH—C(=O)—CH₂—§§;

§—CH₂—S—CH₂CH(COOH)—NH—C(=O)—(CH₂)₅—§§; §—CH₂—S—(CH₂)₂—C(=O)—NH—((CH₂)₂—O)₂—(CH₂)₂—§§;

§—CH₂—S—(CH₂)₂—C(=O)—NH—((CH₂)₂—O)₂—(CH₂)₅—§§;

§—CH₂—S—(CH₂)₂—C(=O)—NH—(CH₂)₂—NH—C(=O)—CH₂—§§;

§—CH₂—S—(CH₂)₂—C(=O)—NH—(CH₂)₂—NH—C(=O)—CH₅—§§;

§—CH₂—S—CH₂CH(COOH)—NH—C(=O)—(CH₂)₂—NH—C(=O)—CH₂—§§;

§—CH₂—S—CH₂CH(NH₂)—C(=O)—NH—(CH₂)₂—NH—C(=O)—(CH₂)₅—§§;

§—CH₂—S—(CH₂)₂—C(=O)—NH—CH(COOH)—CH₂—NH—C(=O)—CH₂—§§;

§—CH₂—S—(CH₂)₂—C(=O)—NH—((CH₂)₂—O)₂—(CH₂)₂—NH—C(=O)—CH₂—§§;

§—CH₂—S—(CH₂)₂—C(=O)—NH—((CH₂)₂—O)₄—(CH₂)₂—NH—C(=O)—CH₂—§§;

§—CH₂—S—(CH₂)₂—C(=O)—NH—((CH₂)₂—O)₂—(CH₂)₂—NH—C(=O)—(CH₂)₅—§§;

§—CH₂—S—(CH₂)₂—C(=O)—NH—((CH₂)₂—O)₄—(CH₂)₂—NH—C(=O)—(CH₂)₅—§§;

§—CH₂—S—CH₂CH(COOH)—NH—C(=O)—((CH₂)₂—O)₂—(CH₂)₂—NH—C(=O)—CH₂—§§;

§—CH₂—S—CH₂CH(COOH)—NH—C(=O)—((CH₂)₂—O)₄—(CH₂)₂—NH—C(=O)—CH₂—§§;

§—CH₂—S—CH₂CH(COOH)—NH—C(=O)—((CH₂)₂—O)₈—(CH₂)₂—NH—C(=O)—CH₂—§§;

§—CH₂—S—CH₂CH(COOH)—NH—C(=O)—((CH₂)₂—O)₄—(CH₂)₂—NH—C(=O)—(CH₂)₂—§§;

§—CH₂—S—(CH₂)₂—CH(COOH)—NH—C(=O)—((CH₂)₂—O)₄—(CH₂)₂—NH—C(=O)—(CH₂)₂—§§;

§—CH₂—S—(CH₂)₂—C(=O)—NH—CH(C₂H₄COOH)—C(=O)—NH—(CH₂)₂—NH—C(=O)—CH₂—§§;

§—CH₂—S—CH₂CH[NH—C(=O)—(CH₂)₂—COOH]—C(=O)—NH—(CH₂)₂—NH—C(=O)—CH₂—§§;

§—CH₂—S—CH₂CH[NH—C(=O)—((CH₂)₂—O)₄—CH₃]—C(=O)—NH—(CH₂)₂—NH—C(=O)—CH₂—§§;

§—CH₂—S—CH₂CH(COOH)—NH—C(=O)—CH(CH₃)—NH—C(=O)—CH(isoC₃H₇)—NH—C(=O)— CH₂—§§;

§—CH₂—S—CH₂CH[NH—C(=O)—(CH₂)₂—COOH]—C(=O)—NH—(CH₂)₂—S(=O)₂—(CH₂)₂—NH— C(=O)—CH₂—§§;

§—CH₂—S—CH₂CH[NH—C(=O)—(CH₂)₂—COOH]—C(=O)—NH—((CH₂)₂—O)₄—(CH₂)₂—NH— C(=O)—CH₂—§§;

§—CH₂—S—CH₂CH[C(=O)—NH—(CH₂)₂—COOH]—NH—C(=O)—((CH₂)₂—O)₄—(CH₂)₂—NH— C(=O)—CH₂—§§;

-continued

§—CH$_2$—S—CH$_2$CH[C(=O)—NH—(CH$_2$)$_2$—COOH]—NH—C(=O)—((CH$_2$)$_2$—O)$_4$—(CH$_2$)$_2$—NH—C(=O)—(CH$_2$)$_2$—§§;

§—CH$_2$—S—CH$_2$CH(COOH)—NH—C(=O)—(CH$_2$)$_2$CH(COOH)—NH—C(=O)—((CH$_2$)$_2$—O)$_4$—(CH$_2$)$_2$—NH—C(=O)—CH$_2$—§§

§—CH$_2$—S—CH$_2$CH[C(=O)—NH—((CH$_2$)$_2$—O)$_4$—(CH$_2$)$_2$—COOH]—NH—C(=O)—((CH$_2$)$_2$—O)$_4$—(CH$_2$)$_2$—NH—C(=O)—CH$_2$—§§;

§—CH$_2$—S—CH$_2$CH(COOH)—NH—C(=O)—CH[(CH$_2$)$_2$—COOH]—NH—C(=O)—((CH$_2$)$_2$—O)$_4$—(CH$_2$)$_2$—NH—C(=O)—(CH$_2$)$_2$—§§, or

§—CH$_2$—S—(CH$_2$)$_2$—C(=O)—NH—CH(COOH)—CH$_2$—NH—C(=O)—CH$_2$—CH$_2$CH(COOH)—NH—C(=O)—CH(CH$_3$)—NH—C(=O)—CH(isoC$_3$H$_7$)—NH—C(=O)—(CH$_2$)$_5$—§§, wherein
§ is the bond to the drug molecule, and
§ § is the bond to the antibody, and
isoC$_3$H$_7$ is an isopropyl residue, or a salt, a solvate, a salt of the solvate or an epimer thereof.

21. The conjugate according to claim 1, wherein the conjugate has one of the formulae below:

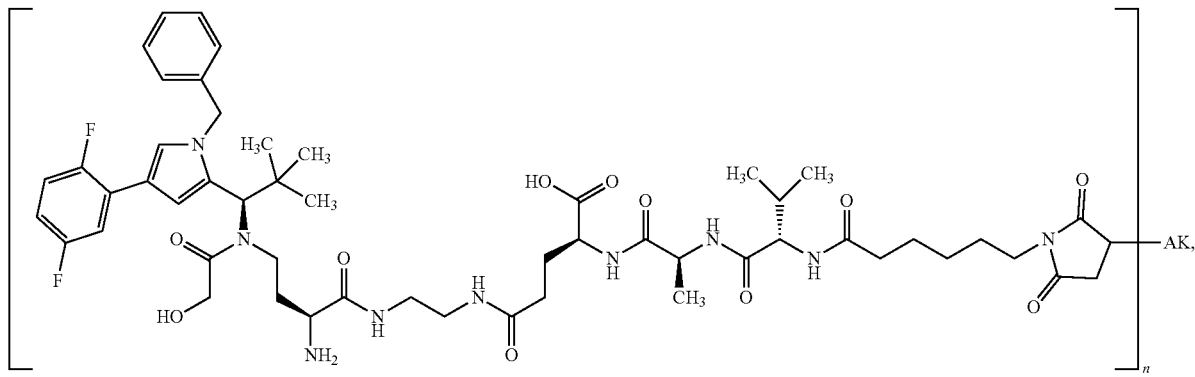

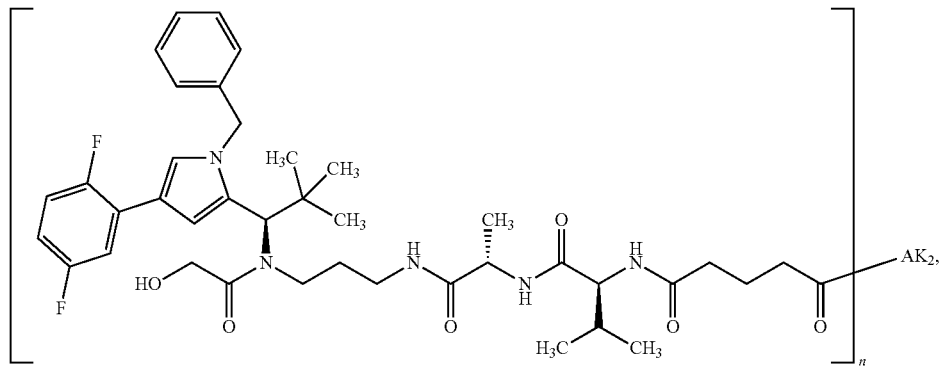

-continued
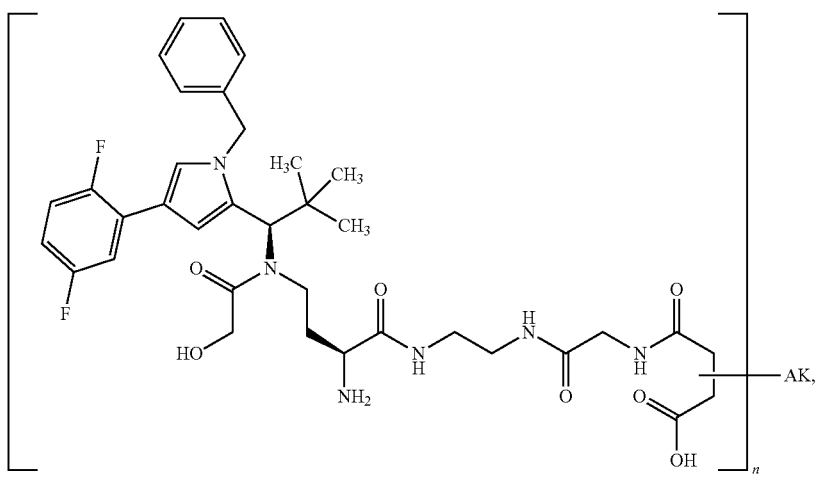
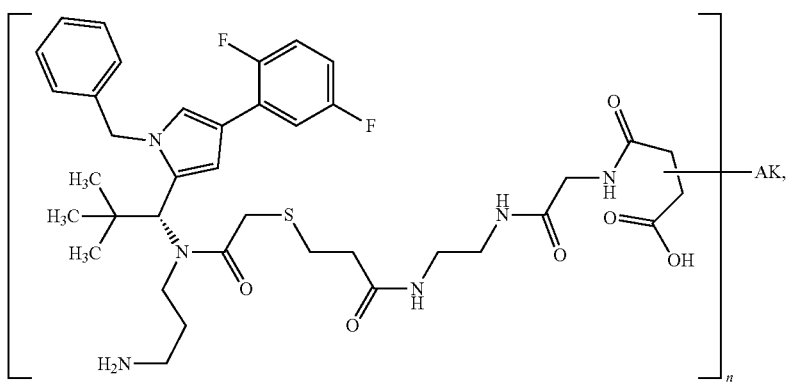
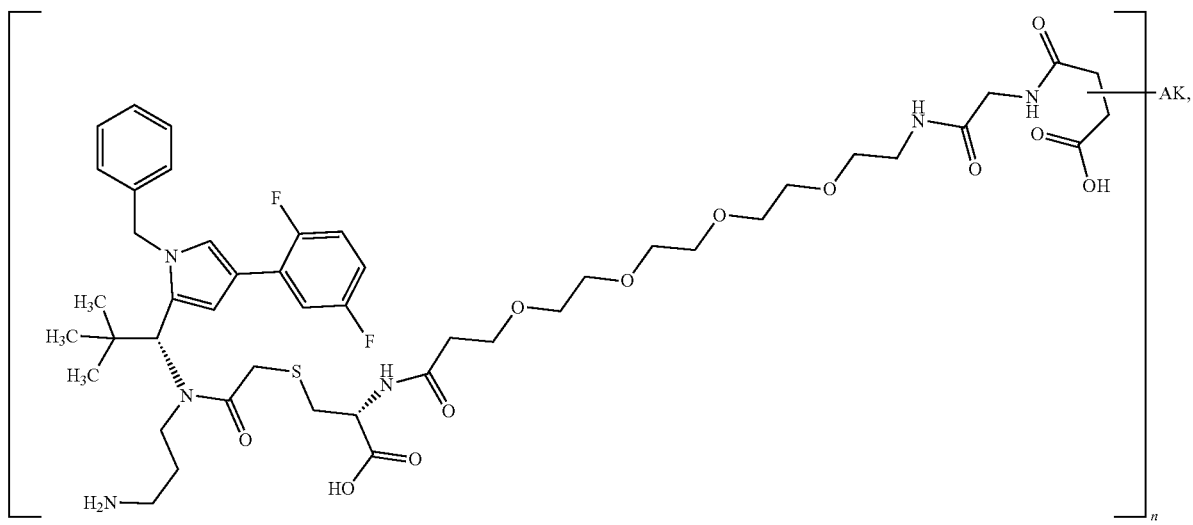

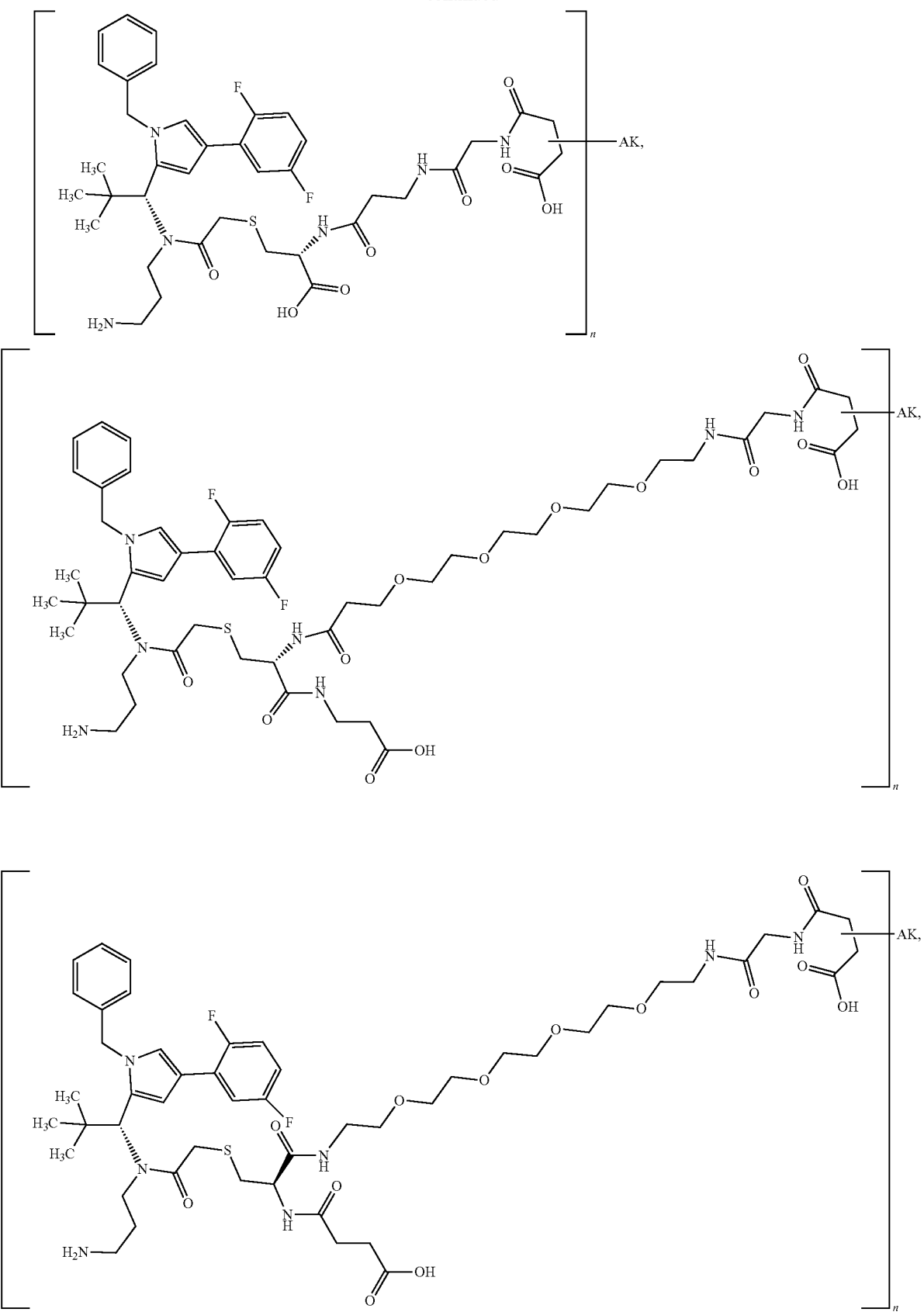

-continued
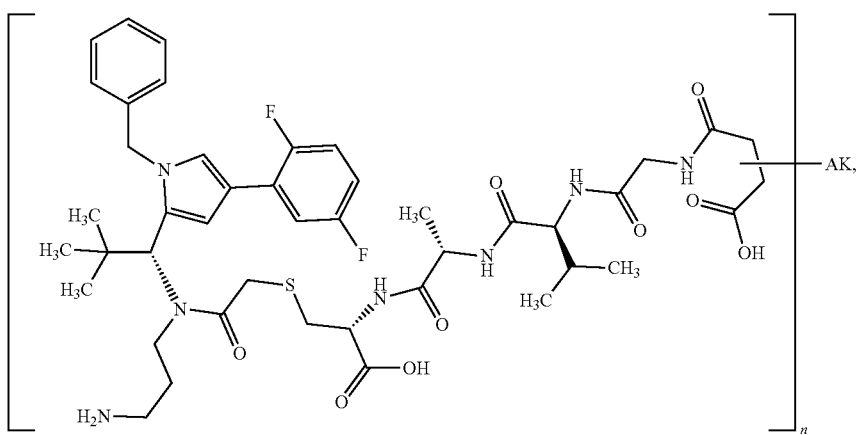
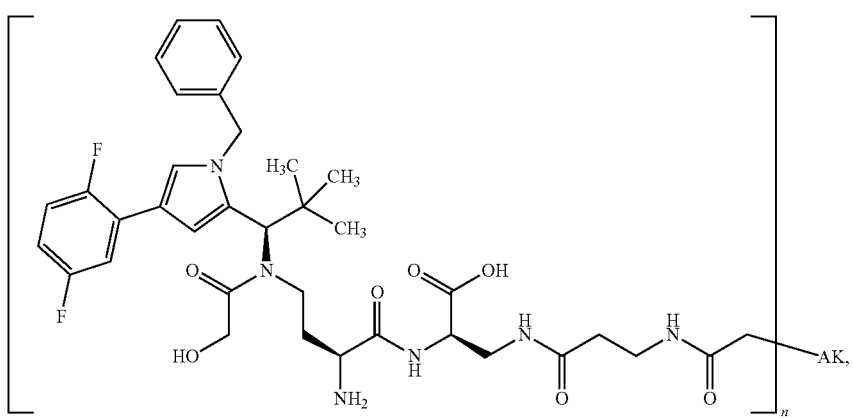
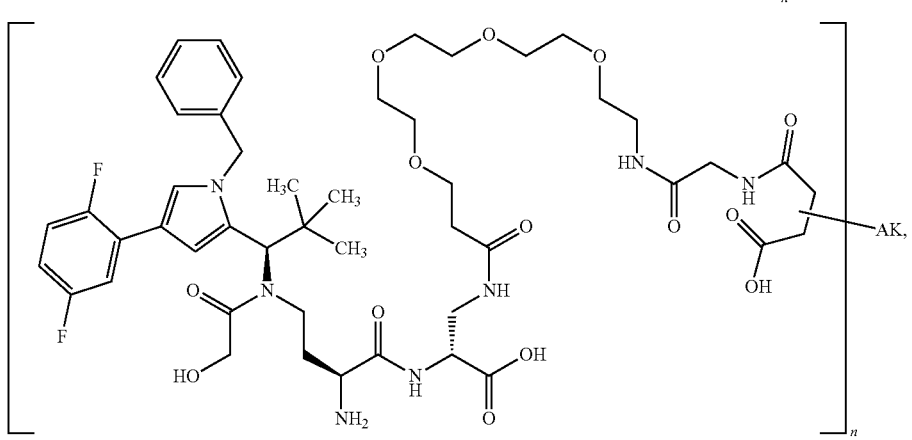
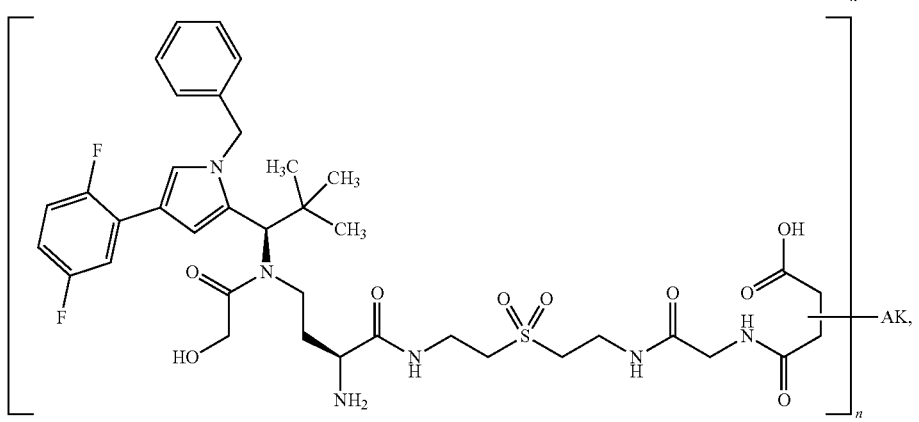

-continued
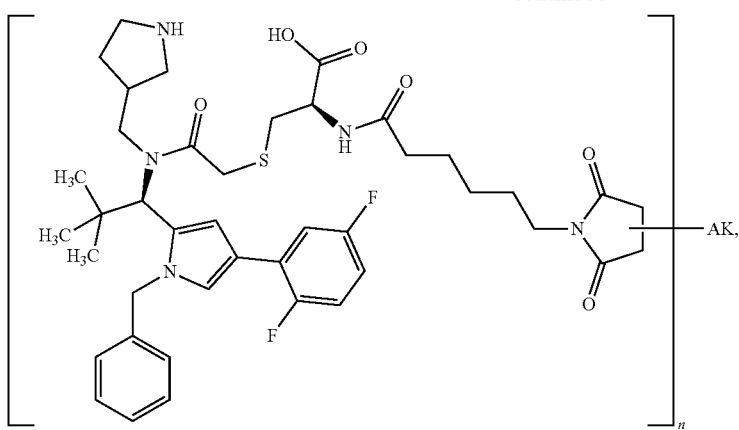
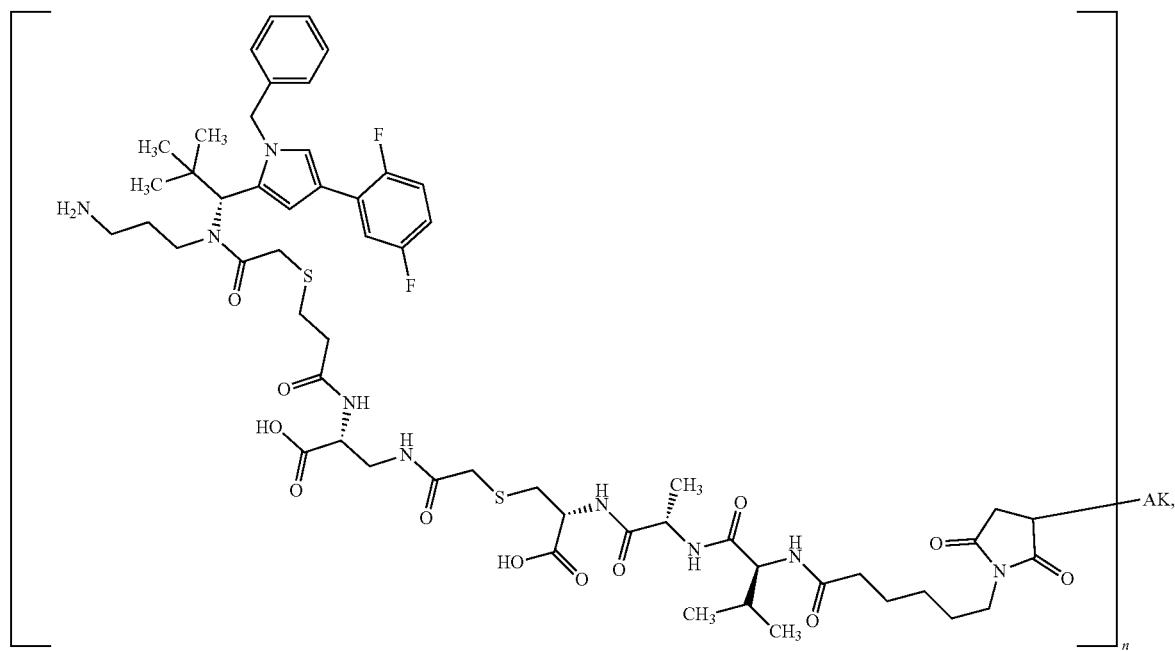
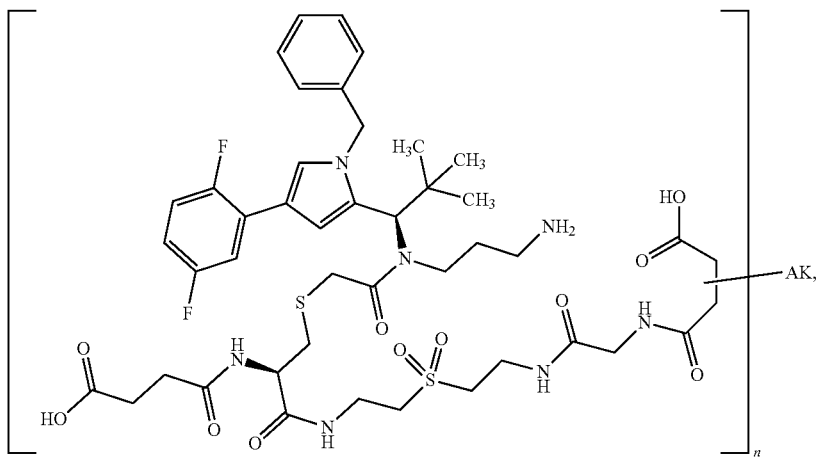

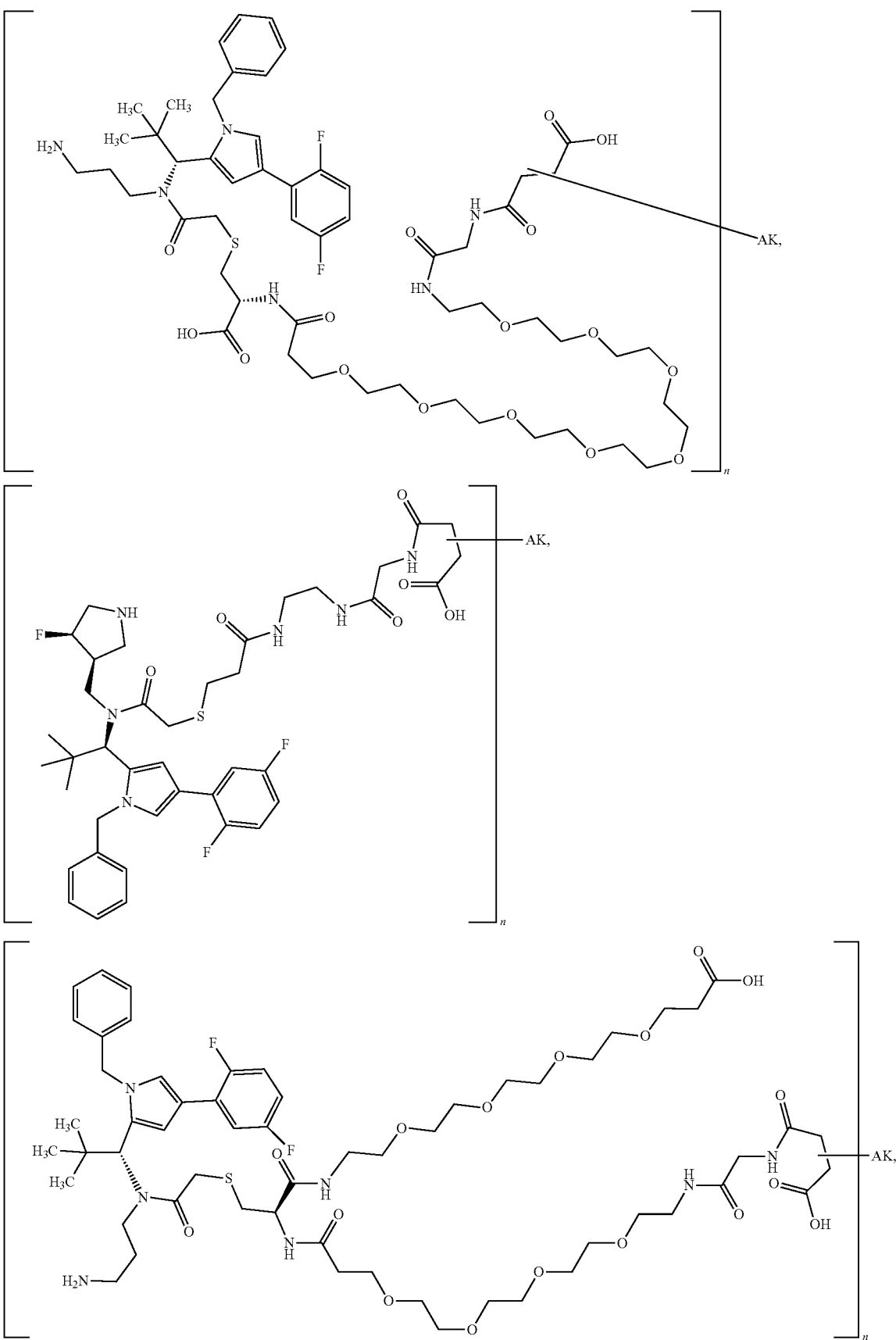

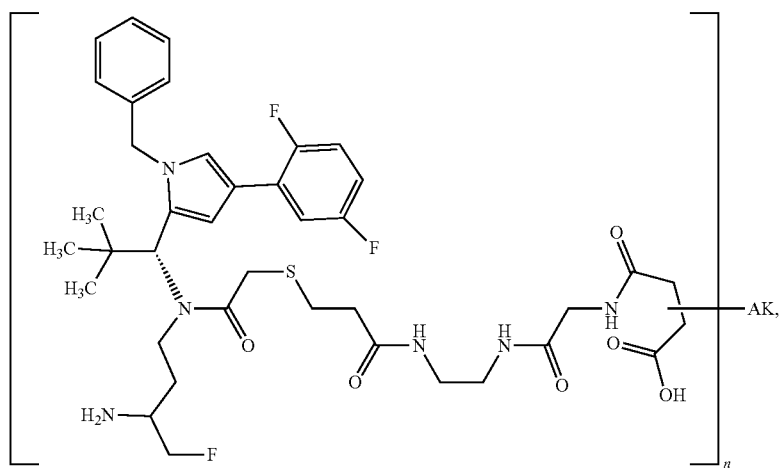
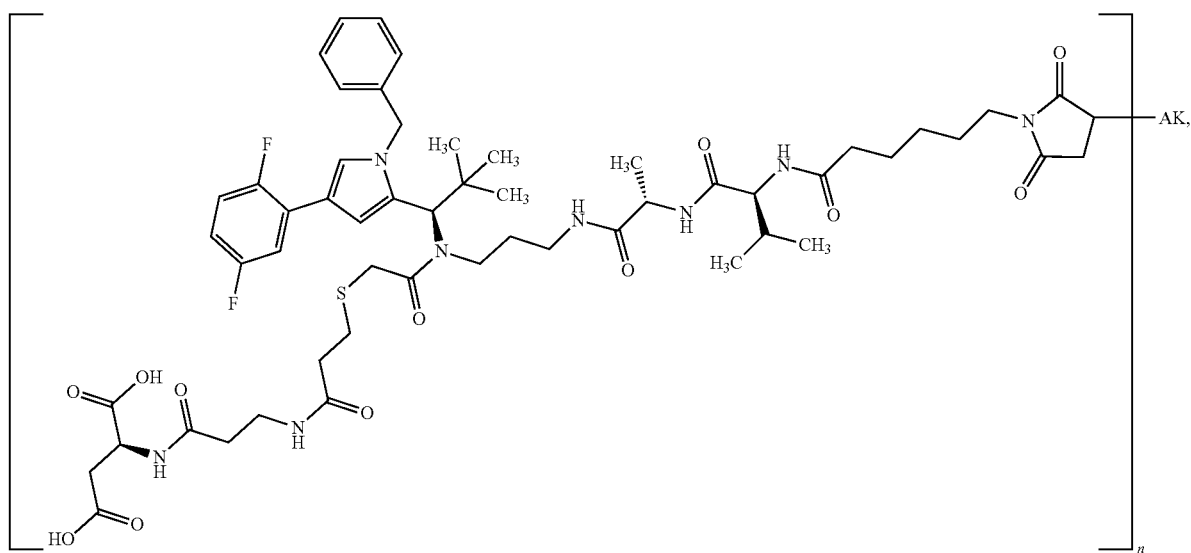
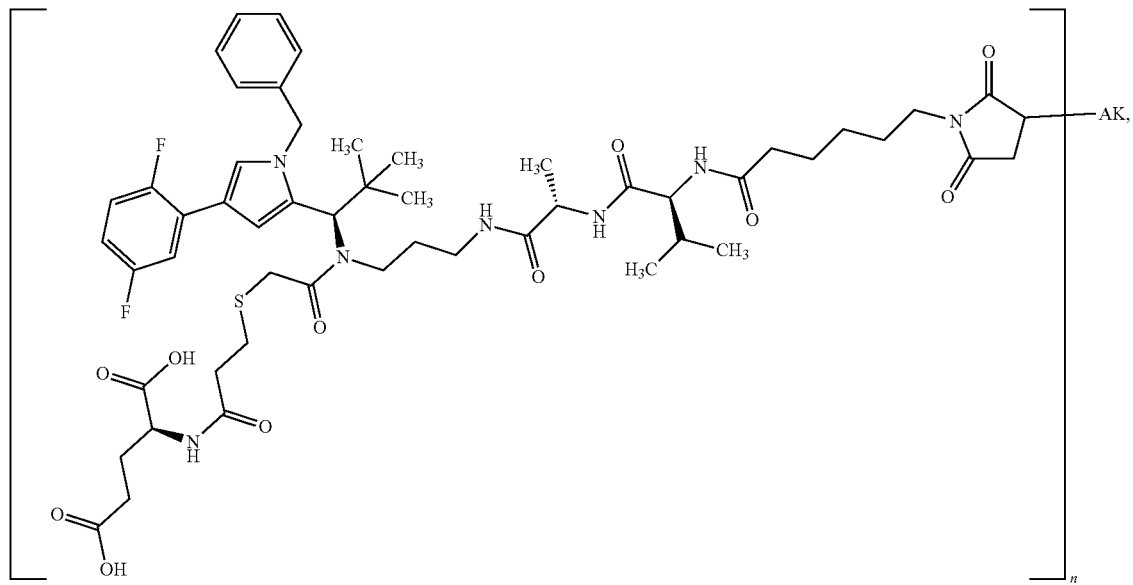

659 660
-continued
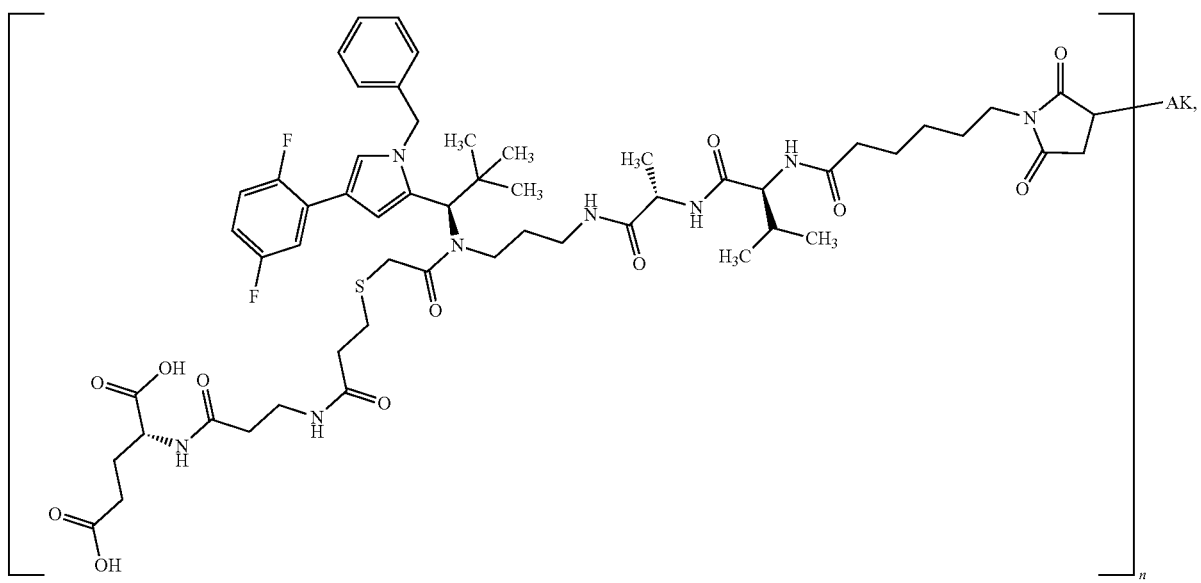
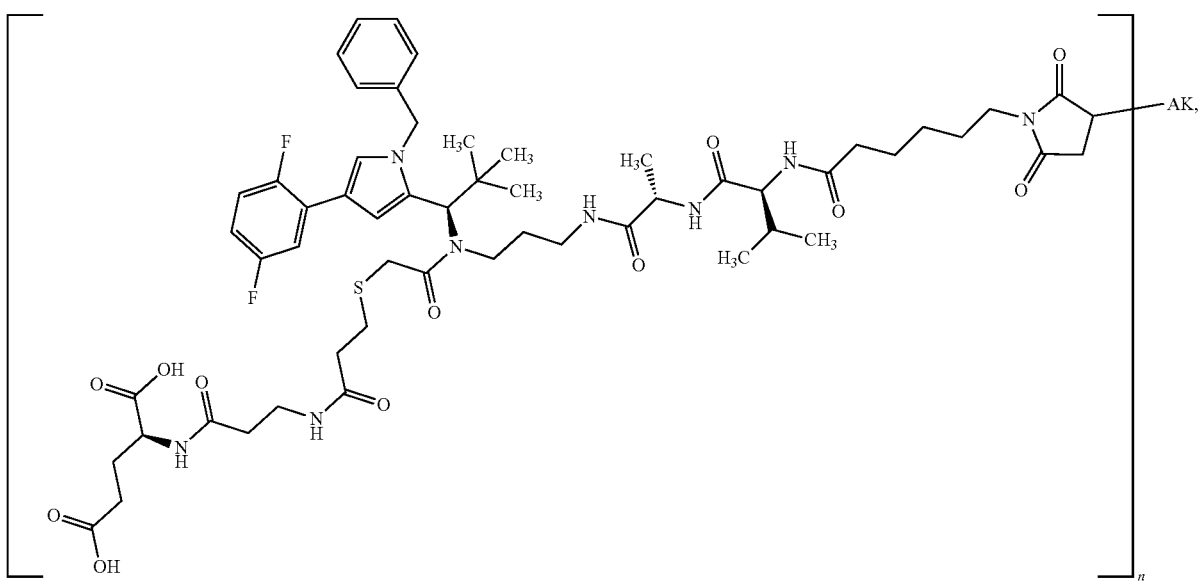

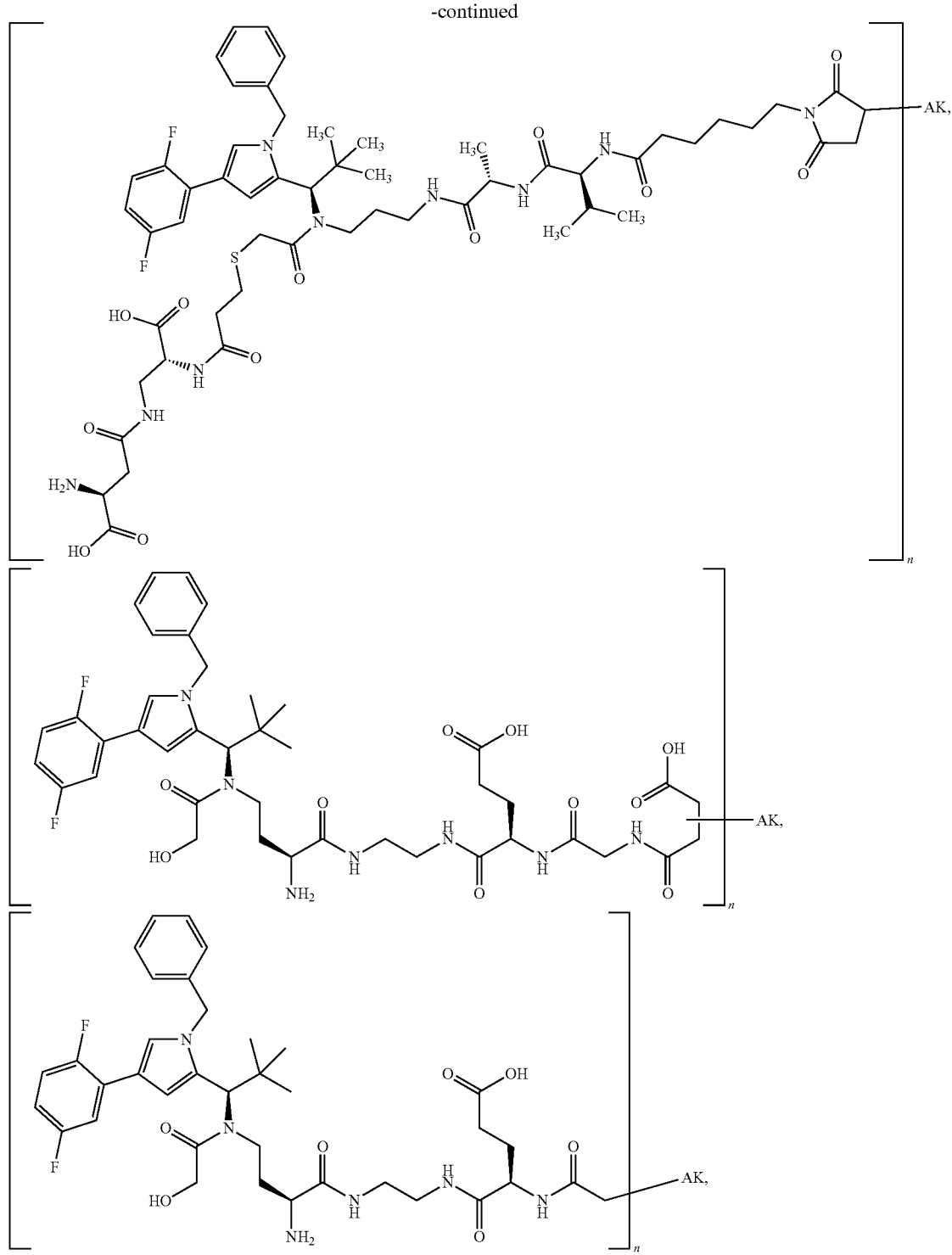

wherein
AK is an antibody linked via cysteine, and
AK$_2$ is an antibody linked via lysine, which binds to B7H3 and is a chimeric or humanized variant of the antibody TPP-6497, and
n is a number from 1 to 20.

22. The conjugate according to claim 1, wherein the anti-B7H3 antibody is an aglycosylated antibody.

23. The conjugate according to claim 1, wherein the anti-B7H3 antibody or the antigen-binding fragment thereof binds to a polypeptide as shown in SEQ ID NO: 52.

24. The conjugate according to claim 1, wherein the anti-B7H3 antibody or the antigen-binding fragment thereof comprises:
   a variable sequence of the heavy chain, as shown in SEQ ID NO: 1 and also a variable sequence of the light chain, as shown in SEQ ID NO: 5; or a variable sequence of the heavy chain, as shown in SEQ ID NO: 11 and also a variable sequence of the light chain, as shown in SEQ ID NO: 15; or a variable sequence of the heavy chain, as shown in SEQ ID NO:21 and also a variable sequence of the light chain, as shown in SEQ ID NO:25; or a variable sequence of the heavy chain, as shown in SEQ ID NO: 31 and also a variable sequence of the light chain, as shown in SEQ ID NO:35; or a variable sequence of the heavy chain, as shown in SEQ ID NO: 41 and also a variable sequence of the light chain, as shown in SEQ ID NO: 45; or a variable sequence of the heavy chain, as shown in SEQ ID NO: 55 and a variable sequence of the light chain, as shown in SEQ ID NO: 57.

25. The conjugate according to claim 1, wherein the anti-B7H3 antibody is an IgG antibody.

26. The conjugate according to claim 1, wherein the anti-B7H3 antibody or the antigen-binding fragment thereof comprises:
   a sequence of the heavy chain, as shown in SEQ ID NO: 9 and also a sequence of the light chain, as shown in SEQ ID NO: 10; or
   a sequence of the heavy chain, as shown in SEQ ID NO: 19 and also a sequence of the light chain, as shown in SEQ ID NO:20; or
   a sequence of the heavy chain, as shown in SEQ ID NO:29 and also a sequence of the light chain, as shown in SEQ ID NO:30; or
   a sequence of the heavy chain, as shown in SEQ ID NO:39 and also a sequence of the light chain, as shown in SEQ ID NO:40; or
   a sequence of the heavy chain, as shown in SEQ ID NO: 49 and also a sequence of the light chain, as shown in SEQ ID NO: 50; or
   a sequence of the heavy chain, as shown in SEQ ID NO: 59 and a sequence of the light chain, as shown in SEQ ID NO: 60; or
   a sequence of the heavy chain, as shown in SEQ ID NO: 61 and a sequence of the light chain, as shown in SEQ ID NO: 60; or
   a sequence of the heavy chain, as shown in SEQ ID NO: 62 and a sequence of the light chain, as shown in SEQ ID NO: 60.

27. The conjugate according claim 1, wherein the anti-B7H3 antibody or the antigen-binding fragment thereof is a humanized variant of one of the antibodies TPP-6497, TPP-6499, TPP-6501, TPP-6502, TPP-6515, TPP-7611, TPP-8382, TPP-8564, TPP-8567, TPP-8322, TPP-8565, TPP-8568, TPP-8748 or TPP-8750.

28. The conjugate according to claim 1, wherein the anti-B7H3 antibody or the antigen-binding fragment thereof is one of the antibodies TPP-8382, TPP-8564 or TPP-8567.

29. The conjugate according to claim 1, wherein the anti-B7H3 antibody or the antigen-binding fragment thereof comprises:
   a sequence of the heavy chain, as shown in SEQ ID NO: 9, which contains at least one amino acid substitution selected from the group consisting of the substitutions R30S, S50A, V51I, A58T, L59Y, T97A, and R98K, and
   a sequence of the light chain, as shown in SEQ ID NO: 10, which contains at least one amino acid substitution selected from the group consisting of the substitutions P33T, G51S, S53N, N54Q, S77T, R80Q, S81A, Q90A, S91A, F92W, F92Y, S94D, K97N, K97S, K98G, an K105Q; or
   a sequence of the heavy chain, as shown in SEQ ID NO: 19, which contains at least one amino acid substitution selected from the group consisting of the substitutions R30S, D31S, F32Y, Y33A, N35S, I37V, S50A, S50Y, A53G, A53S, K56G, K56S, Y57S, Y57T, PI 14S, and PI 14Y, and
   a sequence of the light chain, as shown in SEQ ID NO:20, which contains at least one amino acid substitution selected from the group consisting of the substitutions G25S, Y26S, V29I, G31S, N33Y, N33T, N35Y, G51R, S53N, N54Q, S77T, R80Q, S81A, Q90A, S91A, Y92W, S94D, and K106Q; or
   a sequence of the heavy chain, as shown in SEQ ID NO:29, which contains at least one amino acid substitution selected from the group consisting of the substitutions G33A, H35S, N101Y, L103Y, L103N, and L113T, and
   a sequence of the light chain, as shown in SEQ ID NO: 30, which contains at least one amino acid substitution selected from the group consisting of the substitutions R31S, 133Y, I33T, N35Y, S52N, Q90A, T91A, G93D, T94D, G95S, W96L, V97S, F98G, and K103Q; or
   a sequence of the heavy chain, as shown in SEQ ID NO: 39, which contains at least one amino acid substitution selected from the group consisting of the substitutions T31S, G33A, H35S, T97A, R98K, and L113T, and
   a sequence of the light chain, as shown in SEQ ID NO:40, which contains at least one amino acid substitution selected from the group consisting of the substitutions G25S, P33Y, P33T, N35Y, G51R, S53N, K54Q, Q90A, S91A, Y92W, S94D, W99V, G103E, and K106E; or
   a sequence of the heavy chain, as shown in SEQ ID NO:49, which contains at least one amino acid substitution selected from the group consisting of the substitutions G33A, H35S, V40A, T57S, L104Y, L104W, and Y107S, and
   a sequence of the light chain, as shown in SEQ ID NO:50, which contains at least one amino acid substitution selected from the group consisting of the substitutions T33Y, N35Y, D53N, L56P, L57S, Q90A, S91A, Y92W, S94D, W99V, G103E, and K106E.

30. A pharmaceutical composition comprising a conjugate according to claim 1 in combination with an inert non-toxic pharmaceutically suitable auxiliary.

31. A method for treatment of a cancer in a human in need thereof, comprising administering an effective amount of a conjugate according to claim 1 to the human.

32. A method for treatment of a hyperproliferative or angiogenic disorder in a human in need thereof, comprising administering an effective amount of a conjugate according to claim 1 to the human.

* * * * *

SEQUENCE LISTING

<160> NUMBER OF SEQ ID NOS: 70

<210> SEQ ID NO 1
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6497 VH

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ser Val Ser Gly Ser Gly Gly Ser Ala Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Leu Thr Gly Thr Ser Phe Asp Tyr Trp Gly Gln Gly Thr Leu
            100                 105                 110

Val Thr Val Ser Ser
        115

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6497 H-CDR1

<400> SEQUENCE: 2

Ser Tyr Ala Met Ser
1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6497 H-CDR2

<400> SEQUENCE: 3

Ser Val Ser Gly Ser Gly Gly Ser Ala Leu Tyr Ala Asp Ser Val Lys
1               5                   10                  15

Gly

<210> SEQ ID NO 4
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<223> OTHER INFORMATION: TPP-6497 H-CDR3

<400> SEQUENCE: 4

Leu Thr Gly Thr Ser Phe Asp Tyr
1               5

<210> SEQ ID NO 5
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6497 VL

<400> SEQUENCE: 5

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Phe Asp Ser Leu
                85                  90                  95

Lys Lys Val Phe Gly Gly Gly Thr Lys Leu Thr Val Leu
            100                 105

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6497 L-CDR1

<400> SEQUENCE: 6

Ser Gly Ser Ser Ser Asn Ile Gly Ser Asn Pro Val Asn
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6497 L-CDR2

<400> SEQUENCE: 7

Gly Asn Ser Asn Arg Pro Ser
1               5

<210> SEQ ID NO 8
<211> LENGTH: 10
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6497 L-CDR3

<400> SEQUENCE: 8

Gln Ser Phe Asp Ser Ser Leu Lys Lys Val
1               5                   10

<210> SEQ ID NO 9
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6497 Heavy Chain (IgG)

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ser Val Ser Gly Ser Gly Gly Ser Ala Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Leu Thr Gly Thr Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285
```

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 10
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6497 Light Chain (IgG)

<400> SEQUENCE: 10

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Phe Asp Ser Ser Leu
                85                  90                  95

Lys Lys Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 11
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6499 VH

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Phe
            20                  25                  30

Tyr Met Asn Trp Ile Arg Gln Ala Pro Gly Lys Gly Leu Glu Trp Val
        35                  40                  45

Ser Ser Ile Ser Ala Ser Gly Lys Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Tyr Cys Thr Asn Asp Val Cys Arg Asn Trp Phe
            100                 105                 110

Asp Pro Trp Gly Gln Gly Thr Leu Val Thr Val Ser Ser
        115                 120                 125

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6499 H-CDR1

<400> SEQUENCE: 12

Asp Phe Tyr Met Asn
1               5

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6499 H-CDR2

<400> SEQUENCE: 13

Ser Ile Ser Ala Ser Gly Lys Tyr Thr Tyr Tyr Ala Asp Ser Val Lys
1               5                   10                  15

Gly

```
<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6499 H-CDR3

<400> SEQUENCE: 14

Glu Trp Gly Tyr Cys Thr Asn Asp Val Cys Arg Asn Trp Phe Asp Pro
1               5                   10                  15

<210> SEQ ID NO 15
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6499 VL

<400> SEQUENCE: 15

Gln Ser Val Leu Thr Gln Pro Pro Ser Ala Ser Gly Thr Pro Gly Gln
1               5                   10                  15

Arg Val Thr Ile Ser Cys Ser Gly Gly Tyr Ser Asn Val Gly Gly Asn
                20                  25                  30

Asn Val Asn Trp Tyr Gln Gln Leu Pro Gly Thr Ala Pro Lys Leu Leu
            35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Thr Lys Leu Thr Val Leu
            100                 105                 110

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6499 L-CDR1

<400> SEQUENCE: 16

Ser Gly Gly Tyr Ser Asn Val Gly Gly Asn Asn Val Asn
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6499 L-CDR2

<400> SEQUENCE: 17

Gly Asn Ser Asn Arg Pro Ser
```

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: TPP-6499 L-CDR3

<400> SEQUENCE: 18

```
Gln Ser Tyr Asp Ser Ser Leu Ser Gly Ser Val
1               5                   10
```

<210> SEQ ID NO 19
<211> LENGTH: 454
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: TPP-6499 Heavy Chain (IgG)

<400> SEQUENCE: 19

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Asp Phe
            20                  25                  30

Tyr Met Asn Trp Ile Arg Gln Ala Pro Gly Lys Gly Leu Glu Trp Val
        35                  40                  45

Ser Ser Ile Ser Ala Ser Gly Lys Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Trp Gly Tyr Cys Thr Asn Asp Val Cys Arg Asn Trp Phe
            100                 105                 110

Asp Pro Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255
```

```
Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly
        450

<210> SEQ ID NO 20
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6499 Light Chain (IgG)

<400> SEQUENCE: 20

Gln Ser Val Leu Thr Gln Pro Pro Ser Ala Ser Gly Thr Pro Gly Gln
1               5                   10                  15

Arg Val Thr Ile Ser Cys Ser Gly Gly Tyr Ser Asn Val Gly Gly Asn
            20                  25                  30

Asn Val Asn Trp Tyr Gln Gln Leu Pro Gly Thr Ala Pro Lys Leu Leu
            35                  40                  45

Ile Tyr Gly Asn Ser Asn Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Ser Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
            130                 135                 140
```

```
Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 21
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6501 VH

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Asn Tyr Leu Gly Met Asp Val Trp Gly Gln Gly Thr
            100                 105                 110

Leu Val Thr Val Ser Ser
        115

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6501 H-CDR1

<400> SEQUENCE: 22

Ser Tyr Gly Met His
1               5

<210> SEQ ID NO 23
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6501 H-CDR2
```

```
<400> SEQUENCE: 23

Ala Ile Ser Gly Ser Gly Gly Ser Thr Tyr Tyr Ala Asp Ser Val Lys
1               5                   10                  15

Gly

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6501 H-CDR3

<400> SEQUENCE: 24

Gly Ser Asn Tyr Leu Gly Met Asp Val
1               5

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6501 VL

<400> SEQUENCE: 25

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
            20                  25                  30

Ile Val Asn Trp Tyr Gln Gln Leu Pro Gly Thr Ala Pro Lys Leu Leu
        35                  40                  45

Ile Tyr Arg Ser Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Thr Trp Gly Thr Gly Trp
                85                  90                  95

Val Phe Gly Gly Gly Thr Lys Leu Thr Val Leu
            100                 105

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6501 L-CDR1

<400> SEQUENCE: 26

Ser Gly Ser Ser Ser Asn Ile Gly Arg Asn Ile Val Asn
1               5                   10

<210> SEQ ID NO 27
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: TPP-6501 L-CDR2

<400> SEQUENCE: 27

Arg Ser Asn Gln Arg Pro Ser
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6501 L-CDR3

<400> SEQUENCE: 28

Gln Thr Trp Gly Thr Gly Trp Val
1               5

<210> SEQ ID NO 29
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6501 Heavy Chain (IgG)

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Asn Tyr Leu Gly Met Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
```

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 30
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6501 Light Chain (IgG)

<400> SEQUENCE: 30

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Arg Asn
            20                  25                  30

Ile Val Asn Trp Tyr Gln Gln Leu Pro Gly Thr Ala Pro Lys Leu Leu
        35                  40                  45

Ile Tyr Arg Ser Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Thr Trp Gly Thr Gly Trp
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala

```
            115                 120                 125
Asn Lys Ala Thr Leu Val Cys Leu Ile Ser Asp Phe Tyr Pro Gly Ala
        130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 31
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6502 VH

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Tyr Tyr Tyr Tyr Gly Met Asp Val Trp Gly Gln Gly Thr
            100                 105                 110

Leu Val Thr Val Ser Ser
        115

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6502 H-CDR1

<400> SEQUENCE: 32

Thr Tyr Gly Met His
1               5

<210> SEQ ID NO 33
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: TPP-6502 H-CDR2

<400> SEQUENCE: 33

Ala Ile Ser Gly Ser Gly Gly Ser Thr Tyr Tyr Ala Asp Ser Val Lys
1               5                   10                  15

Gly

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6502 H-CDR3

<400> SEQUENCE: 34

Gly Tyr Tyr Tyr Tyr Gly Met Asp Val
1               5

<210> SEQ ID NO 35
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6502 VL

<400> SEQUENCE: 35

Gln Ser Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Gly Asn Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Trp Val Phe Gly Gly Gly Thr Lys Leu Thr Val Leu
            100                 105                 110

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6502 L-CDR1

<400> SEQUENCE: 36

Ser Gly Gly Ser Ser Asn Ile Gly Ser Asn Pro Val Asn
1               5                   10
```

```
<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6502 L-CDR2

<400> SEQUENCE: 37

Gly Asn Ser Lys Arg Pro Ser
1               5

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6502 L-CDR3

<400> SEQUENCE: 38

Gln Ser Tyr Asp Ser Ser Leu Ser Gly Trp Val
1               5                   10

<210> SEQ ID NO 39
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6502 Heavy Chain (IgG)

<400> SEQUENCE: 39

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Tyr Tyr Tyr Gly Met Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190
```

```
Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 40
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6502 Light Chain (IgG)

<400> SEQUENCE: 40

Gln Ser Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Gly Asn Ser Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95
```

```
Ser Gly Trp Val Phe Gly Gly Thr Lys Leu Thr Val Leu Gly Gln
            100                 105                 110

Pro Lys Ala Ala Pro Ser Val Thr Leu Phe Pro Pro Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
            165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
            210                 215

<210> SEQ ID NO 41
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6515 VH

<400> SEQUENCE: 41

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Val Pro Gly Lys Gly Leu Glu Trp Val
        35                  40                  45

Ser Ala Ile Ser Gly Ser Gly Gly Thr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Gly Gly Tyr His Phe Leu Phe Asp Tyr Trp Gly Gln Gly Thr
            100                 105                 110

Leu Val Thr Val Ser Ser
        115

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6515 H-CDR1

<400> SEQUENCE: 42

Ser Tyr Gly Met His
1               5
```

-continued

```
<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6515 H-CDR2

<400> SEQUENCE: 43

Ala Ile Ser Gly Ser Gly Gly Thr Thr Tyr Tyr Ala Asp Ser Val Lys
1               5                   10                  15

Gly

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6515 H-CDR3

<400> SEQUENCE: 44

Gly Gly Tyr His Phe Leu Phe Asp Tyr
1               5

<210> SEQ ID NO 45
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6515 VL

<400> SEQUENCE: 45

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Thr Val Asn Trp Tyr Gln Gln Leu Pro Gly Thr Ala Pro Lys Leu Leu
            35                  40                  45

Ile Tyr Arg Asn Asp Gln Arg Leu Leu Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Trp Val Phe Gly Gly Gly Thr Lys Leu Thr Val Leu
            100                 105                 110

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6515 L-CDR1

<400> SEQUENCE: 46
```

Ser Gly Ser Ser Asn Ile Gly Ser Asn Thr Val Asn
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6515 L-CDR2

<400> SEQUENCE: 47

Arg Asn Asp Gln Arg Leu Leu
1               5

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-6515 L-CDR3

<400> SEQUENCE: 48

Gln Ser Tyr Asp Ser Ser Leu Ser Gly Trp Val
1               5                   10

<210> SEQ ID NO 49
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6515 Heavy Chain (IgG)

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Val Pro Gly Lys Gly Leu Glu Trp Val
        35                  40                  45

Ser Ala Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr His Phe Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

```
Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
            435                 440                 445

<210> SEQ ID NO 50
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-6515 Light Chain (IgG)

<400> SEQUENCE: 50

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Arg Asn Asp Gln Arg Leu Leu Gly Val Pro Asp Arg Phe Ser
        50                  55                  60
```

```
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Gln Ser Tyr Asp Ser Ser Leu
                 85                  90                  95

Ser Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 51
<211> LENGTH: 296
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-2202

<400> SEQUENCE: 51

Glu Gln Ala Pro Gly Thr Ala Pro Cys Ser Arg Gly Ser Ser Trp Ser
  1               5                  10                  15

Ala Asp Leu Asp Lys Cys Met Asp Cys Ala Ser Cys Arg Ala Arg Pro
             20                  25                  30

His Ser Asp Phe Cys Leu Gly Cys Ala Ala Ala Pro Pro Ala Pro Phe
         35                  40                  45

Arg Leu Leu Trp Pro Ile Glu Gly Arg Met Asp Pro Lys Ser Cys Asp
 50                  55                  60

Lys Thr His Thr Cys Pro Pro Cys Pro Ala Pro Glu Leu Leu Gly Gly
 65                  70                  75                  80

Pro Ser Val Phe Leu Phe Pro Pro Lys Pro Lys Asp Thr Leu Met Ile
             85                  90                  95

Ser Arg Thr Pro Glu Val Thr Cys Val Val Val Asp Val Ser His Glu
            100                 105                 110

Asp Pro Glu Val Lys Phe Asn Trp Tyr Val Asp Gly Val Glu Val His
        115                 120                 125

Asn Ala Lys Thr Lys Pro Arg Glu Glu Gln Tyr Asn Ser Thr Tyr Arg
    130                 135                 140

Val Val Ser Val Leu Thr Val Leu His Gln Asp Trp Leu Asn Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Ala Lys Gly Gln Pro Arg Glu Pro Gln Val Tyr
            180                 185                 190
```

-continued

```
Thr Leu Pro Pro Ser Arg Glu Glu Met Thr Lys Asn Gln Val Ser Leu
            195                 200                 205
Thr Cys Leu Val Lys Gly Phe Tyr Pro Ser Asp Ile Ala Val Glu Trp
    210                 215                 220
Glu Ser Asn Gly Gln Pro Glu Asn Asn Tyr Lys Thr Thr Pro Pro Val
225                 230                 235                 240
Leu Asp Ser Asp Gly Ser Phe Phe Leu Tyr Ser Lys Leu Thr Val Asp
                245                 250                 255
Lys Ser Arg Trp Gln Gln Gly Asn Val Phe Ser Cys Ser Val Met His
                260                 265                 270
Glu Ala Leu His Asn His Tyr Thr Gln Lys Ser Leu Ser Leu Ser Pro
            275                 280                 285
Gly Lys His His His His His His
    290                 295

<210> SEQ ID NO 52
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-3760

<400> SEQUENCE: 52

Gly Ala Leu Glu Val Gln Val Pro Glu Asp Pro Val Val Ala Leu Val
1               5                   10                  15
Gly Thr Asp Ala Thr Leu Cys Cys Ser Phe Ser Pro Glu Pro Gly Phe
            20                  25                  30
Ser Leu Ala Gln Leu Asn Leu Ile Trp Gln Leu Thr Asp Thr Lys Gln
        35                  40                  45
Leu Val His Ser Phe Ala Glu Gly Gln Asp Gln Gly Ser Ala Tyr Ala
    50                  55                  60
Asn Arg Thr Ala Leu Phe Pro Asp Leu Leu Ala Gln Gly Asn Ala Ser
65                  70                  75                  80
Leu Arg Leu Gln Arg Val Arg Val Ala Asp Glu Gly Ser Phe Thr Cys
                85                  90                  95
Phe Val Ser Ile Arg Asp Phe Gly Ser Ala Ala Val Ser Leu Gln Val
            100                 105                 110
Ala Ala Pro Tyr Ser Lys Pro Ser Met Thr Leu Glu Pro Asn Lys Asp
        115                 120                 125
Leu Arg Pro Gly Asp Thr Val Thr Ile Thr Cys Ser Ser Tyr Gln Gly
    130                 135                 140
Tyr Pro Glu Ala Glu Val Phe Trp Gln Asp Gly Gln Gly Val Pro Leu
145                 150                 155                 160
Thr Gly Asn Val Thr Thr Ser Gln Met Ala Asn Glu Gln Gly Leu Phe
                165                 170                 175
Asp Val His Ser Ile Leu Arg Val Val Leu Gly Ala Asn Gly Thr Tyr
            180                 185                 190
Ser Cys Leu Val Arg Asn Pro Val Leu Gln Gln Asp Ala His Ser Ser
        195                 200                 205
Val Thr Ile Thr Pro Gln Arg Ser Pro Thr Gly Ala Val Glu Val Gln
    210                 215                 220
Val Pro Glu Asp Pro Val Val Ala Leu Val Gly Thr Asp Ala Thr Leu
225                 230                 235                 240
```

```
Arg Cys Ser Phe Ser Pro Glu Pro Gly Phe Ser Leu Ala Gln Leu Asn
                245                 250                 255

Leu Ile Trp Gln Leu Thr Asp Thr Lys Gln Leu Val His Ser Phe Thr
            260                 265                 270

Glu Gly Arg Asp Gln Gly Ser Ala Tyr Ala Asn Arg Thr Ala Leu Phe
        275                 280                 285

Pro Asp Leu Leu Ala Gln Gly Asn Ala Ser Leu Arg Leu Gln Arg Val
    290                 295                 300

Arg Val Ala Asp Glu Gly Ser Phe Thr Cys Phe Val Ser Ile Arg Asp
305                 310                 315                 320

Phe Gly Ser Ala Ala Val Ser Leu Gln Val Ala Ala Pro Tyr Ser Lys
                325                 330                 335

Pro Ser Met Thr Leu Glu Pro Asn Lys Asp Leu Arg Pro Gly Asp Thr
            340                 345                 350

Val Thr Ile Thr Cys Ser Ser Tyr Arg Gly Tyr Pro Glu Ala Glu Val
        355                 360                 365

Phe Trp Gln Asp Gly Gln Gly Val Pro Leu Thr Gly Asn Val Thr Thr
    370                 375                 380

Ser Gln Met Ala Asn Glu Gln Gly Leu Phe Asp Val His Ser Val Leu
385                 390                 395                 400

Arg Val Val Leu Gly Ala Asn Gly Thr Tyr Ser Cys Leu Val Arg Asn
                405                 410                 415

Pro Val Leu Gln Gln Asp Ala His Gly Ser Val Thr Ile Thr Gly Gln
            420                 425                 430

Pro Met Thr
        435

<210> SEQ ID NO 53
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-3762

<400> SEQUENCE: 53

Val Glu Val Gln Val Ser Glu Asp Pro Val Ala Leu Val Asp Thr
1               5                   10                  15

Asp Ala Thr Leu Arg Cys Ser Phe Ser Pro Glu Pro Gly Phe Ser Leu
                20                  25                  30

Ala Gln Leu Asn Leu Ile Trp Gln Leu Thr Asp Thr Lys Gln Leu Val
            35                  40                  45

His Ser Phe Thr Glu Gly Arg Asp Gln Gly Ser Ala Tyr Ser Asn Arg
        50                  55                  60

Thr Ala Leu Phe Pro Asp Leu Leu Val Gln Gly Asn Ala Ser Leu Arg
65                  70                  75                  80

Leu Gln Arg Val Arg Val Thr Asp Glu Gly Ser Tyr Thr Cys Phe Val
                85                  90                  95

Ser Ile Gln Asp Phe Asp Ser Ala Ala Val Ser Leu Gln Val Ala Ala
            100                 105                 110

Pro Tyr Ser Lys Pro Ser Met Thr Leu Glu Pro Asn Lys Asp Leu Arg
        115                 120                 125

Pro Gly Asn Met Val Thr Ile Thr Cys Ser Ser Tyr Gln Gly Tyr Pro
    130                 135                 140
```

```
Glu Ala Glu Val Phe Trp Lys Asp Gly Gln Gly Val Pro Leu Thr Gly
145                 150                 155                 160

Asn Val Thr Thr Ser Gln Met Ala Asn Glu Arg Gly Leu Phe Asp Val
                165                 170                 175

His Ser Val Leu Arg Val Val Leu Gly Ala Asn Gly Thr Tyr Ser Cys
            180                 185                 190

Leu Val Arg Asn Pro Val Leu Gln Gln Asp Ala His Gly Ser Val Thr
        195                 200                 205

Ile Thr Gly Gln Pro Leu Thr Phe
    210                 215

<210> SEQ ID NO 54
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-7611 Heavy Chain (IgG)

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ser Val Ser Gly Ser Gly Ser Ala Leu Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Thr Arg Leu Thr Gly Thr Ser Phe Asp Tyr Trp Gly Gln Gly Thr Leu
        100                 105                 110

Val Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

```
Val Lys Phe Asn Trp Tyr Val Asp Gly Val Glu Val His Asn Ala Lys
            275                 280                 285

Thr Lys Pro Arg Glu Glu Gln Tyr Ala Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 55
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-8382 VH

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ser Ile Ser Gly Ser Gly Gly Ser Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Thr Gly Thr Ser Phe Asp Tyr Trp Gly Gln Gly Thr Leu
            100                 105                 110

Val Thr Val Ser Ser
        115

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

-continued

<223> OTHER INFORMATION: TPP-8382 H-CDR2

<400> SEQUENCE: 56

Ser Ile Ser Gly Ser Gly Gly Ser Thr Leu Tyr Ala Asp Ser Val Lys
1               5                   10                  15

Gly

<210> SEQ ID NO 57
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-8382 VL

<400> SEQUENCE: 57

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Phe Asp Ser Ser Leu
                85                  90                  95

Lys Lys Val Phe Gly Gly Gly Thr Lys Leu Thr Val Leu
            100                 105

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-8382 L-CDR2

<400> SEQUENCE: 58

Ser Asn Asn Gln Arg Pro Ser
1               5

<210> SEQ ID NO 59
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-8382 Heavy Chain (IgG)

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val 35                  40                  45
Ser Ser Ile Ser Gly Ser Gly Gly Ser Thr Leu Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Thr Gly Thr Ser Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 60

<211> LENGTH: 215
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: TPP-8382 Light Chain (IgG)

<400> SEQUENCE: 60

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ser
50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ser Phe Asp Ser Ser Leu
                85                  90                  95

Lys Lys Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

<210> SEQ ID NO 61
<211> LENGTH: 446
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: TPP-8564 Heavy Chain (IgG)

<400> SEQUENCE: 61

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Gly Ser Thr Leu Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                        85                  90                  95

Ala Lys Leu Thr Gly Thr Ser Phe Asp Tyr Trp Gly Gln Gly Thr Leu
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Ala Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
                435                 440                 445

<210> SEQ ID NO 62
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: TPP-8567 Heavy Chain (IgG)

<400> SEQUENCE: 62

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Gly Ser Gly Gly Ser Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Thr Gly Thr Ser Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Gln Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400
```

```
Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly
        435                 440                 445

<210> SEQ ID NO 63
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-8322 VH

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Tyr Tyr Gly Met Asp Val Trp Gly Gln Gly Thr
            100                 105                 110

Leu Val Thr Val Ser Ser
        115

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TPP-8322 H-CDR1

<400> SEQUENCE: 64

Ser Tyr Gly Met His
1               5

<210> SEQ ID NO 65
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-8322 Heavy Chain (IgG)

<400> SEQUENCE: 65

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
         20                  25                  30

Gly Met His Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
65                   70                  75                  80

Leu Gln Met Asn Ser Leu Arg Ala Glu Asp Thr Ala Val Tyr Tyr Cys
                 85                  90                  95

Ala Arg Gly Tyr Tyr Tyr Gly Met Asp Val Trp Gly Gln Gly Thr
                 100                 105                 110

Leu Val Thr Val Ser Ser Ala Ser Thr Lys Gly Pro Ser Val Phe Pro
         115                 120                 125

Leu Ala Pro Ser Ser Lys Ser Thr Ser Gly Gly Thr Ala Ala Leu Gly
         130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                 165                 170                 175

Ser Ser Gly Leu Tyr Ser Leu Ser Ser Val Val Thr Val Pro Ser Ser
                 180                 185                 190

Ser Leu Gly Thr Gln Thr Tyr Ile Cys Asn Val Asn His Lys Pro Ser
                 195                 200                 205

Asn Thr Lys Val Asp Lys Lys Val Glu Pro Lys Ser Cys Asp Lys Thr
         210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                 245                 250                 255

Thr Pro Glu Val Thr Cys Val Val Val Asp Val Ser His Glu Asp Pro
                 260                 265                 270

Glu Val Lys Phe Asn Trp Tyr Val Asp Gly Val Glu Val His Asn Ala
         275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                 325                 330                 335

Ile Ser Lys Ala Lys Gly Gln Pro Arg Glu Pro Gln Val Tyr Thr Leu
                 340                 345                 350

Pro Pro Ser Arg Asp Glu Leu Thr Lys Asn Gln Val Ser Leu Thr Cys
         355                 360                 365

Leu Val Lys Gly Phe Tyr Pro Ser Asp Ile Ala Val Glu Trp Glu Ser
         370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                 405                 410                 415

Arg Trp Gln Gln Gly Asn Val Phe Ser Cys Ser Val Met His Glu Ala
         420                 425                 430

Leu His Asn His Tyr Thr Gln Lys Ser Leu Ser Leu Ser Pro Gly
```

<210> SEQ ID NO 66
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: TPP-8565 Heavy Chain (IgG)

<400> SEQUENCE: 66

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Tyr Gly Met Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu

```
              340                 345                 350
Pro Pro Ser Arg Asp Glu Leu Thr Lys Asn Gln Val Ser Leu Thr Cys
            355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
        435                 440                 445
```

<210> SEQ ID NO 67
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: TPP-8568 Heavy Chain (IgG)

<400> SEQUENCE: 67

```
Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Tyr Tyr Tyr Tyr Gly Met Asp Val Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
```

```
                    245                 250                 255
Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Gln Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 68
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-8748 VL

<400> SEQUENCE: 68

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Gly Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Trp Val Phe Gly Gly Gly Thr Lys Leu Thr Val Leu
            100                 105                 110

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
      peptide
<220> FEATURE:
<223> OTHER INFORMATION: TPP-8748 L-CDR2

<400> SEQUENCE: 69

Gly Asn Asn Lys Arg Pro Ser
1               5

<210> SEQ ID NO 70
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: TPP-8748 Light Chain (IgG)

<400> SEQUENCE: 70

Gln Ser Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Ser Asn
            20                  25                  30

Pro Val Asn Trp Tyr Gln Gln Leu Pro Gly Thr Ala Pro Lys Leu Leu
        35                  40                  45

Ile Tyr Gly Asn Asn Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Trp Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```